US011891642B2

(12) United States Patent
Steele et al.

(10) Patent No.: US 11,891,642 B2
(45) Date of Patent: Feb. 6, 2024

(54) BIOCATALYTIC TECHNIQUES

(71) Applicant: HYPHA DISCOVERY LIMITED, Abingdon (GB)

(72) Inventors: Jonathan Charles Paul Steele, Maidenhead (GB); Antonio De Riso, London (GB); Francesco Falcioni, Manchester (GB); Richard Kerry Phipps, Aylesbury (GB); Stephen Keith Wrigley, High Wycombe (GB); Emily Jade Hopkins, Reading (GB); Aksana Rimu Khan, Slough (GB); Tetsuo Kokubun, Egham (GB); Kinga Linda Nytko, Slough (GB); Vincent Poon, Bicester (GB); Sebastian Schulz, Schenkendoebern (DE); John Maxim Ward, London (GB); Mariacristina Bawn, Royston (GB)

(73) Assignee: HYPHA DISCOVERY LIMITED, Abingdon (GB)

( * ) Notice: Subject to any disclaimer, the term of this patent is extended or adjusted under 35 U.S.C. 154(b) by 381 days.

(21) Appl. No.: 17/296,772

(22) PCT Filed: Nov. 26, 2019

(86) PCT No.: PCT/GB2019/053337
§ 371 (c)(1),
(2) Date: May 25, 2021

(87) PCT Pub. No.: WO2020/109776
PCT Pub. Date: Jun. 4, 2020

(65) Prior Publication Data

US 2022/0025416 A1 Jan. 27, 2022

(30) Foreign Application Priority Data

Nov. 26, 2018 (GB) ..................................... 1819209

(51) Int. Cl.
*C12P 13/00* (2006.01)
*C12N 9/02* (2006.01)
(Continued)

(52) U.S. Cl.
CPC .......... *C12P 13/005* (2013.01); *C12N 9/0077* (2013.01); *C12P 7/42* (2013.01);
(Continued)

(58) Field of Classification Search
None
See application file for complete search history.

(56) References Cited

U.S. PATENT DOCUMENTS 6,884,608 B2 4/2005 Basch et al.
8,293,979 B2 † 10/2012 Nakajima et al.
(Continued)

FOREIGN PATENT DOCUMENTS

CN 109022515 † 12/2018
WO 02/083062 10/2002
(Continued)

OTHER PUBLICATIONS

International Search Report and Written Opinion of the International Searching Authority dated Jun. 23, 2020 in International (PCT) Application No. PCT/GB2019/053337.
(Continued)

*Primary Examiner* — Robert J Yamasaki
*Assistant Examiner* — Charles Zoltan Constantine
(74) *Attorney, Agent, or Firm* — Wenderoth, Lind & Ponack, L.L.P.

(57) ABSTRACT

A method for the use of a cytochrome P450 enzyme comprising any of SEQ ID NO: 1-118, or mutants thereof or a variant enzyme having at least 70% identity thereto and having CYP450 activity, for the hydroxylation and or dealkylation of an organic compound.

-continued
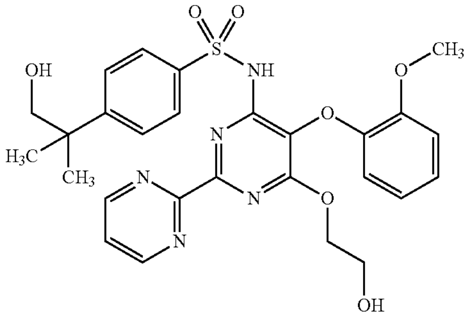
(b)
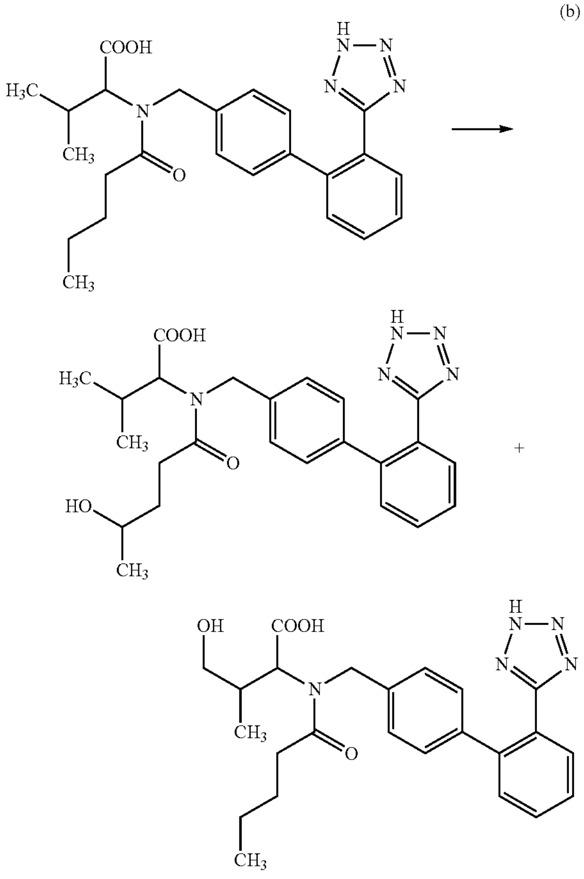
Figure 1(c) (d)
(c)
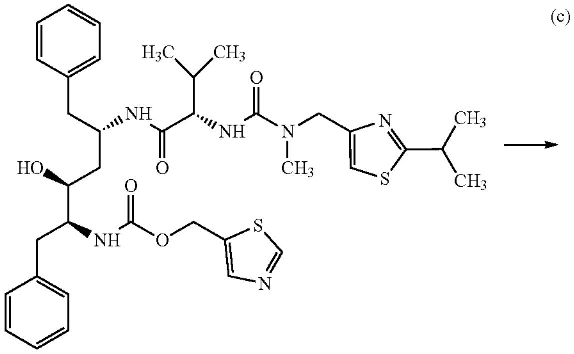
-continued
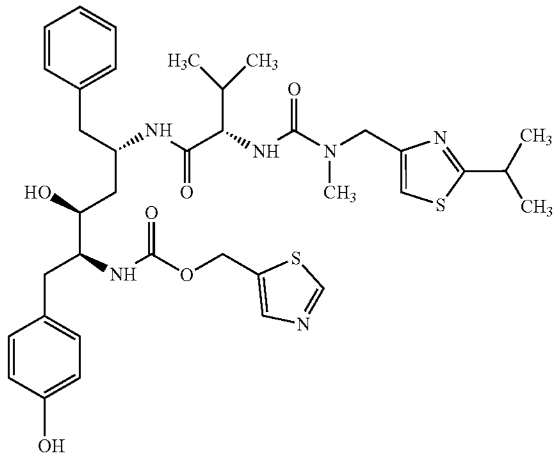
(d)
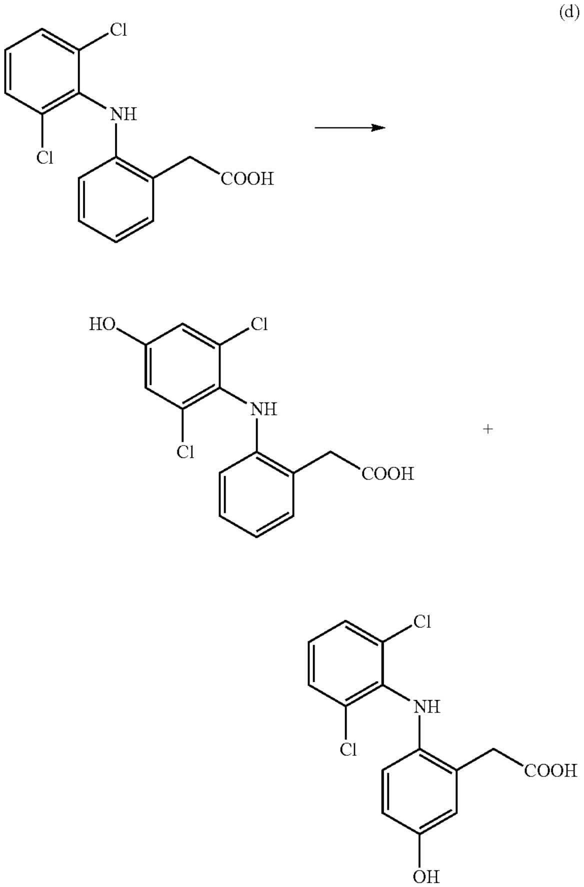
Figure 1(e)
(e)
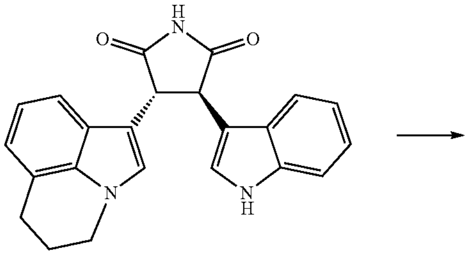

-continued

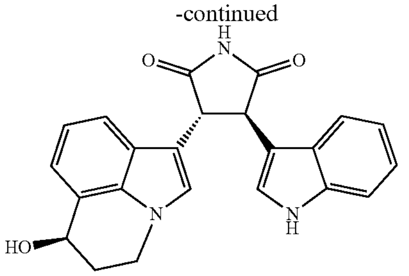

+

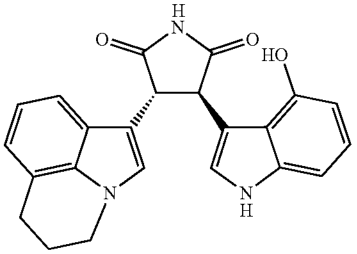

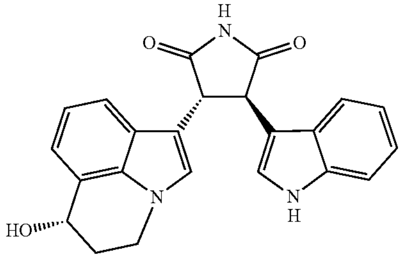

+

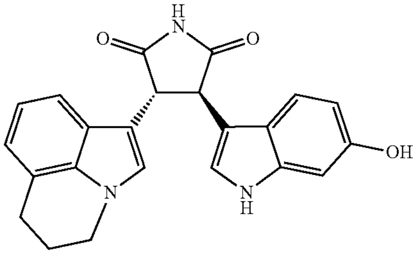

22 Claims, 111 Drawing Sheets

Specification includes a Sequence Listing.

(51) Int. Cl.

| | |
|---|---|
| ***C12P 7/42*** | (2006.01) |
| ***C12P 17/16*** | (2006.01) |
| ***C12P 17/18*** | (2006.01) |

(52) U.S. Cl.

CPC ........... *C12P 17/165* (2013.01); *C12P 17/167* (2013.01); *C12P 17/182* (2013.01)

(56) References Cited

U.S. PATENT DOCUMENTS

2010/0313300 A1 12/2010 Nakajima et al.
2014/0038850 A1† 2/2014 Fasan et al.

FOREIGN PATENT DOCUMENTS

WO 02/092801 11/2002
WO 03/057830 7/2003
WO 2004/078978 9/2004
WO 2011/038313 3/2011
WO 2012/109586 8/2012
WO 2013/073775 5/2013
WO 2016/007623 1/2016
WO 2018/091885 5/2018
WO 2019/220093 11/2019

OTHER PUBLICATIONS

Adam, Waldemar et al., "Biocatalytic Asymmetric Hydroxylation of Hydrocarbons with the Topsoil-Microorganism Bacillus megaterium", Journal of Organic Chemistry, 2000, vol. 65, No. 3, pp. 878-882.

Appleby, C.A. "A soluble haemoprotein P 450 from nitrogen-fixing Rhizobium bacterois", Preliminary Notes, Biochimica et Biophysica Acta, 1967, vol. 147, No. 2, pp. 399-402.

Basch, Jonathan et al., "Cloning and expression of a cytochrome P450 hydroxylase gene from Amcolatopis orientalis: hydroxylation of epothilone B for the production of epothilone F", J Ind Microbiol Biotechnol, vol. 34, 2007, pp. 171-176.

Broadbent, D.A. et al., "Bacterial attack on phenolic ethers Electron acceptor-substrate binding proteins in bacterial O-dealklases: purification and characterization P450npd of Nocardia", Microbios, 1974, vol. 9, pp. 119-130.

Danielson, P.B., "The Cytochrome P450 Superfamily: Biochemistry, Evolution and Drug Metabolism in Humans", Current Drug Metabolism, 2002, vol. 3, No. 6, pp. 561-597.

Denning, A., "Engineering of cytochrome P450 monooxy genases for application in phenol synthesis", Aachen University, 2013, pp. 1-222.

Fasan, Rudi, "Turning P450 Enzymes as Oxidation Catalysts", ACS Catalysis, 2012, vol. 2, pp. 647-666.

Hanukoglu, Israel, "Electron Transfer Proteins of Cytochrome P450 Systems", Advances in Molecular and Cell Biology, 1996, vol. 14, pp. 29-56.

Hussain, Haitham A. et al., "Enhanced Heterologous Expression of Two Streptomyces griseolus Cytochrome P450s and Streptomyces coelicolor Ferredoxin Reductase as Potentially Efficient Hydroxylation Catalysts", Applied and Environmental Microbiology, Jan. 2003, vol. 69, No. 1, pp. 373-382.

Lamb, David C. et al., "The First Virally Encoded Cytochrome P450", Journal of Virology, Aug. 2009, vol. 83, No. 16, pp. 8266-8269.

Le Gal, Annabelle et al., "Diversity of selective environmental substrates for human cytochrome P450 2A6: alkoxyethers, nicotine, coumarin, N-nitrosodiethylamine, and N-nitrosobenzylmethylamine", Toxicology Letters, 2003, vol. 144, pp. 77-91.

Lepri, Susan et al., "Metabolism study and biological evaluation of bosentan derivatives", European Journal of Medicinal Chemistry, 2016, vol. 121, pp. 658-670.

Mäntylä, Antti et al., "Synthesis and antileishmanial activity of novel buparvaquone oxime derivatives", Bioorganic & Medicinal Chemistry, 2004, vol. 12, pp. 3497-3502.

Nakamura, Katsunori et al., "Coumarin Substrates for Cytochrome P450 2D6 Fluorescence Assays", Analytical Biochemistry, 2001, vol. 292, pp. 280-286.

Narhi, Linda Owers et al., "Characterization of a Catalytically Self-sufficient 119,000-Dalton Cytochrome P-450 Monooxygenase Induced by Barbiturates in Bacillus megaterium", Journal of Biological Chemistry, vol. 261, No. 10, 1986, pp. 7160-7169.

Ohta, Kazuo et al., "Production of Human Metabolites of Cyclosporin A, AM1, AM4N and AM9, by Microbial Conversion", Journal of Bioscience and Bioengineering, vol. 99, No. 4, 2005, pp. 390-395.

Roper, Laila et al., "Biocatalysis for Organic Chemists: Hydroxylations", Chapter 8, Organic Synthesis Using Biocatalysis, 2016, pp. 213-241.

Rudolf, Jeffrey D. et al., "Cytochromes P450 for natrual product biosynthesis in Streptomyces: sequence, structure, and function", Natural Product Reports, vol. 34, No. 9, 2017, pp. 1141-1172.

Sariaslani, F. Sima et al., "Induction of Cytochrome P-450 In Streptomyces griseus by Soybean Flour", Biochemical and Biophysical Research Communications, 1986, vol. 141, No. 2, pp. 405-410.

(56) References Cited

OTHER PUBLICATIONS

Schwalb, Herzl et al., "Purification and characterization of pentobarbital-induced cytochrome P-450BM-1 from Bacillus megaterium ATCC 14581", Biochimica et Biophysica Acta. 1985, vol. 838, pp. 302-311.
Sherwood, Emma J. et al., "Cloning and Analysis of the Planosporicin Lantibiotic Biosynthetic Gene Cluster of Planomonospora alba", Journal of Bacteriology, 2013, vol. 195, No. 10, pp. 2309-2321.
Summers, D.K. et al., "Resolutioon of ColE1 dimers requires a DNA sequence implicated in the three-dimensional organization of the cer site", The EMBO Journal, vol. 7, No. 3, 1988, pp. 851-858.
Metal Ions in Life Sciences, vol. 3 "The Ubiquitous Roles of Cytochrome P450 Proteins", Sigel, A., Sigel, H and Sigel R.K.O. eds., John Wiley & Sons Ltd, 2007, pp. 1-667, XP055611890.
Thompson, Julie D. et al., "Clustal W: improving the sensitivity of progressive multiple sequence alignment through sequence weighting, position-specific gap penalties and weight matrix choice", Nucleic Acids Research, 1994, vol. 22, No. 22, pp. 4673-4680.
Worsch, Anne et al., "A novel cytochrome P450 mono-oxygenase from Streptomyces platensis resembles activitites of human drug metabolizing P450s", Biotechnology and Bioengineering, 2018, vol. 115, pp. 2156-2166.
Yu, C-A. et al., "Cytochrome P-450cam", The Journal of Biological Chemistry, 1974, vol. 249, No. 1, pp. 94-101.
UniProt: L8EFR2, "SubName: Full=Cytochrome P450-like enzyme {ECO:0000313/ EMBL: ELQ78055.1}", Apr. 3, 2012, XP002797538—cited in ISR/WO, copy not provided by the Searching Authority.
Shafiee, A. et al., "Macrolide Antibiotic Biosynthesis: Isolation and Properties of two forms of 6-deoxyerythronolide B hydroxylase from Saccharopolyspora erythraea (*Streptomyces erythreus*)", Biochemistry, vol. 26, No. 19, pp. 6204-6210, 1987.†
Di Nardo, G. et al., "Optimization of the bacterial cytochrome P450 BM3 system for the production of human drug metabolites", International Journal of Molecular Sciences, vol. 13, p. 15901-15924, 2012.†
Girvan, H.M. et al., "Applications of microbial cytochrom P450 enymes in biotechnology and synthetic biology", Current Opinion in Chemical Biology, vol. 31, pp. 136-145, 2016.†
Lamb, D.C. et al., "Unusual properties of the cytochrome P450 superfamily", Philosophical Transactions of the Royal Society B, vol. 368, pp. 1-13, 2013.†
Weber, J.M. et al., "Organization of a cluster of erythromycin genes in Saccharopolyspora erythraea", Journal of Bacteriology, vol. 172, No. 5, pp. 2372-2383, May 1990.†
Machida, K. et al., "Increase in Pladienolide D Production Rate Using a Streptomyces Strain Overexpressing a Cytochrome P450 Gene", J. Biosci. Bioengin., vol. 105, No. 6, pp. 649-654, 2008.†
Moody, S.C. et al., "CYP105-diverse structures, functions and roles in an intriguing family of enzymes in Streptomyces", Journal of Applied Microbiology, vol. 117, No. 6, pp. 1549-1563, 2014.†
Hayashi, K. et al., "Structure-based design of a highly active vitamin D hydroxylase from Streptomyces griseolus CYP105A1", Biochemistry, vol. 47, No. 46, pp. 11964-11972, 2008.†
Sugimoto, H. et al., "Crystal structure of CYP105A1 (P450SU-1) in complex with 1-α-25-dihydroxyvitamin D3", Biochemistry, vol. 47, No. 13, pp. 4017-4027, 2008.†
Xu, L-H. et al., "Structural basis for the 4'-hydroxylation of diclofenac by a microbial cytochrome P450 monoxygenase", Appl. Microbiol Biotechnol, DOI 10.1007/s00253-014-6148-y, Oct. 2014.†
Yao, Q. et al., "Hydroxylation of compacting (ML-236B) by CYP105D7 (SAV-7469) from Streptomyces avermitilis", J. Microbiol Biotechnol, vol. 27, No. 5, pp. 956-964, 2017.†
Bell, S.G. et al., "Engineering the CYP101 system for in vivo oxidation of unnatural substrates", Protein Engineering, vol. 14, No. 10, pp. 797-802, 2001.†
Kabumoto, H. et al., "Directed evolution of the actinomycete cytochrom P450 MoxA (CYP105) for enhanced activity", Biosci. Biotechnol. Biochem., vol. 73, No. 9, pp. 1922-1927, 2009.†
Liu, L. et al., "Hydroxylation of flavanones by Cytochrome P450105D7 from Streptomyces avermitilis", Journal of Molecular Catalysis B: Enzymatic, vol. 132, pp. 91-97, 2017.†

† cited by third party (a)

(b)

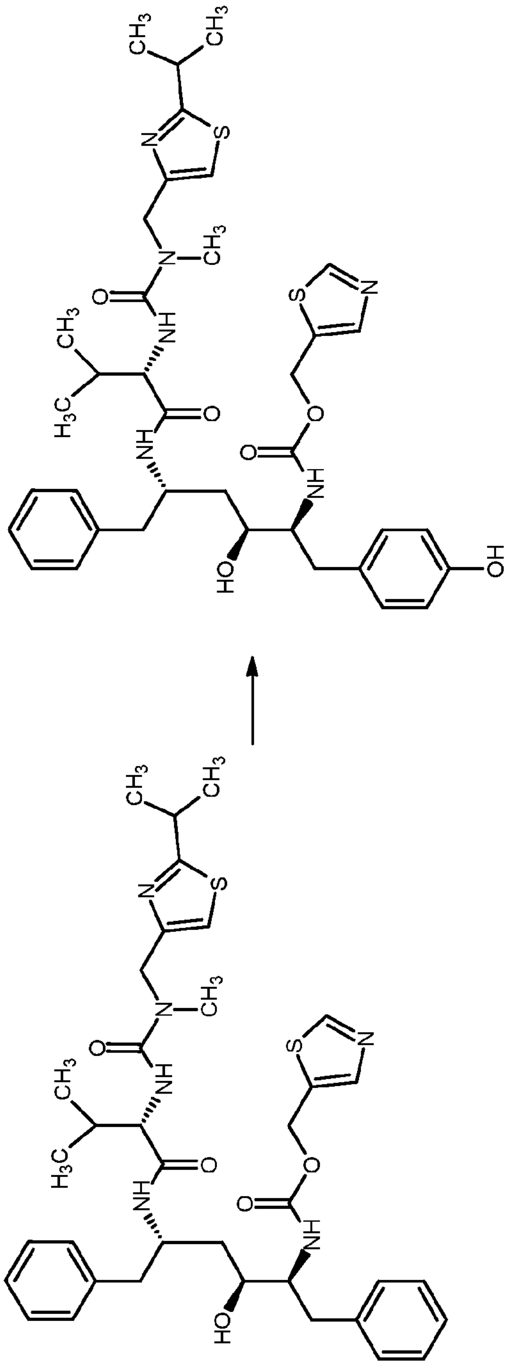
(c)
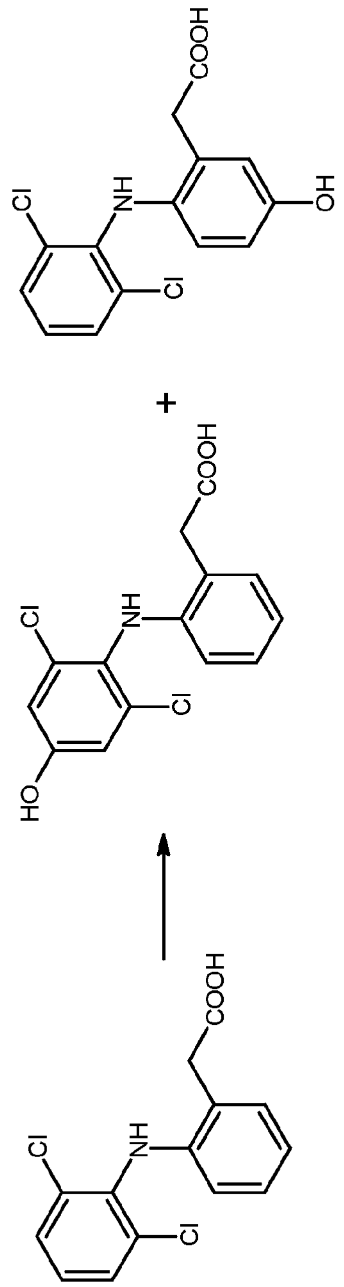
(d)
Figure 1(c) (d)

SEQ ID NO: 1 (coding sequence of sriC01)
P450 sriC01: SRIM_16590

*ATG**ACCGAGACGATCCCGTTCGAAGCAGTCGACGGCGCGGTGCGCCCGTCCG*
*AGGAGGTGCCGGTCGTCGACCTGTCGGCCACCGGCCTCAGCGACACCCCCCT*
*CCAGCAGGCCATGGGCCTGGCCCGCGAGCACGGCGCGGTGTACCGGCGGCG*
*GCTGCACGGCCATGAGGCACTGCTCGTGTCCTCCCTGGAGCTGGTCACCGAA*
*CTGGCCGACGAGAACCGCTTCGCCAAGGGCGTCTCGGTCGCCCTGGAGAACG*
*TCCGCGAGTTCGCCGGCGACGGCCTGTTCACCGCGTACAACGACGAACCGAA*
*CTGGGCCAAGGCGCACGACATCCTCATGCCGGCCTTCGCCCTCGGCTCGATG*
*CGCACGTACCACCCGGCGATGCTGAAGGTCGCCCGCCGGGTGATCGGCAGCT*
*GGGACCGGCGCGCGGCCGACGGCACACCCGTCGACGTCCCCGACGACATGA*
*CCCGGATGACGCTCGACACCATCGGCCTGGCGGGCTTCGGCTTCGACTTCGA*
*GTCCTTCTCCCGCGCGACCATGCACCCCTTCGTCGAGGCGATGGTGCGTTGC*
*CTGGAATGGAGCATGAAACGCCTCGGCCGGGAGCCGGACGGCGACTACACC*
*GAGGAGGACGCTGCCTTCCGGGCCGACGCGGACTACCTCGCCTCGGTCGTG*
*GACGAGGTCATCGCCTCCCGTACGGGTGCGGACGGCACCCCGGGCGAGGAG*
*GCGGGCGACGACCTCCTCGGCCTGATGCTCGGCGCCACCCACCCCGCCGAC*
*GGCACCACGCTCGACCTCGCCAACATCCGCAACCAGGTCATCACCTTCCTCAT*
*CGCCGGTCACGAAACGACCTCCGGCGCGCTGTCCTTCGCCCTGTACCACCTG*
*CTCAAGGACCCGGCCGCCCTGCGCCTGGCGCAGCGCGAGGCCGACGAGCTG*
*TGGGGCGACCAGACCGACCCCGACCCGTCCTTCGAGGACATCGGCCGACTGC*
*CCTACACCCGCCAGGTCCTCAACGAGGCGCTGCGCCTGTGGCCCACCGCCGC*
*CGCCTTCTCCCGCCAGGCCCGTACGGACACCCTGCTCGGCGGCCGCATCCCA*
*CTGAAGGCGGGCCAGCTGGTCACCGTCCTCACGCCGATGCTGCACCGCGACC*
*CGGCCTGGGGCGACAACCCGGAGCTGTTCGACCCCACGCGGTTCGCGCCGG*
*AGGCCGAGGCGGCCCGCTCCCCGCACGCGTACAAGCCCTTCGGTACGGGCG*
*AGCGGGCCTGCATCGGCCGCCAGTTCGCGCTGCACGAGGCGACGATGCTGCT*
*CGCCATGCTGGTGCACCGCTACCGCCTCATCGACCACAGCGACTACCGCCTG*
*AGCATCAAGGAAACCCTGACCCTCAAGCCGGACGGCTTCACCCTCACCCTCGC*
*CCGGCGCACCCCCGCCGACCGCGCGGGCCTGCGCGCCGCCCTCGCCGTACT*
*GCCCGGCGGAGCCGCGGAGCCGGACGGCACCGAGTCCGGTACGGACGACG*
*GCCTGCCGACGCGGGTCCGCCAGGACACCGCCCTGCTCCTCCTCCACGGCAC*
*CAACTACGGCACCTGCCGCGACTTCGCCGAGCGCATCGCCGACGAGGCCACC*
*GGCCTCGGCTTCACCACCGAGGTGGCCCCGCTGGACGCCGCGACCGGCGCG*
*CTCCCCACGGACCGCCCGGTCGTGATCGTCACCGCGTCCTACAACGGACAGC*
*CGACCGATGACGCGGCGCGCTTCGTCGAATGGCTTTCCGGCGACGAAGCCCG*
*GGCCGAAGGCGTCCCCTACGCCGTCCTCGGCGTCGGCGACCGCAACTGGGC*
*CGCCACCTACCAGCGCGTGCCCACGCTTTTGGACGAGCGGCTGGCCGCCCTC*
*GGCGCCGAGCGGCTCCTCCCGCGCGGCGAGGCCGACGCATCCGGCGACCTG*
*AACGGCGCCGTCAAGGCGTTCACGGCCACCCTGCGCACCGAACTGCTCGTAC*
*GCTACGGCGATCCCGCGACCATCGGCGCGAGCACACCGGCCGACGCCACGG*
*ACGCGTCCTACACCGTCCGCGAGGTCACCGGCGGCCCCCTGGACGCACTCGC*
*CGCCCGCCACGGCCTCCAGCCGATGACCGTCACCGAGGCGTACGACCTCACC*
*GCCCCCGGCTACCCGCGCGTCAAGCGCTTCCTGCGCCTCACCCTCCCCGAAG*
*GCGTTACGTACCGTACGGCCGACCACCTCGCCGTACTTCCCGCCAACGGCGC*
*GGCGGCGGTCGAACGCGCCGCGCAGGTGCTGGGCGTATCACTGGAAGCGGT*
*CCTCGACATCCGCGCGGGCGCTGGTCGCGGCGGCCGGGACACGCTCCCCGT*
*GGACCGCCCGCTCACGGTACGTCAGCTCCTCACCCACCACCTGGAGCTGAAC*
*GCCCGACCGACTGCCGCGCAACGGGCGGTGCTCGCCGACCACAACCCCTGT*
*CCGCCCGAGCGTGCCGCCCTCCAGGCCATCCCCGACGACGACCCGCGCACC*
*ACCCTGGACCTCATCGAGGAACACCCGGCCCTGCGCGGTGTGCTGCCCTGGC*
*CGGTACTCCTCGACCTGCTCCCGGCCCTGCGCATCCGCCACTACTCCCTCTCG*

Figure 4 (continued)

*TCCTCGCCCGCCGCCGACCCCCGCCACGCCGACCTGATGGTCTCGCTGCTCC*
*CCGGCGGCACCGGCTCCGGCCACCTGCACACACTGCGGCCCGGCGACACGG*
*TCCTGGCCCGGGTCCAGCCCTGCCGGGAGGCGTTCCGCCTCGACCCGGCCG*
*ACCCGACACCGGTCATCCTGGTAGCGGCCGGCACCGGCCTGGCGCCCTTCCG*
*GGGCGCGGTCGCCGACCGCCTGGCCGCCACCCAACTTGCCCCTGCTCTGCTC*
*TACTTCGGCTGCGATGCCCTCGAAGCCGACTACCTGCACGCCGAAGAACTCCA*
*GGCCGCCGAGGCAGCCGGGGCCGTGTCCCTGCGCCCCGCGTTCAGCGCCCG*
*CCCGGTGGACGGCTGCCGTTACGTCCAGCACCGCATCGCCGCCGAGGCGGA*
*GGAAGTGGGGGCGCTGCTGGACGCCGGAGCCCGGGTGTACGTCTGCGGCGA*
*CGGCAACCGGATGGCCCCGGGCGTACGCGCCGCCTTCCGCGAGCTGTACGC*
*GGCCCGTACCGGCGCCACGCAGGAGGAGGCCGAGGTCTGGCTGCGAGAGCT*
*CACGGCGGCCGGCCGGTATGTGGAGGATGTCTATGTGACGGGGTAA*

Legend
*P450 (italics)*
Start and stop codons in bold

Protein sequence
(Translated using Expasy from DNA sequences above)

SEQ ID NO: 2 (amino acid sequence of cytochrome SriC01 (1064 aa))
MTETIPFEAVDGAVRPSEEVPVVDLSATGLSDTPLQQAMGLAREHGAVYRRRLHG
HEALLVSSLELVTELADENRFAKGVSVALENVREFAGDGLFTAYNDEPNWAKAHDI
LMPAFALGSMRTYHPAMLKVARRVIGSWDRRAADGTPVDVPDDMTRMTLDTIGLA
GFGFDFESFSRATMHPFVEAMVRCLEWSMKRLGREPDGDYTEEDAAFRADADYL
ASVVDEVIASRTGADGTPGEEAGDDLLGLMLGATHPADGTTLDLANIRNQVITFLIA
GHETTSGALSFALYHLLKDPAALRLAQREADELWGDQTDPDPSFEDIGRLPYTRQ
VLNEALRLWPTAAAFSRQARTDTLLGGRIPLKAGQLVTVLTPMLHRDPAWGDNPE
LFDPTRFAPEAEAARSPHAYKPFGTGERACIGRQFALHEATMLLAMLVHRYRLIDH
SDYRLSIKETLTLKPDGFTLTLARRTPADRAGLRAALAVLPGGAAEPDGTESGTDD
GLPTRVRQDTALLLLHGTNYGTCRDFAERIADEATGLGFTTEVAPLDAATGALPTD
RPVVIVTASYNGQPTDDAARFVEWLSGDEARAEGVPYAVLGVGDRNWAATYQRV
PTLLDERLAALGAERLLPRGEADASGDLNGAVKAFTATLRTELLVRYGDPATIGAST
PADATDASYTVREVTGGPLDALAARHGLQPMTVTEAYDLTAPGYPRVKRFLRLTL
PEGVTYRTADHLAVLPANGAAAVERAAQVLGVSLEAVLDIRAGAGRGGRDTLPVD
RPLTVRQLLTHHLELNARPTAAQRAVLADHNPCPPERAALQAIPDDDPRTTLDLIEE
HPALRGVLPWPVLLDLLPALRIRHYSLSSSPAADPRHADLMVSLLPGGTGSGHLHT
LRPGDTVLARVQPCREAFRLDPADPTPVILVAAGTGLAPFRGAVADRLAATQLAPA
LLYFGCDALEADYLHAEELQAAEAAGAVSLRPAFSARPVDGCRYVQHRIAAEAEEV
GALLDAGARVYVCGDGNRMAPGVRAAFRELYAARTGATQEEAEVWLRELTAAGR
YVEDVYVTG-

SEQ ID NO: 3 (coding sequence of sriC02)
P450 sriC01: SRIM_23771
*ATGACCGGCGTATCCGCCCGCGAACCCGCAGCGGGCCGCACCGACGCCTCC*
*CGGTGGCTGCTGCGCCGCCGGGTGCTGTCGGACCCCGCGCTGCGGCTGATC*
*TGCTTCCCGCACGCCGGGGGCGCCGCGACCTTCTTCCACGGGTGGCAGGAC*
*CGGGTACCGGCCGGTACCGAGGTCGGCGCGGTCTGCTATCCGGGGCGGCAG*
*AACCGGATCGCCGAGCCGCCGCTCACCTCCATGGACGACCTCGCCGACCAGG*
*CGCACGCGGCGCTGCGCGGGCTGCTCGACCGCCCGCTGGCGCTCTTCGGGC*
*ACAGCATGGGCGCGGTCGTCGCGTATGAGGTGGCCGTGCGGCTCGCCGAAC*
*GCGACGGCACCGCACCGGTGGCCCTGCTGGTGTCCGGGCACGGCGCCCCGT*
*ATCTGTGCGTGGCCGGGCCGCCGCCGGACACCGCGGCGGACGACCGGGAGA*
*TCGCCGAGCTGGCGATGGCCGCCGACCCGGCGCTGCGCGGCTCGCCCCAGC*

Figure 4 (continued)

*TGCTGGACCTGGTCATGCCGGTGCTCCGCGCCGACCACGCGCTGCTCCGCGC
CTACCGGCCCGTACGCACCCCGCGGATCACCGCGCCGATCGTCGCCTACCGT
GGCGCGGACGACCCCAGGGCGAGCGAGGACGACATGTGGTCCTGGCGCGCG
ATGACCGGCGCCGCCTTCCGGCTCCGTACGCTGCCCGGCAACCACTTCTACC
TGGCCACCGAGGAGGCCGGGCTGGTGGCCGATGTCATGGACGCCTGTCGGG
GCGGTGCGAACGGCGCCGCCGGAAGCACCGCGACCGGCCCGGCCACCGCCT
CCGCCGTACCGCTGTTCGTACGCCGCTCCGGCGCCTGCCCCTTCGACCCGGC
GGAGGACTTCGCCCGGCTGCGCGCCGAGCGGCCCGTGGTCCGCACCACCTT
GCCGACCGGGGCCCGCGCCTGGATGGTCACGCGCTACGCCGACGCCCGCCG
CGTCATCGCCGACCAGCGGCGCTTCAGCTCCCGGGCCGCCGTGAACGGCCC
GGTGCCGCCCCCGGAACCGCCCGAAGGCTTTCCGCCGCCGCGGCCCGGCGT
CTTCTACACGTACGAGCCCGAGGAGCACGGCCGCATCCGCCGGATGCTCACC
CCGGAGTTCAGCGCCCAGCGTGCCCGCGTCCTGGAGCCGCGCGCGGAAACC
CTGGCCGACCGGCACCTCGACGCCATCGAGCGGGCCGGGCCGCCCGCCGAC
CTGATCGCCGACTTCGTGCTGCCGGTGCCCCGGCTGCTGTTCCTGGAACTGCT
GGGCGTGCCCCTCCAGGACGCCGGGCGCCTCCACCACGACCTGGCGCTCCT
GCACGACTTCCACCCCATCCACGAGGCGCAGGCGGGAGCGTTCCGCCGGCTC
GACGCGTACCTGCGGGAACTGGTGGAAACCGCACGCGCCACACCCGGCGAC
AACGTCCTGGGCCACCTGGTCGCCGCGCACGGCGCCGAGCTGAGCGACGAC
GAACTCGCCGGAATCGCCTGCCAGTTGCTGCTGGCCGGATACGCGACGATCG
CCGGCACCCTGGGCCTGTCCCTGCTCGCCCTGATCCTCGACCCCGTACAGGC
GGAGCTGGTGCGCGACGGGCGCGCCCGGCCCGACCGGATGGCCGAGGAACT
GATCCGCCACCTGTCGGTGGTGACCTTCGGCAAGGTCTTCCAGGCGAAGGAG
GACGTCACGATCGCGGACCAGGACATCGCGGCGGGCGAGTACGTGCTGTGC
CATCTGCCGTCCGCCAACCGCGATCCGGCGCTGGCCGACGGCCTCGACCGC
CTCGACGTCACCCGTGAGCCGACGCCCCACCTCGCCCTCGGCCACGGCGCG
CACCACTGCCTGGGCGCCGAACTGGCCCGGATGGAACTGCGGGTCTGCGTGC
CCCGTGTCCTGCGGCGGCTGCCGGGTCTGCGCTTGCGCGTCCCCGTCGAGG
AGCTGCGCTTCACACCACTGAACGCCGCGTACGGAGTGGAATCCCTGCCGGT
CGCCTGGTAA*

Legend

*P450 (italics)*

Start and stop codons in bold

Protein sequence

(Translated using Expasy from DNA sequences above)

SEQ ID NO: 4 (amino acid sequence of cytochrome SriC02 (670 aa))

MTGVSAREPAAGRTDASRWLLRRRVLSDPALRLICFPHAGGAATFFHGWQDRVP
AGTEVGAVCYPGRQNRIAEPPLTSMDDLADQAHAALRGLLDRPLALFGHSMGAVV
AYEVAVRLAERDGTAPVALLVSGHGAPYLCVAGPPPDTAADDREIAELAMAADPAL
RGSPQLLDLVMPVLRADHALLRAYRPVRTPRITAPIVAYRGADDPRASEDDMWSW
RAMTGAAFRLRTLPGNHFYLATEEAGLVADVMDACRGGANGAAGSTATGPATAS
AVPLFVRRSGACPFDPAEDFARLRAERPVVRTTLPTGARAWMVTRYADARRVIAD
QRRFSSRAAVNGPVPPPEPPEGFPPPRPGVFYTYEPEEHGRIRRMLTPEFSAQRA
RVLEPRAETLADRHLDAIERAGPPADLIADFVLPVPRLLFLELLGVPLQDAGRLHHD
LALLHDFHPIHEAQAGAFRRLDAYLRELVETARATPGDNVLGHLVAAHGAELSDDE
LAGIACQLLLAGYATIAGTLGLSLLALILDPVQAELVRDGRARPDRMAEELIRHLSVV
TFGKVFQAKEDVTIADQDIAAGEYVLCHLPSANRDPALADGLDRLDVTREPTPHLA
LGHGAHHCLGAELARMELRVCVPRVLRRLPGLRLRVPVEELRFTPLNAAYGVESL
PVAW-

Figure 4 (continued)

SEQ ID NO: 5 (coding sequence of sriC03-sriF01)
P450 sriC03: SRIM_10361
Ferredoxin sriF01: SRIM_10356
*ATG**CCGGACGAGTCCCAGCACCAGTTCGACCACGCCCGCCGGGCGGGCTTC*
*GGCCCGTCGGACGACATCCGCCGGCAGCGCGCCCAGGGCGCCCTCGTCCGG*
*GAAGAGGTGGCCCCGGCGCCCGGCGCCGCACCCGAGCCCATCTGGATGGCC*
*CTGAGCTACGAGGCCGTGCGCCAGGTCATGGGCGACCACGTCCGCTTCAGCA*
*ACCAGCGCCGGTTCCGCGCCCAGGCCATCCGCGGCGGGAGCAAGCACCGCC*
*CGCAGGAGATGTCCGGCCACCTCATGGACTACGACCAGCCCGAGCACACCCG*
*GCTGCGCAAGATGCTCACGCCGGAGTTCACGGTCCGCCGCATCCAGCGGCTC*
*AAGCCGGTGACCGAGGCGATCGCGGAACGCTGCCTGGACGCCATGGAGCGC*
*AAGGGGCGGCCCGCCGACCTCGTCGAGCTGTACGCGAGCCCGATCTCCGGC*
*GCGGTGCTGTGCGAACTGCTCGGCGTGCCCCGCGACGACCGGCGCGAGTTC*
*CTGGTCAAGCACCAGTGGCAGCTGGAGCAGGACCGCAGCCGCAAGGAGCGC*
*GCCGCGGCTCAGGCGTACACCTCCAACTACCTGCGCGCGCTGGTCAAACGGC*
*AGCGCAAGGACCCCGACGAGGGCTTCATCGGCCAGCTCATCCGCGACCACGG*
*CGACAACTTCGACGACGAGGAACTGATCGGCATCTGCGGCCTGATGGTGCTG*
*GCCGGCCTGGACAACGTCAACGGCATGATCAGCCTCGGTGTGCTGGCCCTCC*
*TGGAACACCCGGACCAGCTCGCCGTCCTGCTGGCGGACCCCGAGAACACCGT*
*GGACCGGGTGGTGGACGAACTGCTGCGCTTCCTGTCCGTGGCGCACGCGCC*
*GACCCCGCGCACCGCCGTCGAGGACGTGGTCGTGGCCGGGCAGCTGATCAA*
*GGCGGGGGAGGAGGTCGTCTGCTCGATCCCGATGGCCAACCGCGACCCGGT*
*ACTCGCCCCCGACGTCGACCGGTTCGACGTCAACCGCGAGCCGCTGCCGCAC*
*ATCGCCTTCGGGCACGGCATCCACCACTGCATCGGCGCCGCGCTCGGCCGGA*
*TGGAACTGCGCACCGCCTACCTGGCGCTGTGGCGCCGGTTCCCGGACCTGCG*
*GCTGGCCGTGCCCGCCGACCAGGTGCCGCACAAGACGAATTCCATCGCGTAC*
*GGCCTGGAGCGCCTGCCGGTCGCCTGG**TGA*CGGCGGCCCGGCCACGGCGC
GCGGCGCCCGCGGAAGAGGAGGGACGATGGTCGAGGTACGGGTCGACGCG
GAGATCTGCGCGGCGTCCGGCATGTGCACGCTGCTGGTGCCCGCGGTCTTCG
ACCAGTCGGAGGAGGACGGCACGGTGGTGCTCGCCGATCCGGCGCCGCCCG
CGGAACTGGCGGCGAAGGTGCGGACGGCGGCGCTGCGGTGCCCGGCCGGC
GCGATCTCGGTGCACGAGCGGGAGGCGGACGGCCCGGGTACGTAA
Legend
*P450 (italics)*
Ferredoxin
Start and stop codons in bold

Protein sequence
(Translated using Expasy from DNA sequences above)

SEQ ID NO: 6 (amino acid sequence of cytochrome SriC03 (404 aa))
MPDESQHQFDHARRAGFGPSDDIRRQRAQGALVREEVAPAPGAAPEPIWMALSY
EAVRQVMGDHVRFSNQRRFRAQAIRGGSKHRPQEMSGHLMDYDQPEHTRLRKM
LTPEFTVRRIQRLKPVTEAIAERCLDAMERKGRPADLVELYASPISGAVLCELLGVP
RDDRREFLVKHQWQLEQDRSRKERAAAQAYTSNYLRALVKRQRKDPDEGFIGQLI
RDHGDNFDDEELIGICGLMVLAGLDNVNGMISLGVLALLEHPDQLAVLLADPENTV
DRVVDELLRFLSVAHAPTPRTAVEDVVVAGQLIKAGEEVVCSIPMANRDPVLAPDV
DRFDVNREPLPHIAFGHGIHHCIGAALGRMELRTAYLALWRRFPDLRLAVPADQVP
HKTNSIAYGLERLPVAW-

SEQ ID NO: 7 (amino acid sequence of ferredoxin SriF01 (73 aa))
MVEVRVDAEICAASGMCTLLVPAVFDQSEEDGTVVLADPAPPAELAAKVRTAALR
CPAGAISVHEREADGPGT-

Figure 4 (continued)

SEQ ID NO: 8 (coding sequence of sriC04)
P450 sriC04: SRIM_15030

*ATG**GCGAGCCGTACCCGTATCGATACGCCTGGTCGTAACGAGCACCGGCTGC*
*ACACCGTCCCCCTGCGCCATGTCCTCGGCGGCCTGCGGGCGGGTGGTCCGC*
*TGGGGCTGATGGAACGTACCGGGCGCCGGTCGCAGGGCGCGCTGACCCGGC*
*TGGAGCTGGGCGCCTTCCGGCCCTTCCTGGTCACCCACCCCGATCATCTGCG*
*GCACGTCCTGCGCGACCACGGTGCGAACTACCGCCGGGGCACCGCGATGTG*
*GAAGGCGATGGGGCGGCTGACGGGGATGGGGATCGCGGGCGAGGGGCCGC*
*AGTGGCGGGCCAGCCGTGAGCTGTGGTGCCGGGGACTGTCGGGCGGTGCGC*
*ACGTCTTCGCCGACGGGACGGCCGACGCGGTCGCCGGGGCGGTGGCGGACC*
*TGGAGCGGCGGGTGGCGGCGGGCGCGACGGTGGACGCGCTGACGGAGATG*
*ACCCGTGTCGTGCTCCGGGTCGTGAATCCGGCGTTCTTCGGCTCGCGCATTCC*
*GCAGGGGGAGTGCGACCGGCTCGCCGCGGCGGTCGCCGTCGCGTTCGACTC*
*GCTGCTGTGGCGCATGGCGCTGCCTTTCGTACCGCTCGCCGTGCCGTTGCCG*
*GGCGATCGCGCCTTCACCCGCGCCACCCGTACGGTCAACGGCATCCTGCTGC*
*CGCTGATCCGCCGGGCACGGCACGCGCACCACCGCGGCCCGGACCTGATGA*
*GCACGCTGCTCGACGGGGCGGACGCGGACGGCCGGGCGCTGGGCGACGCG*
*CATGTGGCCCAGGACATCGTGGCCATGTTCGTGGCGGGTTCGGAGTCCAGCG*
*CCCTGACGCTGACGTGGGCCTGGGTCGCCCTCGCCGGGCATGCCGACATCG*
*CGGCGGAGGTGCGCCGGGAGGCCGACGCGGTGCTCGGCGGCGGGCCGCCC*
*CGGCCCGAGCACGCCCGCCGGCTGGTGTTCACCCGGAGGGTGCTGGCCGAG*
*GTCTGCCGCCTGTACGCGATGGCGTGGGCGGTGCCGCGGACGGCCGTCGCC*
*GAGGACGTCATCGGCGGGGTGACCGTTCCGGCCGGCGCCACGCTGGTGCTG*
*TCCCCGTACCTGACCCACCGGCTGCCCGCCTTCTGGGAGCGGCCGCTGCGCT*
*TCGACCCCGGCCGTTTCACCGACGAGCGCGTACGGGGCCGGCACCCGCTGG*
*CGTACCTGCCGTTCGGCGACGGACCCCACCAGTGCGTCGGCCAGTCGTTCTT*
*CTTCCAGCAGGCGGCCCTCGTCGTGGCCACGATGATGAGCCGTTTCCGTATC*
*GCCGTGCCGACGCCGGCCGAGCCCAGGGCCGCGGTCGCGCTGCGCCCGCG*
*GAGCCGTGTCGATCTGGCGCTCACCCCGCGCGGC**TAA*
Legend
*P450 (italics)*
Start and stop codons in bold

Protein sequence
(Translated using Expasy from DNA sequences above)

SEQ ID NO: 9 (amino acid sequence of cytochrome SriC04 (455 aa))
MASRTRIDTPGRNEHRLHTVPLRHVLGGLRAGGPLGLMERTGRRSQGALTRLELG
AFRPFLVTHPDHLRHVLRDHGANYRRGTAMWKAMGRLTGMGIAGEGPQWRASR
ELWCRGLSGGAHVFADGTADAVAGAVADLERRVAAGATVDALTEMTRVVLRVVN
PAFFGSRIPQGECDRLAAAVAVAFDSLLWRMALPFVPLAVPLPGDRAFTRATRTVN
GILLPLIRRARHAHHRGPDLMSTLLDGADADGRALGDAHVAQDIVAMFVAGSESSA
LTLTWAWVALAGHADIAAEVRREADAVLGGGPPRPEHARRLVFTRRVLAEVCRLY
AMAWAVPRTAVAEDVIGGVTVPAGATLVLSPYLTHRLPAFWERPLRFDPGRFTDE
RVRGRHPLAYLPFGDGPHQCVGQSFFFQQAALVVATMMSRFRIAVPTPAEPRAAV
ALRPRSRVDLALTPRG-

SEQ ID NO: 10 (coding sequence of sriC05-sriF02)
P450 sriC05: SRIM_15540
Ferredoxin sriF02: SRIM_15535
*ATG**TCGTACAACCCGACGGCCCCCGACACCACCGCCGACGGCACCACCGGAG*
*AACCGCCCACCCTGCCCACCGACCGGCGCACCGGCTGCCCCTTCGACCCGCC*

Figure 4 (continued)

*CGGCGAACTCACCGCGCTGAGCGACCGGCCCCTGCGCCGCATGCGCTACGC*
*CGACGGGCACATAGGCTGGCTGGCCACCGGCCACGCCGCCGCCCGCGCGGT*
*CCTGTCCGACCCGCGCTTCAGCTCCCGCTACGAACTCCTGCACCTGCCGGTA*
*CCGATGCCGGGCATGGAGGGGATGACGGCGGTGCCGCCGGCGCCGACCGG*
*CGACTTCCTCGGCCTCGACGCCCCCGAGCACACCCGCTACCGGCGGCTGCTC*
*ACCGGCAAGTTCACGGTCCGCCGGATGCGTCAGCTCTCCGAACGCGTGGAGC*
*AGTTCACCCACGAGTGCCTGGACGCCATGGAGCAGGCCGGGCCCACCGTCGA*
*CCTGGTGGAGGCGTTCGCGCGGCCGGTGCCCGCGCTCATGATCTGCGAACTG*
*CTCGGCGTGCCGTACGCCGACCGGGACCGCTTCCAGGAGCATGTGGCGACC*
*CTCTTCGACCAGGCCGCGGACGCGGAGGCGAGGGGCGCGGCGTTCGCCGCC*
*GTCGGCCGCTTCATGGGCGAACTCGTGGCCGCCAAGCGCGCCGAGCCCACC*
*GACGACCTGCTCAGCGACCTGACCACCTCCGACCTCACGGAGGAAGAGCTGA*
*TCGGGGTCGGCGGGGTGCTCCTGGCCGCCGGTCTCGACACCACCGCCAACAT*
*GCTCGGGCTCGGCACCTTCGCCCTGCTCAGCAACCCCGACCAGCTGGACGCC*
*CTGCGCGCCGACCCGGGCCTCGCCGGGCAGACCGTCGAGGAGCTGCTGCGC*
*TACCTCAGCGTGGCCGACCCCATCCCGCGCGCCGCCCTGGAGGACGTCGAGA*
*TCGAAGGCCGGCTGGTCAGGGCCGGTGAGACGGTGACCGTCTCGGTCCAGG*
*CCGCCAACCGCGACCCGCTGAAGTTCCCCGACCCCGACCGGTTCGACATCCA*
*CCGCAAGGCCACCGGGCACGTCTCCTTCGGCCACGGCCCCCACCAGTGCCTC*
*GGCCAGCAGCTCGCCCGCGTCGAGATGACCGTCGCGTTCCCGGCGCTCTTCG*
*CCCGCTTCCCCACCCTGCGCCTCGCGGTTCCGCCGCAGGAGGTGCCGCTGC*
*GCGACCGCGCCAACATCTACGGCGTGATCAGCCTGCCCGTCACCTGGGACAA*
*GGAGTAA*CCCCATGAGCGAGCCACAAGAGCGGCTGCGTCTGAGCGTCGACC
GTGACCGCTGCGTCGGCGCCGGGATGTGCGCCCTGACCGCTCCCGAGGTCTT
CGACCAGGACGACGAAGAGGGCCTGGTGGTGCTCAAGCACCCCGTACCGGC
CCCCGGCAGCCTGGCCGCCGCCCGGATGGCCGCCGGCCTCTGCCCCGCCGG
AGCCATCACCCTCCACTCCCCGGAACCCACGGACCCGTAA

Legend
*P450 (italics)*
Ferredoxin
Start and stop codons in bold

Protein sequence
(Translated using Expasy from DNA sequences above)

SEQ ID NO: 11 (amino acid sequence of cytochrome SriC05 (414 aa))
MSYNPTAPDTTADGTTGEPPTLPTDRRTGCPFDPPGELTALSDRPLRRMRYADG
HIGWLATGHAAARAVLSDPRFSSRYELLHLPVPMPGMEGMTAVPPAPTGDFLGLD
APEHTRYRRLLTGKFTVRRMRQLSERVEQFTHECLDAMEQAGPTVDLVEAFARPV
PALMICELLGVPYADRDRFQEHVATLFDQAADAEARGAAFAAVGRFMGELVAAKR
AEPTDDLLSDLTTSDLTEEELIGVGGVLLAAGLDTTANMLGLGTFALLSNPDQLDAL
RADPGLAGQTVEELLRYLSVADPIPRAALEDVEIEGRLVRAGETVTVSVQAANRDP
LKFPDPDRFDIHRKATGHVSFGHGPHQCLGQQLARVEMTVAFPALFARFPTLRLA
VPPQEVPLRDRANIYGVISLPVTWDKE-

SEQ ID NO: 12 (amino acid sequence of ferredoxin SriF02 (77 aa))
MSEPQERLRLSVDRDRCVGAGMCALTAPEVFDQDDEEGLVVLKHPVPAPGSLAA
ARMAAGLCPAGAITLHSPEPTDP-

SEQ ID NO: 13 (coding sequence of sriC06)
P450 sriC06: SRIM_13998
*ATGAGCGACCCGGCCGCGGTACGCCGGGCCCTGCGCGCGCTGTTCAGCCCGCTGGGCTGCCCCGAC*

Figure 4 (continued)

*CCGTACCCGCACTACGCGGTGCTGCGGGAGCACGGGCCGGTCTCCCGGCTGCCGGACGGCACCGTC*
*GTCGTCAGCCGGCACGCCGACTGCGACCGCGTGCTGCGCGATCCGCTCTTCCGGGTCGAGGACGAC*
*GCGTACCTCGCCCGTACCTGGCCCGAGGGCCGCGACCACCTCAGCGTCTTCTCCCTGATGGGCGAGA*
*TGGTCAACCAGAACTCGCCGCACCACGAGCGGCTGCGCCGCCTGGTGGGCCGCGCCTTCACCCCGC*
*GCCGGGTGGCCGGGCTGCGGCCCGCGGTGGAGAAGCTGGTCGACGGCCTGCTGGACGGCCTCGCC*
*GAACGGGCCGCCGGGGGCGCTCCGGTGGATCTGATGGAGCACTTCGCGCTGCCGCTGCCGATCACC*
*GTCATCGGCGAGCTGCTCGGCATCCCCGAGGAGGACCGCGCCTGGTTCGCGCCGCGCGTGCAGGCC*
*GTCACCTCCGCGATCGAGCAGAACCTCGCCGGGGAGGCGCTGGAGCGCGCGGACGAGGCCACCGC*
*GGAGCTGTGGGACCGGCTCGGCGCGCTGGCCGCCCGGCGCCAGGAGGACCCGCGCGCCGACCTGG*
*TCAGCACGCTCATCGCGGTACGCGAGGAGGACGGCGACCGGCTCACCCGGCGCGAACTGCTCGCCA*
*ACCTGGTGCTGCTGTACTCCGCCGGCTACGAGACCACCAGCAACCTCATCGGCAACGGCACGGCCGT*
*CCTGCTGGACCGCCCGGACCTGCTCGCGCGGCTGCGCGGCGAGCCGGAGCGGATCGACGCCTGGG*
*TCGAGGAGATGCTGCGCTTCGACCCGCCCATCCAGATCGCCTCCCGCTGGGCGGGGGAGGACACCG*
*AGCTGGGCGGGGTGGCCGTGGCGCAGGGCTCCCAAGTGGTGGCCCTGCTCGCCAGCGCCAACCGC*
*GATCCTGCGCGCCACGGGGACCCGGACGTCTTCCGGCCGGACCGGGCGCCGGGCGGCTCGCTCACC*
*TTCGGCGCGGGCGCGCACTACTGCCTGGGCGCCGCACTGGCCCGCCTGGAGGCGGCCATCGCCTTC*
*CCCCGGCTGCTGGCCCGCTTCCCCTCGATCGCGCACGCGGGCACCGGGGCGCCGCGCAACCGTATG*
*ACGTCCCTGCGCGGCTACGCCGAGCTGCCCCTGCTCCTGTCGTAA*

Legend

*P450 (italics)*

Start and stop codons in bold

Protein sequence

(Translated using Expasy from DNA sequences above)

SEQ ID NO: 14 (amino acid sequence of cytochrome SriC06 (409 aa))

MSDPAAVRRALRALFSPLGCPDPYPHYAVLREHGPVSRLPDGTVVVSRHADCDR
VLRDPLFRVEDDAYLARTWPEGRDHLSVFSLMGEMVNQNSPHHERLRRLVGRAF
TPRRVAGLRPAVEKLVDGLLDGLAERAAGGAPVDLMEHFALPLPITVIGELLGIPEE
DRAWFAPRVQAVTSAIEQNLAGEALERADEATAELWDRLGALAARRQEDPRADLV
STLIAVREEDGDRLTRRELLANLVLLYSAGYETTSNLIGNGTAVLLDRPDLLARLRG
EPERIDAWVEEMLRFDPPIQIASRWAGEDTELGGVAVAQGSQVVALLASANRDPA
RHGDPDVFRPDRAPGGSLTFGAGAHYCLGAALARLEAAIAFPRLLARFPSIAHAGT
GAPRNRMTSLRGYAELPLLLS-

SEQ ID NO: 15 (coding sequence of sriC07)

P450 sriC07: SRIM_16290

*ATGGACATCGATGGCGCGGAGCCCGGCGGCGGCCCTTCCGGTGAGTACGGC*
*TCGTGTGTGCGCCTCGACCCGGAAGCGCGCGATCCCCGCTCCCGCCCGGAC*
*CCGCTGTGCGCCGCGGGCCCTGTGGTGCCCGTCCTGCTGCCGGGTGGGGTG*
*ACGGCCTGGCTGGTGACCCGGCATCAGGCCGGGAAGGCGGTGCTGGCGGAC*
*GGCCGCTTCGTCAAGGACATCGGGGCCTGGCGCGCCTGGCGCGGCGGCGAG*
*GTCCCGCGCTCCTGGCCGCTGGCGCCGCTGCTGACCGTCGCGAACATGACCA*
*CCGCGACGGCGGGCGACCACACCCGGCTGCGCGCGCCGCTGGCCCGCGCG*
*TTCACCGCGCGCCGCGTGGCGGGGCTGCGGCCGCGCGTCGAGGAGCTGGCC*
*GGGGAGCTGCTGGACGGCCTCGCCGCCGAGGGGCCGGCGGGCCCCGTCGA*
*GCTGCGGGCCCGCTTCGCCCACCCGCTGCCGATACGGGTCATCTGCGAGCTG*
*TTCGGCGTGTCCGACGACCGCCGTCCCCGGCTGCAGTCGCTGTGCCAGGCCC*
*TGTTCGCCGCCCCGGCGGGCCCGGCCGATGCCCTGGCCACCCACCGCGAGC*
*TGCGGGCCGCGCTCGCCGATCTGCTCCGCGCCAAGCGCGAGGACCCCGGGG*
*ACGACCTGACGAGCGCGCTGGTGGCCCCCGGCCACGGCCTCAGCGGGAGCG*

Figure 4 (continued)

*AACTCGTCGACACGCTGTTGCTGATGATTGTCGCGGGCCATGAGACCACGGTG*
*AACCTGCTGGTCAACGCGGTGTACGCGCTGCTGACCCACCCCGGTCAGCTCA*
*CTCTCGTACGCGGCGGGCAGGTGCCCTGGAGCGCGGTGGTCGAGGAGACGC*
*TGCGCTGGGACCCGCCGGTCGCCAACTTCCCGTTCCGCTACGCGCTGTGCGA*
*CGTGGACCTGGCCGGCCGGACCATTCGCGCGGGCGATCCGGTGATGCTGTC*
*GTACGCCGCCTTCGGCCGCGACCCGCGGCAGCACGGGCCCGGGGCCGACCG*
*CTTCGACGTCACCCGGCCGCCCACCCGCCATCTGGCCTTCGGGCACGGCATC*
*CACCACTGCCTCGGTGCGCCGCTCGCCCGCCTGGAGGCGGCGGTCGCCCTC*
*CCCGCGCTGTTCGACCGCTTCCCCGGCCTCGCCCTGGACGACCCCGGGCAG*
*CGTCCGCTCCGCCGCCCGTCCATGGTCTTCAACGGCCTGCGGGAGCTGCCGG*
*TCGTCCTCGGCCCGCCCGGCGGTTCATAA*

Legend

*P450 (italics)*

Start and stop codons in bold

Protein sequence

(Translated using Expasy from DNA sequences above)

SEQ ID NO: 16 (amino acid sequence of cytochrome SriC07 (419 aa))

MDIDGAEPGGGPSGEYGSCVRLDPEARDPRSRPDPLCAAGPVVPVLLPGGVTAW
LVTRHQAGKAVLADGRFVKDIGAWRAWRGGEVPRSWPLAPLLTVANMTTATAGD
HTRLRAPLARAFTARRVAGLRPRVEELAGELLDGLAAEGPAGPVELRARFAHPLPI
RVICELFGVSDDRRPRLQSLCQALFAAPAGPADALATHRELRAALADLLRAKREDP
GDDLTSALVAPGHGLSGSELVDTLLLMIVAGHETTVNLLVNAVYALLTHPGQLTLVR
GGQVPWSAVVEETLRWDPPVANFPFRYALCDVDLAGRTIRAGDPVMLSYAAFGR
DPRQHGPGADRFDVTRPPTRHLAFGHGIHHCLGAPLARLEAAVALPALFDRFPGL
ALDDPGQRPLRRPSMVFNGLRELPVVLGPPGGS-

SEQ ID NO: 17 (coding sequence of sriC08)

P450 sriC08: SRIM_20579

*ATGGCTGAGTCCACCCACACTGCCCGCACCGCCCACGCCGTCCCGCCGCTGC*
*CCACCGGGCCCCGGGCCGGCTGCCCCTTCTCCCCGCCGAAGGAACTGCTCG*
*ACGCCCGCGAGCAGGGCCCGATCGGCCACTACACCCACCCCGGCGGCAAGC*
*CCGGCTGGATGATCACCGGGTACGACATGGTGCGGTCCGTGCTCGCCGACCC*
*GCGGTTCAGCTCGCGCAAGGAGCTGATGAACGTGGTCGATTTCGAGATTCCG*
*CCGCCGCCACCCGGCGAGTTCGTCCTCATGGACGACCCGCAGCACCGGCGCT*
*ACCGCAAGCCGCTGATGGGGAAGTTCACCGTGCGGCGGATGCGGCTGCTGAC*
*CGAGCGCATCGAGCAGGTCACCGCCGAGTGCCTGGACGCCATGGAGAAGGC*
*GGGCCCGCCGGTGGACCTGGTGGCCGCGTTCGCCAAGCCCATCCCCGCCAT*
*CGTGATCTGCGAGCTGCTGGGCGTGCCGTACGAGGACCGCGGCTTCTTCCAG*
*GGGCGGATCGACTCGTTCATGAACGGTGAGACGAGCGACGAGGACCTGATGG*
*CGGCCTACACCGAGGTCCAGAACTACCTCGCGGACCTGGTGGCCGCCAAGCG*
*CGCGAACCCCACCGACGACGTGCTCAGCGACCTCACCGACACCGACCTCACC*
*GACGAGGAGTTGAAGGGCATCAGCCTGGTCCTGCTGACGGCCGGGCTCGACA*
*CGACCACGAATGTGCTGGGGCTGGGCACCTTCGCGCTGTTGCAGCACCCTGA*
*GCAACTGGCCGCGCTGCGCGCCGATCCCGCGCTTGTCGACGGAGCGGTGGA*
*GGAGCTGCTGCGGTACCTCAGCGTCGGCAAGCAGTTCTGGCGTACGGCGCTG*
*GAGGATGTCGAGCTGGGCGGTCAGACCGTGAAGGCCGGCACGACGGTCGCC*
*CTGTCGCTCAGCACCGCCAACCGCGACCCCGAGCGCTTCGCCGACCCCGATG*
*TGCTCGATCTCCGGCGGCAGGGCGGCGGACACCTGGCCTTCGGTCACGGCG*
*TTCACCAGTGCCTTGGGCAGCAAGTGGCCCGCATCGAGCTGCGGGTGGCGTT*
*CTCCGCGCTGTTCGACCGCTTCCCCACGCTGCGTCTGGCCGTACCGGCCGAA*

Figure 4 (continued)

*GAGGTCGAACTGCGTCCGGAGTCCGCGGACGTCTTCGGGGTGAAGCGTCTTC*
*CGGTCGCCTGGGATGTGTAA*

Legend
*P450 (italics)*
Start and stop codons in bold

Protein sequence
(Translated using Expasy from DNA sequences above)

SEQ ID NO: 18 (amino acid sequence of cytochrome SriC08 (402 aa))
MAESTHTARTAHAVPPLPTGPRAGCPFSPPKELLDAREQGPIGHYTHPGGKPGW
MITGYDMVRSVLADPRFSSRKELMNVVDFEIPPPPPGEFVLMDDPQHRRYRKPLM
GKFTVRRMRLLTERIEQVTAECLDAMEKAGPPVDLVAAFAKPIPAIVICELLGVPYE
DRGFFQGRIDSFMNGETSDEDLMAAYTEVQNYLADLVAAKRANPTDDVLSDLTDT
DLTDEELKGISLVLLTAGLDTTTNVLGLGTFALLQHPEQLAALRADPALVDGAVEEL
LRYLSVGKQFWRTALEDVELGGQTVKAGTTVALSLSTANRDPERFADPDVLDLRR
QGGGHLAFGHGVHQCLGQQVARIELRVAFSALFDRFPTLRLAVPAEEVELRPESA
DVFGVKRLPVAWDV-

SEQ ID NO: 19 (coding sequence of sriC09-sriF03-sriFR01)
P450 sriC09: SRIM_20449
Ferredoxin sriF03: SRIM_20454
Ferredoxin reductase: sriFR01: SRIM_20459

*ATGACCCCCTCTCCCGCTTCCCCCGCCACCGCCGCCGCACCGGCGCTTCCCGTGCAGCCGCCGCAGG*
*GCTGCCCGTTCGACCCGCCCGCCGAGTTCGCGCGGCTGCGCACCGAGGCGCCGCTGTCGAAGATCT*
*CCCTGCCGGACGGCACCGAAGCCTGGCTCGCCACCCGCTACGCCGACATCCGCGCCATCCTCGGCGA*
*CACCCGCTTCAGCTCCGACACCACCCGCCCCGGCTACCCGCTCAGCGGCATGACCGGCGGCGCCACC*
*ACCGAACACCGCGGCTTCATCCGCATGGACCCGCCCGAGCACACCCGGCTGCGCCGCATGGTCACCC*
*GGGAGTTCATGGTCAAGCGCGTCGAGGCGATGCGCCCGGAGATCCAGCGCCTGACCGACGAACTG*
*TGCGACGCCATGGAGAAGCGCGCCGGCCAGGACGTGGACCTCATCGAGGCGCTGGCCCTGCCGGT*
*GCCGTCGCTCGTCATCAGCCTGCTGCTCGGCGTTCCGTACGACGATCACGAGCTGTTCCAGCGGCTG*
*ACCGGCACCCTGCTGTCCCGTACGGTCACCGACGCGGAGCGGGAGAGCGCGCGGGCCGAACTGCG*
*CGCCTACCTGCACCAGTTGGTGAGCGCCAAGGAGGCCGCGCCCGGCGACGACATCCTCGGCCGCCT*
*GATCGCCGAGCAGCAGGTACCGGGCGAGATCACCCACGACGACGTGGTCGCCTTCGCCGCCCTGCT*
*GCTCATCGCGGGCCACGAGACCACCGCCAACATGATCGGCCTGAGCGCGCTGACCCTGATGCGCGA*
*CCGGGAGACCGCGGACCGGCTGCGCGCCGAACCCGCCCTGATCCGCGGCGCCGTCGAGGAACTGCT*
*GCGCTTCCACAGCATCATCCGCAACGGGCCGCGCCGCGCCGCCACCGAGGACATCGAGATCGGCGG*
*GCAGCTGATCCGGGCCGGGGAGGGCGTCGTGGTGGCCGTACCGTCCGCCAACCGCGACCCGGAGG*
*TCTTCGCGGACCCCGACGCGCTCGACGTCTGCCGCCCCAACGCCCAGCACCACGTCGCCTTCGGCTA*
*CGGCATCCACCAGTGCCTCGGCCAGGCCCTGGCCCGCGTCGAGCTCCAGGTCGTCATCGGCACCCTG*
*CTGCGCCGCTTCCCGGAGATGCGGCCCGCGGTCCCGGTGGACGAGATCCCGTTCCGCAGCGACATG*
*GCGATCTACGGCTGCCACACCCTGCCCGTCACCTGGTGA*CACCCCGCCCGACCGTTCCCCTTCCTCCT
CAGGAGTCTCCTGCCATGAACATCACCCTCGACGCCGACAAGTGCTGCGCCGCAGGCCAGTGCGTA
CTGATCGCCCCCGAGGTCTTCGACCAGCGGGACGAGGACGGCATCGTCGTCCTCCTGGACGCCGCT
CCGCCCGCCGACCAGCACGACGCGGTCCGCGAGGCCGCCGCCATCTGTCCGGCCGCGGTCATCAAG
GTGGACGA*GTGAGCCCCCGCCGCATCGCCGTCGTGGGCGCCTCGGCGGCGGGCCTCGCCGCCGCC*
*GAGGCCCTGCGCCGCTTCGGCTGGACCGGCACCCTGACCCTCGTCGGCGACGAGCCCCACCCGCCG*
*TACGACCGTCCGCCGCTGTCCAAGCAGCTCCTTCAGGGCGCCTGGCAGCCCGACAAGCTGCATCTGC*
*GCGCCGCCGAACAGCTCGACGCGCTCGGCCTCGACCTGCGCCTGGGCACCCGGGCGACCGGCCTGG*
*ACACCGCGACCCGCACCCTGACCCTGGACGGTGGCGAGCGGCTGGCCTGCGACGGCGTGATCGTCG*

Figure 4 (continued)

*CGACCGGCGTCGCGGCCCGCACCCTCCCGGCGGCCGCCGGGCTCGACGGCGTGCACACGCTGCGCA*
*CCCTGGACGACGCGCTCGCCCTCAAGGAACGGCTGTCCGGTACCGGCCATCGCCTGGTCGTCGTCG*
*GCAACGGCGTACTGGGCTGCGAGGCCGCGGCCGTGGCCCGCGAGCTGGGTCACGAGGTCACACTC*
*GTCGGGCGCGAGGCGCTGCCGATGGCCCGTACGGTCGGCACGGAGATCGGCGAGCTGCTGGCGGC*
*CGAGCACCGGGAGCGCGGCGTCCAGCTGCGCACCGCGGCCGTCGACGGCTTCGAGGCGGACGGGG*
*ACGGGCCCGCGCGGCACGTGAGCGCCGTACGGCTGGCCGACGGCACCCGCCTGCCCGCCGACACC*
*GTGCTCGTCGCCATCGGCTCGGAGCCCGCCGTCGGCTGGCTGCACGGCGACCCGGCCCTGGACACC*
*ACCGACGGACTGCGCTGCGACGCGTACTGCGCCGCCGCACCCGGCGTCTACGCGGCCGGTGACGTG*
*GCCCGCTGGCAGCACCCGGTACACGGCCGCCACCTGCGCGTCGAGCACCGGATGAACGCCACCGAG*
*CAGGGCATGGCCGCCGCCCGCAACCTCCTAGCCGAACTGGAGGAGACCCTGCCGGGGGACGAGGC*
*ACTGGCCCCCGCCGCGGGCCGCGAGCGCCGCCCCTTCACACCGGTGCCGTACTTCTGGTCCGACCAG*
*TACGGCCTGAAGCTCCAGGCGTACGGCGTGCTGTCCGGCGCCGACCGGTCCGAGACGACCGTCCTG*
*GACCCGGACGCCAGGAAGGCCGTGGCCCTCTACGGCAGTGACGGCCAGGCCACCGGCGTACTGGC*
*GATCGGTGTGCCGCCGCGCCAGGTCCGGGGCCTGCGGGCGCTGATCGCCACGCCCGTGCCCTGGGA*
*AGAAGCTCGCGAGGGGCTGCACAACGCCCGCGCGTAA*

Legend
*P450 (italics)*
Ferredoxin
*Ferredoxin reductase (italics underlined)*
Start and stop codons in bold

Protein sequence
(Translated using Expasy from DNA sequences above)

SEQ ID NO: 20 (amino acid sequence of cytochrome SriC09 (409 aa))
MTPSPASPATAAAPALPVQPPQGCPFDPPAEFARLRTEAPLSKISLPDGTEAWLAT
RYADIRAILGDTRFSSDTTRPGYPLSGMTGGATTEHRGFIRMDPPEHTRLRRMVTR
EFMVKRVEAMRPEIQRLTDELCDAMEKRAGQDVDLIEALALPVPSLVISLLLGVPYD
DHELFQRLTGTLLSRTVTDAERESARAELRAYLHQLVSAKEAAPGDDILGRLIAEQ
QVPGEITHDDVVAFAALLLIAGHETTANMIGLSALTLMRDRETADRLRAEPALIRGA
VEELLRFHSIIRNGPRRAATEDIEIGGQLIRAGEGVVVAVPSANRDPEVFADPDALD
VCRPNAQHHVAFGYGIHQCLGQALARVELQVVIGTLLRRFPEMRPAVPVDEIPFRS
DMAIYGCHTLPVTW-

SEQ ID NO: 21 (amino acid sequence of ferredoxin SriF03 (64 aa))
MNITLDADKCCAAGQCVLIAPEVFDQRDEDGIVVLLDAAPPADQHDAVREAAAICP
AAVIKVDE-

SEQ ID NO: 22 (amino acid sequence of ferredoxin reductase SriFR01 (425 aa))
VSPRRIAVVGASAAGLAAAEALRRFGWTGTLTLVGDEPHPPYDRPPLSKQLLQGA
WQPDKLHLRAAEQLDALGLDLRLGTRATGLDTATRTLTLDGGERLACDGVIVATGV
AARTLPAAAGLDGVHTLRTLDDALALKERLSGTGHRLVVVGNGVLGCEAAAVARE
LGHEVTLVGREALPMARTVGTEIGELLAAEHRERGVQLRTAAVDGFEADGDGPAR
HVSAVRLADGTRLPADTVLVAIGSEPAVGWLHGDPALDTTDGLRCDAYCAAAPGV
YAAGDVARWQHPVHGRHLRVEHRMNATEQGMAAARNLLAELEETLPGDEALAPA
AGRERRPFTPVPYFWSDQYGLKLQAYGVLSGADRSETTVLDPDARKAVALYGSD
GQATGVLAIGVPPRQVRGLRALIATPVPWEEAREGLHNARA-

SEQ ID NO: 23 (coding sequence of sriC10)
P450 sriC10: SRIM_16925

Figure 4 (continued)

*ATG**ACCCTCACCACACGATCCGGCCCGGCGATACCGGGCCCCCGGGGCGTA*
*CCGTTCCTGGGCTCGATGTTCGACCTGCGGCGCAGCACGCTCGACACGTTCG*
*CGCGCGCCCGCCGTGACCACGGCGACCTGGTGCGCTTCACGGCCGGTCCGC*
*CCGGCCTGCGCAGCGTCTTCTACGGCGTGTTCTCGCCCGAGGGCAGTCAGCG*
*GATCCTCGCCTCCGAGGCCGCCAACTTCCGCAAGGACCACCCGTTCTACGAA*
*GAGGTCCGGCAGTCGTTCGGCAACGGCCTGCTGACCAGCCAGGACGACGACT*
*ATCTCCGCCAGCGGCGGATCGTGCGGCCGCTGTTCACCAAGCGCCGGGTCGA*
*CGGCTACGCGTCGGCCGTGGCCGCGGATGCGCAGGCCGTCGCCGAGCGCTG*
*GCGGACCCCGCCCGGCGGCACGGTCGACCTGGTGGGCGAGATGAACCGGCT*
*CGCGCTGCGCACCGTCTCCCGCATCCTGTTCGGCACGGACGTGGAGGCCGC*
*GGTCGCCACCGTGCACCGCTGCTTCCCGGTGATCAACTCGTATGTCGTACGG*
*CGCGGCTTCTCGCCGCGCAACCCGCCGCGCCACTGGCCCACCCCCGCCAAC*
*CGCCGGGCCGCCGCCGCGACGGCCGAACTGCACTCGGTCTGCGACCGGATC*
*GTGGCCGGGCGGCAGACCGCCGGCGCACTGGAGGACGGCGCCGACCTGCTG*
*TCCCTGCTCACCCGCGCGGGCAACGCGGCGGACGGCGGCCTGGACGCCACC*
*GAGATCCGCGATCAGGTCCTGGTCTTCCTGCTCGCCGGCCACGAGACGACCG*
*CGACGTCCCTGGCCTTCACCCTCCACCTGCTCGCCCGGCATCCGGAGGAACA*
*GGTCCTGGTACGGGAGGAGATCGACGCCGTACTGGGGGACCGGGAGCCGGA*
*AGCCGCCGACCTGGAGCGGTTGCCGCGGCTGACGATGGCCCTCAAGGAGGC*
*CATGCGGCTGTACCCGGCGGCGCCCGTGGTGAGCCGGCGCGGCGTCGCGGC*
*CACCGAGATCGGCGGCCACCGGATACCGGACGGCGCCGATGTGATCGTCTCG*
*CCGTGGGTGACCCACCGGCACCCCGGCCTGTGGGAGGACCCGGAGCGCTTC*
*GATCCGCGGCGGTTCACCCCGGAGCGGGAGGCGGCGCGCCACCGCTACGCG*
*TGGTTCCCGTTCGGCGGCGGCCCGCGGGCGTGCATCGGGCAGCACTTCTCGA*
*TGCTGGAGTCGGTGCTGGCGGCAGCGGTACTGCTGCGCTCGTACGAGCTGAC*
*GGCGGTCGACCGGGAGGTGCCGCTCACCGCGGGCATCACCTTGCAGGCGGC*
*GGGCCCGGCGCGGGTGCGGCTGAGGGGAGTGGGC**TAA*

Legend

*P450 (italics)*

Start and stop codons in bold

Protein sequence

(Translated using Expasy from DNA sequences above)

SEQ ID NO: 24 (amino acid sequence of cytochrome SriC10 (457 aa))

MTLTTRSGPAIPGPRGVPFLGSMFDLRRSTLDTFARARRDHGDLVRFTAGPPGLR
SVFYGVFSPEGSQRILASEAANFRKDHPFYEEVRQSFGNGLLTSQDDDYLRQRRI
VRPLFTKRRVDGYASAVAADAQAVAERWRTPPGGTVDLVGEMNRLALRTVSRILF
GTDVEAAVATVHRCFPVINSYVVRRGFSPRNPPRHWPTPANRRAAAATAELHSVC
DRIVAGRQTAGALEDGADLLSLLTRAGNAADGGLDATEIRDQVLVFLLAGHETTAT
SLAFTLHLLARHPEEQVLVREEIDAVLGDREPEAADLERLPRLTMALKEAMRLYPA
APVVSRRGVAATEIGGHRIPDGADVIVSPWVTHRHPGLWEDPERFDPRRFTPERE
AARHRYAWFPFGGGPRACIGQHFSMLESVLAAAVLLRSYELTAVDREVPLTAGITL
QAAGPARVRLRGVG-

SEQ ID NO: 25 (coding sequence of sriC11-sriF04)

P450 sriC11: SRIM_33256

Ferredoxin sriF04: SRIM_33251

*ATG**ACGCACACCGAACCGGCCGCGCCGGCCACCTGCCCGGTCACGGGAGCG*
*ACGGCCGGGGCCACGGACACGACGGATTCGACCGGGCACGGAACGGACCCG*
*CTGGTCGTCGACTTTCCGCTGCGCGCGCCCGGCATACCCTTCCCGCCGCCCG*
*AATACGCCGATTACCGCGACAAGAAGGGGCTGGTGCTCTCGCACCTGCCCGA*

Figure 4 (continued)

*CGGCAAACGGGTGTGGCTGGTCACCCGGCACGAGGACGTACGCGCCGTCCT*
*GACCAACCCGGCCATCAGCTCCAACCCCAGCACCCGGGCTTTCCCAATGTC*
*GGCGAGACGATCGGCGTACCCAGGCAGGACCAGATACCCGGCTGGTTCGTGG*
*GAATGGACTCGCCCGAACACGACCGGTTCCGCAAGGCCCTCATCCCGGAGTT*
*CACCGTGCGGCGCGTCCGCGCGATGAAACCCGCGATCGAGCGCACGGTGGA*
*CGCGCAACTGGACGCGATGCTGGCCGCGGGCAACACCGCCGACCTCGTCGC*
*CGACTTCACCCTGCCCATTCCCTCCCTGGTGATCTCGGCACTGCTCGGCGTGC*
*CGCCCGCCGACCGCGAGTTCTTCGAATCCAGGACCCGCGTCCTGGTCTCGTT*
*CCGTGCGTACTCCGACGAGGACCGCCTGGCCGCCGGCAAGGACCTCATGCG*
*GTACATCAACCGGCTGATCGAGATCAAGAAGAACTGGGGCGGCGACGACATC*
*GTCACCCGGCTGCTGGCCACCGGCGCCATCGGTGCCCACGAAATGTCCGGCG*
*TACTGATGCTGCTGCTCATCGCCGGCCACGAGACCACGGCCAACAACATCGC*
*GCTCGGTGTGGTCACCCTGCTGAAGAATCCCCAGTGGATCGGTGACGAACGG*
*GCCGTCGAGGAAACCCTGCGCTTCCACTCGGTCGCCGACCTGGTGTCCCTGC*
*GGGTGGCCGTCGAGGACGTGGAGATCGCCGGGCAGCACATCAAGGCGGGCG*
*AGGGCATCGTGCCGCTGGTCGCCGCCGCCAATCACGACGAGGAACTCTTCGC*
*GTGCCCCCACGCGTTCGACCCCTCCCGCTCCGCCCGCGGCCATGTGGCCTTC*
*GGCTACGGCGTACACCAGTGCCTGGGGCAGAACCTGGTACGGGTCGAGATGG*
*AGGTCGCGTACCGCAAGCTCTTCGAGCGCATTCCCAACCTCCGGCTCGACGT*
*GCCCGAGGACGGACTGAACATCAAGTACGACGGCGTGCTCTACGGCCTGCAC*
*GAGCTGCCCGTCCGCTGGTGA*CCTGACCAGAGAACCCGCGCCCGCCCGGCG
GCACGCCTCACCGGCCGCCGGGCGGCCCCCATCCACCGCAGGAGAGAAACC
CGACATGCGTATCACCGTTGACTCCGACCGCTGCGTCGGGGCGGGCCAGTGC
GTACTGAACGCGCCCGCGGTCTTCGACCAGGACGACGACGGGCTCGTCACCC
TTCTCGCCGAGCCCGGCGCCGACCAGGAGGCCGCCGCCAAACTGGCCGGTG
CCCTGTGCCCGTCCGGGGCCATCACCGTGCACGAGGGCTAA

Legend
*P450 (italics)*
Ferredoxin
Start and stop codons in bold

Protein sequence
(Translated using Expasy from DNA sequences above)

SEQ ID NO: 26 (amino acid sequence of cytochrome SriC11 (420 aa))
MTHTEPAAPATCPVTGATAGATDTTDSTGHGTDPLVVDFPLRAPGIPFPPPEYADY
RDKKGLVLSHLPDGKRVWLVTRHEDVRAVLTNPAISSNPQHPGFPNVGETIGVPR
QDQIPGWFVGMDSPEHDRFRKALIPEFTVRRVRAMKPAIERTVDAQLDAMLAAGN
TADLVADFTLPIPSLVISALLGVPPADREFFESRTRVLVSFRAYSDEDRLAAGKDLM
RYINRLIEIKKNWGGDDIVTRLLATGAIGAHEMSGVLMLLLIAGHETTANNIALGVVTL
LKNPQWIGDERAVEETLRFHSVADLVSLRVAVEDVEIAGQHIKAGEGIVPLVAAANH
DEELFACPHAFDPSRSARGHVAFGYGVHQCLGQNLVRVEMEVAYRKLFERIPNLR
LDVPEDGLNIKYDGVLYGLHELPVRW-

SEQ ID NO: 27 (amino acid sequence of ferredoxin SriF04 (63 aa))
MRITVDSDRCVGAGQCVLNAPAVFDQDDDGLVTLLAEPGADQEAAAKLAGALCPS
GAITVHEG-

SEQ ID NO: 28 (coding sequence of sriC12-sriF05)
P450 sriC12: SRIM_15095
Ferredoxin sriF05: SRIM_15100

Figure 4 (continued)

*ATGACCGAGGCGCTGCCCTTCCCGCAGGACCGGACCTGTCCCTACGACCCGC*
*CCGCCGGCTACCAGCCCCTGCGCGACAGCCGCCCCCTGTCCCGCGTGACGC*
*TCTACGACGGGCGCCCCGCCTGGGTGGTGACCGGGCACGCCGAATCGCGGG*
*CGCTGCTCACCGACCCGCGCCTGTCCGCCGACCGGCAGAATCCGGCGTTCCC*
*CTCCCCCGCCCCGCGCTTCGAGACGCTGCGCAAGGTGCGGACCCCGCTGCT*
*GGGCGTCGACGACCCCGAACACAACACCCAGCGCCGGATGCTGATACCGAGC*
*TTCAGCGTCAAGCGCGCCGCCGCGCTGCGCCCCCGCATCCAGGAGATCGTGG*
*ACCGGCTGCTGGACGCCATGGAGCAGCAGGGCCCGCCCGCCGAGCTGGTGT*
*CCGCCTTCGCGCTGCCGGTGCCGTCCATGGTGATCTGCGCGCTCCTCGGCGT*
*CCCGTACGCCGACCACGAGCTGTTCGAGGGCCTGTCCCGGACGCTCCTGCAG*
*AGCGCCGACCCGCAGGAGGTCACCGAGGCCCGCGACAAGCTGGAGGACTAC*
*TTCACCGCCCTGGTGGAGCGCAAACGGAAGGAGCCGGGCGACGGCCTGCTG*
*GACGAGCTGATCGCCGAGCGGCTGGACTCCGGCGAGCTGGGCCACCGCGAA*
*CTGGTCCGGATGGCCATGCTGCTGCTGGTGGCCGGCCACGAGACCACCTCCA*
*ACATGCTGTCCCTGGGCACCTTCACGCTGCTGGAACACCCCGAGCAGTTCGC*
*CGCCCTGCGCGCCGACCCGTCGCTGCTCCCGGCCGCGGTCGAGGAGCTGCT*
*GAGGTTCCTGTCCATCGCCGACGGCATGGTGCGGGTGGCGACCGAGGACATC*
*GAGATCGGCGGCGTGACGATCCGGGCGGACGACGGCGTGATCTTCTCCACCT*
*CGGTCGTCAACCGGGACGGCGCCGCCTACGCCTCGCCGGACACCCTGGACT*
*GGGAGCGCTCCGCCCGCCACCACGTCGCCTTCGGCTTCGGCGTCCACCAGTG*
*CCTGGGCCAGAACCTGGCCCGCGCGGAGATGGAGATCGCCTTCGGGGCGCT*
*CTTCGCCCGCTTCCCCGGTCTGCGCCTGGCGGTGCCCGCCGCCGAGATACCC*
*GTCAAACCCGCCCACGCCCTCCAGGGCCTGGTCGAACTGCCCGTCACCTGGT*
*AG*CGGCGGACCGCCGCCCACACCCTGTACCCGTCAACGGAGGAGAGCCACC
ATGAAGATCGACATCGATACGTCCGTGTGCATCGGCTCGGGCCAGTGCGTGC
TGACCGCGCCGGGGGTGTTCACCCAGGACGACGACGGTTTCAGCACCCTGCT
GCCCGGCCGCGAGGACGGCACGGGCGACCCGCTCGTACGCGAGGCCGCCC
GCGCTTGTCCGGTTCAGGCGATCGCGGTCACGGACGACTAA

Legend
*P450 (italics)*
Ferredoxin
Start and stop codons in bold

Protein sequence
(Translated using Expasy from DNA sequences above)
SEQ ID NO: 29 (amino acid sequence of cytochrome SriC12 (395 aa))
MTEALPFPQDRTCPYDPPAGYQPLRDSRPLSRVTLYDGRPAWVVTGHAESRALLT
DPRLSADRQNPAFPSPAPRFETLRKVRTPLLGVDDPEHNTQRRMLIPSFSVKRAA
ALRPRIQEIVDRLLDAMEQQGPPAELVSAFALPVPSMVICALLGVPYADHELFEGLS
RTLLQSADPQEVTEARDKLEDYFTALVERKRKEPGDGLLDELIAERLDSGELGHRE
LVRMAMLLLVAGHETTSNMLSLGTFTLLEHPEQFAALRADPSLLPAAVEELLRFLSI
ADGMVRVATEDIEIGGVTIRADDGVIFSTSVVNRDGAAYASPDTLDWERSARHHVA
FGFGVHQCLGQNLARAEMEIAFGALFARFPGLRLAVPAAEIPVKPAHALQGLVELP
VTW-

SEQ ID NO: 30 (amino acid sequence of ferredoxin SriF05 (64 aa))
MKIDIDTSVCIGSGQCVLTAPGVFTQDDDGFSTLLPGREDGTGDPLVREAARACPV
QAIAVTDD-

SEQ ID NO: 31 (coding sequence of sriC13)
P450 sriC13: SRIM_13731

Figure 4 (continued)

*ATGACCGCGGCCGCGCAGGAACTGGAAATCGCCCGCGCCTGCCCCTACTCCC
CGAATGCGCAGCACATCGCATTCCAGCAGCAGGGCCGCCCCGTCAAGGTCAC
CCTGGCGACCTTGGGGCCGGGTGCGCCGGTCTGGGCGGTGAGCAATCACGC
CGATATCCGCACCATGCTCAACGACGCCCGATTCAGCGCCGACCGGCAGCAG
CAGGGCTTTCCCTTCCAGGTCGACGGGCAGCCGGGCAACTTCCGCCGGACGA
TGATTTCCATGGACGGGGCGGAACACCGGGAAGTCCGCCGTTCCGTGACCGG
CGAATTCACCCTCAAGCGCATGAAGGCCCTGCAGCCGCGGATCCAGCAGATC
GTGGACGACTGCATCGACACCATGCTGGCCGGTCCGAAACCCGCTGACCTGG
TCAGCGCGCTCGCGCTCCCCGTTCCCTCGCTGGTGATCTGTGAACAGCTCGG
TGTGCCCTACGAAGGCCACGACTTCTTCCAGTCCCGGTCCCACATGCTGTTGC
TACGCGGCGCTTCGGCGGAAGAGCGGCTGCGCGCGCTGGACGAACTCATCG
ATTTTCTCGGCGACCTCATCACCGAGAAGGAGGCCGAGCCGACCGACGACCT
GCTCGGGCGCCAGATCGTGAAGCTGCGCGAGGCGGGGACGTACCGCCACCA
GGACCTGGCGCGCATGGCCTTTCTGCTGCTGGTCGCCGGACACGAGACCACC
GCGAACATGATTTCGCTGGGCACCATGGCCCTGCTCGACCGCCCCGCGGACG
CGGACGCCCTGCGCGCGGACCCGAGCAAGCTCCCGGTCGCGGTGGAGGAAC
TCCTGCGGTACTTCACCATCGCCGAGTTCATTCCCACGCGCGTCGCCACCGAG
GACGTGGAACTGGGCGGCAGCCTCATCAAGGCGGGCGATGTCCTCGTGGCG
CTGTGCAATGTGGCCAACCGCGACCCCTCGGTGTTTCCCGACGGCGACACAC
TGGACCTGCAACGCGGAGCCCGTCACCAACTGGCGTTCGGCTTCGGGGCTCA
TCAGTGCCTGGGGCAGAATCTCGCCCGCATGGAACTGGAGATCGTCTATGCG
ACGCTGCTCCGGCGGATACCGACGCTGCGCTCCGCGATACCGACCCGTGAAC
TGCCGTTCAAGCACGACGCGGACATCTACGGTATCCACGCATTCCCGGTCACC
TGGTAA*

Legend

*P450 (italics)*

Start and stop codons in bold

Protein sequence

(Translated using Expasy from DNA sequences above)

SEQ ID NO: 32 (amino acid sequence of cytochrome SriC13 (399 aa))

MTAAAQELEIARACPYSPNAQHIAFQQQGRPVKVTLATLGPGAPVWAVSNHADIR
TMLNDARFSADRQQQGFPFQVDGQPGNFRRTMISMDGAEHREVRRSVTGEFTLK
RMKALQPRIQQIVDDCIDTMLAGPKPADLVSALALPVPSLVICEQLGVPYEGHDFFQ
SRSHMLLLRGASAEERLRALDELIDFLGDLITEKEAEPTDDLLGRQIVKLREAGTYR
HQDLARMAFLLLVAGHETTANMISLGTMALLDRPADADALRADPSKLPVAVEELLR
YFTIAEFIPTRVATEDVELGGSLIKAGDVLVALCNVANRDPSVFPDGDTLDLQRGAR
HQLAFGFGAHQCLGQNLARMELEIVYATLLRRIPTLRSAIPTRELPFKHDADIYGIHA
FPVTW-

SEQ ID NO: 33 (coding sequence of sriC14-sriF06)

P450 sriC14: SRIM_07333

Ferredoxin sriF06: SRIM_07328

*ATGACCGAGACCTCCACCGCCTTCCCGGCCCAAGACGCTCCTGCCTTCCCCA
GCGACCGTACCTGCCCGTACGGGCTGCCCGAGACGTACGCACGGTTACGCGA
CAGCGAGGACGCGCTGCGCCCCGTGACCCTCTTCGACGGCCGCACCGCCTG
GGTCGTCACCAAGCACGAGACCGCCCGCACCCTGCTCGCCGACCCGCGGCTC
TCCTCGAACCGCACCCACCCCGACTTCCCTCTCACCTCCCCGCGCCTGGCGG
GCCTGCGCGATCGCCGCCCCGCCTTCATCAGCATGGACCCGCCCGAGCACGG
GCCCCGGCGCCGGATGACGATCAGCGAATTCACCGTCAAGCGCATCAAGGGC
ATGCGACCGGACATCGAGCGAATCGTGCACGGCTTCCTCGACGAGATGCTCG*

Figure 4 (continued)

*CCGCGGGCCCGCCCGCCGACCTGGTCAGCCGGTTCGCGCTGCCGGTGCCCT*
*CCATGGTGATCTGCCAACTGCTCGGTGTCCCCTACGCCGACCACGACTTCTTC*
*CAGGACGCCAGTCGGCGCCTGGTGCAGTCGACCAGCGCGGAGGAGGCGACC*
*GGCGCGCGCGACGACCTGGAACGCTACCTGGACGGGCTGATCACCACCCTG*
*GAGTCCGAGCCCGGGCCCGGACTCCTCGGCGCGCTGGTCACCCGGCAGCTC*
*GCGGACGGCGCCATCGACCGCGACGAACTGATCTCGAACGCGCTGCTGCTGC*
*TCGTCGCCGGCCACGAGACCACCGCCTCCATGACCTCCCTGAGCGTCATCAC*
*CCTGCTCGAACACCCCGAGCAGCACGCCGCCCTGCGCGACGATCCGTCCCTG*
*ATCCCGGGCGCGGTCGAGGAACTGCTGCGCTACCTCGCCATCGCCGACGTGG*
*CGGGCGCCCGCGTCGCCACCGCCGACATCGAAGTGGACGGACAGGTCATCC*
*GGGCCGGCGAGGGCGTGATCGTCGTCCACTCCATCGCCAACCGCGACGCCG*
*GGGTGTTCGAGAACCCGGACACCTTCGACATTCACCGCTCGGCCCGCCACCA*
*CCTCTCCTTCGGCTACGGCGTCCACCAGTGCCTCGGCCAGAATCTGGCCCGC*
*CTCGAACTCGAAATCATCCTGAGCGCGCTGTTCGAACGCATCCCCACGCTGCG*
*GCTGGCCACACCGGTCGAGCGCTTGACCCTGCGGCCCGGCAGCACCATCCAG*
*GGCGTCAACGAACTCCCCGTCACCTGGTGA*GCGGGGCGAAGGAGCGACCA
TGCACGTGACCGCCGACCGCGACGTGTGCGTCGGTGCCGGGATGTGCGCCC
TGACCGCGCCCGGCGTCTTCGACCAGGACGACGACGGGCTCGTCACCGTCCT
GACCTCCGATATCGGAGAGAACGACCGGGACGCCGTGCGCGAGGCCGGCAT
GCTGTGCCCGTCCGGGGCCCTTCGGGTCACGGAGTAA

Legend

*P450 (italics)*

Ferredoxin

Start and stop codons in bold

Protein sequence

(Translated using Expasy from DNA sequences above)

SEQ ID NO: 34 (amino acid sequence of cytochrome SriC14 (406 aa))

MTETSTAFPAQDAPAFPSDRTCPYGLPETYARLRDSEDALRPVTLFDGRTAWVVT
KHETARTLLADPRLSSNRTHPDFPLTSPRLAGLRDRRPAFISMDPPEHGPRRRMTI
SEFTVKRIKGMRPDIERIVHGFLDEMLAAGPPADLVSRFALPVPSMVICQLLGVPYA
DHDFFQDASRRLVQSTSAEEATGARDDLERYLDGLITTLESEPGPGLLGALVTRQL
ADGAIDRDELISNALLLLVAGHETTASMTSLSVITLLEHPEQHAALRDDPSLIPGAVE
ELLRYLAIADVAGARVATADIEVDGQVIRAGEGVIVVHSIANRDAGVFENPDTFDIHR
SARHHLSFGYGVHQCLGQNLARLELEIILSALFERIPTLRLATPVERLTLRPGSTIQG
VNELPVTW-

SEQ ID NO: 35 (amino acid sequence of ferredoxin SriF06 (63 aa))

MHVTADRDVCVGAGMCALTAPGVFDQDDDGLVTVLTSDIGENDRDAVREAGMLC
PSGALRVTE-

SEQ ID NO: 36 (coding sequence of sriC15)

P450 sriC15: SRIM_05911

*ATGGCTGCACACGCCGATGAGCCGATCCGCCTGGCGGTGGGGGAACTGGCA*
*CGGTTTCTCGGCGCGGACGTCGACGACCCCGCCTTTCTGACCGATCCTCACA*
*GATGTCTGACGCCCGGGATACGCGAGAAATCCGTGCACCGGCTGCCCGGAGG*
*CGCCCTGGCCGTTCTCGGTTACACGGCGTGCGCCGAGGTGCTGCGTGATACA*
*CGGTTCGGCCACGGTGCCCGCGAACTGTACGAGACCACCCTGCTGGGGCTGC*
*CGGCCCGGTCTTTTCTCCAACTGGACGCACCGGGGCACACCCGGCTGCGCGG*
*CCAGGTCGCGCGGCATTTCACCGCACGGCGAGTACGGGCCTTGGCCGAGAAC*
*GTCGGGTATTACAGCACTGCTCTCGTACGGGAGCACGCGGGCCGCCCGGGG*
*GATTTCGTGGCGGATTTCGCCGAGCCGCTGGCGATGTCGGTCATCAGCGACG*

Figure 4 (continued)

*TACTGGGCGTGCCGCCCGAGGATCGCCCCGCCTTCCACCGTGACGCCCGGCT*
*GGTCGTCCGCGGACTGGACCAGCCGGCCCGCGCCATGGACGAACGGGCCGT*
*CGCCCAGGCGCGGTTCCGCTTCGTACGGTTCTTCCGCCGCCGGGCGCAGGC*
*GCGCCGCCAGGCCGGGACGCGGCACCGGGCGCCCCGGGACGGCCTGCTGG*
*ACGCCTTGTCGCACCGGCCGGACGGCAGCCCGGCCGACATCCGCGAGCTGG*
*TCACCACGTGCAGCCTGCTGCTGAGCGCCGGATACGACACCACGGTCAGCCT*
*GCTGTCGCACGCGGTGGCGGAACTGGGCGGCGCACCGTCCGGGCAGGGGTG*
*GGCGCTGGCCCGGGACCCGCAGACGGTGGGCGCGGTCGTGGAGGAGGTGCT*
*GCGTCTGCACTCTCCCGTGCAGATCGCTCCGCGCGCCGCGGTGCGTGACGCG*
*GCCCTGGACGGGCTGCCGGTGGCCCGCGGCACGATCGTGCTGCCCCTGCTG*
*CCGGCGGCCAACCGGGACCCGGACATCTTCGACAGCCCGCACACCTTCCGGC*
*CCCGGCGCTATCTCGCCCCGGCAGCTCAAGGCCGTTCGACAGCAAGGCATTT*
*GGCGTTCGGAGCGGGCGCGCATTTCTGTCTGGGGGCGGCCCTGGCCCGGCT*
*GACCGCCCACAGCGCGCTGGCTGTTCTGGCCGCCTGCCCGCCCAGACCGCG*
*CGACGCGCCCCGTACGTACAGCGAAGGCGTCGTCGTACGCGGCCTGCGCAGT*
*CTGCCGGTCACCTGGCCGCACCGGCCCGCGGAACGGCCCCCGCACCCTCCG*
*GCCGACGGCGCGGCCGCGTACGTCGAGCCGTCGTGCCCCATCCCCCACGCG*
*CAAAGGAGCGTCACATAA*

Legend
*P450 (italics)*
Start and stop codons in bold

Protein sequence
(Translated using Expasy from DNA sequences above)

SEQ ID NO: 37 (amino acid sequence of cytochrome SriC15 (451 aa))
MAAHADEPIRLAVGELARFLGADVDDPAFLTDPHRCLTPGIREKSVHRLPGGALAV
LGYTACAEVLRDTRFGHGARELYETTLLGLPARSFLQLDAPGHTRLRGQVARHFT
ARRVRALAENVGYYSTALVREHAGRPGDFVADFAEPLAMSVISDVLGVPPEDRPA
FHRDARLVVRGLDQPARAMDERAVAQARFRFVRFFRRRAQARRQAGTRHRAPR
DGLLDALSHRPDGSPADIRELVTTCSLLLSAGYDTTVSLLSHAVAELGGAPSGQGW
ALARDPQTVGAVVEEVLRLHSPVQIAPRAAVRDAALDGLPVARGTIVLPLLPAANR
DPDIFDSPHTFRPRRYLAPAAQGRSTARHLAFGAGAHFCLGAALARLTAHSALAVL
AACPPRPRDAPRTYSEGVVVRGLRSLPVTWPHRPAERPPHPPADGAAAYVEPSC
PIPHAQRSVT-

SEQ ID NO: 38 (coding sequence of sriC16)
P450 sriC16: SRIM_06201
*ATGCCGGGCGCCTTGCCCCTCGTCGGGCACGCGCCCGCGCTCATTCGTGATC*
*CCTTCGGCTTCTTCCTGTCGCTGCGGGACCACGCCGACGACCGCGGCCTGGT*
*CCGCATCCGGCTCGGCTCGATGCCCGTCTACATGGCCACCACCCCTGAGCGG*
*CTGCACGAGGTCCTGGTGGACAAGGGGCGGTGGTTCGAGAAGGGCCGGTTCT*
*TCCAGCGCCTCAAGCGGCTGGCCGGCGAGGGGCTGAGCACCGCGGACGGGG*
*AGCTGCACAAACGTAACCGCCGCTTCCTCGCGCCCCTTTTCGGCGCGCAGCG*
*CATCAAGGACTACTCCCTGGTCATGAGCCGCAATGCCCGGCGCCTGTCCCAGT*
*CCTGGCAGCCGGATCAGCAGGTGGACATCTACAAGGAGGCCGCCGCTTATTC*
*CATCGACTCCATCGCCATGTCGCTGTTCAGTACAGACGTCGGAACGCCGGCG*
*GTGGAAACGATCCGTACCGAACTGCCGGTGCTGCTGGACATGCTCCTCAAGC*
*GCGCTGCCTCACCGAAGATCCTGGATCGCCTGCCGGTACGCTACAACCGCGT*
*TTTCGACCGGGCGTCCGCGCAGTTGACCGGGGTGATCGACCAGGTCATCACC*
*ACCGCACACGCCGGCGGCCACGCCGAGGAGCACGACGACCTGCTCGCGCAG*
*CTGCTGCGGGCGCAGGTCCACGACGACGTTCCGGTCCGCCTCAGTGACGTTC*
*AGATCCGCGACGAGGTGGCCACGCTGCTGTTCGCCGGGGCCGAGACCACGG*

Figure 4 (continued)

*CGTCGACCCTGGCCTGGGCCTGGCACTACCTGGCGCACCACCCCGAGGTCGA*
*CCGGCAGGTGGTGGACGAGGTCCTGGAGGTCGTGGCCCCGACCGCGCGGT*
*GACCATCGAAGACGTCCCCCGGCTGACCGTGATCCGCCGGGTGCTGGACGAG*
*GTGATCCGCCTGCACGGTGTCACGTTCCTGATGCGCCGCAGCACCGCGCCGG*
*TGACCCTCGCCGATGTCACGCTGCCCGCGGGCACCGAGGTGGCGTTCAGCAT*
*GTACGCCATCCACCGTGATCCCGAGGCTTTCGAGGACCCCCACACCTTCAACC*
*CGGACCGGTGGCTGGACCCCGGGGCCAAACGGTCGTTCATGCCCTTCGGCG*
*GCGGCAACCGCAAGTGCATCGGCGATCAGTTCGCCCTGGCCGAGACCACCAT*
*CGCCGTCGCGGAGGTGCTGCGCGACTGGCGCATGACCCCCGCCGGCGGCCA*
*CACTCCGCAGCAGGTGATCTCCGCTGTCGCCCGGCCCGACCGGGTACCCATG*
*ACCGTACGGCCGCGTAACCCCGCACCCAGCCGGCCGAGCAACTAA*

Legend

*P450 (italics)*

Start and stop codons in bold

Protein sequence

(Translated using Expasy from DNA sequences above)

SEQ ID NO: 39 (amino acid sequence of cytochrome SriC16 (446 aa))

MPGALPLVGHAPALIRDPFGFFLSLRDHADDRGLVRIRLGSMPVYMATTPERLHEV
LVDKGRWFEKGRFFQRLKRLAGEGLSTADGELHKRNRRFLAPLFGAQRIKDYSLV
MSRNARRLSQSWQPDQQVDIYKEAAAYSIDSIAMSLFSTDVGTPAVETIRTELPVLL
DMLLKRAASPKILDRLPVRYNRVFDRASAQLTGVIDQVITTAHAGGHAEEHDDLLA
QLLRAQVHDDVPVRLSDVQIRDEVATLLFAGAETTASTLAWAWHYLAHHPEVDRQ
VVDEVLEVVGPDRAVTIEDVPRLTVIRRVLDEVIRLHGVTFLMRRSTAPVTLADVTL
PAGTEVAFSMYAIHRDPEAFEDPHTFNPDRWLDPGAKRSFMPFGGGNRKCIGDQ
FALAETTIAVAEVLRDWRMTPAGGHTPQQVISAVARPDRVPMTVRPRNPAPSRPS
N-

SEQ ID NO: 40 (coding sequence of sriC17)

P450 sriC17: SRIM_22544

*ATGCCGGTCCAGCTCCCCGGCGGCATCCCCGGCCACGCCGTGACCCGCCAC*
*CACGCCCTGCGCGACTTCCTCACCCACCCGGAAGTGGCCAAGGACGCCTGCC*
*ACTTCGCCGCGCTGCGCGAGGGCCGCATCCCGCCCGGCTGGCCGCTCACCA*
*CCTTCGCGACCGTGGACGGGATGACGACGGCCGACGGCGCGGACCACCGGC*
*GGCTGCGGGAACCGGCCGTCAAGGCGCTCTCGCCCCGGCGGGTGGCGGCGC*
*TGCGGCCGCGGGTGGAGCGGCTGACCGCCGAGCTGCTCGACGGGCTGCCCG*
*CCCTGGCCGCGCGGGGCGGCGGGACGGTCGATCTCCGGCACGCCTTCGCCT*
*ATCCGCTGCCCATGCGGGTGATCAGTGAACTCATCGGCGTGGACGAGGAGTT*
*CCGGGACCGGCTGCACCAGCTGTCCGGGCTGGTCGTGAGCACCGTCATCGAC*
*CCGGAGGCGGCGCTGGCGGCCAACCGGGAGCTGGTCGGGGTCCTCGGGCA*
*GGTCGTGGCGGCCCGCCGCGCGGCGCCGGGCGACGACCTGACCAGCGCGC*
*TCATCGCGGCCTGTGACGAGGCGGACGCCCGGCTGAGCGAACGGGAGCTGA*
*TCGGCACCCTGTTGCTGATGATCGCCGCCGGGCACCAGACCACCCTCGACTT*
*GATCACCAACGCCGTACGGGCCCTCTGCGCCCACCGCGACCAGCTGGACCTG*
*GTCCGCGCGGGGCGGGCGGACTGGGCGGACGTGGTCGAGGAGACGCTGCG*
*CCACGACAGCCCGGTGGCCCACTTCCCGTTCCGCTACCCGACCCGGGACCTG*
*GACGTCGGCGGCACGGTGATCCCCCGGGGGACGCCGGTGCTCGCCTCGTAC*
*GCGGCGGCCGGGCGCGACCCGGAGGCGTACGGGCCGGACGCGGACCGCTT*
*CGACGTGACGCGACGGCCCGCCGTCCGGCACCTGTCCTTCGGGCACGGGCC*
*GCATGTCTGTCCGGGCGCACCGCTGGCCCGCTTGGAGGCGCGGATCGCCCT*
*GCGCGCGCTGTTCACCCGCTTCCCTGATCTGGCCCTGGCCGTACCGGAGGCG*
*GACCTGCGGCCGCTGCCCACGTTCGTGGGCAACAGCGTCGCGGAGCTTCCG*

Figure 4 (continued)

*GTACGGCCGGGTCGGGACGTCGGGACGGCCGGTCAGGACGCGTCGGCCACC*
*AGCCCCGGCGCCGGG*TAA

Legend
*P450 (italics)*
Start and stop codons in bold

Protein sequence
(Translated using Expasy from DNA sequences above)

SEQ ID NO: 41 (amino acid sequence of cytochrome SriC17 (397 aa))
MPVQLPGGIPGHAVTRHHALRDFLTHPEVAKDACHFAALREGRIPPGWPLTTFATV
DGMTTADGADHRRLREPAVKALSPRRVAALRPRVERLTAELLDGLPALAARGGGT
VDLRHAFAYPLPMRVISELIGVDEEFRDRLHQLSGLVVSTVIDPEAALAANRELVGV
LGQVVAARRAAPGDDLTSALIAACDEADARLSERELIGTLLLMIAAGHQTTLDLITNA
VRALCAHRDQLDLVRAGRADWADVVEETLRHDSPVAHFPFRYPTRDLDVGGTVIP
RGTPVLASYAAAGRDPEAYGPDADRFDVTRRPAVRHLSFGHGPHVCPGAPLARL
EARIALRALFTRFPDLALAVPEADLRPLPTFVGNSVAELPVRPGRDVGTAGQDASA
TSPGAG-

SEQ ID NO: 42 (coding sequence of sriC18)
P450 sriC18: SRIM_21739
*ATG**ACGACCGTTCCCGATCTTCCCGACGCCACAGAGGCGCTGGAGCACTTCC*
*CCTTCGACGACGGCCGTGGCATCGAGGTCCACGAGCGGTTCCGGGAGCTGC*
*GGGAGCGCGCGGGGCTGCTCCGGGTGCGGCTCGACTACGGTGAACCCACCT*
*GGCTGGTCACCCGTTACGCGGACGCCCGGCTGGTGCTGGGCGACGCGCGGT*
*TCAGCCGTGCCATGTCGGTCGGCCGGGACTTCCCGCGCCAGGAGGAAGCGA*
*CGGAACTGGCCGGGCTGATCACCATGGACGCCCCCGAACACACCCGGCTGCG*
*CACACTGTTGGTCAAAGCCCTCAGCAAATCCCGTATCGACGCGCAGCGCCCGA*
*CGGTGCGCGCGACGGCGGACGCGCTGCTGTCGTCGGCGATGGACGCCGGGC*
*CGGGCATGGACATCGTGGTGGACTACGCGCAGCAGATGAGCGTGCTGTCCAT*
*CTGCGACCTGCTCGGCGTGCCGGCCTCGGACCGGGAGGCGTTCGAGTCGAC*
*CAGCGCGGCACTGCTCCCCGGCAGCGCCGTCGGCGCCGAGGACATGATGCG*
*GCGGTTCGGTGAGCTGCGCGCCTGCACCGAGCGGCTCATCGCCGAGCGCCG*
*GGCCCGCCCCCGCGACGACCTGATGTCGGCGATGATCCAGGCCCGGGACGA*
*GGAGGACCGGCTCACCGACGCCGAGCTGATCGAGCTGGTCGTCAGCATGCTG*
*CTGGCCAGGTTCGAGGCGATCATCACCCAGATCCCGAACTGCGTCTACGTTCT*
*CACGCGGGGCGACCGGGCGCTCTGGAACCGGCTGCGTGCGAATCCGGCCGA*
*GCTGCCCGCGGCGGTCGAGGAGCTGCTGCGCAACAACGCCTCCGCCGGCGC*
*GGGCCTGTTCGTCCGCTATGCGCGGGAGGATGTCAACGTCGGCGGCACGCTG*
*GTGCGCGCGGGCGAAGCCCTGACCATCGCCGTCGAGTCGGCCAACCACGAC*
*CCGGCCCGGTTCGAGGACCCCGACGCGATCGATTTCACCCGGCCACCCGGC*
*GGGCACCTCACCTTCGGTTATGGCGCGCACTACTGCGTCGGCGCCCAGCTCG*
*GGCGCATCGACCTCCAGGAAGGGCTGCGGGTGCTGCTCACCAGGGCCCCGG*
*AGCTGACCGTCCGCGACCTCACGTGGAGAGTACGGCCGCACATCCGGGACC*
*GGTGGCGATGCGCGTGACCTGGCAGGGCGACCCGGAA*TAA

Legend
*P450 (italics)*
Start and stop codons in bold

Protein sequence
(Translated using Expasy from DNA sequences above)

Figure 4 (continued)

SEQ ID NO: 43 (amino acid sequence of cytochrome SriC18 (407 aa))
MTTVPDLPDATEALEHFPFDDGRGIEVHERFRELRERAGLLRVRLDYGEPTWLVT
RYADARLVLGDARFSRAMSVGRDFPRQEEATELAGLITMDAPEHTRLRTLLVKALS
KSRIDAQRPTVRATADALLSSAMDAGPGMDIVVDYAQQMSVLSICDLLGVPASDRE
AFESTSAALLPGSAVGAEDMMRRFGELRACTERLIAERRARPRDDLMSAMIQARD
EEDRLTDAELIELVVSMLLARFEAIITQIPNCVYVLTRGDRALWNRLRANPAELPAAV
EELLRNNASAGAGLFVRYAREDVNVGGTLVRAGEALTIAVESANHDPARFEDPDAI
DFTRPPGGHLTFGYGAHYCVGAQLGRIDLQEGLRVLLTRAPELTVRDLTWRVRPHI
RGPVAMRVTWQGDPE-

SEQ ID NO: 44 (coding sequence of sriC19)
P450 sriC19: SRIM_24386
*ATG**CAGAACACCGCCGAGACCGGCCCCGACGACCTCATTGACGTGACGCAGC*
*TTCTGGACGATCCGCACGCCGGGTACGCGGTGTTGCGGGAGGCGGGGCCCG*
*TCCATCGGATTGCCGGGCCGGACGGGCAGCCCGCGTGGCTGGTGACGCGGT*
*ACGAGGATGTGCGGCGGTGTCTGTCCGATCCGCGGCTTTCCCTGGACAAGCG*
*GAACGCGCGGGGCGGCTATCGCGGGTTCGCGCTGCCGCCCGCGCTGGACGC*
*GAATCTGCTCAACATGGATCCGCCGGACCACACCCGGGTGCGCCGGCTGGTG*
*GCCAAGGCATTCACGCCCGCGCGGGTCGAGAAGCTGCGGGAGCCCGTACGG*
*CGGCTGGCGGACGGGTTGCTGGACGCGGTCGCGGACGCCGGGCGGGCCGA*
*CCTGATGGAGTGTTACGCCGGTCCGCTGCCCATCATCGTCATCTGCGACCTGC*
*TGGGCGTACCGGAGGACGACCGGCCGGACTTCCGGGCCTGGACGGACGCGC*
*TGATCACGCCCGACCCGGCCCGGCCGGAGCGGGCGAAGGAGGCCGTCGGG*
*GCGATGATGCGCTACTACACGGGGCTGATCACGGCCAAGCGGGCCGCGCCG*
*GGGGACGATCTGCTCTCCGACCTGATCCTGGTGCGGGACGGCGCGGCGGCG*
*GAGGGTGGCGCGGGGGACCGGCTCGGTGAGGACGAGCTGACCTCGTTGGCG*
*TTCCTCCTGCTCTTCGCCGGTTACGAGAACACCGTTCACCTCATCGGTAACTCA*
*GTCCTCGCCCTGCTCGACCACCCCGAACACCTCATGGCGTTGCGTACGAATCC*
*AGCCGAACTGTCGGCGGCCGTGGAAGAGTTCGCACGCTATGACGGACCGGCC*
*TCGCTGGCCATCCGCCGGTTCCCCCTGGAGGACGTGGAAATCGGCGGCGTAC*
*GGGTGCCCGCGGGCGAGAGTGTGCTGCTCTCCCTTGCCTCGGCGAACCGCG*
*ACCCGCACCGCTTCGCCGACCCCGGGACGCTCGATCCGGGCCGCGACGCCA*
*CGGGTCAGCTGATGTTCGGGCACGGCATCCACTACTGCCTCGGCGCGGCCCT*
*GGCGCGCCTGCAGACCGAGACCGCGCTGACCGCTCTCATCAGCCGTTTTCCC*
*GGGTTGCGGCTGGATGTGCCACGGTCGGAACTGCGCCACCGCCGCACCCTG*
*CGGGCACGTGGCTTGATCTCGCTCCCCGTCGCCTGG**TAA*
Legend
*P450 (italics)*
Start and stop codons in bold

Protein sequence
(Translated using Expasy from DNA sequences above)

SEQ ID NO: 45 (amino acid sequence of cytochrome SriC19 (407 aa))
MQNTAETGPDDLIDVTQLLDDPHAGYAVLREAGPVHRIAGPDGQPAWLVTRYEDV
RRCLSDPRLSLDKRNARGGYRGFALPPALDANLLNMDPPDHTRVRRLVAKAFTPA
RVEKLREPVRRLADGLLDAVADAGRADLMECYAGPLPIIVICDLLGVPEDDRPDFR
AWTDALITPDPARPERAKEAVGAMMRYYTGLITAKRAAPGDDLLSDLILVRDGAAA
EGGAGDRLGEDELTSLAFLLLFAGYENTVHLIGNSVLALLDHPEHLMALRTNPAELS
AAVEEFARYDGPASLAIRRFPLEDVEIGGVRVPAGESVLLSLASANRDPHRFADPG
TLDPGRDATGQLMFGHGIHYCLGAALARLQTETALTALISRFPGLRLDVPRSELRH
RRTLRARGLISLPVAW-

Figure 4 (continued)

SEQ ID NO: 46 (coding sequence of sriC20)
P450 sriC20: SRIM_22019
*ATG**CCGGAAATCATCGACCTGGGCGCGTACGGCCCGGACTTCGTCGCCGACC*
*CGCATCCGTACTACGCCAAGCTGCGCGCCCAGGGCCCGGTCCACCGGGTCC*
*GCGCCCCGGAGATGGAGCCGGAGTTCCCGCAGGCCTGGCTGATCGTCGGATA*
*CGACGAAGCGCGGGCCGTGCTGGCCGACAACCGCTTCGCCAAGGACTGGTC*
*CCGGGCGAACGGCTCCCTCGCCGACAGCGAGGTCCTGGCCGAGTGGCAGCT*
*GATGAACATGCTCGACGCCGACCCGCCGCAGCACACCCGGCTGCGCAAGCTG*
*GTGGCCCGGGAGTTCACCACCCGCCGCGTCGAGGCGCTGCGCCCGCGCGTC*
*CAGCAGATCACCGACGAGCTGCTGGACGCCATGCTGGCCGCCCCGGACGGC*
*CGCGCCGACCTCGTGGAGGCGCTCGCCTTCCCGCTCCCGATGACCGTCATCT*
*GCGAACTCCTCGGCGTGCCCGACATCGAGCGGGACACCTTCCGCGCCTGGTC*
*CAACGAACTGGTCTCGCCGACCGACAACGAGGCGACGATGACCGCCGCCCGC*
*GAGATGGCCGCCTATCTGGACGGCCTGATCGAAAGCAAGCGGAGCTCGCCGG*
*GCGAGGACCTGCTGAGCGCGCTGGTGCGCACGAGCGATGAGGACGGCGACC*
*AGCTCTCCCGGCAGGAACTGCTCGGCATGGCCTTCCTCCTGCTCGTGGCCGG*
*CCACGAAACCACCGTCAACCTGATCTCCAACGGCGTACGGGCCCTGCTCCAG*
*CACCCCGCGCAACTGGCCGCACTGCGCGCCGATCCCTCGCTTCTCGACAACG*
*CCGTCGAGGAGATGCTGCGCTACGACGGCCCCGTGGAGACCGCCACCTGGC*
*GCTTCACCGCCGAGCCCGTCGGGATCGGCGGCGTGGAGATCCCGGCCGGTG*
*AGATCGTCCTCGTCGGCCTGGCCGGGGCGGACCGCGACCCGGAGCGCTTCG*
*AGGCCCCCGACACCTTCGACATCACCCGCGAGACCCGCGGCCACGTCGCCTT*
*CGGCCACGGCATTCACTTCTGCCTCGGCGCCCCACTGGCCCGCGTCGAGGGC*
*CGTATCGCGGTGCGCACTCTCCTGGACCGCTGCCCGGACCTGGCCCTGGACA*
*CCGCTCCCGAGGCGCTGACCTGGCGCGCGGGCATGACGATACGAGGGCCCC*
*AGCACCTGCCGGTGCGGTGGCGG**TAA*
Legend
*P450 (italics)*
Start and stop codons in bold

Protein sequence
(Translated using Expasy from DNA sequences above)

SEQ ID NO: 47 (amino acid sequence of cytochrome SriC20 (403 aa))
MPEIIDLGAYGPDFVADPHPYYAKLRAQGPVHRVRAPEMEPEFPQAWLIVGYDEA
RAVLADNRFAKDWSRANGSLADSEVLAEWQLMNMLDADPPQHTRLRKLVAREFT
TRRVEALRPRVQQITDELLDAMLAAPDGRADLVEALAFPLPMTVICELLGVPDIERD
TFRAWSNELVSPTDNEATMTAAREMAAYLDGLIESKRSSPGEDLLSALVRTSDED
GDQLSRQELLGMAFLLLVAGHETTVNLISNGVRALLQHPAQLAALRADPSLLDNAV
EEMLRYDGPVETATWRFTAEPVGIGGVEIPAGEIVLVGLAGADRDPERFEAPDTFD
ITRETRGHVAFGHGIHFCLGAPLARVEGRIAVRTLLDRCPDLALDTAPEALTWRAG
MTIRGPQHLPVRWR-

SEQ ID NO: 48 (coding sequence of sriC21)
P450 sriC21: SRIM_08633
*ATG**TCAGTGCCGAGCCGCCCGCCGGCCACCGTGCTCGACAACCCGCTGCACG*
*CCCTGCTCGACCGGGAGGTGCTCGCGAACCCCTACCCGCTGTTCGAGCGGTG*
*GCGGGAGCAAGGTCCGATGTGGACGTCGGACGGTTCCCTGCTGCTGAGCGAC*
*CACGCCAGTTGTCTGGCGGTGCTCAAGAGCCACCCGACCATGGGCAGTGACA*
*CGTTCAACGCGCCGGGGATGCGGGAACTCTTCGGCGACCGCGGCGACGAGC*
*CGGTGCTCAACTCGATCTTCTTCATGGACGATCCGGACACGGGCGGCAGCG*
*GAACCTGGTCAGCAAGGCATTCACACCACGGATCACCGCGCGCTTCGAGCCG*

Figure 4 (continued)

*TGGATCCGCGAGATCGTGGACGAACTGCTTCGCGACTGCCTGGCCGACGGCG
AGTTCGACGGCGTGCAGGACCTGGCCGCGGTGCTCTCGCTGCGGGTCATCGC
GACGCTCCTGGGCATCCCGCGCGAGGACATCCCGATGCTGCGGGAGTGGTCC
AGCGACATGGCGCTGTCCACGGAGCTGCCCACGCTGGTGGCCAGCTTCCACT
CCACCGCGATGTTCGACCGCGAGGAACTCGTCCGCATCATCCGTACCACCAC
CGAACTGCACGGCTACTTCGCGAACCTCATCCACAAGCGCCGCCGCAACCCC
GGCGAGGACCTCATCTCCAGTCTGATCTCCACGCAGGAGAACGGGCGCGGAC
TGAGCCGGCGTGAGGTGACGAACGTCGTGGTGACCGTGTTCACCGCGGCCCA
CGAGTCCACCACGAACCTGATCACCAACGGCCTGCTCGCGATGTCGCGCCAC
CCGGAGCAGTTCCAGCTGCTCCGGCAGAACCCGGCGATCGTCGGCGACGTG
GTCGGCGAGGCGCTGCGCTACGACTGCCCGATCATGCTGACCGGCCGGGTC
GCGCTGCGGTCCGACCGGATCAACGGCATCGACATCCCCGAGGGCTCGGTG
GTCACCCTGGTCCTCGCGTCCGGCAACAGGGACGAGCGGGTGCACCCGAAG
GCGGATCGGTTCATCGCGGACCGGAAGCCGGCCGTGATGAACCTCGCCTTCG
GCGCCGGCGCGCACTTCTGCCTCGGTAGCAGTCTGGCCCGGCTGGAGGCGG
AGATCGTGTTCGGTGAGCTGGCTCGCCGGCTGCGCGGCTTTCACGTGCACGA
GGACTCACTGAGCTATCGCAGGCACGTGGTCGTCCGCGGCCTCGACACCGAA
CGGATCACTTTCCAACTC*TAA*

Legend
*P450 (italics)*
Start and stop codons in bold

Protein sequence
(Translated using Expasy from DNA sequences above)

SEQ ID NO: 49 (amino acid sequence of cytochrome SriC21 (420 aa))
MSVPSRPPATVLDNPLHALLDREVLANPYPLFERWREQGPMWTSDGSLLLSDHA
SCLAVLKSHPTMGSDTFNAPGMRELFGDRGDEPVLNSIFFMDDPGHGRQRNLVS
KAFTPRITARFEPWIREIVDELLRDCLADGEFDGVQDLAAVLSLRVIATLLGIPREDIP
MLREWSSDMALSTELPTLVASFHSTAMFDREELVRIIRTTTELHGYFANLIHKRRRN
PGEDLISSLISTQENGRGLSRREVTNVVVTVFTAAHESTTNLITNGLLAMSRHPEQF
QLLRQNPAIVGDVVGEALRYDCPIMLTGRVALRSDRINGIDIPEGSVVTLVLASGNR
DERVHPKADRFIADRKPAVMNLAFGAGAHFCLGSSLARLEAEIVFGELARRLRGFH
VHEDSLSYRRHVVVRGLDTERITFQL-

SEQ ID NO: 50 (coding sequence of sriC22)
P450 sriC22: SRIM_26382
*ATG**ACCACATCGCCCACCGAGTCCACCACGGCCACCCCGCCCGACTCCACCA
CCGCCTCCGCCCCCGGCACCCCGCCGGACGCCCTGCCGTCCTACGTCGGCC
TGCACCCGGGCGAGCCGAACGTGATGGAGCCGGAGCTGCTCAACGACCCGTA
CGCCGGTTACGGGAAGCTGCGCGAACAGGGCGCCCTGGTGCGCGGCCGGTT
TCTCGACGACTCGCCCGTCTGGCTCGTGACCCGCTTCGACGTGGTACGCGAG
GTCATGCGCGACCCGCGGTTCATCAACAACCCGTCCCGCCTGCCCGGCCGCA
CGGAGAAGGACCCGCGCGCCCAGCTGATCGAGCTGTTCGGCATCCCCGACCA
CATGGCCCGGTACCTGGTGGACACCATCCTCACCAGCGACCCGCCGGACCAC
ACCCGGCTGCGGCGCCTGGTCTCGCGGGCCTTCACCGCCCGCCGCATCCAG
GACCTGCGGCCGCGGGTGGAGGCGATCACCGACGAGCTGCTGGACCGGTTG
CCGGCCCACGCGCAGGACGGCGTCGTCGACCTCGTCGAGCACTTCGCGTACC
CGCTGCCCATCACCGTGATCTGCGAACTGGTCGGCATCGACGAGGAGGACCG
GCCGCTGTGGCGGCAGTTCGGCGCCGACCTCACCTCCCTGGAGCCGAAGCG
GATCGGCGCCACGGTACCGGCCATGGTCGAGCACATCCACAAGGTGATCGGC
GAGCGCCAATCGGCCCTGCGGGACGACCTGCTCAGCGCGCTCATCCGGGCC
CGGGACGACGACGGCGGCCGGCTGAGCGAGACCGAGATGGTCACCATGGTC*

Figure 4 (continued)

*CTCACGCTGGTACTGGCCGGCCACGAGACCACCGCCCACCTCATCAGCAACG*
*GCACCCTCGCCCTGCTCACCCACCCCGACCAGCGGCGCCTGCTCACCGAGGA*
*CCCGGGCCTGCTCCCCCGCGCGGTCCACGAGCTGATGCGCTGGTGCGGGCC*
*GATCCAGGCCACCCAGCTGCGGTACGCCTCCGAGGACGTCGAGGTGGCCGG*
*CACCCAGGTCCACAAGGGCGACGCCCTGATGTTCAGCCTCGTGGCGGCCAAC*
*CACGACCCGCGCCACTACACCGAGCCGGAAAAACTCGACCTGACACGCCAGC*
*CGGCGGGCCGCGCCGAGGACCACGTCGGCTTCGGACACGGCATGCACTACT*
*GCCTGGGCGCCTCACTCGCCCGGCAGGAAGGCGAAGTCGCCTTCGGCAAGCT*
*GCTCGCACGCTATCCGGAGGTGGCACTCGCCCTGCCCCATGAGCAGCTGGAG*
*GAGCAAGAGCGCATACGCCAGCCCGGGTCCTGGCGACTGCGGCGGCTGCCG*
*TTGCGGCTGCGTCCGGAGGACTAA*
Legend
*P450 (italics)*
Start and stop codons in bold

Protein sequence
(Translated using Expasy from DNA sequences above)

SEQ ID NO: 51 (amino acid sequence of cytochrome SriC22 (454 aa))
MTTSPTESTTATPPDSTTASAPGTPPDALPSYVGLHPGEPNVMEPELLNDPYAGY
GKLREQGALVRGRFLDDSPVWLVTRFDVVREVMRDPRFINNPSRLPGRTEKDPR
AQLIELFGIPDHMARYLVDTILTSDPPDHTRLRRLVSRAFTARRIQDLRPRVEAITDE
LLDRLPAHAQDGVVDLVEHFAYPLPITVICELVGIDEEDRPLWRQFGADLTSLEPKR
IGATVPAMVEHIHKVIGERQSALRDDLLSALIRARDDDGGRLSETEMVTMVLTLVLA
GHETTAHLISNGTLALLTHPDQRRLLTEDPGLLPRAVHELMRWCGPIQATQLRYAS
EDVEVAGTQVHKGDALMFSLVAANHDPRHYTEPEKLDLTRQPAGRAEDHVGFGH
GMHYCLGASLARQEGEVAFGKLLARYPEVALALPHEQLEEQERIRQPGSWRLRRL
PLRLRPED-

SEQ ID NO: 52 (coding sequence of sriC23)
P450 sriC23: SRIM_05961
*ATGACCGCCGAGAACCACACCGCGCAGCCCCAGGCGCCCGCGCCCGACGGG*
*ATCCCGTACGACGAGCCCCTTCCGCACTACCCCTTCAGCACCAAGGGGGACC*
*GGCTCGCCCCCGAACTCGACGAGCTGCGCAGCCGCTGCCCCGTGGCCCGGG*
*TCAGCACCAACTCCGGTGAACAGGCGTGGCTGGTGACCGACTACGGGCTCGC*
*CCAGCACGTACTGCGGGACCGCGCCTTCGCCCGCTCCGTGCTGGGCGAGGC*
*GGACAGCCCCGCCCAGGACGCCCCGATCCTCGCGCCCGAACTGCTCGACGC*
*CATGAACCACCTCCAGCAGGCCGGGCTGCGTGCCGAAGTGCTCCGCTCGCTC*
*GGCCGCGACCAGCCCGACCTGCCCGCCGACTGGGTCGCGCGGGTCACCGGC*
*GAAGGGCTGGACGCGATGATCCGCGAAGGCGCCCCCGGCGACCTCCAGCGC*
*CACTTCGCTGAGTGGGTCGCCGCCCAGTGCATGTGCCGCCTCCTCGGCGTGC*
*CCTTCGAGGACCATGCCTGGCTCGCCGTACGGGCGGACCTGGACCTGACCAT*
*GGTCACCCCCACCCCCGAGGAACTCGCCCGCAACTGGGAGGAGATCCGCGC*
*CTACATGGCCGCGCACATGACGGCCCGCCGCCCCGGCGAGCCCCGAGGCCT*
*CGTGGACCGCCTCGCCGACCTCAACGCCGCGCACCAAGGGCTGACGGAGCG*
*GCAGCTGTCGAACATCGTGTCCGTCCTCTTCGTCAGCGGCTACGAGGACTTCG*
*CGAGCTTCCTGGGCGTCGCGGCCTACAACCTGCTCCAGCACCCGGAGACCAT*
*CAGCGCGGTGCGCGCCGAGCCGGAGACCATGCCGCAGTGCGTGGAGGAGCT*
*GCTGCGGTGCAGCGTCGTGCTGGGCAACGCGATTCCCCGCTTTGTCACCGCC*
*GACGCGCGGATCGGCCCGTCCCAGGTCAAAAAGGGCGACATGGTCCTGCTCT*
*CCCTGGACGCGGTCAACTACGACTCGACCGCGTTCCCCGACCCCAAGACCTT*
*CGACCCCACCCGCTCACCCAACCCCCACCTGCGCTTCGGCTACGGCCGCCAC*
*CACTGCCCCGGCGCCCACCTGGTCCGCCGCCAGTCCGAGGTCGCCTTCCGC*

Figure 4 (continued)

*GTCCTCCTCGACCGCCTGCCCGGCATCCACCTGGTGGTGCCGCCGCAAGAGG*
*TTCCCTGGCACCCGAACCGCATGGCGATCATGGCGGCGGAGATTCCGGTGGC*
*GTGGTAA*

Legend

*P450 (italics)*

Start and stop codons in bold

Protein sequence

(Translated using Expasy from DNA sequences above)

SEQ ID NO: 53 (amino acid sequence of cytochrome SriC23 (414 aa))

MTAENHTAQPQAPAPDGIPYDEPLPHYPFSTKGDRLAPELDELRSRCPVARVSTN
SGEQAWLVTDYGLAQHVLRDRAFARSVLGEADSPAQDAPILAPELLDAMNHLQQA
GLRAEVLRSLGRDQPDLPADWVARVTGEGLDAMIREGAPGDLQRHFAEWVAAQC
MCRLLGVPFEDHAWLAVRADLDLTMVTPTPEELARNWEEIRAYMAAHMTARRPG
EPRGLVDRLADLNAAHQGLTERQLSNIVSVLFVSGYEDFASFLGVAAYNLLQHPETI
SAVRAEPETMPQCVEELLRCSVVLGNAIPRFVTADARIGPSQVKKGDMVLLSLDAV
NYDSTAFPDPKTFDPTRSPNPHLRFGYGRHHCPGAHLVRRQSEVAFRVLLDRLPG
IHLVVPPQEVPWHPNRMAIMAAEIPVAW-

SEQ ID NO: 54 (coding sequence of sriC24)

P450 sriC24: SRIM_09151

*ATGCCGCAGGACACCTCCCGCCGGTTCGAGCGAGCGCCCAGGGCCGCCTTC*
*GGCCCCGACGCCCACACCCGCGAGCTGCACGGGAAAGCACCGGTCAGCAAA*
*GTCGACATGGGCCCGATACCCGACTCGGACGCCGGCCGCGCCACGGTCTGG*
*CTGGTCACGGGCTACCACGAGGTACGCCAGGTCCTCGGCGACCACGTACGGT*
*TCGGCAACGGCTTCGCCTCCGGCCCGGTGTACGGACCGCGAGCCGCTTCC*
*GGCCCCCGGAGGTCGTCGGGCACCTGATGGACTACGACCCGCCGGAGCACA*
*CCCGGCTGCGCCGGATGCTGACCCCGGCGTTCACGGTCCGGCGGATGCGGC*
*AGCTGGAGCCCCGTATCGAAGAGGTCGTGGCGCGCTGCCTGGACGGCGTGG*
*CGAAGGCCGGGCAGCCCGCCGACCTGGTGGAACGGTTCGCCCGCCCGGTGT*
*CGGGCGAGGCGCTGTGCGAACTGCTCGGGGTGCCGCGCGACGACCGTACGG*
*ACTTCGTGCGCCGCGTCCAGTGGCAGCTGGAGCAGGACCGGCCGCGCAGGC*
*AGCGGGCCGACGCGGGCGAGTCCTACCTGCGCTACCTCGGCGCGATGGTGC*
*GCCGCCGTCGCAAGGACCCCGACGACAGCTTCATCGGCACGCTCGTACGCGA*
*GCACGGCGACAGCATCACCGACGAGGAACTGCGCGGCGTCTGCGGCCTGAT*
*GATGCTCGCCGGGCTCGACAACGTCTCCGGCATGATCAGCCTGGGCATCCTC*
*GTCCTGCTCCAGCACCCCGACCAGCTCGCCGCGCTGCACGCCGGCACCGCGT*
*CCGCGGACCGCGTGGTCGACGAGCTGCTGCGCTACCTGTCGGTGGCGCACG*
*CACCGCAGCGGCGGATCGCCCTGGCGGACGTCACCGTCGCGGGCCAGGTGA*
*TCAAAAAGGGGGAGCAGGTCCTGTGCTCCCTCCAGATGGCCAACCGCGACCC*
*GGCCTTCCTCCCGCACCCCGACCGCTTCGACGCCACCCGCGACCCCGCGCCC*
*CACGTCGCCTTCGGCCATGGCATCCACCACTGCATCGGCGCCGCGATGTCCA*
*GGATGGAACTGCGCATCGCCTACCGCGCCCTGTGGCACCGCTTCCCCGGACT*
*GCGGCTGGCCGTCCCCGTGGAGGAGATCGCGTATCGGACCAATGCGGTGGC*
*GGACGGGGTGGTGAGGCTGCCTGTGGTGTGGTAA*

Legend

*P450 (italics)*

Start and stop codons in bold

Protein sequence

(Translated using Expasy from DNA sequences above)

Figure 4 (continued)

SEQ ID NO: 55 (amino acid sequence of cytochrome SriC24 (404 aa))
MPQDTSRRFERAPRAAFGPDAHTRELHGKAPVSKVDMGPIPDSDAGRATVWLVT
GYHEVRQVLGDHVRFGNGFASGPVYGTASRFRPPEVVGHLMDYDPPEHTRLRR
MLTPAFTVRRMRQLEPRIEEVVARCLDGVAKAGQPADLVERFARPVSGEALCELL
GVPRDDRTDFVRRVQWQLEQDRPRRQRADAGESYLRYLGAMVRRRRKDPDDSF
IGTLVREHGDSITDEELRGVCGLMMLAGLDNVSGMISLGILVLLQHPDQLAALHAGT
ASADRVVDELLRYLSVAHAPQRRIALADVTVAGQVIKKGEQVLCSLQMANRDPAFL
PHPDRFDATRDPAPHVAFGHGIHHCIGAAMSRMELRIAYRALWHRFPGLRLAVPV
EEIAYRTNAVADGVVRLPVVW-

SEQ ID NO: 56 (coding sequence of sriC25)
P450 sriC25: SRIM_03476
*ATG**GATGAGTCGCCCGTCTTCGTCCTGGATCCCGCAGGCCGTGACCGGCACG
GTGAGGACGCCCGGTTGCGCGCCCGTGGCCCGCTCACCCGGGTGGACGTGC
TCGGCGTCGAAGCCTGGGCGGTCTCCGACCCTGTTCTGCTGCGTCGGCTCCT
CATGGACCCGCGCGTCTCCAAGGATGCCCGCCGTCACTGGCCTGCCTATCCC
GGCCGGATCGCGGGGGTCTGGCCGCTGGAGCTGTGGGTGGCGGTGGACAAC
ATGTTCACCGCCTACGGTGACGAACACCGTCGGCTCCGCCGCATCATCAGCCA
GGTCTTCACCGCGCGGCACGTCAACGCCCTGGCACCCGTCATCGAACGCATC
GCCGGAGAGCTGCTCGACGGCCTTGCTGCCACACCGCCCGGTACGCCGGTG
GACCTGCGTGAACGCTTCGCGTCGCCGTTGCCGATCAGGGTCGTCAGCCACT
TGGTGGGCCTGTCCGAAGCGGACGGGCCACGCTTCCGCCGTACCGTCGACAA
GGTCTTCTCCACCAGTCTGGACCCGGTGGAGGCAGGCGCCAACGTCGCTGAA
CTGTACGCGCTGCTGACCGGCCTGGTCGCCGCGAAACGGGCCGAGCCCGGC
GACGACCTGGCCTCCAAGCTCATCACCGCGCGGGACAGTGAGGGCGACGGAT
CACGTCTCACCGAGACCGAACTGATCGACACTCTCCTCCTGGTGATCAACGCC
GGGTTCGAGACCACCGTCAACCTGATCGACCAAGCCGTCACGGCCTTGCTCA
CCCACCCCGGCCGGCTCGCCCTCGCGCGAGCGGGCCGCGTCGGCTGGCAGG
ACGTCGTGGAGGAGACGCTGCGCTGGGAGGCCCCGGTACCGTACCTGCCCAT
GCGCTACGCGGTGGAGGACATCCCGCTGCCCGGCCACGGCCCGACGATCCG
CAAAGGGGACGCGATCCTCGCCTCGTACGGCGCCGCCAACCGGCACCCGGA
CCTCCACGGTCCCACCGCCGATCAGTTCGACCCCGCCAGGACGGACAAATCC
CACCTCTCCTTCGGACACGGAGTGCACGCCTGCCTGGGTGCCGCACTCGCCC
GGCTGGAAGGCACGATCGCCCTGCGCGGCCTCTTCGAACGCTTCCCCGATCT
CGCTCTCGCCGTCCCGGCACACCGGCTGCGCCCCCTGCCGAGCTTCGTCTCC
AACGGCCACCGCGAACTACCGGTTGTGCTCCGCTCCGCGCCGGCCGGGGAA
GCAGGGGGA**TAA*
Legend
*P450 (italics)*
Start and stop codons in bold

Protein sequence
(Translated using Expasy from DNA sequences above)

SEQ ID NO: 57 (amino acid sequence of cytochrome SriC25 (417 aa))
MDESPVFVLDPAGRDRHGEDARLRARGPLTRVDVLGVEAWAVSDPVLLRRLLMD
PRVSKDARRHWPAYPGRIAGVWPLELWVAVDNMFTAYGDEHRRLRRIISQVFTAR
HVNALAPVIERIAGELLDGLAATPPGTPVDLRERFASPLPIRVVSHLVGLSEADGPR
FRRTVDKVFSTSLDPVEAGANVAELYALLTGLVAAKRAEPGDDLASKLITARDSEG
DGSRLTETELIDTLLLVINAGFETTVNLIDQAVTALLTHPGRLALARAGRVGWQDVV
EETLRWEAPVPYLPMRYAVEDIPLPGHGPTIRKGDAILASYGAANRHPDLHGPTAD
QFDPARTDKSHLSFGHGVHACLGAALARLEGTIALRGLFERFPDLALAVPAHRLRP
LPSFVSNGHRELPVVLRSAPAGEAGG-

Figure 4 (continued)

SEQ ID NO: 58 (coding sequence of sriC26)
P450 sriC26: SRIM_36636
*ATG**GAGACTGCCCCGCTCCGCCCCGTACCCGGCCCGCGCGGCCTGCCGTGG*
*CTCGGAAACCTGCCCGCCTTCGGCAAGGACCCGCTGGCGTTCCTGACCCGGC*
*TGCGGGACGCCGGCGACGCCGTGACGTGGTCCCTCGGCCCGCGGCGCAGCC*
*TGTTCCTCTCCCACCCGCAGCACATCGCCGAATTCCTCGGCTCCCGGGGCGG*
*CGCCTACGACGTCCTGCGAATCGGCTGGCCATGCACCAGCTCGTCGGCGAG*
*AGCGTCCTGCTCACCGCGGGGGCCGAGTGGCGCCGCAAGCGCGGCATGGTC*
*CAGCCGACCGTCCGCCCGCGCCAGGTCCGCCGCTTCGCCCGGACCATGGTC*
*GACAGCGCCCTCGCGGCGGTCGGCGGCTGGCGCGACGGCGACCGCTTCGAC*
*CTGCGGCGGGAGATGACGCTCATCACTCAGCGCATCGTGCTCCGTACGCTGT*
*TCGGCAACGACCTCGGGGACCGGACCCAGGCCCTCGGCGAGGCGATGGCGA*
*CGGCCGAACGCGCGGTCGCCACCGAGATCCGCGGCCTGCCTCTGATCCTCCC*
*GCCATGGGTGCCGCTGCCCTACCGCCGGCGTCATCTCGGCGCCGTCGCCACC*
*ATCGACGCCGAGATGCGGCGGCTGATCGACGCCCGGCGGGCCGGGGCGGAC*
*GGCGGGGACGGTGCCGGTGCGGACGGCGGCCAGGGCGGCGATCTGCTGAC*
*CCGGCTGCTCGCGGCGCGGGACGAGGAAGGGCGCCCGCTGTCCGCCAAAGA*
*GGTCCAGGACGAGGCGGTGACGCTCTGGGCGGCCGGTCACGAGACGACCTC*
*CACCGCGTTGACGTGGACCTGGTACCTGCTGTCCCGGTCGCCCGAGGCGCGG*
*GCCCGGCTGGACGACGAGGTCGACCGCGTCCTGGGCGGCCGCCCACCCACC*
*GAGGAGGACTACGAACGGCTGGTCTGGACCCGGCAGATCGTCAAGGAGAGCC*
*TGCGGATGTATCCGCCGGTCTGGCTCGTCCCCGCCGTGGCCAAGGAGGGCGT*
*CGTCCTGGGCGGCCGCGCCATTCCCGCCGGTACGACGGTGTGGTGCAGCCA*
*GTGGACGGTCCACCGGGACCCGCGCTGGTTCCGCGACCCCCAGGTGTTCCG*
*CCCTGAACGCTGGGACGCCGACGCTCCCGACGTCATCCCCGAACACGCTTGG*
*TTCCCGTTCGGCGGCGGCTCCCGCGGCTGTATCGGCGCCCGGTTCGCCCAGA*
*TGGAGGCGGCTTTGCTCATCGCCGCCGTGGCGCAGCGCTTCCACCTGGACGT*
*GACGCCGAAGGAGGCGACGCCGCGCATGGGCATGGTCATTCAGCCGGCCGT*
*GCCGCTGATCGCCACGGTGCGCGCTCGTTCGCGTCCG**TAA*
Legend
*P450 (italics)*
Start and stop codons in bold

Protein sequence
(Translated using Expasy from DNA sequences above)

SEQ ID NO: 59 (amino acid sequence of cytochrome SriC26 (458 aa))
METAPLRPVPGPRGLPWLGNLPAFGKDPLAFLTRLRDAGDAVTWSLGPRRSLFLS
HPQHIAEFLGSRGGAYDVLRIGWAMHQLVGESVLLTAGAEWRRKRGMVQPTVRP
RQVRRFARTMVDSALAAVGGWRDGDRFDLRREMTLITQRIVLRTLFGNDLGDRTQ
ALGEAMATAERAVATEIRGLPLILPPWVPLPYRRRHLGAVATIDAEMRRLIDARRAG
ADGGDGAGADGGQGGDLLTRLLAARDEEGRPLSAKEVQDEAVTLWAAGHETTST
ALTWTWYLLSRSPEARARLDDEVDRVLGGRPPTEEDYERLVWTRQIVKESLRMYP
PVWLVPAVAKEGVVLGGRAIPAGTTVWCSQWTVHRDPRWFRDPQVFRPERWDA
DAPDVIPEHAWFPFGGGSRGCIGARFAQMEAALLIAAVAQRFHLDVTPKEATPRM
GMVIQPAVPLIATVRARSRP-

SEQ ID NO: 60 (coding sequence of sriC27)
P450 sriC27: SRIM_28831
*ATG**CGCGATCCGGTCCGCTACTTCGAGACGTTGCGCCGGCGCTACGGTCCGG*
*TGTTCCGTATGAAATTGCTCGGCTTCCCGCCCCAGGTCGTGGTCTCGACCGCG*
*GAGCTGGCCGCGGAGATCTACCGTATGGACGGCGACGGCAACCGCGCCGGA*

Figure 4 (continued)

*GCGCTGCGCGCGGGGTACGTGCCGTGGGTCGGACAGCACTCGCTGCTCACC
AACGACGGCGAGGAATGGTGGCGCCACCGCAAGCTGCTCAGCCCCACCCTGC
ACGGCAGGTCCATCGCGAACTATCCCGAGCTGATCGCCGAGATCGCCGCGAA
GGACATCGGGACGTGGCCGCTCGGCAGGCCGTTCACCCTGCGCGAGCACAT
GCAGGCCATCACCCTGGAGGTCATCCTGCGGCTGGTCTTCGGGGTCCGGGAC
ACCGAGCAGGGGGCCCGGTTACGGGCCGGTCTCATCGACCTGTCCAAGGCCA
CCGGCTCCGCCGCCCTGTTCCTGACGCCCGCCCGGCTGCGGGCCTGGGCGC
AACGGTCTCCGCTGGCGATGCGCCTGCCGTTCCTGCCGACGACCCGCGCCGC
GCAGGCCGTCGAGACGGTGGACCACATCCTGTTCGCCGAGATCGCCCGGCGC
CGGGCCGAGGAGGACGCGGACGCCGACGACGTCCTGGGGCGGCTGCTCCGC
GCCCGGGACGACCAGGGCCGCCCGCTCAGCGACCAGGAGATCCGCGACGAA
CTGCTCACCCTGCTGGAGGCCGGCCTGGAGACCACGGCGACCGGCCTGTCAT
GGACCTTCGAGCGGCTGATGCGCAATCCGCGGGTGCTCGCGCGGCTCCAGG
AGGAGGTGGAGCAGGGCGAGGACGACACCTACCTCGACGCGGTCGTCAAGG
AGGCGCTGCGGTCCCGTCCGGTGATCTTCGGCATGGGGCGGCTGCTGGACAA
GCCGTTGCGGGTCGGTGGGTTCGAGGTGCCGGCCGGCTGGGTGGCCATCCC
GATGTTCTCGCTGATCCTCCAGGACCGTGCGGTGTACCCGGACGCCGGGGAG
TTCCGGCCGGAACGCTTCCTCGGTGAGGGCGCCAAGGCGGCGCAGAAGTCGT
TCCTGCCGTTCGGCGGCGGCCGCCGTTACTGCGTCGGCGCCCAACTCGCCAC
GCTGGAGATGAAGATCATCACTCGCGAGGTGCTCCGGCACGTCCATCTGGCC
CCCGCCGACCCCGCGCCGGAGGCCCAGCGCATGTGGCACGCCACCCTCATC
CCCGGCAAGCAGGTCGTCGCGGTGGCCCGCAAGCAACCGCCGAAGCGGCGG
GCGCCGGTCCAGGAGGCGAAGTGCCCCGTACATCCGGCTCTTTCGGACGACG
CGGGGTAA*

Legend

*P450 (italics)*

Start and stop codons in bold

Protein sequence

(Translated using Expasy from DNA sequences above)

SEQ ID NO: 61 (amino acid sequence of cytochrome SriC27 (449 aa))

MRDPVRYFETLRRRYGPVFRMKLLGFPPQVVVSTAELAAEIYRMDGDGNRAGALR
AGYVPWVGQHSLLTNDGEEWWRHRKLLSPTLHGRSIANYPELIAEIAAKDIGTWPL
GRPFTLREHMQAITLEVILRLVFGVRDTEQGARLRAGLIDLSKATGSAALFLTPARL
RAWAQRSPLAMRLPFLPTTRAAQAVETVDHILFAEIARRRAEEDADADDVLGRLLR
ARDDQGRPLSDQEIRDELLTLLEAGLETTATGLSWTFERLMRNPRVLARLQEEVE
QGEDDTYLDAVVKEALRSRPVIFGMGRLLDKPLRVGGFEVPAGWVAIPMFSLILQD
RAVYPDAGEFRPERFLGEGAKAAQKSFLPFGGGRRYCVGAQLATLEMKIITREVLR
HVHLAPADPAPEAQRMWHATLIPGKQVVAVARKQPPKRRAPVQEAKCPVHPALS
DDAG-

SEQ ID NO: 62 (coding sequence of sriC28)

P450 sriC28: SRIM_16485

*ATGTTCACACCCCGCACGTACGCCACCGCGGTCCCGTACGAACTCTTCAGGG
AACTGCGGGCGACCCGGCCGGTGTGCTGGATCGAGGAACCGGCGGTCGACG
GCTGGCCCGCCGGGCCCGGCTACTGGGCCGTGCTGCGGCACGCCGACGTCA
AACACGTCCTGCGTACCCCCGAGATCTACTCCTCGTACCTGGGCGCGACCCA
GATCCGCGACCCCGACACCGAGGAGGACCTCGCGTTCGTCCGGGCGATGATG
CTCAACCAGGACCCTCCGGACCACGCGCGCATCCGGCGTGTCGTCGCCGCG
GCCTTCACCCCGCGCGCGGTACGGGAACTGGCGGACGTCATCGACGCGCGG
GCACGGGAGCTGGTGGCGGAGGTGGCACGGCGGGCGAGGCGGACTTCGT
GACCGTGGCCGCCGACCTGCCGGTGTGGACGCTGGCGCACGTCATGGGCGT*

Figure 4 (continued)

*CCCGGAGGAGGACCGGCAGCTGCTCTTCGACTGGTCGAACCGCGTCATCGGC*
*TACCAGGACGACGCGTACGCCACCTCCAGCACTGCCGACCCCGCCCGCCTCA*
*GCCCGATGGGACGGCCGCCCTGCGCCACCGGCCCGCACCGGCGCTCCGCC*
*CGGACGGACGCCCGGTCAACCCGCGCTCGCGCCGCGCACTGGCCGACATGT*
*TCGCGTACGCCCACGCGCTGGCCGAGCACCCGCGCCCCGGCACCGTGATGG*
*CCCACCTACGGGAAGGCGGCCTGACCCGCGCCGAGTTCGAGAACACGTTCTT*
*CCTCTTCGCCGTGGCCGGCAACGAAACCCTGCGCAACGGCATCCCGGGCGGC*
*CTGCTCACCCTCCTCCAGCACCCGGACCAGTTCGCCCGCCTCCGCCGGGAAC*
*CGGACCTGACCGACAGCGCGGTGGAGGAAATGCTGCGCTACTGGCCCCCGGT*
*GATCGACTTCCGCCGCACCGCCACCCGCGACACCGAACTCGCCGGACAGCAC*
*ATCCGCCGCGGCGACAAGGTCGTCGTCTACCACGCCTCCGCCAACCGCGACG*
*AAACCGTCTTCCCCACCCCCGACCACTTCAACATCACCCGCACCCCCAACGAC*
*CACCTCAGCTTCGGCTTCGGCCCACACTTCTGCCTGGGCAGCCACCTCGCCC*
*GCCTCCAGATGCGGGCGGTACTCCGGCATGTGCTGGAGCGGCTGCCGGGGG*
*TGGAGCTGGCGGGGGAGCCGGTGCGGTTGGTTTCCAACTTTCAGAACGGGTT*
*GCGGCGGTTGCCGGTGCGGGTGGGGGCGTAA*

Legend
*P450 (italics)*
Start and stop codons in bold

Protein sequence
(Translated using Expasy from DNA sequences above)

SEQ ID NO: 63 (amino acid sequence of cytochrome SriC28 (422 aa))
MFTPRTYATAVPYELFRELRATRPVCWIEEPAVDGWPAGPGYWAVLRHADVKHV
LRTPEIYSSYLGATQIRDPDTEEDLAFVRAMMLNQDPPDHARIRRVVAAAFTPRAV
RELADVIDARARELVAEVARAGEADFVTVAADLPVWTLAHVMGVPEEDRQLLFDW
SNRVIGYQDDAYATSSTADPARLSPMGRAALRHRPAPALRPDGRPVNPRSRRALA
DMFAYAHALAEHPRPGTVMAHLREGGLTRAEFENTFFLFAVAGNETLRNGIPGGL
LTLLQHPDQFARLRREPDLTDSAVEEMLRYWPPVIDFRRTATRDTELAGQHIRRGD
KVVVYHASANRDETVFPTPDHFNITRTPNDHLSFGFGPHFCLGSHLARLQMRAVL
RHVLERLPGVELAGEPVRLVSNFQNGLRRLPVRVGA-

SEQ ID NO: 64 (coding sequence of sriC30)
P450 sriC30: SRIM_10366
*ATGACCACGGACGACGACGAAGAAGAGGATCAGCGGATGCCCGAGACACCCG*
*AGATTCCCGCGCACTACCGGCGGGACCGCTTCGACCCGGTACCCGAACTCGT*
*CCGGATGGCCAGGGAGACGCCGCTGGTCGAGACCGACGTCACGATCGGTCC*
*CTCCGAGCAGGTGGGCTGGGTGGCCACCGGGCACGCCGAGGTGCGGGCGGT*
*GCTGGCCGACGCGGAGCGGTTCAGCACCCGCCCGCCCGCCGACAGCGAGGA*
*GGACGCCGAGAGCCTGGTCCAGGCCGGGAACCTGCTCCAGTACGACCCGCC*
*CGACCACACCCGGCTGCGCAAGCTGCTCACGCCGGAGTACACGGTGCGCAAG*
*ATGCGCCGCCTGGAGCCCCGCATCGAGGAGATCGTCCAGGACTGCCTGGACA*
*CCATGGAGCGCGTCGGCCGCCCGGCCGACCTCGTACGCTACTTCGCCTGGCC*
*GATCCCGGGCCTCGCCAGCTGCGAACTGCTCGGCGTCCCCCGCGACGACCA*
*GACGGAACTGGCGCGCTACCTGGACATCACCCGGGACGTGGCCGCAGCCA*
*GGAACAGCAGCTGGCCGCCGGGAAGGCGTACTGGGCGTACATGGGCCAGCT*
*CGCCGAGCGCCGCCGCCGCAACCCCGGCGACGACATGCTCGGCAGTCTCGT*
*CCGCGAACAGGGCGCGGCCGTCTCCGACGCGGAACTGGCGGGCATCGGCGC*
*GACGGTGATGGCCGCCGGCTTCGAACAGGTCGCCAGCATCCTGGGGCTGGG*
*CACCCTGCTGCTGCTGGAACACCCCGACCAGCTCGCCCTGTGGCGCGAACAG*
*CCCGAACTGACCGACCGCGCGGTCGAGGAAGTGCTGCGCTACCTCACGGTCA*
*TCCACACCGCCTCGCCCCGTACGGCACTGGTGGACGTGACGATCGGCGGGCA*

Figure 4 (continued)

*GACCATCAAGGCCGGGGAGAGCGTGGCCTGTTCGCTGCTGGCCGCCAACCG*
*CGTACCGGCCCCCGGTGAGCCCGCCGACCGCTTCGACATCACCCGTGAGCCG*
*GCCACCCACATGGCCTTCGGCCACGGCATCCACCACTGCCTCGGCGCCCCGC*
*TGGCCCGGATGGAACTGCGCATCGCCTTCCCGGCCCTGCTGCGCCGCTTCCC*
*GGACCTGCGGCTCGCCGTGCCGCACGAGCGGGTCCGGTTCCGGCCCGCCCG*
*GTCCCGCCAGTACGCCCTGGAATCGTTGCCCGTCGCATGGTAA*
Legend
*P450 (italics)*
Start and stop codons in bold

Protein sequence
(Translated using Expasy from DNA sequences above)

SEQ ID NO: 65 (amino acid sequence of cytochrome SriC30 (408 aa))
MTTDDDEEEDQRMPETPEIPAHYRRDRFDPVPELVRMARETPLVETDVTIGPSEQ
VGWVATGHAEVRAVLADAERFSTRPPADSEEDAESLVQAGNLLQYDPPDHTRLR
KLLTPEYTVRKMRRLEPRIEEIVQDCLDTMERVGRPADLVRYFAWPIPGLASCELL
GVPRDDQTELARYLDITRDVGRSQEQQLAAGKAYWAYMGQLAERRRRNPGDDM
LGSLVREQGAAVSDAELAGIGATVMAAGFEQVASILGLGTLLLLEHPDQLALWREQ
PELTDRAVEEVLRYLTVIHTASPRTALVDVTIGGQTIKAGESVACSLLAANRVPAPG
EPADRFDITREPATHMAFGHGIHHCLGAPLARMELRIAFPALLRRFPDLRLAVPHER
VRFRPARSRQYALESLPVAW-

SEQ ID NO: 66 (coding sequence of sriC31)
P450 sriC31: SRIM_26287
*ATGTTGATGCCGCTGCGGCGTCAGGGGCTGGACCCGGTGGGCGAGCTGGCG*
*ACGGTGCGCGAGCAGGAGCCCATCTCCAAGCTGCCGGTGCCGATCGCCGCCA*
*ATGTGTGGCTCGTCACCGGGTACGACGAGGTCAAGGCGGTACTGGCAAGGC*
*CAACGCCTTCAGCTCGGACTTCACCAACCTCATCGGCCAGGCCGGTGCCAGC*
*ACCGACCAGAACCCCGGCGGCCTCGGATTCGCCGACCCGCCGGTGCACACC*
*CGGCTGCGCCGTCTGCTGACCCCCGAATTCACCATGCGCCGGCTCGGGCGGC*
*TCACGCCCCGTATCCACGAGATCGTGGAGGAGCGGCTGGACGCCATGGAGAA*
*GGCCGGCAGCTCCGGCGAGCCGGTCGACATCGTGGAAACCTTTGCGCTGCCG*
*ATTCCGTCCTTGGTCATTTGCGAACTGCTCGGTGTGCCGTACGAGGACCGCGC*
*GGACTTCGAGCGGCTGAGCGCCGCGCGCTTCGACCTCTTCAGCGGCGCCAAC*
*GCGTCCTTCGGCGCCATATCGGAATCGCTCGCCTATTTCCGTGAGGTGGTCAA*
*GAAGCAGCGGCAGAACCCGGGCGACGGCCTGCTCGGCATGATCGTCAAGGAA*
*CACGGCGACTCGGTCAGCGACGAGGAGCTGGCGGGCCTGGCCGACGGCGTG*
*CTGACCGGCGGCTTCGAGACCACCGCGAGCATGCTGGCGCTGGGCGCCCTG*
*GTCCTCCTCCAGGACCCCGAGCACTTCGCCGCCCTCAAGGACGGCGACGAGG*
*CGGCCGAGCGCTACGTCGAGGAGCTGCTGCGCTACCTCACCGTCGTCCAGGT*
*CGCCTTCCCCCGCTTCGCGCGCGAGGACATGGAGATCGCCGGTGTGCCGATC*
*GCCAAGGGCGACGTGGTGCTGTGCTCGCTCAGCGGCGCCGACCGGGACGGC*
*AAGCTCGGTCCCGACATGGAGCGCTTCGACCCGTCCCGCAACGTTCCCTCGC*
*ACCTGGCCTTCGGCTACGGCATACACCGCTGCGTCGGCGCCGAGCTGGCCCG*
*TATGGAGCTGCGCGCCGCCTACCCCGCGCTGGTACGGCGGTTCCCGAACATG*
*CGGCTCGCGGTGGAGCCGGACGCGCTGGAATTCCGCAAGCTGTCGATCGTGT*
*ACGGAATCGAGTCGCTGCCGGTGCACCTCGGCGGCTAA*
Legend
*P450 (italics)*
Start and stop codons in bold

Figure 4 (continued)

Protein sequence
(Translated using Expasy from DNA sequences above)

SEQ ID NO: 67 (amino acid sequence of cytochrome SriC31 (392 aa))
MLMPLRRQGLDPVGELATVREQEPISKLPVPIAANVWLVTGYDEVKAVLGKANAFS
SDFTNLIGQAGASTDQNPGGLGFADPPVHTRLRRLLTPEFTMRRLGRLTPRIHEIV
EERLDAMEKAGSSGEPVDIVETFALPIPSLVICELLGVPYEDRADFERLSAARFDLF
SGANASFGAISESLAYFREVVKKQRQNPGDGLLGMIVKEHGDSVSDEELAGLADG
VLTGGFETTASMLALGALVLLQDPEHFAALKDGDEAAERYVEELLRYLTVVQVAFP
RFAREDMEIAGVPIAKGDVVLCSLSGADRDGKLGPDMERFDPSRNVPSHLAFGYG
IHRCVGAELARMELRAAYPALVRRFPNMRLAVEPDALEFRKLSIVYGIESLPVHLGG
-

SEQ ID NO: 68 (coding sequence of sriC32)
P450 sriC32: SRIM_08623
*ATG**CTCGGCGACGCCCGGTTCAGCTCCGACCGCTCGCACCCGGACTTCCCGT*
*GGATGCGCGTCGGCGAGACCGTTTTCCCCGGCTTCAGGCCCTCGCTGATCGA*
*GATGGACCCGCCCGAGCACGGCCCCGCCCGTCGTGCGGTCGCCGGCGAGTT*
*CACCATCCACCGCATGCGGGAGCTGCGCCCCAAGATTCAGCGCATTGTTGAC*
*GGTCTGCTCGACGATGTGCTGGCCGGTGCCAAGCCCGCCGACCTGGTGTCCG*
*CGCTGGCCGTGCCGCTGTCCGGTCTGGTGCTGTGTGAGCTGCTCGGGATCCC*
*GACCGGTTACCGGGAGGAGCTCACCACCAACACCGCGGTGTTGGTGGCCCAC*
*GACTCCGCTGATGCGGATCGCGCCGAGTCCTTCCGCTCCCTGAGCGAGTATTT*
*CGACGCGCTGTGTGCCACGAAGATGACCGAGCGGCCCGGGGACCTGCTGGG*
*CAGGCTGGCGGGCCACCGGCTCTTCAGCGGTGACGAGAGTCGCTGGGCCAT*
*GGTCGAACTGTGCATACTCCTGGTCGTCGCGGGCCTGGAGACCACCGCCACG*
*ATGACCGCACTCGGAATCCTGGCTCTCCTCGAACACCCCGGCCAGCTCGCCC*
*TCCTCACCGCCGACCCGGGCCTGACCCCGGGAGCGGTGGATGAATTGCTGAG*
*GTTCTTCTCCATTGCCGAGCTGTCCCTGATGCGCCGCGCCACGGCGGACGTT*
*GAGATCGGCGGCACTCTGGTACGTACGGGTGAGGGCGTCGCCGCCCTGTCC*
*GCCGCCGCCAACCGCGACCCCGCGGTCTTCGCCGACCCGGACACGTTCGATG*
*TCACCAGGGACAACCGCAGGCATCTGGCTTTCGGTTCGGGACCGCACCAGTG*
*CCTCGGCAAGAACCTGGCCCGGATGGAGCTGCGCATCGTTCTCGATACCCTG*
*TTCCGGCGCATCCCCACTCTCCGCCTGGCCACGCCACGCGACGAATTGCGCT*
*TCGTCAACGGCTCCGGGTTCTCGGTATCGGCACTCCCGGTCACTTGG**TAA*
Legend
*P450 (italics)*
Start and stop codons in bold

Protein sequence
(Translated using Expasy from DNA sequences above)

SEQ ID NO: 69 (amino acid sequence of cytochrome SriC32 (344 aa))
MLGDARFSSDRSHPDFPWMRVGETVFPGFRPSLIEMDPPEHGPARRAVAGEFTIH
RMRELRPKIQRIVDGLLDDVLAGAKPADLVSALAVPLSGLVLCELLGIPTGYREELT
TNTAVLVAHDSADADRAESFRSLSEYFDALCATKMTERPGDLLGRLAGHRLFSGD
ESRWAMVELCILLVVAGLETTATMTALGILALLEHPGQLALLTADPGLTPGAVDELL
RFFSIAELSLMRRATADVEIGGTLVRTGEGVAALSAAANRDPAVFADPDTFDVTRD
NRRHLAFGSGPHQCLGKNLARMELRIVLDTLFRRIPTLRLATPRDELRFVNGSGFS
VSALPVTW-

SEQ ID NO: 70 (coding sequence of sriC33)
P450 sriC33: SRIM_23746

Figure 4 (continued)

*ATG**GACACACACCCCGAACCCATCGATTACCCTTTTCCGAGCCGTCCGGGCT
CACCGTCGATCCGGAATACGAGGACTGCCGCAGCCGCCCCGGCCTGACGTGG
ATCCGGCCGCCGTACGGTGACCACGCCTGGCTGGTGACGCGCTACGCGGACA
TCCGCTTCGTCCTGCGGGACCGGCGGTTCGTCCGCACGCCCCCGCCGGGCA
GCGACGAGGCGCGGCTGACCCCGCTGCCGCTGCAGGACAGCATCCTGAACA
CCGATCCGCCCCAGCAGCCCCGCCTGCGCAAGGCCCTCGCCCAGGGCCTCA
AGTTCAACGCCGAGCACGTCCGTGAGCTGGAGGAACTGGCCACCGGGGAGG
CGCGGCGGCTGCTGGCCCGCTGCACGGCGGAGCCGCCCCCGGCCGATCTGG
CCGCCGCGTACACCAAGCCGCTCACCGTGGCCATCCTCTGCCCGCTGATCGG
CATCCCCGAAGAGGACCTGGCGGTCTTCCTCGACTGGTTCGAGGGGTTCGCG
GGCACCGGCCTGCCCGCCGACGTGGTGGAGTCGCGTATCGAGGAGATCTCCC
GCTACACGGCCCGGCTCATCGCCGACCGCCGGCAGCGGCCGCGGGAGGACC
TGGTCAGCCGCCTGGTGGCCCGGCTGGGCCAGGACGACGGGCTGTCGATGG
AGGAGCTGGGCGAGCTGGTCAACGACATCCTGCTCGCCGTCGACAACGTCAC
CACCCAGCTCACCAACGCCTGTTACGTGCTGCTCTCCTCCCCCGCCCACTTCC
GGGAGCTGGCGGCCGACCCGGACCTGCTGCCGCGGGCGGCCGACGAGCTG
CTGCGCTACGCGCCGTTCCCCTCGCACGTCACCTTCGCCCGGTACGCCACCG
AGGACGTGGAGGTCGGCGGCACCCTCGTACGGGCCGGTGAGCAGGTGCTGC
CCGCGCTGCCGGCCGGCAACCACGACCCGCGGATGTTCGCCGAGCCGGAGC
GGCTGGACTTCCACCGCGGCGGCAACCCGCATCTGTCCTTCGGCCACGGCAC
CCATCACTGCATGGGGCCGCCGCTGGTGCGGATGCTGGTGAAGGTGGCCGTG
GCCGCCCTGCTCGGCCACCCCGGCCTGCGGCTGGCCGCGCCGGACGAGGAG
CTGCCGTGGCGCGCCGACCTGATCATCCGGCGGATCGAGGAGCTGCCGGTCA
CCTGG**TAA*

Legend

*P450 (italics)*

Start and stop codons in bold

Protein sequence

(Translated using Expasy from DNA sequences above)

SEQ ID NO: 71 (amino acid sequence of cytochrome SriC33 (397 aa))

MDTHPEPIDYPFSEPSGLTVDPEYEDCRSRPGLTWIRPPYGDHAWLVTRYADIRFV
LRDRRFVRTPPPGSDEARLTPLPLQDSILNTDPPQQPRLRKALAQGLKFNAEHVRE
LEELATGEARRLLARCTAEPPPADLAAAYTKPLTVAILCPLIGIPEEDLAVFLDWFEG
FAGTGLPADVVESRIEEISRYTARLIADRRQRPREDLVSRLVARLGQDDGLSMEEL
GELVNDILLAVDNVTTQLTNACYVLLSSPAHFRELAADPDLLPRAADELLRYAPFPS
HVTFARYATEDVEVGGTLVRAGEQVLPALPAGNHDPRMFAEPERLDFHRGGNPH
LSFGHGTHHCMGPPLVRMLVKVAVAALLGHPGLRLAAPDEELPWRADLIIRRIEEL
PVTW-

SEQ ID NO: 72 (coding sequence of sriC34)

P450 sriC34: SRIM_09156

*ATG**ACGCAGCCGGACACCAGGACGAACCAGCCGGACACCGGGCCGGGCCGG
CCCGAGCAGATACCCGCCCACCTGCGGCGGGACCGTTTCGACCCGGTTCCCG
AACTCCGGCGGCAGGTCCGGGAGGCGCCGCTCGTGGTGGCCGACGTCGAAT
TCGGGCTCTTCGGCCGGGTGAAGTGGGTGGCCACCGGCGAGGCCGAAATCC
GGGAGGTGCTGGGCGACCTGAAACGTTTCAGCTCCCGGCTGCCCGACGACGG
CCAGGACACGTCCGGGGCCCGCGCCGCACCCGGCAACCTCCTGCAGTGCGA
CCCACCCGACCACACCCGCCTCCGGCGCATGGTGGCACCGGAATTCACGGCG
CGGCGGACCCGGCGGCTGGAACCGCGCATCACCGCGATCGTCGAAGAGTGC
CTGGACATCATGGAGCGCGTCGGACCGCCGACCGACTTCATGCGAAACTTCG
CCTGGCCCGTGGCAGGGCTGATCACCTGCGAGCTGCTGGGCATTCCCCGCGA*

Figure 4 (continued)

*CGACCGGGCGGAACTGTCCCGCTATCTCGACATCGCCCAGGACGAATCCGCG
CCCCCGGAACAGCAGACGGCCGTCGGCAAGGCGTACTGGGCCTATATGGTGC
GGCTCGCCAAACGGCAGCGCCGCAGCCCCGGCGACGGCCTCTTCGGCCACG
TGGTGCGCGAGCACGGCGCGGACATCGGCGACGACGAACTGGCGGGTGTCG
GCGCGACCTTCGTCTCCGACGGCTTCCTCCAGGTCTCCAGCATGCTGGGGCT
GGGCGCGCTGGCGCTGCTGGACCACCCCGGCCAGCTGCGGCTGCTGCGGGA
ACGGCCGGAGCTGATCGACCGGGCCGTGGAAGAACTGCTGCGCTACGTCACC
GTCATCCACACCGTCTCGCCCCGCACCGCCCTGGAGGACGTGACCATCGGGA
ACCAGGTGATCAAGGCGGGCGAGATGGTCGCCTGCTCGCTGTTCGCCGTCAA
CCGGGCGCAGGGCGGACCGGGGGCGGACGCGTTCGACATCACCCGCGAGTC
CGCCCCGCACCTGGCCTTCGGCCACGGCATGCACCACTGCGTCGCCGCGCC
GCTGGTCAAGCTGGAGATGCGCATCGCCTACCCGGCACTGCTGCGCCGGTTC
CCCGGGCTGCGGCCCGCGGTGGCGCCGGACGGCATCCGCTTCCGGTCCGCG
CAGACGCGGCAGTTCAGCCTGGACGCGCTGCCCGTCGCCTGG*TAA*

Legend

*P450 (italics)*

Start and stop codons in bold

Protein sequence

(Translated using Expasy from DNA sequences above)

SEQ ID NO: 73 (amino acid sequence of cytochrome SriC34 (409 aa))

MTQPDTRTNQPDTGPGRPEQIPAHLRRDRFDPVPELRRQVREAPLVVADVEFGLF
GRVKWVATGEAEIREVLGDLKRFSSRLPDDGQDTSGARAAPGNLLQCDPPDHTR
LRRMVAPEFTARRTRRLEPRITAIVEECLDIMERVGPPTDFMRNFAWPVAGLITCEL
LGIPRDDRAELSRYLDIAQDESAPPEQQTAVGKAYWAYMVRLAKRQRRSPGDGLF
GHVVREHGADIGDDELAGVGATFVSDGFLQVSSMLGLGALALLDHPGQLRLLRER
PELIDRAVEELLRYVTVIHTVSPRTALEDVTIGNQVIKAGEMVACSLFAVNRAQGGP
GADAFDITRESAPHLAFGHGMHHCVAAPLVKLEMRIAYPALLRRFPGLRPAVAPDG
IRFRSAQTRQFSLDALPVAW-

SEQ ID NO: 74 (coding sequence of sriC35)

P450 sriC35: SRIM_29141

*ATG**CCGGACGCCGGACGTCTCCCTCGATACCCTTTCGCCTTCCGGGGCGACCAGCTCGCGCCCGAGC
TGGCCGCATCGGTGGTCCACCGCCCGATCCAGCGCGTACGGACCAACACCGGTACCGACGCCTGGC
TGGTGACCGGCCACGAGCTGGTGCGCTCGGTGCTCCGGGACCGCCGCTTCAGCCTCACCCTCACCTC
CGACCCCTGGATGCCCCGGCAGGACCCCCTCATCCCACCGCTCTCGGTCACCGACATCCGCACCCAGT
GCGAGAACGCGGGCCTCCTCCAGGACCTCTTCCAAGGCGTGGGACCGCACCAGCGGTACCTGACAC
CGGGCCGCGTCCGGGAGATCGCCGACGGGCTGCTGGACACCTTCCTGGCCGGAGAGCAACCCGGC
GACCTGATGGACGGGTTCATCATGCCGCTCTCCCGCGCGCTCACCATGGAACTGCTGGGCCTGGACC
CGGAAGGCTGCCCGGACAACGCCGAAATCTTCAACATCTTCCGTACCGGCCCGGAAAGCATGCAGG
GCGTGCCGGAGAGCTGGAACCTGGCCCTTACGTGGATGCTCGGACGGCTTCCCGGGCTGCGCGCGT
CCGGCGCAGGGCTGCTGGGCCGCCTCATCACCCTCAGCGACGCGTCCGGCGTACTGAGCGAGGAG
GAGGTCGCCGACCTCTTCGTCTTCCTCCTCATCTCCCAGTTCGGCAACCCCGCCACCTTCCTCGGCGC
GGCGACCGTGGGGCTGATGCAGCACCCGGAGGTGACGGCCCGGCTGCGGAAGGACCCCGGGCTG
CTGCCACGGGCCGTCGACGAGCTGCTGCGCTGGACGGTCTTCCTGGGCGACGCACTGCCCCGCAAC
GCGCGCGAGGACGTGCTGCTGGACGGCGTTCTCGTACGGGAGGGCGACCTCGTGCTGGTGTCCACC
GACGCGGCCAACCGCGACCCGCGGGTCTTCCCCGACCCGCACCGCCTCGACATCGACCGGGAGCCC
GGCCCGCACCTGCGGTTCAGCGACGGGCGGCACCGCTGTCCGGGCGGCCCGGTCTCCCGCATGCAG
GCCGCGGAGACGCTGCGCGTACTGCTGGGGCGGACCGCCGATCTGCGCCTGGCCGTGCCCGCCGAC
GAGATCGAATGGCACCGCTACTACGCGGTCACACTGCCGGTGGCGGTGCCGGTCAACTGGACGCTC*

Figure 4 (continued)

*CCCGGAGCGGCCACTCCCGGGACCGGCGACGGTAAGCCCCGCGGAGCGGCCGTTCCCAGGCCCGA*
*TGGCGGGACGCTCACTCCG*TAA

Legend
*P450 (italics)*
Start and stop codons in bold

Protein sequence
(Translated using Expasy from DNA sequences above)

SEQ ID NO: 75 (amino acid sequence of cytochrome SriC35 (425 aa))
MPDAGRLPRYPFAFRGDQLAPELAASVVHRPIQRVRTNTGTDAWLVTGHELVRSV
LRDRRFSLTLTSDPWMPRQDPLIPPLSVTDIRTQCENAGLLQDLFQGVGPHQRYLT
PGRVREIADGLLDTFLAGEQPGDLMDGFIMPLSRALTMELLGLDPEGCPDNAEIFNI
FRTGPESMQGVPESWNLALTWMLGRLPGLRASGAGLLGRLITLSDASGVLSEEEV
ADLFVFLLISQFGNPATFLGAATVGLMQHPEVTARLRKDPGLLPRAVDELLRWTVF
LGDALPRNAREDVLLDGVLVREGDLVLVSTDAANRDPRVFPDPHRLDIDREPGPH
LRFSDGRHRCPGGPVSRMQAAETLRVLLGRTADLRLAVPADEIEWHRYYAVTLPV
AVPVNWTLPGAATPGTGDGKPRGAAVPRPDGGTLTP-

SEQ ID NO: 76 (coding sequence of sriC36)
P450 sriC36: SRIM_10261
*ATG**GAGTCACCGGAGTTCTTCCGCGACCCGTACCCGCTGCTCGCCGCGCTGC*
*GCGAGCGCGGTCCCGTCCAGCAGGTACGGTCCGGGCCGCACGGCGCGACGT*
*GGCTCGTCACCGGCTGGGCCGAGGCCCGTACGGCGCTGGCGGAGCCCCGGC*
*TCTCCAAGGACACCACCCGCTACTTCGCCGACAAGCCGTCCAAGCGCAACCTG*
*GCGCCCGCCGTCAGCGCCACCATGCTGGCCACCGACCCGCCGGACCACACC*
*CGGCTGCGCCGGCTGGCCGTCAAGGCGTTCACGCCGGCGGCGGTGGCCCGC*
*CTGGAGCCGCGGGTGGCGGAGATCGCGGACGGTCTGCTGGACCGGATGGCC*
*GACGGCGGCGATTCGGCCGATCTCGTCGAGGACTTCGCCGTACCGCTGCCCA*
*TCGAGGTCATCGGCGACCTGCTCGGCGTTCCCCGCGAGGACCGCCCGGCGC*
*TGCGCCGCTGGTCCAACGACCTCTTCGCGGCCGGCGCGCCGGACAGCATCGA*
*CGCGGCCTCGCACGCCATCAGCGACTACATGACGGAGCTGATCGCGAAGAAG*
*CGCGCCGAAGGTACCGGGGCCGATCTGCTCACCGAGCTGATCGCCGCGCGC*
*GACGAGGGCGACCGGCTCAGCGAGTTCGAACTGGTCTCGCTGGCCGTCCTGC*
*TGGTCGTCGCCGGGCACGAGACGACCACCAACCTGATCGGCAACGGCGCGCT*
*CGCGCTCCTCCGGGACGACGCGCTCCGTACCCGCCTGCGGCAGGACCCGGC*
*GCTCATCCCGGACGCCGTGGAGGAACTGCTCCGCTATGACTCCCCGATCACC*
*ACGGCCACGTTCCGGTACGCGGCCGAACCGCTCACCCTCGGCGGCGCCGAG*
*ATCGCGGCGGGCGATGTCGTCCTGGTCTCCCCGGGCGCCGCCAACCGTGAC*
*CCGGCCCGGTTCCCCGACCCGGACACGGTCACCCCCGGCCGTTCCGCCGGG*
*CATCTCTCCTTCGGCCACGGTCCGCACCACTGCCTGGGCGCGCCCCTGGCCC*
*GCCTGGAAGCCCGTATCGCCTTCCGAGCGCTGCTCACCCGCTTCCCCGGCCT*
*GCGGCTGGCCGTCCCGCCCGGCGAACTCCCGTGGCGCCACACCCGCCTGAT*
*GCGCGGTCTGTCGCACCTCCCGGTCACCTGGTCCGCACAGGTCACGGATTGT*
*TAA*

Legend
*P450 (italics)*
Start and stop codons in bold

Protein sequence
(Translated using Expasy from DNA sequences above)

Figure 4 (continued)

SEQ ID NO: 77 (amino acid sequence of cytochrome SriC36 (395 aa))
MESPEFFRDPYPLLAALRERGPVQQVRSGPHGATWLVTGWAEARTALAEPRLSK
DTTRYFADKPSKRNLAPAVSATMLATDPPDHTRLRRLAVKAFTPAAVARLEPRVAE
IADGLLDRMADGGDSADLVEDFAVPLPIEVIGDLLGVPREDRPALRRWSNDLFAAG
APDSIDAASHAISDYMTELIAKKRAEGTGADLLTELIAARDEGDRLSEFELVSLAVLL
VVAGHETTTNLIGNGALALLRDDALRTRLRQDPALIPDAVEELLRYDSPITTATFRYA
AEPLTLGGAEIAAGDVVLVSPGAANRDPARFPDPDTVTPGRSAGHLSFGHGPHHC
LGAPLARLEARIAFRALLTRFPGLRLAVPPGELPWRHTRLMRGLSHLPVTWSAQVT
DC-

SEQ ID NO: 78 (coding sequence of sriC37)
P450 sriC37: SRIM_03326
*ATG**AAGTCGTCCGCGACGCGGTCCGGGGCCGGCGGACACGCCCGTACCCCGTGCGATGCCGCGGC*
*CCGCGCCCACTCCAGCGGCCCGCTGGATCTCTTGCGCGCCGAGTTCGACGGCGTGCACGACGTGTG*
*GCGCTCGGCCTCGGGAATGGTGTACGTGGCCGGCCCGGAGGCGGCGCGGGCGGTGCTGGGCAACC*
*GGCCGGCCATCGTGGCCGAGACGTCCGACTTCTACCGGACCCGGCACGGCGTCTTCGGGCCGCGGG*
*CCGCGCAGGCGGAGATCGGCCGTGCGGCCCGCGCCCTGATGCACCACCACCTCGACGCCCGGCGGT*
*CGCAGCTGCCCCGGCTGATCCACGAGCGCCTCGCGCCCCGCAGTTCCTGGCCGGACGCGGGGAACC*
*TGCTGGTCCACGAGCACCTGGCGGATGTCCTGCTGCACCCGGGCGCGCCGATCTCCCTGCGTACGAC*
*GGTCGGCAAGGTCGTCACCCGCGCCGTGCTGGCGGGTGCCCGCAGGCGCCACGCACCGCCGTCCAG*
*GCTCCTCCTCCGCCACCGCGCGTCCGCCGCGCTGCAGGCCGAGATACGCGCCCGGCAGCACCGGCG*
*ACAGCACCACGGCGGCAGCGCCGGCCCCCGCGACCTGCTCGATGTCGTGGTGGACGGCTGCGGTCC*
*CGCGACGGCATCCGACGATCTCGCCGAGGTCTACCTGTCTTTCCTGTTCGCCGCGGTGGGCTCCATC*
*GGCTTCGCCCTCGGATGGTCGGTCCACCTTCTCGGCACCCATCCCGGCTGCCCGGCGGCACCGGACC*
*GGATCGTGCGCGAGGCCCTGCGCCTGTGGCCGGTGGCCTGGCTGTTCGCCCGTACGCCGCTGCGGG*
*CCGTGGAGCTCGGCGGGATGACGGTGACACCCGAGGACCAGCTCGCCGTGTGCACCTACCTGGTGC*
*ACCGGCATCCCGCGTACTGGGAGCGACCCGACGAGTTCCTCCCGCAGCGCTGGGCGGCACCCGTCT*
*CCCGGGCCGCCTACCTCCCCTTCGGGCACGGGCCGCACACCTGCGCCGGAGCGACCGTCACCCTGCA*
*ACTCCTCAAGGACATCGTCGGCCTGCTCATCCATGACTGGCGGCTGTCGGTCATCCACGACGGCGGC*
*GGTCCTCAGGTGGGCCCGGCGCTGGCTCCGCCGCGCTTCACCGCGGTGCTGAGCCCACGTGCCAAC*
*AGCTCCGGAAGGAGG**TAA*

Legend
*P450 (italics)*
Start and stop codons in bold

Protein sequence
(Translated using Expasy from DNA sequences above)

SEQ ID NO: 79 (amino acid sequence of cytochrome SriC37 (402 aa))
MKSSATRSGAGGHARTPCDAAARAHSSGPLDLLRAEFDGVHDVWRSASGMVYV
AGPEAARAVLGNRPAIVAETSDFYRTRHGVFGPRAAQAEIGRAARALMHHHLDAR
RSQLPRLIHERLAPRSSWPDAGNLLVHEHLADVLLHPGAPISLRTTVGKVVTRAVL
AGARRRHAPPSRLLLRHRASAALQAEIRARQHRRQHHGGSAGPRDLLDVVVDGC
GPATASDDLAEVYLSFLFAAVGSIGFALGWSVHLLGTHPGCPAAPDRIVREALRLW
PVAWLFARTPLRAVELGGMTVTPEDQLAVCTYLVHRHPAYWERPDEFLPQRWAA
PVSRAAYLPFGHGPHTCAGATVTLQLLKDIVGLLIHDWRLSVIHDGGGPQVGPALA
PPRFTAVLSPRANSSGRR-

SEQ ID NO: 80 (coding sequence of sriC38)
P450 sriC38: SRIM_04368
*ATG**CGCCCACCCCGCCTACCCGAACCGCTCCCCCTCTACGGGGAGGACTACA*
*AGCGCGACCCGTACCCCCTGTACGCCGAGCTGCGCGAGCGCGGCCCCGTCC*

Figure 4 (continued)

*ACCGGGTCAGGTTCCCGAGCGGCGTGCACGCCTGGCTCGTCACCGGATACGA
GGCCGCTCACCGGGCGCTGAACGATCCCCGGCTGGGCAAGCACCACTCCCG
CGGCAACGCCGCCTGGCGCGCCCGTGCCTCGATCATGCCCGAGCCGCAGCA
TTCGCGGCTCCAGGTCCACCTGCTGCACCAGGACCCGCCCCGGCACACCGCC
ATGCGGCGCCTGATCACCGACGCCTTCGCACCCAGGCGGATCGCCGGACTCC
GGCCGCGGTTCGAGCGCTTGGCGGAGGCGCTGTTGGATGAACTGCCGCCCG
CAGGGCCGAGCGGCGAAGGCGGTCCGGAGCGGGGCGCCCGCGCCGACCTG
GTCGCCTCGTTCGCGGCGCGCTTCCCCTTCCTCGTGCTCGCCGAGGTCATCG
GCCTGCCGGACGCGTTCACCGCGCGCTTCGACCGCGACTGGGGCAAGGTCG
TCCAGCCCGTCGGCCCGGACGATCCCGGCCGTCCGGCGTACGAGGCCCGGC
TGCGCGGCTTGCAGGGCTATATCGCCGACCTCGTACAACACAAGCGGCGGGA
ACGCGGCACCGACCTGCTCTCCCGTCTGGTCACCGCCCGCGACGCCGGGGA
ACTGGACGATGCCGAGCTGGACTCCATGATCTTCCAACTCCTCGTCGCCGGAC
AGGAACCCGTCACCAACCAGATCACCACAGCGCTGACCGCCCTGCTCCGGCA
CCCGGAACACCTCGCGCGGCTGCGCGACGACCCCGCGCTCCTCCCCCGCGC
GGTGGAGGAACTGCTCCGCTACGACAGTGCTTTCGAGCTGACGACCTGGCGG
TTCCTCGCGGCGGACGCGGACGTGTCGGGCACGCGGATTCCGGCCGGCGAC
TCCGTGATCGTCTCGCTGTGCGCGGCCAACCGCGACCCCGCCCGCTTCCCCG
CCCCCGACACGCTCGACTTCGACCGTACGCCCAACCCGCATCTCGCCTTCGG
CCACGGCATCCACTTCTGCCCGGGCGCCACGCTCGCCCGTACCGAACTGCAC
ATCGCTCTGGAAACGCTGCTCCGCCGCCTGCCGGGCCTGCGCCTGGCCGTGC
CGGATGCCGACTTGAGGTGGATACCGGCGGTGCTGGCGCGCGGGGTGGATG
AGCTTCCGGTCTCGTACGGGGCGGTTGGCGGGGCTGCGGGCAGCGATGGCG
GGGTGGGTACAGAACCGGCCGGATCGGGTACAGAACCGGCCGGTACTCCTGC
GGGCAGAGGCGGCGGGTCGGGTACAGAACCCGCCGGACCGCCTCCGTACGC
CTGCCCCTTCAGCGGCTCTGCCGGAGAGGCCGCCACCCGA*_TAA_

Legend
*P450 (italics)*
Start and stop codons in bold

Protein sequence
(Translated using Expasy from DNA sequences above)

SEQ ID NO: 81 (amino acid sequence of cytochrome SriC38 (477 aa))
MRPPRLPEPLPLYGEDYKRDPYPLYAELRERGPVHRVRFPSGVHAWLVTGYEAA
HRALNDPRLGKHHSRGNAAWRARASIMPEPQHSRLQVHLLHQDPPRHTAMRRLI
TDAFAPRRIAGLRPRFERLAEALLDELPPAGPSGEGGPERGARADLVASFAARFPF
LVLAEVIGLPDAFTARFDRDWGKVVQPVGPDDPGRPAYEARLRGLQGYIADLVQH
KRRERGTDLLSRLVTARDAGELDDAELDSMIFQLLVAGQEPVTNQITTALTALLRHP
EHLARLRDDPALLPRAVEELLRYDSAFELTTWRFLAADADVSGTRIPAGDSVIVSLC
AANRDPARFPAPDTLDFDRTPNPHLAFGHGIHFCPGATLARTELHIALETLLRRLPG
LRLAVPDADLRWIPAVLARGVDELPVSYGAVGGAAGSDGGVGTEPAGSGTEPAG
TPAGRGGGSGTEPAGPPPYACPFSGSAGEAATR-

SEQ ID NO: 82 (coding sequence of sriC39)
P450 sriC39: SRIM_32206
_ATG_*GAAGGAGTCCAGGCAGTCTTCGATCCCTGGTCGCCGGATTTCGTCGCCG
ACCCGTATCCCGCCTACGCCGAGCTGCGCGCCCGCGGCCGGGTGCACTATTT
CGCGCCCTCCAACCAGTGGCTCGTCCCGCGCCACGCGGACGTCGCGGCGCT
GCTCCGCGACCGCCGGCTGGGCCGTACGTACCGGCACCGCTTCACGCACGA
GGAGTTCGGCCGTACCGCTCCGCCACCCGAGCACGAGCCGTTCCACGTGCTC
AACGACAACGGCATGCTCGACCTGGAGGCGCCCGCCCACACCCGCATCCGCC
GTCTGGTCTCGAAGGCGTTCACCGCCCGTACGGTCGAGCGGCTGCGGCCCTA*

Figure 4 (continued)

*CGTCGAAGCCCTGGCGGACCGGCTGGCCGCGGATCTGGTCGCGGACGGCGG*
*CGGGGACCTGGTGGCGCGGGTCGCGGAGCCGCTGCCCGTCGCGGTGATCGC*
*CGAAATGCTCGGCATCCCCGAGGCCGACCGGCATGCGCTGCGCCCCTGGTCG*
*GCCGCCATCTGCGGCATGTACGAGCTGAACCCGCCGGAGGAGACGGCCCGG*
*CGCGCGGTGGCCGCTTCGCTGGAATTCTCCGGCTACCTGCGGGAATTGATCG*
*CCGCTCGGCGCAGTGCGCCGGGGGACGACCTGATCTCCGGGCTGATCGCCG*
*CGTACGACGAGGGCGAGTCGCTGAGCGAACAGGAGATGATCTCGACCTGTGT*
*CCTGCTGCTGAACGCGGGCCACGAGGCCACTGTCAACGCGACGGCCAACGG*
*CTGGTACGCGCTCTTCCGCCACCCGGAGCAGTTGGCGGCCCTGCGCGCGGC*
*CCCGGCCGCGCTGCTGCCCACCGCCGTGGAGGAGTTGCTGCGCCACGACAC*
*GCCGCTCCAGCTCTTCGAACGCTGGGTGCTGGACGACATCGAGATCGGCGGT*
*ACGGTCGTGCCGCGCGGCAGCGAGATCGCGCTACTCTTCGGCTCGGCCAACC*
*ACGACCCGGCAGCCTTCGACCACCCCGAACGGCTCGACCTCGCCCGTAAGGA*
*CAACCCGCACATCTCCTTCAGCGCCGGTATCCACTACTGCATCGGCGCGCCCC*
*TGGCCCGTATCGAACTGGCCGCCTCGCTGGCGGCGTTGCTCCGCCGGGCCC*
*CTGACCTGCGCCTGGCCGCCACTCCGGAACGCAAGCCGAACTTCGTGATCCG*
*AGGACTGCGCGAGCTGCTGGTCGCGGTG**TAA*

Legend

*P450 (italics)*

Start and stop codons in bold

Protein sequence

(Translated using Expasy from DNA sequences above)

SEQ ID NO: 83 (amino acid sequence of cytochrome SriC39 (405 aa))

MEGVQAVFDPWSPDFVADPYPAYAELRARGRVHYFAPSNQWLVPRHADVAALLR
DRRLGRTYRHRFTHEEFGRTAPPPEHEPFHVLNDNGMLDLEAPAHTRIRRLVSKA
FTARTVERLRPYVEALADRLAADLVADGGGDLVARVAEPLPVAVIAEMLGIPEADR
HALRPWSAAICGMYELNPPEETARRAVAASLEFSGYLRELIAARRSAPGDDLISGLI
AAYDEGESLSEQEMISTCVLLLNAGHEATVNATANGWYALFRHPEQLAALRAAPA
ALLPTAVEELLRHDTPLQLFERWVLDDIEIGGTVVPRGSEIALLFGSANHDPAAFDH
PERLDLARKDNPHISFSAGIHYCIGAPLARIELAASLAALLRRAPDLRLAATPERKPN
FVIRGLRELLVAV-

SEQ ID NO: 84 (coding sequence of sriC40-sriF07-sriFR02)

P450 sriC40: SRIM_03496

Ferredoxin sriF07: SRIM_03491

Ferredoxin reductase sriFR02: SRIM_03491

ATGCAGATCGTCGTGGACCTCACCCGCTGTCAGGCGTACGCGCAATGCGTCTTCCTCGCGCCGGAG
GTCTTCCGGCTGCCCAGGGAGGAGAGCCTGCTGTACCGCCCGGACGTTCCCGAGGACCAGATGGA
GCGCGTGCGCCAGGCCGCGGCGGCGTGCCCGGTGCAGGCGATCCTGATGGGAGAGGCGGTGAGT
CCCG*GTG*_CCCGG_*TGA*_CCTGCGGGACGGCCGGATCGTCATCGTCGGCGCGTCGCTGGCCGGACTGC_
*GCGCCGCGGAGACGCTGCGCGACGAGGGCTTCACCGGTTCGCTGACCGTGCTGGGCGAGGAGCCG*
*TGGCCGCCGTACGACAGGCCGCCGCTGACCAAGCAGGTGCTCCTCGGCACCGCGGCCCCGGAGAGC*
*ACCGGGCTGCCGATGCGCCGGGACGTGGACGCCGACTGGCGGCTCGGGGTACGCGCCGACGGGCT*
*CGATCCGATCGGCAAGCGTGTGCTGCTGGCCGGCGGCGAGGCGCTGCCGTACGACCGGCTGCTGAT*
*CGCCACCGGTACCCGGGCGCGCCCCTGGCCCCACCCGGAACAGGCCGCTCTGGACGGGGTACTGGC*
*CGTGCGTACCCGCGACGACGCCGCGCATCTGGCCGACCGGCTGGCCGCCGGTCCGCGCCGGGTGCT*
*GGTCATCGGCGGCGGCTTCACCGGCTCGGAGATCGCCTCGGCCTGCCGGGAACGGGACATCGAGG*
*TCACGGTCGCCGAACGCGGCCCCGGACCGCTGGTGGGCGCGCTCGGCGGCACGTTGGCGAAGCTC*
*GCCGCCGGCCTGCAACGGGCCCACGGCGTGGACCTGCGCTGCGGCGTGACGGTCACCGCACTGCGC*
*GGGGACGACAAGGGCCGCTTCACCGGGGCGGATCTCTCCGACGGCAGCCGCATCGACGCGGACGT*

Figure 4 (continued)

GTGCGTCATCGCGTTGGGCGCGGTGCGCAACGTCGAATGGCTGGCGGACTCCGGGCTGGCGGCGG
GCCCCCACGGAGTCGCCTGCGACGCCGGATGCCGTGCCTTCACCCGGTACGGGATCGTCACCGACG
ACGTCTTCGTGGCCGGTGACGTCTCCCGCTTCCCGCATCCGCTCTTCGACTACCAGATGCTCTCCCTG
GAACATTGGGGCAACGCGGTCGCCCAGGCCGAGGTGGCGGCCCACAACATGGTCAGCCCGGGGCC
GCTGCGCCGTCCGCACCTCGGCGTTCCGGTGTTCTGGTCGAACCACTTCGGGATCAGCATCAAGTCC
GTGGGCGTCCCCACCTTCTCCGACCAGGTGGTCGTCGCCCAAGGCTCGGTGGCCGAACGCCGGCTG
GCGGCGGTCTACGGCTACCAGGGCCGCGTCACCGCCGCGGTCACCGTCGACATGGGCAAGTGGCTG
GAGCACTACCAGCGACTGATCGAGACCGCCGCCCCGTTCCCGCCCGCTCCCGGCGCGGCCGACGGC
CACCCGCTGATCAGCGAACTCCCGGTGCCCTCCGACGTACCGGACCCCGCGGGGCTCTCCCACGGCC
CCACCGTCGCGCTCACCGGTCATCTGCCGGACCGCCGGCTCACCGTGCGGCATTCCGGCACCTGACT
CCTCAGCTCTGTTGTCAGTCCCTCCCGTCCGAGGAGCCGTCATGGCCGTCGACACCCTGCTGGAGCG
GATCACCGACTACGCCAGCCGTCCCGACCCCTACCCGCTGTACGCGGAGCTGCGCGAGGCGGGCGT
GGCGCGGCAGACGGACGGCAGCTACCTGATCGGCGGGTATCACGACATCGTCGCGTTGCTGCACG
ACCCGCGGCTCAGTTCCGACCGCCGCAACCGCGCCGCGCCCTACCACGGTCTGCGCGAGGACGAGG
AGACGCTGGTCCCCTTCCTCCGGCTCGACGACCCCGAGCACCACCGGCTGCGCGCGCTGGCCATGCG
GCCGTTCGGGCCACCGCACAGCCCGGGCCGGGTCGACGCGATGCGCGGTGAAATCGCCCGTATCAC
CCGGGAACTGGCCGAGGCGTTCCGCGGCCGTACGCACCTCGACCTCGTCGACGACTTCGCCTACCCG
CTGCCCGTCACCGTGATCTGCCGGCTGCTCGGCGTCCCGCGCGAGGACGAGCCGGTCTTCCGTGACT
GGTCCACCACGATCATCGACGCCTTCGACGTCCGGTCCGGCGAGGACGCCGACAAGCGTCAACGGG
CCGGTGCCCAGGCCCGCACGGAGATGGGCCGCTACCTGGTGGACCTCGCCGAGCGGCGCCGCGGA
CAGCCGGACGACACCATGCTCTCCGCGTTCGTCAACGCCCCGGCCGCGGACGGCGTGCTCATCCGCG
AGGAACTGGCGGCCACCGCAGTCCTGTTGCTGGTCGCCGGACACGAGACCACCGTCAACCTGATCA
CCAACGGCGTACTCACCCTGCTGCGCCACCCCGACCAGCTGGACCGACTCCTGCGGGAGCCGCAGCT
GATGCCCACGGCGGTGGAGGAACTGCTGCGCTACGAGCCACCCGTACACCTGCTACAACGCGTACC
CCTCGCCCACATAGACGTCGCGGGCACAACCCTCCCCAAGGGCGTGCCGGTGGTACTCGCCGTGGC
CTCGGGCAGCCGCGACCCCAGGCGCTTCCAGAACCCCGACCGGTTCGACCCCACCCGCCAGGACAA
CCAGCACCTCGGCTTCGGCAGCGGCATCCACCTCTGCTACGGCGCCCCCCTCGCCCGCATAGAAGCC
CAAACCGCCCTCACGGCACTCCTGCCCCACCTCAGCACAGCAACGCTCACCGAAGACCCACCCCCTTA
CCGCCACAGCGCCCTCCTGCGCGGTCCTCGGCACCTGCCCCTCGATTTGGCGTCGCCTCGAAATAAA
GGGTAA

Legend

*P450 (italics)*

Ferredoxin

*Ferredoxin reductase (italics underlined)*

Start and stop codons in bold

Protein sequence

(Translated using Expasy from DNA sequences above)

SEQ ID NO: 85 (amino acid sequence of cytochrome SriC40 (408 aa))

MAVDTLLERITDYASRPDPYPLYAELREAGVARQTDGSYLIGGYHDIVALLHDPRLS
SDRRNRAAPYHGLREDEETLVPFLRLDDPEHHRLRALAMRPFGPPHSPGRVDAM
RGEIARITRELAEAFRGRTHLDLVDDFAYPLPVTVICRLLGVPREDEPVFRDWSTTII
DAFDVRSGEDADKRQRAGAQARTEMGRYLVDLAERRRGQPDDTMLSAFVNAPA
ADGVLIREELAATAVLLLVAGHETTVNLITNGVLTLLRHPDQLDRLLREPQLMPTAV
EELLRYEPPVHLLQRVPLAHIDVAGTTLPKGVPVVLAVASGSRDPRRFQNPDRFDP
TRQDNQHLGFGSGIHLCYGAPLARIEAQTALTALLPHLSTATLTEDPPPYRHSALLR
GPRHLPLDLASPRNKG-

SEQ ID NO: 86 (amino acid sequence of ferredoxin SriF07 (69 aa))

Figure 4 (continued)

MQIVVDLTRCQAYAQCVFLAPEVFRLPREESLLYRPDVPEDQMERVRQAAAACPV
QAILMGEAVSPGAR-

SEQ ID NO: 87 (amino acid sequence of ferredoxin reductase SriFR02 (458 aa))
VPGDLRDGRIVIVGASLAGLRAAETLRDEGFTGSLTVLGEEPWPPYDRPPLTKQVL
LGTAAPESTGLPMRRDVDADWRLGVRADGLDPIGKRVLLAGGEALPYDRLLIATGT
RARPWPHPEQAALDGVLAVRTRDDAAHLADRLAAGPRRVLVIGGGFTGSEIASAC
RERDIEVTVAERGPGPLVGALGGTLAKLAAGLQRAHGVDLRCGVTVTALRGDDKG
RFTGADLSDGSRIDADVCVIALGAVRNVEWLADSGLAAGPHGVACDAGCRAFTRY
GIVTDDVFVAGDVSRFPHPLFDYQMLSLEHWGNAVAQAEVAAHNMVSPGPLRRP
HLGVPVFWSNHFGISIKSVGVPTFSDQVVVAQGSVAERRLAAVYGYQGRVTAAVT
VDMGKWLEHYQRLIETAAPFPPAPGAADGHPLISELPVPSDVPDPAGLSHGPTVAL
TGHLPDRRLTVRHSGT-

SEQ ID NO: 88 (coding sequence of sriC41)
P450 sriC41: SRIM_38074
*ATG**TCCGGCCACGGACCGGCGGCCGTCCCGCCCTGTCCGGAACTGTTCACGT*
*GGGAGTTCGCCGCCGACCCGTACCCGGCGTACGCCTGGCTGCGCGAGCACG*
*CGCCCGTACACCGCACCCGGCTGCCCAGCGGTGTCGAAGCCTGGCTGGTGAC*
*CCGGTACGCGGACGCGCGGCAGGCGCTCGCCGACACCCGGCTGTCGAAGAA*
*CCCGGTGCACCACAGCGAGGCCGCGCACGGCAAGGGCAAGGTCGGCATCCC*
*CGGCGAGCGGGGCGCCAACCTGATGACGCACCTGCTCAACATCGACCCACCG*
*GACCACACCCGGCTGCGCCGCCTGGTCTCCAAAGCCTTCACCCCGCGCCGCA*
*TCGCCCGGTTCGCGCCGCGCGTACAGGAACTGACCGACGCGCTGATCGACTC*
*CTTCGCGGAGCGCGGCGAGGCCGATCTCATCCACGAGTTCGCCTTCCCGCTC*
*CCCATCTACGCCATCTGCGATCTGCTCGGTGTCCCGCGCGAGGACCAGGACG*
*ACTTCCGCGACTGGGCCGGGATGATGATCCGGCACGGCGGCGGGCCGCGCG*
*GCGGCGTCGCCCGGTCGGTGAAGAAGATGCGCGGCTACCTCGCCGAGCTGAT*
*CCACCGCAAGCGCGAGGCCCTGGGGGAGGAAGGGGCCGACGACCTCATCTC*
*CGGCCTGATCCGCGCCTCCGACCACGGCGAGCACCTGACGGAGAACGAGGC*
*CGCCGCGATGGCCTTCATCCTGCTGTTCGCGGGCTTCGAGACCACCGTCAATC*
*TCATCGGCAACGGCGTGTACCAGCTGCTGCGCCACCCTGACCAGCGCGCACT*
*GCTCCAGAAGGCCGCTGCGGCGGGCGATACGGAGCTGCTCGCCGCCGGGGT*
*CGAGGAGCTGCTGCGCTACGACGGCCCGGTCGAGCTGGCCACCTGGCGCTT*
*CGCGACCCGGGACCTGACCCTGGGCGGGCAGCGCATCGCCGAGGGAGATCC*
*GGTCCTGGTCGTGCTCGCCGCCGCCGACCGCGACCCGCGGCGCTTCGCGGA*
*ACCGGACGTACTGGACCTGCGCCGCCGCGACAATCAGCACCTCGGATACGGC*
*CACGGCATCCACTACTGCCTGGGCGCGCCGCTGGCCCGTCTCGAAGGCCAGG*
*CCGCCATCGCCACGCTGCTGACCCGGCTGCCGGACCTGGCACTCGCCGCCG*
*ACCCGGACGATCTGCGGTGGCGCGGCGGGCTGATCATGCGAGGGCTGCGGG*
*CCCTGCCGGTGGAGTTCACGCCCGTACGGAAG**TAA*
Legend
*P450 (italics)*
Start and stop codons in bold

Protein sequence
(Translated using Expasy from DNA sequences above)

SEQ ID NO: 89 (amino acid sequence of cytochrome SriC41 (423 aa))
MSGHGPAAVPPCPELFTWEFAADPYPAYAWLREHAPVHRTRLPSGVEAWLVTRY
ADARQALADTRLSKNPVHHSEAAHGKGKVGIPGERGANLMTHLLNIDPPDHTRLR
RLVSKAFTPRRIARFAPRVQELTDALIDSFAERGEADLIHEFAFPLPIYAICDLLGVPR

Figure 4 (continued)

EDQDDFRDWAGMMIRHGGGPRGGVARSVKKMRGYLAELIHRKREALGEEGADD
LISGLIRASDHGEHLTENEAAAMAFILLFAGFETTVNLIGNGVYQLLRHPDQRALLQK
AAAAGDTELLAAGVEELLRYDGPVELATWRFATRDLTLGGQRIAEGDPVLVVLAAA
DRDPRRFAEPDVLDLRRRDNQHLGYGHGIHYCLGAPLARLEGQAAIATLLTRLPDL
ALAADPDDLRWRGGLIMRGLRALPVEFTPVRK-

SEQ ID NO: 90 (coding sequence of sriC42)
P450 sriC42: SRIM_27319
*ATG**CCATGCCCCGCGCTGCCCGACGGGTTCGACTTCACCGACCCCGACGTCT*
*ACCAGAGCCGTGTACCGCTGCCCGAGTTCGCGCGGCTGCGGCGTACCACCCC*
*CGTCTGGTGGAACGCCCAGCCGCACGGCATCGCCGGGTTCGGCGACGACGG*
*GTACTGGGTGGTGACCCGCCACGAGGACGTCAAGGAGGTCTCCACCCGGCCG*
*GAGGTCTTCTCGGCGAGCACCAACACCTCGATCATCCGGTTCAACGCGGCCAT*
*GACCCGCGACCGGATCGACGTCCAGAAGCTGATCATGCTGAACATGGACCCG*
*CCGGAGCACACCCGGGTCCGCCAGATCGTCCAGCGCGGCTTCACGCCCCGC*
*GCCATCCGCGCCCTGGAGGACGCGCTGCGCACCCGCGCGCGGACCATCGTC*
*GCCGAGGCGCGGCGCAAGGAGTCCGGCGACTTCGTCACCGATGTCGCCTGT*
*GAACTGCCCCTCCAGGCCATCGCCGAGCTGATCGGCATCCCCCAGGACGACC*
*GGGCCCGGATCTTCGACTGGTCGAACAAGATGGTCGCGTACGACGATCCCGA*
*GCTGGCCATCACCGAGGAGGTCGGCAACACCGCGGCGGCGGAGCTGATCTC*
*GTACGCGATGAACCTGGCCGCGGACCGCAAGGAGTGCCCCGCCCAGGACATC*
*GTCAGCCGGCTCGTCGCGGCGGAGGACGAGGGCAACCTCGCGTCCGACGAG*
*TTCGGGTTCTTCGTCCTGCTGCTGGCCGTCGCGGGCAACGAGACCACGCGCA*
*ACGCGATCACGCACGGCATGCACGCGTTCCTGACGCACCCCGACCAGTGGGA*
*GCTGTACAAGCGCGAGCGGCCGAGCACCACGGCCGAGGAGATCGTGCGCTG*
*GGCGACGCCCGTCGTCTCCTTCCAGCGCACGGCCACCCAGGACACCACCCTG*
*GGCGGCGCGCGGATCGAAAAGGGGCAGCGCGTCGGCCTCTTCTACGCCTCC*
*GCCAACCACGACCCCGAGGTCTTCGCGCACCCGGAGACGTTCGACATCACCC*
*GCGACCCCAACCCCCATCTGGGCTTCGGCGGGGGCGGCCCGCACTTCTGCCT*
*CGGCAAGTCGCTCGCCGTCCTGGAGATCGACCTGATCTTCCAGGCCATCGCC*
*GACGCCATGCCGGACATCGCCCTCGTGGGCACCCCGCGCCGGCTGCGGTCG*
*GCGTGGCTCAACGGGGTGAAGGAGCTGCGGGTCCGGTACGTG**TAA*
Legend
*P450 (italics)*
Start and stop codons in bold
Protein sequence
(Translated using Expasy from DNA sequences above)

SEQ ID NO: 91 (amino acid sequence of cytochrome SriC42 (410 aa))
MPCPALPDGFDFTDPDVYQSRVPLPEFARLRRTTPVWWNAQPHGIAGFGDDGY
WVVTRHEDVKEVSTRPEVFSASTNTSIIRFNAAMTRDRIDVQKLIMLNMDPPEHTR
VRQIVQRGFTPRAIRALEDALRTRARTIVAEARRKESGDFVTDVACELPLQAIAELIG
IPQDDRARIFDWSNKMVAYDDPELAITEEVGNTAAAELISYAMNLAADRKECPAQDI
VSRLVAAEDEGNLASDEFGFFVLLLAVAGNETTRNAITHGMHAFLTHPDQWELYK
RERPSTTAEEIVRWATPVVSFQRTATQDTTLGGARIEKGQRVGLFYASANHDPEV
FAHPETFDITRDPNPHLGFGGGGPHFCLGKSLAVLEIDLIFQAIADAMPDIALVGTPR
RLRSAWLNGVKELRVRYV-

SEQ ID NO: 92 (coding sequence of sriC43)
P450 sriC43: SRIM_18450
*ATG**GACGCGCGGGTCCGCCACAGCCCCGAGGCCGAGCGCATCGACACCCGC*
*GGCGAACCGCCGGTGTGGCGCGCGGAGCTGCCCGACGGCTCCACCGCCTGG*

Figure 4 (continued)

*GTCGCGTCCGGGTACGACGCCGCGCGCCAGGTGCTGACGGACTCCGGCTTC*
*GCGAAACCGGCCGTCCGGGGCGGCGAGCGCTGGACGGACTATCTGGCCTTC*
*ACCGGCAAGGAGGTCACCGACAGCATCGTGCGCAGCATGCTCAACACCGACG*
*GCGACCTGCACCGGCAGCTGCGCGAACTGGGCGCGTCGGCGTTCACGCCCG*
*AGCGGGTGCGGGAGACCGCCGACCGCGCGGAAACGCTCGCCGAGACCCTGC*
*TCGACGAGATCGCGGGACGCGGCCGCGCCGACCTCGTCCACGAATTCGCCCA*
*CCCCTTCGCCGTCCGGGCCATCACCGAACACCTCGGCTATCCGCCCGATTTCA*
*TCCGGCGCGCCCTGGAGCTGCGGCGCTGGGGCCCGTCCCCGCTGTTCGATC*
*CCCCCGGCTCCCCGGACCGCGCGCGCTACGCCGCCGACCGCACGGCCATGA*
*GCGAGCTGCTGCACGACCTGGTGGCCTTCCGGCGCGGCAGCCCCGGGCCCG*
*ACGCCGTCAGCGGGATGATCGCGCGCGCCGACGCCGCGGGCCTGGACGAAG*
*GGCAGCTGACCTCCACCCTCTTCCTGCTGCTCGTCTCCGCCTACGAACCGGTC*
*GCCGACTTCCTCACGTCGAGCCTGTACTCCCTCTGGCACCGCCCCGACCTGCT*
*CGCCGACCCCGCCCGGGTGGCCGACGGCCTCGGCGAGCTGCTGCGCTACAC*
*CTCCCCGCTGGCCGCCACCATGCCGCGCTTCGCCACCCGCCCGATGGAGCTG*
*TACGGCGCCGAGCTGGCGCCGGGGGACGCGGTGATCGTGCACCTGGCCCTC*
*GCCAACCGCGACCCGCGCCGCTTCACCGCCCCCAACCGCCTCGACCTCGACC*
*GGGAAACCGGCCAGGACCTGGTCTTCGCGCACGGCCCGCACTTCTGCCTCGG*
*CAGCCAGTTCGCGGTCCGGCTGTGCCGTACGGCCCTCGGCGCCGTGCTGCG*
*CCGCCTGCCCGGACTCGCCGCCGCCCGGCCGCTCGACACACTGCCCTGGCA*
*GCGCGGCTCCACGGGCGGCATCACCCATCTGCACGTCACCGCGGGCCTGAC*
*GGAGCTGCCCGTCACCTTCCAGCCCCGGCACGCGGTGGTCTCCTAA*

Legend
*P450 (italics)*
Start and stop codons in bold

Protein sequence
(Translated using Expasy from DNA sequences above)

SEQ ID NO: 93 (amino acid sequence of cytochrome SriC43 (409 aa))
MDARVRHSPEAERIDTRGEPPVWRAELPDGSTAWVASGYDAARQVLTDSGFAKP
AVRGGERWTDYLAFTGKEVTDSIVRSMLNTDGDLHRQLRELGASAFTPERVRETA
DRAETLAETLLDEIAGRGRADLVHEFAHPFAVRAITEHLGYPPDFIRRALELRRWGP
SPLFDPPGSPDRARYAADRTAMSELLHDLVAFRRGSPGPDAVSGMIARADAAGLD
EGQLTSTLFLLLVSAYEPVADFLTSSLYSLWHRPDLLADPARVADGLGELLRYTSPL
AATMPRFATRPMELYGAELAPGDAVIVHLALANRDPRRFTAPNRLDLDRETGQDL
VFAHGPHFCLGSQFAVRLCRTALGAVLRRLPGLAAARPLDTLPWQRGSTGGITHL
HVTAGLTELPVTFQPRHAVVS-

SEQ ID NO: 94 (coding sequence of sriC44)
P450 sriC44: SRIM_16375
*ATGGGTATACGTGGTGCGGCGGGCGTCCGCGCGGCCCGCGGTCCCGCCCCG*
*CACAGCTGGACCGTGTCGACGGCACCCGGCGGCGTACCGCTGCTGGGACAC*
*GCGCTCCCGCTGTGGCGGCGCCCGCTGGACTTCCTCGCCTCGCTGCCCGCG*
*CACGGCGACCTGGTCGCGATCCGCCTCGGACCGCAGCGCGTGTGGCTCGCC*
*TGCGACCCGGCGCTGGTGCAGCAGATCCTCATGGACCCGCGCACGTACGACA*
*AGGGCGGTCCGCTCTACGACACCATGCGCATGGTGCTCGGCAACGGGCTGGT*
*CACCTGCACCCAGGACGTGCACCGCAGGCAGCGCCGGCTGGCCCAGCCCTG*
*CTTCCGCCCGTCCCGGATCGCCGACTACGCGCAGGTGATGAGCGCCGAGATC*
*GACGCCGCCGTCGGAAAGTGGCGGCCCGGACAGACGCTGGACGTCACCGAC*
*GCGATGATGGACCTCTCGGCCCGGGTCACCACCGGCGTGCTGATGTCCACGT*
*CCCTCGACCCGGGCCTCGCCGCCGAGGTACGCGCCTGCCTGTCGACCGTCAT*
*GCGCGGCGTCCTGCTGCGCGCGGTCGTCCCGCTCGGCCCGCTCTACAGACTC*

Figure 4 (continued)

*CCCACGCCCGGCAACCGCCGCTTCGACCGGGCTCTCGCCCGGCTGCACCACA*
*TCATCGACGGGATCATCGCCGAACGCCGCGGCAGCACCGCCCGGCACGGCG*
*ACCTGCTCGACACCCTCCTGGGAGCCACGGACGACGCCCCCGGACCGGACG*
*GCCGCGCCGTACCCGAAGGCCTTGCCCAGGACTGCCCCCACGCCACCGCCG*
*CGCCCACCCCCCAGGAGGCACCCCACGATCAGGAACCGCTCACCGACCAAGA*
*GGCGCACGACCAGTTGATGACCTTCCTCGTGGCCGGCATCGAGACCACCGCG*
*CTGGCCCTCGCCTGGACGCTCCACCTCCTGGCGGCCCACCCCGAGGAAGAAC*
*GCCGGCTGCACGCCGAGGTGGACTCCGTGCTCGCCGGCCGGCCGCCCGCGC*
*CGGACGATCTGCCCCGGCTCGGCCACGCCCGGCGCGTGGTCACCGAAGCCC*
*TGCGCATGTACCCGCCGGGCTGGGCCCTGACCCGGGTGACCACCACCGAGA*
*CCACGCTGGCCGGCCACCGGCTGGCACCGGGAAGCACCGTCCTGTACAGCG*
*CGTACGTGCTCCACCAGGACCCGGTGGCCTTCCCCGACCCCCAGCGTTTCGA*
*CCCCGACCGATGGTTGCCGGAACGGCAGGGGGCGTTCCGGGCGGTGCGAT*
*GCTCCCGTTCGCCGCCGGCAACCGCAAGTGCATCGGCGACCACTTCGCGATG*
*ACCGAAGCCGTGCTCGTCCTTGCCGCCATCGCCGCGCGCTGGCGCCTGCGCC*
*CGCCGTCCCCCAGGACCGTACGACCGGTCCCGGCGGCCGTGCTGAGCCCGG*
*GCCCGCTGCCCATGGTCTGCGCCTCACGCCGCGGACCGGACGGCCCAGCGC*
*CGGCCGTGCCATCTGAAGCACCGTAA*

Legend

*P450 (italics)*

Start and stop codons in bold

Protein sequence

(Translated using Expasy from DNA sequences above)

SEQ ID NO: 95 (amino acid sequence of cytochrome SriC44 (505 aa))

MGIRGAAGVRAARGPAPHSWTVSTAPGGVPLLGHALPLWRRPLDFLASLPAHGD
LVAIRLGPQRVWLACDPALVQQILMDPRTYDKGGPLYDTMRMVLGNGLVTCTQDV
HRRQRRLAQPCFRPSRIADYAQVMSAEIDAAVGKWRPGQTLDVTDAMMDLSARV
TTGVLMSTSLDPGLAAEVRACLSTVMRGVLLRAVVPLGPLYRLPTPGNRRFDRAL
ARLHHIIDGIIAERRGSTARHGDLLDTLLGATDDAPGPDGRAVPEGLAQDCPHATA
APTPQEAPHDQEPLTDQEAHDQLMTFLVAGIETTALALAWTLHLLAAHPEEERRLH
AEVDSVLAGRPPAPDDLPRLGHARRVVTEALRMYPPGWALTRVTTTETTLAGHRL
APGSTVLYSAYVLHQDPVAFPDPQRFDPDRWLPERAGGVPGGAMLPFAAGNRKC
IGDHFAMTEAVLVLAAIAARWRLRPPSPRTVRPVPAAVLSPGPLPMVCASRRGPD
GPAPAVPSEAP-

SEQ ID NO: 96 (coding sequence of sriC45)

P450 sriC45: SRIM_16660

*ATGGGTACGCACATTCCTGGACCCGAACCCCGGCCGGACGGCGGGGTGGAT*
*GCTGTCGCGGCGGCGGGTGGGCTGCACCGGTATCAGTTGTGGCTGCATGCC*
*GAGTACGGGCCCGTGGTGCGGTTCCAGCTGCCGGGGGCGGAGACGGCCGTT*
*TCGGTGGCGGATCCGGTGCTGCTGGAGGCCACGGCGCACATCGACAAGCGG*
*CCGGAGCGGTTGTTCGAGTTTCTGGCACCGCTGTGCGAGGCGGGCAATCTGC*
*AGGTGTTGCCGGCCGAGGAGCACACCCCGTGGCGTCGGGTGCTGTTGTCGGT*
*GCTGGCCGGGCGGCCGTCGCACGAACGGCACTTCGAGCGGTTCACCGAGCT*
*GACGACGTCCCTCGCGGACCGGTGGGCCGGGCAGGGCGAACAGGAACCGGT*
*CGCGTTGCAGAAGGAACTGACCGCACTGTCGTTGCGGATGATCGGTGCGTAC*
*GCGCTGGGGGGCGACGCGGCGGATCCGGAGAAGGTCATCGCGGCCTTCGAG*
*GAGGTGCTCACCGAGTATCTGGGGCGGCTCTACCAGGTGCCCGTGCCGGGTA*
*CGGAGGAGGAGCGCGCCCGGCGGGCGGAGCAGGCCCTCGCGTATCTGCGG*
*GCGACCGTCGACCGGGTGCTGACGGCGCACCGCCCTGACAGCCGTACGGAC*
*CGGAGCGATCTGATCGGGGCCCTCGTGGCGGCCGGTGAGGACCCGGCGCGG*

Figure 4 (continued)

*ATCCGTGACACGGTGATGGTGGCGATGCTGGCCGCGCACCACACGACGGGC*
*GTGGCCGTGTCGTGGACCCTGCACCTGCTGGGACGCCACCCCGAGGTGGCC*
*GAACGCGTCGCCGGGGAGCTGGACCGCGTGCTCGGCGACCGTGCGGTGCCC*
*GGGTACGCCGATCTGCGGCGCCTGACGTATCTGGACATGGTCCTGAAGGAGT*
*CGATGCGGCTGTTCCCGCCCGGTCCGTACGGTGCACGGGAGACGACCGAGG*
*CGCTGGTCCTGGGCGCGTACGAGGTTCCGGCCGGGACGGTGATCTTCTATCC*
*GTTCTGGGCCGTCCATCTGAACCCCGATCACTGGCCCGAGCCCGAGAGGTTC*
*GTGCCCGAGCGGTTCCTTCCGGAAGAGGTGGCCAAGCGTCCGAGGCTGGCGT*
*ACATCCCGTTCGGCCTCGGGCCGCGCAGCTGTGAGGGCGCCGGTCTGGCCA*
*CGGTCGAGGCGCAACTGGTCCTGGCCGTACTGCTCAAGCGCTTCCGGTTCCG*
*GCCTGTGCCAGGGCATGAGGTGACGCCGATCGAGCGGTTCGTGCTGTGGGC*
*GGCCGATGACATCCGGATGTTCGTGAGTCGGCGGGAGGTGGGGGCGGGGAG*
*CCCGTAA*

Legend

*P450 (italics)*

Start and stop codons in bold

Protein sequence

(Translated using Expasy from DNA sequences above)

SEQ ID NO: 97 (amino acid sequence of cytochrome SriC45 (446 aa))

MGTHIPGPEPRPDGGVDAVAAAGGLHRYQLWLHAEYGPVVRFQLPGAETAVSVA
DPVLLEATAHIDKRPERLFEFLAPLCEAGNLQVLPAEEHTPWRRVLLSVLAGRPSH
ERHFERFTELTTSLADRWAGQGEQEPVALQKELTALSLRMIGAYALGGDAADPEK
VIAAFEEVLTEYLGRLYQVPVPGTEEERARRAEQALAYLRATVDRVLTAHRPDSRT
DRSDLIGALVAAGEDPARIRDTVMVAMLAAHHTTGVAVSWTLHLLGRHPEVAERV
AGELDRVLGDRAVPGYADLRRLTYLDMVLKESMRLFPPGPYGARETTEALVLGAY
EVPAGTVIFYPFWAVHLNPDHWPEPERFVPERFLPEEVAKRPRLAYIPFGLGPRSC
EGAGLATVEAQLVLAVLLKRFRFRPVPGHEVTPIERFVLWAADDIRMFVSRREVGA
GSP-

SEQ ID NO: 98 (coding sequence of sriC46)

P450 sriC46: SRIM_03331

*ATGACCACCCCCCAGCACCCCGACGACTTCCTGCGTCTCCTGCGAATGCGCA*
*GCGCGGCCGAGGACGGGATCTTCCGGGTCGACGAGGAACGGCTCGCCGTGT*
*TCGATCCGGAAGCGGCCCGCCGGATCAGCGCCGCGAACTGGCACCGGTTCGT*
*CATGCACGACCGCCTGGTCGACATGGTGCGGCGGCGCCGGAGTCCCGAGGT*
*GCGGTGGAGCCAGGTACGGTCCGCCTGGCTCACCCAGCTGCACGCGCTGGC*
*CACGCCGGAACAGCACGGCCGGCTGATCGAGCGCATGGCACAGATCATGGAC*
*GCGCGGCTCGGCCGGGACGTGGATCTCACCATGCTCAGCCAGGACGTGGCC*
*GTGCGGTCGCTGCTGCCGCTCGCGCTGTCGGGCCTCACCACCGGCGAGGCG*
*GATCTCGTCCGCCGGGACCTGGAGATGAAGCTGCTGCGGCTGGTCTCGCCCG*
*ACCCGGGCAGCACCTGGCACCACCTGCGGTTCGTCGCGGTCCAGATACGGTC*
*GGGACTGGTCGTGCGCCGGGTCCTGCGCCAACGCGCCCGCGGGCGCCGGG*
*GCCGCGAGCCGGACCTCGCCGACCCGATCGTCGACCTGCTGCCCGCACTCG*
*GCATGGACCGCGCCCTGGACGTGGTGACGGCCGTCCTCACCGCCATCGGCG*
*GCCCGCCGGGCACGGCCGCCGCGAGCGTGCTGTACGAGTTCGCCCGCCGCC*
*CCGAGTGGCAGCGGCGGCTCGCCGATGAGCTGGGCGCCGTCGACCCCGTCG*
*CGTTCCGTACGGCACCGCCGGACGCGGCCCCGGTGACCCACCGCTTCGTCAA*
*GGAAGTGCTGCGCCTGTGGAGTCCGCCGCTGCTGCTGGTACGACGCTCCACG*
*GTCCCGTTCGACCTCGGGAAGACACGCCTGGCGCCGGGCGACTGGTACTTGC*
*TGAGCCCGCACATGATCCATCGCGATGACCGCGTCTGGAAACGGCCCGACCT*
*CTTCGACCCGGACCGATTTCTGCCCGGTGCGCCCCACGGCCCGGCGGACCG*

Figure 4 (continued)

*CACGTGCTACGTGCCGTTCGGCTGGGCGCCCAAGAAGTGCATCGGCGCGAAC*
*ATCGCCATCGTCCAGCTGATGGCCCTGTGCCACCTGCTGTGCACCCGGTACC*
*GCCTGACCGTGCACCGGCCGGACGAGGTCACGATGGCCTTGCGTTTCGCTCC*
*GGTACCGGAGAACTTCCGGGGGGAGCTGGCCTTCCGGTAA*
Legend
*P450 (italics)*
Start and stop codons in bold

Protein sequence
(Translated using Expasy from DNA sequences above)

SEQ ID NO: 99 (amino acid sequence of cytochrome SriC46 (407 aa))
MTTPQHPDDFLRLLRMRSAAEDGIFRVDEERLAVFDPEAARRISAANWHRFVMHD
RLVDMVRRRRSPEVRWSQVRSAWLTQLHALATPEQHGRLIERMAQIMDARLGRD
VDLTMLSQDVAVRSLLPLALSGLTTGEADLVRRDLEMKLLRLVSPDPGSTWHHLRF
VAVQIRSGLVVRRVLRQRARGRRGREPDLADPIVDLLPALGMDRALDVVTAVLTAI
GGPPGTAAASVLYEFARRPEWQRRLADELGAVDPVAFRTAPPDAAPVTHRFVKE
VLRLWSPPLLLVRRSTVPFDLGKTRLAPGDWYLLSPHMIHRDDRVWKRPDLFDPD
RFLPGAPHGPADRTCYVPFGWAPKKCIGANIAIVQLMALCHLLCTRYRLTVHRPDE
VTMALRFAPVPENFRGELAFR-

SEQ ID NO: 100 (coding sequence of sriC47)
P450 sriC47: SRIM_32706
*ATGACTTTCCCTTTTCCCGAACAGCCCGGCACCACGTGGGCCGCCACGCCGC*
*CTCCGGAGTGCCCGGCACACGCCCGGCCCGGCGCCGCCGACGGGCTGGCG*
*CGGCTCTTCGGCCCCGAGGCGGCCGCCGACCCCATGGGCCTGTACGAGCGC*
*CTGCGCGCCCGGCACGGGGCCGTCGCGCCCGTCCTGCTGGACGGCGACCTG*
*CCCGCCTGGCTCGTCCTCGGCTACCGAGAGATCCTGGAGGTCGCCGGTACGC*
*CCGCCCGTTTCAGCCGCGATTCGCGCAACTGGCGCTGGTTCAGGGAGGGGCG*
*GGTCCCGCCGGACTCGCCGCTGCTCCCGATGATCGCCTGGCAGCCGGTGTGC*
*CTGTTCCTGGACGGGGAGGAGCGCAACCGGCTGCGCCTGGCCGTCACCGAC*
*AGCCTGGACCGCTTCAACCGCCGGGGCATCCGGCGGCACATCACCCGCTTCA*
*CCCACCAGCTGGTGGACGGCTTCATCGAGCGCGGGGAGGCGGACCTGGCCG*
*AGGAGTTCTGCGAACACCTGCCCATGCTCGTGCTGACCCAGCTCCTGGGCAT*
*GCCGGACGAGTACGGGCCCCGGCTGGTCGCGGCCAGCCGGGACATGGTGGC*
*GGGCACCGCGACCTCGGTGGCCAGCAACGCGTTCATCGTGGACACCCTCATG*
*GAGCTGGTACGGAGCAAGCACACCACCCGCGGGCACGACATCACGTCCTGGC*
*TGATCGACCACTCCTCCCGGCTGACCGACGAGGAGGTGTGGAACCACCTGCG*
*GGTCGTCCTGATCGCCGCGAACGAGACCACCGTCAACCTCCTCAAGAGCACG*
*CTGCGGATGGTGCTGACCGACCCCCGGTGCCACGCGTCGCTGGCCGGCGGG*
*CAGATGACGCTGCCCGACGTGGTGGAGCAGGTGCTGTGGAGCGAACCGCCG*
*CTGATGACCATCCCCGGCCGCTGGGCCGCGGTGGACACGGAGGTCGGCGGC*
*CAGAAGATCGAGGCGGGGGACATGCTGCTGCTCAGCCTGGCCGCCGGGAAC*
*CACGATCCGGCCGTCCGGCCGGACCCGTCGATCCCGCTGCACGGCAACCGCT*
*CGCACCTCGCCTTCAGCAGCGGCCCGCAGGAGTGCCCCGGCCAGAACATCG*
*GCCGCGCCATCGCCGACACCGGCATCGACACGCTGATGGCACGGCTGCCCG*
*ACGTACGGCTGCGCATCCCCGAGGAGGAGCTGCGCTGGACGTCGGGCTGGA*
*TGACGCGCCATCTGACCAGCCTTCCGGTGACGTTCAGCGCCTCCCGGCCCGC*
*GCACTCCGGCGCGACCGCCGGTACGGCCTTCGAACGCCCGCCGGGCACCAC*
*CCCGCACGACGGCTCCCTGCCCGCGGCCGAGCCCCCGGCCACGCCCCCGCC*
*CGGCCCGCCTCCGGCGGCTCCCGTGCCCAGGGGGCGTACGTCCTGGTGGGC*
*CGCGTTGAAGGCTTGGCTGCGCGGCTAA*
Legend

Figure 4 (continued)

*P450 (italics)*
Start and stop codons in bold

Protein sequence
(Translated using Expasy from DNA sequences above)

SEQ ID NO: 101 (amino acid sequence of cytochrome SriC47 (488 aa))
MTFPFPEQPGTTWAATPPPECPAHARPGAADGLARLFGPEAAADPMGLYERLRA
RHGAVAPVLLDGDLPAWLVLGYREILEVAGTPARFSRDSRNWRWFREGRVPPDS
PLLPMIAWQPVCLFLDGEERNRLRLAVTDSLDRFNRRGIRRHITRFTHQLVDGFIER
GEADLAEEFCEHLPMLVLTQLLGMPDEYGPRLVAASRDMVAGTATSVASNAFIVD
TLMELVRSKHTTRGHDITSWLIDHSSRLTDEEVWNHLRVVLIAANETTVNLLKSTLR
MVLTDPRCHASLAGGQMTLPDVVEQVLWSEPPLMTIPGRWAAVDTEVGGQKIEA
GDMLLLSLAAGNHDPAVRPDPSIPLHGNRSHLAFSSGPQECPGQNIGRAIADTGID
TLMARLPDVRLRIPEEELRWTSGWMTRHLTSLPVTFSASRPAHSGATAGTAFERP
PGTTPHDGSLPAAEPPATPPPGPPPAAPVPRGRTSWWAALKAWLRG-

SEQ ID NO: 102 (coding sequence of sriC48)
P450 sriC48: SRIM_06206
*ATG**CTGGAACAGCTGCGCAGGCAGTACGGGGACGTCGCACCGGTCCTCGTCC
CCGGCGACATCCCGGCCTACCTGGTCCTGGGATACAACGCGACACGCGATGT
CATGCAGAGCAACTCCCGCGTGGTCTGCGACTCCCGCCGCGGCCGTGTCTAC
CAGGACGGCCGGATCCCGGCGGACCACCCCCTGGCGCCGATGACCGCGTAC
CAGCCGGTCGTGGCGTTCGAGGACGGCGTGCCCCACGCCCGCCTGCGCAGC
GCCGTGGTCGACAGCCTGGACTTCAACCGGCACTCCCTGCGCCGCTACATCG
GCCGGTACGCCAACCGCCTCATCGACTGCGTCGCCTCCCGCGGCACCGCCGA
CCTGGTCAGCGAGTACGCCGCGCAGCTGCCGGCCCTCGTGATGGCCTGGATG
TACGGCATGCCCGAGGAGGAGAGCCCCGCCCTGGTGGCCGCGGTACGGGAC
CTGACCAGCGGCAACGAGCGGGCCGCCGAGGGCAACGCGTTCGTCACCCGC
ACGATGGAGGAACTCGTCCGGCGCAGGCGGGCCGGCGAGGGCGCCGACAAC
ACCATCGGCGGCCGGGACTTCGTCAGCCGTCTCCTGGACCACGAGGCGGGC
CTCAGCGATCAGGAGGTCGTCGAGCACCTGCGCATGATCTTCGTCGCCGGCT
ACACGCCGACGGTCGCGCTGATCGCAAACACGCTGCTGGTGCTGCTGACCCA
GCGTCAGTTCAGCCGTGACCTGACCAGCGGCCAGATGACGCTGCCCGAGGCC
CTGGAACGCGTGCTCTGGGACCACCCGCCGATCGGGCTGCTGCCCACCCGCT
GGGCGGCCGGGGACATGACCATCGCCGGCCAGCAGATCAAGGCCGGAGACA
TGATCATCCTGGGGATCGAGGCTGCCAACGCGGACCCCGCCGCCCGGGAACC
CGGACGCCCCGTAGTCCACAATTCGGGACACCTCGCCTTCTCCACCGGCCCC
CACGAGTGTCCCGGCCGCGACATCGGACAGGCCATCGCGGAGACCGGCATC
GACATCCTGCTGAGCACGCTCAGGGACCTGGAACTGGCGGTGCCCGAGGCAG
AGCTGCAGTGGCAGTCGGCTTGGGTCTCGCGTCGCCTGCTGTCCTTGCCGGT
GACGTTCACTCCGCCGCGGGTCAGGGGGGTGCGGGCTCCGCAGCCGGAGGC
TGCTGTGGCGGGAGTGGGTAGGTCGGTTGGTACTGCC*TAA*
Legend
*P450 (italics)*
Start and stop codons in bold

Protein sequence
(Translated using Expasy from DNA sequences above)

SEQ ID NO: 103 (amino acid sequence of cytochrome SriC48 (408 aa))

Figure 4 (continued)

MLEQLRRQYGDVAPVLVPGDIPAYLVLGYNATRDVMQSNSRVVCDSRRGRVYQD
GRIPADHPLAPMTAYQPVVAFEDGVPHARLRSAVVDSLDFNRHSLRRYIGRYANR
LIDCVASRGTADLVSEYAAQLPALVMAWMYGMPEEESPALVAAVRDLTSGNERAA
EGNAFVTRTMEELVRRRRAGEGADNTIGGRDFVSRLLDHEAGLSDQEVVEHLRMI
FVAGYTPTVALIANTLLVLLTQRQFSRDLTSGQMTLPEALERVLWDHPPIGLLPTRW
AAGDMTIAGQQIKAGDMIILGIEAANADPAAREPGRPVVHNSGHLAFSTGPHECPG
RDIGQAIAETGIDILLSTLRDLELAVPEAELQWQSAWVSRRLLSLPVTFTPPRVRGV
RAPQPEAAVAGVGRSVGTA-

SEQ ID NO: 104 (coding sequence of sriC49)
P450 sriC49: SRIM_09586
*ATG**AACACCCTCCGCACCGCCAAGCTGCTCGCCGCCGCGGCCGGTCTCCTCT*
*CCGTCCCGTACTGGCTGCCGCGCTCCGTCGTCGCCGCCCGCGTCGCGCTCTT*
*CGCGCGGATCAACGGCGACGAGGGCATCGCCTTCCCGAGCGCCGACGTCCC*
*CGCCGACCGCTTCCAGGAGATCTACTCCCACCCCGCCGCCAACGGCCGCAGC*
*CGGGGCGCCGCCCTCTCGGACCTCTTCTGGTACTGGCTGGCGCCCGGCCCC*
*GAGGTGCACCAGGAGCACCTGGAGGACGGCCCGCGCTACGACGAGGTCGCC*
*CGTACCACCCTCGCCGTGCTGGGCGGTCCCAGCCGCGAGCTGTCCGCCGCG*
*GTGGCCCGCCGTACCGCCGCCGTGCTCGACGAACTGGTCACCGGCCGGGCC*
*GAGTTGGTCCGGCTGCGCGACCTGATGATGCCGGTGTGGGCGGAGTTCTTCT*
*ACGGACTCGTGTTCCGCGAACCGTGCCCGCCGTACGTCCGGCGCCTGATCGT*
*GGACAACGCCGCCGACGTGGTCAACTCCCTGAAGTGCACCCGGCTCCGCCAC*
*CCGGCCCGCCGCGCCCGCCTCACCCGCCACCTGCGGCAGCGCATCGCCGCC*
*GGGACCGTACCGCCGCACCACCTGCCGGGCTCCCTCACGCCCGACGAGCAG*
*GCGTACTACCTCCAGGGCACCTTCTTCAACACGGCCATCGTCCAGATGTCCGA*
*GGCCATGGCCCACCTGCTGCTGGTCCTCGCCCAGCACCCGGAGGCGCAGCG*
*CAGGCTCGCCGCCGGACCGGACGACGACCGGTACTTCTCCAACGTCCTCAAC*
*GAGACGCTGCGGCTCTACCCGCTCTTCGGCGTCGCCCACCGCATCAGCACGG*
*ACGACATCCCGCTCGGCCCCGGCACGGCCATCCCCGCCGGCTCCGTCCTGTG*
*CTTCAACTACCCCGACTACCACGCCACCGGCTACACCGACCCCGAGGTCTTCG*
*ACCCCGCCCGCTGGGACCGCCTGGTGGCCAAGGAGCAGCACCACATCCCGTT*
*CGGCGTCGCCGCCAACCGGCCGTGCCCGGCCTGGCGGCTCGCCCCGCTGGC*
*CATGCACGCCGCGACCCGCGAGGTGCTGCGCCGCTTCACCCTCCACTCCACC*
*GTCGCCCACACCCGCTCCATCCCGCACCGCGCCCCCTGCCTGCTGGTCCGGC*
*GCGACCGTCCGCTGCCGAAGCACCGGCTGCTCGCCGCCCGGGTCTTCCTGAG*
*GGTGCGCGACCGGTGGGAGGACGTGTGGCGCAGCTGCGTCCAGCTCGTCCT*
*CGGTACGTGGATGGTGCTCGACGCCCGCCGCCTGCGCCCGGCCGAGCGCTA*
*CTTCGCCACCCACGACACGCAGGGCGTCCCGCTGCCGGGCACCGCCCCCGC*
*CCCGGCGCGCTGTCCGTACCCGCACGCC**TAA*
Legend
*P450 (italics)*
Start and stop codons in bold

Protein sequence
(Translated using Expasy from DNA sequences above)

SEQ ID NO: 105 (amino acid sequence of cytochrome SriC49 (474 aa))
MNTLRTAKLLAAAAGLLSVPYWLPRSVVAARVALFARINGDEGIAFPSADVPADRF
QEIYSHPAANGRSRGAALSDLFWYWLAPGPEVHQEHLEDGPRYDEVARTTLAVL
GGPSRELSAAVARRTAAVLDELVTGRAELVRLRDLMMPVWAEFFYGLVFREPCPP
YVRRLIVDNAADVVNSLKCTRLRHPARRARLTRHLRQRIAAGTVPPHHLPGSLTPD
EQAYYLQGTFFNTAIVQMSEAMAHLLLVLAQHPEAQRRLAAGPDDDRYFSNVLNE
TLRLYPLFGVAHRISTDDIPLGPGTAIPAGSVLCFNYPDYHATGYTDPEVFDPARW

Figure 4 (continued)

DRLVAKEQHHIPFGVAANRPCPAWRLAPLAMHAATREVLRRFTLHSTVAHTRSIPH
RAPCLLVRRDRPLPKHRLLAARVFLRVRDRWEDVWRSCVQLVLGTWMVLDARRL
RPAERYFATHDTQGVPLPGTAPAPARCPYPHA-

SEQ ID NO: 106 (coding sequence of sriC50)
P450 sriC50: SRIM_32731
*ATG**CGTACGTACGGTACGGAACGGAGCGACCGGGTCACGGTCTTCACGCCGC*
*GGCTCGGCCGGCTCCTCAGTGAGCACCGCGGCGCGGACGTCTTCCGGCTGG*
*AGGCCGACACGGTCGGCGTCGCCGGACCCGGGCTGATCGACGCCGTGCTGC*
*GCAGCAGACCGGCCAACGCGGCCGAACGGCCCACTTTCAAACCCCTACAGGG*
*CCGGCCCATCAGCCGCCCCGAATCCTCCGCGGTCATGCGGGCCGTTTCCCTG*
*GACGTGCGCGCGGCACTGGAAAAGCCCGACGGGAAAGGCGGCCCGGCGGCC*
*GATCTGTCGGGGGAATGGCCGCGGGTGGCACACCTTTATCTGCGGGACCTGG*
*TTTTCGGGTCCGATCCGATGCGGCTGCGCGTACTCGTGGACCGCAAGCTGGA*
*ATGGACGCCCAAACTGACGTGGACCGTGATCGCGGCGGGCGCGGCGCTGCC*
*GGGCTGCCCGGGGGCCGGTGCGCCGGTGTCCCGGCTGGCGGGTCTCGCCG*
*CCGCCGCGGCCGGTTACGGGGACCGGCGGTACGCGATGGGCCTGTACCGGC*
*GGGCGGCGGCACCGGTGTGCTTCACCGTGTCCACGCTGGTCGCCAACGCCCT*
*CTGGCTCGGGTCGCCCTTCGAGGACCACATACCGAACCGTCACATCCTGTACG*
*AGTCGATGCGGCTGCTGCCGCCTTCGTGGAACCTCCTGCGCGTGGCGTCACC*
*GGAGTTCGCGGCCCTCGACGACCGGATCGGCGCGGGCGACGACGTCCTGCT*
*GCTGCCGCTGCTCAGCCACCGCGATCCGCGGCTGTGGGACGCGCCGGACGC*
*GTTCCGGCCCGAGCGCTGGGCGGCCCTCGACGCCGACGACCAGCCCGGCTA*
*CCTGCCCTTCGGGCACGCGAACGAGCGGTGCTGGGGGCGGCACATGGTCAT*
*GCCGCTGGCCGAACGGCTGCTGGACCTGGTGCGGGAACAGGGCCTGGCGGT*
*GAGCCCGGAGCAGAAGTCCGCCGAGGTGCCGCTGGCCGGGCTGCTCGGGGT*
*GTCGCGGGTGTCGGTCGTACGGCGC**TAA*
Legend
*P450 (italics)*
Start and stop codons in bold

Protein sequence
(Translated using Expasy from DNA sequences above)

SEQ ID NO: 107 (amino acid sequence of cytochrome SriC50 (351 aa))
MRTYGTERSDRVTVFTPRLGRLLSEHRGADVFRLEADTVGVAGPGLIDAVLRSRP
ANAAERPTFKPLQGRPISRPESSAVMRAVSLDVRAALEKPDGKGGPAADLSGEWP
RVAHLYLRDLVFGSDPMRLRVLVDRKLEWTPKLTWTVIAAGAALPGCPGAGAPVS
RLAGLAAAAAGYGDRRYAMGLYRRAAAPVCFTVSTLVANALWLGSPFEDHIPNRH
ILYESMRLLPPSWNLLRVASPEFAALDDRIGAGDDVLLLPLLSHRDPRLWDAPDAF
RPERWAALDADDQPGYLPFGHANERCWGRHMVMPLAERLLDLVREQGLAVSPE
QKSAEVPLAGLLGVSRVSVVRR-

SEQ ID NO: 108 (coding sequence of sriC51-sriF08)
P450 sriC51: SRIM_37486
Ferredoxin sriF08: SRIM_37491
*ATG**ACCACAGCCGACACGATGCCCCTTGCCTACCCGTTCAACGACGCCGACGGACTGGCTCTGTCCG*
*AGACCTACGAACAGGTCCGCGACCGGCCCGGACTGCTCCGGGTACAGATGGCGTACGGCGAACCG*
*GCCTGGCTCGCCACCCGCTACGCCGACGCCCGGCTGGTCCTCGGCGACCGGCGCTTCAGCCGCGCG*
*GAAGGGCTCGAACGCGACGAGCCGCGGCAGTCGGAGGGCCAGCGGGACAGCGGGATACTGAGCA*
*TGGACCCGCCCGACCACACCCGGCTGCGCACCCTGGTCGCCAAGGCGTTCACCGTGCACCAGGTGG*
*AGAAACTCCGGCCGTGGGTGCGCGAGTTGACACACGGCCTGATCGACGAGCTGGAGGCCGCGGGC*

Figure 4 (continued)

*CCGCCCGTGGACCTCGTGGACCGCTACGCGCTGCCCATCCCGGTCGCGGTGATCTGCCGGATGCTCG*
*GCGTACCGGAAGAGGACCGGCCCAAGTTCCGTACGTGGAGCGACGCCGCACTGTCCACCAGCTCGC*
*TGACGGCCGAGGAGTTCGAGGCCAACCGCGAGGAACTGCGCGCCTACATGGCGAAGTTGATCGAG*
*GATCACCGCACGACGCCGCGGGACGACCTGATGACGCGGCTGATCGAGGCCCGGGACGTCGGCGA*
*CCGGCTCTCCGAGCTGGAGCTGATCGACCTGTGCGTCGGCATCCTGGTCGCCGGACACGAGACAAC*
*GGCCACCCAGATCCCCAACTTCGTCCTGTCGCTGCTGGACCACCCGGGCGAGCTGGAGCGGCTGCG*
*CGCCGAACCCGCGCTGATCAAGAGCGCCGTCGAGGAACTGCTGCGCTTCGTACCGCTCGGCAGCGG*
*CGCGGGCTTCCCGCGCTACGCCACCGAGGACATCGAGGTGGGCGGCACACTCGTCCGTGCGGGTGA*
*ACCGGTACTGGTCGCCGTCGGCGCGGCCAACCGGGACGCGCTGCGCTTCGACGAGCCGGGCACCCT*
*CAACATCACCCGCGACGGCAACCAGCACCTCGGCTTCGGACACGGCGTGCACCACTGCCTCGGCGC*
*GCCGCTGGCCCGGCTGGAACTCCAGGAGGCGCTGATCGCCCTGATCACCCGGTTCCCGAAGCTGCA*
*TGTGGCCGGGGACGTGGTGTGGAAGGACCAGATGCTGGTCCGCGGCCCGCGCGTGATGCCGGTGG*
*GGTGGTGA*GCCGGATGACGTGGAAAGCGGCGATCGACGGACAGCAGTGCATGGCGTCCGGCATG
TGCGCGGGCATCGCCCCGGACCTCTTCGTCCTGGACGGCCCGCACGCCCGACCGCTCCAGGAGGAG
ATCCCCGAGGACGAGGCCGCGCTCGACGCGGCGGACTCCTGCCCCGCCATGGCGATCCTGATCCGG
GACGGGGAGAAGGTGGTGGGGCCGCGGCCCTAA

Legend
*P450 (italics)*
Ferredoxin
Start and stop codons in bold

Protein sequence
(Translated using Expasy from DNA sequences above)

SEQ ID NO: 109 (amino acid sequence of cytochrome SriC51 (396 aa))
MTTADTMPLAYPFNDADGLALSETYEQVRDRPGLLRVQMAYGEPAWLATRYADA
RLVLGDRRFSRAEGLERDEPRQSEGQRDSGILSMDPPDHTRLRTLVAKAFTVHQV
EKLRPWVRELTHGLIDELEAAGPPVDLVDRYALPIPVAVICRMLGVPEEDRPKFRT
WSDAALSTSSLTAEEFEANREELRAYMAKLIEDHRTTPRDDLMTRLIEARDVGDRL
SELELIDLCVGILVAGHETTATQIPNFVLSLLDHPGELERLRAEPALIKSAVEELLRFV
PLGSGAGFPRYATEDIEVGGTLVRAGEPVLVAVGAANRDALRFDEPGTLNITRDGN
QHLGFGHGVHHCLGAPLARLELQEALIALITRFPKLHVAGDVVWKDQMLVRGPRV
MPVGW-

SEQ ID NO: 110 (amino acid sequence of ferredoxin SriF08 (71 aa))
MTWKAAIDGQQCMASGMCAGIAPDLFVLDGPHARPLQEEIPEDEALDAADSCPA
MAILIRDGEKVVGPRP-

SEQ ID NO: 111 (coding sequence of sriC52)
P450 sriC52: SRIM_10981
*ATG**GCGTGGCTCCAGGACGCGGACGCGCCCAGTTGGTTCGTGAGCCGGTAC*
*GACGACGTCCGTGCGGTGATCGGGGATCCACGGCTGGTCAGGCCGAGTGTCA*
*ACGGCTGGTCCTTCATGCCGGAGCAGGACCGGCCGGACGGCATGGAACTGAT*
*CACGATGATGGAGATGGAGGGCCCGCGGCACACGGCGCTGCGCAGGGCCCT*
*GTCCGGGGCGTTCAGCGCACGGTCCGTACGGCGCCGTCTGCCGCGTATCCG*
*CCGGAGCGCCGAGCGGCTGCTGGACGAGTTCGCCGACGGCGGCGCACCCGG*
*CGATCTGATCGCCGGTTACACCGAGCCCTTTCCGCTGCTGGTGGTGTGCGAAT*
*CGGTGGGCATCCCGTACGAGGACCGCGACTACTACCTGCCCATGGCGGACGC*
*GGCTCTGGGGGCGCTGCTCACCGTGGAGGAGGCGCGGCGGGTCACGCCGCT*
*GCTACGGGACTACGTCCGGTCACTGATCGTCCAACGGCGGCGGGCGCCCGC*
*GGACGACATCCTCGGCGACCTGGTCCGCAGGTGTGACCGGGGCGAGCTGGA*

Figure 4 (continued)

*CGAGGAGAGCGTGCTCAGCTTCGGGCTGTCGATGCTCGTCGCCGGTTACCGC*
*ACGACGACCATGTTCCTGTCCGACGCCGTCCTGGCGCTGCTGGCCGATCCGG*
*ACCAGTACGTCCGGCTGCGCGACGACCGCGGCCTGCTGCCCGGCGCGGTGG*
*AGGAGTTCCTGCGCTACGTCCCGGCGATGAACGGGGTGGTGGTGCTGCAGGC*
*CACCGAGGACTTCGAACTGGGCGGGCAGACGATCCGGGCGGGGGACGCGGT*
*CCTGCCGGCACTGGCCTCCGCCAACCGCGACGAGACCGTGTTCGATGAGCCC*
*GAACGGCTCGATGTGTGCCGGCGGCCGAACCCGCACATCGCGTTCGGCCGG*
*GGCCCGCACAACTGCATCGGCGCCCACCTGGCGCGGGCGGAGCTGACCGTG*
*GGCCTGGAAACGCTCCTGGACCGTTTCCCGCACCTGCGCCTGGCCGAGGGAC*
*ACAGCCCCACCTGGGACGACGCCTCCCCGTCCAAGTCGCCTCTCACCCTTCC*
*GGTCAGCTGGTAA*

Legend

*P450 (italics)*

Start and stop codons in bold

Protein sequence

(Translated using Expasy from DNA sequences above)

SEQ ID NO: 112 (amino acid sequence of cytochrome SriC52 (364 aa))

MAWLQDADAPSWFVSRYDDVRAVIGDPRLVRPSVNGWSFMPEQDRPDGMELIT
MMEMEGPRHTALRRALSGAFSARSVRRRLPRIRRSAERLLDEFADGGAPGDLIAG
YTEPFPLLVVCESVGIPYEDRDYYLPMADAALGALLTVEEARRVTPLLRDYVRSLIV
QRRRAPADDILGDLVRRCDRGELDEESVLSFGLSMLVAGYRTTTMFLSDAVLALLA
DPDQYVRLRDDRGLLPGAVEEFLRYVPAMNGVVVLQATEDFELGGQTIRAGDAVL
PALASANRDETVFDEPERLDVCRRPNPHIAFGRGPHNCIGAHLARAELTVGLETLL
DRFPHLRLAEGHSPTWDDASPSKSPLTLPVSW-

SEQ ID NO: 113 (coding sequence of sriC54)

P450 sriC54: SRIM_05956

*ATGAGCCACCCCGAAGCCCTCATACCGGTCCCGGAGGTCGAGCCCGGTACCGCGGGGCCGCCGTGC*
*GCCTACGCCCGGCTGCGGACCGAGGCGCCCGTGGTCAAGGCGCAGCTGCCCAACGGCGAGACGGG*
*CTGGCTGATCAGCCGCTACGAGGACGCCCGCGCCGCGTTCGCCGACCCCCGGCTCGTACGGCCGCT*
*GCTGTCGGCCTGGCCGCCCCGCGAGGGAAGCGACGCCCCGCCGCCGTGCCTGCCCACCTTCCTGGA*
*GATGACCGGCGCCCACCACGAACGCGTGCGCCGCACCGTACTGCCGCTGTTCGGCAGGCGGCGGCT*
*CGCCTTCATGGAGCCCCGCGTCCGGGCGATGGCGGAGGAACTCCTCGACACGATGGTGGCCGGGG*
*CCGACGGGGGAGTGGCGGATCTCGTCGCCTCCTACGCCGAGCCGCTGCCGCTGCGGGTGCTGTGCG*
*CGACCGTCGGCCTGCCGTACGAGGACCGCGAGACCTACCTGCCGCACACCCTCGCGCTCCTGGGCG*
*CGTCCGGCCTCACGATGGAGGAGGTACTCGCGGCCCTGTACGCGCTGCAGGACTATGCGGACGACC*
*TCATCTCCCGTAAGGAGAAGACGGACGGCGAGGACGAGGACTACATCCGGCTGCTGCTGGCGGAG*
*GCACGCCGGCCGGACAGCGAGATCACCCGCGACGACGTCGTCAGCTTCGTCGTCACCATGCTGATG*
*GCCGGCTACAAGACCAACATCCAGCACACCGGCAACGCCCTGCTCGCGCTGCTCACCCACCCCGAGC*
*AGCTGAAGGCGCTGCGCGAGGCGCCCGAGCGGACCGGCGCCGCGGTGGAGGAACTGCTGCGGTA*
*CGTCCCGCTGATGAACGCCATCAACATCCTCGTCGCCACCGAGGACTTCACCCTCCACGGGCAGAAC*
*ATCAGGGCCGGGGACGCGGTCGTGCCCGTACCGGCGTCCGCCAACCGCGACCCGGACGCCTTCGCC*
*GAACCCGACCGCCTCGACCTGACGCGGACTCCGAACGCGCACATCGCGTTCGGGCACGGCCCCCAC*
*GCCTGCACCGGCGGCCACCTGACCCGTATGCAGCTCGGTATCGCCATCCAGGTACTGCTGGAACGG*
*CTGCCCGGCATCGAACTGGCCGTCGCGGCGGACACCATCCCCTGGGACGAGTCCACTCCACTGCGC*
*GCACCGGCCCGGCTCCCCGTGCGCTGGTAA*

Legend

*P450 (italics)*

Figure 4 (continued)

Start and stop codons in bold

Protein sequence
(Translated using Expasy from DNA sequences above)

SEQ ID NO: 114 (amino acid sequence of cytochrome SriC54 (404 aa))
MSHPEALIPVPEVEPGTAGPPCAYARLRTEAPVVKAQLPNGETGWLISRYEDARA
AFADPRLVRPLLSAWPPREGSDAPPPCLPTFLEMTGAHHERVRRTVLPLFGRRRL
AFMEPRVRAMAEELLDTMVAGADGGVADLVASYAEPLPLRVLCATVGLPYEDRET
YLPHTLALLGASGLTMEEVLAALYALQDYADDLISRKEKTDGEDEDYIRLLLAEARR
PDSEITRDDVVSFVVTMLMAGYKTNIQHTGNALLALLTHPEQLKALREAPERTGAA
VEELLRYVPLMNAINILVATEDFTLHGQNIRAGDAVVPVPASANRDPDAFAEPDRLD
LTRTPNAHIAFGHGPHACTGGHLTRMQLGIAIQVLLERLPGIELAVAADTIPWDEST
PLRAPARLPVRW-

SEQ ID NO: 115 (coding sequence of sriC59)
P450 sriC59: SRIM_05430
*ATG**GGCCCGGGCGCGCTCACCGACCCGGACTGGGTGGTGCCGCCGGTGCCC*
*CAGGACGTACCGGAGGGCGGGATGGCCTGGCTGCGGGCGCGGGTCGCCCG*
*CTTCAGCAGCGGGGAGGCGCACGTACGGCGCCGGGCGCTGGCGGTCGGCCC*
*GCTCGGCGGGGGAGACGCGGCCGACGCGCTGCGCGACACCGCCCGCGTAC*
*GGACGCAAGCGCTGCTGGACGGGGCGGGGGTGGGGCCGGGATCGGGGCCG*
*GGGACGGTGGACGTGATGGCGCTGGTGGCGCGCGTCGTGCCCGTCGAAGTG*
*CTTGCCGATTTCGTCGGGCTGCCGGTCACGGCGGAGACGGCCGGGCTGGTC*
*GGGCACGTCGCCCGCGCGTACCACGCACACGGCGAGACCGTCCCGGCCGCC*
*GACCGCGCCCTCGCCCGGCTCGTAACGGTGTGCGGCGGTACGTGGGACGAG*
*GCCACGGCGGCCCGCATCGGGCTGCTGGTGCAGGCGTACGACGCGACGGCG*
*GGGCTGATCGGCAACGCGGCGCATCGGATGCTGTCCTGCGATACAGGCGATA*
*CGGGGAGTGCGAGCGGTACGGGGGATACGCCGGAGGGCTCCGCCGAGTCTG*
*CCGCCGATGTCGTCACCGCCTCGCTCGACCGGACGCTGAGCGCCGACCCACC*
*CGTACGGGGCACCCTCCGCGCCCCTGCGAACGGCGGTGATCCAGTACGGATC*
*GCCCTGCTCACGGACGACGGATCGCTCGCCTTCGGTGCCGGCCCGCACGCCT*
*GCCCCGGGCGCGCCCACGCCCGGGCGCTCGCGGCCGGAGTGCTGGACGCG*
*CTGCTCGGGCGCGGCTGCCGCCTCGTCCGGCCGGACCTCGCGTACGAGCCG*
*TCCCCGAACCTGCGGGTGCCGGTGCGGCTGGAGGTGACGTGCACA**TAA*
Legend
*P450 (italics)*
Start and stop codons in bold

Protein sequence
(Translated using Expasy from DNA sequences above)

SEQ ID NO: 116 (amino acid sequence of cytochrome SriC59 (304 aa))
MGPGALTDPDWVVPPVPQDVPEGGMAWLRARVARFSSGEAHVRRRALAVGPLG
GGDAADALRDTARVRTQALLDGAGVGPGSGPGTVDVMALVARVVPVEVLADFVG
LPVTAETAGLVGHVARAYHAHGETVPAADRALARLVTVCGGTWDEATAARIGLLV
QAYDATAGLIGNAAHRMLSCDTGDTGSASGTGDTPEGSAESAADVVTASLDRTLS
ADPPVRGTLRAPANGGDPVRIALLTDDGSLAFGAGPHACPGRAHARALAAGVLDA
LLGRGCRLVRPDLAYEPSPNLRVPVRLEVTCT-

SEQ ID NO: 117 (coding sequence of sriC60)
P450 sriC60: SRIM_00906

Figure 4 (continued)

*ATG**GACAATCCCTACCCCCTGTACCGGCGGCTGCGCGAAACCTCCCCCGTTCT*
*GTGGGATCCCGTACGCCATCACTGGACCGTCACCCGCCACCAGGAAGTCACC*
*CAGGCACTGCGCTCCCCGGCCCTGCACGCCGTACCCCGCCGCCTCGGCCCC*
*CGCACACCCCCCACCCTGCGCCTGCTCAACAGCGCCATGCTCGACTCCGATC*
*CGCCCGAGCACACCCGCCGCCGTCGCGTCTTCACCCAAGCCTTCACCCCGCG*
*CCTGACCGCAGACCTCGCACCCGCCATCACCCACCGCGTCGACGCCCTCCTC*
*GACCGCGTGCACGAAAGCGGCCACATGGACCTCATCGAAGACCTGGCCACTC*
*CACTGCCCCTGCACGTCATCGGCCAGCTGCTCGGCATACCCCCGCAAGACCG*
*CCCCCGCCTGCACGCCGGAGCCCGCGGCTACGCCCGACTGTGGGGCGGCGA*
*CGACACCGACCAGACCACCATCGGCCAAGCCGTCACCGACATCACCAGAGCC*
*ATCGACCACTGCCGCGAGCTGATCACCCAGCGTCGCAACGCTCCCCGCTCCG*
*ACCTGATCAGCCGTCTGGCCTCACCAGCCGGCCGGGCGGGCTCGCTCAGCGA*
*CGGCGAACTGGCCGCCAACCTCTTCATGGTCTTCACCGCAGGCCACTACACGA*
*CCACCGACTTCCTGGGAAACTCCGTCCTCGCACTGGCACACCACCCGCACCA*
*GTGGCAACAACTGTGCACGGACCCGGCACTGGCCTCCTCGGCCGTCACCGAA*
*CTGCTGCGCTACGAAGCCCCCGTCCAGTTCGTCATCCGCCTGGCCGCACAAG*
*ACCTCACCCTCGCCGGCCAGCGCATCACAGCCGGCCAGCTCGTCGTCCTTCT*
*GCTCGCCGCAGCGAACCGCGACCCACGGGCCTTCCCCGACCCCGACCGCCT*
*CGACCTCACACGCACTCCCAACCACCACCTCACCCTCGGCTTCGGCATCCACT*
*CCTGCCTGGGCACCGCCCTGGCCCGGCTCCAAGGCGAGATCACCCTGAGCC*
*GCCTGGCCGCCCGCATGCCCCGTCTCCGCCCGGCCGGCGACACCATCCGCT*
*GGAAGACCACCACCGGACTCCGCGGACCTCTCCGTCTATCCGTCCACTGGGA*
*CT**TAA*

Legend
*P450 (italics)*
Start and stop codons in bold

Protein sequence
(Translated using Expasy from DNA sequences above)

SEQ ID NO: 118 (amino acid sequence of cytochrome SriC60 (381 aa))
MDNPYPLYRRLRETSPVLWDPVRHHWTVTRHQEVTQALRSPALHAVPRRLGPRT
PPTLRLLNSAMLDSDPPEHTRRRRVFTQAFTPRLTADLAPAITHRVDALLDRVHES
GHMDLIEDLATPLPLHVIGQLLGIPPQDRPRLHAGARGYARLWGGDDTDQTTIGQA
VTDITRAIDHCRELITQRRNAPRSDLISRLASPAGRAGSLSDGELAANLFMVFTAGH
YTTTDFLGNSVLALAHHPHQWQQLCTDPALASSAVTELLRYEAPVQFVIRLAAQDL
TLAGQRITAGQLVVLLLAAANRDPRAFPDPDRLDLTRTPNHHLTLGFGIHSCLGTAL
ARLQGEITLSRLAARMPRLRPAGDTIRWKTTTGLRGPLRLSVHWD-

SEQ ID NO: 229 (synthetic DNA sequence of full optimization of SriC12, SriF05 and ribosome binding site of SriF05 by DNA2.0)
CAT*ATG**ACCGAAGCACTGCCTTTCCCACAAGACCGCACCTGTCCGTACGACCC*
*ACCGGCTGGCTACCAGCCGCTGAGAGATAGCCGTCCACTGAGCCGTGTTACG*
*TTGTATGATGGCCGTCCGGCGTGGGTCGTGACGGGCCACGCAGAGAGCCGTG*
*CACTGCTGACGGACCCGCGCTTGTCGGCTGATCGCCAGAACCCGGCGTTCCC*
*GTCCCCGGCTCCGCGTTTTGAGACTCTGCGTAAGGTCCGTACCCCGCTGCTG*
*GGCGTGGACGATCCGGAGCACAATACGCAGCGTCGTATGTTGATTCCGTCCTT*
*CAGCGTGAAGCGTGCAGCAGCACTGCGCCCGCGTATCCAAGAAATCGTGGAT*
*CGCCTGTTGGACGCTATGGAACAGCAAGGTCCTCCGGCGGAACTGGTTTCTG*
*CGTTCGCACTGCCGGTCCCGAGCATGGTCATCTGCGCCTTGCTGGGTGTCCC*
*GTACGCTGACCATGAACTGTTTGAGGGCCTGAGCCGTACTCTGCTGCAGAGCG*
*CAGACCCGCAAGAGGTCACCGAAGCCCGCGATAAACTGGAAGATTACTTTACC*
*GCACTGGTGGAGCGTAAGCGCAAAGAACCGGGTGACGGTCTGCTGGATGAAC*

Figure 4 (continued)

*TGATTGCGGAGCGCCTGGACAGCGGCGAGCTGGGCCATCGTGAACTGGTCCG*
*TATGGCGATGCTGCTGCTGGTTGCGGGTCATGAAACCACCTCCAACATGTTGA*
*GCCTGGGCACGTTCACCCTGCTGGAGCACCCGGAGCAATTTGCGGCGCTGCG*
*CGCTGATCCTAGCCTGCTGCCGGCGGCAGTGGAAGAATTGCTGCGTTTCCTGT*
*CTATCGCCGACGGCATGGTTCGTGTTGCGACCGAAGATATCGAGATCGGTGG*
*CGTTACGATTCGCGCGGATGATGGTGTGATCTTCAGCACGAGCGTGGTTAATC*
*GCGACGGTGCGGCGTATGCCTCACCGGATACCCTGGACTGGGAGCGTAGCGC*
*GCGTCACCATGTCGCTTTTGGTTTCGGTGTTCACCAGTGCCTGGGTCAGAACC*
*TGGCCCGTGCCGAGATGGAAATTGCATTTGGTGCGTTATTCGCCCGTTTTCCG*
*GGTCTGCGTCTTGCAGTGCCTGCGGCCGAGATTCCGGTGAAACCGGCGCACG*
*CGTTGCAAGGTCTGGTTGAGCTGCCGGTGACCTGGTGA*TAACGGCGGACCGC
CGCCCACACCCTGTACCCGTCAACGGAGGAGAGAAAAAATGAAAATTGACATT
GACACGAGCGTTTGTATCGGTAGCGGCCAATGTGTTCTGACTGCCCCGGGTGT
TTTTACCCAAGATGATGATGGTTTCAGCACGCTGCTGCCGGGTCGCGAAGATG
GTACGGGCGACCCATTAGTTCGTGAAGCCGCGCGCGTGCCCGGTGCAAGC
AATCGCGGTGACCGACGACTAATAATAGGAAGCTT

Legend
*P450 (italics)*
Ferredoxin

SEQ ID NO: 230 (coding sequence of R63W mutant of codon optimised sriC12)
*ATG**ACCGAAGCACTGCCTTTCCCACAAGACCGCACCTGTCCGTACGACCCACC*
*GGCTGGCTACCAGCCGCTGAGAGATAGCCGTCCACTGAGCCGTGTTACGTTG*
*TATGATGGCCGTCCGGCGTGGGTCGTGACGGGCCACGCAGAGAGCCGTGCA*
*CTGCTGACGGACCCGCGCTTGTCGGCTGATTGGCAGAACCCGGCGTTCCCGT*
*CCCCGGCTCCGCGTTTTGAGACTCTGCGTAAGGTCCGTACCCCGCTGCTGGG*
*CGTGGACGATCCGGAGCACAATACGCAGCGTCGTATGTTGATTCCGTCCTTCA*
*GCGTGAAGCGTGCAGCAGCACTGCGCCCGCGTATCCAAGAAATCGTGGATCG*
*CCTGTTGGACGCTATGGAACAGCAAGGTCCTCCGGCGGAACTGGTTTCTGCGT*
*TCGCACTGCCGGTCCCGAGCATGGTCATCTGCGCCTTGCTGGGTGTCCCGTA*
*CGCTGACCATGAACTGTTTGAGGGCCTGAGCCGTACTCTGCTGCAGAGCGCA*
*GACCCGCAAGAGGTCACCGAAGCCCGCGATAAACTGGAAGATTACTTTACCGC*
*ACTGGTGGAGCGTAAGCGCAAAGAACCGGGTGACGGTCTGCTGGATGAACTG*
*ATTGCGGAGCGCCTGGACAGCGGCGAGCTGGGCCATCGTGAACTGGTCCGTA*
*TGGCGATGCTGCTGCTGGTTGCGGGTCATGAAACCACCTCCAACATGTTGAGC*
*CTGGGCACGTTCACCCTGCTGGAGCACCCGGAGCAATTTGCGGCGCTGCGCG*
*CTGATCCTAGCCTGCTGCCGGCGGCAGTGGAAGAATTGCTGCGTTTCCTGTCT*
*ATCGCCGACGGCATGGTTCGTGTTGCGACCGAAGATATCGAGATCGGTGGCG*
*TTACGATTCGCGCGGATGATGGTGTGATCTTCAGCACGAGCGTGGTTAATCGC*
*GACGGTGCGGCGTATGCCTCACCGGATACCCTGGACTGGGAGCGTAGCGCGC*
*GTCACCATGTCGCTTTTGGTTTCGGTGTTCACCAGTGCCTGGGTCAGAACCTG*
*GCCCGTGCCGAGATGGAAATTGCATTTGGTGCGTTATTCGCCCGTTTTCCGGG*
*TCTGCGTCTTGCAGTGCCTGCGGCCGAGATTCCGGTGAAACCGGCGCACGCG*
*TTGCAAGGTCTGGTTGAGCTGCCGGTGACCTGGTGA*

Legend
*P450 (italics)*
Start and stop codons in bold

Protein sequence
(Translated using Expasy from DNA sequences above)

Figure 4 (continued)

SEQ ID NO: 231 (amino acid sequence of R63W mutant of codon optimised cytochrome SriC12 (395 aa))
MTEALPFPQDRTCPYDPPAGYQPLRDSRPLSRVTLYDGRPAWVVTGHAESRALLT
DPRLSADWQNPAFPSPAPRFETLRKVRTPLLGVDDPEHNTQRRMLIPSFSVKRAA
ALRPRIQEIVDRLLDAMEQQGPPAELVSAFALPVPSMVICALLGVPYADHELFEGLS
RTLLQSADPQEVTEARDKLEDYFTALVERKRKEPGDGLLDELIAERLDSGELGHRE
LVRMAMLLLVAGHETTSNMLSLGTFTLLEHPEQFAALRADPSLLPAAVEELLRFLSI
ADGMVRVATEDIEIGGVTIRADDGVIFSTSVVNRDGAAYASPDTLDWERSARHHVA
FGFGVHQCLGQNLARAEMEIAFGALFARFPGLRLAVPAAEIPVKPAHALQGLVELP
VTW-

SEQ ID NO: 232 (coding sequence of R63Y mutant of codon optimised sriC12)
*ATG**ACCGAAGCACTGCCTTTCCCACAAGACCGCACCTGTCCGTACGACCCACCGGCTGGCTACCAGC*
*CGCTGAGAGATAGCCGTCCACTGAGCCGTGTTACGTTGTATGATGGCCGTCCGGCGTGGGTCGTGA*
*CGGGCCACGCAGAGAGCCGTGCACTGCTGACGGACCCGCGCTTGTCGGCTGATTATCAGAACCCGG*
*CGTTCCCGTCCCCGGCTCCGCGTTTTGAGACTCTGCGTAAGGTCCGTACCCCGCTGCTGGGCGTGGA*
*CGATCCGGAGCACAATACGCAGCGTCGTATGTTGATTCCGTCCTTCAGCGTGAAGCGTGCAGCAGC*
*ACTGCGCCCGCGTATCCAAGAAATCGTGGATCGCCTGTTGGACGCTATGGAACAGCAAGGTCCTCC*
*GGCGGAACTGGTTTCTGCGTTCGCACTGCCGGTCCCGAGCATGGTCATCTGCGCCTTGCTGGGTGTC*
*CCGTACGCTGACCATGAACTGTTTGAGGGCCTGAGCCGTACTCTGCTGCAGAGCGCAGACCCGCAA*
*GAGGTCACCGAAGCCCGCGATAAACTGGAAGATTACTTTACCGCACTGGTGGAGCGTAAGCGCAAA*
*GAACCGGGTGACGGTCTGCTGGATGAACTGATTGCGGAGCGCCTGGACAGCGGCGAGCTGGGCCA*
*TCGTGAACTGGTCCGTATGGCGATGCTGCTGCTGGTTGCGGGTCATGAAACCACCTCCAACATGTTG*
*AGCCTGGGCACGTTCACCCTGCTGGAGCACCCGGAGCAATTTGCGGCGCTGCGCGCTGATCCTAGC*
*CTGCTGCCGGCGGCAGTGGAAGAATTGCTGCGTTTCCTGTCTATCGCCGACGGCATGGTTCGTGTTG*
*CGACCGAAGATATCGAGATCGGTGGCGTTACGATTCGCGCGGATGATGGTGTGATCTTCAGCACGA*
*GCGTGGTTAATCGCGACGGTGCGGCGTATGCCTCACCGGATACCCTGGACTGGGAGCGTAGCGCGC*
*GTCACCATGTCGCTTTTGGTTTCGGTGTTCACCAGTGCCTGGGTCAGAACCTGGCCCGTGCCGAGAT*
*GGAAATTGCATTTGGTGCGTTATTCGCCCGTTTTCCGGGTCTGCGTCTTGCAGTGCCTGCGGCCGAG*
*ATTCCGGTGAAACCGGCGCACGCGTTGCAAGGTCTGGTTGAGCTGCCGGTGACCTGG**TGA*

Legend
*P450 (italics)*
Start and stop codons in bold

Protein sequence
(Translated using Expasy from DNA sequences above)

SEQ ID NO: 233 (amino acid sequence of R63Y mutant of codon optimized cytochrome SriC12 (395 aa))
MTEALPFPQDRTCPYDPPAGYQPLRDSRPLSRVTLYDGRPAWVVTGHAESRALLT
DPRLSADYQNPAFPSPAPRFETLRKVRTPLLGVDDPEHNTQRRMLIPSFSVKRAAA
LRPRIQEIVDRLLDAMEQQGPPAELVSAFALPVPSMVICALLGVPYADHELFEGLSR
TLLQSADPQEVTEARDKLEDYFTALVERKRKEPGDGLLDELIAERLDSGELGHREL
VRMAMLLLVAGHETTSNMLSLGTFTLLEHPEQFAALRADPSLLPAAVEELLRFLSIA
DGMVRVATEDIEIGGVTIRADDGVIFSTSVVNRDGAAYASPDTLDWERSARHHVAF
GFGVHQCLGQNLARAEMEIAFGALFARFPGLRLAVPAAEIPVKPAHALQGLVELPV
TW-

SEQ ID NO: 234 (coding sequence of L171I mutant of codon optimised sriC12)
*ATG**ACCGAAGCACTGCCTTTCCCACAAGACCGCACCTGTCCGTACGACCCACCGGCTGGCTACCAGC*
*CGCTGAGAGATAGCCGTCCACTGAGCCGTGTTACGTTGTATGATGGCCGTCCGGCGTGGGTCGTGA*
*CGGGCCACGCAGAGAGCCGTGCACTGCTGACGGACCCGCGCTTGTCGGCTGATCGCCAGAACCCGG*

Figure 4 (continued)

*CGTTCCCGTCCCCGGCTCCGCGTTTTGAGACTCTGCGTAAGGTCCGTACCCCGCTGCTGGGCGTGGA*
*CGATCCGGAGCACAATACGCAGCGTCGTATGTTGATTCCGTCCTTCAGCGTGAAGCGTGCAGCAGC*
*ACTGCGCCCGCGTATCCAAGAAATCGTGGATCGCCTGTTGGACGCTATGGAACAGCAAGGTCCTCC*
*GGCGGAACTGGTTTCTGCGTTCGCACTGCCGGTCCCGAGCATGGTCATCTGCGCCTTGCTGGGTGTC*
*CCGTACGCTGACCATGAACTGTTTGAGGGCCTGAGCCGTACTCTGATTCAGAGCGCAGACCCGCAA*
*GAGGTCACCGAAGCCCGCGATAAACTGGAAGATTACTTTACCGCACTGGTGGAGCGTAAGCGCAAA*
*GAACCGGGTGACGGTCTGCTGGATGAACTGATTGCGGAGCGCCTGGACAGCGGCGAGCTGGGCCA*
*TCGTGAACTGGTCCGTATGGCGATGCTGCTGCTGGTTGCGGGTCATGAAACCACCTCCAACATGTTG*
*AGCCTGGGCACGTTCACCCTGCTGGAGCACCCGGAGCAATTTGCGGCGCTGCGCGCTGATCCTAGC*
*CTGCTGCCGGCGGCAGTGGAAGAATTGCTGCGTTTCCTGTCTATCGCCGACGGCATGGTTCGTGTTG*
*CGACCGAAGATATCGAGATCGGTGGCGTTACGATTCGCGCGGATGATGGTGTGATCTTCAGCACGA*
*GCGTGGTTAATCGCGACGGTGCGGCGTATGCCTCACCGGATACCCTGGACTGGGAGCGTAGCGCGC*
*GTCACCATGTCGCTTTTGGTTTCGGTGTTCACCAGTGCCTGGGTCAGAACCTGGCCCGTGCCGAGAT*
*GGAAATTGCATTTGGTGCGTTATTCGCCCGTTTTCCGGGTCTGCGTCTTGCAGTGCCTGCGGCCGAG*
*ATTCCGGTGAAACCGGCGCACGCGTTGCAAGGTCTGGTTGAGCTGCCGGTGACCTGG*TGA
Legend
*P450 (italics)*
Start and stop codons in bold

Protein sequence
(Translated using Expasy from DNA sequences above)

SEQ ID NO: 235 (amino acid sequence of L171I mutant of codon optimized cytochrome SriC12 (395 aa))
MTEALPFPQDRTCPYDPPAGYQPLRDSRPLSRVTLYDGRPAWVVTGHAESRALLT
DPRLSADRQNPAFPSPAPRFETLRKVRTPLLGVDDPEHNTQRRMLIPSFSVKRAA
ALRPRIQEIVDRLLDAMEQQGPPAELVSAFALPVPSMVICALLGVPYADHELFEGLS
RTLIQSADPQEVTEARDKLEDYFTALVERKRKEPGDGLLDELIAERLDSGELGHRE
LVRMAMLLLVAGHETTSNMLSLGTFTLLEHPEQFAALRADPSLLPAAVEELLRFLSI
ADGMVRVATEDIEIGGVTIRADDGVIFSTSVVNRDGAAYASPDTLDWERSARHHVA
FGFGVHQCLGQNLARAEMEIAFGALFARFPGLRLAVPAAEIPVKPAHALQGLVELP
VTW-

SEQ ID NO: 236 (coding sequence of L230I mutant of codon optimised sriC12)
*ATG**ACCGAAGCACTGCCTTTCCCACAAGACCGCACCTGTCCGTACGACCCACC*
*GGCTGGCTACCAGCCGCTGAGAGATAGCCGTCCACTGAGCCGTGTTACGTTG*
*TATGATGGCCGTCCGGCGTGGGTCGTGACGGGCCACGCAGAGAGCCGTGCA*
*CTGCTGACGGACCCGCGCTTGTCGGCTGATCGCCAGAACCCGGCGTTCCCGT*
*CCCCGGCTCCGCGTTTTGAGACTCTGCGTAAGGTCCGTACCCCGCTGCTGGG*
*CGTGGACGATCCGGAGCACAATACGCAGCGTCGTATGTTGATTCCGTCCTTCA*
*GCGTGAAGCGTGCAGCAGCACTGCGCCCGCGTATCCAAGAAATCGTGGATCG*
*CCTGTTGGACGCTATGGAACAGCAAGGTCCTCCGGCGGAACTGGTTTCTGCGT*
*TCGCACTGCCGGTCCCGAGCATGGTCATCTGCGCCTTGCTGGGTGTCCCGTA*
*CGCTGACCATGAACTGTTTGAGGGCCTGAGCCGTACTCTGCTGCAGAGCGCA*
*GACCCGCAAGAGGTCACCGAAGCCCGCGATAAACTGGAAGATTACTTTACCGC*
*ACTGGTGGAGCGTAAGCGCAAAGAACCGGGTGACGGTCTGCTGGATGAACTG*
*ATTGCGGAGCGCCTGGACAGCGGCGAGCTGGGCCATCGTGAACTGGTCCGTA*
*TGGCGATGATTCTGCTGGTTGCGGGTCATGAAACCACCTCCAACATGTTGAGC*
*CTGGGCACGTTCACCCTGCTGGAGCACCCGGAGCAATTTGCGGCGCTGCGCG*
*CTGATCCTAGCCTGCTGCCGGCGGCAGTGGAAGAATTGCTGCGTTTCCTGTCT*
*ATCGCCGACGGCATGGTTCGTGTTGCGACCGAAGATATCGAGATCGGTGGCG*
*TTACGATTCGCGCGGATGATGGTGTGATCTTCAGCACGAGCGTGGTTAATCGC*

Figure 4 (continued)

*GACGGTGCGGCGTATGCCTCACCGGATACCCTGGACTGGGAGCGTAGCGCGC*
*GTCACCATGTCGCTTTTGGTTTCGGTGTTCACCAGTGCCTGGGTCAGAACCTG*
*GCCCGTGCCGAGATGGAAATTGCATTTGGTGCGTTATTCGCCCGTTTTCCGGG*
*TCTGCGTCTTGCAGTGCCTGCGGCCGAGATTCCGGTGAAACCGGCGCACGCG*
*TTGCAAGGTCTGGTTGAGCTGCCGGTGACCTGGTGA*

Legend
*P450 (italics)*
Start and stop codons in bold

Protein sequence
(Translated using Expasy from DNA sequences above)

SEQ ID NO: 237 (amino acid sequence of L230I mutant of codon optimized cytochrome SriC12 (395 aa))
MTEALPFPQDRTCPYDPPAGYQPLRDSRPLSRVTLYDGRPAWVVTGHAESRALLT
DPRLSADRQNPAFPSPAPRFETLRKVRTPLLGVDDPEHNTQRRMLIPSFSVKRAA
ALRPRIQEIVDRLLDAMEQQGPPAELVSAFALPVPSMVICALLGVPYADHELFEGLS
RTLLQSADPQEVTEARDKLEDYFTALVERKRKEPGDGLLDELIAERLDSGELGHRE
LVRMAMILLVAGHETTSNMLSLGTFTLLEHPEQFAALRADPSLLPAAVEELLRFLSIA
DGMVRVATEDIEIGGVTIRADDGVIFSTSVVNRDGAAYASPDTLDWERSARHHVAF
GFGVHQCLGQNLARAEMEIAFGALFARFPGLRLAVPAAEIPVKPAHALQGLVELPV
TW-

SEQ ID NO: 250 (coding sequence of R63W R74Y mutant of codon optimised sriC12)
*ATGACCGAAGCACTGCCTTTCCCACAAGACCGCACCTGTCCGTACGACCCACC*
*GGCTGGCTACCAGCCGCTGAGAGATAGCCGTCCACTGAGCCGTGTTACGTTG*
*TATGATGGCCGTCCGGCGTGGGTCGTGACGGGCCACGCAGAGAGCCGTGCA*
*CTGCTGACGGACCCGCGCTTGTCGGCTGATTGGCAGAACCCGGCGTTCCCGT*
*CCCCGGCTCCGTATTTTGAGACTCTGCGTAAGGTCCGTACCCCGCTGCTGGGC*
*GTGGACGATCCGGAGCACAATACGCAGCGTCGTATGTTGATTCCGTCCTTCAG*
*CGTGAAGCGTGCAGCAGCACTGCGCCCGCGTATCCAAGAAATCGTGGATCGC*
*CTGTTGGACGCTATGGAACAGCAAGGTCCTCCGGCGGAACTGGTTTCTGCGTT*
*CGCACTGCCGGTCCCGAGCATGGTCATCTGCGCCTTGCTGGGTGTCCCGTAC*
*GCTGACCATGAACTGTTTGAGGGCCTGAGCCGTACTCTGCTGCAGAGCGCAG*
*ACCCGCAAGAGGTCACCGAAGCCCGCGATAAACTGGAAGATTACTTTACCGCA*
*CTGGTGGAGCGTAAGCGCAAAGAACCGGGTGACGGTCTGCTGGATGAACTGA*
*TTGCGGAGCGCCTGGACAGCGGCGAGCTGGGCCATCGTGAACTGGTCCGTAT*
*GGCGATGCTGCTGCTGGTTGCGGGTCATGAAACCACCTCCAACATGTTGAGCC*
*TGGGCACGTTCACCCTGCTGGAGCACCCGGAGCAATTTGCGGCGCTGCGCGC*
*TGATCCTAGCCTGCTGCCGGCGGCAGTGGAAGAATTGCTGCGTTTCCTGTCTA*
*TCGCCGACGGCATGGTTCGTGTTGCGACCGAAGATATCGAGATCGGTGGCGT*
*TACGATTCGCGCGGATGATGGTGTGATCTTCAGCACGAGCGTGGTTAATCGCG*
*ACGGTGCGGCGTATGCCTCACCGGATACCCTGGACTGGGAGCGTAGCGCGCG*
*TCACCATGTCGCTTTTGGTTTCGGTGTTCACCAGTGCCTGGGTCAGAACCTGG*
*CCCGTGCCGAGATGGAAATTGCATTTGGTGCGTTATTCGCCCGTTTTCCGGGT*
*CTGCGTCTTGCAGTGCCTGCGGCCGAGATTCCGGTGAAACCGGCGCACGCGT*
*TGCAAGGTCTGGTTGAGCTGCCGGTGACCTGGTGA*

Legend
*P450 (italics)*
Start and stop codons in bold

Figure 4 (continued)

Protein sequence
(Translated using Expasy from DNA sequences above)

SEQ ID NO: 251 (amino acid sequence of R63W R74Y mutant of codon optimized cytochrome SriC12 (395 aa))
MTEALPFPQDRTCPYDPPAGYQPLRDSRPLSRVTLYDGRPAWVVTGHAESRALLT
DPRLSADWQNPAFPSPAPYFETLRKVRTPLLGVDDPEHNTQRRMLIPSFSVKRAA
ALRPRIQEIVDRLLDAMEQQGPPAELVSAFALPVPSMVICALLGVPYADHELFEGLS
RTLLQSADPQEVTEARDKLEDYFTALVERKRKEPGDGLLDELIAERLDSGELGHRE
LVRMAMLLLVAGHETTSNMLSLGTFTLLEHPEQFAALRADPSLLPAAVEELLRFLSI
ADGMVRVATEDIEIGGVTIRADDGVIFSTSVVNRDGAAYASPDTLDWERSARHHVA
FGFGVHQCLGQNLARAEMEIAFGALFARFPGLRLAVPAAEIPVKPAHALQGLVELP
VTW-

SEQ ID NO: 252 (coding sequence of R63W L171A mutant of codon optimised sriC12)
*ATG**ACCGAAGCACTGCCTTTCCCACAAGACCGCACCTGTCCGTACGACCCACC*
*GGCTGGCTACCAGCCGCTGAGAGATAGCCGTCCACTGAGCCGTGTTACGTTG*
*TATGATGGCCGTCCGGCGTGGGTCGTGACGGGCCACGCAGAGAGCCGTGCA*
*CTGCTGACGGACCCGCGCTTGTCGGCTGATTGGCAGAACCCGGCGTTCCCGT*
*CCCCGGCTCCGCGTTTTGAGACTCTGCGTAAGGTCCGTACCCCGCTGCTGGG*
*CGTGGACGATCCGGAGCACAATACGCAGCGTCGTATGTTGATTCCGTCCTTCA*
*GCGTGAAGCGTGCAGCAGCACTGCGCCCGCGTATCCAAGAAATCGTGGATCG*
*CCTGTTGGACGCTATGGAACAGCAAGGTCCTCCGGCGGAACTGGTTTCTGCGT*
*TCGCACTGCCGGTCCCGAGCATGGTCATCTGCGCCTTGCTGGGTGTCCCGTA*
*CGCTGACCATGAACTGTTTGAGGGCCTGAGCCGTACTCTGGCGCAGAGCGCA*
*GACCCGCAAGAGGTCACCGAAGCCCGCGATAAACTGGAAGATTACTTTACCGC*
*ACTGGTGGAGCGTAAGCGCAAAGAACCGGGTGACGGTCTGCTGGATGAACTG*
*ATTGCGGAGCGCCTGGACAGCGGCGAGCTGGGCCATCGTGAACTGGTCCGTA*
*TGGCGATGCTGCTGCTGGTTGCGGGTCATGAAACCACCTCCAACATGTTGAGC*
*CTGGGCACGTTCACCCTGCTGGAGCACCCGGAGCAATTTGCGGCGCTGCGCG*
*CTGATCCTAGCCTGCTGCCGGCGGCAGTGGAAGAATTGCTGCGTTTCCTGTCT*
*ATCGCCGACGGCATGGTTCGTGTTGCGACCGAAGATATCGAGATCGGTGGCG*
*TTACGATTCGCGCGGATGATGGTGTGATCTTCAGCACGAGCGTGGTTAATCGC*
*GACGGTGCGGCGTATGCCTCACCGGATACCCTGGACTGGGAGCGTAGCGCGC*
*GTCACCATGTCGCTTTTGGTTTCGGTGTTCACCAGTGCCTGGGTCAGAACCTG*
*GCCCGTGCCGAGATGGAAATTGCATTTGGTGCGTTATTCGCCCGTTTTCCGGG*
*TCTGCGTCTTGCAGTGCCTGCGGCCGAGATTCCGGTGAAACCGGCGCACGCG*
*TTGCAAGGTCTGGTTGAGCTGCCGGTGACCTGG**TGA*

Legend
*P450 (italics)*
Start and stop codons in bold

Protein sequence
(Translated using Expasy from DNA sequences above)

SEQ ID NO: 253 (amino acid sequence of R63W L171A mutant of codon optimized cytochrome SriC12 (395 aa))
MTEALPFPQDRTCPYDPPAGYQPLRDSRPLSRVTLYDGRPAWVVTGHAESRALLT
DPRLSADWQNPAFPSPAPRFETLRKVRTPLLGVDDPEHNTQRRMLIPSFSVKRAA
ALRPRIQEIVDRLLDAMEQQGPPAELVSAFALPVPSMVICALLGVPYADHELFEGLS

Figure 4 (continued)

RTLAQSADPQEVTEARDKLEDYFTALVERKRKEPGDGLLDELIAERLDSGELGHRE
LVRMAMLLLVAGHETTSNMLSLGTFTLLEHPEQFAALRADPSLLPAAVEELLRFLSI
ADGMVRVATEDIEIGGVTIRADDGVIFSTSVVNRDGAAYASPDTLDWERSARHHVA
FGFGVHQCLGQNLARAEMEIAFGALFARFPGLRLAVPAAEIPVKPAHALQGLVELP
VTW-

SEQ ID NO: 254 (coding sequence of R74Y L171I R183W mutant of codon optimised sriC12)
*ATG**ACCGAAGCACTGCCTTTCCCACAAGACCGCACCTGTCCGTACGACCCACC*
*GGCTGGCTACCAGCCGCTGAGAGATAGCCGTCCACTGAGCCGTGTTACGTTG*
*TATGATGGCCGTCCGGCGTGGGTCGTGACGGGCCACGCAGAGAGCCGTGCA*
*CTGCTGACGGACCCGCGCTTGTCGGCTGATCGCCAGAACCCGGCGTTCCCGT*
*CCCCGGCTCCGTATTTTGAGACTCTGCGTAAGGTCCGTACCCCGCTGCTGGGC*
*GTGGACGATCCGGAGCACAATACGCAGCGTCGTATGTTGATTCCGTCCTTCAG*
*CGTGAAGCGTGCAGCAGCACTGCGCCCGCGTATCCAAGAAATCGTGGATCGC*
*CTGTTGGACGCTATGGAACAGCAAGGTCCTCCGGCGGAACTGGTTTCTGCGTT*
*CGCACTGCCGGTCCCGAGCATGGTCATCTGCGCCTTGCTGGGTGTCCCGTAC*
*GCTGACCATGAACTGTTTGAGGGCCTGAGCCGTACTCTGGCGCAGAGCGCAG*
*ACCCGCAAGAGGTCACCGAAGCCTGGGATAAACTGGAAGATTACTTTACCGCA*
*CTGGTGGAGCGTAAGCGCAAAGAACCGGGTGACGGTCTGCTGGATGAACTGA*
*TTGCGGAGCGCCTGGACAGCGGCGAGCTGGGCCATCGTGAACTGGTCCGTAT*
*GGCGATGCTGCTGCTGGTTGCGGGTCATGAAACCACCTCCAACATGTTGAGCC*
*TGGGCACGTTCACCCTGCTGGAGCACCCGGAGCAATTTGCGGCGCTGCGCGC*
*TGATCCTAGCCTGCTGCCGGCGGCAGTGGAAGAATTGCTGCGTTTCCTGTCTA*
*TCGCCGACGGCATGGTTCGTGTTGCGACCGAAGATATCGAGATCGGTGGCGT*
*TACGATTCGCGCGGATGATGGTGTGATCTTCAGCACGAGCGTGGTTAATCGCG*
*ACGGTGCGGCGTATGCCTCACCGGATACCCTGGACTGGGAGCGTAGCGCGCG*
*TCACCATGTCGCTTTTGGTTTCGGTGTTCACCAGTGCCTGGGTCAGAACCTGG*
*CCCGTGCCGAGATGGAAATTGCATTTGGTGCGTTATTCGCCCGTTTTCCGGGT*
*CTGCGTCTTGCAGTGCCTGCGGCCGAGATTCCGGTGAAACCGGCGCACGCGT*
*TGCAAGGTCTGGTTGAGCTGCCGGTGACCTGG**TGA*

Legend
*P450 (italics)*
Start and stop codons in bold

Protein sequence
(Translated using Expasy from DNA sequences above)

SEQ ID NO: 255 (amino acid sequence of R74Y L171A R183W mutant of codon optimized cytochrome SriC12 (395 aa))
MTEALPFPQDRTCPYDPPAGYQPLRDSRPLSRVTLYDGRPAWVVTGHAESRA
LLTDPRLSADRQNPAFPSPAPYFETLRKVRTPLLGVDDPEHNTQRRMLIPSFSV
KRAAALRPRIQEIVDRLLDAMEQQGPPAELVSAFALPVPSMVICALLGVPYADH
ELFEGLSRTLAQSADPQEVTEAWDKLEDYFTALVERKRKEPGDGLLDELIAERL
DSGELGHRELVRMAMLLLVAGHETTSNMLSLGTFTLLEHPEQFAALRADPSLL
PAAVEELLRFLSIADGMVRVATEDIEIGGVTIRADDGVIFSTSVVNRDGAAYASP
DTLDWERSARHHVAFGFGVHQCLGQNLARAEMEIAFGALFARFPGLRLAVPA
AEIPVKPAHALQGLVELPVTW-

Figure 4 (continued)

SEQ ID NO: 256 (coding sequence of R63W R74Y L171A mutant of codon optimised sriC12)
*ATG**ACCGAAGCACTGCCTTTCCCACAAGACCGCACCTGTCCGTACGACCCACC
GGCTGGCTACCAGCCGCTGAGAGATAGCCGTCCACTGAGCCGTGTTACGTTG
TATGATGGCCGTCCGGCGTGGGTCGTGACGGGCCACGCAGAGAGCCGTGCA
CTGCTGACGGACCCGCGCTTGTCGGCTGATTGGCAGAACCCGGCGTTCCCGT
CCCCGGCTCCGTATTTTGAGACTCTGCGTAAGGTCCGTACCCCGCTGCTGGGC
GTGGACGATCCGGAGCACAATACGCAGCGTCGTATGTTGATTCCGTCCTTCAG
CGTGAAGCGTGCAGCAGCACTGCGCCCGCGTATCCAAGAAATCGTGGATCGC
CTGTTGGACGCTATGGAACAGCAAGGTCCTCCGGCGGAACTGGTTTCTGCGTT
CGCACTGCCGGTCCCGAGCATGGTCATCTGCGCCTTGCTGGGTGTCCCGTAC
GCTGACCATGAACTGTTTGAGGGCCTGAGCCGTACTCTGGCGCAGAGCGCAG
ACCCGCAAGAGGTCACCGAAGCCCGCGATAAACTGGAAGATTACTTTACCGCA
CTGGTGGAGCGTAAGCGCAAAGAACCGGGTGACGGTCTGCTGGATGAACTGA
TTGCGGAGCGCCTGGACAGCGGCGAGCTGGGCCATCGTGAACTGGTCCGTAT
GGCGATGCTGCTGCTGGTTGCGGGTCATGAAACCACCTCCAACATGTTGAGCC
TGGGCACGTTCACCCTGCTGGAGCACCCGGAGCAATTTGCGGCGCTGCGCGC
TGATCCTAGCCTGCTGCCGGCGGCAGTGGAAGAATTGCTGCGTTTCCTGTCTA
TCGCCGACGGCATGGTTCGTGTTGCGACCGAAGATATCGAGATCGGTGGCGT
TACGATTCGCGCGGATGATGGTGTGATCTTCAGCACGAGCGTGGTTAATCGCG
ACGGTGCGGCGTATGCCTCACCGGATACCCTGGACTGGGAGCGTAGCGCGCG
TCACCATGTCGCTTTTGGTTTCGGTGTTCACCAGTGCCTGGGTCAGAACCTGG
CCCGTGCCGAGATGGAAATTGCATTTGGTGCGTTATTCGCCCGTTTTCCGGGT
CTGCGTCTTGCAGTGCCTGCGGCCGAGATTCCGGTGAAACCGGCGCACGCGT
TGCAAGGTCTGGTTGAGCTGCCGGTGACCTGG**TGA*

Legend
*P450 (italics)*
Start and stop codons in bold

Protein sequence
(Translated using Expasy from DNA sequences above)

SEQ ID NO: 257 (amino acid sequence of R63W R74Y L171A mutant of codon optimized cytochrome SriC12 (395 aa))
MTEALPFPQDRTCPYDPPAGYQPLRDSRPLSRVTLYDGRPAWVVTGHAESRA
LLTDPRLSADWQNPAFPSPAPYFETLRKVRTPLLGVDDPEHNTQRRMLIPSFS
VKRAAALRPRIQEIVDRLLDAMEQQGPPAELVSAFALPVPSMVICALLGVPYAD
HELFEGLSRTLAQSADPQEVTEARDKLEDYFTALVERKRKEPGDGLLDELIAER
LDSGELGHRELVRMAMLLLVAGHETTSNMLSLGTFTLLEHPEQFAALRADPSL
LPAAVEELLRFLSIADGMVRVATEDIEIGGVTIRADDGVIFSTSVVNRDGAAYAS
PDTLDWERSARHHVAFGFGVHQCLGQNLARAEMEIAFGALFARFPGLRLAVP
AAEIPVKPAHALQGLVELPVTW- Chromatograms of post-reaction extract using lyophilised material of recombinant $P450_{SriC12}$, $ferredoxin_{SriF05}$ and ferredoxin $reductase_{SCF15A}$, as described in example 5, dosed with 100 mg/L bosentan. Top to bottom is $UV_{268nm}$, $EIC_{552m/z}$ (bosentan (1.80 mins)), $EIC_{568m/z}$ (hydroxy-bosentan, (1.47 mins, 2.8 % yield of parent-derived products) and $EIC_{538m/z}$ (*O*-demethyl-bosentan (1.71 mins, 3.3 % yield).

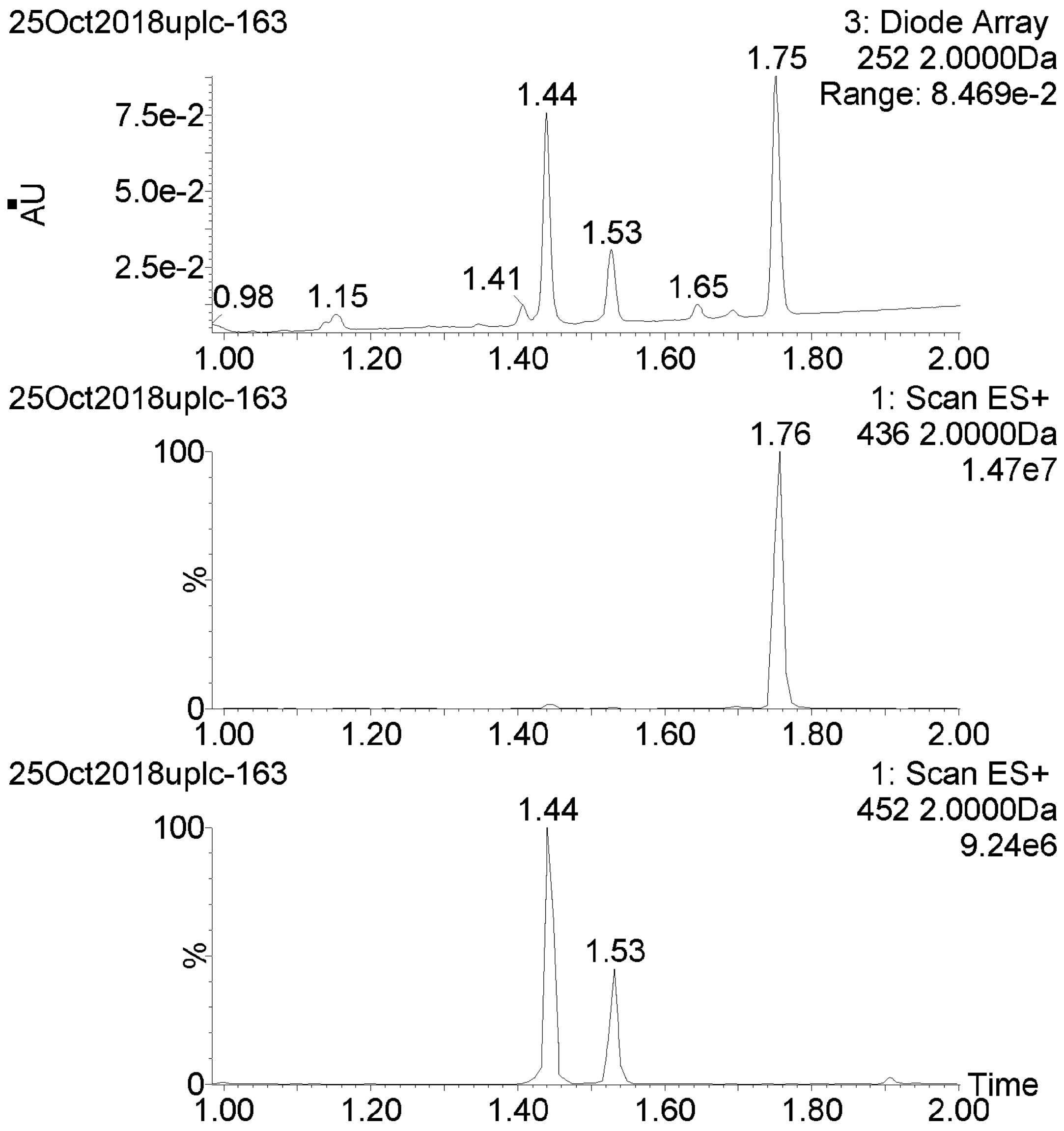

Chromatograms of post-reaction extract using lyophilised material of recombinant $P450_{SriC12}$, $ferredoxin_{SriF05}$ and ferredoxin $reductase_{SCF15A}$, as described in example 5, dosed with 100 mg/L valsartan. Top to bottom is $UV_{252nm}$, $EIC_{436m/z}$ (valsartan (1.75 mins)) and $EIC_{452m/z}$ (hydroxy-valsartan derivatives, (1.44 mins, 38.6 % yield, and 1.53 mins, 14.8 % yield of parent-derived products, respectively).

Figure 15b

Chromatograms of post-reaction extract using lyophilised material of recombinant $P450_{SriC12}$, $ferredoxin_{SriF05}$ and ferredoxin $reductase_{SCF15A}$, as described in example 5, dosed with 100 mg/L ritonavir. Top to bottom is $UV_{225nm}$, $EIC_{721m/z}$ (ritonavir (1.88 mins)) and $EIC_{737m/z}$ (hydroxy-ritonavir derivative, (1.72 mins, 14.2 % yield of parent-derived products).

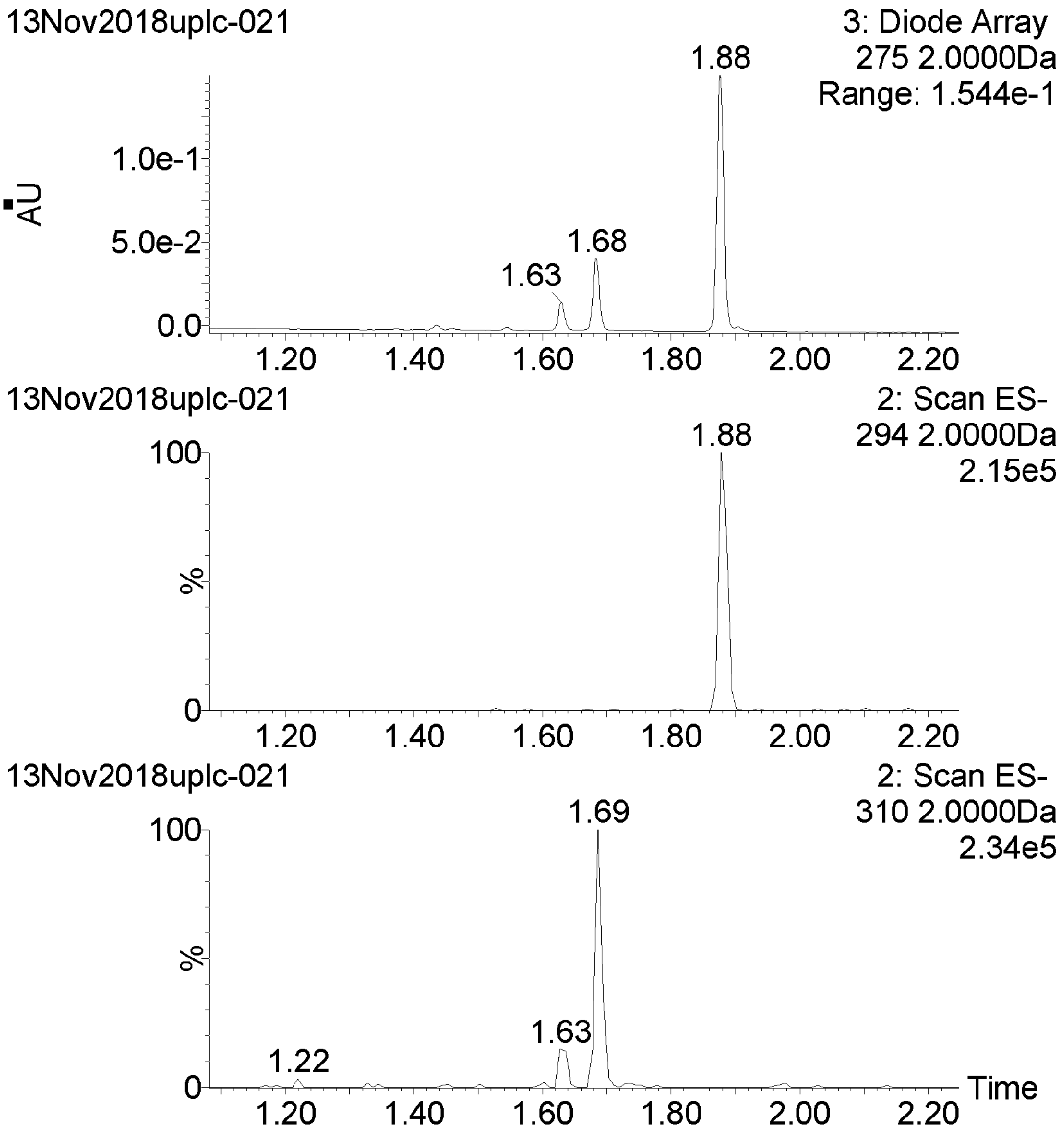

Chromatograms of post-reaction extract using lyophilised material of recombinant $P450_{SriC12}$, $ferredoxin_{SriF05}$ and ferredoxin $reductase_{SCF15A}$, as described in example 5, dosed with 100 mg/L diclofenac. Top to bottom is $UV_{275nm}$, $EIC_{294m/z}$ (diclofenac (1.88 mins)) and $EIC_{310m/z}$ (hydroxy-diclofenac derivatives, (1.63 mins, 7.6 % yield, and 1.69 mins, 19.7 % yield of parent-derived products, respectively).

Figure 15d

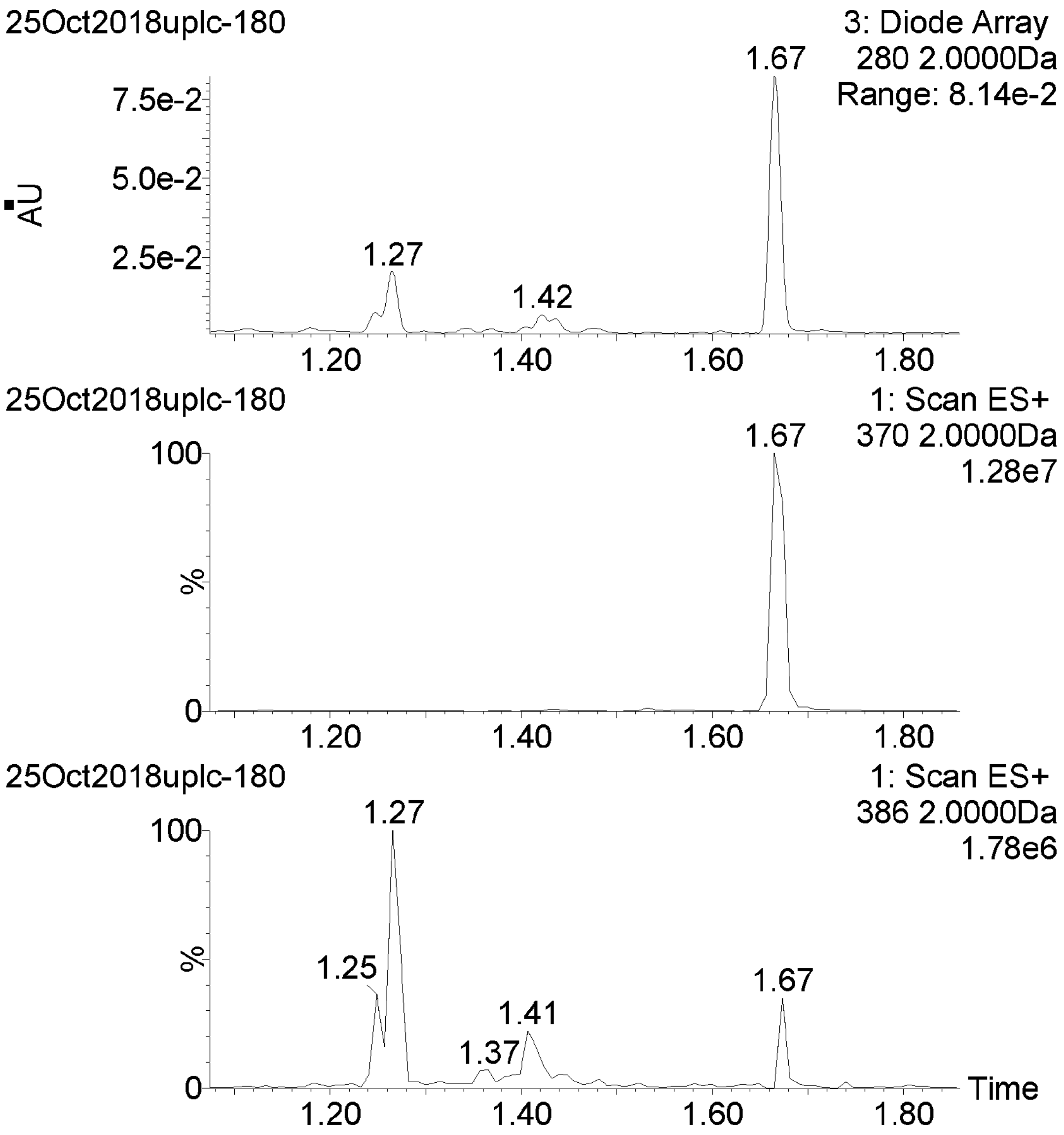

Chromatograms of post-reaction extract using lyophilised material of recombinant $P450_{SriC12}$, $ferredoxin_{SriF05}$ and ferredoxin $reductase_{SCF15A}$, as described in example 5, dosed with 100 mg/L tivantinib. Top to bottom is $UV_{280nm}$, $EIC_{370m/z}$ (tivantinib (1.67 mins)) and $EIC_{386m/z}$ (hydroxy-tivantinib derivatives, (1.25 mins, 5.2 % yield; 1.27 mins, 18.4 % yield; 1.37 mins, 1.2 % yield; and 1.41 mins, 5.2 % yield of parent-derived products, respectively).

Figure 15e

Chromatograms of post-reaction extract using lyophilised material of recombinant $P450_{SriC20}$, $ferredoxin_{Fd1}$ and ferredoxin $reductase_{SCF15A}$, as described in example 5, dosed with 100 mg/L vanoxerine. Top to bottom is $UV_{220nm}$, $EIC_{451m/z}$ (vanoxerine (1.41 mins)) and $EIC_{467m/z}$ (hydroxy-vanoxerine derivative, (1.28 mins, 22.9 % yield of parent-derived product).

Chromatograms of post-reaction extract using lyophilised material of recombinant $P450_{SriC20}$, $ferredoxin_{Fd1}$ and ferredoxin $reductase_{SCF15A}$, as described in example 5, dosed with 100 mg/L bosentan. Top to bottom is $UV_{268nm}$, $EIC_{552m/z}$ (bosentan (1.81 mins)) and $EIC_{568m/z}$ (hydroxy-bosentan derivative, (1.48 mins, 23.9 % yield of parent-derived product).

Chromatograms of post-reaction extract using lyophilised material of recombinant $P450_{SriC20}$, $ferredoxin_{Fd1}$ and ferredoxin $reductase_{SCF15A}$, as described in example 5, dosed with 100 mg/L ritonavir. Top to bottom is $UV_{225nm}$, $EIC_{721m/z}$ (ritonavir (1.91 mins)) and $EIC_{737m/z}$ (hydroxy-bosentan derivative, (1.68 mins, 43.7 % yield of parent-derived product).

Chromatograms of post-reaction extract using lyophilised material of recombinant $P450_{SriC20}$, $ferredoxin_{Fd1}$ and ferredoxin $reductase_{SCF15A}$, as described in example 5, dosed with 100 mg/L cyclosporin. Top to bottom is $EIC_{1203+1225m/z}$ (cyclosporine A (2.37 mins)) and $EIC_{1219+1241m/z}$ (hydroxy-cyclosporine A derivative, (2.11 mins, 4.1 % yield of parent-derived product).

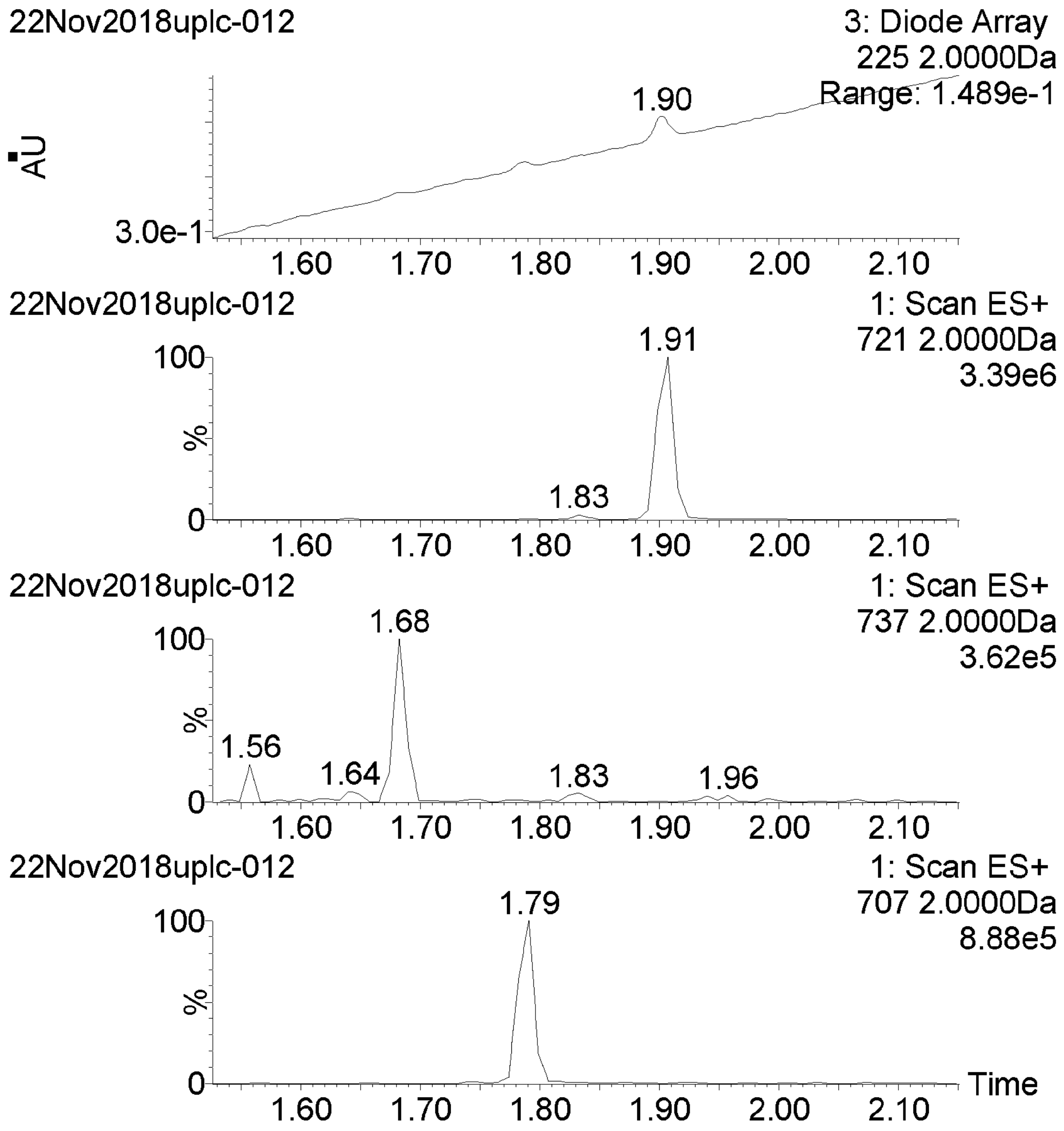

Chromatograms of post-reaction extract using lyophilised material of recombinant $P450_{SriC22}$, $ferredoxin_{Fd1}$ and ferredoxin $reductase_{SCF15A}$, as described in example 5, dosed with 100 mg/L ritonavir. Top to bottom is $UV_{225nm}$, $EIC_{721m/z}$ (ritonavir (1.90 mins)), $EIC_{737m/z}$ (hydroxyisopropyl-ritonavir, (1.68 mins, 11.7 % yield of parent-derived products) and $EIC_{707m/z}$ (*N*-demethyl-ritonavir (1.79 mins, 20.7 % yield).

Figure 15j

Chromatograms of post-reaction extract using lyophilised material of recombinant $P450_{SriC22}$, $ferredoxin_{Fd1}$ and ferredoxin $reductase_{SCF15A}$, as described in example 5, dosed with 100 mg/L cyclosporin. Top to bottom is $EIC_{1203+1225m/z}$ (cyclosporine A (2.37 mins)) and $EIC_{1219+1241m/z}$ (hydroxy-cyclosporine A derivative, (2.18 mins, 38.8 % yield of parent-derived product).

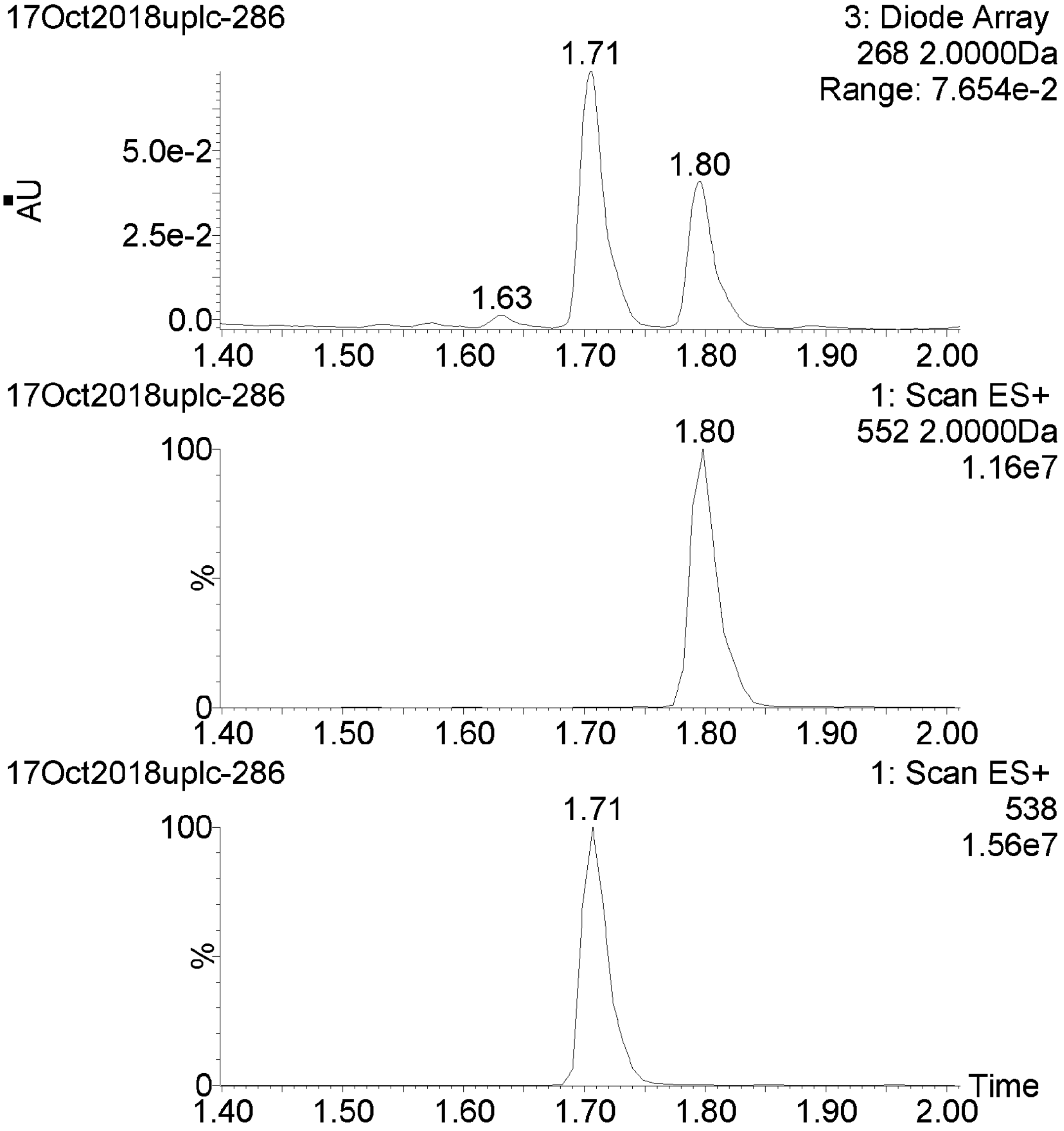

Chromatograms of post-reaction extract using lyophilised material of recombinant R63W mutant of codon-optimised P450$_{SriC12}$ [SEQ ID No: 231], ferredoxin$_{SriF05}$ and ferredoxin reductase$_{SCF15A}$, as described in example 5, dosed with 100 mg/L bosentan. Top to bottom is UV$_{268nm}$, EIC$_{552m/z}$ (bosentan (1.80 mins)) and EIC$_{538m/z}$ (*O*-demethyl-bosentan (1.71 mins, 63.2 % yield). The yield of *O*-demethyl-bosentan is considerably increased in comparison with that produced with the native P450$_{SriC12}$ (see Figure 15a).

Figure 15l

Chromatograms of post-reaction extract using lyophilised material of $P450_{SriC01}$ [SEQ ID No: 2], as described in example 5, dosed with 100 mg/L 7-ethoxycoumarin. Top to bottom is $UV_{322nm}$, $EIC_{191m/z}$ (7-ethoxycoumarin (1.44 mins)), $EIC_{177m/z}$ (unidentified hydroxylated 7-hydroxycoumarin derivatives (0.91, 0.83, 0.81 mins, 19.4 % combined yield)) and $EIC_{161m/z}$ (7-hydroxycoumarin (0.99 mins, 70.9 % yield).

Chromatograms of post-reaction extract using lyophilised material of $P450_{SriC01}$ [SEQ ID No: 2], as described in example 5A, dosed with 100 mg/L vanoxerine. Top to bottom is $UV_{220nm}$, $EIC_{451m/z}$ (vanoxerine (1.39 mins)) and $EIC_{467m/z}$ (unidentified hydroxy-vanoxerine derivatives, (1.32, 1.28, 1.24, 1.20 mins, combined yield 87.3 %)).

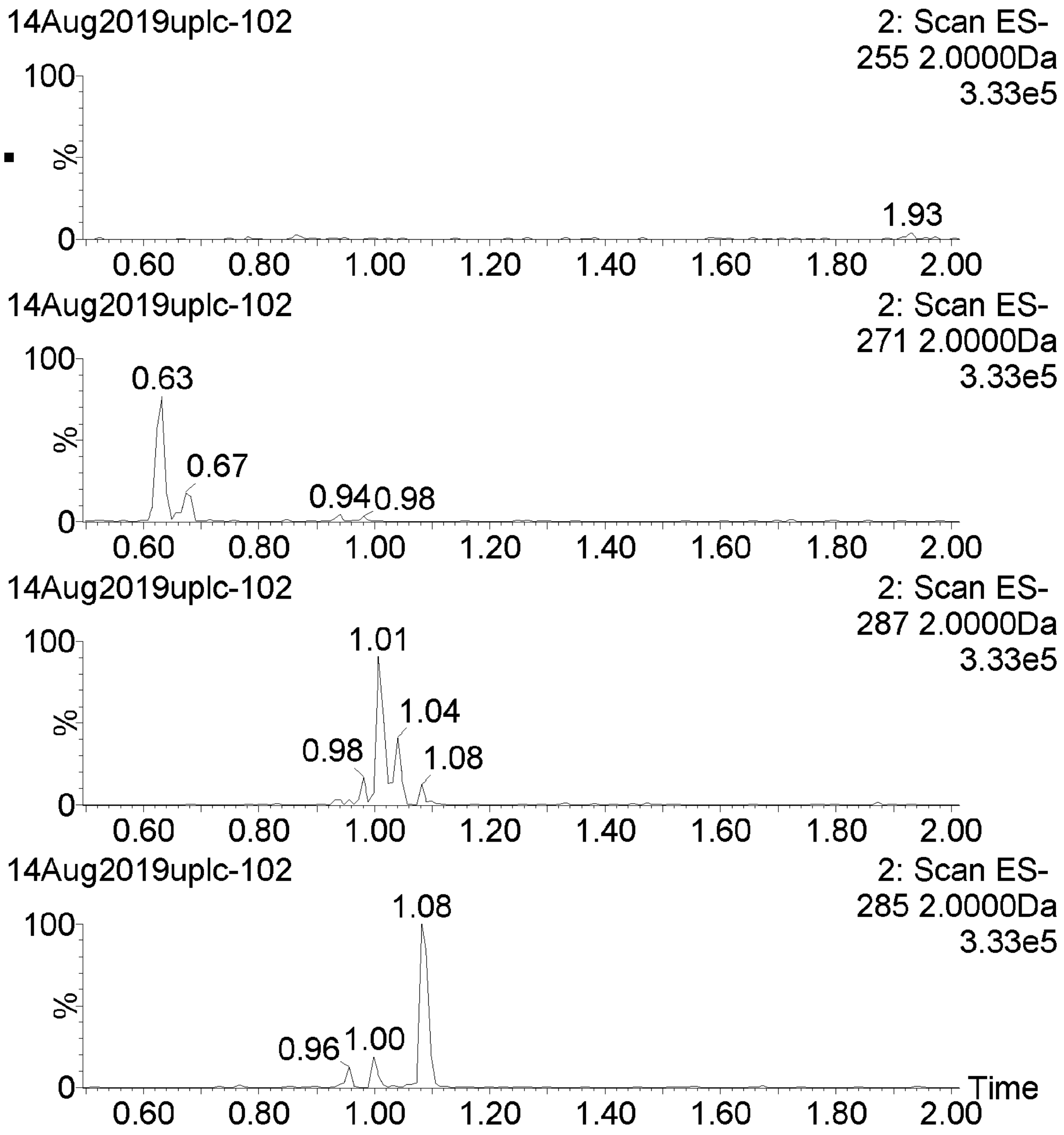

Chromatograms of post-reaction extract using lyophilised material of $P450_{SriC01}$ [SEQ ID No: 2], as described in example 5A, dosed with 100 mg/L palmitic acid. Top to bottom is $EIC_{255m/z}$ (palmitic acid (1.93 mins)), $EIC_{271m/z}$ (unidentified hydroxy-palmitic acid derivatives, (0.67, 0.63 mins, combined yield 29.8 %)), $EIC_{287m/z}$ (unidentified dihydroxy-palmitic acid derivatives, (1.04, 1.01 mins, combined yield 39.4 %) and $EIC_{285m/z}$ (unidentified hydroxyketo-palmitic acid derivative, (1.08 mins, yield 29.6 %)).

Figure 15o

Chromatograms of post-reaction extract using lyophilised material of $P450_{SriC14}$ [SEQ ID No: 14], $ferredoxin_{SriF06}$ and ferredoxin $reductase_{SCF15A}$, as described in example 5, dosed with 100 mg/L diclofenac. Top to bottom is $UV_{275nm}$, $EIC_{294m/z}$ (diclofenac (1.83 mins)) and $EIC_{310m/z}$ (4'-hydroxydiclofenac (1.69 mins, 47.9 % yield)).

Chromatograms of post-reaction extract using lyophilised material of $P450_{SriC14}$ [SEQ ID No: 14], $ferredoxin_{SriF06}$ and ferredoxin $reductase_{SCF15A}$, as described in example 5, dosed with 100 mg/L valsartan. Top to bottom is $UV_{254nm}$, $EIC_{436m/z}$ (valsartan (1.68 mins)) and $EIC_{452m/z}$ (4-hydroxyvaleryl-valsartan, (24.3 % yield). Component at 1.47 mins is unrelated.

Chromatograms of post-reaction extract using lyophilised material of P450$_{SriC01}$ [SEQ ID No: 2], as described in example 5, dosed with 100 mg/L progesterone. Top to bottom is UV$_{240nm}$, EIC$_{315m/z}$ (progesterone (1.90 mins)) and EIC$_{331m/z}$ & EIC$_{347m/z}$ (hydroxy-progesterone & dihydroxy-progesterone derivatives, (1.44 - 1.64 mins & 1.17 - 1.24mins; 80.1 % combined yield).

Chromatograms of post-reaction extract using lyophilised material of $P450_{SriC01}$ [SEQ ID No: 2], as described in example 5, dosed with 100 mg/L prednisolone. Top to bottom is $UV_{240nm}$, $EIC_{361m/z}$ (prednisolone (1.26 mins)) and $EIC_{377m/z}$ (hydroxy-prednisolone derivatives 0.84, 0.89, 0.98 & 1.19 mins) & $EIC_{393m/z}$ (dihydroxy-prednisolone derivative 0.82 mins), (64.2 % combined yield). Component at 1.16 mins is unrelated.

Chromatograms of post-reaction extract using lyophilised material of as described in example 5, $P450_{SriC01}$ [SEQ ID No: 2], dosed with 100 mg/L diclofenac. Top to bottom is $UV_{275nm}$, $EIC_{294m/z}$ (diclofenac (1.81 mins)) and $EIC_{310m/z}$ (5-hydroxydiclofenac and 4'-hydroxydiclofenac, (1.57 mins, 11.6 % yield, and 1.62 mins, 25.4 % yield, respectively).

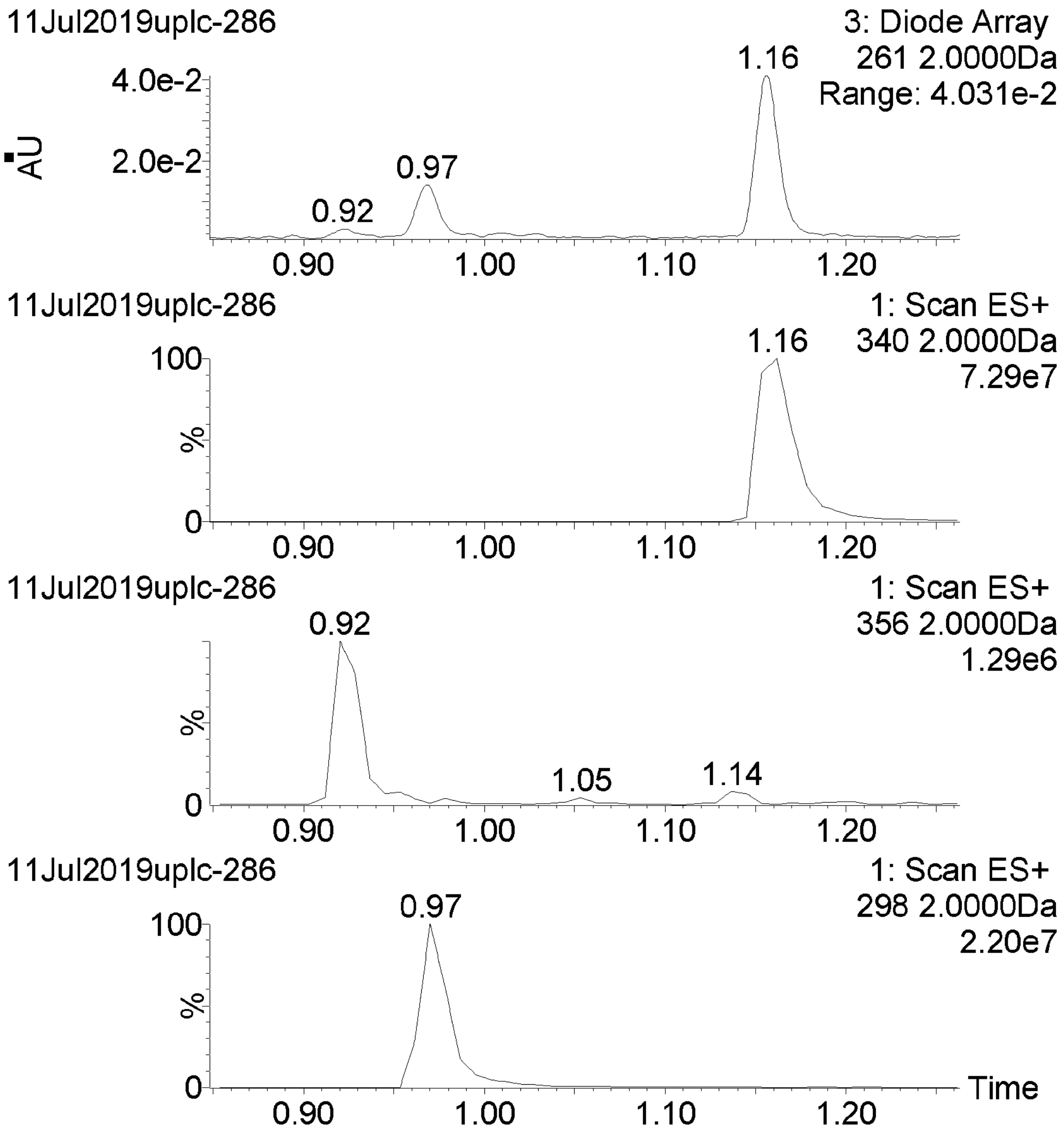

Chromatograms of post-reaction extract using lyophilised material of recombinant R63W, R74Y mutant of codon-optimised $P450_{SriC12}$ [SEQ ID No: 251], $ferredoxin_{SriF05}$ and ferredoxin $reductase_{SCF15A}$, as described in example 5, dosed with 100 mg/L disopyramide. Top to bottom is $UV_{261nm}$, $EIC_{340m/z}$ (disopyramide (1.16 mins)), $EIC_{356m/z}$ (hydroxy-disopyramide, (0.92 mins, 4.6 % yield) and $EIC_{298m/z}$ (*N*-deisopropyl-disopyramide (0.97 mins, 22.6 % yield). These products are not observed with the native $P450_{SriC12}$ or its R63W mutant.

Figure 15u

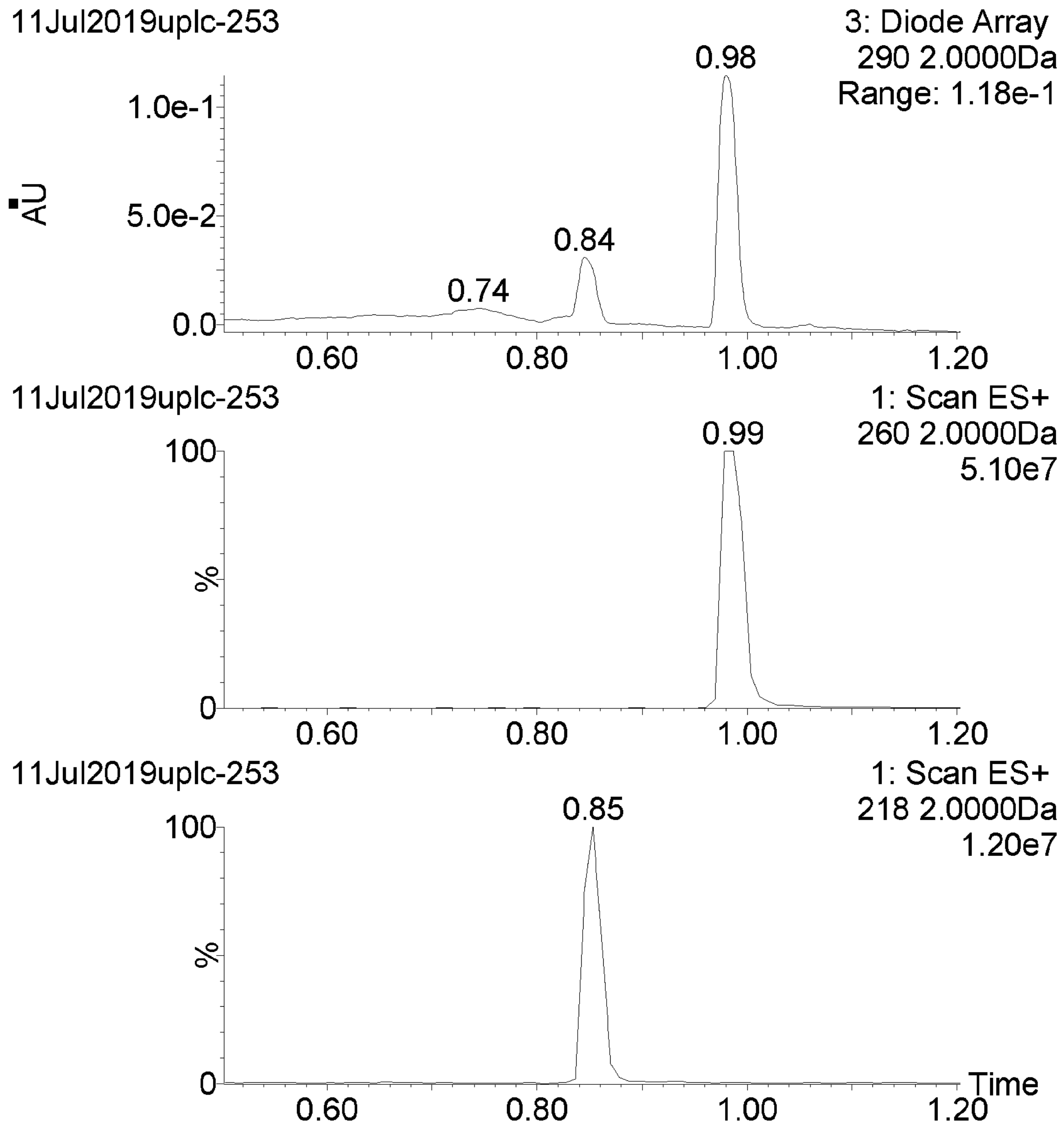

Chromatograms of post-reaction extract using lyophilised material of recombinant R63W, R74Y mutant of codon-optimised $P450_{SriC12}$ [SEQ ID No: 251], $ferredoxin_{SriF05}$ and ferredoxin $reductase_{SCF15A}$, as described in example 5, dosed with 100 mg/L propranolol. Top to bottom is $UV_{290nm}$, $EIC_{260m/z}$ (propranolol (0.99 mins)) and $EIC_{218m/z}$ (*N*-deisopropyl-propranolol (0.85 mins, 22.2 % yield). This product is not observed with the native $P450_{SriC12}$ or its R63W mutant.

Figure 15v

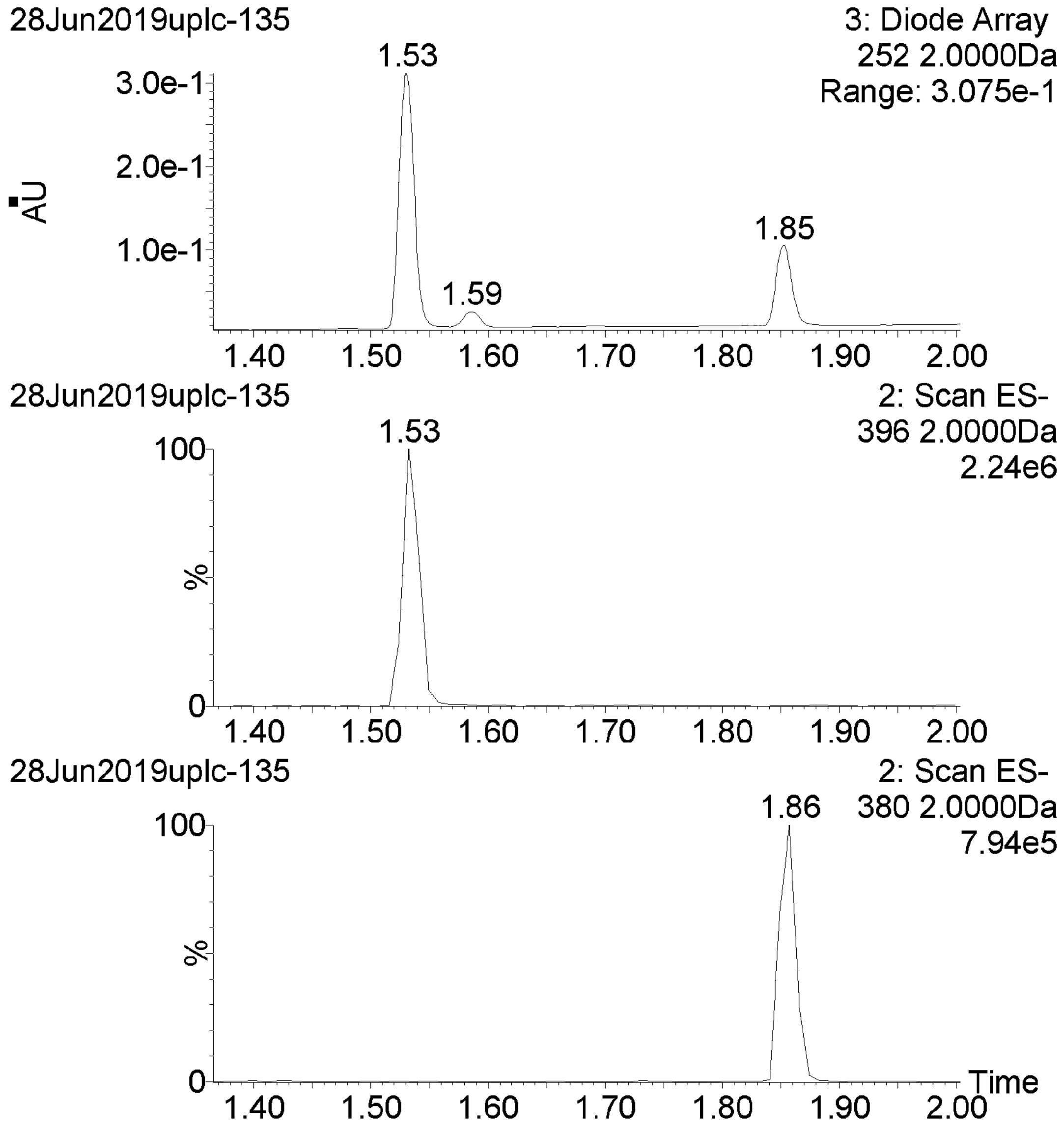

Chromatograms of post-reaction extract using lyophilised material of recombinant R63W, R74Y mutant of codon-optimised $P450_{SriC12}$ [SEQ ID No: 251], $ferredoxin_{SriF05}$ and ferredoxin $reductase_{SCF15A}$, as described in example 5, dosed with 100 mg/L celecoxib. Top to bottom is $UV_{252nm}$, $EIC_{380m/z}$ (celecoxib (1.86 mins)) and $EIC_{396m/z}$ (hydroxy-celecoxib (1.53 mins, 75.6 % yield). The yield of this product is significantly increased compared to reactions with the native $P450_{SriC12}$ or its R63W mutant.

Figure 15w

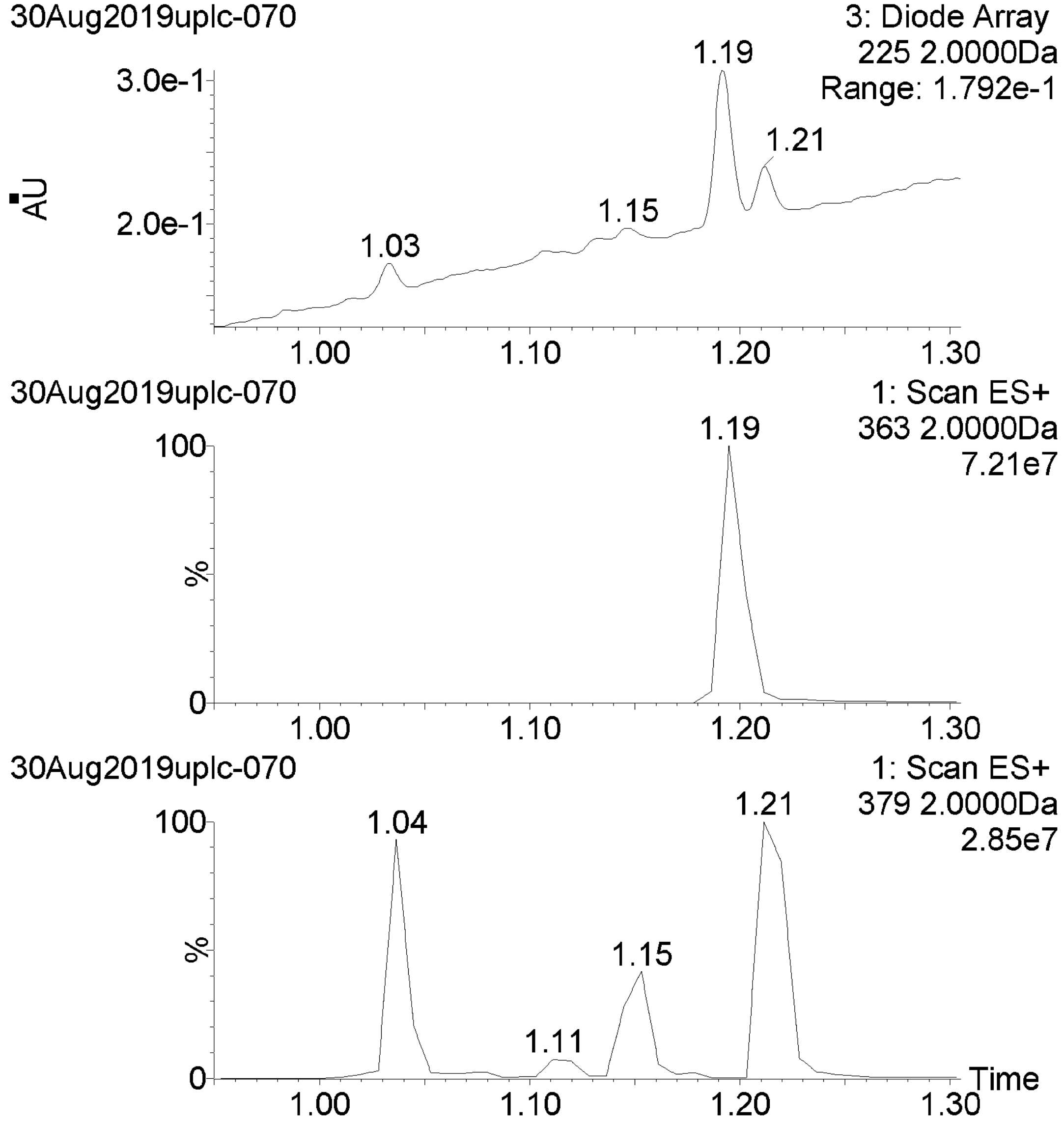

Chromatograms of post-reaction extract using lyophilised material of recombinant R63W, R74Y mutant of codon-optimised $P450_{SriC12}$ [SEQ ID No: 251], $ferredoxin_{SriF05}$ and ferredoxin $reductase_{SCF15A}$, as described in example 5, dosed with 100 mg/L solifenacin. Top to bottom is $UV_{225nm}$, $EIC_{363m/z}$ (solifenacin (1.19 mins)) and $EIC_{379m/z}$ (hydroxylated/*N*-oxidated solifenacin derivatives (1.04, 1.11, 1.15, 1.21 mins, combined yield 59 %). These products are not observed with the native $P450_{SriC12}$ or its R63W mutant.

Figure 15x

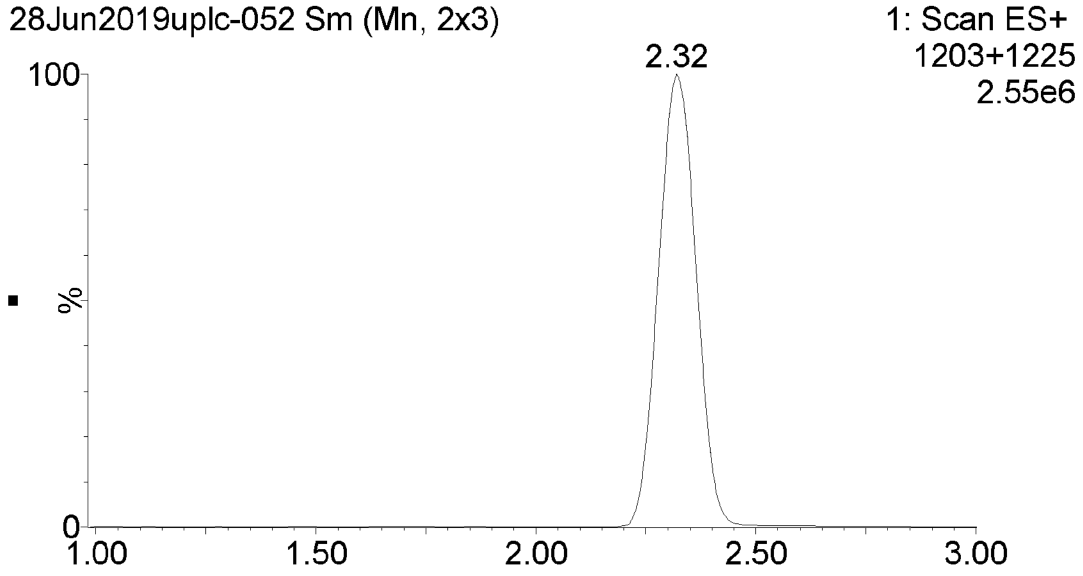

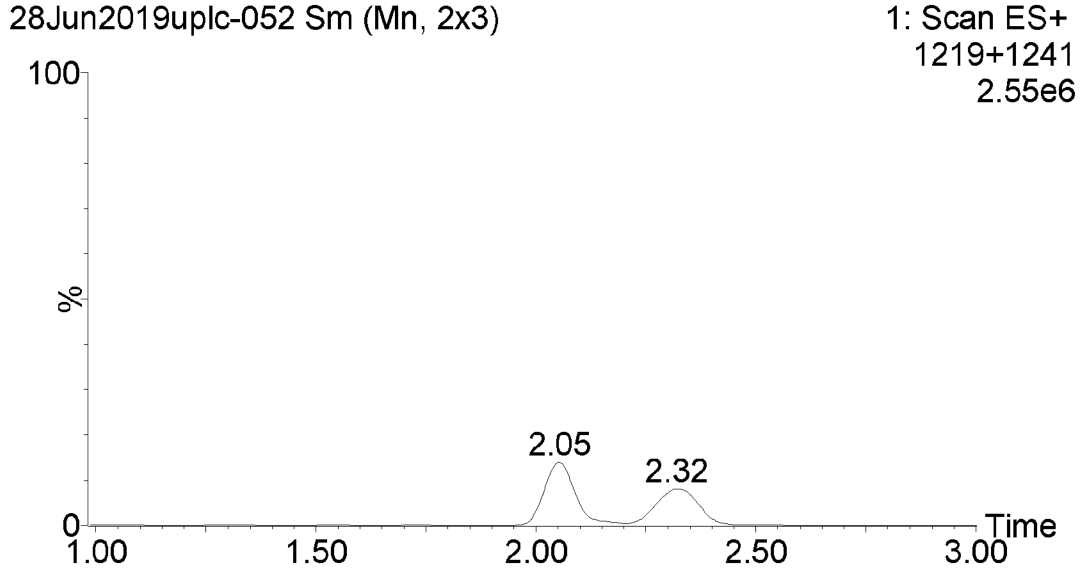

Chromatograms of post-reaction extract using lyophilised material of recombinant R63W, R74Y, L171A mutant of codon-optimised $P450_{SriC12}$ [SEQ ID No: 257], $ferredoxin_{SriF05}$ and ferredoxin $reductase_{SCF15A}$, as described in example 5, dosed with 100 mg/L cyclosporin. Top to bottom is $EIC_{1203+1225m/z}$ (cyclosporin (2.32 mins)) and $EIC_{1219+1241m/z}$ (AM1 hydroxy-cyclosporin derivative, (2.05 mins, 8.5 % yield of parent-derived product). This product is not observed with the native $P450_{SriC12}$ and only to a much lesser extent with the R63W, R74Y mutant.

Figure 15y

500 MHz ¹H-NMR spectrum in CDCl₃ of purified cyclosporin A metabolite AM1 produced using recombinant P450sriC20, ferredoxinFd1 and ferredoxin reductasescF15A as described in Example 7.

(a)

(b)

(c)

(a)

(b)

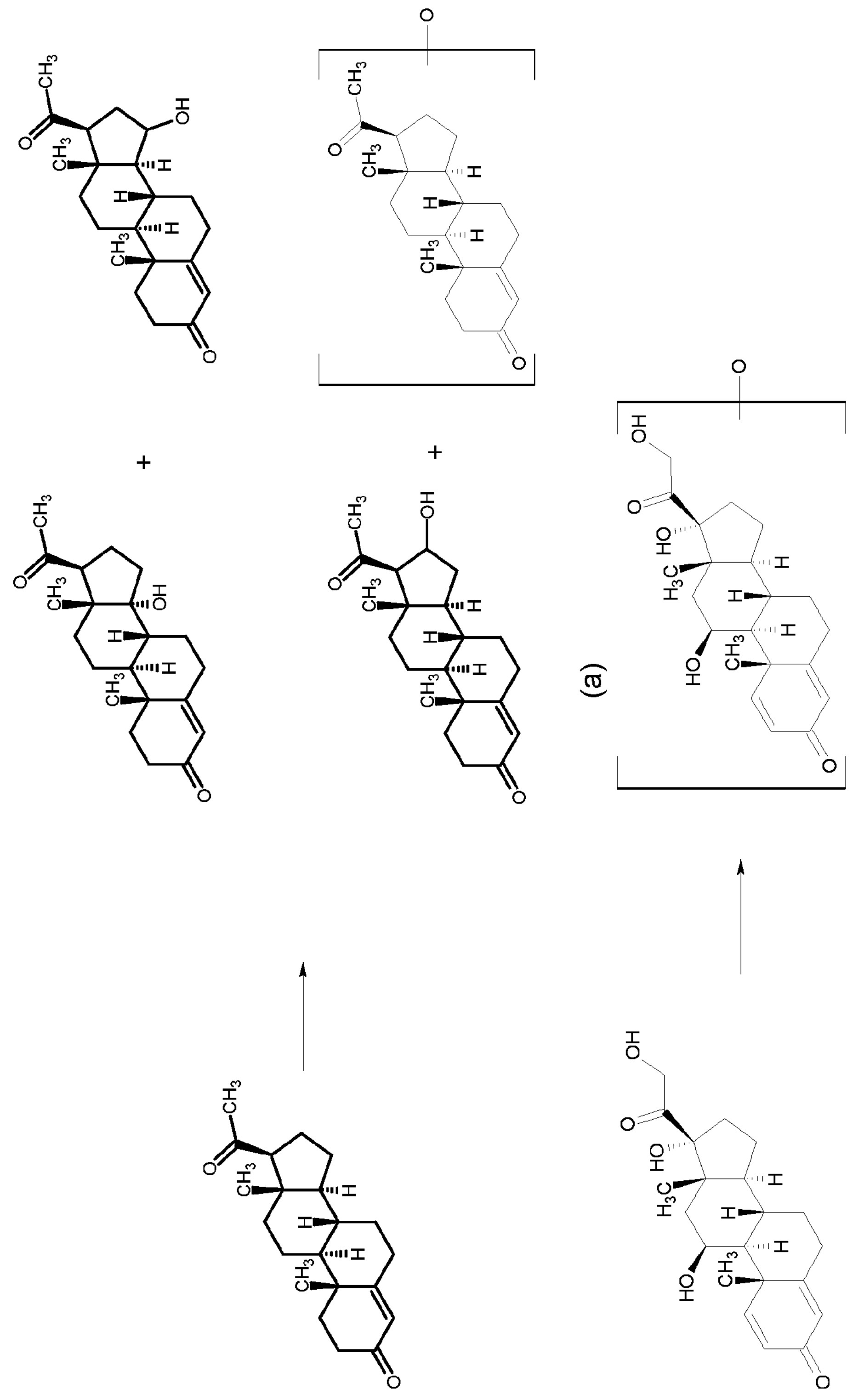
(a)
(b)
Figure 24 (a) (b)

(c)

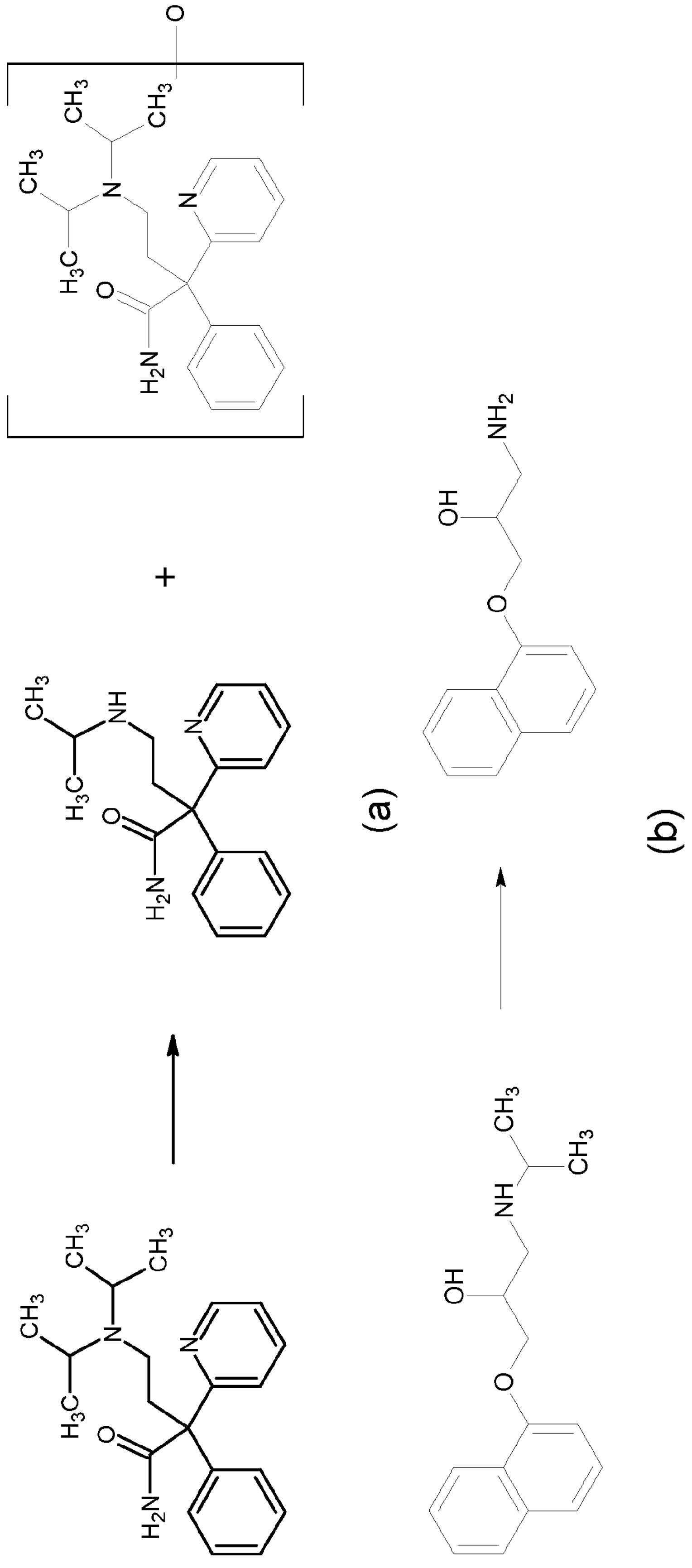
(a)
(b)
Figure 25 (a) (b)

(c)

(d)

BIOCATALYTIC TECHNIQUES

SEQUENCE LISTING

A sequence listing in electronic (ASCII text file) format is filed with this application and incorporated herein by reference. The name of the ASCII text file is "2021_0995A_ST25.txt"; the file was created on Feb. 10, 2022; the size of the file is 383 KB.

FIELD OF THE INVENTION

The present invention relates to the use of cytochrome P450 enzymes from *Streptomyces rimosus* NRRL-2234 for catalysing the hydroxylation and dealkylation of organic substrates.

BACKGROUND OF INVENTION

Cytochrome P450 (CYP450) is a superfamily of haem-thiolate proteins named for the spectral absorbance peak of their carbon-monoxide bound species at 450 nm. They are found in all kingdoms of life such as animals, plants, fungi, protists, bacteria, archaea, and furthermore a putative P450 from giant virus *Acanthamoeba polyphaga* has been recently proposed, Lamb, D C; Lei, L; Warrilow, A G; Lepesheva, G I; Mullins, J G; Waterman, M R; Kelly, S L (2009). "*The first virally encoded cytochrome P*450". *Journal of Virology.* 83 (16): pp 8266-9. Cytochrome P450 have not been identified in *E. coli*, Roland Sigel; Sigel, Astrid; Sigel, Helmut (2007). The Ubiquitous Roles of Cytochrome P450 Proteins: Metal Ions in Life Sciences. New York: Wiley. ISBN 0-470-01672-8; Danielson PB (December 2002). "The cytochrome P450 superfamily: biochemistry, evolution and drug metabolism in humans". Curr. Drug Metab. 3 (6): pp 561-97.

Cytochrome P450s show extraordinary diversity in their reaction chemistry supporting the oxidative, peroxidative and reductive metabolism of a diversity and range of endogenous and xenobiotic substrates.

In humans, cytochrome P450s are best known for their central role in phase I drug metabolism where they are of critical importance for two of the most significant problems in clinical pharmacology: drug-drug interactions and inter-individual variability in drug metabolism.

The most common reaction catalyzed by cytochromes P450 is a mono-oxygenase reaction. Cytochrome P450 mono-oxygenases use a haem group to oxidase molecules, often making them more water-soluble by either adding or unmasking a polar group. In general, the reactions catalysed by these enzymes can be summarised as:

Carbon oxidation

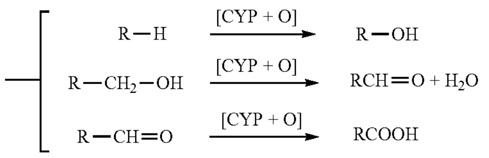

Heteroatom oxidation

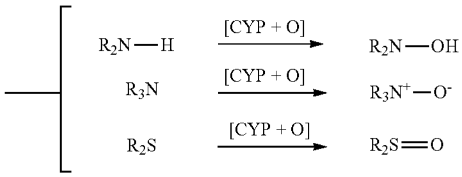

Dealkylation

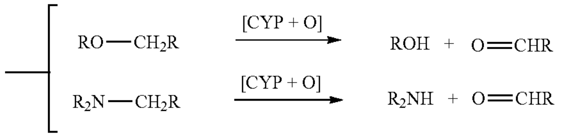

Epoxide formation

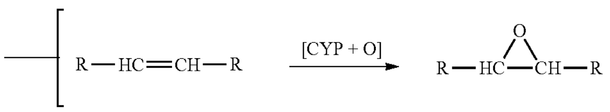

In the first line example, R—H is the substrate and R—OH is the oxygenated substrate. The oxygen is bound to the haem group in the core of the CYP enzyme, protons ($H^+$) are usually derived from the reduced cofactor NADH or NADPH through specific amino acids in the CYP enzyme. CYP enzymes can receive electrons from a range of redox partner proteins such as cytochrome b5, a ferredoxin reductase and a ferredoxin, and adrenodoxin reductase and adrenodoxin.

Although classification and nomenclature of cytochrome P450 is quite complex, they can be classified by their redox partner transfer protein system, proposed by I. Hanukoglu (1996). "*Electron Transfer Proteins of Cytochrome P450 Systems*". Advances in Molecular and Cell Biology. Advances in Molecular and Cell Biology. 14: 29-56. In summary, cytochrome P450s can be classified into the following groups:

- Microsomal P450 systems which utilise cytochrome P450 reductase or cytochrome b5 to transfer electrons from cofactor to cytochrome P450;
- Mitochondrial P450 systems which utilise adrenodoxin reductase and adrenodoxin to transfer electrons from reduced cofactor to cytochrome P450;
- Bacterial P450 systems which utilise ferredoxin reductase and ferredoxin to transfer electrons from reduced cofactor to cytochrome P450;
- CYB5R-cytb5-P450 systems, which utilise cytochrome b5 for the electron transfer from the cofactor to the cytochrome P450;
- FMN-Fd-P450 systems in which the electron partner reductase is a fused FMN domain;
- P450 only systems that do not require redox partner proteins.

Isolated bacterial cytochrome P450 enzymes are known, including $P450_{cam}$ from *Pseudomonas putida*, J Biol Chem (1974) 249, 94; $P450_{BM\text{-}1}$ and $P450_{BM\text{-}3}$ both from *Bacillus megaterium* ATCC 14581, Biochim Hiophys Acta (1985) 838, 302, and J Biol Chem (1986) 261, 1986, 7160; P450a, P450b, and P450c from *Rhizobium japonicum*, Biochim Biophys Acta (1967) 147, 399; and P450npd from *Nocardia* sp. NHI, Microbios (1974) 9, 119.

However, cytochrome P450 enzymes purified from Actinomycete microorganisms remain relatively unreported. The induction of a cytochrome P450 in *Streptomyces griseus* by soybean flour ($P450_{soy}$) is described in Biochem and Biophys Res Comm (1986) 141, 405. Other reported examples include the isolation and properties of two forms of a P450 effecting pesticide inactivation ($P450_{SU1}$ & $_{SU2}$) and two forms of 6-deoxyerythronolide B hydroxylase from *Saccharopolyspora erythraea* (originally classified as *Streptomyces erythraeus*) as described in Biochemistry (1987) 26, 6204. U.S. Pat. No. 6,884,608 describes enzymatic hydroxylation of epothilone B to epothilone F, effected with a hydroxylation enzyme produced by a strain of Amycolatopsis *orientalis* (originally classified as *Streptomyces orientalis*).

In the field of medicinal chemistry, modifications to chemical compounds are used to modify the properties of such chemical compounds. For example, tertiary butyl moieties are often used by medicinal chemists in the synthesis of drug-like molecules for introduction of hydrophobicity. However, further modifications thereof can be used to improve potency, selectivity and solubility profiles of such compounds, for example hydroxylations can be used. Hydroxylations are also the main route of metabolic degradation, another important aspect of pharmacology and medicinal chemistry. Methods for the production of these hydroxylated metabolites are sought using biotransformation with animal tissues.

SUMMARY OF THE INVENTION

It has surprisingly been found that specific cytochrome P450 enzymes found in *Streptomyces rimosus* NRRL-2234 can be used for the hydroxylation and/or dealkylation of organic substrates.

In particular, cytochrome P450 enzymes having the SEQ ID NOs: 2, 29, 34, 47, 51 and 109, and mutants thereof, can be used for the hydroxylation and/or dealkylation of organic compounds in order to activate or modify the compound's physicochemical and pharmacological properties. In a particularly preferred embodiment, the cytochrome P450 enzyme having the SEQ ID NO: 2, 29, 34, 47, 51 and 109, and mutants thereof, are useful for the hydroxylation of a variety of aliphatic and aromatic moieties, or chemicals containing such moieties, for the purposes of C—H activation or modification of the compound's physicochemical and pharmacological properties, as well as dealkylation such as the removal of a alkyl moieties from alkoxyl moieties or alkylamines.

A first aspect of the invention provides the use of a cytochrome P450 enzyme selected from SEQ ID NO's: 1-118, and mutants thereof, or a variant enzyme having at least 70% identity thereto and having CYP450 activity, for the hydroxylation and/or dealkylation of an organic compound.

A second aspect of the invention provides a method for the production of a hydroxylated or dealkylated organic compound, comprising reacting the organic compound with an enzyme preparation containing in part cytochrome P450 enzyme selected from SEQ ID NO's: 1-118, and mutants thereof, or a variant enzyme having at least 70% identity thereto and having CYP450 activity.

A third aspect of the invention provides a kit comprising i) a cytochrome P450 enzyme selected from SEQ ID NO's: 1-118, and mutants thereof, or a variant enzyme having at least 70% identity thereto and having CYP450 activity, or ii) a microorganism that expresses a cytochrome P450 enzyme comprising SEQ ID NO's: 1-118, and mutants thereof, or a variant enzyme having at least 70% identity thereto and having CYP450 activity, wherein the kit further comprises instructions and other cofactor reagents for use for the hydroxylation and/or dealkylation of an organic compound.

BRIEF DESCRIPTION OF THE FIGURES

FIG. 1(*a*) shows 0-de-methylation and hydroxylation of bosentan, FIG. 1(*b*) shows the hydroxylation of valsartan in two aliphatic positions; FIG. 1(*c*) shows aromatic hydroxylation of ritonavir; FIG. 1(*d*) shows aromatic hydroxylation of diclofenac; FIG. 1(*e*) shows benzylic and aromatic hydroxylation of tivantinib.

FIG. 2(*a*) shows the aromatic hydroxylation of vanoxerine; FIG. 2(*b*) shows the t-butyl hydroxylation of bosentan; FIG. 2(*c*) shows the isopropyl hydroxylation of ritonavir; FIG. 2(*d*) shows the hydroxylation of cyclosporin.

FIG. 3(*a*) shows the N-demethylation and isopropyl hydroxylation of ritonavir; FIG. 3(*b*) shows the hydroxylation of cyclosporin.

FIG. 4 shows various ID sequences. SEQ ID NO: 1 is the coding sequence of sriC01; SEQ ID NO: 2 is the amino acid sequence of cytochrome SriC01; SEQ ID NO: 3 is the coding sequence of sriCO2; SEQ ID NO: 4 is the amino acid sequence of cytochrome SriCO2; SEQ ID NO: 5 is the coding sequence of sriC03-sriF01; SEQ ID NO: 6 is the amino acid sequence of cytochrome SriC03; SEQ ID NO: 7 is the amino acid sequence of ferredoxin SriF01; SEQ ID NO: 8 is the coding sequence of sriC04; SEQ ID NO: 9 is the amino acid sequence of cytochrome SriC04; SEQ ID NO: 10 is the coding sequence of sriC05-sriF02; SEQ ID NO: 11 is the amino acid sequence of cytochrome SriC05; SEQ ID NO: 12 is the amino acid sequence of ferredoxin SriF02; SEQ ID NO: 13 is the coding sequence of sriC06; SEQ ID NO: 14 is the amino acid sequence of cytochrome SriC06; SEQ ID NO: 15 is the coding sequence of sriC07; SEQ ID NO: 16 is the amino acid sequence of cytochrome SriC07; SEQ ID NO: 17 is the coding sequence of sriC08; SEQ ID NO: 18 is the amino acid sequence of cytochrome SriC08; SEQ ID NO: 19 is the coding sequence of sriC09-sriF03-sriFRO1; SEQ ID NO: 20 is the amino acid sequence of cytochrome SriC09; SEQ ID NO: 21 is the amino acid sequence of ferredoxin SriF03; SEQ ID NO: 22 is the amino acid sequence of ferredoxin reductase SriFR01; SEQ ID NO: 23 is the coding sequence of sriC10; SEQ ID NO: 24 is the amino acid sequence of cytochrome SriC10; SEQ ID NO: 25 is the coding sequence of sriC11-sriF04; SEQ ID NO: 26 is the amino acid sequence of cytochrome SriC11; SEQ ID NO: 27 is the amino acid sequence of ferredoxin SriF04; SEQ ID NO: 28 is the coding sequence of sriC12-sriF05; SEQ ID NO: 29 is the amino acid sequence of cytochrome SriC12; SEQ ID NO: 30 is the amino acid sequence of ferredoxin SriF05; SEQ ID NO: 31 is the coding sequence of sriC13; SEQ ID NO: 32 is the amino acid sequence of cytochrome sriC13; SEQ ID NO: 33 is the coding sequence of sriC14-sriF06; SEQ ID NO: 34 is the amino acid sequence of cytochrome SriC14; SEQ ID NO: 35 is the amino acid sequence of ferredoxin SriF06; SEQ ID NO: 36 is the coding sequence of sriC15; SEQ ID NO: 37 is the amino acid sequence of cytochrome SriC15; SEQ ID NO: 38 is the coding sequence of sriC16; SEQ ID NO: 39 is the amino acid sequence of cytochrome SriC16; SEQ ID NO: 40 is the coding sequence of sriC17; SEQ ID NO: 41 is the amino acid sequence of cytochrome SriC17; SEQ ID NO: 42 is the coding sequence of sriC18; SEQ ID NO: 43 is the amino acid sequence of SriC18; SEQ ID NO: 44 is the coding sequence of sriC19; SEQ ID NO: 45 is the amino acid sequence of cytochrome SriC19; SEQ ID NO: 46 is the coding sequence of sriC20; SEQ ID NO: 47 is the amino acid sequence of cytochrome SriC20; SEQ ID NO: 48 is the coding sequence of sriC21; SEQ ID NO: 49 is the amino acid sequence of cytochrome SriC21; SEQ ID NO: 50 is the coding sequence of sriC22; SEQ ID NO: 51 is the amino acid sequence of cytochrome SriC22; SEQ ID NO: 52 is the coding sequence of sriC23; SEQ ID NO: 53 is the amino acid sequence of cytochrome SriC23; SEQ ID NO: 54 is the coding sequence of sriC24; SEQ ID NO: 55 is the amino acid sequence of cytochrome SriC24; SEQ ID NO: 56 is the coding sequence of sriC25; SEQ ID NO: 57 is the amino acid sequence of cytochrome SriC25; SEQ ID NO: 58 is the coding sequence of sriC26; SEQ ID NO: 59 is the amino acid sequence of cytochrome SriC26; SEQ ID NO: 60 is the coding sequence of sriC27; SEQ ID NO: 61 is the amino acid sequence of cytochrome SriC27; SEQ ID NO: 62 is the coding sequence of sriC28; SEQ ID NO: 63 is the amino acid sequence of cytochrome SriC28; SEQ ID NO: 64 is the coding sequence of sriC30; SEQ ID NO: 65 is the amino acid sequence of cytochrome SriC30; SEQ ID NO: 66 is the coding sequence of sriC31; SEQ ID NO: 67 is the amino acid sequence of cytochrome SriC31; SEQ ID NO: 68 is the coding sequence of sriC32; SEQ ID NO: 69 is the amino acid sequence of SriC32; SEQ ID NO: 70 is the coding sequence of sriC33; SEQ ID NO: 71 is the amino acid sequence of cytochrome SriC33; SEQ ID NO: 72 is the coding sequence of sriC34; SEQ ID NO: 73 is the amino acid sequence of cytochrome SriC34; SEQ ID NO: 74 is the coding sequence of sriC35; SEQ ID NO: 75 is the amino acid sequence of cytochrome SriC35; SEQ ID NO: 76 is the coding sequence of sriC36; SEQ ID NO: 77 is the amino acid sequence of cytochrome SriC36; SEQ ID NO: 78 is the coding sequence of sriC37; SEQ ID NO: 79 is the amino acid sequence of cytochrome SriC37; SEQ ID NO: 80 is the coding sequence of sriC38; SEQ ID NO: 81 is the amino acid sequence of SriC38; SEQ ID NO: 82 is the coding sequence of sriC39; SEQ ID NO: 83 is the amino acid sequence of cytochrome SriC39; SEQ ID NO: 84 is the coding sequence of sriC40-sriF07-sriFR02; SEQ ID NO: 85 is the amino acid sequence of cytochrome SriC40; SEQ ID NO: 86 is the amino acid sequence of ferredoxin SriF07; SEQ ID NO: 87 is the amino acid sequence of ferredoxin reductase SriFRO2; SEQ ID NO: 88 is the coding sequence of sriC41; SEQ ID NO: 89 is the amino acid sequence of cytochrome SriC41; SEQ ID NO: 90 is the coding sequence of sriC42; SEQ ID NO: 91 is the amino acid sequence of SriC42; SEQ ID NO: 92 is the coding sequence of sriC43; SEQ ID NO: 93 is the amino acid sequence of cytochrome SriC43; SEQ ID NO: 94 is the coding sequence of sriC44; SEQ ID NO: 95 is the amino acid sequence of cytochrome SriC44; SEQ ID NO: 96 is the coding sequence of sriC45; SEQ ID NO: 97 is the amino acid sequence of cytochrome SriC45; SEQ ID NO: 98 is the coding sequence of sriC46; SEQ ID NO: 99 is the amino acid sequence of cytochrome SriC46; SEQ ID NO: 100 is the coding sequence of sriC47; SEQ ID NO: 101 is the amino acid sequence of SriC47; SEQ ID NO: 102 is the coding sequence of sriC48; SEQ ID NO: 103 is the amino acid sequence of cytochrome SriC48; SEQ ID NO: 104 is the coding sequence of sriC49; SEQ ID NO: 105 is the amino acid sequence of cytochrome SriC49; SEQ ID NO: 106 is the coding sequence of sriC50; SEQ ID NO: 107 is the amino acid sequence of cytochrome SriC50; SEQ ID NO: 108 is the coding sequence of sriC51-sriF08; SEQ ID NO: 109 is the amino acid sequence of cytochrome sriC51; SEQ ID NO: 110 is the amino acid sequence of ferredoxin sriF08; SEQ ID NO: 111 is the coding sequence of sriC52; SEQ ID NO: 112 is the amino acid sequence of cytochrome SriC52; SEQ ID NO: 113 is the coding sequence of sriC54; SEQ ID NO: 114 is the amino acid sequence of cytochrome SriC54; SEQ ID NO: 115 is the coding sequence of sriC59; SEQ ID NO: 116 is the amino acid sequence of cytochrome SriC59; SEQ ID NO: 117 is the coding sequence of sriC60; SEQ ID NO: 118 is the amino acid sequence of cytochrome SriC60; SEQ ID NO: 229 is the synthetic DNA sequence of full optimization of SriC12, SriF05 and ribosome binding site of SriF05 by DNA2.0); SEQ ID NO: 230 is the coding sequence of R63W mutant of codon optimised sriC12; SEQ ID NO: 231 is the amino acid sequence of R63W mutant of codon optimised cytochrome SriC12; SEQ ID NO: 232 is the coding sequence of R63Y mutant of codon optimised sriC12; SEQ ID NO: 233 is the amino acid sequence of R63Y mutant of codon optimised cytochrome SriC12; SEQ ID NO: 234 is the coding sequence of L1711 mutant of codon optimised sriC12; SEQ ID NO: 235 is the amino acid sequence of L1711 mutant of codon optimised cytochrome SriC12; SEQ ID NO: 236 is the coding sequence of L2301 mutant of codon optimised sriC12; SEQ ID NO: 237 is the amino acid sequence of L2301 mutant of codon optimised cytochrome SriC12; SEQ ID NO: 250 is the coding sequence of R63W R74Y mutant of codon optimised cytochrome sriC12; SEQ ID NO: 251 is the amino acid sequence of R63W R74Y mutant of codon optimised cytochrome SriC12; SEQ ID NO: 252 is the coding sequence of R63W L171A mutant of codon optimised cytochrome sriC12; SEQ ID NO: 253 is the amino acid sequence of R63W L171A mutant of codon optimised cytochrome SriC12; SEQ ID NO: 254 is the coding sequence of R74Y L171A R183W mutant of codon optimised cytochrome sriC12; SEQ ID NO: 255 is the amino acid sequence of R74Y L171A R183W mutant of codon optimised cytochrome SriC12; SEQ ID NO: 256 is the coding sequence of R63W R74Y L171A mutant of codon optimised cytochrome sriC12; SEQ ID NO: 257 is the amino acid sequence of R63W R74Y L171A mutant of codon optimised cytochrome SriC12.

FIG. 22(*a*) shows the O-de-ethylation and hydroxylation of 7-ethoxycoumarin; FIG. 22(*b*) shows the hydroxylation of vanoxerine; FIG. 22(*c*) shows the hydroxylation of palmitic acid.

FIG. 23(*a*) shows the hydroxylation of diclofenac; FIG. 23(*b*) shows the hydroxylation of valsartan.

FIG. 24(*a*) shows the hydroxylation of progesterone; FIG. 24(*b*) shows the hydroxylation of prednisolone; FIG. 24(*c*) shows the hydroxylation of diclofenac.

FIG. 25(*a*) shows the dealkylation and hydroxylation of disopyramide; FIG. 25(*b*) shows the dealkylation of propranolol; FIG. 25(*c*) shows the hydroxylation of celecoxib; FIG. 25(*d*) shows the hydroxylation of solifenacin.

DESCRIPTION OF THE PREFERRED EMBODIMENTS

Figure 1A:
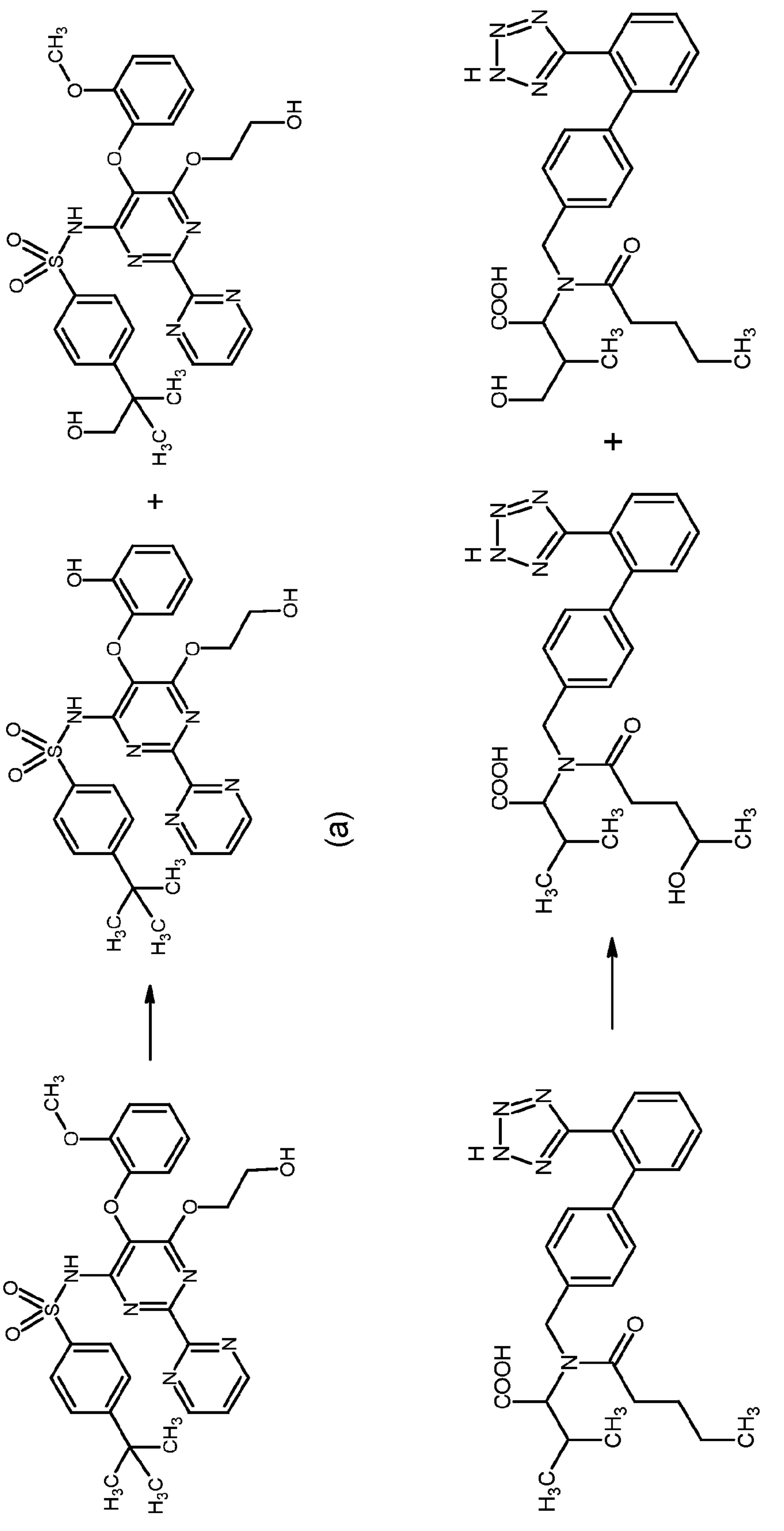
FIG. 1 shows schematic examples of the biotransformation effected by the use of a cytochrome P450 enzyme comprising SEQ ID NO: 29 of the present invention.
Figure 1E:
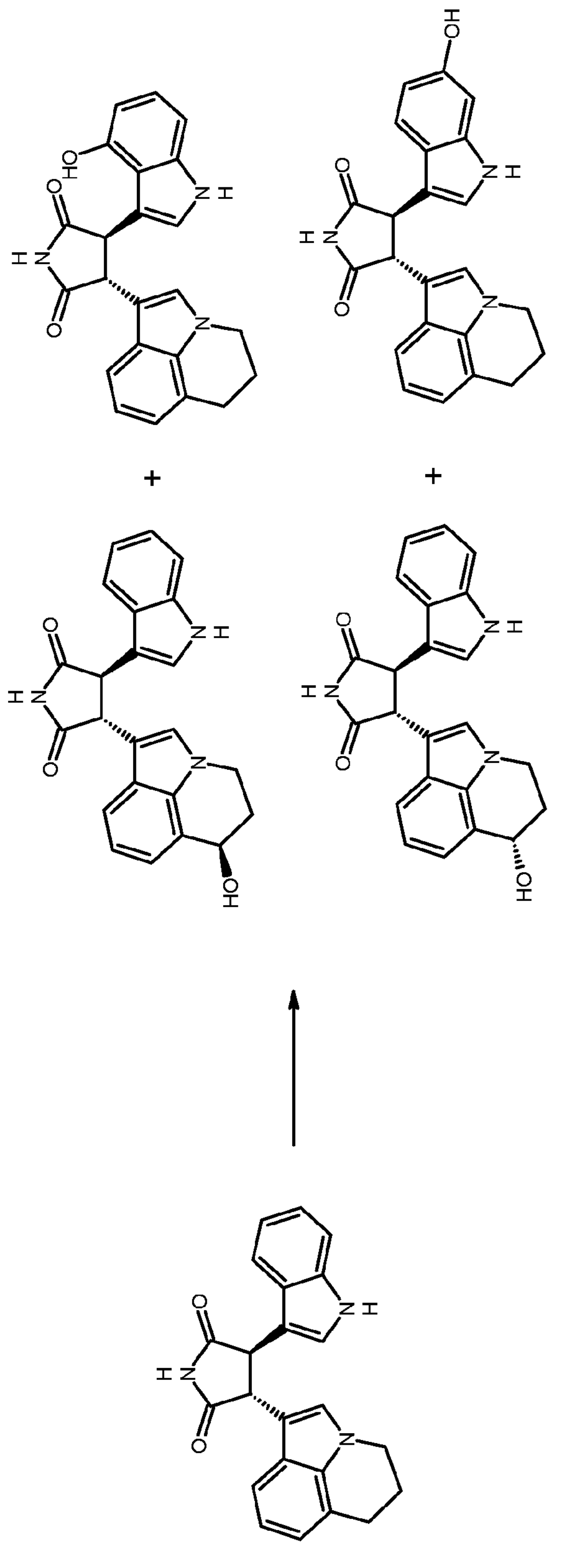
Figure 2A:
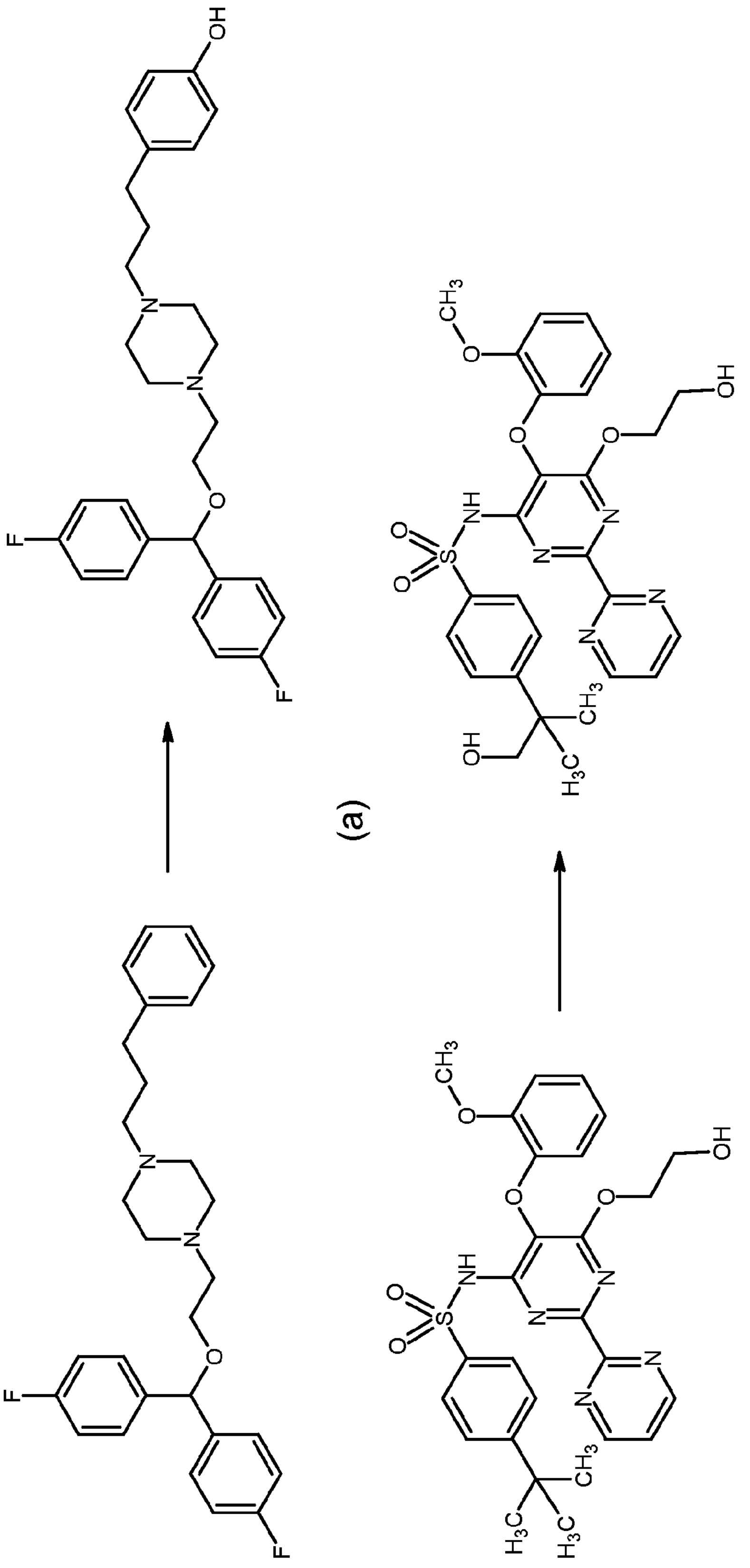
FIG. 2 shows examples of the biotransformation effected by the use of a cytochrome P450 enzyme comprising SEQ ID NO: 47, of the present invention.
Figure 2C:
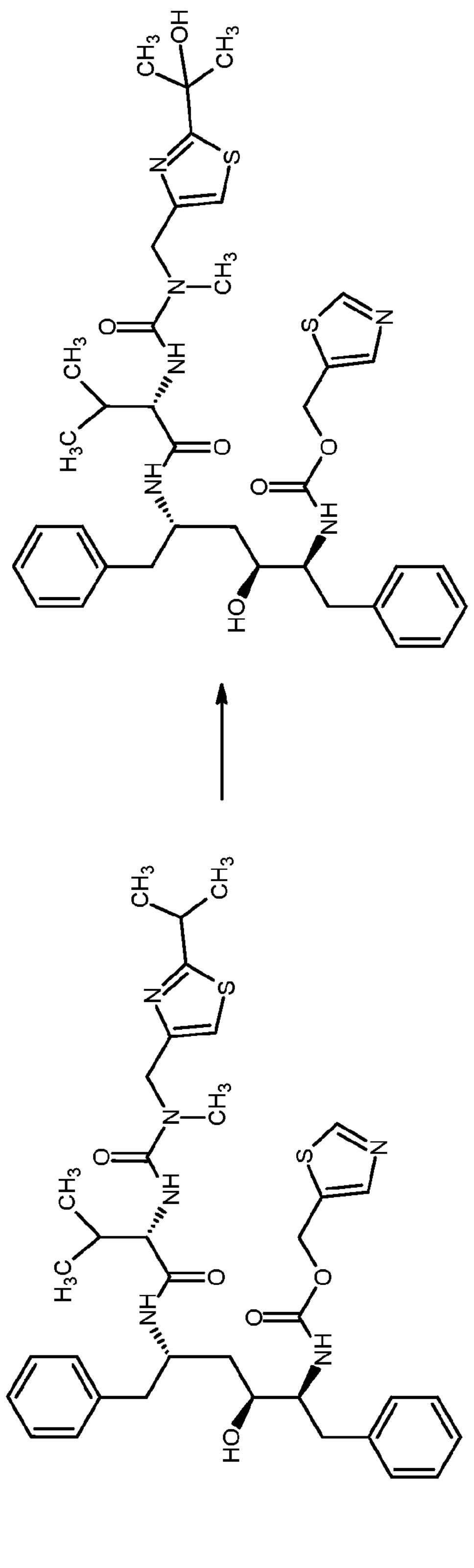
Figure 2D:
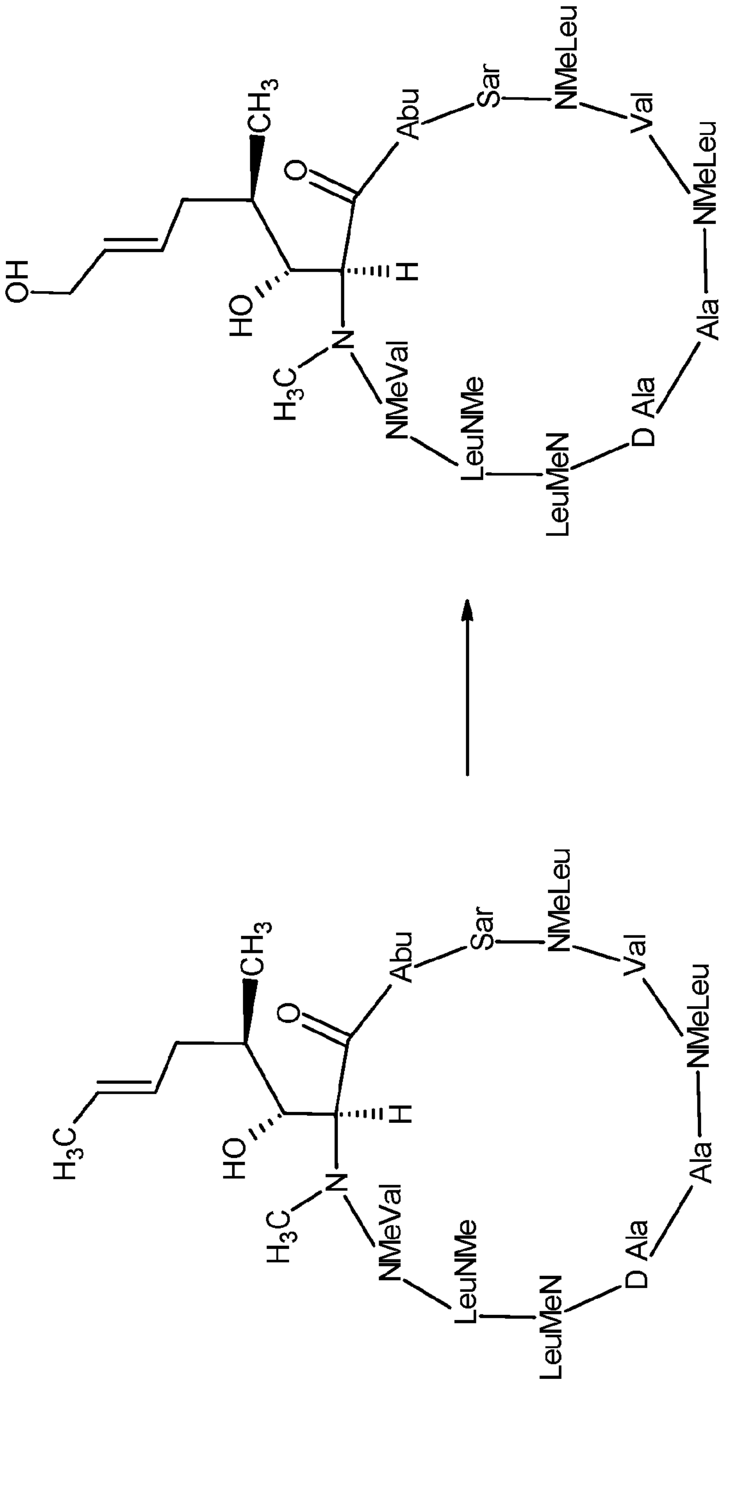
Figure 3A:
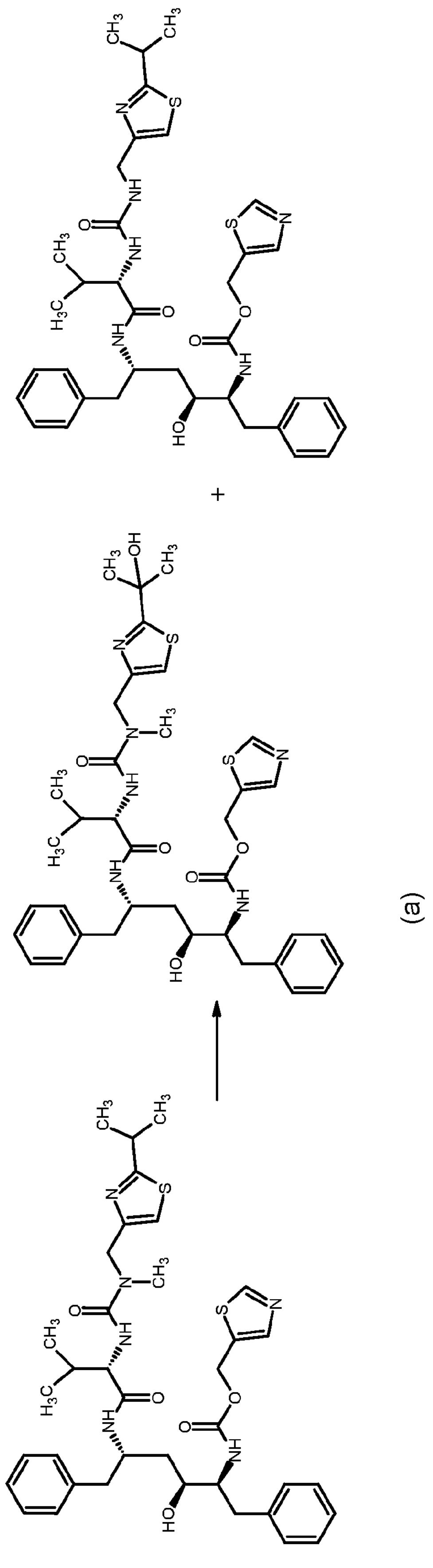
FIG. 3 shows examples of the biotransformation effected by the use of a cytochrome P450 enzyme comprising SEQ ID NO: 51, of the present invention.
Figure 3B:
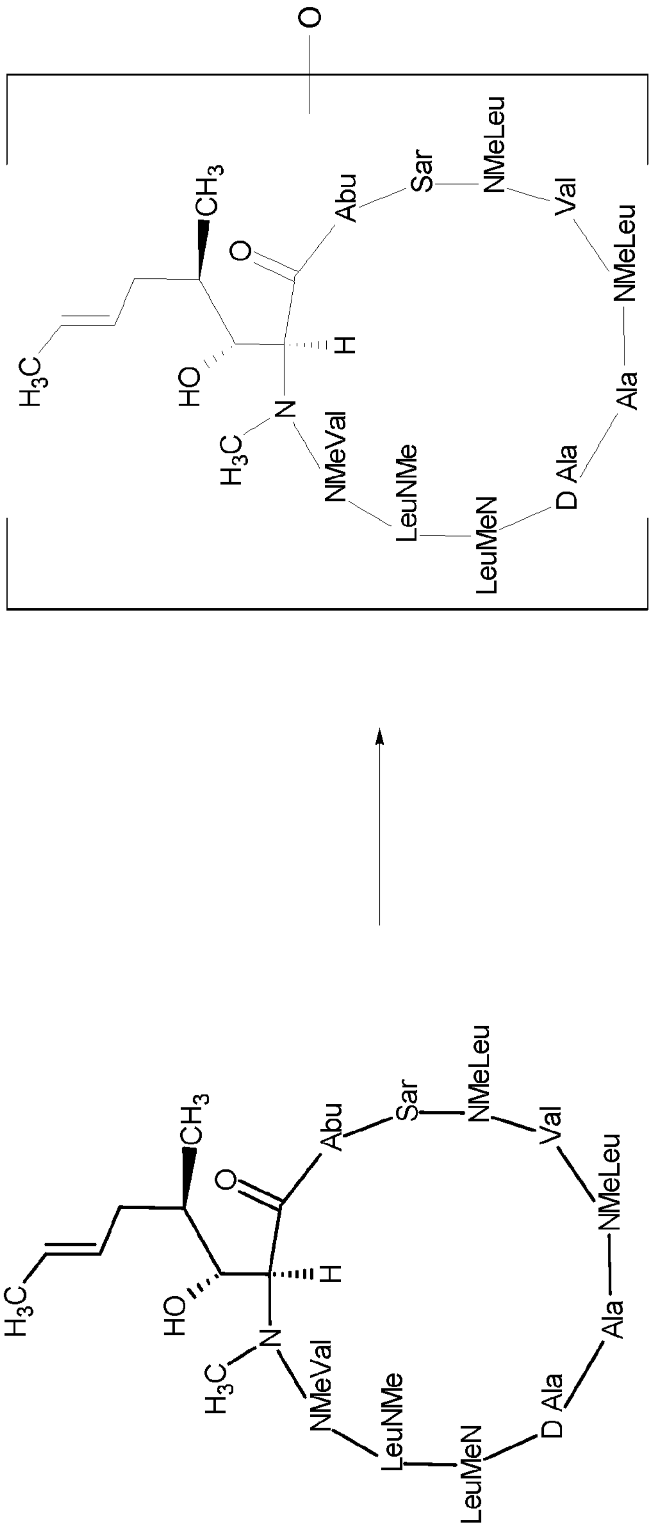
Figure 5:
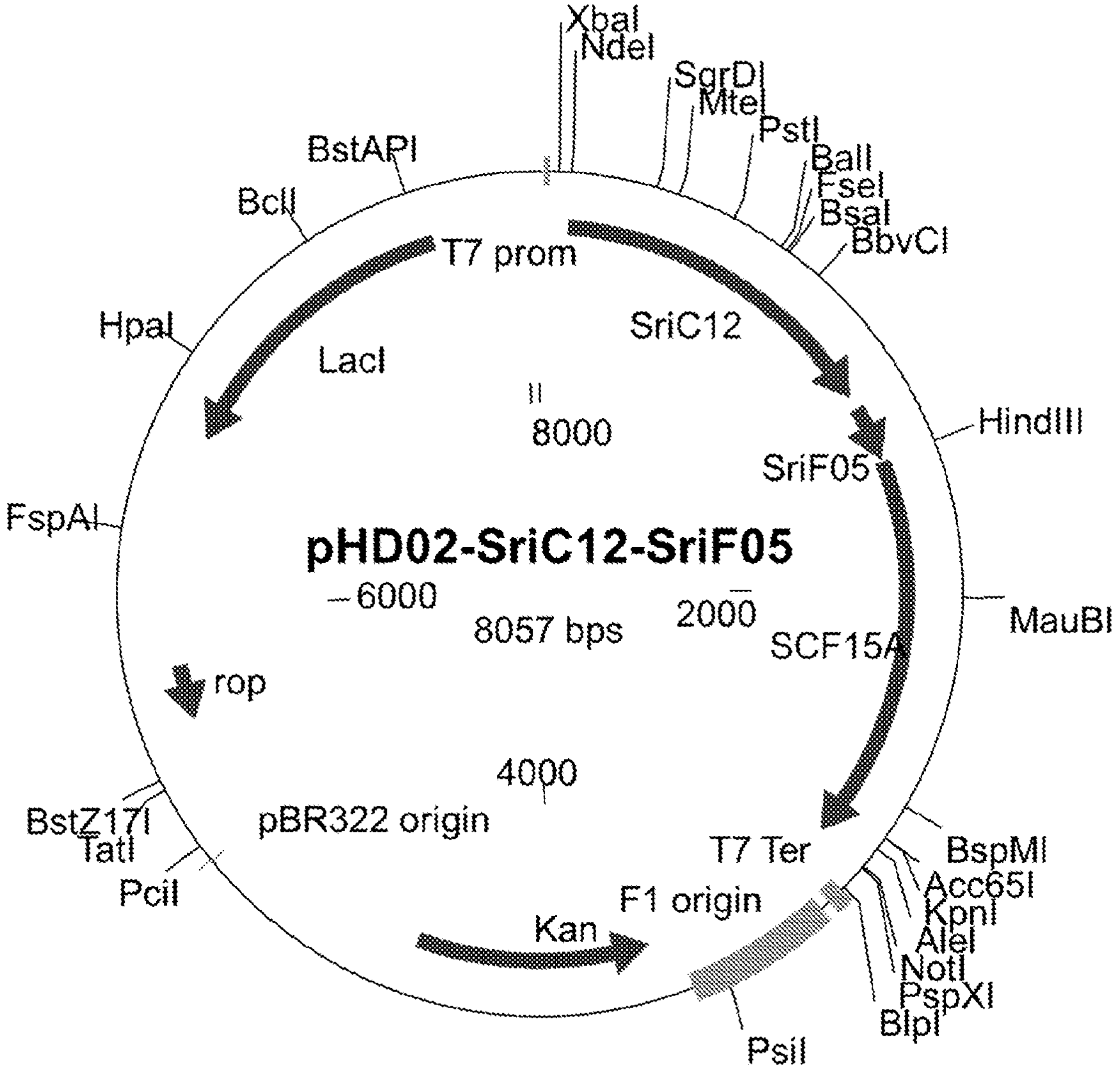
FIG. 5 shows expression plasmid pHD02-SriC12-SriF05
Figure 6:
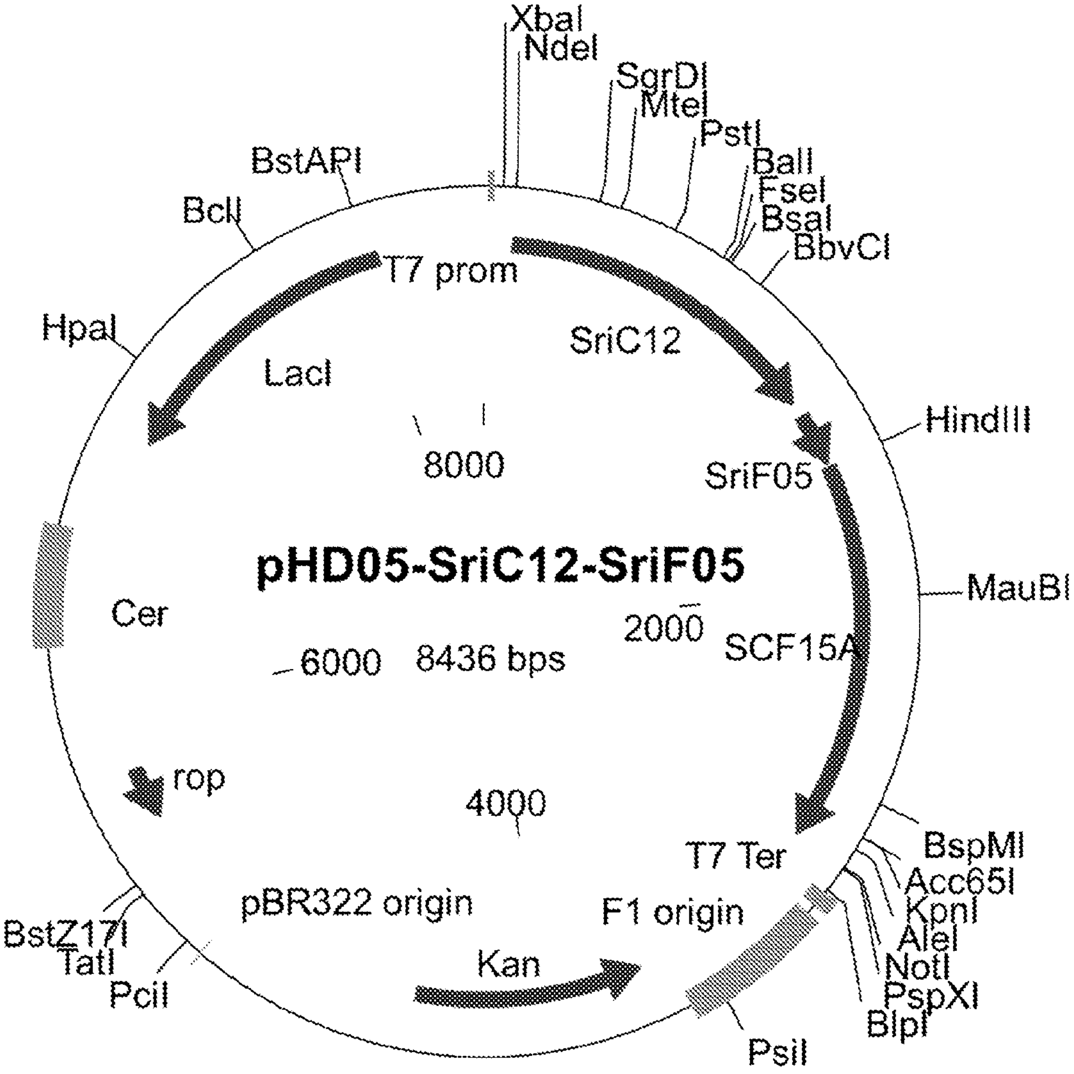
FIG. 6 shows expression plasmid pHD05-SriC12-SriF05
Figure 7:
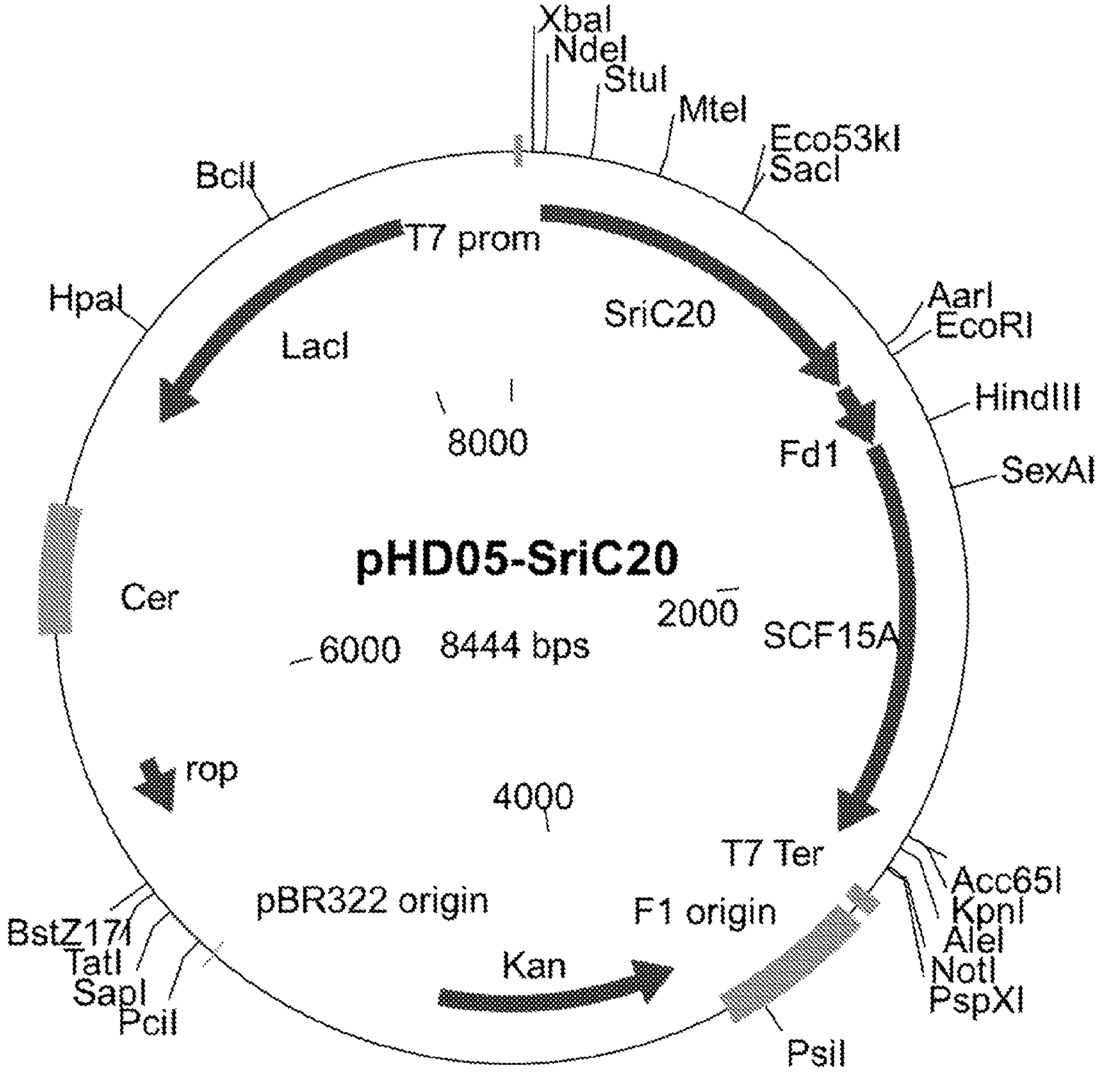
FIG. 7 shows expression plasmid pHD05-SriC20
Figure 8:
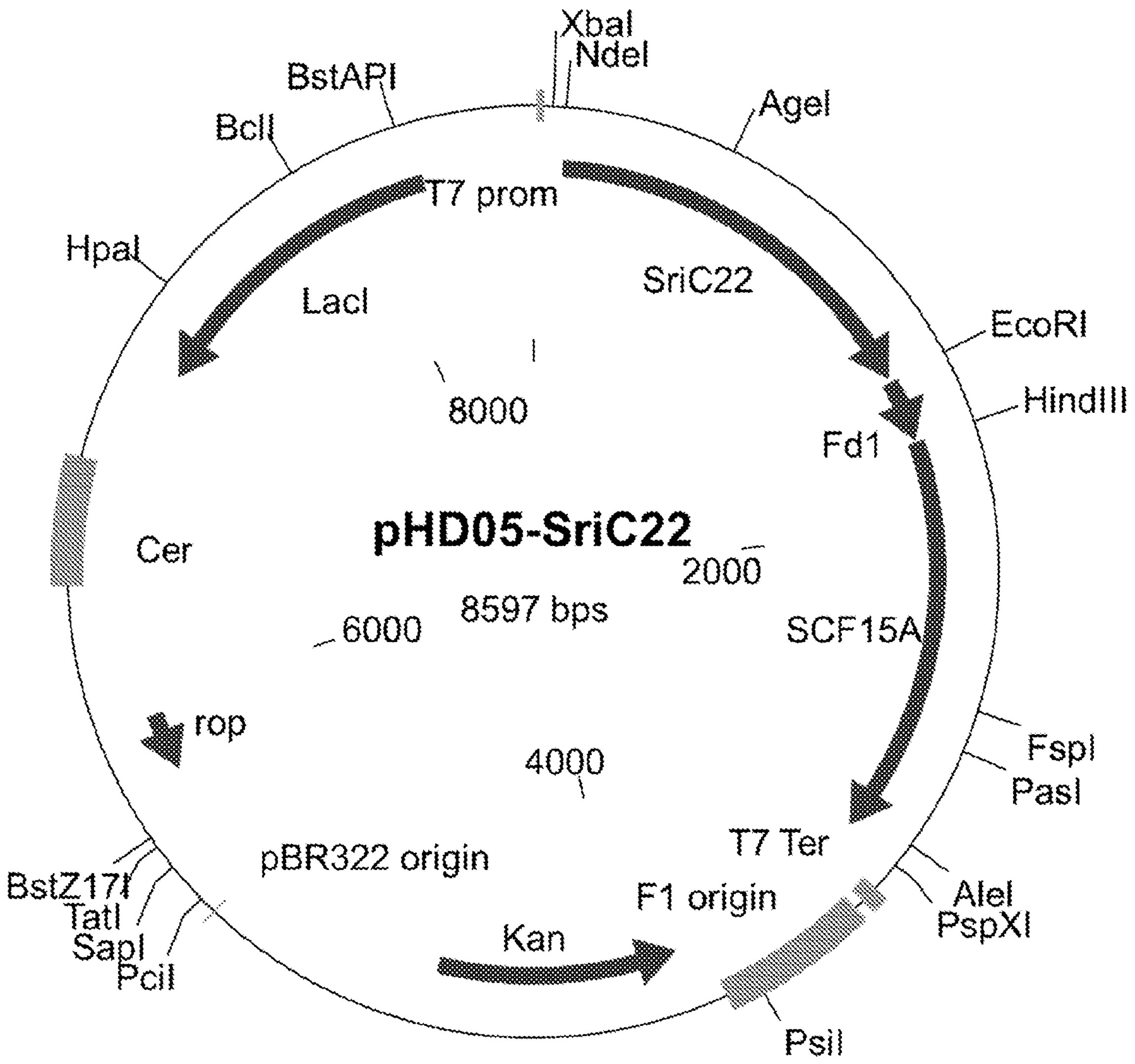
FIG. 8 shows expression plasmid pHD05-SriC22

A first aspect of the invention provides the use of cytochrome P450 enzymes comprising SEQ ID NO: 2, 29, 34, 47, 51 and 109, and mutants thereof, or a variant enzyme having at least 70% identity thereto and having CYP450 activity, for the hydroxylation of an organic compound.

Specifically, the present invention provides the use of the enzymes cytochrome $P450_{SriC01}$, $P450_{SriC12}$, $P450_{SriC14}$, $P450_{SriC20}$, $P450_{SriC22}$ and $P450_{SriC51}$, and mutants thereof. These enzymes have amino acid sequences as shown in SEQ ID NO: 2, 29, 34, 47, 51 and 109, respectively.

These enzymes are present in the strain *Streptomyces rimosus*, a deposit in the ARS Culture Collection, National Center for Agricultural Utilization Research, 1815 North University Street, Peoria, Illinois 61604, USA, under the Accession number NRRL-2234. The strain has also been deposited with various other Culture Collection, with the accession numbers ATCC 10970, ATCC 23955, BUCSAV 18,3, Boots 883, CBS 938.68, CCM 3231, ETH 20240, FD 10326, IAM W6-3, IFO 12907, IFO 3390, IMRU 3558, ISP 5260, NCIB 8229, PSA 47, Pfizer S-3279, RIA 1185.

When these enzymes, and mutants thereof or variants thereof, are combined with suitable reductase components, it is able to hydroxylate and dealkylate organic compounds.

The enzymes cytochrome $P450_{SriC01}$, $P450_{SriC12}$, $P450_{SriC14}$, $P450_{SriC20}$, $P450_{SriC22}$ & $P450_{SriC51}$ can be extracted, with or without purification from the known *Streptomyces rimosus* NRRL-2234, or other bacterial strain, or similarly extracted, with or without purification from a recombinant expression system via cloning of cytochrome $P450_{SriC01}$, $P450_{SriC12}$, $P450_{SriC14}$, $P450_{SriC20}$, $P450_{SriC22}$ and $P450_{SriC51}$ genes into an expression system, such as *E. coli*, as will be understood by the skilled person.

Actinomycetes including *Streptomyces rimosus* NRRL-2234 readily undergo mutation both through natural causes and as a result of artificial treatments such as UV irradiation, radiation treatment and chemical treatment. The present invention embraces all productive mutants of *Streptomyces rimosus* NRRL-2234. These mutant strains also include any strains obtained by gene manipulation such as gene recombination, transduction and transformation. It is also well-known that the properties of Actinomycetes change in some degree even for the same strain after successive cultures. Therefore, strains cannot always be differentiated taxonomically because of a slight difference in culture properties. This invention embraces all strains that can produce one or more of the cytochromes P450 enzymes, and especially strains that cannot be clearly differentiated from strain NRRL-2234 or its mutants.

One of skill in the art will appreciate that the present invention can include variants of those particular amino acids sequences which are exemplified herein. Particularly preferred are variants having an amino acid sequence similar to that of the amino acid sequences disclosed herein, in which one or more amino acids residues are substituted, deleted or added in any combination. Especially preferred are silent substitutions, additions and deletions, which do not alter the properties and activities of the protein of the present invention. Various amino acids have similar properties, and one or more such amino acids of a substance can often be substituted by one or more other amino acids without eliminating a desired activity of that substance. Thus, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Variants include naturally occurring and artificial variants. Artificial variants may be generated using mutagenesis techniques, including those applied to nucleic acid molecules, cells or organisms. Preferably, the variants have substantial identity to the amino acid sequences exemplified herein. As used herein, the term "variant" or "mutant thereof" refers to amino acid sequences which have "substantial identity", preferably having at least 70%, 80%, 90%, 91%, 92%, 93%, 94%, 95% 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.1%, 99.8% or 99.9% identity with any of the claimed sequences, in particular with the sequences identified herein as SEQ ID NO: 2, 29, 34, 47, 51 and 109, and having CYP450 activity. Desirably, the term "substantial identity" indicates that said sequence has a greater degree of identity with any of the sequences described herein than with prior art amino acid sequences. One can use a program such as the online tool using CLUSTAL W algorithm (Thompson, J. D., Higgins, D. G. and Gibson, T. J. (1994). Nucleic Acids Research, 22: 4673-4680.) to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. The above applied mutatis mutandis to all amino acid sequences disclosed in the present application.

A variety of different compounds can be hydroxylated and/or dealkylated using the claimed cytochrome P450 enzymes. In a preferred embodiment, the organic compound to be hydroxylated will have a rate of conversion to the resulting derivative of at least 3%, more preferably at least 5%, more preferably at least 10%, more preferably at least 25%, more preferably at least 50%, even more preferably at least 70% and most preferably a rate of conversion to the resulting derivative of 100%, using the same or similar conditions to those described in Example 5 herein.

The compound to be hydroxylated by the cytochrome P450 enzyme may have an optionally substituted or unsubstituted linear or branched alkyl group, such as, but not limited to, methyl, isopropyl, tert-butyl or pentyl, which is hydroxylated; or an aromatic group, such as an optionally substituted or unsubstituted aryl or heteroaryl, which is hydroxylated.

There is a particularly high conversion rate from these compounds to their hydroxylated derivatives when using the claimed cytochrome P450 enzyme.

Preferably, the compound to be hydroxylated is of formula I:

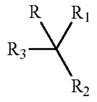

(I)

where R represents the rest of the compound, and where $R^1$, $R^2$ and $R^3$ are independently selected from H or $C_{1-12}$ alkyl or $C_{6-10}$ aryl, or wherein any two of $R^1$, $R^2$ and $R^3$ may be joined to form an optionally substituted cycloalkyl or heterocycloalkyl or $R^1$, $R^2$ and $R^3$ may be joined together with their bridging carbon to form an olefin, aryl or heteroaryl.

Preferably R is an optionally substituted alkyl; an optionally substituted olefin, an optionally substituted aryl, optionally substituted heteroaryl or optionally substituted heterocycloalkyl.

As used herein "alkyl" means a $C_1$-$C_{10}$ alkyl group, which can be linear or branched or cyclic. Examples include propyl and butyl, pentyl, hexyl, cyclopentyl and cyclohexyl. Preferably, it is a $C_3$-$C_{10}$ alkyl moiety. More preferably it is a $C_5$-$C_6$ alkyl moiety. Preferably the alkyl is an optionally substituted cyclohexyl.

The compound to be dealkylated by the cytochrome P450 enzyme may have an optionally substituted linear or branched alkyl group, such as but not limited to methyl, ethyl, propyl, isopropyl or tert-butyl bonded to the rest of the compound via an oxygen (ether linkage) or nitrogen.

There is a particularly high conversion rate from these compounds to their dealkylated derivatives when using the claimed cytochrome P450 enzyme.

Preferably, the compound to be dealkylated is of formula II:

$$R_{(y)}—X—R^1 \qquad (II)$$

where R represents the rest of the compound, y is the number of bonded moieties depending on the valency of X, X is oxygen or nitrogen, and where $R^1$ is the leaving moiety independently selected from $C_{1-12}$ alkyl or $C_{6-10}$ aryl, or wherein R and $R^1$ may be joined to form an optionally substituted cycloalkyl or heterocycloalkyl or R and $R^1$ may be joined together with their bridging carbon to form an olefin, aryl or heteroaryl.

Preferably R is an optionally substituted alkyl; an optionally substituted olefin, an optionally substituted aryl, optionally substituted heteroaryl or optionally substituted heterocycloalkyl. Demethylation of methyl-amides in linear- or cyclic-peptide residues is a particularly useful reaction.

As used herein "alkyl" means a $C_1$-$C_{10}$ alkyl group, which can be linear or branched or cyclic. Examples include propyl and butyl, pentyl, hexyl, cyclopentyl and cyclohexyl. Preferably, it is a $C_3$-$C_{10}$ alkyl moiety. More preferably it is a $C_5$-$C_6$ alkyl moiety. Preferably the alkyl is an optionally substituted cyclohexyl.

For the avoidance of any doubt, the term cycloalkyl is a cyclic alkyl group.

As used herein "aryl" means an optionally substituted monocyclic, bicyclic or tricyclic aromatic radical, such as phenyl, biphenyl, naphthyl, anthracenyl. Preferably the aryl is an optionally substituted C aryl.

As used herein "heteroaryl" means an optionally substituted monocyclic, bicyclic or tricyclic aromatic radical containing at least one and up to four heteroatoms selected from oxygen, nitrogen and sulfur, such as furanyl, pyrrolyl, thiazolyl, isothiazolyl, tetrazolyl, imidazolyl, oxazolyl, isoxazolyl, thienyl, pyrazolyl, pyridinyl, pyrazinyl, pyrimidinyl, indolyl, azaindolyl, isoindolyl, quinolyl, isoquinolyl, triazolyl, thiadiazolyl, oxadiazolyl. Preferably the heteroaryl is an optionally substituted thioazole.

As used herein heterocycloalkyl means an optionally substituted cycloalkyl wherein one to four carbon atoms have been substituted with a heteroatom. Preferably, the heteroatoms are selected from nitrogen, oxygen, sulphur or phosphorous.

As used herein the term "optionally substituted" means an H has been removed from a compound and replaced with an organic fragment such as those those comprising a combination of any of carbon, hydrogen, nitrogen, oxygen and sulphur.

Preferably the compounds of formula I and formula II have a molecular weight of from 50 to 1500, such as from 100 to 800, more preferably from 200 to 500.

Preferably at least 2 of $R^1$, $R^2$ and $R^3$ are selected from $C_{1-12}$ alkyl or $C_{6-10}$ aryl. Preferably, $R^1$, $R^2$ and $R^3$ are independently selected from H, $C_{1-6}$ alkyl or $C_{6-10}$ aryl, preferably with the proviso that either one or none of $R^1$, $R^2$ and $R^3$ is H. Most preferably, $R^1$, $R^2$ and $R^3$ are independently selected from H, methyl, ethyl, propyl, butyl, t-butyl, pentyl and hexyl preferably with the proviso that either one or none of $R^1$, $R^2$ and $R^3$ is H.

In a particularly preferred embodiment, the cytochrome P450 enzymes are reacted with a compound such as bosentan, cyclosporine A, diclofenac, ritonavir, tivantinib, valsartan orvanoxerine. Most preferably, the cytochrome P450 enzyme is reacted with bosentan, cyclosporine A, or ritonavir.

The compounds of formula I and formula II are exemplified as being typically of the following structural formulae:

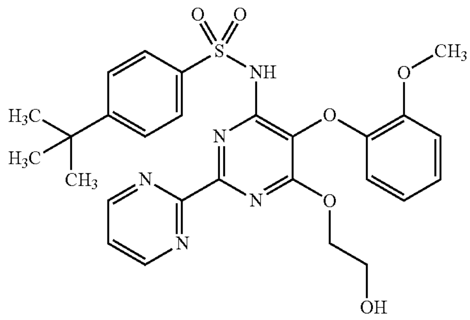

(ii)

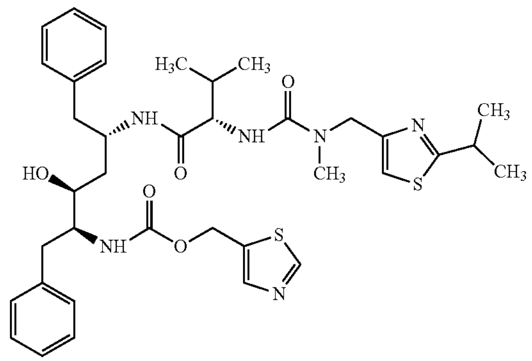

(iii)

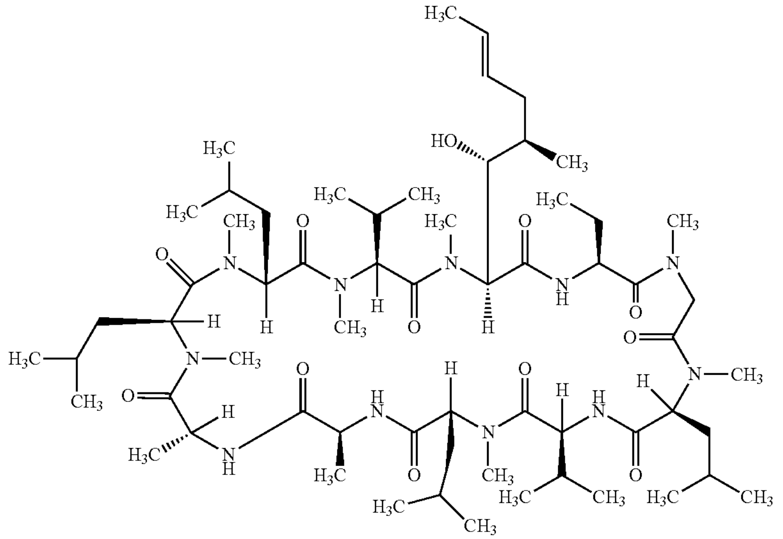

(iv)

-continued (v)

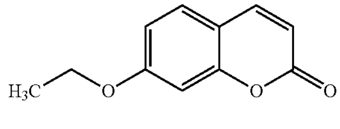

(vi)

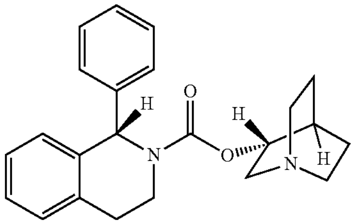

(vii)

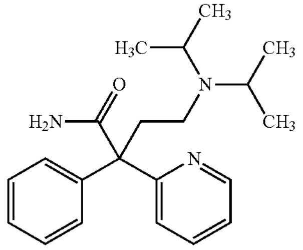

(viii)

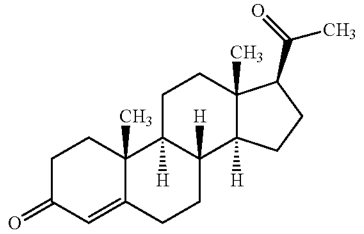

(ix)

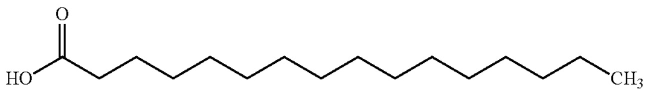

The cytochrome P450 enzyme may optionally be used in combination with reductase components, which activate the cytochrome P450. In a preferred embodiment, ferredoxin and ferredoxin reductase components are used. Any components which activate the cytochrome P450 may also be used, including those fused directly or by peptide linkage, protein or chemical in nature. In a particularly preferred embodiment, the enzyme cytochrome $P450_{SriC01}$, $P450_{SriC12}$, $P450_{SriC14}$, $P450_{SriC20}$, $P450_{SriC22}$ and $P450_{SriC51}$ having SEQ ID NO: 2, 29, 34, 47, 51 and 109, respectively, mutants thereof or a variant enzyme having at least 70% identity thereto and having CYP450 activity, is combined with suitable ferredoxin and ferredoxin reductase components to give an effective system to convert a substrate compound to a resulting derivative, hydroxylated and/or dealkylated.

In a preferred embodiment, the cytochrome P450 enzymes or variant thereof is present in *Streptomyces rimosus* NRRL-2234 cells.

In another preferred embodiment, the cytochrome P450 enzymes or variant thereof is expressed by at least one recombinant microorganism comprising heterologous nucleic acid encoding the enzyme, derived from *Streptomyces rimosus* NRRL-2234. As used herein the term "comprising" is intended to mean containing at least the claimed sequences, but may include other sequences. In one embodiment, the recombinant microorganism comprises a heterologous nucleic acid encoding the enzyme or variant thereof. In an alternative embodiment, the recombinant microorganism also comprises a heterologous nucleic acid encoding a reductase agent.

In another aspect of the invention, there is provided a method for the production of a hydroxylated organic compound, comprising reacting the organic compound with a cytochrome P450 enzyme comprising SEQ ID NO: 2, 29, 34, 47, 51 or 109, mutants thereof or a variant enzyme having at least 70% identity thereto and having CYP450 activity.

The choice of compound to be hydroxylated is discussed above.

In another aspect of the invention, there is provided a method for the production of a dealkylated organic compound, comprising reacting the organic compound with a cytochrome P450 enzymes comprising SEQ ID NO: 2, 29, 34, 47, 51 or 109, mutants thereof or a variant enzyme having at least 70% identity thereto and having CYP450 activity.

The choice of compound to be dealkylated is discussed above.

In a preferred embodiment, the enzymes are used to catalyse the hydroxylation or removal of an alkyl or aryl group, more preferably hydroxylation of an isopropyl or isobutyl group or tert-butyl group or removal of a methyl group. Most preferably, the enzymes are used to catalyse demethylation of O-methyl and N-methyl moieties. The cytochrome $P450_{SriC12}$ enzyme is able to catalyse the substrate compound with an O-methyl moiety to an O-demethylated derivative. The cytochrome $P450_{SriC22}$ enzyme is able to catalyse the substrate compound with an N-methyl moiety to a N-demethylated derivative.

In a particularly preferred embodiment, the compound to be hydroxylated is bosentan, cyclosporin, solifenacin, palmitic acid or progesterone. Most preferably, the compound to be dealkylated is bosentan, disopyramide or ritonavir.

Optionally, one or more additional component(s) may be used to activate the cytochrome P450 enzyme. In an embodiment according to the present invention, the cytochrome P450 enzyme is used in combination with reductase components, preferably with ferredoxin and ferredoxin reductase components.

In a preferred embodiment of the invention, the cytochrome P450 enzymes or variants thereof are present in *Streptomyces rimosus* NRRL-2234 cells. The cells may be dosed with the organic compound to be hydroxylated and/or dealkylated. The method may optionally comprise an additional step wherein the cells are subsequently harvested and purified to obtain the hydroxylated compound.

Culture of the *Streptomyces rimosus* NRRL-2234 to produce the P450 enzyme extracts is suitably performed by seeding of a conventional culture medium containing nutrients well-known for use with such microorganisms. Thus, the culture medium contains sources of assimilable carbon and of assimilable nitrogen. The culture medium may also contain inorganic salts. Examples of sources of assimilable carbon include glucose, sucrose, starch, glycerin, millet jelly, molasses and soybean oil. Examples of sources of assimilable nitrogen include soybean solids (such as soybean meal or soybean flour), wheat germ, meat extracts, peptone, corn steep liquor, dried yeast and ammonium salts, such as ammonium sulphate. If required, inorganic salts, such as sodium chloride, potassium chloride, calcium carbonate and various phosphates, may also be included. The medium is preferably sterilized and has a pH adjusted to 5 to 8.

The skilled person will understand that the particular cultivation technique employed is not critical to the invention and any technique commonly used for the cultivation of Actinomycete bacteria may equally be employed with the present invention. In general, the techniques employed will be chosen having regard to industrial efficiency. Thus, liquid culture is generally preferred and the submerged culture method is most convenient from the industrial point of view. Cultivation is preferably carried out under aerobic conditions.

The enzymes of this invention are inducible enzymes, and are not produced unless an induction agent is present. For preference, but not limited to, the induction agent is selected to be the same as the intended substrate for the isolated enzyme. When from 4 hours to 3 days have elapsed after inoculation, preferably 0.05 to 5 mM, more preferably 0.2 mM of induction agent is added, and then cultivation is continued for 2 hours to 1 week, preferably for about one day. The temperature of cultivation is typically 20° to 45° C., preferably 25° to 30° C., optimally about 27° C. Shake culture or aeration techniques can be adopted.

The cells obtained by the cultivation may be disrupted by cell disruption techniques such as high-pressure homogenisation in buffer® solution. The supernatant obtained by centrifugation gives the crude enzyme solution. For example, the enzyme of the present invention can be obtained in a supernatant produced by centrifugation at 38,000×g for 20 minutes.

In an alternative embodiment, the cytochrome P450 enzymes or variants thereof are expressed by at least one recombinant microorganism comprising heterologous nucleic acid encoding the enzyme, derived from *Streptomyces rimosus* NRRL-2234.

Here, the at least one recombinant microorganism can be dosed with an organic compound to be hydroxylated. This method may optionally comprise a purification step to obtain the hydroxylated compound.

In a preferred embodiment, this can be achieved by the recombinant expression of the functional cytochrome $P450_{SriC01}$, $P450_{SriC12}$, $P450_{SriC14}$, $P450_{SriC20}$, $P450_{SriC22}$ and $P450_{SriC51}$ proteins with intact haem. Each can be expressed with any or all of the cofactor enzymes. In a particularly preferred embodiment, ferredoxin and ferredoxin reductase may be expressed. This can be achieved by polycistronic plasmid use or via fusion, either via linkers or directly into a single protein product.

Alternatively, the functional cytochrome $P450_{SriC01}$, $P450_{SriC12}$, $P450_{SriC14}$, $P450_{SriC20}$, $P450_{SriC22}$ and $P450_{SriC51}$ proteins may be expressed alone without mixing with cofactor enzymes. In a preferred embodiment, cofactor enzymes may be titrated in to provide the active enzyme reaction after material production. The cofactors may be obtained by extraction from wild-type or recombinant materials derived from plants or microbial fermentation. Hussain & Ward, Appl Environ Microbiol. 2003; 69(1):373-382, describe the cloning techniques that may be used.

The native organism, host strain expressing the recombinant enzyme or extracted enzyme is contacted directly with the substrate, preferably in an aqueous medium, either mono or biphasic. Reaction conditions, including choice of pH and temperature will be evident to the skilled person, based on conventional techniques. For example, a selected microbial growth medium or phosphate buffer solution at a pH value in the range of from 5 to 11, more preferably 6.5 to 9.0, most preferably around 8 may be used. The reaction temperature is preferably within the range from 20° to 45° C., more preferably from 25° to 30° C. The concentration of the substrate in the reaction medium is preferably within the range from 0.01 to 5.0% by weight. The time allowed for the reaction is normally from 1 minute to 5 days, more usually from 1 day to 5 days, although this may vary, depending upon the concentration of substrate in the reaction mixture, the reaction temperature, and other factors. The extracted enzyme material can either be used directly after extraction, after storage in frozen solution. In a particularly preferred embodiment, the extracted enzyme material can be dried, preferably by lyophilisation, sealed with or without vacuum, for later use with or without the addition of other components required for reaction, such as other enzyme cofactor components.

After completion of the conversion reaction, the resulting compound (hydroxylated and/or dealkylated) can be isolated using conventional procedures, including, for instance, filtration, solvent extraction, chromatography, crystallization, and other isolation procedures. Such procedures will be selected having due regard to the identity of the product. Before, during or after the isolation, the product may or may not be derivatised, as desired.

The starting materials as substrates for the enzyme may by either derived from synthetic routes, naturally occurring, either via natural biomass such as plant material, or produced by fermentation, or by mixed routes thereof. Enzyme reactions can also be performed using pure or non-purified materials, the resulting reaction may be used to aid later purifications of reacted or unreacted components.

Of the substrate compounds used as starting materials, free bases, alkali metal salts, e.g. the sodium or potassium salts, or acid salts of organic or inorganic nature such as tosylate or hydrochlorides, are suitable for use.

After completion of the conversion reaction, the desired compound can be obtained from the reaction system, collected, isolated and purified by conventional means if required, or onward used directly in unpurified form. For example, the reaction product is centrifuged or filtered and the supernatant or filtrate is extracted with a hydrophobic resin, ion-exchange resin or water-immiscible organic solvent such as ethyl acetate. After evaporation of the solvent of the extract, the remaining crude, for example the remaining crude hydroxylated and/or dealkylated compound, may be purified by subjecting it to column chromatography using silica gel or alumina or reversed-phase stationary phase, and by eluting with a suitable eluent. If the starting material is a mixture, then the product can be isolated as a mixture of hydroxylated and/or dealkylated compounds which if desired can be separated using chromatography or other suitable techniques.

In general, the resulting compound (hydroxylated and/or dealkylated) may have improved pharmaceutical or agrochemical properties, such as bioactivity potency, improved solubility characteristics, reduced off-target interactions, or simply of further utility, such as for onward synthesis, or be useful for an analytical standard. Particularly preferred are the hydroxylated and dealkylated compounds of formulas (I) & (II) discussed above.

When the cytochrome P450 enzyme preparations of this invention is reacted with substrate compound at pH 7.4 for 5 minutes with (a) ferredoxin, (b) ferredoxin-$NADP^+$-reductase, (c) $NADP^+$, (d) NADPH regeneration system, and (e) dissolved oxygen, the temperature of reaction ranges at least from 4° C. to 60° C.

The use of ferredoxin, ferredoxin-$NADP^+$-reductase, oxygen and NADPH is not essential. Any components which can activate the cytochrome P450 may be adopted.

Measurement of the enzyme activity is normally effected in one of two ways:

(i) Measurement on cytochrome P450

Measurement is performed according to the method of Omura and Sato et al. (J Biol Chem, 239. 1964, 2370). That is to say, cytochrome P450 is analyzed quantitatively using the following formula, based on the difference in the absorbance of the reduced CO versus the reduced difference spectrum at 450 nm and 490 nm.

$$\text{Cytochrome } P450(\text{mM}) = \frac{\text{Abs(450 nm)} - \text{Abs(490 nm)}}{91(\text{mM cm}^{-1}) \times l(\text{cm})}$$

(ii) Measurement of rate of formation of hydroxylated or dealkylated substrate compound from substrate compound The following cocktail of components is employed:

| | |
|---|---|
| Potassium phosphate buffer pH 8 | 100 mM |
| $MgCl_2$ | 5 mM |
| Enzyme solution containing expressed Fd, FdR, P450 concentration when pellet extracted at a rate of 0.3 g cell wet weight per ml extraction buffer | Native |
| $NADP^+$ | 1 mM |
| Glucose-6-phosphate | 5 mM |
| Glucose-6-phosphate dehydrogenase | 1 UN/ml |
| Substrate compound | 0.1 mg/ml |
| Total volume | 0.1-0.5 ml |

To measure enzyme activity the components of the table are mixed, the solution is shaken at 30° C. for 16-20 hours, and then 100-500 µl of ACN is added and the reaction stopped. The amount of hydroxylated/dealkylated substrate formed by the enzyme system is determined with HPLC or UPLC.

Using the test methods for determining activity, the loss of activity with change in temperature and pH can be determined.

In a further aspect, the invention provides a kit comprising i) a cytochrome P450 enzyme comprising SEQ ID NO: 2, 29, 34, 47, 51 or 109, or mutant thereof or a variant enzyme having at least 70% identity thereto and having CYP450 activity, or ii) a microorganism that expresses a cytochrome P450 enzyme comprising SEQ ID NO: 2, 29, 34, 47, 51 or 109, or mutant thereof or a variant enzyme having at least 70% identity thereto and having CYP450 activity, and wherein the kit further comprises instructions for use for the hydroxylation and/or dealkylation of an organic compound.

The kit allows the user to screen for the hydroxylation and/or dealkylation of compounds of interest.

In a preferred embodiment, the kit further comprises electron donating agents. The kit may preferably comprise as the electron donating agents ferredoxin reductase and a ferredoxin with cofactors NADH or NADPH or cofactor regeneration systems such as NAD+ or NADP+, glucose or glucose-6-phosphate, and glucose-dehydrogenase or glucose-6-phosphate dehydrogenase. However, any suitable electron donating agents may be used.

Optionally, the kit may further comprise a buffer, either separately or contained with the other components.

Preferably, the kit may further comprise one or more other CYP450 enzymes.

Preferably, the cytochrome P450 enzyme or microorganism is lyophilised or immobilised or tethered to other macromolecules or support materials such alginate beads, Nickel columns and electrochemical electrodes.

The methods of the present invention are demonstrated in the examples below. These examples are provided as an illustration only and should not be construed as limiting on the present invention.

EXAMPLES

Example 1: Cloning of P450s, Ferredoxins and Ferredoxin Reductases from *Streptomyces rimosus* NRRL-2234

Extraction of Genomic DNA from *Streptomyces rimosus* NRRL-2234

Genomic DNA (gDNA) was isolated from cell pellet of fermentation material of *Streptomyces rimosus* NRRL-2234. Culture medium containing 4 g/L yeast extract; 10 g/L malt extract; 4 g/L glucose and adjusted to pH 7.0. Two Erlenmeyer flasks of 250 ml volume, each of which contained 50 ml of the medium, were sterilized 115° C. for 20 minutes. *Streptomyces rimosus* NRRL-2234 was recovered from cryovial stocks stored in liquid nitrogen and inoculated into the two flasks containing 50 ml of the above growth medium. After 2 days of growth at 27° C. and 200 rpm, 50 mls of culture were transferred to 50 ml centrifuge tubes and centrifuged to collect the pelleted cells. The pellet was washed once with an isotonic buffer to remove residual medium components before freezing the pellet at −80° C. for later extraction of genomic DNA as described below. The cell pellet was defrosted and resuspended in 7.5 ml TE buffer (10 mM Tris-HCl pH 7.5, 1 mM $Na_2EDTA$). Seventy-five µl of 20 mg/ml lysozyme solution was added and the solution was incubated at 37° C. for 1 hour, followed by addition of 750 µl of 10% (w/v) SDS and mixing by inverting. After addition of 20 µl of 20 mg/ml pronase and incubation at 37° C. for 1.5 hours, the solution was supplemented with 16 µl of 10 mg/ml RNase solution, followed by another incubation step at 37° C. for 1 hour and 50° C. for 1 hour. Nine hundred µl of 0.5 M NaCl solution was added before the solution was extracted twice with an equal volume of phenol-chloroform-isoamylalcohol (25:24:1; Sigma-Aldrich). The aqueous layers were collected and gDNA was precipitated with 1 volume of isopropanol and centrifugation (10,000×g, 30 min, 20° C.). The gDNA pellet was washed once with 100% ethanol and twice with 70% ethanol (~30 ml each wash step). The gDNA pellet was air-dried and resuspended in 5 ml TE buffer. Concentration and purity of the gDNA was measured using a NanoDrop instrument (Thermo Scientific) and gDNA integrity was assessed by agarose gel electrophoresis.

PCR Reactions

Fifty-four cytochrome P450s (SEQ ID NO: 1-118) were cloned from *Streptomyces rimosus* NRRL-2234 in a total reaction volume of 50 µl using primers in Table 1. PCR reactions contained 10 µl of 5×GC Green buffer (Thermo Scientific), 2.5 μl of DMSO (Sigma), 10 μL of 5M betaine (Sigma) and 1 μL of formamide (Sigma), 1 μl of 10 mM of dNTPs (Thermo Scientific), 1 unit of HotStart II Phusion© High-Fidelity DNA Polymerase (Thermo Scientific), ~ 90 ng of genomic DNA, 0.5 μM of each forward and reverse primer and the reaction was filled up to a total volume of 50 μl with MilliQ®-$H_2O$. PCR reactions were performed on an Eppendorf Mastercycler ep Gradient system with the following cycling conditions: 98° C. for 2 minutes, 35 cycles (98° C. for 45 seconds, 72° C. for 30 seconds, 72° C. for 2 minute), 72° C. for 15 minutes. The PCR reaction was analysed by agarose gel electrophoresis and products were extracted from the agarose gel using the Thermofisher GeneJet Gel Extraction Kit and Qiagen QIAquick 96 PCR Purification Kit. The DNA concentration of the purified DNA product were measured using the Biochrome Genequant 1300 instrument and on the Molecular Devices Spectramax 384 plus plate reader.

TABLE 1 primers used to amplify the 54 cytochrome P450s and their neighbouring redox partners from *S. rimosus* NRRL-2234

| Target | | | Primer sequences (5' to 3')<br>Forward primer<br>Reverse primer |
|---|---|---|---|
| P450 | Fd | FdR | |
| SriC01 | | | ATTTTGTTTAACTTTAAGAAGGAGATATACATATGACCGAGACGATCCCGTT CGAAG (SEQ ID NO: 119)<br>GTGGTGGTGGTGGTGGTGCTCGAGTGCGGCCGCTAATTACCCCGTCACA TAGACATCCTC (SEQ ID NO: 120) |
| SriC02 | | | ATTTTGTTTAACTTTAAGAAGGAGATATACATATGACCGGCGTATCCGCCC GCGAAC (SEQ ID NO: 121)<br>CGATCCGCACTCACCCGCATGGTCATGAATTCTGTTTCCTATAATTACCAG GCGACCGGCAGGGATTC (SEQ ID NO: 122) |
| SriC03 | SriF01 | | ATTTTGTTTAACTTTAAGAAGGAGATATACATATGCCGGACGAGTCCCAGC ACCAGTTC (SEQ ID NO: 123)<br>CTACCCGCAGAGGGCGGGGCATAAGCTTCCTATTACGTACCCGGGCCGT CCGCCTCCCGCTC (SEQ ID NO: 124) |
| SriC04 | | | ATTTTGTTTAACTTTAAGAAGGAGATATACATATGGCGAGCCGTACCCGTA TCGATAC (SEQ ID NO: 125)<br>CGATCCGCACTCACCCGCATGGTCATGAATTCTGTTTCCTATAATTAGCCG CGCGGGGTGAGCGCCAGATC (SEQ ID NO: 126) |
| SriC05 | SriF02 | | ATTTTGTTTAACTTTAAGAAGGAGATATACATATGTCGTACAACCCGACGG CCCCCGAC (SEQ ID NO: 127)<br>CTACCCGCAGAGGGCGGGGCATAAGCTTCCTATTACGGGTCCGTGGGTT CCGGGGAG (SEQ ID NO: 128) |
| SriC06 | | | ATTTTGTTTAACTTTAAGAAGGAGATATACATATGAGCGACCCGGCCGCGG TAC (SEQ ID NO: 129)<br>CGATCCGCACTCACCCGCATGGTCATGAATTCTGTTTCCTATAATTACGAC AGGAGCAGGGGCAGCTC (SEQ ID NO: 130) |
| SriC07 | | | ATTTTGTTTAACTTTAAGAAGGAGATATACATATGGACATCGATGGCGCGG AGCCCGGCGGCGGCCCTTC (SEQ ID NO: 131)<br>CGATCCGCACTCACCCGCATGGTCATGAATTCTGTTTCCTATAATTATGAA CCGCCGGGCGGGCCGAGGAC (SEQ ID NO: 132) |
| SriC08 | | | ATTTTGTTTAACTTTAAGAAGGAGATATACATATGGCTGAGTCCACCCACA CTG (SEQ ID NO: 133)<br>CGATCCGCACTCACCCGCATGGTCATGAATTCTGTTTCCTATAATTACACA TCCCAGGCGACCGGAAGAC (SEQ ID NO: 134) |
| SriC09 | SriF03 | SriFR01 | ATTTTGTTTAACTTTAAGAAGGAGATATACATATGACCCCCTCTCCCGCTTC CCCCGCCAC (SEQ ID NO: 135)<br>GTGGTGGTGGTGGTGGTGCTCGAGTGCGGCCGCTAATTACGCGCGGGCG TTGTGCAGCCCCTCGCGAG (SEQ ID NO: 136) |
| SriC10 | | | ATTTTGTTTAACTTTAAGAAGGAGATATACATATGACCCTCACCACACGATC CGGCCCGGCGA (SEQ ID NO: 137)<br>CGATCCGCACTCACCCGCATGGTCATGAATTCTGTTTCCTATAATTAGCCC ACTCCCCTCAGCCGCACCCGCGCCGGGCCCGCCGCCTG (SEQ ID NO: 138) |
| SriC11 | SriF04 | | ATTTTGTTTAACTTTAAGAAGGAGATATACATATGACGCACACCGAACCGG CCGCGCCGGCCACCTG (SEQ ID NO: 139)<br>CTACCCGCAGAGGGCGGGGCATAAGCTTCCTATTAGCCCTCGTGCACGG TGATGGCCCCGGAC (SEQ ID NO: 140) |
| SriC12 | SriF05 | | ATTTTGTTTAACTTTAAGAAGGAGATATACATATGACCGAGGCGCTGCCCT TCCCGCAG (SEQ ID NO: 141)<br>CTACCCGCAGAGGGCGGGGCATAAGCTTCCTATTAGTCGTCCGTGACCG CGATCGCCTGAAC (SEQ ID NO: 142) |

TABLE 1-continued primers used to amplify the 54 cytochrome P450s and their neighbouring redox partners from *S. rimosus* NRRL-2234

| Target | | | Primer sequences (5' to 3') Forward primer |
|---|---|---|---|
| P450 | Fd | FdR | Reverse primer |
| SriC13 | | | ATTTTGTTTAACTTTAAGAAGGAGATATACATATGACCGCGGCCGCGCAGGAACTGGAAATC (SEQ ID NO: 143)<br>CGATCCGCACTCACCCGCATGGTCATGAATTCTGTTTCCTATAATTACCAGGTGACCGGGAATGCGTGGATAC (SEQ ID NO: 144) |
| SriC14 | SriF06 | | ATTTTGTTTAACTTTAAGAAGGAGATATACATATGACCGAGACCTCCACCGCCTTCCCGGCCCAAGAC (SEQ ID NO: 145)<br>CTACCCGCAGAGGGCGGGGCATAAGCTTCCTATTACTCCGTGACCCGAAGGGCCCCGGACGGGCACAGCATG (SEQ ID NO: 146) |
| SriC15 | | | ATTTTGTTTAACTTTAAGAAGGAGATATACATATGGCTGCACACGCCGATGAGCCGATC (SEQ ID NO: 147)<br>CGATCCGCACTCACCCGCATGGTCATGAATTCTGTTTCCTATAATTATGTGACGCTCCTTTGCGCGTGGGGGATG (SEQ ID NO: 148) |
| SriC16 | | | ATTTTGTTTAACTTTAAGAAGGAGATATACATATGCCGGGCGCCTTGCCCCTCGTCGGGCAC (SEQ ID NO: 149)<br>CGATCCGCACTCACCCGCATGGTCATGAATTCTGTTTCCTATAATTAGTTGCTCGGCCGGCTGGGTGCGGGGTTAC (SEQ ID NO: 150) |
| SriC17 | | | ATTTTGTTTAACTTTAAGAAGGAGATATACATATGCCGGTCCAGCTCCCCGGCGGCATC (SEQ ID NO: 151)<br>CGATCCGCACTCACCCGCATGGTCATGAATTCTGTTTCCTATAATTACCCGGCGCCGGGGCTGGTGGCCGAC (SEQ ID NO: 152) |
| SriC18 | | | ATTTTGTTTAACTTTAAGAAGGAGATATACATATGACGACCGTTCCCGATCTTCCCGACGCCACAG (SEQ ID NO: 153)<br>CGATCCGCACTCACCCGCATGGTCATGAATTCTGTTTCCTATAATTATTCCGGGTCGCCCTGCCAGGTCAC (SEQ ID NO: 154) |
| SriC19 | | | ATTTTGTTTAACTTTAAGAAGGAGATATACATATGCAGAACACCGCCGAGACCGGCCCCGAC (SEQ ID NO: 155)<br>CGATCCGCACTCACCCGCATGGTCATGAATTCTGTTTCCTATAATTACCAGGCGACGGGGAGCGAGATCAAG (SEQ ID NO: 156) |
| SriC20 | | | ATTTTGTTTAACTTTAAGAAGGAGATATACATATGCCGGAAATCATCGACCTG (SEQ ID NO: 157)<br>CGATCCGCACTCACCCGCATGGTCATGAATTCTGTTTCCTATAATTACCGCCACCGCACCGGCAGGTG (SEQ ID NO: 158) |
| SriC21 | | | ATTTTGTTTAACTTTAAGAAGGAGATATACATATGTCAGTGCCGAGCCGCCCGCCGGCCAC (SEQ ID NO: 159)<br>CGATCCGCACTCACCCGCATGGTCATGAATTCTGTTTCCTATAATTAGAGTTGGAAAGTGATCCGTTCGGTG (SEQ ID NO: 160) |
| SriC22 | | | ATTTTGTTTAACTTTAAGAAGGAGATATACATATGACCACATCGCCCACCGAGTCCAC (SEQ ID NO: 161)<br>CGATCCGCACTCACCCGCATGGTCATGAATTCTGTTTCCTATAATTAGTCCTCCGGACGCAGCCGCAACGGCAG (SEQ ID NO: 162) |
| SriC23 | | | ATTTTGTTTAACTTTAAGAAGGAGATATACATATGACCGCCGAGAACCACACCGCGCAG (SEQ ID NO: 163)<br>CGATCCGCACTCACCCGCATGGTCATGAATTCTGTTTCCTATAATTACCACGCCACCGGAATCTCCGCCGCCATG (SEQ ID NO: 164) |
| SriC24 | | | ATTTTGTTTAACTTTAAGAAGGAGATATACATATGCCGCAGGACACCTCCCGCCGGTTC (SEQ ID NO: 165)<br>CGATCCGCACTCACCCGCATGGTCATGAATTCTGTTTCCTATAATTACCACACCACAGGCAGCCTCACCAC (SEQ ID NO: 166) |
| SriC25 | | | ATTTTGTTTAACTTTAAGAAGGAGATATACATATGGATGAGTCGCCCGTCTTCGTCCTGGATC (SEQ ID NO: 167)<br>CGATCCGCACTCACCCGCATGGTCATGAATTCTGTTTCCTATAATTATCCCCCTGCTTCCCCGGCCGGCGCGGAGCGGAG (SEQ ID NO: 168) |
| SriC26 | | | ATTTTGTTTAACTTTAAGAAGGAGATATACATATGGAGACTGCCCCGCTCCGCCCCGTAC (SEQ ID NO: 169)<br>CGATCCGCACTCACCCGCATGGTCATGAATTCTGTTTCCTATAATTACGGACGCGAACGAGCGCGCACCGTG (SEQ ID NO: 170) |

TABLE 1-continued primers used to amplify the 54 cytochrome P450s and their neighbouring redox partners from *S. rimosus* NRRL-2234

| Target P450 | Fd | FdR | Primer sequences (5' to 3') Forward primer Reverse primer |
|---|---|---|---|
| SriC27 | | | ATTTTGTTTAACTTTAAGAAGGAGATATACATATGCGCGATCCGGTCCGCTACTTCGAGAC (SEQ ID NO: 171)<br>CGATCCGCACTCACCCGCATGGTCATGAATTCTGTTTCCTATAATTACCCCGCGTCGTCCGAAAGAGCCGGATG (SEQ ID NO: 172) |
| SriC28 | | | ATTTTGTTTAACTTTAAGAAGGAGATATACATATGTTCACACCCCGCACGTACGCCAC (SEQ ID NO: 173)<br>CGATCCGCACTCACCCGCATGGTCATGAATTCTGTTTCCTATAATTACGCCCCCACCCGCACCGGCAACCGCCGCAAC (SEQ ID NO: 174) |
| SriC30 | | | ATTTTGTTTAACTTTAAGAAGGAGATATACATATGACCACGGACGACGACGAAGAAGAGGATCAG (SEQ ID NO: 175)<br>CGATCCGCACTCACCCGCATGGTCATGAATTCTGTTTCCTATAATTACCATGCGACGGGCAACGATTCCAG (SEQ ID NO: 176) |
| SriC31 | | | ATTTTGTTTAACTTTAAGAAGGAGATATACATATGTTGATGCCGCTGCGGCGTCAGGGGCTG (SEQ ID NO: 177)<br>CGATCCGCACTCACCCGCATGGTCATGAATTCTGTTTCCTATAATTAGCCGCCGAGGTGCACCGGCAGCGAC (SEQ ID NO: 178) |
| SriC32 | | | ATTTTGTTTAACTTTAAGAAGGAGATATACATATGCTCGGCGACGCCCGGTTCAGCTC (SEQ ID NO: 179)<br>CGATCCGCACTCACCCGCATGGTCATGAATTCTGTTTCCTATAATTACCAAGTGACCGGGAGTGCCGATAC (SEQ ID NO: 180) |
| SriC33 | | | ATTTTGTTTAACTTTAAGAAGGAGATATACATATGGACACACACCCCGAACCCATCGATTAC (SEQ ID NO: 181)<br>CGATCCGCACTCACCCGCATGGTCATGAATTCTGTTTCCTATAATTACCAGGTGACCGGCAGCTCCTCGATC (SEQ ID NO: 182) |
| SriC34 | | | ATTTTGTTTAACTTTAAGAAGGAGATATACATATGACGCAGCCGGACACCAGGACGAAC (SEQ ID NO: 183)<br>CGATCCGCACTCACCCGCATGGTCATGAATTCTGTTTCCTATAATTACCAGGCGACGGGCAGCGCGTCCAG (SEQ ID NO: 184) |
| SriC35 | | | ATTTTGTTTAACTTTAAGAAGGAGATATACATATGCCGGACGCCGGACGTCTCCCTC (SEQ ID NO: 185)<br>CGATCCGCACTCACCCGCATGGTCATGAATTCTGTTTCCTATAATTACGGAGTGAGCGTCCCGCCATCGGGCCTG (SEQ ID NO: 186) |
| SriC36 | | | ATTTTGTTTAACTTTAAGAAGGAGATATACATATGGAGTCACCGGAGTTCTTCCGCGAC (SEQ ID NO: 187)<br>CGATCCGCACTCACCCGCATGGTCATGAATTCTGTTTCCTATAATTAACAATCCGTGACCTGTGCGGACCAG (SEQ ID NO: 188) |
| SriC37 | | | ATTTTGTTTAACTTTAAGAAGGAGATATACATATGAAGTCGTCCGCGACGCGGTCCGGGGCCGGCGGAC (SEQ ID NO: 189)<br>CGATCCGCACTCACCCGCATGGTCATGAATTCTGTTTCCTATAATTACCTCCTTCCGGAGCTGTTGGCACGTG (SEQ ID NO: 190) |
| SriC38 | | | ATTTTGTTTAACTTTAAGAAGGAGATATACATATGCGCCCACCCCGCCTACCCGAAC (SEQ ID NO: 191)<br>CGATCCGCACTCACCCGCATGGTCATGAATTCTGTTTCCTATAATTATCGGGTGGCGGCCTCTCCGGCAG (SEQ ID NO: 192) |
| SriC39 | | | ATTTTGTTTAACTTTAAGAAGGAGATATACATATGGAAGGAGTCCAGGCAGTCTTC (SEQ ID NO: 193)<br>CGATCCGCACTCACCCGCATGGTCATGAATTCTGTTTCCTATAATTACACCGCGACCAGCAGCTCGCGCAG (SEQ ID NO: 194) |
| SriC40 | SriF07 | SriFR02 | ATTTTGTTTAACTTTAAGAAGGAGATATACATATGCAGATCGTCGTGGACCTCAC (SEQ ID NO: 195)<br>GTGGTGGTGGTGGTGGTGCTCGAGTGCGGCCGCTAATTACCCTTTATTTCGAGGCGACGCCAAATC (SEQ ID NO: 196) |
| SriC41 | | | ATTTTGTTTAACTTTAAGAAGGAGATATACATATGTCCGGCCACGGACCGGCGGCCGTC (SEQ ID NO: 197)<br>CGATCCGCACTCACCCGCATGGTCATGAATTCTGTTTCCTATAATTACTTCCGTACGGGCGTGAACTCCAC (SEQ ID NO: 198) |

TABLE 1-continued primers used to amplify the 54 cytochrome P450s and their neighbouring redox partners from *S. rimosus* NRRL-2234

| Target | | | Primer sequences (5' to 3') Forward primer |
|---|---|---|---|
| P450 | Fd | FdR | Reverse primer |
| SriC42 | | | ATTTTGTTTAACTTTAAGAAGGAGATATACATATGCCATGCCCCGCGCTGCCCGAC (SEQ ID NO: 199)<br>CGATCCGCACTCACCCGCATGGTCATGAATTCTGTTTCCTATAATTACACGTACCGGACCCGCAGCTCCTTC (SEQ ID NO: 200) |
| SriC43 | | | ATTTTGTTTAACTTTAAGAAGGAGATATACATATGGACGCGCGGGTCCGCCACAGCCCCGAG (SEQ ID NO: 201)<br>CGATCCGCACTCACCCGCATGGTCATGAATTCTGTTTCCTATAATTAGGAGACCACCGCGTGCCGGGGCTG (SEQ ID NO: 202) |
| SriC44 | | | ATTTTGTTTAACTTTAAGAAGGAGATATACATATGGGTATACGTGGTGCGGCGGGCGTCCGCGCGGCCCGCGGTC (SEQ ID NO: 203)<br>CGATCCGCACTCACCCGCATGGTCATGAATTCTGTTTCCTATAATTACGGTGCTTCAGATGGCACGGCCGGCGCTGGGCCGTC (SEQ ID NO: 204) |
| SriC45 | | | ATTTTGTTTAACTTTAAGAAGGAGATATACATATGGGTACGCACATTCCTGGACCCGAAC (SEQ ID NO: 205)<br>CGATCCGCACTCACCCGCATGGTCATGAATTCTGTTTCCTATAATTACGGGCTCCCCGCCCCCACCTCCCGCCGAC (SEQ ID NO: 206) |
| SriC46 | | | ATTTTGTTTAACTTTAAGAAGGAGATATACATATGACCACCCCCCAGCACCCCGACGAC (SEQ ID NO: 207)<br>CGATCCGCACTCACCCGCATGGTCATGAATTCTGTTTCCTATAATTACCGGAAGGCCAGCTCCCCCCGGAAG (SEQ ID NO: 208) |
| SriC47 | | | ATTTTGTTTAACTTTAAGAAGGAGATATACATATGACTTTCCCTTTTCCCGAACAGCCCGGCAC (SEQ ID NO: 209)<br>CGATCCGCACTCACCCGCATGGTCATGAATTCTGTTTCCTATAATTAGCCGCGCAGCCAAGCCTTCAACGCGGCCCAC (SEQ ID NO: 210) |
| SriC48 | | | ATTTTGTTTAACTTTAAGAAGGAGATATACATATGCTGGAACAGCTGCGCAGGCAGTAC (SEQ ID NO: 211)<br>CGATCCGCACTCACCCGCATGGTCATGAATTCTGTTTCCTATAATTAGGCAGTACCAACCGACCTACCCACTC (SEQ ID NO: 212) |
| SriC49 | | | ATTTTGTTTAACTTTAAGAAGGAGATATACATATGAACACCCTCCGCACCGCCAAGCTGCTC (SEQ ID NO: 213)<br>CGATCCGCACTCACCCGCATGGTCATGAATTCTGTTTCCTATAATTAGGCGTGCGGGTACGGACAGCGCGCCGGGGCGGGGGCGGTGCCCGGCAG (SEQ ID NO: 214) |
| SriC50 | | | ATTTTGTTTAACTTTAAGAAGGAGATATACATATGCGTACGTACGGTACGGAACGGAG (SEQ ID NO: 215)<br>CGATCCGCACTCACCCGCATGGTCATGAATTCTGTTTCCTATAATTAGCGCCGTACGACCGACACCCGCGAC (SEQ ID NO: 216) |
| SriC51 | SriF08 | | ATTTTGTTTAACTTTAAGAAGGAGATATACATATGACCACAGCCGACACGATGCCCCTTGCCTACCCGTTC (SEQ ID NO: 217)<br>CTACCCGCAGAGGGCGGGGCATAAGCTTCCTATTAGGGCCGCGGCCCCACCACCTTCTCCCCGTC (SEQ ID NO: 218) |
| SriC52 | | | ATTTTGTTTAACTTTAAGAAGGAGATATACATATGGCGTGGCTCCAGGACGCGGAC (SEQ ID NO: 219)<br>CGATCCGCACTCACCCGCATGGTCATGAATTCTGTTTCCTATAATTACCAGCTGACCGGAAGGGTGAG (SEQ ID NO: 220) |
| SriC54 | | | ATTTTGTTTAACTTTAAGAAGGAGATATACATATGAGCCACCCCGAAGCCCTCATAC (SEQ ID NO: 221)<br>CGATCCGCACTCACCCGCATGGTCATGAATTCTGTTTCCTATAATTACCAGCGCACGGGGAGCCGGGCCGGTG (SEQ ID NO: 222) |
| SriC59 | | | ATTTTGTTTAACTTTAAGAAGGAGATATACATATGGGCCCGGGCGCGCTCACCGAC (SEQ ID NO: 223)<br>CGATCCGCACTCACCCGCATGGTCATGAATTCTGTTTCCTATAATTATGTGCACGTCACCTCCAGCCGCAC (SEQ ID NO: 224) |
| SriC60 | | | ATTTTGTTTAACTTTAAGAAGGAGATATACATATGGACAATCCCTACCCCCTGTAC (SEQ ID NO: 225)<br>CGATCCGCACTCACCCGCATGGTCATGAATTCTGTTTCCTATAATTAGTCCCAGTGGACGGATAGAC (SEQ ID NO: 226) |

Construction of pHD05 Vector

The pHD05 vector is a derivative of pHD02 (See WO2018091885A1) containing the cer sequence. The cer sequence was amplified from pKS450 plasmid (Summers and Sherratt., EMBO J. 1988; 7(3):851-858.) by PCR using the primers ser_f (5'-primer sequence-3': GGGTCCT-CAACGACAGGAGCACGATCATGCCGGAAATACAG-GAACGCACG CTG) (SEQ ID NO: 227) and ser_r (5'-primer sequence-3': TTATCGCCGGCATGGCGGC-CCCACGGGTGCCGGGGCACAACTCAATTTGC GGGTAC) (SEQ ID NO: 228). The expected 439 bp amplicon was extracted from the agarose gel using the Thermofisher GeneJet Gel Extraction Kit and cloned into the FspAI site of pHD02 by Gibson assembly. The plasmids containing the cer sequence were analysed by PCR screening and DNA sequence was confirmed by Sanger sequencing at LGC Genomics (Germany). The plasmid containing the cer sequence was designated as pHD05.

Cloning of Cytochrome P450 (with Redox Partners) into pHD05 Plasmid

The purified amplicons were assembled into pHD05 vector digested with NdeI and either EcorI, HindIII and NotI so that that the cytochrome P450 (with its redox partner) is introduced into a polycistronic operon containing at least one ferredoxin and ferredoxin reductase. The vector was digested with restriction endonuclease (New England Biolabs). Restriction digestion was carried out for 16 h at 37° C. in a total volume of 100 μl containing 10 μl of 10× CutSmart Buffer®, 2 μl of each restriction endonuclease (40 units, New England Biolabs), ~ 5 μg of plasmid DNA. The reaction was stopped by inactivation of the restriction endonuclease at 65° C. for 20 min. The expected digested products were purified using the Thermo Scientific GeneJET Gel Extraction Kit and Qiagen QIAquick 96 PCR Purification Kit. The purified digested vector and purified P450 amplicon were assembled together using Gibson assembly in a total volume of 20 μL containing ~100 ng of digested vector and 1:3 (vector:insert) molar concentration of insert, 6.65% PEG 8000, 133 mM Tris-HCl (Fisher), pH7.5, 13.3 mM $MgCl_2$ (Sigma), 13.3 mM DTT (Sigma), 0.266 mM dNTP (New England Biolabs), 1.33 mM NAD (New England Biolabs), 0.495 Unit of Phusion DNA polymerase (New England Biolabs), 79.5 Units of Taq DNA ligase (New England Biolabs) and 0.075 Units of T5 exonuclease (New England Biolabs). The reaction mixture was incubated at 50° C. for 1 hour and 1 μL was introduced into 25 μL of chemically competent cells *E. coli* DH5a (Invitrogen) by chemical transformation. Clones were selected on Miller's Luria broth (LB) plates containing 50 μg/mL kanamycin after 16 hours of incubation at 37° C. Clones were picked and cultivated in 5 mL LB containing the same antibiotic and recombinant plasmids were isolated from the cultures using the Thermo Scientific GeneJET Plasmid Extraction Kit. DNA sequences of the P450, ferredoxin and ferredoxin reductase were analysed by PCR screening and DNA sequence was confirmed by Sanger sequencing at LGC genomics (Germany).

Construction of the Recombinant Expression Strain

The strains *E. coli* BL21 (DE3) Rosetta2 & Tuner (Merck) were used as a host for recombinant expression of P450, ferredoxin and ferredoxin reductase. To construct this expression strain, *E. coli* BL21 (DE3) Rosetta2 & Tuner cells were transformed with the expression plasmid using chemical transformation. Twenty-five μl of chemically competent cells were mixed with 1 μl (~100 ng) of plasmid followed by incubation on ice for 30 min. Heat shock was performed at 30 sec in a water bath at 42° C. and cells were subsequently chilled on ice for 2 min. One millilitre of LB was added to the cells and incubated for 1 hour at 37° C. and shaking at 250 rpm. The transformation mixture was plated onto LB plates containing 50 μg/ml kanamycin. Plates were incubated at 37° C. for 16 hours. To prepare glycerol stocks of this expression strain, several colonies was picked with a sterile loop and inoculated into 5 ml LB media containing the same antibiotics and cultivated at 37° C. and 250 rpm for 16 h. Five hundred millilitres of this culture were mixed with 500 μl of 50% (w/v) glycerol in cryovials and stored at −80° C.

Example 2: Expression of Recombinant P450

Preculture: Five milliliters of LB Miller media (Sigma) supplemented with 50 μg/ml of kanamycin was inoculated with a loop scraped from a cryovial containing *E. coli* BL21 (DE3) Rosetta2 & Tuner cells harbouring the expression plasmid. Cells were grown overnight at 37° C. and 250 rpm in a New Brunswick Scientific Innova 4230.

Seed: Into a 250 ml baffled flask, 50 ml of PCM8.1 media supplemented with 50 μg/ml of kanamycin was inoculated with the overnight preculture to an OD600 of 0.1 and incubated at 37° C. and 200 rpm until the end of the day.

The components of PCM8.1 were $MgSO_4$ (0.49 $gL^{-1}$), $Na_2HPO_4$*$7H_2O$ (6.7 $gL^{-1}$), $KH_2PO_4$ (3.4 $gL^{-1}$), $NH_4Cl$ (2.68 $gL^{-1}$), $Na_2SO_4$ (0.71 $gL^{-1}$), arginine (0.2 $gL^{-1}$), histidine (0.15 $gL^{-1}$), lysine (0.2 $gL^{-1}$), phenylalanine (0.2 $gL^{-1}$), serine (0.2 $gL^{-1}$), threonine (0.2 $gL^{-1}$), tryptophan (0.2 $gL^{-1}$), methionine (0.2 $gL^{-1}$), monosodium glutamate (8 $gL^{-1}$), glucose (0.5 $gL^{-1}$), glycerol (10 $gL^{-1}$) and a 1000-fold diluted trace element solution with $FeCl_3$ (81.1 $gL^{-1}$), $CaCl_2$*$6H_2O$ (4.38 $gL^{-1}$), $MnCl_2$*$4H_2O$ (1.98 $gL^{-1}$), $ZnSO_4$*$7H_2O$ (2.88 $gL^{-1}$), $CoCl_2$*$6H_2O$ (0.48 $gL^{-1}$), $CuCl_2$*$2H_2O$ (0.34 $gL^{-1}$), $NiCl_2$*$6H_2O$ (0.48 $gL^{-1}$), $Na_2MoO_4$*$2H_2O$ (0.48 $gL^{-1}$), $Na_2SeO_3$ (0.35 $gL^{-1}$), and $H_3BO_3$ (0.12 $gL^{-1}$).

Production: At the end of the day, a 1 L baffled flask containing 200 mL of PCM8.1 media supplemented with 50 μg/ml of kanamycin, 23.8 μg/ml of IPTG, 320 μg/ml of 5'-aminolevulinic acid and 55 μg/ml of $FeSO_4$*$7H_2O$ were inoculated with the seed cultures to an OD of 0.6. The induced production cultures were incubated at 27° C. and 200 rpm until the cultures had reached stationary phase (approximately 16-20 hours). The cultures were harvested by centrifugation at 3,000 rpm for 15 minutes. The pellets were washed with 30 mL of wash buffer (isotonic 0.85% NaCl with 5% glycerol) and transferred into a fresh 50 mL falcon tube. The cells were further centrifuged at 4,000 rpm for 25-35 minutes and the pellet was stored at −20° C. for processing.

Example 3: Extraction & Processing of Enzyme Materials

Suspended cell pellets were provided as described in Example 2, containing recombinant P450, ferredoxin and ferredoxin reductase in 0.1 M potassium phosphate buffer pH 8, 5 mM $MgCl_2$, 0.5 mM TCEP, and 1 mM PMSF in a ratio of 15 ml of buffer per 1 g of cells. Lysed cells were produced by high pressure disruption using three cycles of 30 kpsi. Lysed material was centrifuged at 38,000×g for 30 minutes (4° C.) and the supernatant was sterilized by passing through 0.2 micron filter to provide the enzyme preparation containing recombinant P450, ferredoxin and ferredoxin reductase. The crude extract was then dispensed into glass vials (0.5 ml per 2 ml vial), frozen and lyophilised using an Edwards Supermodulyo Freeze-dryer before being sealed under vacuum stored in a standard laboratory freezer at −20° C. until required for use.

Measurement of the concentration of cytochrome P450 were performed according to the method of Omura and Sato et al. (J Biol Chem, 239. 1964, 2370). Cytochrome P450 concentrations of cell-free extracts of induced *E. coli* BL21 (DE3) Rosetta2 & Tuner cells harbouring either pHD05-SriC01, pHD02-SriC12-SriF05, pHD05-SriC14-SriF06, pHD05-SriC20, pHD05-SriC22 or pHD05-SriC51-SriF08 are shown in Table 2. Carbon monoxide difference spectra for $P450_{SriC01}$, $P450_{SriC12}$, $P450_{SriC14}$, $P450_{SriC20}$, $P450_{SriC22}$ and $P450_{SriC51}$ are shown in FIGS. 9, 10, 11, 19, 20 & 21 respectively.

TABLE 2

Concentration of cytochrome P450 from *S. rimosus* NRRL-2234 expressed in *E. coli* BL21 (DE3) Rosetta2 & Tuner cells

| Cytochrome P450 | P450 concentration (microM) |
|---|---|
| SriC01 | 33.5 |
| SriC12-SriF05 | 3.6 |
| SriC14-SriF06 | 15.4 |
| SriC20 | 18.8 |
| SriC22 | 18.4 |
| SriC51-SriF08 | 25.0 |

Example 4: Codon Optimisation of P450 SriC12 and Ferredoxin SriF05

The DNA sequence $P450_{sriC12}$ and $ferredoxin_{sriF05}$ operon (SEQ ID NO: 28) was optimised for *E. coli* to determine whether the expression or the folding of the cytochrome P450 could be further improved. The DNA sequence was modified but the amino acid sequence is exactly the same as in SEQ ID NO: 29 & 30 A synthetic DNA (SEQ ID NO: 119) containing codon optimisation of $P450_{sriC12}$ and $ferredoxin_{sriF05}$ and altered $ferredoxin_{sriF05}$ ribosome binding site was produced by DNA2.0. The synthetic DNA was digested with NdeI and HindIII as described above and sub-cloned into pHD02 in a total volume of 20 μL containing 1.5 μL T4 DNA ligase, 4 μL T4 ligase buffer and digested insert (48 ng) and vector (64.4 ng). The reaction was incubated at room temperature for 15 minutes and then moved to 4° C. overnight. The ligation mixture was introduced into DH5a cells by chemical transformation as described in Example 1. The recombinant vector was screened by restriction enzyme digestion and DNA sequencing. The constructed plasmid was designated as pHD02-SriC12CO-SriFO5CO.

Figure 9:
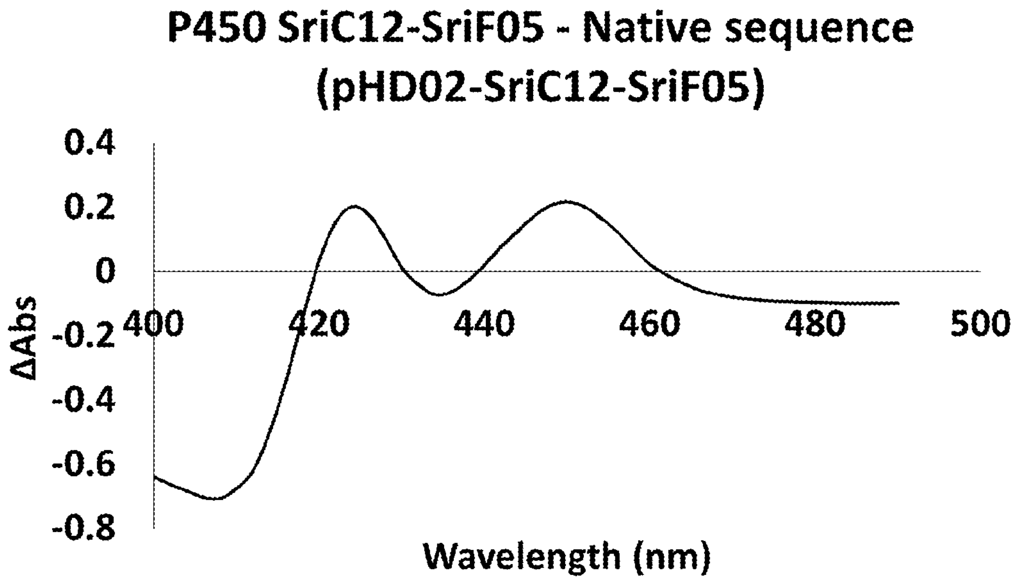
FIG. 9 shows the carbon monoxide difference spectrum of the crude enzyme extract containing $P450_{SriC12-SriF05}$ protein. The sample was prepared from IPTG-induced culture of *E. coli* BL21 (DE3) Rosetta2 cells containing the pHD02-SriC12-SriF05 plasmid.
Figure 10:
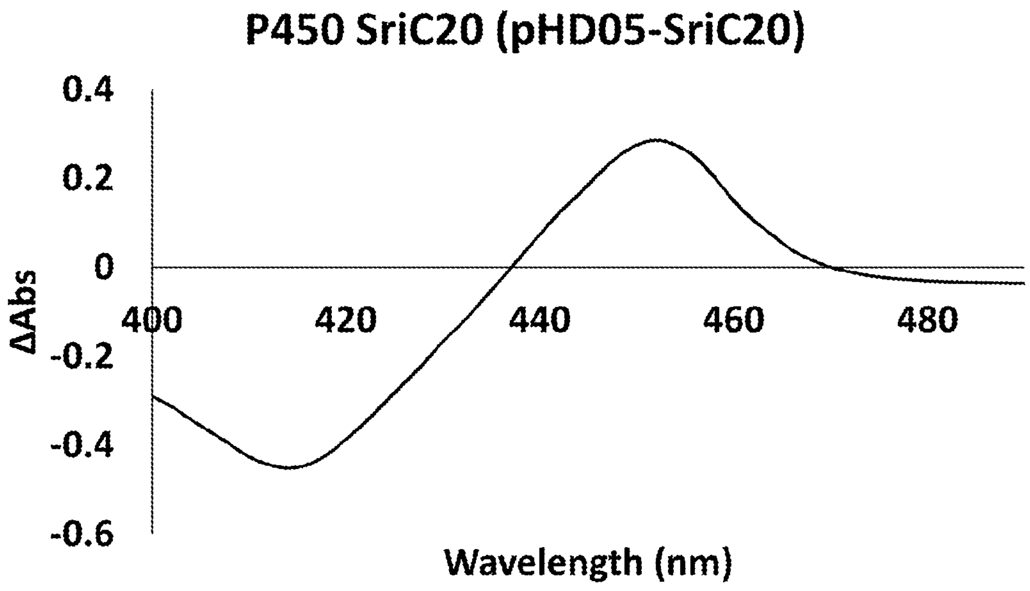
FIG. 10 shows the carbon monoxide difference spectrum of the crude enzyme extract containing $P450_{SriC20}$ protein. The sample was prepared from IPTG-induced culture of *E. coli* BL21 (DE3) Rosetta2 cells containing the pHD05-SriC20 plasmid.
Figure 11:
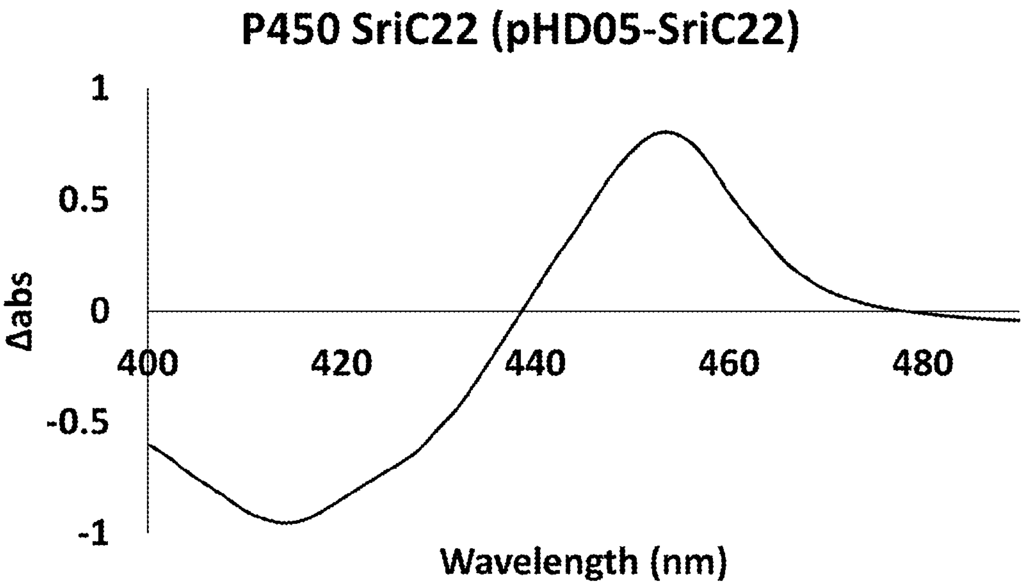
FIG. 11 shows the carbon monoxide difference spectrum of the crude enzyme extract containing $P450_{SriC22}$ protein. The sample was prepared from IPTG-induced culture of *E. coli* BL21 (DE3) Rosetta2 cells containing the pHD05-SriC22 plasmid.
Figure 12:
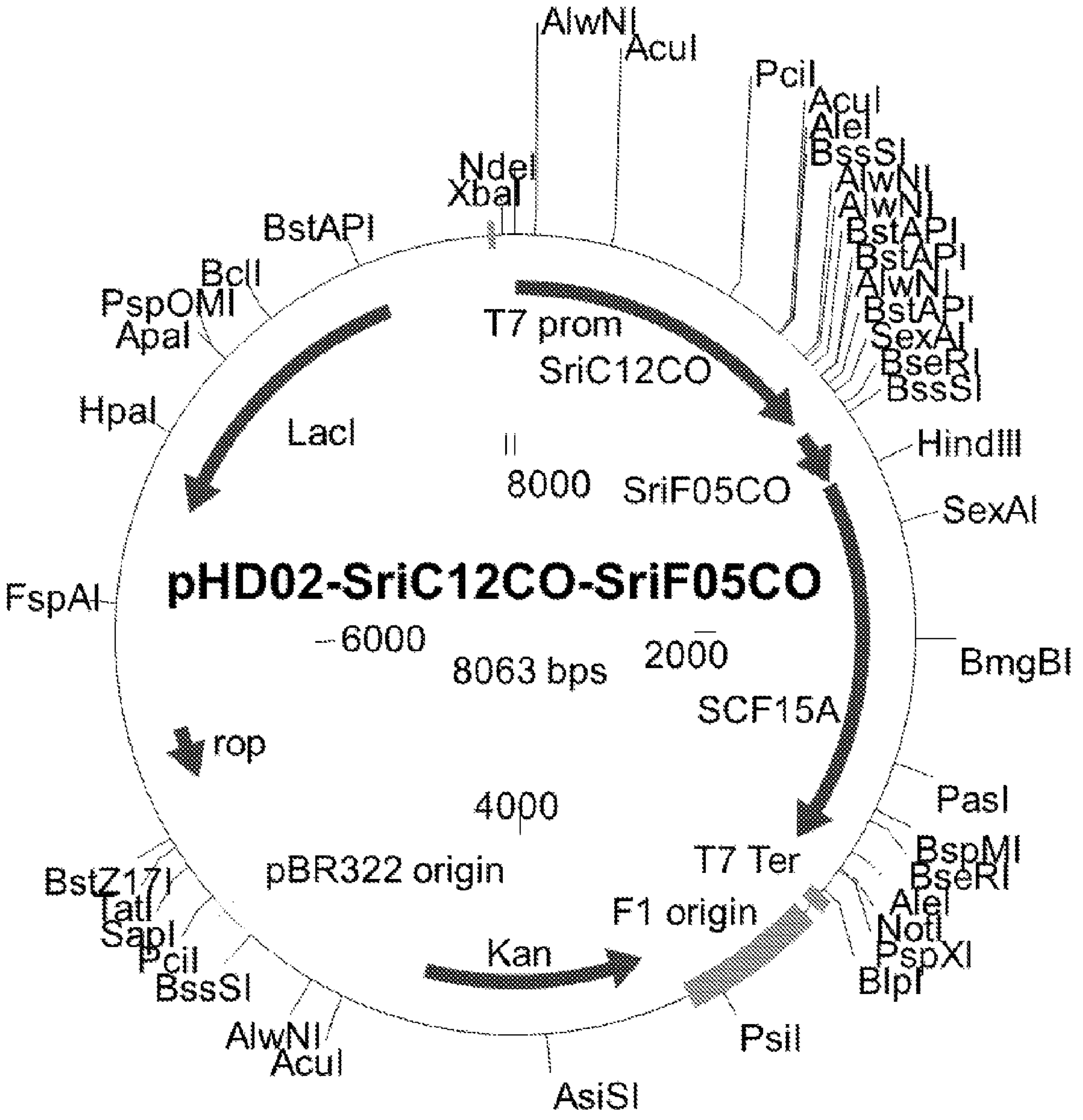
FIG. 12 shows expression plasmid pHD02-SriC12CO-SriF05CO
Figure 13:
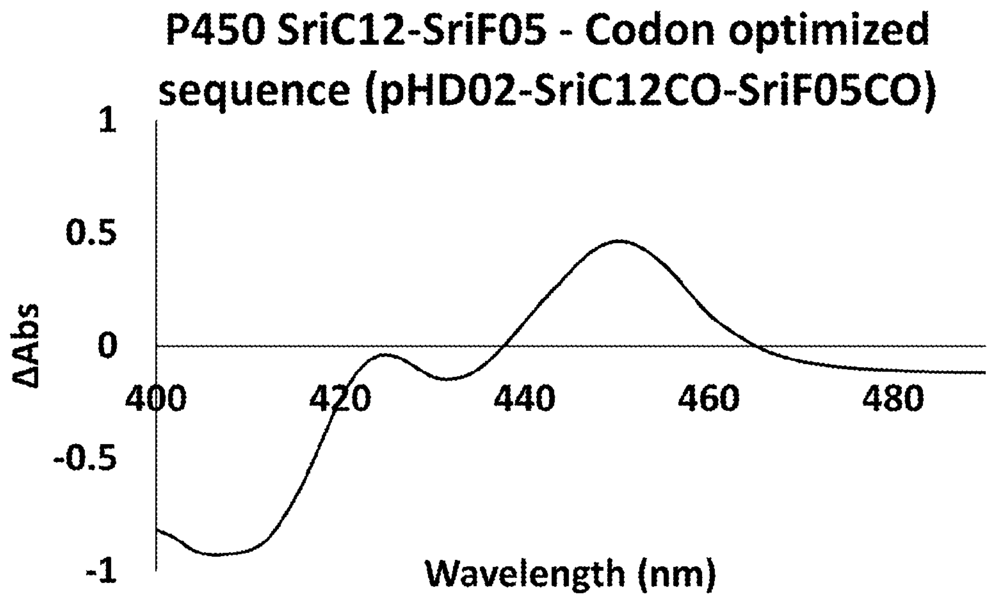
FIG. 13 shows the carbon monoxide difference spectrum of the crude enzyme extract containing codon optimised $P450_{SriC12-SriF05}$ protein. The sample was prepared from IPTG-induced culture of *E. coli* BL21 (DE3) cells containing the pHD02-SriC12CO-SriF05CO plasmid.

The native and codon optimised $P450_{sriC12}$ and $ferredoxin_{sriF05}$ in pHD02-SriC12-SriF05 and pHD02-SriC12CO-SriF05CO respectively were introduced into *E. coli* BL21 (DE3). The recombinant strains were cultured and proteins were induced as in Example 2. The cell-free extract material was obtained as in Example 3 and carbon monoxide difference spectrums were measure to calculate the concentration of cytochrome P450. Codon optimisation of the operon resulted in a significantly increase in $P450_{sriC12}$ expression; the codon optimised sequenced produced almost double the concentration made by the native sequence. Results are shown in Table 3. Notable differences were also observed in the carbon-monoxide difference spectrum; a 420 nm signal, which is indicative of poor folding of the $P450_{SriC12}$ can be observed in the native sequence (pHD02-SriC12-SriF05), and is significantly reduced in the codon optimised sequence (pHD02-SriC12CO-SriF05CO). Carbon monoxide difference spectra results of native and codon optimised sequence P450 SriC12 are shown in FIGS. 9 & 13 respectively.

TABLE 3

Effect of codon optimisation on the expression of P450 SriC12

| Strain | P450 concentration (microM ± SD) |
|---|---|
| Native sequence (pHD02-SriC12-SriF05) | 3.6 ± 0.3 |
| Codon optimised sequence (pHD02-SriC12CO-SriF05CO) | 6.5 ± 0.8 |

Example 5: Hydroxylase/Dealkylase Activity/Spectrum Testing Cell-Free Assay

Lyophilised material of recombinant P450, ferredoxin and ferredoxin reductase proteins was made as described in Example 3 and reconstituted in high purity water to 90% the original volume. Biocatalysis was performed at 27° C. in the following conditions: 50 mM potassium phosphate pH 7.4, 5 mM $MgCl_2$, 0.1 mg/ml substrate compound such as bosentan, cyclosporine A, diclofenac, ritonavir, tivantinib, valsartan or vanoxerine, native concentration of P450, ferredoxin and ferredoxin reductase as extracted (Example 3). Reactions were initiated by addition of 10× stock of cofactor mixture (50 mM G6P, 10 mM NADP, 10 UN/ml G6PDH) to provide a final volume of e.g., 100 μL. After 16-20 hours, reactions were extracted with an equal volume of acetonitrile, centrifuged to remove precipitated proteins and conversion assessed by UPLC-MS analysis.

UPLC data was obtained as follows:

Acidic Analysis Conditions

Column: Acquity UPLC BEH Shield RP18 1.7 μm 2.1 mm i.d. 50 mm length

Column temperature: 45° C.

Solvents: $H_2O$, B: Acetonitrile, both with 0.1% Formic acid

Flow rate: 1.0 ml/min

Gradient (A9%/B %): t=0 mins: 98/2 to 2/98 at t=2.4 mins and held for a further 0.4 mins (2.8 mins total), return to 98/2 over 0.05 mins and re-equilibrated for 0.15 mins (t=3 mins) at a flow-rate of 1.0 mL/min.

Basic Analysis Conditions

Column: Waters Acquity UPLC BEH C18 1.7 μm 2.1 mm i.d. 50 mm length

Column temperature: 45° C.

Solvents: A: 10 mM ammonium bicarbonate in $H_2O$, B: Acetonitrile

Gradient (A %/B %): t=0 mins: 98/2 to 2/98 at t=2.4 mins and held for a further 0.4 mins (2.8 mins total), return to 98/2 over 0.05 mins and re-equilibrated for 0.15 mins (t=3 mins) at a flow-rate of 1.0 mL/min.

Detector: Waters Acquity UPLC PDA (UV-Vis detection) and Waters Acquity UPLC QDA (MS)

To confirm the identities of reaction products their chromatographic retention time, mass and ultraviolet spectra were compared with those of authentic metabolite standards.

Biotransformation Using Resuspended Cells Containing Cytochrome P450 and Redox Partner Protein.

Induced cell pellets containing cytochrome P450, ferredoxin and ferredoxin reductase were produced as described in Example 2. The cell pellets were resuspended in 50 mM potassium phosphate pH 7.4, 100 mM glucose, 5 mM $MgCl_2$, to a volume equal to one quarter of the original culture volume, dosed with 0.1 mg/ml substrate compound such as bosentan, cyclosporine A, diclofenac, ritonavir, tivantinib, valsartan or vanoxerine. Reaction volumes are typically 1 mL. After 16-20 hours, reactions were extracted with an equal volume of acetonitrile, centrifuged to remove precipitated proteins and conversion assessed by UPLC-MS analysis as described above.

Example 6: Construction, Expression and Testing of $P450_{sriC12}$ Mutants PCR-Based Site Directed Mutagenesis Site directed mutagenesis by PCR of positions R63, R74, L171 and L230 in the $P450_{SriC12}$ enzyme was performed in which the above codons were altered to new amino acids: R63W, R63Y, R74Y, L1711, L171A, R183W & L2301, (SEQ ID NO: 230-237 and SEQ ID NO: 250-257). The sequences of primers used for amplification and mutagenesis are shown in Table 4.

DNA of a plasmid containing the codon optimised $P450_{sric12}$ gene (Example 4) was used as the template DNA and the mutagenic primers are shown in Table 4 below. PCR reactions contained 12.5 µl of Phusion® High-Fidelity PCR Master Mix (1 U/µl; New England Biolabs), ~ 2 ng of template DNA, 1.25 µl DMSO, 0.5 µM of each forward and reverse primer and the reaction mixture was made up to a total volume of 25 µl with MilliQ®-$H_2O$. Since the whole of the plasmid was amplified leading to long PCR products, reactions were supplemented with 5% DMSO. Amplification reactions were identical for all mutagenic reactions. Reactions were performed on a Techne™ TC-512 Thermal Cycler with the following cycling conditions: 98° C. for 30 seconds, 16 cycles (98° C. for 30 seconds, annealing temperature for 1 minute, 72° C. for 8 minutes), 72° C. for 10 minutes. Amplifications were then subjected to DpnI digestion to remove the template DNA.

DpnI Digestion

1 µl DpnI (20 U/µl; New England Biolabs), 1 µl Cutsmart buffer (New England Biolabs) was added to 8 µl of the PCR reaction. Unmutated template DNA was digested for 60 min at 37° C.

Cloning of Mutants

DpnI reactions were used to transform 50 µl chemically competent *E. coli* DH5a cells. Clones were selected on lysogeny broth (LB) plates containing 50 µg/ml kanamycin after 16 hours of incubation at 37° C. Clones were picked and cultivated in 5 ml LB containing 50 µg/ml kanamycin for 16 hours at 37° C. and 250 rpm. Recombinant plasmids were isolated from these cultures using the QIAprep® Spin Miniprep Kit (Qiagen) and analysed via DNA sequencing.

DNA Sequencing and Analysis

DNA sequences of the cloned mutants and the reductase part of the vector backbone were confirmed by Sanger sequencing at Eurofins Genomics (Germany).

TABLE 4 primers used for the site-directed mutagenesis of codon optimised $P450_{sriC12}$

| Mutant | Primer Sequences (5' to 3') |
|---|---|
| Mutant 1 R63W | |
| Forward primer | GTCGGCTGATTGGCAGAACCCGG (SEQ ID NO: 238) |
| Reverse primer | CCGGGTTCTGGCGATCAGCCGAC (SEQ ID NO: 239) |

TABLE 4-continued primers used for the site-directed mutagenesis of codon optimised $P450_{sriC12}$

| Mutant | Primer Sequences (5' to 3') |
|---|---|
| Mutant 2 R63Y | |
| Forward primer | GTCGGCTGATTATCAGAACCCGG (SEQ ID NO: 240) |
| Reverse primer | CCGGGTTCTGATAATCAGCCGAC (SEQ ID NO: 241) |
| Mutant 4 R74Y R183W | Additional R183W mutation obtained (random cloning error) |
| Forward primer | CCCGGCTCCGTATTTTGAGACTC (SEQ ID NO: 242) |
| Reverse primer | GAGTCTCAAAATACGGAGCCGGG (SEQ ID NO: 243) |
| Mutant 9 L171A | |
| Forward primer | CCGTACTCTGGCGCAGAGCGCAG (SEQ ID NO: 244) |
| Reverse primer | CTGCGCTCTGCGCCAGAGTACGG (SEQ ID NO: 245) |
| Mutant 10 L171I | |
| Forward primer | CCGTACTCTGATTCAGAGCGCAG (SEQ ID NO: 246) |
| Reverse primer | CAACCAGCAGAATCATCGCCATA (SEQ ID NO: 247) |
| Mutant 14 L230I | |
| Forward primer | TATGGCGATGATTCTGCTGGTTG-3' (SEQ ID NO: 248) |
| Reverse primer | CATGACCCGCCAGCAGCAGCAGC-3' (SEQ ID NO: 249) |
| Mutant 17 R63W R74Y | Using Mutant 1 as template |
| Forward primer | CCCGGCTCCGTATTTTGAGACTC (SEQ ID NO: 242) |
| Reverse primer | GAGTCTCAAAATACGGAGCCGGG (SEQ ID NO: 243) |
| Mutant 18 R63W L171A | Using Mutant 1 as template |
| Forward primer | CCGTACTCTGGCGCAGAGCGCAG (SEQ ID NO: 244) |
| Reverse primer | CTGCGCTCTGCGCCAGAGTACGG (SEQ ID NO: 245) |
| Mutant 20 R74Y L171A R183W | Using Mutant 4 as template Unexpected R183W mutation obtained |
| Forward primer | CCGTACTCTGGCGCAGAGCGCAG (SEQ ID NO: 244) |
| Reverse primer | CTGCGCTCTGCGCCAGAGTACGG (SEQ ID NO: 245) |
| Mutant 22 R63W R74Y L171A | Using Mutant 17 as template |
| Forward primer | CCGTACTCTGGCGCAGAGCGCAG (SEQ ID NO: 244) |
| Reverse primer | CTGCGCTCTGCGCCAGAGTACGG (SEQ ID NO: 245) |

Expression and Testing of Mutants

Figure 14:
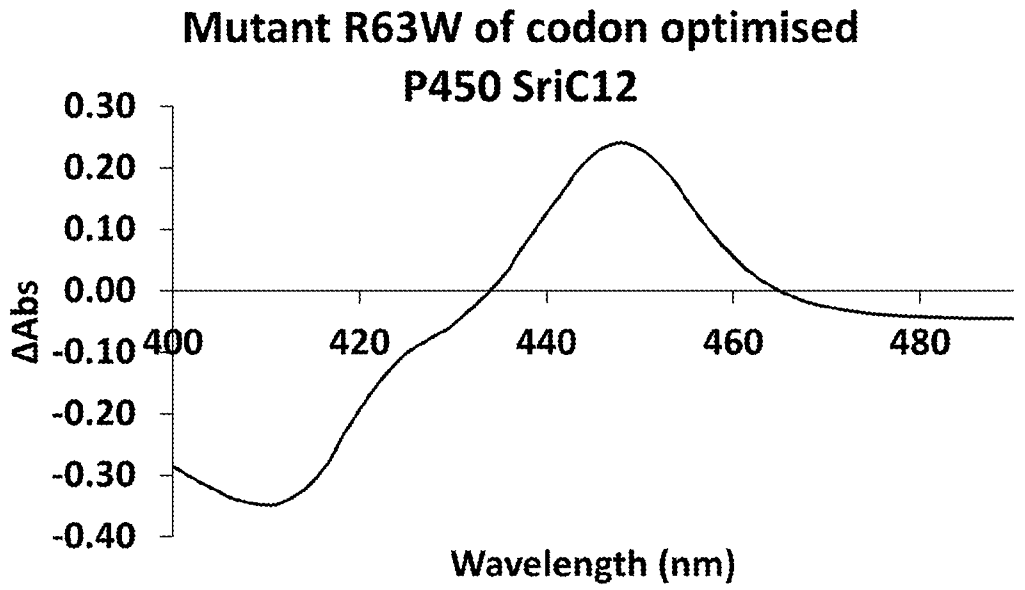
FIG. 14 shows the carbon monoxide difference spectrum of the crude enzyme extract containing R63W mutant of codon optimised $P450_{SriC12-SriF05}$ protein. The sample was prepared from IPTG-induced culture of *E. coli* BL21 (DE3) cells containing the pHD02-SriC12M1_CO-SriF05_CO plasmid.

The resulting plasmids containing the new mutants genes were transformed into recombinant *E. coli* strains for expression as described in Example 1, cultured and induced as described in Example 2, extracted and processed as described in Example 3 and tested for biocatalytic activity as described in Example 5 above. The carbon monoxide difference spectrum result of R63W mutant of codon optimised $P450_{SriC12}$ is shown in FIG. 14 and the cytochrome P450 concentration of mutant $P450_{SriC12}$ are shown in Table 5.

TABLE 5

| Concentration of mutant $P450_{SriC12}$ expressed in *E. coli* BL21 (DE3) | |
|---|---|
| Mutant $P450_{SriC12}$ | P450 concentration (microM) |
| Mutant 1 R63W | 17.6 |
| Mutant 2 R63Y | 6.2 |
| Mutant 4 R74Y R183W | 15.4 |
| Mutant 9 L171A | 8.2 |
| Mutant 10 L171I | 12.4 |
| Mutant 14 L230I | 3.5 |
| Mutant 17 R63W R74Y | 27.6 |
| Mutant 18 R63W L171A | 22.4 |
| Mutant 20 R74Y L171A R183W | 14.1 |
| Mutant 22 R63W R74Y L171A | 19.9 |

Figure 15A:
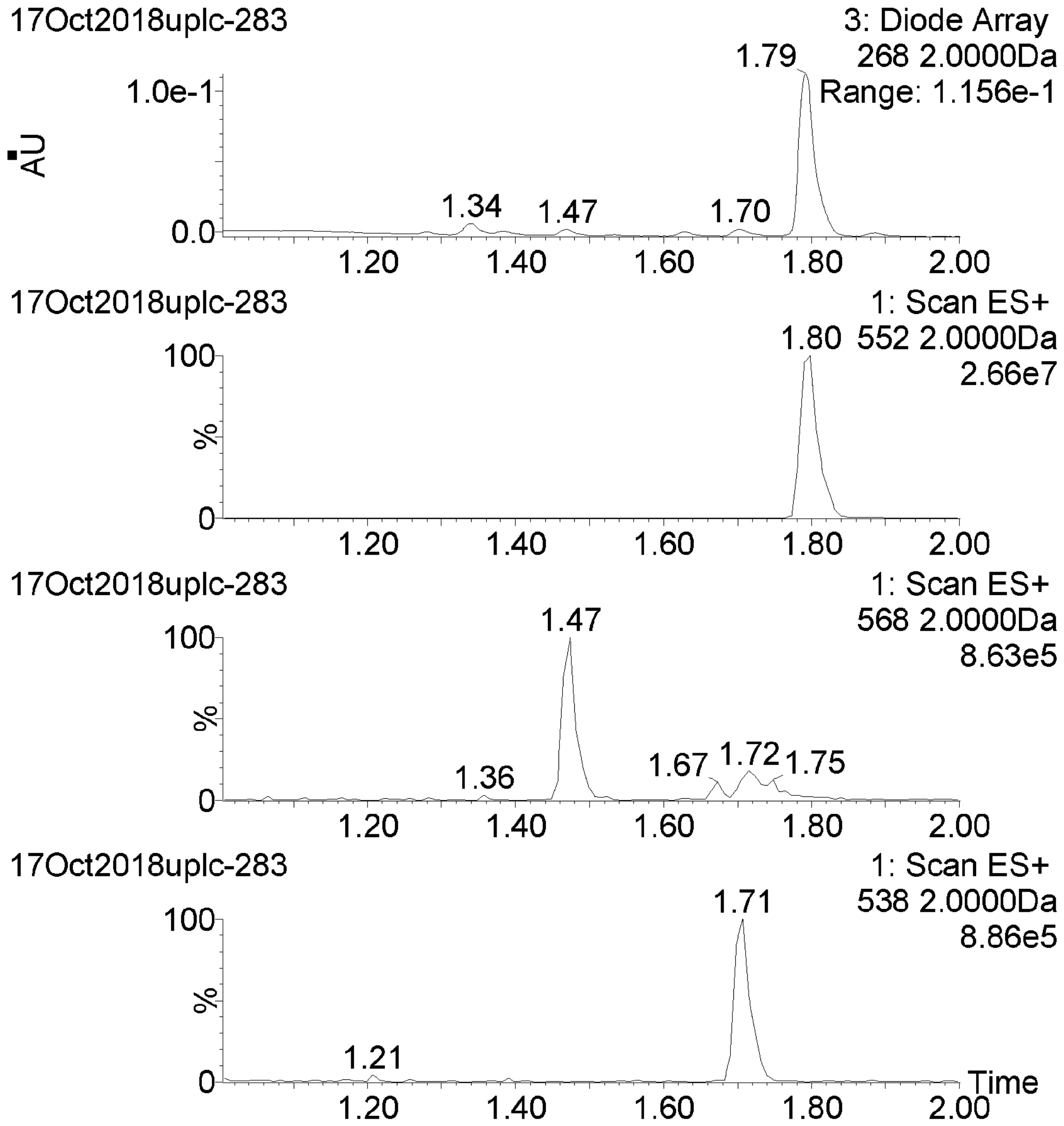
FIGS. 15*a-z* show UPLC-MS chromatograms of various reactions performed at 100 uL screening scale and a proton NMR spectrum of a purified metabolite.
Figure 15C:
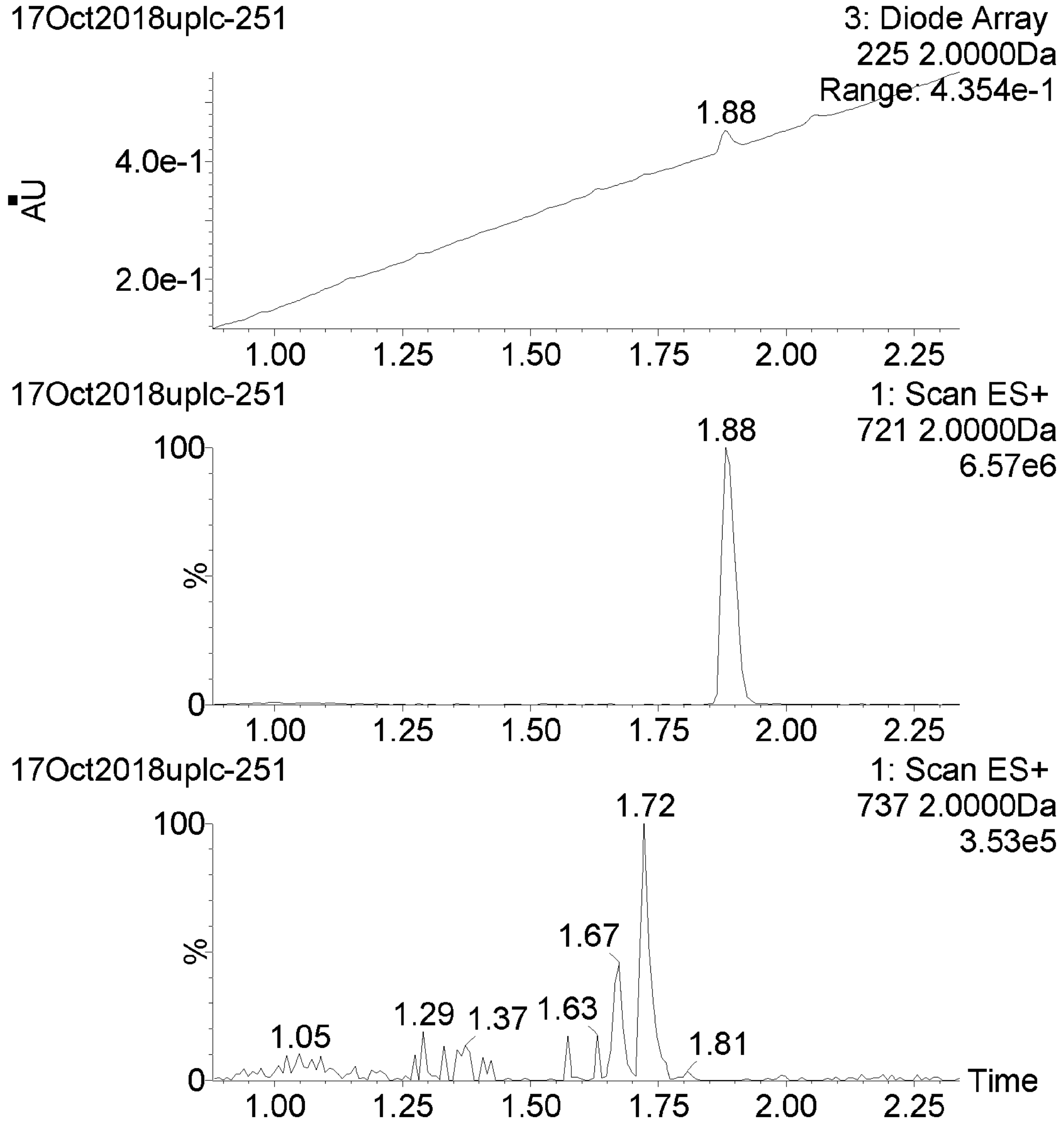
Figure 15F:
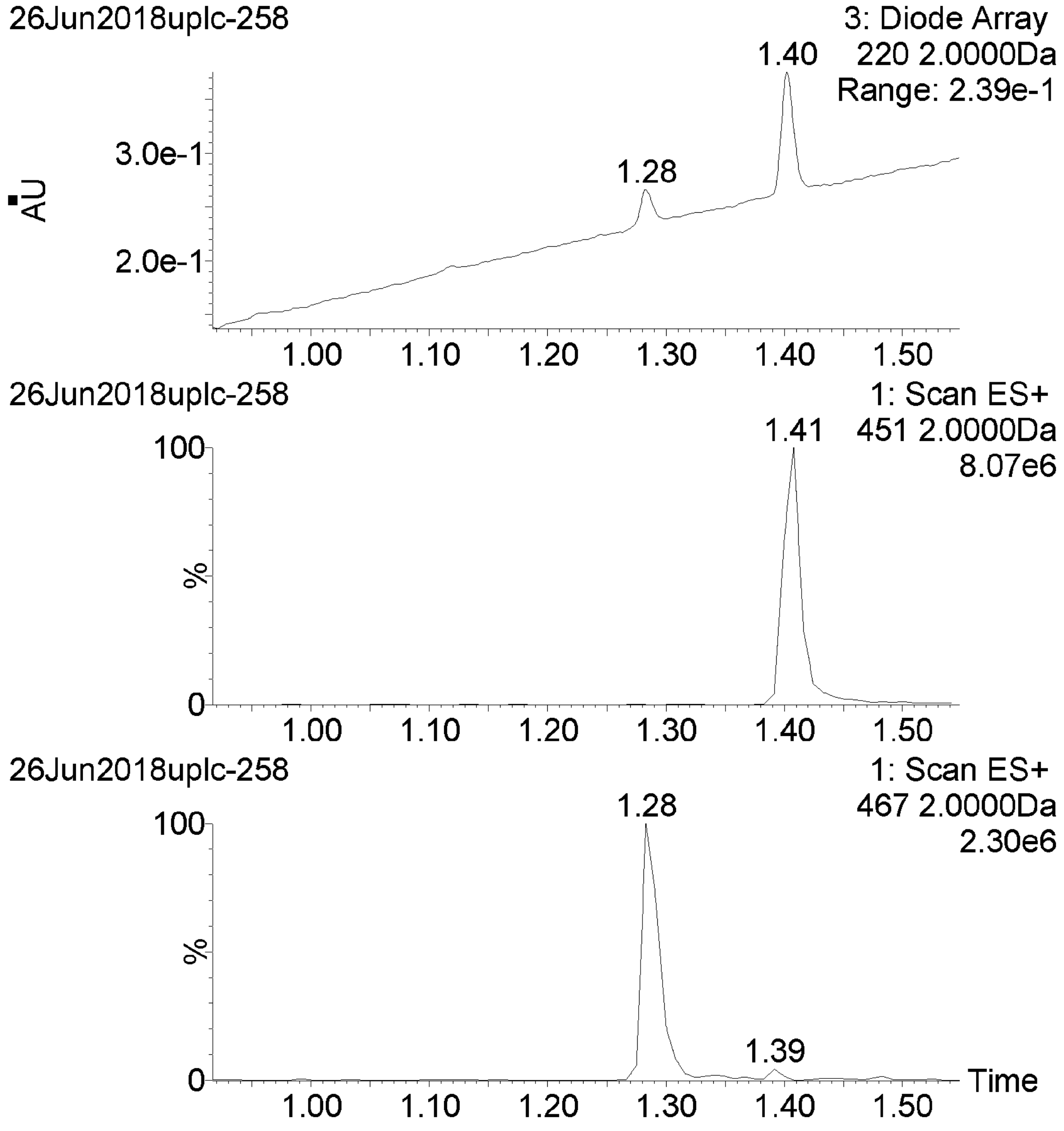
Figure 15G:
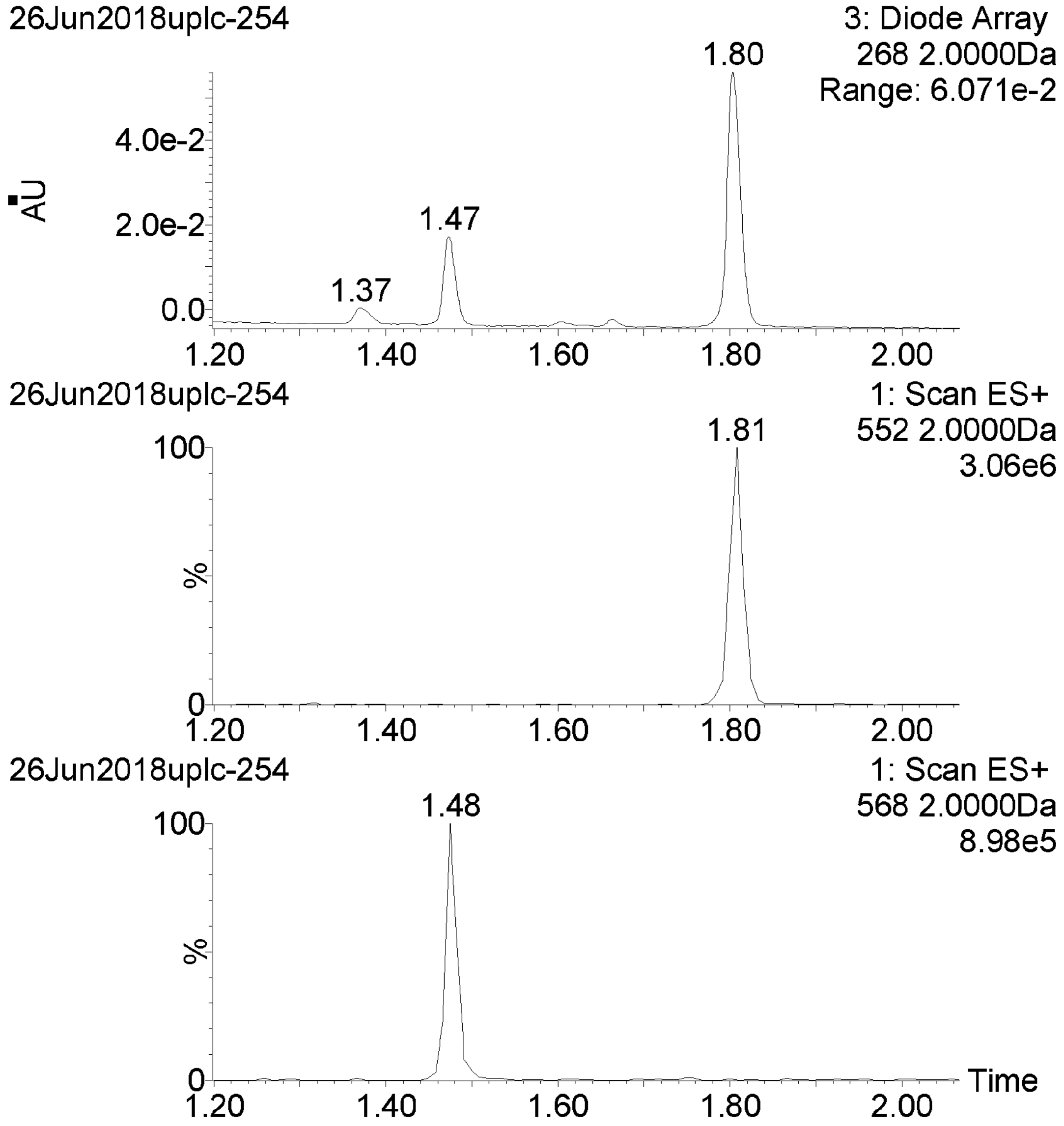
Figure 15H:
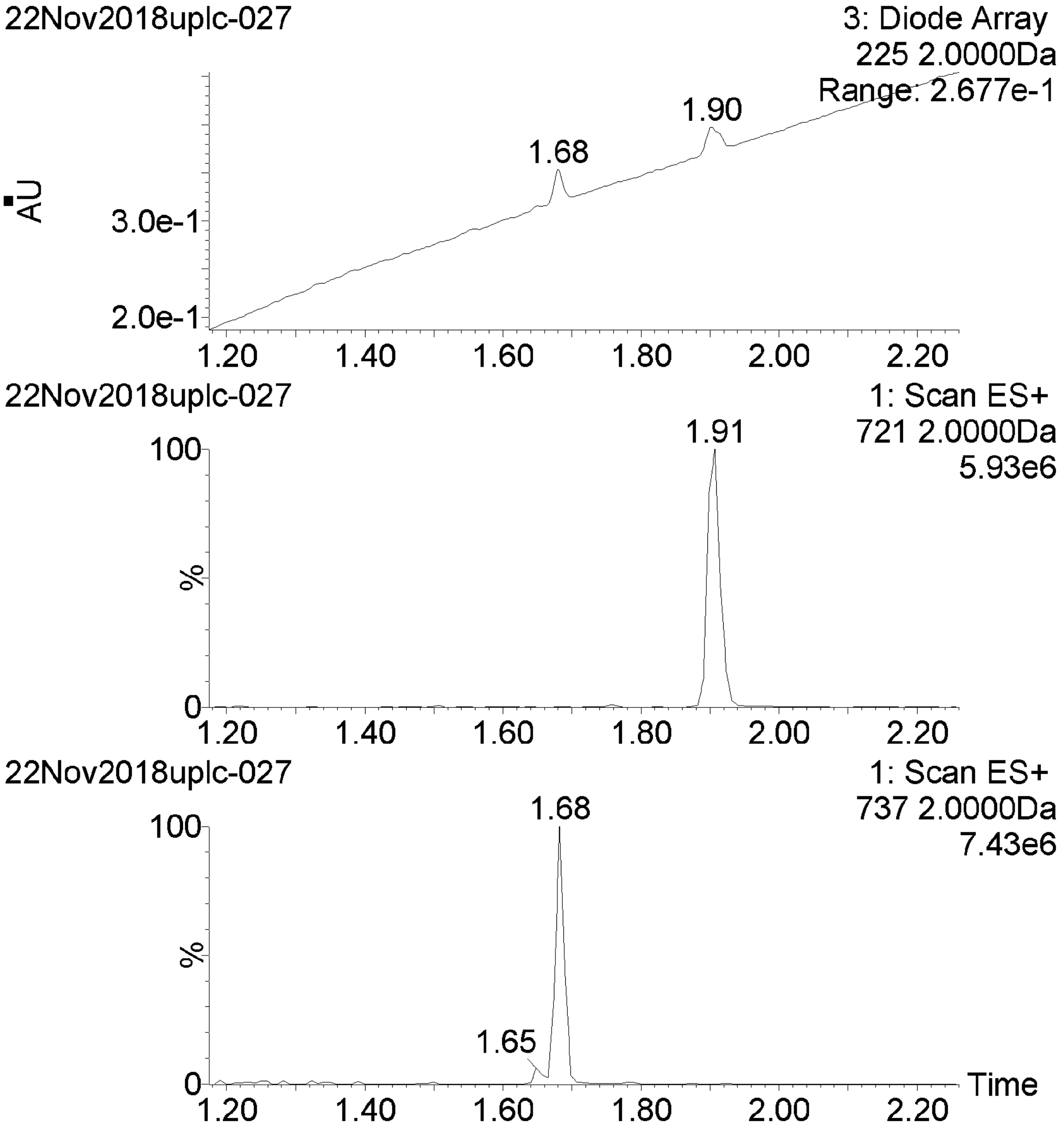
Figure 15I:
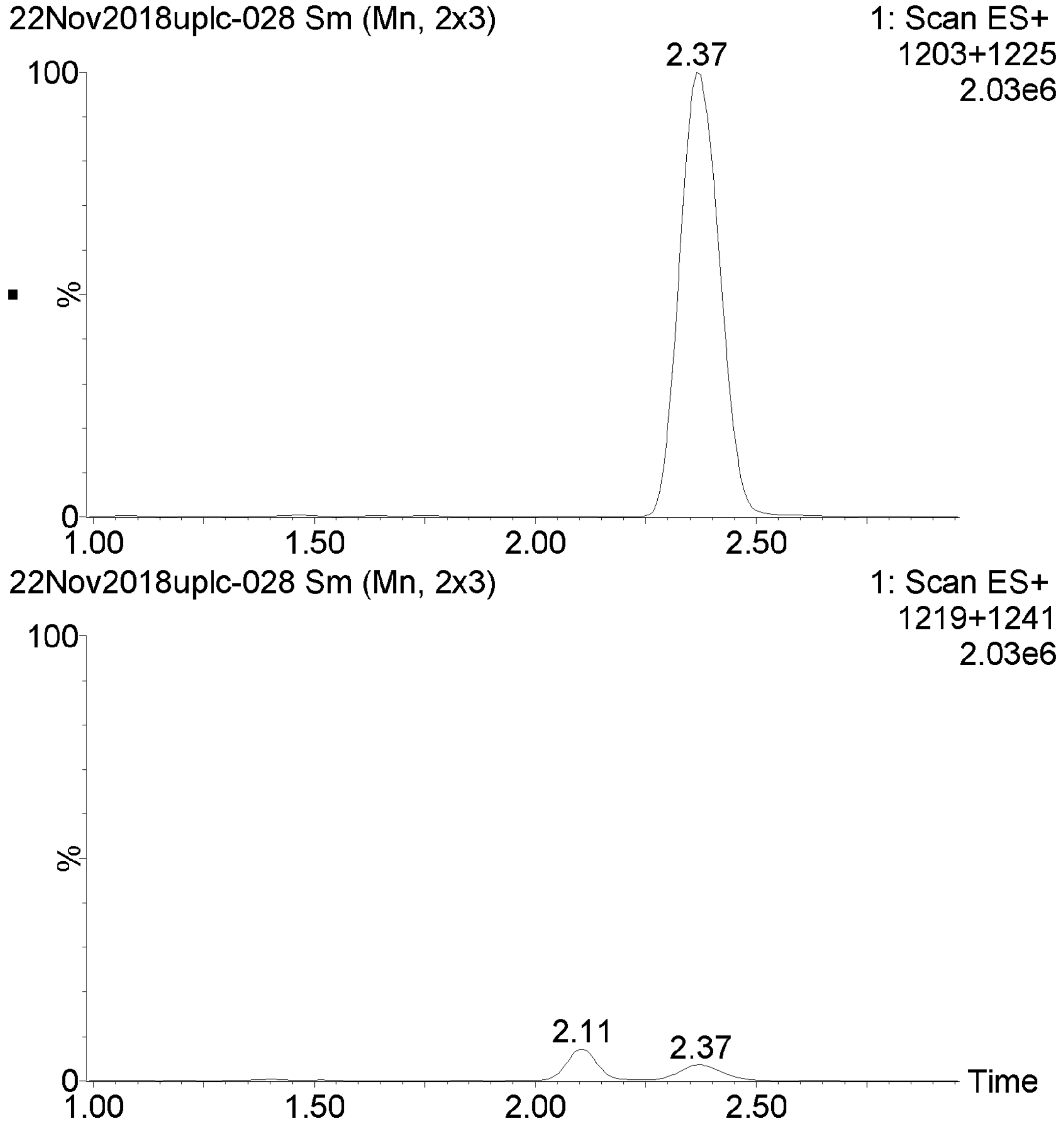
Figure 15K:
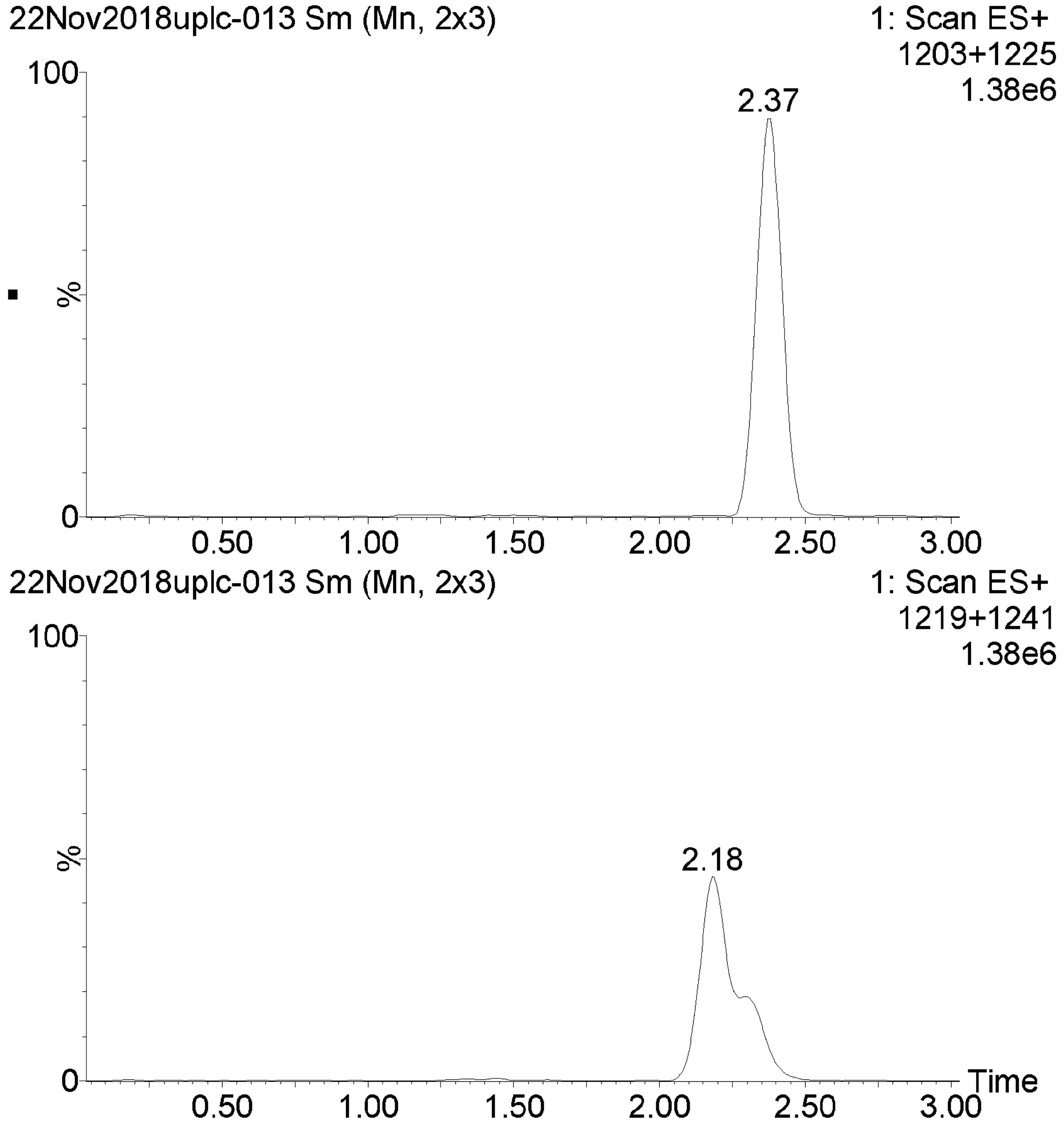
Figure 15M:
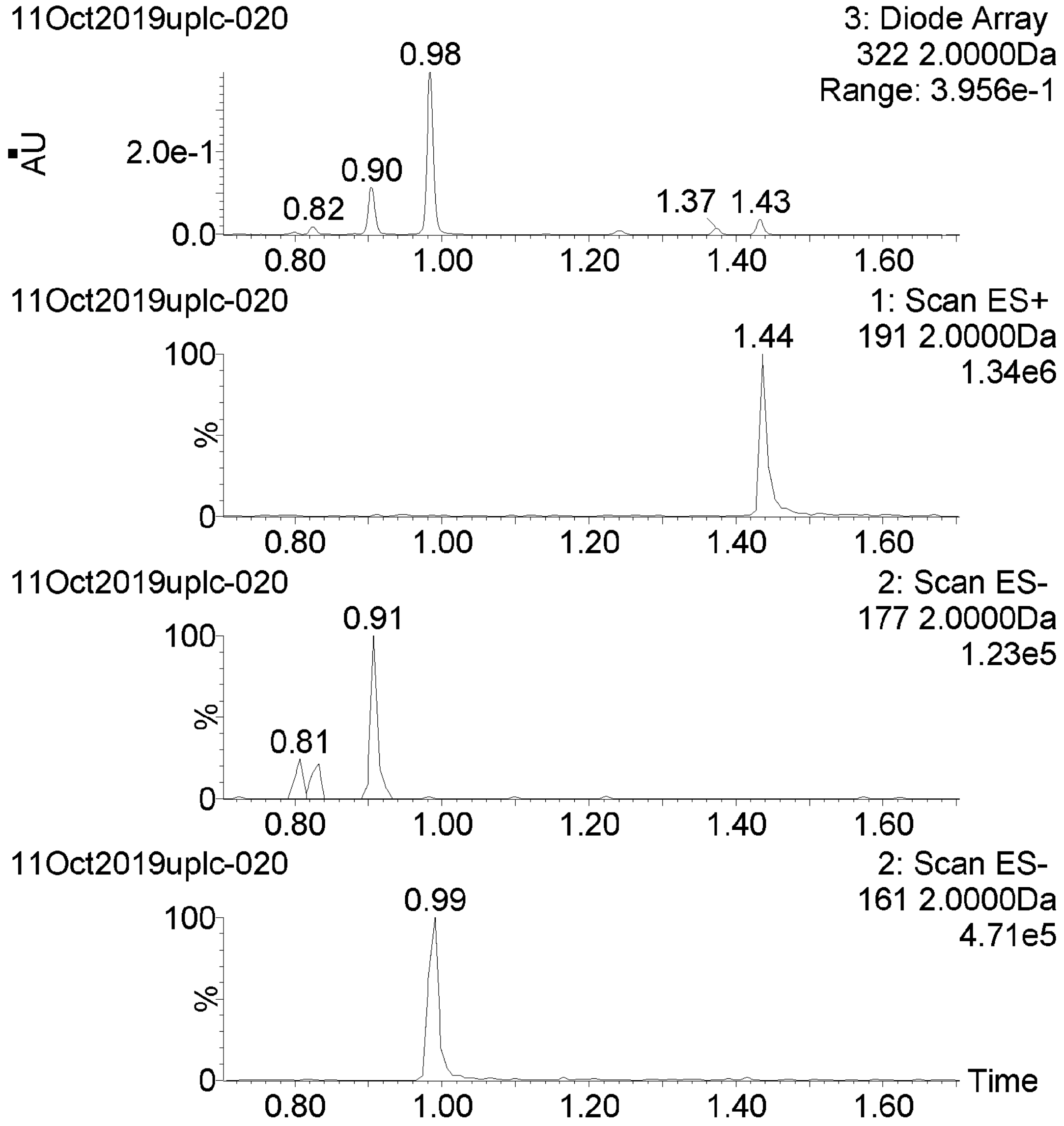
Figure 15N:
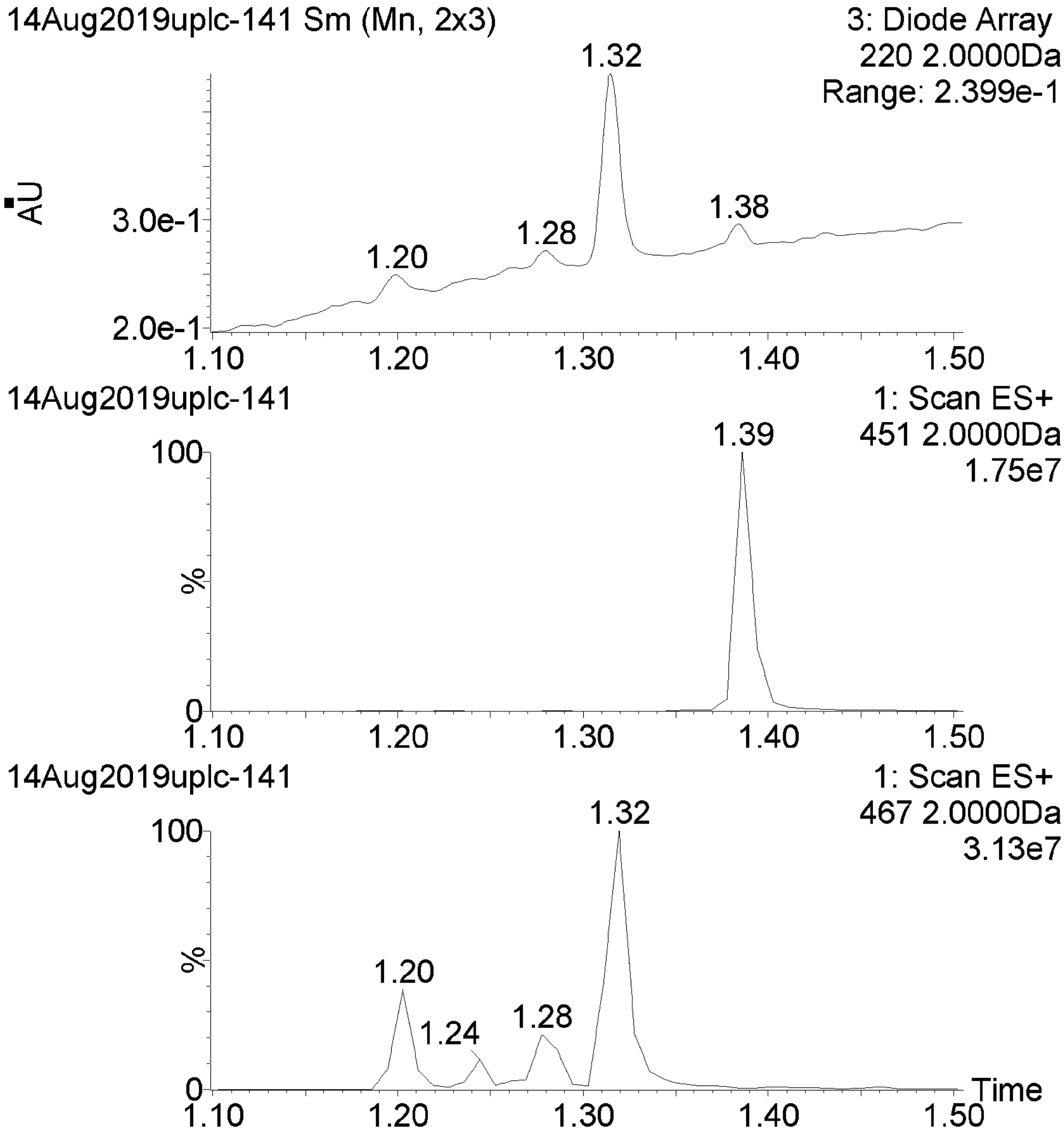
Figure 15P:
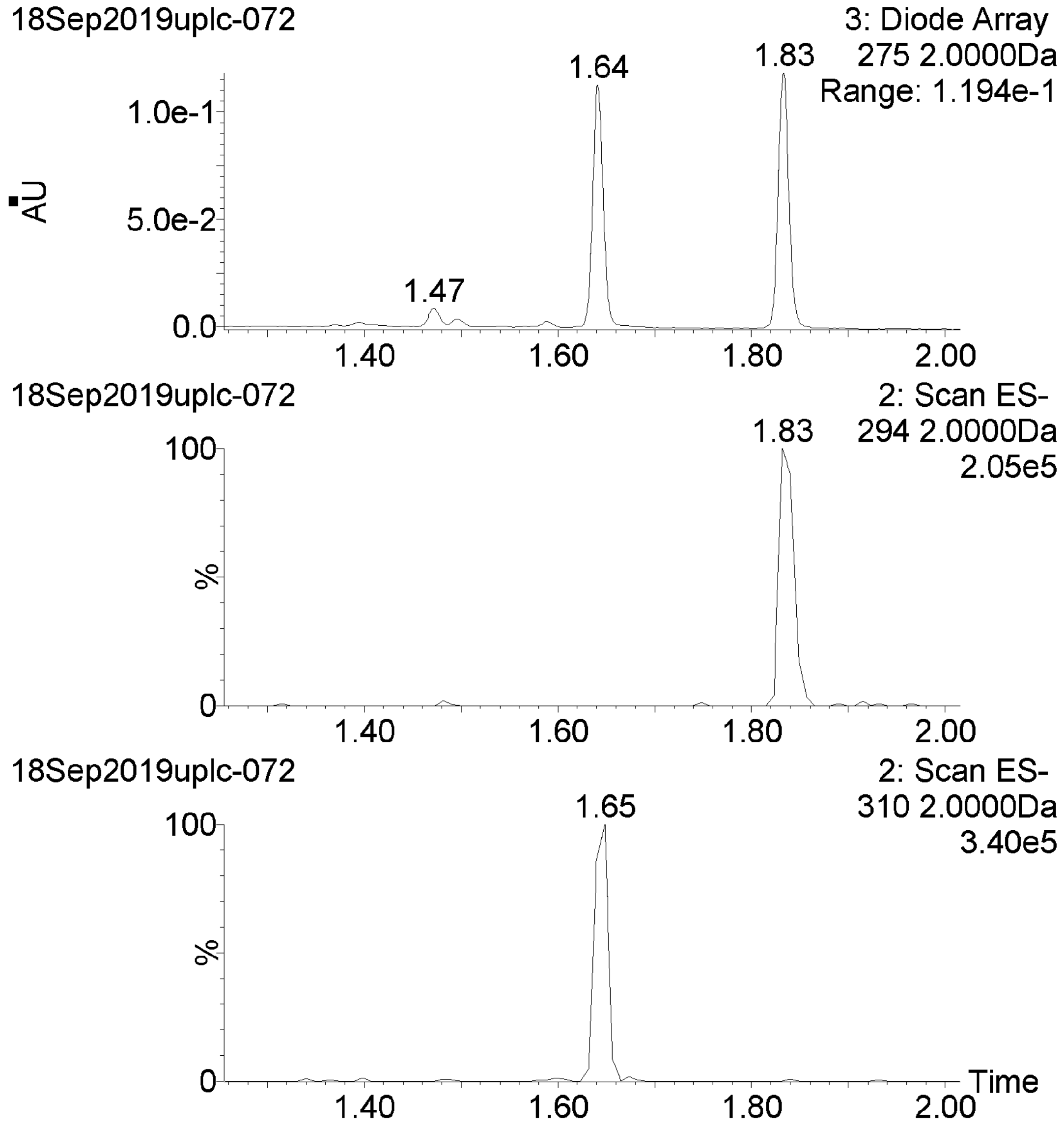
Figure 15Q:
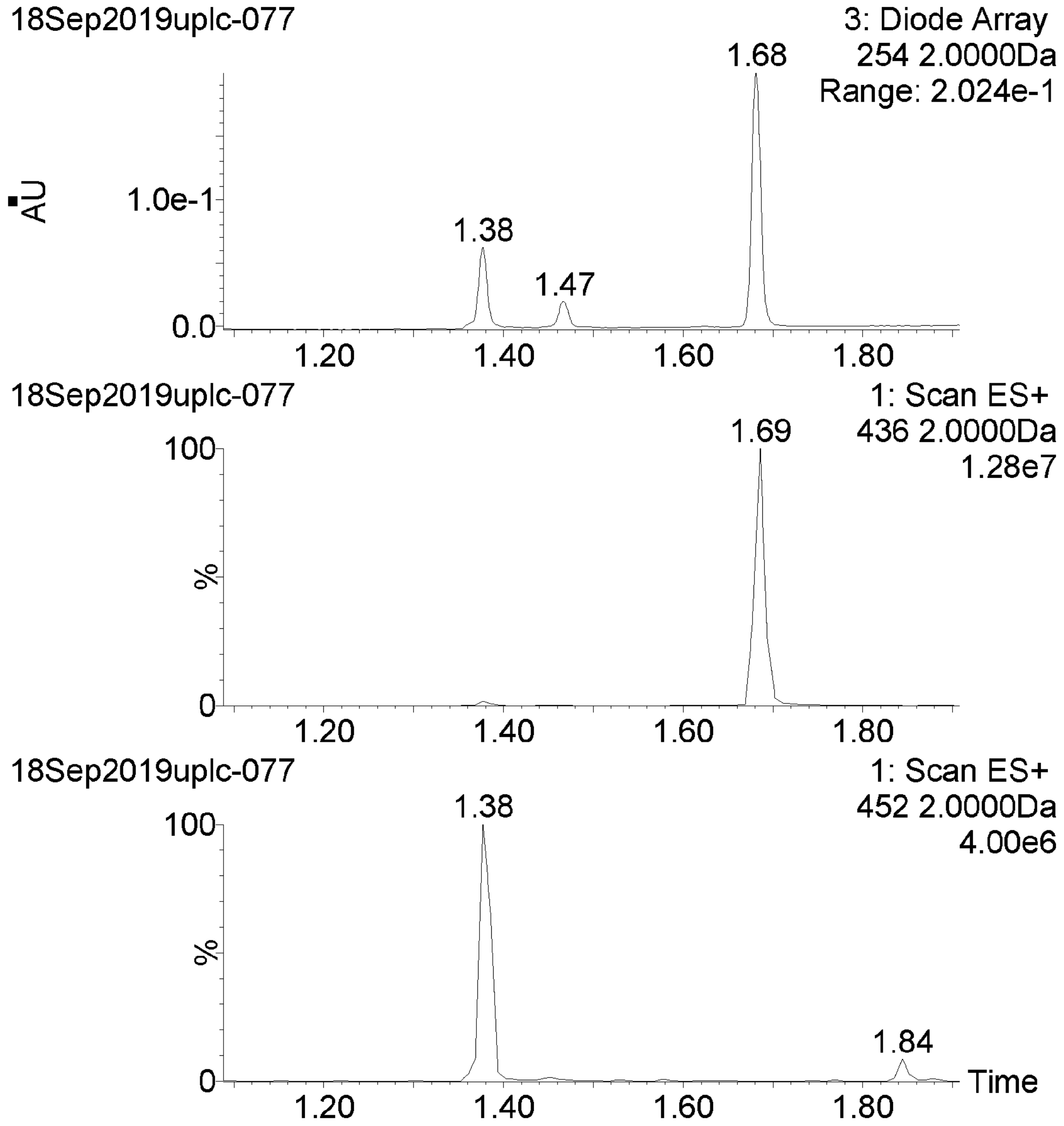
Figure 15R:
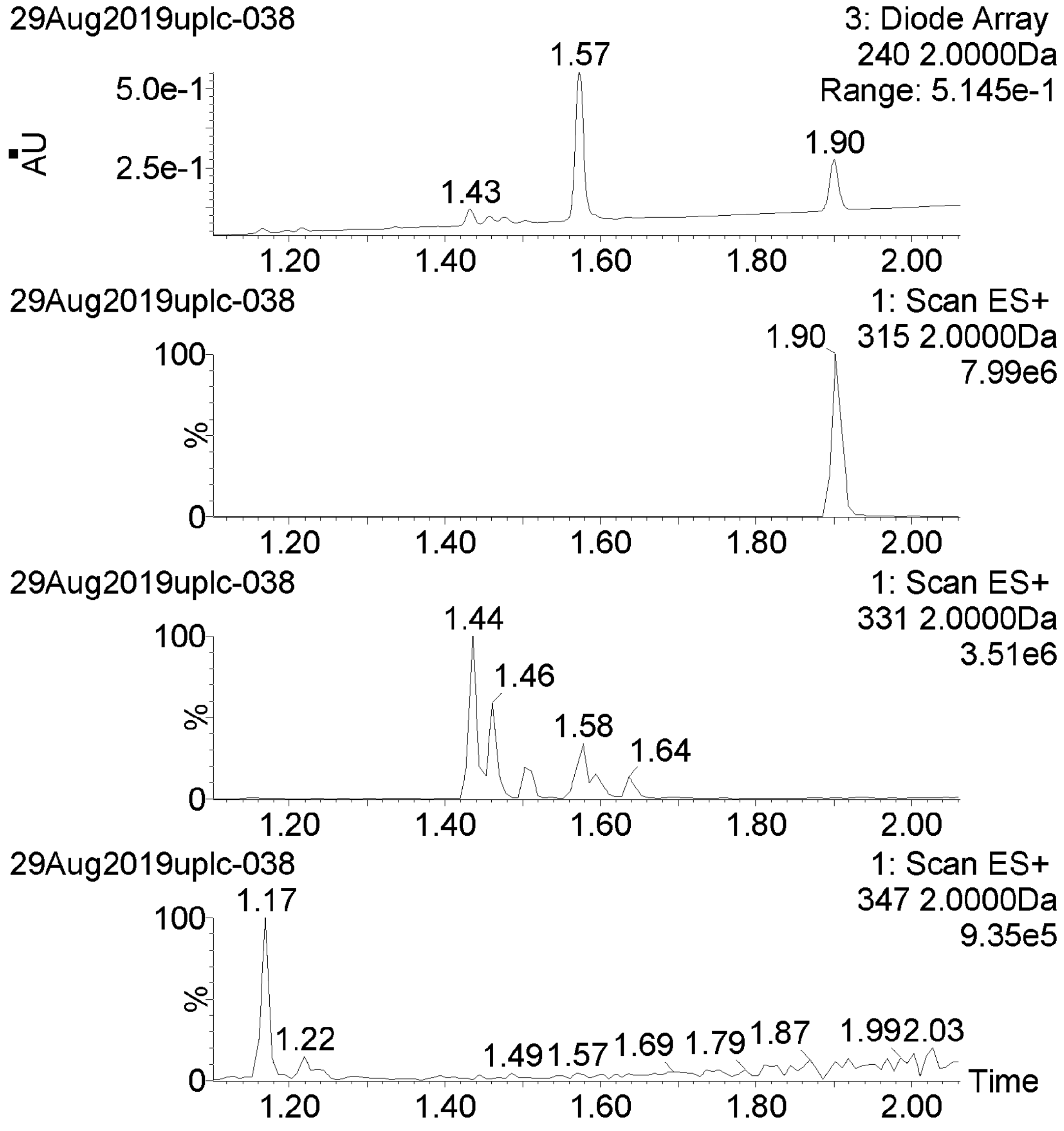
Figure 15S:
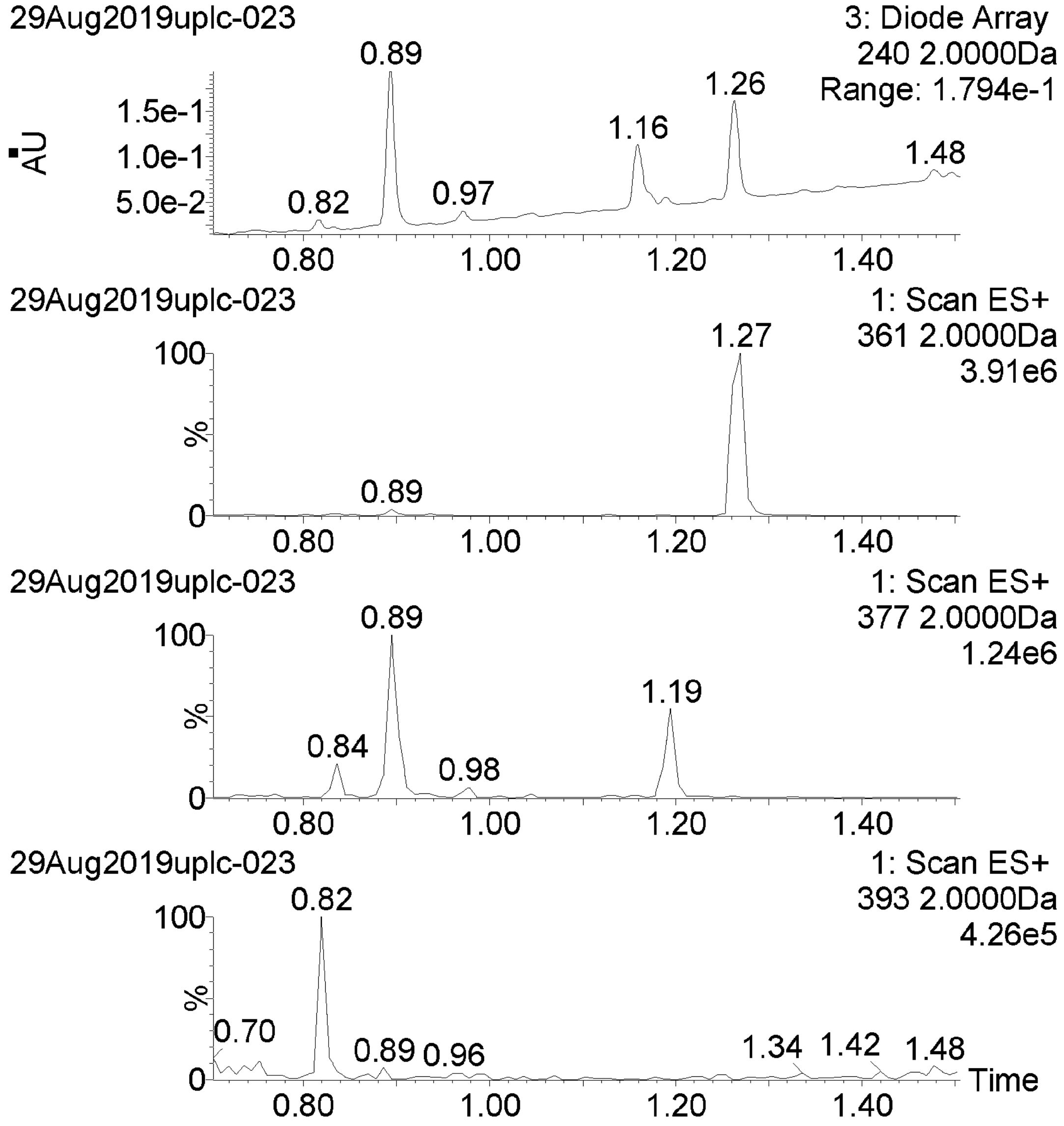
Figure 15T:
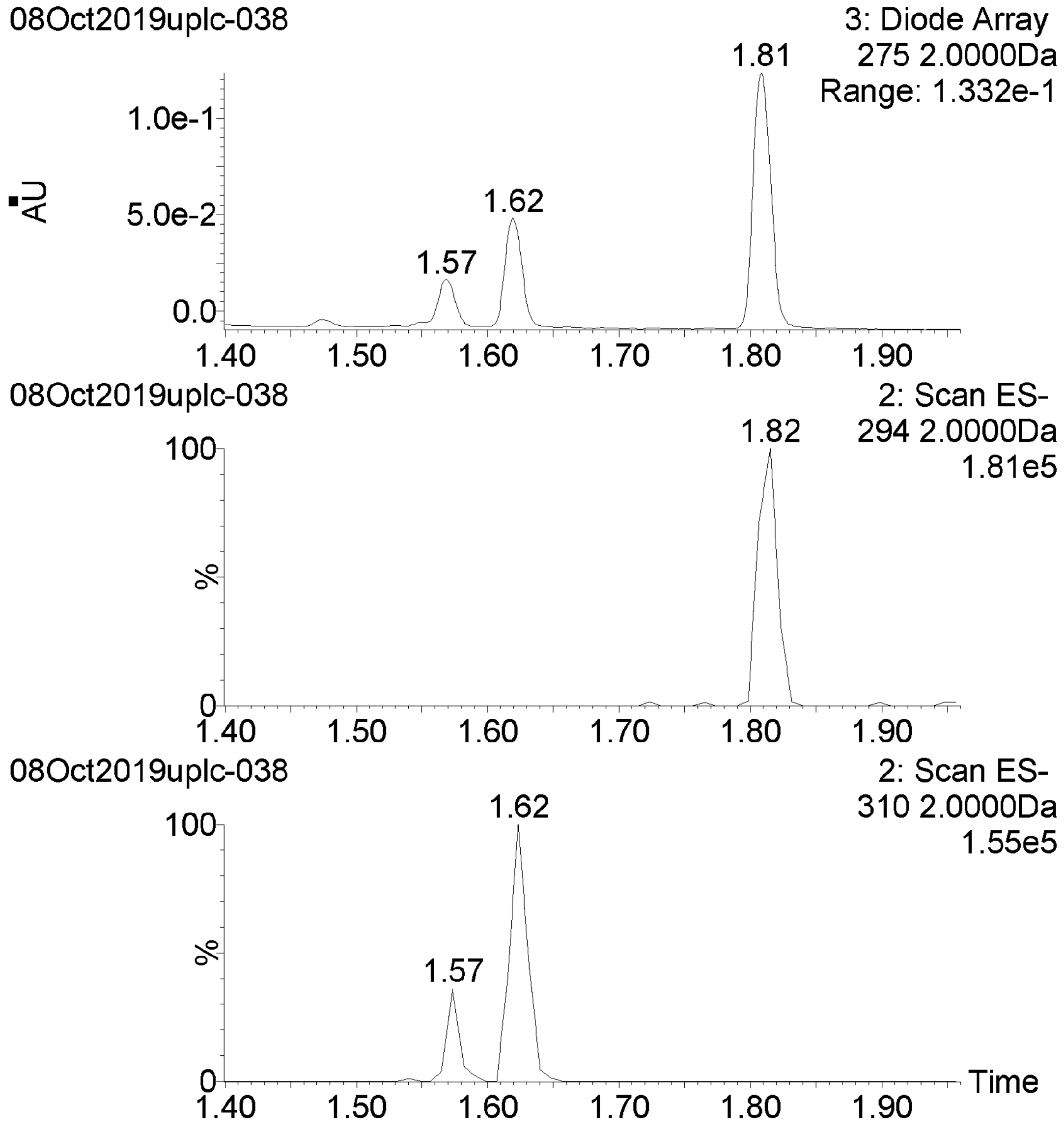

The chromatographic analysis of the post-reaction extract following incubation with bosentan of the lyophilised extract of the R63W mutant of codon optimised $P450_{SriC12}$ is shown in FIG. 15I. Compared to the corresponding extract containing the native codon optimised $P450_{SriC12}$ (FIG. 15*a*) the yield of the O-demethyl-bosentan product had increased from 3.3 to 63.2%, while no hydroxy-bosentan product was detected. This demonstrates the capacity of site-directed mutation to significantly alter the reactivity of these enzymes.

Figure 15Z:
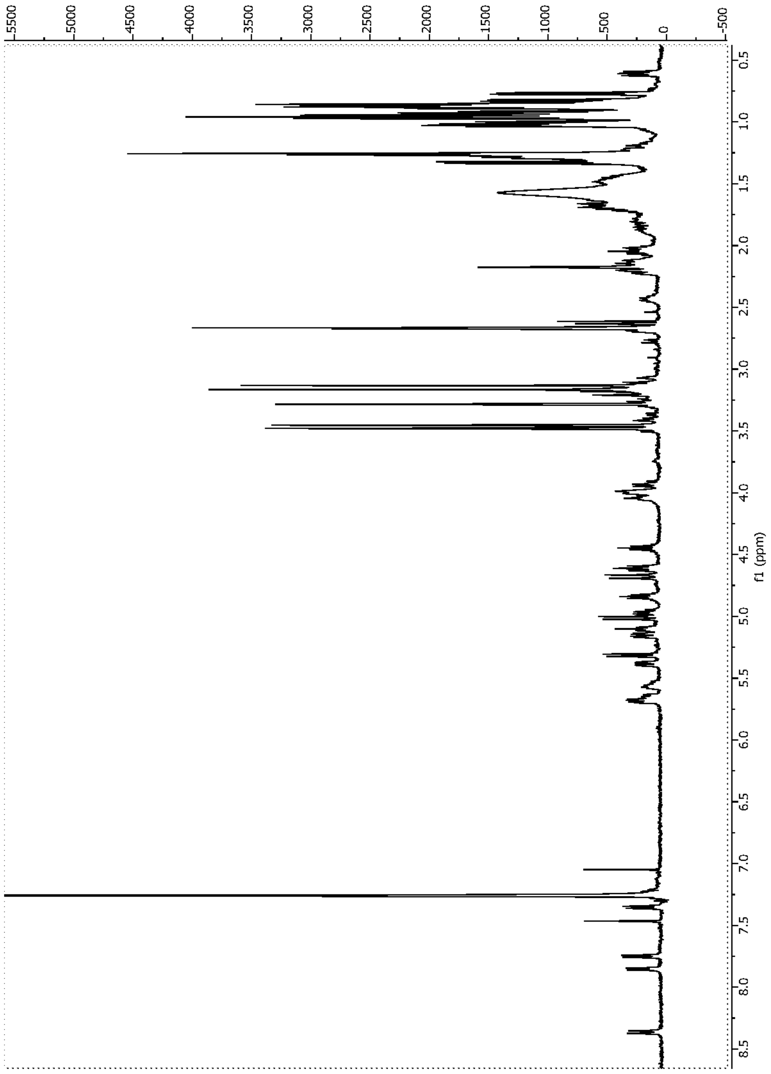
Figure 16:
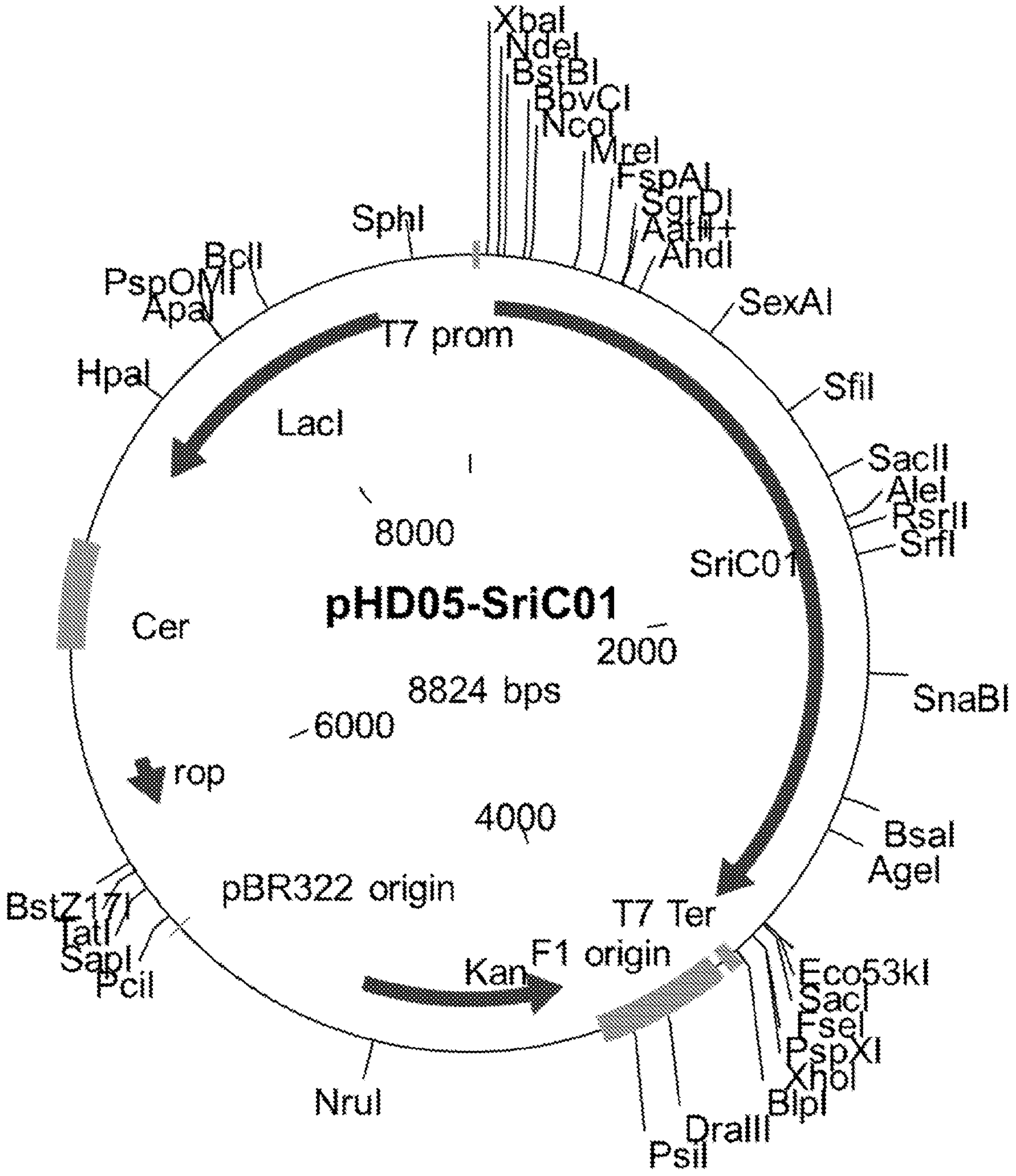
FIG. 16 shows expression plasmid pHD05-SriC01
Figure 17:
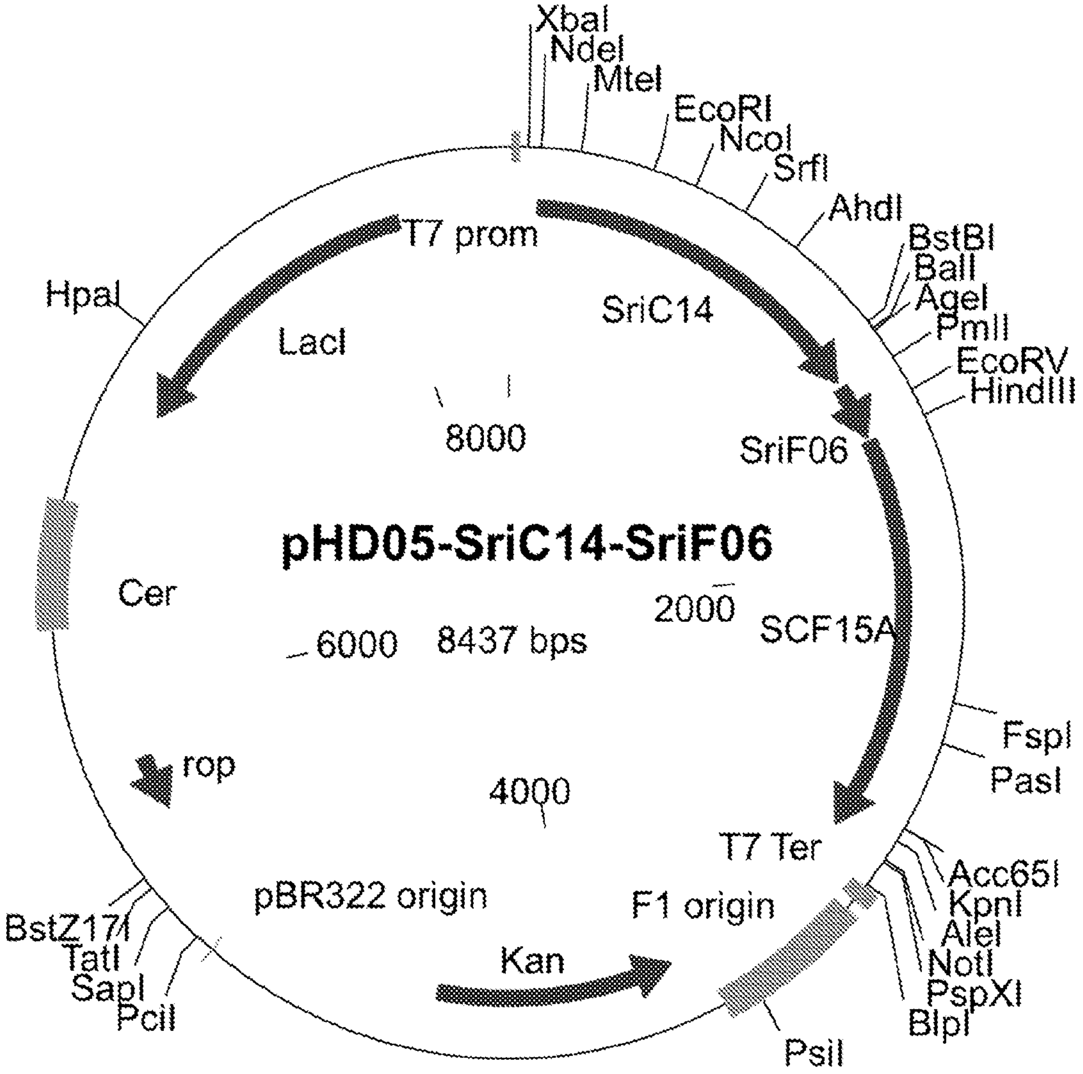
FIG. 17 shows expression plasmid pHD05-SriC14-SriF06
Figure 18:
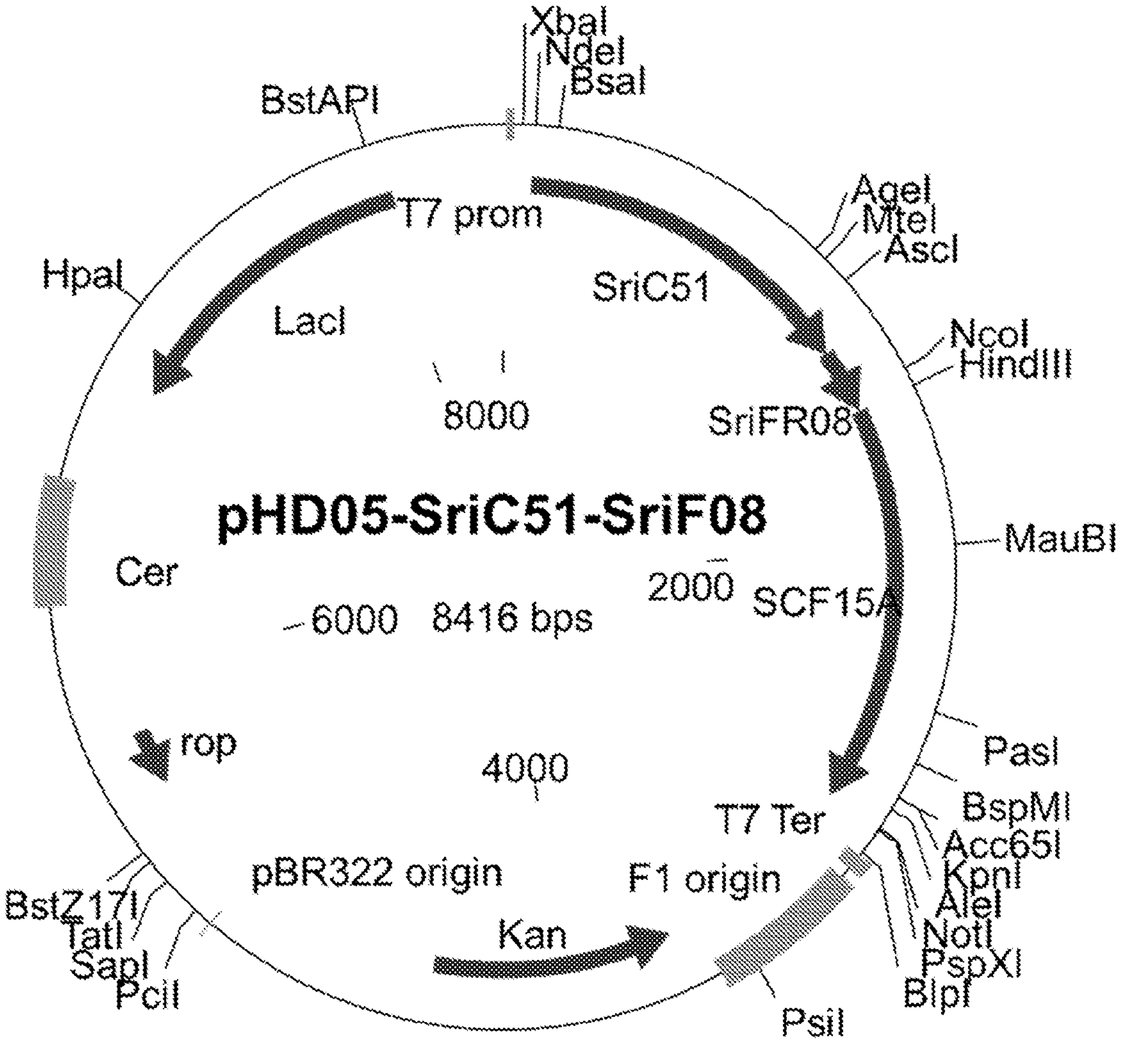
FIG. 18 shows expression plasmid pHD05-SriC51-SriF08
Figure 19:
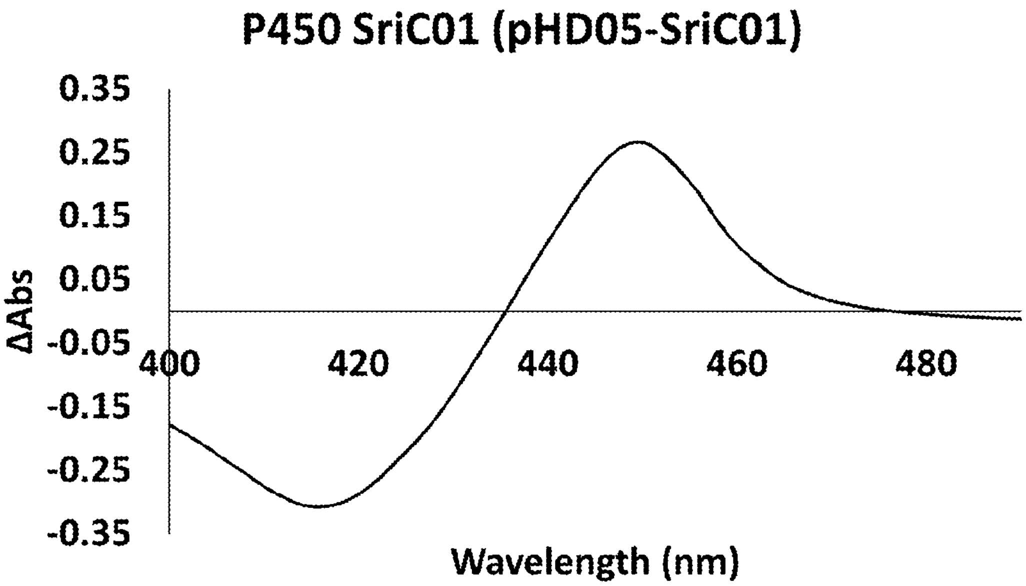
FIG. 19 shows the carbon monoxide difference spectrum of the crude enzyme extract containing codon optimised $P450_{SriC01}$ protein. The sample was prepared from IPTG-induced culture of *E. coli* BL21 (DE3) Rosetta2 cells containing the pHD05-SriC01 plasmid.
Figure 20:
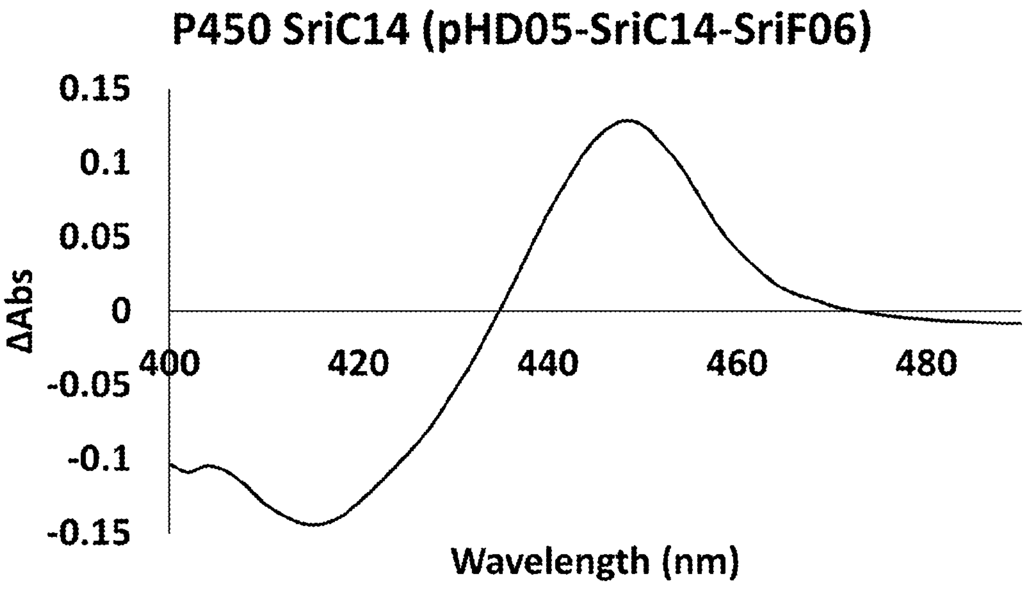
FIG. 20 shows the carbon monoxide difference spectrum of the crude enzyme extract containing codon optimised $P450_{SriC14-SriF06}$ protein. The sample was prepared from IPTG-induced culture of *E. coli* BL21 (DE3) Tuner cells containing the pHD05-SriC14-SriF06 plasmid.
Figure 21:
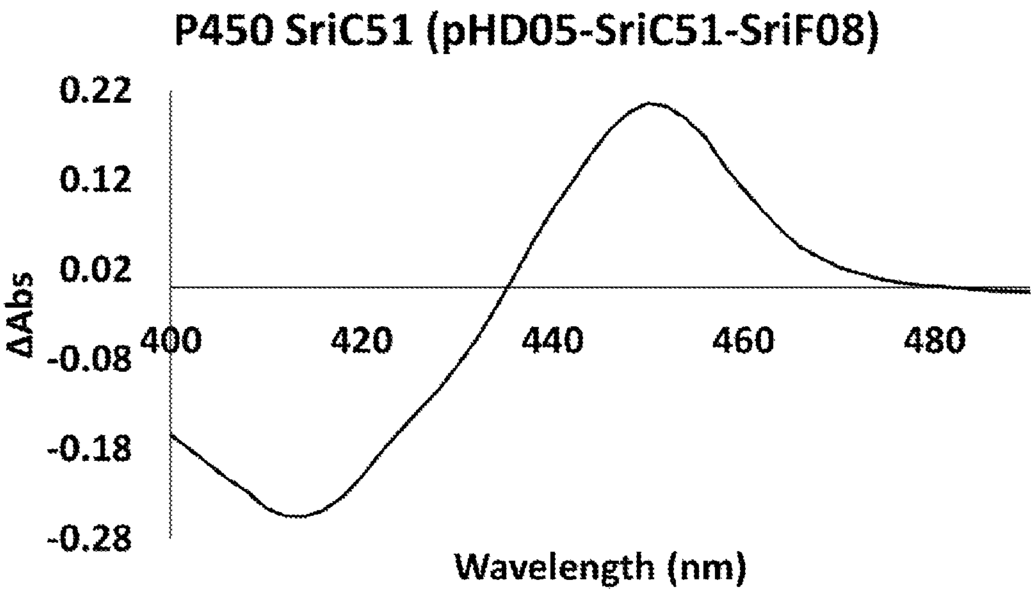
FIG. 21 shows the carbon monoxide difference spectrum of the crude enzyme extract containing codon optimised $P450_{SriC51-SriF08}$ protein. The sample was prepared from IPTG-induced culture of *E. coli* BL21 (DE3) Tuner cells containing the pHD05-SriC51-SriF08 plasmid.
Figure 22:
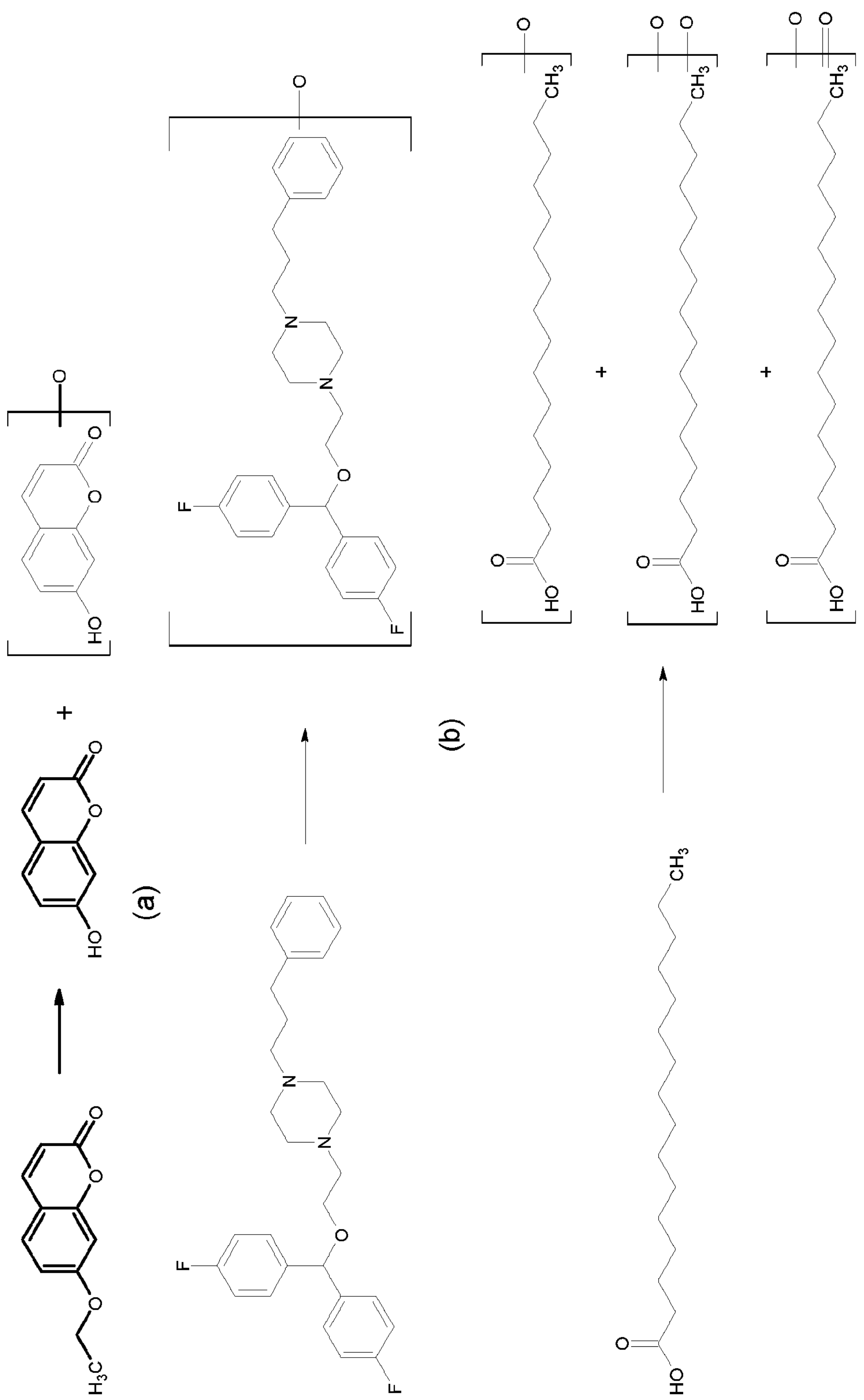
FIG. 22 shows examples of the biotransformation effected by the use of a cytochrome P450 enzyme comprising SEQ ID NO: 2, of the present invention.
Figure 23:
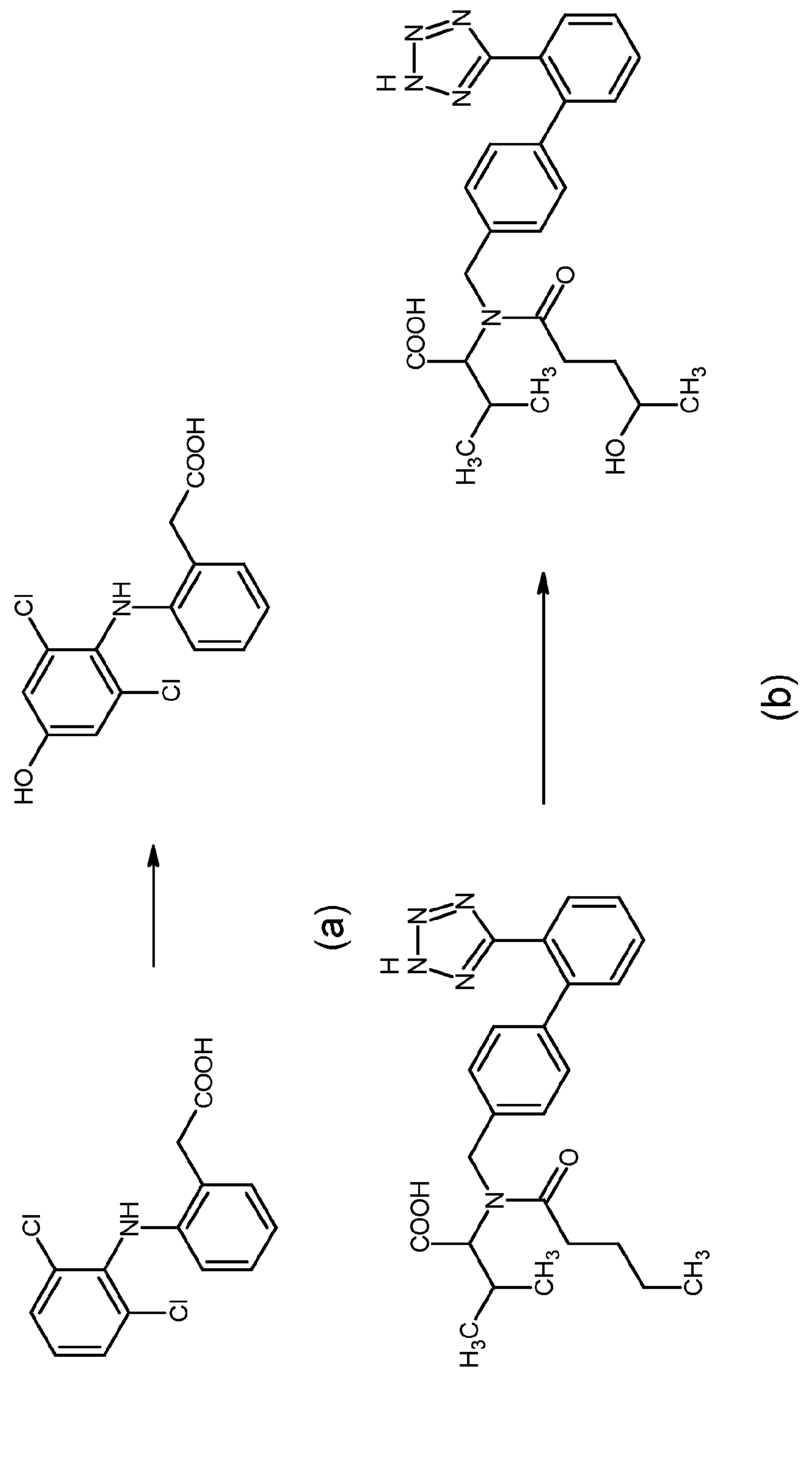
FIG. 23 shows examples of the biotransformation effected by the use of a cytochrome P450 enzyme comprising SEQ ID NO: 34, of the present invention.
Figure 24C:
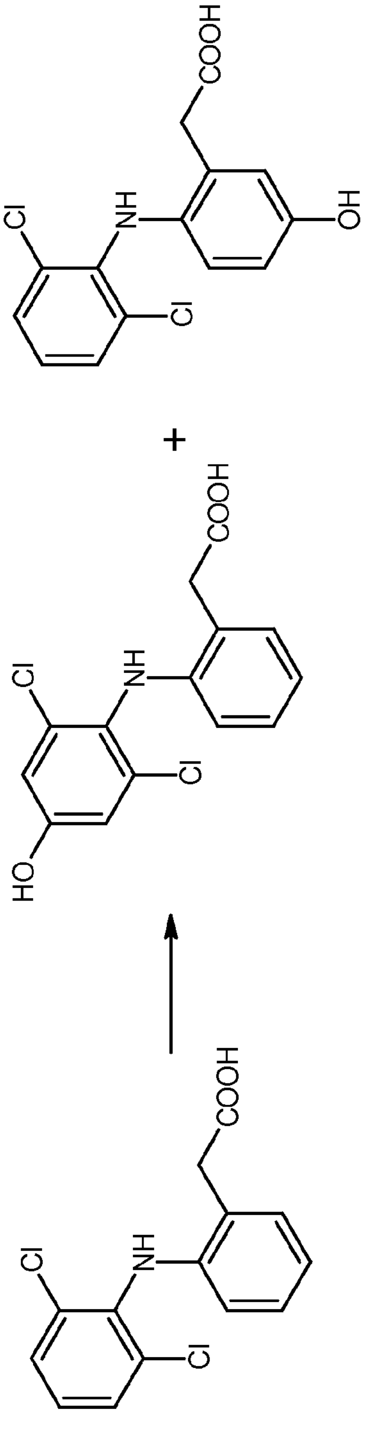
FIG. 24 shows examples of the biotransformation effected by the use of a cytochrome P450 enzyme comprising SEQ ID NO: 109, of the present invention.
Figure 25C:
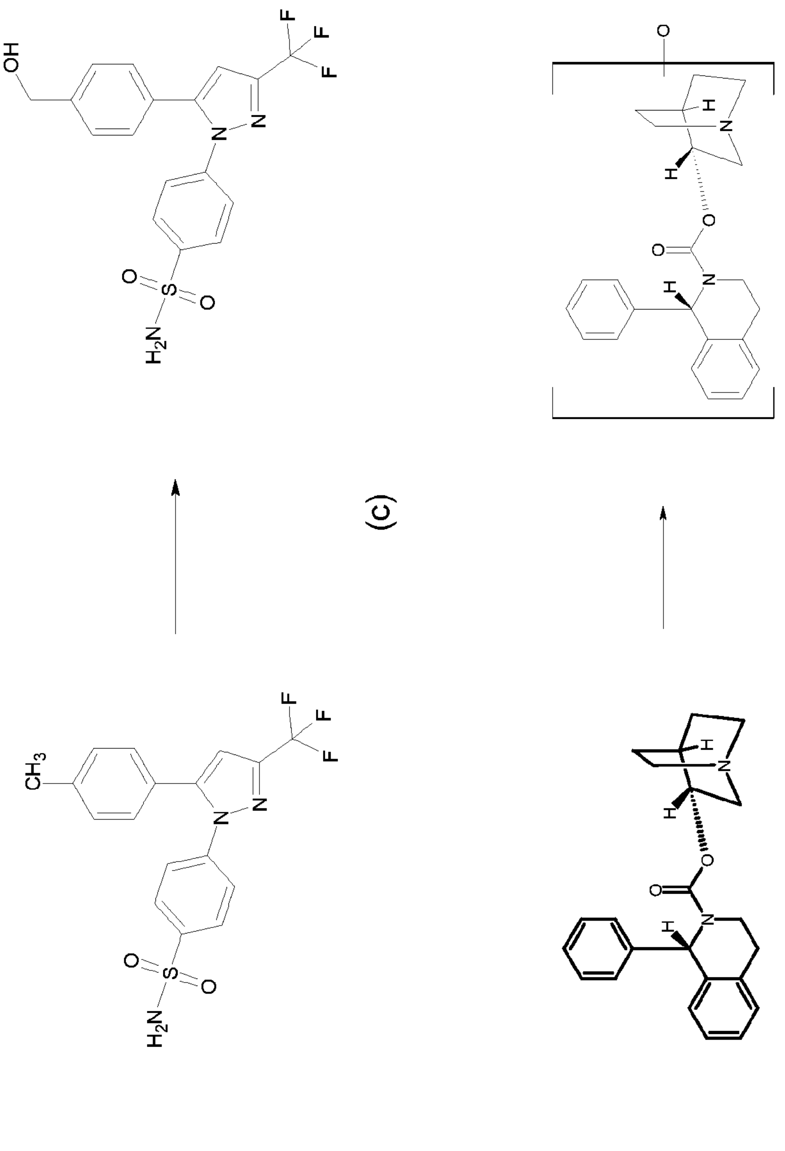
FIG. 25 shows examples of the biotransformation effected by the use of a cytochrome P450 enzyme comprising SEQ ID NO: 251, of the present invention.
Figure 26:
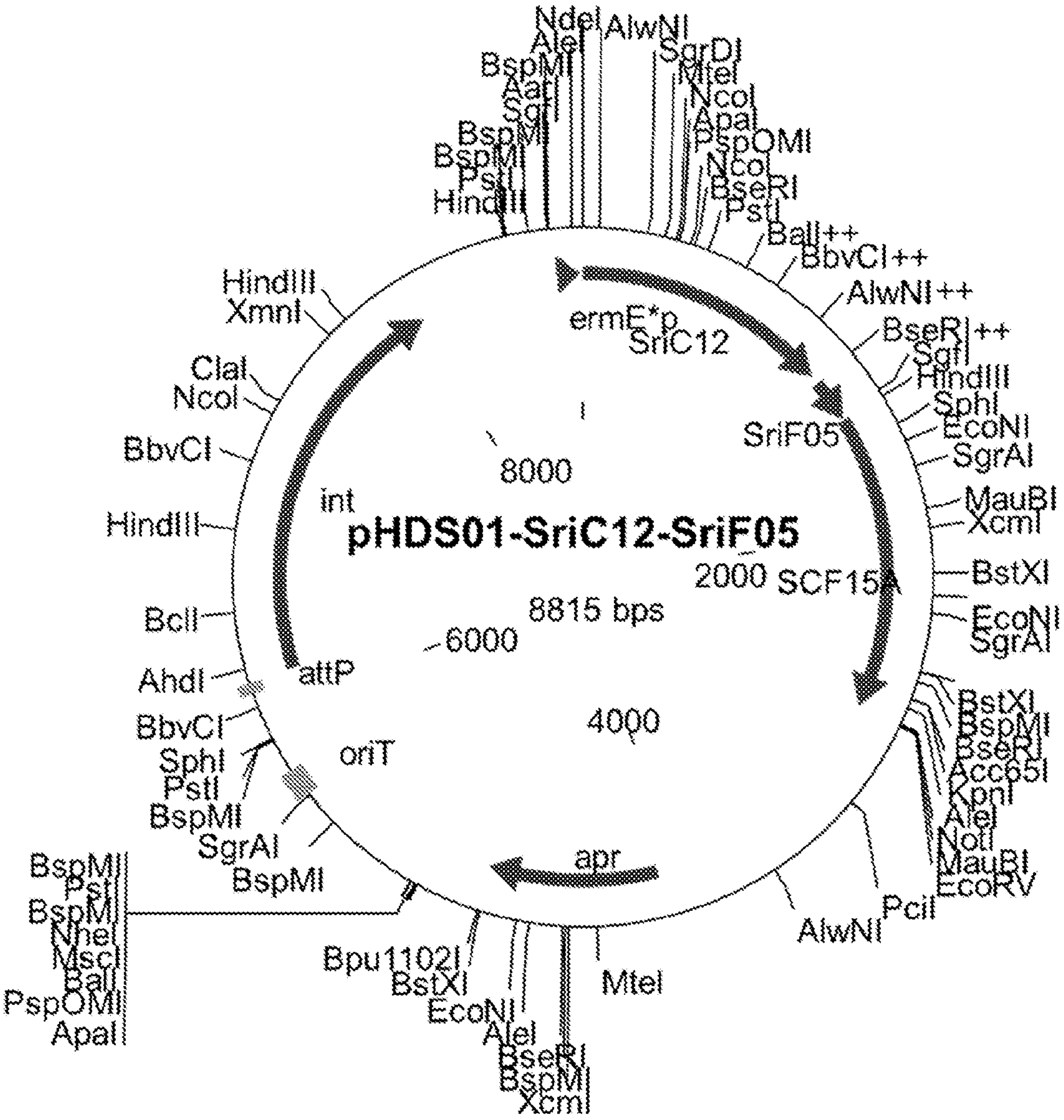
FIG. 26 shows expression plasmid pHDSO1-SriC12-SriFO5.

Example 7: Scale-Up of the Biotransformation of Cyclosporin a by Recombinant $P450_{SriC20}$, Ferredoxin$_{Fd1}$ and Ferredoxin Reductase$_{SCF15A}$ The biotransformation of cyclosporin A by recombinant $P450_{SriC20}$, ferredoxin$_{Fd1}$ and ferredoxin reductase$_{SCF15A}$ as illustrated in FIG. 15*i* was conducted on a larger scale as follows to further characterise the main metabolite produced. Induced cell pellets containing $P450_{SriC20}$, ferredoxin$_{Fd1}$ and ferredoxin reductase$_{SCF15A}$ were produced in a similar manner as in Example 2 by fed-batch bioreactor as would be understood by a person skilled in the art and stored at −20° C. A bulk cell pellet was defrosted, resuspended and processed as in Example 3. The lysed material (total volume 490 ml) was dosed with cyclosporin A (55.0 mg as a 25 mg/ml stock solution in DMSO) in 250 ml Erlenmeyer flasks containing 50 ml reaction per flask, and the reactions initiated by addition of the cofactor mixture as in Example 5 (total reaction volume 550 ml). The flasks were shaken at 150 rpm and 27° C. for 18 hours before the flask contents were combined and frozen at −20° C. The frozen reaction mixture was then thawed and extracted with ethyl acetate (3×500 ml). The combined ethyl acetate layers were concentrated to dryness to yield 381 mg crude extract containing the hydroxylated cyclosporin metabolite of interest, unreacted cyclosporin A and other minor products. This extract was resuspended in heptane-ethyl acetate (1:1) and applied to a column of silica gel (35-70 m particle size, 2 cm diam.×16.2 cm) packed in heptane. The column was eluted with heptane-ethyl acetate-methanol mixtures increasing in ethyl acetate and then methanol content, with the final eluents consisting of ethyl acetate-methanol (90:10) followed by pure acetone, and the fractions collected from these last elutions were found to contain the hydroxylated cyclosporin metabolite of interest as well as cyclosporine A. These fractions (combined weight 39 mg) were redissolved in acetonitrile-water (3:1) and further purified by semi-preparative reversed phase HPLC on a Waters SymmetryShield RP8 column (5 m, 10 mm i.d.×100 mm) eluted with a linear gradient increasing from 45% to 60% acetone in water in the presence of 0.1% formic acid at a flow rate of 4.0 ml/minute and a temperature of 65° C. Iterative injections were made, and fractions were collected every 15 seconds and analysed by HPLC-MS. Fractions containing the hydroxylated metabolite of interest ($MH^+$ at m/z 1218.7) were combined and concentrated to dryness to yield 1.9 mg material (overall purified yield 3.4%). The 500 MHz $^1H$ NMR spectrum of a 0.5 mg aliquot of this material dissolved in $CDCl_3$ is shown in FIG. 15*z*. The signals present in the spectrum are consistent with its identity as cyclosporin A metabolite AM1 based on comparison with literature information (K. Ohta et al. (2005): Production of human metabolites of cyclosporin A, AM1, AM4N and AM9, by microbial conversion. *J. Biosci. Bioeng.* 99: 390-395).

Example 8: Whole-Cell Biotransformation of Ritonavir by Recombinant $P450_{SriC12}$, Ferredoxin$_{SriF05}$ and Ferredoxin Reductase$_{SCF15A}$ Expressed in *Streptomyces lividans* TK24

Construction of *Streptomyces lividans* HD002

The polycistronic operon containing $P450_{SriC12}$, ferredoxin$_{SriF05}$ and ferredoxin reductase$_{SCF15A}$ was sub-cloned from pHD02-SriC12-SriF05 into pIJ12551 vector (Sherwood, E. J. et al. (2013). J Bacteriol. 195(10): 2309-2321) via NdeI and NotI as in Example 4. The DNA sequence was confirmed by Sanger sequencing at LGC genomics (Germany). The plasmid was designated as pHDSO1-SriC12-SriFO5.

Triparental conjugation was performed to introduce pHDSO1-SriC12-SriFO5 into *Streptomyces lividans* TK24 (John Innes Centre, UK). Single colonies of *E. coli* DH5a harbouring pHDSO1-SriC12-SriFO5 and *E. coli* DH5α harbouring pUB307 were inoculated into LB media containing 50 μg/mL apramycin and 50 μg/mL kanamycin respectively and incubated shaking overnight at 37° C. and 200 rpm. Next morning, precultures were sub-cultured into fresh LB media with appropriate antibiotics and incubated at 37° C. and 200 rpm until OD600 reached between 0.35 and 0.4. The *E. coli* cultures were centrifuged at 2,000 rpm for 10 minutes at 4° C. and washed twice with 10 mL of fresh LB media to remove antibiotics. While washing, 10 μL of *Streptomyces lividans* TK24 concentrated spore stock was heat-shocked in 500 μL of 2×YT media at 50° C. for 10 minutes. After washing the *E. coli* cells, the pellet was resuspended in 500 μL of LB media. A mixture containing 500 μL of *E. coli* DH5α harbour pHDSO1-SriC12-SriFO5, 500 μL of *E. coli* DH5a harbour pUB307 and 500 μL of heat-shocked *S. lividans* TK24 spores were briefly centrifuged at 5,000 rpm for 30 seconds. The supernatant was poured off and the pellet was resuspended in 500 μL of sterile water. The conjugation mixture was serially diluted from 10-1 to 104 and 100 μL of the dilutions were plated onto SFM agar with 10 mM $MgCl_2$ (Kieser, T. et al. (2000). Practical *Streptomyces* Genetics. The John Innes Foundation.) and incubated overnight at 30° C. The next morning, the conjugation plates were overlaid with 1 mL of water containing 0.5 mg nalidixic acid and 1.25 mg apramycin and allowed to dry. The plates were further incubated at 30° C. until spore colonies were observed. Exconjugants were further streaked across an entire plate of SFM agar containing 25 μg/mL nalidixic acid and 50 μg/mL apramycin and incubated at 30°

C. until sporulation. Concentrated spore stocks were made as in Kieser, T. et al. (2000). Practical *Streptomyces* Genetics. The John Innes Foundation. *S. lividans* TK24 harbouring pHDSO1-SriC12-SriFO5 was designated as *S. lividans* HD002.

As a negative control, an empty plJ12551 expression vector was introduced into *S. lividans* TK24 by triparental conjugation as described above and designated as *S. lividans* HD0000.

Whole-Cell Biotransformations Using *S. lividans* HD002 Against Ritonavir in 24-Well Block Format Approximately $10^8$ cells of *S. lividans* HD000 and *S. lividans* HD000 were inoculated separately into 50 mL of culture medium (containing 5 g/L glycerol; 20 g/L glucose; 5 g/L yeast extract peptone; 2 g/L meat extract; 5 g/L mycological peptone; 1 g/L ammonium phosphate dibasic; 3 g/I sodium chloride; 0.3 g/L magnesium sulphate heptahydrate and 3.5 g/L calcium carbonate, adjusted to pH 7.0 and sterilised at 115° C. for 15 minutes) in 250 mL baffled flasks and incubated shaking at 27° C., 200 rpm for 48 hours. In a 24-well micro-bioreactor block (EnzyScreen, Netherlands), 2.5 mL of *S. lividans* HD000 and *S. lividans* HD002 were dosed with ritonavir at a concentration of 100 mg/L. Ritonavir was formulated with 20% hydroxypropyl-p-cyclodextrin (prepared via 1 in 25 dilution of a stock solution of 25 mg ritonavir in 1 mL DMSO). Cultures were time-coursed daily after dosing to assess the production of the target metabolite hydroxy-ritonavir as in Example 5.

*S. lividans* HD000 negative control strain was unable to hydroxylate ritonavir and only parent metabolite was detected as shown in Table 6. *S. lividans* HD002 expressing $P450_{SriC12}$, $ferredoxin_{SriF05}$, ferredoxin $reductase_{SCF15A}$ was able to hydroxylate ritonavir in whole-cell biotransformations to produce several hydroxylated products (differentiated by their LC-MS retention times) and the percentage conversions of the parent to its metabolites are shown in Table 7. Conversions of ritonavir improved with longer incubations with the drug.

TABLE 6

Hydroxylase activity of *S. lividans* HD000 negative control against ritonavir (parent) to yield hydroxylated (+16 Da) products with different LC-MS retention times.

| Sampling time point (hour) | Parent (1.90 min) % | +16 Da (1.67 min) % | +16 Da (1.72 min) % | +16 Da (1.76 min) % |
|---|---|---|---|---|
| 24 | 100.0 | 0.0 | 0.0 | 0.0 |
| 48 | 100.0 | 0.0 | 0.0 | 0.0 |
| 120 | 100.0 | 0.0 | 0.0 | 0.0 |

TABLE 7

Hydroxylase activity of $P450_{SriC12}$-$ferredoxin_{SriF05}$-ferredoxin $reductase_{SCF15A}$ expressed in *S. lividans* HD002 against ritonavir (parent) to yield hydroxylated (+16 Da) products with different LC-MS retention times.

| Sampling time point (hour) | Parent (1.90 min) % | +16 Da (1.67 min) % | +16 Da (1.72 min) % | +16 Da (1.76 min) % |
|---|---|---|---|---|
| 24 | 68.5 | 7.1 | 18.9 | 1.4 |
| 48 | 58.6 | 8.6 | 23.6 | 2.8 |
| 120 | 51.2 | 9.1 | 28.1 | 1.4 |

The invention claimed is:

1. An enzyme having cytochrome P450 activity and having at least 90% identity to a cytochrome P450 enzyme comprising SEQ ID NO: 29 and comprising at least two of:

(a) a tryptophan residue at the position corresponding to position 63 of SEQ ID NO: 29;

(b) a tyrosine residue at the position corresponding to position 74 of SEQ ID NO: 29; and (c) an alanine residue at the position corresponding to position 171 of SEQ ID NO: 29.

2. The enzyme of claim 1, comprising:

(a) a tryptophan residue at the position corresponding to position 63 of SEQ ID NO: 29 and a tyrosine residue at the position corresponding to position 74 of SEQ ID NO: 29;

(b) a tryptophan residue at the position corresponding to position 63 of SEQ ID NO: 29 and an alanine residue at the position corresponding to position 171 of SEQ ID NO: 29;

(c) a tyrosine residue at the position corresponding to position 74 of SEQ ID NO: 29, an alanine residue at the position corresponding to position 171 of SEQ ID NO: 29 and a tryptophan residue at the position corresponding to position 183 of SEQ ID NO: 29; or (d) a tryptophan residue at the position corresponding to position 63 of SEQ ID NO: 29, a tyrosine residue at the position corresponding to position 74 of SEQ ID NO: 29 and an alanine residue at the position corresponding to position 171 of SEQ ID NO: 29.

3. The enzyme of claim 2, comprising the amino acid sequence set forth in SEQ ID NO: 251, 253, 255 or 257, or a sequence having at least 95% identity thereto.

4. The enzyme of claim 3, comprising the amino acid sequence set forth in SEQ ID NO: 251, 253, 255 or 257.

5. A kit comprising:

(i) an enzyme having cytochrome P450 activity and having at least 90% identity to a cytochrome P450 enzyme comprising SEQ ID NO: 29 and comprising at least two of:

(a) a tryptophan residue at the position corresponding to position 63 of SEQ ID NO: 29;

(b) a tyrosine residue at the position corresponding to position 74 of SEQ ID NO: 29; and (c) an alanine residue at the position corresponding to position 171 of SEQ ID NO: 29; or (ii) a microorganism that expresses an enzyme as defined in (i); or (iii) an extract of the microorganism of (ii) comprising the enzyme of (i).

6. The kit according to claim 5, wherein the enzyme comprises:

(a) a tryptophan residue at the position corresponding to position 63 of SEQ ID NO: 29 and a tyrosine residue at the position corresponding to position 74 of SEQ ID NO: 29;

(b) a tryptophan residue at the position corresponding to position 63 of SEQ ID NO: 29 and an alanine residue at the position corresponding to position 171 of SEQ ID NO: 29;

(c) a tyrosine residue at the position corresponding to position 74 of SEQ ID NO: 29, an alanine residue at the position corresponding to position 171 of SEQ ID NO: 29 and a tryptophan residue at the position corresponding to position 183 of SEQ ID NO: 29; or (d) a tryptophan residue at the position corresponding to position 63 of SEQ ID NO: 29, a tyrosine residue at the position corresponding to position 74 of SEQ ID NO: 29 and an alanine residue at the position corresponding to position 171 of SEQ ID NO: 29.

7. The kit according to claim 6, wherein the enzyme comprises the amino acid sequence set forth in SEQ ID NO: 251, 253, 255 or 257, or a sequence having at least 95% identity thereto.

8. The kit according to claim 6, wherein the enzyme comprises the amino acid sequence set forth in SEQ ID NO: 251, 253, 255 or 257.

9. The kit according to claim 6, wherein the kit comprises (i) at least two enzymes as defined in (a) to (d), (ii) microorganisms expressing at least two enzymes as defined in (a) to (d), or (iii) an extract of the microorganisms in (ii) comprising at least two enzymes as defined in (a) to (d).

10. The kit according to claim 5, comprising a reducing agent.

11. The kit according to claim 10, wherein the kit comprises ferredoxin reductase and a ferredoxin.

12. The kit according to claim 5, further comprising one or more other cytochrome P450 enzymes.

13. The kit according to claim 5, wherein the cytochrome P450 enzyme, microorganism or extract is lyophilised and sealed.

14. The kit according to claim 5, further comprising a buffer.

15. A microorganism expressing an enzyme having cytochrome P450 activity as defined in claim 1.

16. A method for the production of a hydroxylated and/or dealkylated organic compound, comprising reacting the organic compound with an enzyme as defined in claim 1.

17. The method of claim 16, wherein the enzyme comprises the amino acid sequence set forth in SEQ ID NO: 251, 253, 255 or 257, or a sequence having at least 95% identity thereto.

18. The method of claim 16, wherein the enzyme catalyzes the hydroxylation of a propyl group or a butyl group.

19. The method of claim 18, wherein the enzyme catalyzes the hydroxylation of an isopropyl or isobutyl group.

20. The method of claim 18, wherein the enzyme catalyzes the hydroxylation of a tert-butyl group.

21. The method of claim 16, wherein the enzyme is used to catalyse the hydroxylation of a compound of formula (II), where R represents the rest of the compound and where $R^1$ is $CH_3$ or H:

(II)
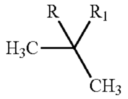
22. The method of claim 16, wherein the enzyme is in purified form, part-purified form, a crude enzyme extract, or in a host cell.
* * * * *

SEQUENCE LISTING

<160> NUMBER OF SEQ ID NOS: 257

<210> SEQ ID NO 1
<211> LENGTH: 3195
<212> TYPE: DNA
<213> ORGANISM: Streptomyces rimosus

<400> SEQUENCE: 1

```
atgaccgaga cgatcccgtt cgaagcagtc gacggcgcgg tgcgcccgtc cgaggaggtg     60
ccggtcgtcg acctgtcggc caccggcctc agcgacaccc ccctccagca ggccatgggc    120
ctggcccgcg agcacggcgc ggtgtaccgg cggcggctgc acggccatga ggcactgctc    180
gtgtcctccc tggagctggt caccgaactg gccgacgaga accgcttcgc caagggcgtc    240
tcggtcgccc tggagaacgt ccgcgagttc gccggcgacg gcctgttcac cgcgtacaac    300
gacgaaccga actgggccaa ggcgcacgac atcctcatgc cggccttcgc cctcggctcg    360
atgcgcacgt accacccggc gatgctgaag gtcgcccgcc gggtgatcgg cagctgggac    420
cggcgcgcgg ccgacggcac acccgtcgac gtccccgacg acatgacccg gatgacgctc    480
gacaccatcg gcctggcggg cttcggcttc gacttcgagt ccttctcccg cgcgaccatg    540
cacccettcg tcgaggcgat ggtgcgttgc ctggaatgga gcatgaaacg cctcggccgg    600
gagccggacg gcgactacac cgaggaggac gctgccttcc gggccgacgc ggactacctc    660
gcctcggtcg tggacgaggt catcgcctcc cgtacgggtg cggacggcac cccgggcgag    720
gaggcgggcg acgacctcct cggcctgatg ctcggcgcca cccaccccgc cgacggcacc    780
acgctcgacc tcgccaacat ccgcaaccag gtcatcacct tcctcatcgc cggtcacgaa    840
```

-continued acgacctccg gcgcgctgtc cttcgccctg taccacctgc tcaaggaccc ggccgccctg 900
cgcctggcgc agcgcgaggc cgacgagctg tggggcgacc agaccgaccc cgacccgtcc 960
ttcgaggaca tcggccgact gccctacacc cgccaggtcc tcaacgaggc gctgcgcctg 1020
tggcccaccg ccgccgcctt ctcccgccag gcccgtacgg acaccctgct cggcggccgc 1080
atcccactga aggcgggcca gctggtcacc gtcctcacgc cgatgctgca ccgcgacccg 1140
gcctggggcg acaacccgga gctgttcgac cccacgcggt tcgcgccgga ggccgaggcg 1200
gcccgctccc cgcacgcgta caagcccttc ggtacgggcg agcgggcctg catcggccgc 1260
cagttcgcgc tgcacgaggc gacgatgctg ctcgccatgc tggtgcaccg ctaccgcctc 1320
atcgaccaca gcgactaccg cctgagcatc aaggaaaccc tgaccctcaa gccggacggc 1380
ttcaccctca ccctcgcccg gcgcaccccc gccgaccgcg cgggcctgcg cgccgccctc 1440
gccgtactgc ccggcggagc cgcggagccg gacggcaccg agtccggtac ggacgacggc 1500
ctgccgacgc gggtccgcca ggacaccgcc ctgctcctcc tccacggcac caactacggc 1560
acctgccgcg acttcgccga gcgcatcgcc gacgaggcca ccggcctcgg cttcaccacc 1620
gaggtggccc cgctggacgc cgcgaccggc gcgctcccca cggaccgccc ggtcgtgatc 1680
gtcaccgcgt cctacaacgg acagccgacc gatgacgcgg cgcgcttcgt cgaatggctt 1740
tccggcgacg aagcccgggc cgaaggcgtc ccctacgccg tcctcggcgt cggcgaccgc 1800
aactgggccg ccacctacca gcgcgtgccc acgcttttgg acgagcggct ggccgccctc 1860
ggcgccgagc ggctcctccc gcgcggcgag gccgacgcat ccggcgacct gaacggcgcc 1920
gtcaaggcgt tcacggccac cctgcgcacc gaactgctcg tacgctacgg cgatcccgcg 1980
accatcggcg cgagcacacc ggccgacgcc acggacgcgt cctacaccgt ccgcgaggtc 2040
accggcggcc ccctggacgc actcgccgcc cgccacggcc tccagccgat gaccgtcacc 2100
gaggcgtacg acctcaccgc ccccggctac ccgcgcgtca agcgcttcct gcgcctcacc 2160
ctccccgaag gcgttacgta ccgtacggcc gaccacctcg ccgtacttcc cgccaacggc 2220
gcggcggcgg tcgaacgcgc cgcgcaggtg ctgggcgtat cactggaagc ggtcctcgac 2280
atccgcgcgg gcgctggtcg cggcggccgg gacacgctcc ccgtggaccg cccgctcacg 2340
gtacgtcagc tcctcaccca ccacctggag ctgaacgccc gaccgactgc cgcgcaacgg 2400
gcggtgctcg ccgaccacaa cccctgtccg cccgagcgtg ccgccctcca ggccatcccc 2460
gacgacgacc cgcgcaccac cctggacctc atcgaggaac acccggccct gcgcggtgtg 2520
ctgccctggc cggtactcct cgacctgctc ccggccctgc gcatccgcca ctactccctc 2580
tcgtcctcgc ccgccgccga cccccgccac gccgacctga tggtctcgct gctccccggc 2640
ggcaccggct ccggccacct gcacacactg cggcccggcg acacggtcct ggcccgggtc 2700
cagccctgcc gggaggcgtt ccgcctcgac ccggccgacc cgacaccggt catcctggta 2760
gcggccggca ccggcctggc gcccttccgg ggcgcggtcg ccgaccgcct ggccgccacc 2820
caacttgccc ctgctctgct ctacttcggc tgcgatgccc tcgaagccga ctacctgcac 2880
gccgaagaac tccaggccgc cgaggcagcc ggggccgtgt ccctgcgccc cgcgttcagc 2940
gcccgcccgg tggacggctg ccgttacgtc cagcaccgca tcgccgccga ggcggaggaa 3000
gtgggggcgc tgctggacgc cggagcccgg gtgtacgtct gcggcgacgg caaccggatg 3060
gccccgggcg tacgcgccgc cttccgcgag ctgtacgcgg cccgtaccgg cgccacgcag 3120
gaggaggccg aggtctggct gcgagagctc acggcggccg gccggtatgt ggaggatgtc 3180

-continued tatgtgacgg ggtaa 3195

<210> SEQ ID NO 2
<211> LENGTH: 1064
<212> TYPE: PRT
<213> ORGANISM: Streptomyces rimosus

<400> SEQUENCE: 2

```
Met Thr Glu Thr Ile Pro Phe Glu Ala Val Asp Gly Ala Val Arg Pro
1               5                   10                  15

Ser Glu Glu Val Pro Val Val Asp Leu Ser Ala Thr Gly Leu Ser Asp
            20                  25                  30

Thr Pro Leu Gln Gln Ala Met Gly Leu Ala Arg Glu His Gly Ala Val
        35                  40                  45

Tyr Arg Arg Arg Leu His Gly His Glu Ala Leu Leu Val Ser Ser Leu
    50                  55                  60

Glu Leu Val Thr Glu Leu Ala Asp Glu Asn Arg Phe Ala Lys Gly Val
65                  70                  75                  80

Ser Val Ala Leu Glu Asn Val Arg Glu Phe Ala Gly Asp Gly Leu Phe
                85                  90                  95

Thr Ala Tyr Asn Asp Glu Pro Asn Trp Ala Lys Ala His Asp Ile Leu
            100                 105                 110

Met Pro Ala Phe Ala Leu Gly Ser Met Arg Thr Tyr His Pro Ala Met
        115                 120                 125

Leu Lys Val Ala Arg Arg Val Ile Gly Ser Trp Asp Arg Arg Ala Ala
    130                 135                 140

Asp Gly Thr Pro Val Asp Val Pro Asp Asp Met Thr Arg Met Thr Leu
145                 150                 155                 160

Asp Thr Ile Gly Leu Ala Gly Phe Gly Phe Asp Phe Glu Ser Phe Ser
                165                 170                 175

Arg Ala Thr Met His Pro Phe Val Glu Ala Met Val Arg Cys Leu Glu
            180                 185                 190

Trp Ser Met Lys Arg Leu Gly Arg Glu Pro Asp Gly Asp Tyr Thr Glu
        195                 200                 205

Glu Asp Ala Ala Phe Arg Ala Asp Ala Asp Tyr Leu Ala Ser Val Val
    210                 215                 220

Asp Glu Val Ile Ala Ser Arg Thr Gly Ala Asp Gly Thr Pro Gly Glu
225                 230                 235                 240

Glu Ala Gly Asp Asp Leu Leu Gly Leu Met Leu Gly Ala Thr His Pro
                245                 250                 255

Ala Asp Gly Thr Thr Leu Asp Leu Ala Asn Ile Arg Asn Gln Val Ile
            260                 265                 270

Thr Phe Leu Ile Ala Gly His Glu Thr Thr Ser Gly Ala Leu Ser Phe
        275                 280                 285

Ala Leu Tyr His Leu Leu Lys Asp Pro Ala Ala Leu Arg Leu Ala Gln
    290                 295                 300

Arg Glu Ala Asp Glu Leu Trp Gly Asp Gln Thr Asp Pro Asp Pro Ser
305                 310                 315                 320

Phe Glu Asp Ile Gly Arg Leu Pro Tyr Thr Arg Gln Val Leu Asn Glu
                325                 330                 335

Ala Leu Arg Leu Trp Pro Thr Ala Ala Ala Phe Ser Arg Gln Ala Arg
            340                 345                 350

Thr Asp Thr Leu Leu Gly Gly Arg Ile Pro Leu Lys Ala Gly Gln Leu
        355                 360                 365
```

-continued

```
Val Thr Val Leu Thr Pro Met Leu His Arg Asp Pro Ala Trp Gly Asp
    370                 375                 380

Asn Pro Glu Leu Phe Asp Pro Thr Arg Phe Ala Pro Glu Ala Glu Ala
385                 390                 395                 400

Ala Arg Ser Pro His Ala Tyr Lys Pro Phe Gly Thr Gly Glu Arg Ala
                405                 410                 415

Cys Ile Gly Arg Gln Phe Ala Leu His Glu Ala Thr Met Leu Leu Ala
            420                 425                 430

Met Leu Val His Arg Tyr Arg Leu Ile Asp His Ser Asp Tyr Arg Leu
        435                 440                 445

Ser Ile Lys Glu Thr Leu Thr Leu Lys Pro Asp Gly Phe Thr Leu Thr
    450                 455                 460

Leu Ala Arg Arg Thr Pro Ala Asp Arg Ala Gly Leu Arg Ala Ala Leu
465                 470                 475                 480

Ala Val Leu Pro Gly Gly Ala Ala Glu Pro Asp Gly Thr Glu Ser Gly
                485                 490                 495

Thr Asp Asp Gly Leu Pro Thr Arg Val Arg Gln Asp Thr Ala Leu Leu
            500                 505                 510

Leu Leu His Gly Thr Asn Tyr Gly Thr Cys Arg Asp Phe Ala Glu Arg
        515                 520                 525

Ile Ala Asp Glu Ala Thr Gly Leu Gly Phe Thr Thr Glu Val Ala Pro
    530                 535                 540

Leu Asp Ala Ala Thr Gly Ala Leu Pro Thr Asp Arg Pro Val Val Ile
545                 550                 555                 560

Val Thr Ala Ser Tyr Asn Gly Gln Pro Thr Asp Asp Ala Ala Arg Phe
                565                 570                 575

Val Glu Trp Leu Ser Gly Asp Glu Ala Arg Ala Glu Gly Val Pro Tyr
            580                 585                 590

Ala Val Leu Gly Val Gly Asp Arg Asn Trp Ala Ala Thr Tyr Gln Arg
        595                 600                 605

Val Pro Thr Leu Leu Asp Glu Arg Leu Ala Ala Leu Gly Ala Glu Arg
    610                 615                 620

Leu Leu Pro Arg Gly Glu Ala Asp Ala Ser Gly Asp Leu Asn Gly Ala
625                 630                 635                 640

Val Lys Ala Phe Thr Ala Thr Leu Arg Thr Glu Leu Leu Val Arg Tyr
                645                 650                 655

Gly Asp Pro Ala Thr Ile Gly Ala Ser Thr Pro Ala Asp Ala Thr Asp
            660                 665                 670

Ala Ser Tyr Thr Val Arg Glu Val Thr Gly Gly Pro Leu Asp Ala Leu
        675                 680                 685

Ala Ala Arg His Gly Leu Gln Pro Met Thr Val Thr Glu Ala Tyr Asp
    690                 695                 700

Leu Thr Ala Pro Gly Tyr Pro Arg Val Lys Arg Phe Leu Arg Leu Thr
705                 710                 715                 720

Leu Pro Glu Gly Val Thr Tyr Arg Thr Ala Asp His Leu Ala Val Leu
                725                 730                 735

Pro Ala Asn Gly Ala Ala Ala Val Glu Arg Ala Ala Gln Val Leu Gly
            740                 745                 750

Val Ser Leu Glu Ala Val Leu Asp Ile Arg Ala Gly Ala Gly Arg Gly
        755                 760                 765

Gly Arg Asp Thr Leu Pro Val Asp Arg Pro Leu Thr Val Arg Gln Leu
    770                 775                 780

Leu Thr His His Leu Glu Leu Asn Ala Arg Pro Thr Ala Ala Gln Arg
```

-continued

```
785                 790                 795                 800

Ala Val Leu Ala Asp His Asn Pro Cys Pro Pro Glu Arg Ala Ala Leu
                805                 810                 815

Gln Ala Ile Pro Asp Asp Asp Pro Arg Thr Thr Leu Asp Leu Ile Glu
            820                 825                 830

Glu His Pro Ala Leu Arg Gly Val Leu Pro Trp Pro Val Leu Leu Asp
        835                 840                 845

Leu Leu Pro Ala Leu Arg Ile Arg His Tyr Ser Leu Ser Ser Ser Pro
    850                 855                 860

Ala Ala Asp Pro Arg His Ala Asp Leu Met Val Ser Leu Leu Pro Gly
865                 870                 875                 880

Gly Thr Gly Ser Gly His Leu His Thr Leu Arg Pro Gly Asp Thr Val
                885                 890                 895

Leu Ala Arg Val Gln Pro Cys Arg Glu Ala Phe Arg Leu Asp Pro Ala
            900                 905                 910

Asp Pro Thr Pro Val Ile Leu Val Ala Ala Gly Thr Gly Leu Ala Pro
        915                 920                 925

Phe Arg Gly Ala Val Ala Asp Arg Leu Ala Ala Thr Gln Leu Ala Pro
    930                 935                 940

Ala Leu Leu Tyr Phe Gly Cys Asp Ala Leu Glu Ala Asp Tyr Leu His
945                 950                 955                 960

Ala Glu Glu Leu Gln Ala Ala Glu Ala Ala Gly Ala Val Ser Leu Arg
                965                 970                 975

Pro Ala Phe Ser Ala Arg Pro Val Asp Gly Cys Arg Tyr Val Gln His
            980                 985                 990

Arg Ile Ala Ala Glu Ala Glu Glu  Val Gly Ala Leu Leu  Asp Ala Gly
        995                 1000                1005

Ala Arg  Val Tyr Val Cys Gly  Asp Gly Asn Arg Met  Ala Pro Gly
    1010                1015                1020

Val Arg  Ala Ala Phe Arg Glu  Leu Tyr Ala Ala Arg  Thr Gly Ala
    1025                1030                1035

Thr Gln  Glu Glu Ala Glu Val  Trp Leu Arg Glu Leu  Thr Ala Ala
    1040                1045                1050

Gly Arg  Tyr Val Glu Asp Val  Tyr Val Thr Gly
    1055                1060


<210> SEQ ID NO 3
<211> LENGTH: 2013
<212> TYPE: DNA
<213> ORGANISM: Streptomyces rimosus

<400> SEQUENCE: 3

atgaccggcg tatccgcccg cgaacccgca gcgggccgca ccgacgcctc ccggtggctg      60

ctgcgccgcc gggtgctgtc ggaccccgcg ctgcggctga tctgcttccc gcacgccggg     120

ggcgccgcga ccttcttcca cgggtggcag gaccgggtac cggccggtac cgaggtcggc     180

gcggtctgct atccggggcg gcagaaccgg atcgccgagc cgccgctcac ctccatggac     240

gacctcgccg accaggcgca cgcggcgctg cgcgggctgc tcgaccgccc gctggcgctc     300

ttcgggcaca gcatgggcgc ggtcgtcgcg tatgaggtgg ccgtgcggct cgccgaacgc     360

gacggcaccg caccggtggc cctgctggtg tccgggcacg gcgccccgta tctgtgcgtg     420

gccgggccgc cgccggacac cgcggcggac gaccgggaga tcgccgagct ggcgatggcc     480

gccgacccgg cgctgcgcgg ctcgccccag ctgctggacc tggtcatgcc ggtgctccgc     540
```

-continued

```
gccgaccacg cgctgctccg cgcctaccgg cccgtacgca ccccgcggat caccgcgccg    600

atcgtcgcct accgtggcgc ggacgacccc agggcgagcg aggacgacat gtggtcctgg    660

cgcgcgatga ccggcgccgc cttccggctc cgtacgctgc ccggcaacca cttctacctg    720

gccaccgagg aggccgggct ggtggccgat gtcatggacg cctgtcgggg cggtgcgaac    780

ggcgccgccg gaagcaccgc gaccggcccg gccaccgcct ccgccgtacc gctgttcgta    840

cgccgctccg gcgcctgccc cttcgacccg gcggaggact tcgcccggct gcgcgccgag    900

cggcccgtgg tccgcaccac cttgccgacc ggggcccgcg cctggatggt cacgcgctac    960

gccgacgccc gccgcgtcat cgccgaccag cggcgcttca gctcccgggc cgccgtgaac   1020

ggcccggtgc cgcccccgga accgcccgaa ggctttccgc cgccgcggcc cggcgtcttc   1080

tacacgtacg agcccgagga gcacggccgc atccgccgga tgctcacccc ggagttcagc   1140

gcccagcgtg cccgcgtcct ggagccgcgc gcggaaaccc tggccgaccg gcacctcgac   1200

gccatcgagc gggccgggcc gcccgccgac ctgatcgccg acttcgtgct gccggtgccc   1260

cggctgctgt tcctggaact gctgggcgtg cccctccagg acgccgggcg cctccaccac   1320

gacctggcgc tcctgcacga cttccacccc atccacgagg cgcaggcggg agcgttccgc   1380

cggctcgacg cgtacctgcg ggaactggtg gaaaccgcac gcgccacacc cggcgacaac   1440

gtcctgggcc acctggtcgc cgcgcacggc gccgagctga gcgacgacga actcgccgga   1500

atcgcctgcc agttgctgct ggccggatac gcgacgatcg ccggcaccct gggcctgtcc   1560

ctgctcgccc tgatcctcga ccccgtacag gcggagctgg tgcgcgacgg gcgcgcccgg   1620

cccgaccgga tggccgagga actgatccgc cacctgtcgg tggtgacctt cggcaaggtc   1680

ttccaggcga aggaggacgt cacgatcgcg gaccaggaca tcgcggcggg cgagtacgtg   1740

ctgtgccatc tgccgtccgc caaccgcgat ccggcgctgg ccgacggcct cgaccgcctc   1800

gacgtcaccc gtgagccgac gccccacctc gccctcggcc acggcgcgca ccactgcctg   1860

ggcgccgaac tggcccggat ggaactgcgg gtctgcgtgc cccgtgtcct gcggcggctg   1920

ccgggtctgc gcttgcgcgt ccccgtcgag gagctgcgct tcacaccact gaacgccgcg   1980

tacggagtgg aatccctgcc ggtcgcctgg taa                                2013
```

<210> SEQ ID NO 4
<211> LENGTH: 670
<212> TYPE: PRT
<213> ORGANISM: Streptomyces rimosus

<400> SEQUENCE: 4

```
Met Thr Gly Val Ser Ala Arg Glu Pro Ala Ala Gly Arg Thr Asp Ala
1               5                   10                  15

Ser Arg Trp Leu Leu Arg Arg Arg Val Leu Ser Asp Pro Ala Leu Arg
            20                  25                  30

Leu Ile Cys Phe Pro His Ala Gly Gly Ala Ala Thr Phe Phe His Gly
        35                  40                  45

Trp Gln Asp Arg Val Pro Ala Gly Thr Glu Val Gly Ala Val Cys Tyr
    50                  55                  60

Pro Gly Arg Gln Asn Arg Ile Ala Glu Pro Pro Leu Thr Ser Met Asp
65                  70                  75                  80

Asp Leu Ala Asp Gln Ala His Ala Ala Leu Arg Gly Leu Leu Asp Arg
                85                  90                  95

Pro Leu Ala Leu Phe Gly His Ser Met Gly Ala Val Val Ala Tyr Glu
            100                 105                 110
```

-continued

```
Val Ala Val Arg Leu Ala Glu Arg Asp Gly Thr Ala Pro Val Ala Leu
        115                 120                 125

Leu Val Ser Gly His Gly Ala Pro Tyr Leu Cys Val Ala Gly Pro Pro
    130                 135                 140

Pro Asp Thr Ala Ala Asp Asp Arg Glu Ile Ala Glu Leu Ala Met Ala
145                 150                 155                 160

Ala Asp Pro Ala Leu Arg Gly Ser Pro Gln Leu Leu Asp Leu Val Met
                165                 170                 175

Pro Val Leu Arg Ala Asp His Ala Leu Leu Arg Ala Tyr Arg Pro Val
            180                 185                 190

Arg Thr Pro Arg Ile Thr Ala Pro Ile Val Ala Tyr Arg Gly Ala Asp
        195                 200                 205

Asp Pro Arg Ala Ser Glu Asp Asp Met Trp Ser Trp Arg Ala Met Thr
    210                 215                 220

Gly Ala Ala Phe Arg Leu Arg Thr Leu Pro Gly Asn His Phe Tyr Leu
225                 230                 235                 240

Ala Thr Glu Glu Ala Gly Leu Val Ala Asp Val Met Asp Ala Cys Arg
                245                 250                 255

Gly Gly Ala Asn Gly Ala Ala Gly Ser Thr Ala Thr Gly Pro Ala Thr
            260                 265                 270

Ala Ser Ala Val Pro Leu Phe Val Arg Arg Ser Gly Ala Cys Pro Phe
        275                 280                 285

Asp Pro Ala Glu Asp Phe Ala Arg Leu Arg Ala Glu Arg Pro Val Val
    290                 295                 300

Arg Thr Thr Leu Pro Thr Gly Ala Arg Ala Trp Met Val Thr Arg Tyr
305                 310                 315                 320

Ala Asp Ala Arg Arg Val Ile Ala Asp Gln Arg Arg Phe Ser Ser Arg
                325                 330                 335

Ala Ala Val Asn Gly Pro Val Pro Pro Pro Glu Pro Pro Glu Gly Phe
            340                 345                 350

Pro Pro Pro Arg Pro Gly Val Phe Tyr Thr Tyr Glu Pro Glu Glu His
        355                 360                 365

Gly Arg Ile Arg Arg Met Leu Thr Pro Glu Phe Ser Ala Gln Arg Ala
    370                 375                 380

Arg Val Leu Glu Pro Arg Ala Glu Thr Leu Ala Asp Arg His Leu Asp
385                 390                 395                 400

Ala Ile Glu Arg Ala Gly Pro Pro Ala Asp Leu Ile Ala Asp Phe Val
                405                 410                 415

Leu Pro Val Pro Arg Leu Leu Phe Leu Glu Leu Leu Gly Val Pro Leu
            420                 425                 430

Gln Asp Ala Gly Arg Leu His His Asp Leu Ala Leu Leu His Asp Phe
        435                 440                 445

His Pro Ile His Glu Ala Gln Ala Gly Ala Phe Arg Arg Leu Asp Ala
    450                 455                 460

Tyr Leu Arg Glu Leu Val Glu Thr Ala Arg Ala Thr Pro Gly Asp Asn
465                 470                 475                 480

Val Leu Gly His Leu Val Ala Ala His Gly Ala Glu Leu Ser Asp Asp
                485                 490                 495

Glu Leu Ala Gly Ile Ala Cys Gln Leu Leu Leu Ala Gly Tyr Ala Thr
            500                 505                 510

Ile Ala Gly Thr Leu Gly Leu Ser Leu Leu Ala Leu Ile Leu Asp Pro
        515                 520                 525

Val Gln Ala Glu Leu Val Arg Asp Gly Arg Ala Arg Pro Asp Arg Met
```

-continued

```
    530                 535                 540

Ala Glu Glu Leu Ile Arg His Leu Ser Val Val Thr Phe Gly Lys Val
545                 550                 555                 560

Phe Gln Ala Lys Glu Asp Val Thr Ile Ala Asp Gln Asp Ile Ala Ala
                565                 570                 575

Gly Glu Tyr Val Leu Cys His Leu Pro Ser Ala Asn Arg Asp Pro Ala
            580                 585                 590

Leu Ala Asp Gly Leu Asp Arg Leu Asp Val Thr Arg Glu Pro Thr Pro
        595                 600                 605

His Leu Ala Leu Gly His Gly Ala His His Cys Leu Gly Ala Glu Leu
    610                 615                 620

Ala Arg Met Glu Leu Arg Val Cys Val Pro Arg Val Leu Arg Arg Leu
625                 630                 635                 640

Pro Gly Leu Arg Leu Arg Val Pro Val Glu Glu Leu Arg Phe Thr Pro
                645                 650                 655

Leu Asn Ala Ala Tyr Gly Val Glu Ser Leu Pro Val Ala Trp
            660                 665                 670


<210> SEQ ID NO 5
<211> LENGTH: 1483
<212> TYPE: DNA
<213> ORGANISM: Streptomyces rimosus

<400> SEQUENCE: 5

atgccggacg agtcccagca ccagttcgac cacgcccgcc gggcgggctt cggcccgtcg     60

gacgacatcc gccggcagcg cgcccagggc gccctcgtcc gggaagaggt ggccccggcg    120

cccggcgccg cacccgagcc catctggatg gccctgagct acgaggccgt gcgccaggtc    180

atgggcgacc acgtccgctt cagcaaccag cgccggttcc gcgcccaggc catccgcggc    240

gggagcaagc accgcccgca ggagatgtcc ggccacctca tggactacga ccagcccgag    300

cacacccggc tgcgcaagat gctcacgccg gagttcacgg tccgccgcat ccagcggctc    360

aagccggtga ccgaggcgat cgcggaacgc tgcctggacg ccatggagcg caaggggcgg    420

cccgccgacc tcgtcgagct gtacgcgagc ccgatctccg gcgcggtgct gtgcgaactg    480

ctcggcgtgc cccgcgacga ccggcgcgag ttcctggtca agcaccagtg gcagctggag    540

caggaccgca gccgcaagga gcgcgccgcg gctcaggcgt acacctccaa ctacctgcgc    600

gcgctggtca aacggcagcg caaggacccc gacgagggct tcatcggcca gctcatccgc    660

gaccacggcg acaacttcga cgacgaggaa ctgatcggca tctgcggcct gatggtgctg    720

gccggcctgg acaacgtcaa cggcatgatc agcctcggtg tgctggccct cctggaacac    780

ccggaccagc tcgccgtcct gctggcggac cccgagaaca ccgtggaccg ggtggtggac    840

gaactgctgc gcttcctgtc cgtggcgcac gcgccgaccc cgcgcaccgc cgtcgaggac    900

gtggtcgtgg ccgggcagct gatcaaggcg ggggaggagg tcgtctgctc gatcccgatg    960

gccaaccgcg acccggtact cgccccccgac gtcgaccggt tcgacgtcaa ccgcgagccg   1020

ctgccgcaca tcgccttcgg gcacggcatc caccactgca tcggcgccgc gctcggccgg   1080

atggaactgc gcaccgccta cctggcgctg tggcgccggt tcccggacct gcggctggcc   1140

gtgcccgccg accaggtgcc gcacaagacg aattccatcg cgtacggcct ggagcgcctg   1200

ccggtcgcct ggtgacggcg gcccggccac ggcgcgcggc gcccgcggaa gaggagggac   1260

gatggtcgag gtacgggtcg acgcggagat ctgcgcggcg tccggcatgt gcacgctgct   1320

ggtgcccgcg gtcttcgacc agtcggagga ggacggcacg gtggtgctcg ccgatccggc   1380
```

gccgcccgcg gaactggcgg cgaaggtgcg gacggcggcg ctgcggtgcc cggccggcgc 1440
gatctcggtg cacgagcggg aggcggacgg cccgggtacg taa 1483

<210> SEQ ID NO 6
<211> LENGTH: 404
<212> TYPE: PRT
<213> ORGANISM: Streptomyces rimosus

<400> SEQUENCE: 6

Met Pro Asp Glu Ser Gln His Gln Phe Asp His Ala Arg Arg Ala Gly
1 5 10 15

Phe Gly Pro Ser Asp Asp Ile Arg Arg Gln Arg Ala Gln Gly Ala Leu
20 25 30

Val Arg Glu Glu Val Ala Pro Ala Pro Gly Ala Ala Pro Glu Pro Ile
35 40 45

Trp Met Ala Leu Ser Tyr Glu Ala Val Arg Gln Val Met Gly Asp His
50 55 60

Val Arg Phe Ser Asn Gln Arg Arg Phe Arg Ala Gln Ala Ile Arg Gly
65 70 75 80

Gly Ser Lys His Arg Pro Gln Glu Met Ser Gly His Leu Met Asp Tyr
85 90 95

Asp Gln Pro Glu His Thr Arg Leu Arg Lys Met Leu Thr Pro Glu Phe
100 105 110

Thr Val Arg Arg Ile Gln Arg Leu Lys Pro Val Thr Glu Ala Ile Ala
115 120 125

Glu Arg Cys Leu Asp Ala Met Glu Arg Lys Gly Arg Pro Ala Asp Leu
130 135 140

Val Glu Leu Tyr Ala Ser Pro Ile Ser Gly Ala Val Leu Cys Glu Leu
145 150 155 160

Leu Gly Val Pro Arg Asp Asp Arg Arg Glu Phe Leu Val Lys His Gln
165 170 175

Trp Gln Leu Glu Gln Asp Arg Ser Arg Lys Glu Arg Ala Ala Ala Gln
180 185 190

Ala Tyr Thr Ser Asn Tyr Leu Arg Ala Leu Val Lys Arg Gln Arg Lys
195 200 205

Asp Pro Asp Glu Gly Phe Ile Gly Gln Leu Ile Arg Asp His Gly Asp
210 215 220

Asn Phe Asp Asp Glu Glu Leu Ile Gly Ile Cys Gly Leu Met Val Leu
225 230 235 240

Ala Gly Leu Asp Asn Val Asn Gly Met Ile Ser Leu Gly Val Leu Ala
245 250 255

Leu Leu Glu His Pro Asp Gln Leu Ala Val Leu Leu Ala Asp Pro Glu
260 265 270

Asn Thr Val Asp Arg Val Val Asp Glu Leu Leu Arg Phe Leu Ser Val
275 280 285

Ala His Ala Pro Thr Pro Arg Thr Ala Val Glu Asp Val Val Val Ala
290 295 300

Gly Gln Leu Ile Lys Ala Gly Glu Glu Val Val Cys Ser Ile Pro Met
305 310 315 320

Ala Asn Arg Asp Pro Val Leu Ala Pro Asp Val Asp Arg Phe Asp Val
325 330 335

Asn Arg Glu Pro Leu Pro His Ile Ala Phe Gly His Gly Ile His His
340 345 350

```
Cys Ile Gly Ala Ala Leu Gly Arg Met Glu Leu Arg Thr Ala Tyr Leu
        355                 360                 365

Ala Leu Trp Arg Arg Phe Pro Asp Leu Arg Leu Ala Val Pro Ala Asp
    370                 375                 380

Gln Val Pro His Lys Thr Asn Ser Ile Ala Tyr Gly Leu Glu Arg Leu
385                 390                 395                 400

Pro Val Ala Trp


<210> SEQ ID NO 7
<211> LENGTH: 73
<212> TYPE: PRT
<213> ORGANISM: Streptomyces rimosus

<400> SEQUENCE: 7

Met Val Glu Val Arg Val Asp Ala Glu Ile Cys Ala Ala Ser Gly Met
1               5                   10                  15

Cys Thr Leu Leu Val Pro Ala Val Phe Asp Gln Ser Glu Glu Asp Gly
            20                  25                  30

Thr Val Val Leu Ala Asp Pro Ala Pro Pro Ala Glu Leu Ala Ala Lys
        35                  40                  45

Val Arg Thr Ala Ala Leu Arg Cys Pro Ala Gly Ala Ile Ser Val His
    50                  55                  60

Glu Arg Glu Ala Asp Gly Pro Gly Thr
65                  70


<210> SEQ ID NO 8
<211> LENGTH: 1368
<212> TYPE: DNA
<213> ORGANISM: Streptomyces rimosus

<400> SEQUENCE: 8

atggcgagcc gtacccgtat cgatacgcct ggtcgtaacg agcaccggct gcacaccgtc     60

cccctgcgcc atgtcctcgg cggcctgcgg gcgggtggtc cgctggggct gatggaacgt    120

accgggcgcc ggtcgcaggg cgcgctgacc cggctggagc tgggcgcctt ccggcccttc    180

ctggtcaccc accccgatca tctgcggcac gtcctgcgcg accacggtgc gaactaccgc    240

cggggcaccg cgatgtggaa ggcgatgggg cggctgacgg ggatggggat cgcgggcgag    300

gggccgcagt ggcgggccag ccgtgagctg tggtgccggg gactgtcggg cggtgcgcac    360

gtcttcgccg acgggacggc cgacgcggtc gccggggcgg tggcggacct ggagcggcgg    420

gtggcggcgg gcgcgacggt ggacgcgctg acggagatga cccgtgtcgt gctccgggtc    480

gtgaatccgg cgttcttcgg ctcgcgcatt ccgcaggggg agtgcgaccg gctcgccgcg    540

gcggtcgccg tcgcgttcga ctcgctgctg tggcgcatgg cgctgccttt cgtaccgctc    600

gccgtgccgt tgccgggcga tcgcgccttc acccgcgcca cccgtacggt caacggcatc    660

ctgctgccgc tgatccgccg ggcacggcac gcgcaccacc gcggcccgga cctgatgagc    720

acgctgctcg acggggcgga cgcggacggc cgggcgctgg gcgacgcgca tgtggcccag    780

gacatcgtgg ccatgttcgt ggcgggttcg gagtccagcg ccctgacgct gacgtgggcc    840

tgggtcgccc tcgccgggca tgccgacatc gcggcggagg tgcgccggga ggccgacgcg    900

gtgctcggcg gcgggccgcc ccggcccgag cacgcccgcc ggctggtgtt cacccggagg    960

gtgctggccg aggtctgccg cctgtacgcg atggcgtggg cggtgccgcg gacggccgtc   1020

gccgaggacg tcatcggcgg ggtgaccgtt ccggccggcg ccacgctggt gctgtccccg   1080

tacctgaccc accggctgcc cgccttctgg gagcggccgc tgcgcttcga ccccggccgt   1140
```

```
ttcaccgacg agcgcgtacg gggccggcac ccgctggcgt acctgccgtt cggcgacgga   1200

ccccaccagt gcgtcggcca gtcgttcttc ttccagcagg cggccctcgt cgtggccacg   1260

atgatgagcc gtttccgtat cgccgtgccg acgccggccg agcccagggc cgcggtcgcg   1320

ctgcgcccgc ggagccgtgt cgatctggcg ctcaccccgc gcggctaa                1368


<210> SEQ ID NO 9
<211> LENGTH: 455
<212> TYPE: PRT
<213> ORGANISM: Streptomyces rimosus

<400> SEQUENCE: 9

Met Ala Ser Arg Thr Arg Ile Asp Thr Pro Gly Arg Asn Glu His Arg
1               5                   10                  15

Leu His Thr Val Pro Leu Arg His Val Leu Gly Gly Leu Arg Ala Gly
            20                  25                  30

Gly Pro Leu Gly Leu Met Glu Arg Thr Gly Arg Arg Ser Gln Gly Ala
        35                  40                  45

Leu Thr Arg Leu Glu Leu Gly Ala Phe Arg Pro Phe Leu Val Thr His
    50                  55                  60

Pro Asp His Leu Arg His Val Leu Arg Asp His Gly Ala Asn Tyr Arg
65                  70                  75                  80

Arg Gly Thr Ala Met Trp Lys Ala Met Gly Arg Leu Thr Gly Met Gly
                85                  90                  95

Ile Ala Gly Glu Gly Pro Gln Trp Arg Ala Ser Arg Glu Leu Trp Cys
            100                 105                 110

Arg Gly Leu Ser Gly Gly Ala His Val Phe Ala Asp Gly Thr Ala Asp
        115                 120                 125

Ala Val Ala Gly Ala Val Ala Asp Leu Glu Arg Arg Val Ala Ala Gly
    130                 135                 140

Ala Thr Val Asp Ala Leu Thr Glu Met Thr Arg Val Val Leu Arg Val
145                 150                 155                 160

Val Asn Pro Ala Phe Phe Gly Ser Arg Ile Pro Gln Gly Glu Cys Asp
                165                 170                 175

Arg Leu Ala Ala Ala Val Ala Val Ala Phe Asp Ser Leu Leu Trp Arg
            180                 185                 190

Met Ala Leu Pro Phe Val Pro Leu Ala Val Pro Leu Pro Gly Asp Arg
        195                 200                 205

Ala Phe Thr Arg Ala Thr Arg Thr Val Asn Gly Ile Leu Leu Pro Leu
    210                 215                 220

Ile Arg Arg Ala Arg His Ala His His Arg Gly Pro Asp Leu Met Ser
225                 230                 235                 240

Thr Leu Leu Asp Gly Ala Asp Ala Asp Gly Arg Ala Leu Gly Asp Ala
                245                 250                 255

His Val Ala Gln Asp Ile Val Ala Met Phe Val Ala Gly Ser Glu Ser
            260                 265                 270

Ser Ala Leu Thr Leu Thr Trp Ala Trp Val Ala Leu Ala Gly His Ala
        275                 280                 285

Asp Ile Ala Ala Glu Val Arg Arg Glu Ala Asp Ala Val Leu Gly Gly
    290                 295                 300

Gly Pro Pro Arg Pro Glu His Ala Arg Arg Leu Val Phe Thr Arg Arg
305                 310                 315                 320

Val Leu Ala Glu Val Cys Arg Leu Tyr Ala Met Ala Trp Ala Val Pro
                325                 330                 335
```

-continued

```
Arg Thr Ala Val Ala Glu Asp Val Ile Gly Gly Val Thr Val Pro Ala
            340                 345                 350

Gly Ala Thr Leu Val Leu Ser Pro Tyr Leu Thr His Arg Leu Pro Ala
        355                 360                 365

Phe Trp Glu Arg Pro Leu Arg Phe Asp Pro Gly Arg Phe Thr Asp Glu
    370                 375                 380

Arg Val Arg Gly Arg His Pro Leu Ala Tyr Leu Pro Phe Gly Asp Gly
385                 390                 395                 400

Pro His Gln Cys Val Gly Gln Ser Phe Phe Phe Gln Gln Ala Ala Leu
                405                 410                 415

Val Val Ala Thr Met Met Ser Arg Phe Arg Ile Ala Val Pro Thr Pro
            420                 425                 430

Ala Glu Pro Arg Ala Ala Val Ala Leu Arg Pro Arg Ser Arg Val Asp
        435                 440                 445

Leu Ala Leu Thr Pro Arg Gly
    450                 455


<210> SEQ ID NO 10
<211> LENGTH: 1483
<212> TYPE: DNA
<213> ORGANISM: Streptomyces rimosus

<400> SEQUENCE: 10

atgtcgtaca acccgacggc ccccgacacc accgccgacg gcaccaccgg agaaccgccc      60

accctgccca ccgaccggcg caccggctgc cccttcgacc cgcccggcga actcaccgcg     120

ctgagcgacc ggcccctgcg ccgcatgcgc tacgccgacg ggcacatagg ctggctggcc     180

accggccacg ccgccgcccg cgcggtcctg tccgacccgc gcttcagctc ccgctacgaa     240

ctcctgcacc tgccggtacc gatgccgggc atggagggga tgacggcggt gccgccggcg     300

ccgaccggcg acttcctcgg cctcgacgcc cccgagcaca cccgctaccg gcggctgctc     360

accggcaagt tcacggtccg ccggatgcgt cagctctccg aacgcgtgga gcagttcacc     420

cacgagtgcc tggacgccat ggagcaggcc gggcccaccg tcgacctggt ggaggcgttc     480

gcgcggccgg tgcccgcgct catgatctgc gaactgctcg gcgtgccgta cgccgaccgg     540

gaccgcttcc aggagcatgt ggcgaccctc ttcgaccagg ccgcggacgc ggaggcgagg     600

ggcgcggcgt tcgccgccgt cggccgcttc atgggcgaac tcgtggccgc caagcgcgcc     660

gagcccaccg acgacctgct cagcgacctg accacctccg acctcacgga ggaagagctg     720

atcggggtcg gcggggtgct cctggccgcc ggtctcgaca ccaccgccaa catgctcggg     780

ctcggcacct tcgccctgct cagcaacccc gaccagctgg acgccctgcg cgccgacccg     840

ggcctcgccg ggcagaccgt cgaggagctg ctgcgctacc tcagcgtggc cgaccccatc     900

ccgcgcgccg ccctggagga cgtcgagatc gaaggccggc tggtcagggc cggtgagacg     960

gtgaccgtct cggtccaggc cgccaaccgc gacccgctga agttccccga ccccgaccgg    1020

ttcgacatcc accgcaaggc caccgggcac gtctccttcg gccacggccc ccaccagtgc    1080

ctcggccagc agctcgcccg cgtcgagatg accgtcgcgt tcccggcgct cttcgcccgc    1140

ttccccaccc tgcgcctcgc ggttccgccg caggaggtgc cgctgcgcga ccgcgccaac    1200

atctacggcg tgatcagcct gcccgtcacc tgggacaagg agtaacccca tgagcgagcc    1260

acaagagcgg ctgcgtctga gcgtcgaccg tgaccgctgc gtcggcgccg ggatgtgcgc    1320

cctgaccgct cccgaggtct tcgaccagga cgacgaagag ggcctggtgg tgctcaagca    1380
```

-continued ccccgtaccg gcccccggca gcctggccgc cgcccggatg gccgccggcc tctgccccgc 1440
cggagccatc accctccact ccccggaacc cacggacccg taa 1483

<210> SEQ ID NO 11
<211> LENGTH: 414
<212> TYPE: PRT
<213> ORGANISM: Streptomyces rimosus

<400> SEQUENCE: 11

```
Met Ser Tyr Asn Pro Thr Ala Pro Asp Thr Thr Ala Asp Gly Thr Thr
1               5                   10                  15

Gly Glu Pro Pro Thr Leu Pro Thr Asp Arg Arg Thr Gly Cys Pro Phe
            20                  25                  30

Asp Pro Pro Gly Glu Leu Thr Ala Leu Ser Asp Arg Pro Leu Arg Arg
        35                  40                  45

Met Arg Tyr Ala Asp Gly His Ile Gly Trp Leu Ala Thr Gly His Ala
    50                  55                  60

Ala Ala Arg Ala Val Leu Ser Asp Pro Arg Phe Ser Ser Arg Tyr Glu
65                  70                  75                  80

Leu Leu His Leu Pro Val Pro Met Pro Gly Met Glu Gly Met Thr Ala
                85                  90                  95

Val Pro Pro Ala Pro Thr Gly Asp Phe Leu Gly Leu Asp Ala Pro Glu
            100                 105                 110

His Thr Arg Tyr Arg Arg Leu Leu Thr Gly Lys Phe Thr Val Arg Arg
        115                 120                 125

Met Arg Gln Leu Ser Glu Arg Val Glu Gln Phe Thr His Glu Cys Leu
    130                 135                 140

Asp Ala Met Glu Gln Ala Gly Pro Thr Val Asp Leu Val Glu Ala Phe
145                 150                 155                 160

Ala Arg Pro Val Pro Ala Leu Met Ile Cys Glu Leu Leu Gly Val Pro
                165                 170                 175

Tyr Ala Asp Arg Asp Arg Phe Gln Glu His Val Ala Thr Leu Phe Asp
            180                 185                 190

Gln Ala Ala Asp Ala Glu Ala Arg Gly Ala Ala Phe Ala Ala Val Gly
        195                 200                 205

Arg Phe Met Gly Glu Leu Val Ala Ala Lys Arg Ala Glu Pro Thr Asp
    210                 215                 220

Asp Leu Leu Ser Asp Leu Thr Thr Ser Asp Leu Thr Glu Glu Glu Leu
225                 230                 235                 240

Ile Gly Val Gly Gly Val Leu Leu Ala Ala Gly Leu Asp Thr Thr Ala
                245                 250                 255

Asn Met Leu Gly Leu Gly Thr Phe Ala Leu Leu Ser Asn Pro Asp Gln
            260                 265                 270

Leu Asp Ala Leu Arg Ala Asp Pro Gly Leu Ala Gly Gln Thr Val Glu
        275                 280                 285

Glu Leu Leu Arg Tyr Leu Ser Val Ala Asp Pro Ile Pro Arg Ala Ala
    290                 295                 300

Leu Glu Asp Val Glu Ile Glu Gly Arg Leu Val Arg Ala Gly Glu Thr
305                 310                 315                 320

Val Thr Val Ser Val Gln Ala Ala Asn Arg Asp Pro Leu Lys Phe Pro
                325                 330                 335

Asp Pro Asp Arg Phe Asp Ile His Arg Lys Ala Thr Gly His Val Ser
            340                 345                 350

Phe Gly His Gly Pro His Gln Cys Leu Gly Gln Gln Leu Ala Arg Val
```

-continued

```
        355                 360                 365

Glu Met Thr Val Ala Phe Pro Ala Leu Phe Ala Arg Phe Pro Thr Leu
    370                 375                 380

Arg Leu Ala Val Pro Pro Gln Glu Val Pro Leu Arg Asp Arg Ala Asn
385                 390                 395                 400

Ile Tyr Gly Val Ile Ser Leu Pro Val Thr Trp Asp Lys Glu
                405                 410


<210> SEQ ID NO 12
<211> LENGTH: 77
<212> TYPE: PRT
<213> ORGANISM: Streptomyces rimosus

<400> SEQUENCE: 12

Met Ser Glu Pro Gln Glu Arg Leu Arg Leu Ser Val Asp Arg Asp Arg
1               5                   10                  15

Cys Val Gly Ala Gly Met Cys Ala Leu Thr Ala Pro Glu Val Phe Asp
            20                  25                  30

Gln Asp Asp Glu Glu Gly Leu Val Val Leu Lys His Pro Val Pro Ala
        35                  40                  45

Pro Gly Ser Leu Ala Ala Ala Arg Met Ala Ala Gly Leu Cys Pro Ala
    50                  55                  60

Gly Ala Ile Thr Leu His Ser Pro Glu Pro Thr Asp Pro
65                  70                  75


<210> SEQ ID NO 13
<211> LENGTH: 1230
<212> TYPE: DNA
<213> ORGANISM: Streptomyces rimosus

<400> SEQUENCE: 13

atgagcgacc cggccgcggt acgccgggcc ctgcgcgcgc tgttcagccc gctgggctgc      60

cccgacccgt acccgcacta cgcggtgctg cgggagcacg ggccggtctc ccggctgccg     120

gacggcaccg tcgtcgtcag ccggcacgcc gactgcgacc gcgtgctgcg cgatccgctc     180

ttccgggtcg aggacgacgc gtacctcgcc cgtacctggc ccgagggccg cgaccacctc     240

agcgtcttct ccctgatggg cgagatggtc aaccagaact cgccgcacca cgagcggctg     300

cgccgcctgg tgggccgcgc cttcaccccg cgccgggtgg ccgggctgcg gcccgcggtg     360

gagaagctgg tcgacggcct gctggacggc ctcgccgaac gggccgccgg gggcgctccg     420

gtggatctga tggagcactt cgcgctgccg ctgccgatca ccgtcatcgg cgagctgctc     480

ggcatccccg aggaggaccg cgcctggttc gcgccgcgcg tgcaggccgt cacctccgcg     540

atcgagcaga acctcgccgg ggaggcgctg gagcgcgcgg acgaggccac cgcggagctg     600

tgggaccggc tcggcgcgct ggccgcccgg cgccaggagg acccgcgcgc cgacctggtc     660

agcacgctca tcgcggtacg cgaggaggac ggcgaccggc tcacccggcg cgaactgctc     720

gccaacctgg tgctgctgta ctccgccggc tacgagacca ccagcaacct catcggcaac     780

ggcacggccg tcctgctgga ccgcccggac ctgctcgcgc ggctgcgcgg cgagccggag     840

cggatcgacg cctgggtcga ggagatgctg cgcttcgacc cgcccatcca gatcgcctcc     900

cgctgggcgg gggaggacac cgagctgggc ggggtggccg tggcgcaggg ctcccaagtg     960

gtggccctgc tcgccagcgc caaccgcgat cctgcgcgcc acggggaccc ggacgtcttc    1020

cggccggacc gggcgccggg cggctcgctc accttcggcg cgggcgcgca ctactgcctg    1080

ggcgccgcac tggcccgcct ggaggcggcc atcgccttcc cccggctgct ggcccgcttc    1140
```

```
ccctcgatcg cgcacgcggg caccggggcg ccgcgcaacc gtatgacgtc cctgcgcggc   1200

tacgccgagc tgcccctgct cctgtcgtaa                                    1230


<210> SEQ ID NO 14
<211> LENGTH: 409
<212> TYPE: PRT
<213> ORGANISM: Streptomyces rimosus

<400> SEQUENCE: 14

Met Ser Asp Pro Ala Ala Val Arg Arg Ala Leu Arg Ala Leu Phe Ser
1               5                   10                  15

Pro Leu Gly Cys Pro Asp Pro Tyr Pro His Tyr Ala Val Leu Arg Glu
            20                  25                  30

His Gly Pro Val Ser Arg Leu Pro Asp Gly Thr Val Val Val Ser Arg
        35                  40                  45

His Ala Asp Cys Asp Arg Val Leu Arg Asp Pro Leu Phe Arg Val Glu
    50                  55                  60

Asp Asp Ala Tyr Leu Ala Arg Thr Trp Pro Glu Gly Arg Asp His Leu
65                  70                  75                  80

Ser Val Phe Ser Leu Met Gly Glu Met Val Asn Gln Asn Ser Pro His
                85                  90                  95

His Glu Arg Leu Arg Arg Leu Val Gly Arg Ala Phe Thr Pro Arg Arg
            100                 105                 110

Val Ala Gly Leu Arg Pro Ala Val Glu Lys Leu Val Asp Gly Leu Leu
        115                 120                 125

Asp Gly Leu Ala Glu Arg Ala Ala Gly Gly Ala Pro Val Asp Leu Met
    130                 135                 140

Glu His Phe Ala Leu Pro Leu Pro Ile Thr Val Ile Gly Glu Leu Leu
145                 150                 155                 160

Gly Ile Pro Glu Glu Asp Arg Ala Trp Phe Ala Pro Arg Val Gln Ala
                165                 170                 175

Val Thr Ser Ala Ile Glu Gln Asn Leu Ala Gly Glu Ala Leu Glu Arg
            180                 185                 190

Ala Asp Glu Ala Thr Ala Glu Leu Trp Asp Arg Leu Gly Ala Leu Ala
        195                 200                 205

Ala Arg Arg Gln Glu Asp Pro Arg Ala Asp Leu Val Ser Thr Leu Ile
    210                 215                 220

Ala Val Arg Glu Glu Asp Gly Asp Arg Leu Thr Arg Arg Glu Leu Leu
225                 230                 235                 240

Ala Asn Leu Val Leu Leu Tyr Ser Ala Gly Tyr Glu Thr Thr Ser Asn
                245                 250                 255

Leu Ile Gly Asn Gly Thr Ala Val Leu Leu Asp Arg Pro Asp Leu Leu
            260                 265                 270

Ala Arg Leu Arg Gly Glu Pro Glu Arg Ile Asp Ala Trp Val Glu Glu
        275                 280                 285

Met Leu Arg Phe Asp Pro Pro Ile Gln Ile Ala Ser Arg Trp Ala Gly
    290                 295                 300

Glu Asp Thr Glu Leu Gly Gly Val Ala Val Ala Gln Gly Ser Gln Val
305                 310                 315                 320

Val Ala Leu Leu Ala Ser Ala Asn Arg Asp Pro Ala Arg His Gly Asp
                325                 330                 335

Pro Asp Val Phe Arg Pro Asp Arg Ala Pro Gly Gly Ser Leu Thr Phe
            340                 345                 350
```

-continued

Gly Ala Gly Ala His Tyr Cys Leu Gly Ala Ala Leu Ala Arg Leu Glu
355 360 365

Ala Ala Ile Ala Phe Pro Arg Leu Leu Ala Arg Phe Pro Ser Ile Ala
370 375 380

His Ala Gly Thr Gly Ala Pro Arg Asn Arg Met Thr Ser Leu Arg Gly
385 390 395 400

Tyr Ala Glu Leu Pro Leu Leu Leu Ser
405

<210> SEQ ID NO 15
<211> LENGTH: 1260
<212> TYPE: DNA
<213> ORGANISM: Streptomyces rimosus

<400> SEQUENCE: 15
atggacatcg atggcgcgga gcccggcggc ggcccttccg gtgagtacgg ctcgtgtgtg 60
cgcctcgacc cggaagcgcg cgatccccgc tcccgcccgg acccgctgtg cgccgcgggc 120
cctgtggtgc ccgtcctgct gccgggtggg gtgacggcct ggctggtgac ccggcatcag 180
gccgggaagg cggtgctggc ggacggccgc ttcgtcaagg acatcggggc ctggcgcgcc 240
tggcgcggcg gcgaggtccc gcgctcctgg ccgctggcgc cgctgctgac cgtcgcgaac 300
atgaccaccg cgacggcggg cgaccacacc cggctgcgcg cgccgctggc ccgcgcgttc 360
accgcgcgcc gcgtggcggg gctgcggccg cgcgtcgagg agctggccgg ggagctgctg 420
gacggcctcg ccgccgaggg gccggcgggc cccgtcgagc tgcgggcccg cttcgcccac 480
ccgctgccga tacgggtcat ctgcgagctg ttcggcgtgt ccgacgaccg ccgtccccgg 540
ctgcagtcgc tgtgccaggc cctgttcgcc gccccggcgg gcccggccga tgccctggcc 600
acccaccgcg agctgcgggc cgcgctcgcc gatctgctcc gcgccaagcg cgaggacccc 660
ggggacgacc tgacgagcgc gctggtggcc cccggccacg gcctcagcgg gagcgaactc 720
gtcgacacgc tgttgctgat gattgtcgcg ggccatgaga ccacggtgaa cctgctggtc 780
aacgcggtgt acgcgctgct gacccacccc ggtcagctca ctctcgtacg cggcgggcag 840
gtgccctgga gcgcggtggt cgaggagacg ctgcgctggg acccgccggt cgccaacttc 900
ccgttccgct acgcgctgtg cgacgtggac ctggccggcc ggaccattcg cgcgggcgat 960
ccggtgatgc tgtcgtacgc cgccttcggc cgcgacccgc ggcagcacgg gcccggggcc 1020
gaccgcttcg acgtcacccg gccgcccacc cgccatctgg ccttcgggca cggcatccac 1080
cactgcctcg gtgcgccgct cgcccgcctg gaggcggcgg tcgccctccc cgcgctgttc 1140
gaccgcttcc ccggcctcgc cctggacgac cccgggcagc gtccgctccg ccgcccgtcc 1200
atggtcttca acggcctgcg ggagctgccg gtcgtcctcg gcccgcccgg cggttcataa 1260

<210> SEQ ID NO 16
<211> LENGTH: 419
<212> TYPE: PRT
<213> ORGANISM: Streptomyces rimosus

<400> SEQUENCE: 16

Met Asp Ile Asp Gly Ala Glu Pro Gly Gly Gly Pro Ser Gly Glu Tyr
1 5 10 15

Gly Ser Cys Val Arg Leu Asp Pro Glu Ala Arg Asp Pro Arg Ser Arg
20 25 30

Pro Asp Pro Leu Cys Ala Ala Gly Pro Val Val Pro Val Leu Leu Pro
35 40 45

```
Gly Gly Val Thr Ala Trp Leu Val Thr Arg His Gln Ala Gly Lys Ala
    50                  55                  60

Val Leu Ala Asp Gly Arg Phe Val Lys Asp Ile Gly Ala Trp Arg Ala
65                  70                  75                  80

Trp Arg Gly Gly Glu Val Pro Arg Ser Trp Pro Leu Ala Pro Leu Leu
                85                  90                  95

Thr Val Ala Asn Met Thr Thr Ala Thr Ala Gly Asp His Thr Arg Leu
            100                 105                 110

Arg Ala Pro Leu Ala Arg Ala Phe Thr Ala Arg Arg Val Ala Gly Leu
        115                 120                 125

Arg Pro Arg Val Glu Glu Leu Ala Gly Glu Leu Leu Asp Gly Leu Ala
    130                 135                 140

Ala Glu Gly Pro Ala Gly Pro Val Glu Leu Arg Ala Arg Phe Ala His
145                 150                 155                 160

Pro Leu Pro Ile Arg Val Ile Cys Glu Leu Phe Gly Val Ser Asp Asp
                165                 170                 175

Arg Arg Pro Arg Leu Gln Ser Leu Cys Gln Ala Leu Phe Ala Ala Pro
            180                 185                 190

Ala Gly Pro Ala Asp Ala Leu Ala Thr His Arg Glu Leu Arg Ala Ala
        195                 200                 205

Leu Ala Asp Leu Leu Arg Ala Lys Arg Glu Asp Pro Gly Asp Asp Leu
    210                 215                 220

Thr Ser Ala Leu Val Ala Pro Gly His Gly Leu Ser Gly Ser Glu Leu
225                 230                 235                 240

Val Asp Thr Leu Leu Leu Met Ile Val Ala Gly His Glu Thr Thr Val
                245                 250                 255

Asn Leu Leu Val Asn Ala Val Tyr Ala Leu Leu Thr His Pro Gly Gln
            260                 265                 270

Leu Thr Leu Val Arg Gly Gly Gln Val Pro Trp Ser Ala Val Val Glu
        275                 280                 285

Glu Thr Leu Arg Trp Asp Pro Pro Val Ala Asn Phe Pro Phe Arg Tyr
    290                 295                 300

Ala Leu Cys Asp Val Asp Leu Ala Gly Arg Thr Ile Arg Ala Gly Asp
305                 310                 315                 320

Pro Val Met Leu Ser Tyr Ala Ala Phe Gly Arg Asp Pro Arg Gln His
                325                 330                 335

Gly Pro Gly Ala Asp Arg Phe Asp Val Thr Arg Pro Pro Thr Arg His
            340                 345                 350

Leu Ala Phe Gly His Gly Ile His His Cys Leu Gly Ala Pro Leu Ala
        355                 360                 365

Arg Leu Glu Ala Ala Val Ala Leu Pro Ala Leu Phe Asp Arg Phe Pro
    370                 375                 380

Gly Leu Ala Leu Asp Asp Pro Gly Gln Arg Pro Leu Arg Arg Pro Ser
385                 390                 395                 400

Met Val Phe Asn Gly Leu Arg Glu Leu Pro Val Val Leu Gly Pro Pro
                405                 410                 415

Gly Gly Ser
```

<210> SEQ ID NO 17
<211> LENGTH: 1200
<212> TYPE: DNA
<213> ORGANISM: Streptomyces rimosus

<400> SEQUENCE: 17

-continued

```
atggctgagt ccacccacac tgcccgcacc gcccacgccg tcccgccgct gcccaccggg     60

ccccgggccg gctgcccctt ctccccgccg aaggaactgc tcgacgcccg cgagcagggc    120

ccgatcggcc actacaccca ccccggcggc aagcccggct ggatgatcac cgggtacgac    180

atggtgcggt ccgtgctcgc cgacccgcgg ttcagctcgc gcaaggagct gatgaacgtg    240

gtcgatttcg agattccgcc gccgccaccc ggcgagttcg tcctcatgga cgacccgcag    300

caccggcgct accgcaagcc gctgatgggg aagttcaccg tgcggcggat gcggctgctg    360

accgagcgca tcgagcaggt caccgccgag tgcctggacg ccatggagaa ggcgggcccg    420

ccggtggacc tggtggccgc gttcgccaag cccatccccg ccatcgtgat ctgcgagctg    480

ctgggcgtgc cgtacgagga ccgcggcttc ttccaggggc ggatcgactc gttcatgaac    540

ggtgagacga gcgacgagga cctgatggcg gcctacaccg aggtccagaa ctacctcgcg    600

gacctggtgg ccgccaagcg cgcgaacccc accgacgacg tgctcagcga cctcaccgac    660

accgacctca ccgacgagga gttgaagggc atcagcctgg tcctgctgac ggccgggctc    720

gacacgacca cgaatgtgct ggggctgggc accttcgcgc tgttgcagca ccctgagcaa    780

ctggccgcgc tgcgcgccga tcccgcgctt gtcgacggag cggtggagga gctgctgcgg    840

tacctcagcg tcggcaagca gttctggcgt acggcgctgg aggatgtcga gctgggcggt    900

cagaccgtga aggccggcac gacggtcgcc ctgtcgctca gcaccgccaa ccgcgacccc    960

gagcgcttcg ccgaccccga tgtgctcgat ctccggcggc agggcggcgg acacctggcc   1020

ttcggtcacg gcgttcacca gtgccttggg cagcaagtgg cccgcatcga gctgcgggtg   1080

gcgttctccg cgctgttcga ccgcttcccc acgctgcgtc tggccgtacc ggccgaagag   1140

gtcgaactgc gtccggagtc cgcggacgtc ttcggggtga agcgtcttcc ggtcgcctgg   1200
```

```
<210> SEQ ID NO 18
<211> LENGTH: 402
<212> TYPE: PRT
<213> ORGANISM: Streptomyces rimosus

<400> SEQUENCE: 18

Met Ala Glu Ser Thr His Thr Ala Arg Thr Ala His Ala Val Pro Pro
1               5                   10                  15

Leu Pro Thr Gly Pro Arg Ala Gly Cys Pro Phe Ser Pro Pro Lys Glu
            20                  25                  30

Leu Leu Asp Ala Arg Glu Gln Gly Pro Ile Gly His Tyr Thr His Pro
        35                  40                  45

Gly Gly Lys Pro Gly Trp Met Ile Thr Gly Tyr Asp Met Val Arg Ser
    50                  55                  60

Val Leu Ala Asp Pro Arg Phe Ser Ser Arg Lys Glu Leu Met Asn Val
65                  70                  75                  80

Val Asp Phe Glu Ile Pro Pro Pro Pro Pro Gly Glu Phe Val Leu Met
                85                  90                  95

Asp Asp Pro Gln His Arg Arg Tyr Arg Lys Pro Leu Met Gly Lys Phe
            100                 105                 110

Thr Val Arg Arg Met Arg Leu Leu Thr Glu Arg Ile Glu Gln Val Thr
        115                 120                 125

Ala Glu Cys Leu Asp Ala Met Glu Lys Ala Gly Pro Pro Val Asp Leu
    130                 135                 140

Val Ala Ala Phe Ala Lys Pro Ile Pro Ala Ile Val Ile Cys Glu Leu
145                 150                 155                 160

Leu Gly Val Pro Tyr Glu Asp Arg Gly Phe Phe Gln Gly Arg Ile Asp
```

-continued

```
                165                 170                 175

Ser Phe Met Asn Gly Glu Thr Ser Asp Glu Asp Leu Met Ala Ala Tyr
            180                 185                 190

Thr Glu Val Gln Asn Tyr Leu Ala Asp Leu Val Ala Ala Lys Arg Ala
        195                 200                 205

Asn Pro Thr Asp Asp Val Leu Ser Asp Leu Thr Asp Thr Asp Leu Thr
    210                 215                 220

Asp Glu Glu Leu Lys Gly Ile Ser Leu Val Leu Leu Thr Ala Gly Leu
225                 230                 235                 240

Asp Thr Thr Thr Asn Val Leu Gly Leu Gly Thr Phe Ala Leu Leu Gln
                245                 250                 255

His Pro Glu Gln Leu Ala Ala Leu Arg Ala Asp Pro Ala Leu Val Asp
            260                 265                 270

Gly Ala Val Glu Glu Leu Leu Arg Tyr Leu Ser Val Gly Lys Gln Phe
        275                 280                 285

Trp Arg Thr Ala Leu Glu Asp Val Glu Leu Gly Gly Gln Thr Val Lys
    290                 295                 300

Ala Gly Thr Thr Val Ala Leu Ser Leu Ser Thr Ala Asn Arg Asp Pro
305                 310                 315                 320

Glu Arg Phe Ala Asp Pro Asp Val Leu Asp Leu Arg Arg Gln Gly Gly
                325                 330                 335

Gly His Leu Ala Phe Gly His Gly Val His Gln Cys Leu Gly Gln Gln
            340                 345                 350

Val Ala Arg Ile Glu Leu Arg Val Ala Phe Ser Ala Leu Phe Asp Arg
        355                 360                 365

Phe Pro Thr Leu Arg Leu Ala Val Pro Ala Glu Glu Val Glu Leu Arg
    370                 375                 380

Pro Glu Ser Ala Asp Val Phe Gly Val Lys Arg Leu Pro Val Ala Trp
385                 390                 395                 400

Asp Val


<210> SEQ ID NO 19
<211> LENGTH: 2743
<212> TYPE: DNA
<213> ORGANISM: Streptomyces rimosus

<400> SEQUENCE: 19

atgaccccct ctcccgcttc ccccgccacc gccgccgcac cggcgcttcc cgtgcagccg      60

ccgcagggct gcccgttcga cccgcccgcc gagttcgcgc ggctgcgcac cgaggcgccg     120

ctgtcgaaga tctccctgcc ggacggcacc gaagcctggc tcgccacccg ctacgccgac     180

atccgcgcca tcctcggcga cacccgcttc agctccgaca ccacccgccc cggctacccg     240

ctcagcggca tgaccggcgg cgccaccacc gaacaccgcg gcttcatccg catggacccg     300

cccgagcaca cccggctgcg ccgcatggtc acccgggagt tcatggtcaa gcgcgtcgag     360

gcgatgcgcc cggagatcca gcgcctgacc gacgaactgt gcgacgccat ggagaagcgc     420

gccggccagg acgtggacct catcgaggcg ctggccctgc cggtgccgtc gctcgtcatc     480

agcctgctgc tcggcgttcc gtacgacgat cacgagctgt tccagcggct gaccggcacc     540

ctgctgtccc gtacggtcac cgacgcggag cgggagagcg cgcgggccga actgcgcgcc     600

tacctgcacc agttggtgag cgccaaggag gccgcgcccg gcgacgacat cctcggccgc     660

ctgatcgccg agcagcaggt accgggcgag atcacccacg acgacgtggt cgccttcgcc     720

gccctgctgc tcatcgcggg ccacgagacc accgccaaca tgatcggcct gagcgcgctg     780
```

```
accctgatgc gcgaccggga gaccgcggac cggctgcgcg ccgaacccgc cctgatccgc    840
ggcgccgtcg aggaactgct gcgcttccac agcatcatcc gcaacgggcc gcgccgcgcc    900
gccaccgagg acatcgagat cggcgggcag ctgatccggg ccggggaggg cgtcgtggtg    960
gccgtaccgt ccgccaaccg cgacccggag gtcttcgcgg accccgacgc gctcgacgtc   1020
tgccgcccca acgcccagca ccacgtcgcc ttcggctacg gcatccacca gtgcctcggc   1080
caggccctgg cccgcgtcga gctccaggtc gtcatcggca ccctgctgcg ccgcttcccg   1140
gagatgcggc ccgcggtccc ggtggacgag atcccgttcc gcagcgacat ggcgatctac   1200
ggctgccaca ccctgcccgt cacctggtga caccccgccc gaccgttccc cttcctcctc   1260
aggagtctcc tgccatgaac atcaccctcg acgccgacaa gtgctgcgcc gcaggccagt   1320
gcgtactgat cgcccccgag gtcttcgacc agcgggacga ggacggcatc gtcgtcctcc   1380
tggacgccgc tccgcccgcc gaccagcacg acgcggtccg cgaggccgcc gccatctgtc   1440
cggccgcggt catcaaggtg gacgagtgag cccccgccgc atcgccgtcg tgggcgcctc   1500
ggcggcgggc ctcgccgccg ccgaggccct gcgccgcttc ggctggaccg gcaccctgac   1560
cctcgtcggc gacgagcccc acccgccgta cgaccgtccg ccgctgtcca agcagctcct   1620
tcagggcgcc tggcagcccg acaagctgca tctgcgcgcc gccgaacagc tcgacgcgct   1680
cggcctcgac ctgcgcctgg gcacccgggc gaccggcctg gacaccgcga cccgcaccct   1740
gaccctggac ggtggcgagc ggctggcctg cgacggcgtg atcgtcgcga ccggcgtcgc   1800
ggcccgcacc ctcccggcgg ccgccgggct cgacggcgtg cacacgctgc gcaccctgga   1860
cgacgcgctc gccctcaagg aacggctgtc cggtaccggc catcgcctgg tcgtcgtcgg   1920
caacggcgta ctgggctgcg aggccgcggc cgtggcccgc gagctgggtc acgaggtcac   1980
actcgtcggg cgcgaggcgc tgccgatggc ccgtacggtc ggcacggaga tcggcgagct   2040
gctggcggcc gagcaccggg agcgcggcgt ccagctgcgc accgcggccg tcgacggctt   2100
cgaggcggac ggggacgggc ccgcgcggca cgtgagcgcc gtacggctgg ccgacggcac   2160
ccgcctgccc gccgacaccg tgctcgtcgc catcggctcg gagcccgccg tcggctggct   2220
gcacggcgac ccggccctgg acaccaccga cggactgcgc tgcgacgcgt actgcgccgc   2280
cgcacccggc gtctacgcgg ccggtgacgt ggcccgctgg cagcacccgg tacacggccg   2340
ccacctgcgc gtcgagcacc ggatgaacgc caccgagcag ggcatggccg ccgcccgcaa   2400
cctcctagcc gaactggagg agaccctgcc gggggacgag gcactggccc ccgccgcggg   2460
ccgcgagcgc cgccccttca caccggtgcc gtacttctgg tccgaccagt acggcctgaa   2520
gctccaggcg tacggcgtgc tgtccggcgc cgaccggtcc gagacgaccg tcctggaccc   2580
ggacgccagg aaggccgtgg ccctctacgg cagtgacggc caggccaccg gcgtactggc   2640
gatcggtgtg ccgccgcgcc aggtccgggg cctgcgggcg ctgatcgcca cgcccgtgcc   2700
ctgggaagaa gctcgcgagg ggctgcacaa cgcccgcgcg taa                     2743
```

<210> SEQ ID NO 20
<211> LENGTH: 409
<212> TYPE: PRT
<213> ORGANISM: Streptomyces rimosus

<400> SEQUENCE: 20

```
Met Thr Pro Ser Pro Ala Ser Pro Ala Thr Ala Ala Ala Pro Ala Leu
1               5                   10                  15

Pro Val Gln Pro Pro Gln Gly Cys Pro Phe Asp Pro Pro Ala Glu Phe
```

-continued

```
            20                  25                  30

Ala Arg Leu Arg Thr Glu Ala Pro Leu Ser Lys Ile Ser Leu Pro Asp
        35                  40                  45

Gly Thr Glu Ala Trp Leu Ala Thr Arg Tyr Ala Asp Ile Arg Ala Ile
    50                  55                  60

Leu Gly Asp Thr Arg Phe Ser Ser Asp Thr Thr Arg Pro Gly Tyr Pro
65                  70                  75                  80

Leu Ser Gly Met Thr Gly Gly Ala Thr Thr Glu His Arg Gly Phe Ile
                85                  90                  95

Arg Met Asp Pro Pro Glu His Thr Arg Leu Arg Arg Met Val Thr Arg
            100                 105                 110

Glu Phe Met Val Lys Arg Val Glu Ala Met Arg Pro Glu Ile Gln Arg
        115                 120                 125

Leu Thr Asp Glu Leu Cys Asp Ala Met Glu Lys Arg Ala Gly Gln Asp
    130                 135                 140

Val Asp Leu Ile Glu Ala Leu Ala Leu Pro Val Pro Ser Leu Val Ile
145                 150                 155                 160

Ser Leu Leu Leu Gly Val Pro Tyr Asp Asp His Glu Leu Phe Gln Arg
                165                 170                 175

Leu Thr Gly Thr Leu Leu Ser Arg Thr Val Thr Asp Ala Glu Arg Glu
            180                 185                 190

Ser Ala Arg Ala Glu Leu Arg Ala Tyr Leu His Gln Leu Val Ser Ala
        195                 200                 205

Lys Glu Ala Ala Pro Gly Asp Asp Ile Leu Gly Arg Leu Ile Ala Glu
    210                 215                 220

Gln Gln Val Pro Gly Glu Ile Thr His Asp Asp Val Val Ala Phe Ala
225                 230                 235                 240

Ala Leu Leu Leu Ile Ala Gly His Glu Thr Thr Ala Asn Met Ile Gly
                245                 250                 255

Leu Ser Ala Leu Thr Leu Met Arg Asp Arg Glu Thr Ala Asp Arg Leu
            260                 265                 270

Arg Ala Glu Pro Ala Leu Ile Arg Gly Ala Val Glu Glu Leu Leu Arg
        275                 280                 285

Phe His Ser Ile Ile Arg Asn Gly Pro Arg Arg Ala Ala Thr Glu Asp
    290                 295                 300

Ile Glu Ile Gly Gly Gln Leu Ile Arg Ala Gly Glu Gly Val Val Val
305                 310                 315                 320

Ala Val Pro Ser Ala Asn Arg Asp Pro Glu Val Phe Ala Asp Pro Asp
                325                 330                 335

Ala Leu Asp Val Cys Arg Pro Asn Ala Gln His His Val Ala Phe Gly
            340                 345                 350

Tyr Gly Ile His Gln Cys Leu Gly Gln Ala Leu Ala Arg Val Glu Leu
        355                 360                 365

Gln Val Val Ile Gly Thr Leu Leu Arg Arg Phe Pro Glu Met Arg Pro
    370                 375                 380

Ala Val Pro Val Asp Glu Ile Pro Phe Arg Ser Asp Met Ala Ile Tyr
385                 390                 395                 400

Gly Cys His Thr Leu Pro Val Thr Trp
                405
```

<210> SEQ ID NO 21
<211> LENGTH: 64
<212> TYPE: PRT
<213> ORGANISM: Streptomyces rimosus

<400> SEQUENCE: 21

```
Met Asn Ile Thr Leu Asp Ala Asp Lys Cys Cys Ala Ala Gly Gln Cys
1               5                   10                  15

Val Leu Ile Ala Pro Glu Val Phe Asp Gln Arg Asp Glu Asp Gly Ile
            20                  25                  30

Val Val Leu Leu Asp Ala Ala Pro Pro Ala Asp Gln His Asp Ala Val
        35                  40                  45

Arg Glu Ala Ala Ala Ile Cys Pro Ala Ala Val Ile Lys Val Asp Glu
    50                  55                  60
```

<210> SEQ ID NO 22
<211> LENGTH: 425
<212> TYPE: PRT
<213> ORGANISM: Streptomyces rimosus

<400> SEQUENCE: 22

```
Val Ser Pro Arg Arg Ile Ala Val Val Gly Ala Ser Ala Ala Gly Leu
1               5                   10                  15

Ala Ala Ala Glu Ala Leu Arg Arg Phe Gly Trp Thr Gly Thr Leu Thr
            20                  25                  30

Leu Val Gly Asp Glu Pro His Pro Pro Tyr Asp Arg Pro Pro Leu Ser
        35                  40                  45

Lys Gln Leu Leu Gln Gly Ala Trp Gln Pro Asp Lys Leu His Leu Arg
    50                  55                  60

Ala Ala Glu Gln Leu Asp Ala Leu Gly Leu Asp Leu Arg Leu Gly Thr
65                  70                  75                  80

Arg Ala Thr Gly Leu Asp Thr Ala Thr Arg Thr Leu Thr Leu Asp Gly
                85                  90                  95

Gly Glu Arg Leu Ala Cys Asp Gly Val Ile Val Ala Thr Gly Val Ala
            100                 105                 110

Ala Arg Thr Leu Pro Ala Ala Ala Gly Leu Asp Gly Val His Thr Leu
        115                 120                 125

Arg Thr Leu Asp Asp Ala Leu Ala Leu Lys Glu Arg Leu Ser Gly Thr
    130                 135                 140

Gly His Arg Leu Val Val Val Gly Asn Gly Val Leu Gly Cys Glu Ala
145                 150                 155                 160

Ala Ala Val Ala Arg Glu Leu Gly His Glu Val Thr Leu Val Gly Arg
                165                 170                 175

Glu Ala Leu Pro Met Ala Arg Thr Val Gly Thr Glu Ile Gly Glu Leu
            180                 185                 190

Leu Ala Ala Glu His Arg Glu Arg Gly Val Gln Leu Arg Thr Ala Ala
        195                 200                 205

Val Asp Gly Phe Glu Ala Asp Gly Asp Gly Pro Ala Arg His Val Ser
    210                 215                 220

Ala Val Arg Leu Ala Asp Gly Thr Arg Leu Pro Ala Asp Thr Val Leu
225                 230                 235                 240

Val Ala Ile Gly Ser Glu Pro Ala Val Gly Trp Leu His Gly Asp Pro
                245                 250                 255

Ala Leu Asp Thr Thr Asp Gly Leu Arg Cys Asp Ala Tyr Cys Ala Ala
            260                 265                 270

Ala Pro Gly Val Tyr Ala Ala Gly Asp Val Ala Arg Trp Gln His Pro
        275                 280                 285

Val His Gly Arg His Leu Arg Val Glu His Arg Met Asn Ala Thr Glu
    290                 295                 300
```

```
Gln Gly Met Ala Ala Ala Arg Asn Leu Leu Ala Glu Leu Glu Glu Thr
305                 310                 315                 320

Leu Pro Gly Asp Glu Ala Leu Ala Pro Ala Ala Gly Arg Glu Arg Arg
                325                 330                 335

Pro Phe Thr Pro Val Pro Tyr Phe Trp Ser Asp Gln Tyr Gly Leu Lys
            340                 345                 350

Leu Gln Ala Tyr Gly Val Leu Ser Gly Ala Asp Arg Ser Glu Thr Thr
        355                 360                 365

Val Leu Asp Pro Asp Ala Arg Lys Ala Val Ala Leu Tyr Gly Ser Asp
    370                 375                 380

Gly Gln Ala Thr Gly Val Leu Ala Ile Gly Val Pro Pro Arg Gln Val
385                 390                 395                 400

Arg Gly Leu Arg Ala Leu Ile Ala Thr Pro Val Pro Trp Glu Glu Ala
                405                 410                 415

Arg Glu Gly Leu His Asn Ala Arg Ala
            420                 425
```

<210> SEQ ID NO 23
<211> LENGTH: 1374
<212> TYPE: DNA
<213> ORGANISM: Streptomyces rimosus

<400> SEQUENCE: 23

```
atgaccctca ccacacgatc cggcccggcg ataccgggcc cccggggcgt accgttcctg     60

ggctcgatgt tcgacctgcg gcgcagcacg ctcgacacgt tcgcgcgcgc ccgccgtgac    120

cacggcgacc tggtgcgctt cacggccggt ccgcccggcc tgcgcagcgt cttctacggc    180

gtgttctcgc ccgagggcag tcagcggatc ctcgcctccg aggccgccaa cttccgcaag    240

gaccacccgt tctacgaaga ggtccggcag tcgttcggca acggcctgct gaccagccag    300

gacgacgact atctccgcca gcggcggatc gtgcggccgc tgttcaccaa gcgccgggtc    360

gacggctacg cgtcggccgt ggccgcggat gcgcaggccg tcgccgagcg ctggcggacc    420

ccgcccggcg gcacggtcga cctggtgggc gagatgaacc ggctcgcgct gcgcaccgtc    480

tcccgcatcc tgttcggcac ggacgtggag gccgcggtcg ccaccgtgca ccgctgcttc    540

ccggtgatca actcgtatgt cgtacggcgc ggcttctcgc cgcgcaaccc gccgcgccac    600

tggcccaccc ccgccaaccg ccgggccgcc gccgcgacgg ccgaactgca ctcggtctgc    660

gaccggatcg tggccgggcg gcagaccgcc ggcgcactgg aggacggcgc cgacctgctg    720

tccctgctca cccgcgcggg caacgcggcg gacggcggcc tggacgccac cgagatccgc    780

gatcaggtcc tggtcttcct gctcgccggc cacgagacga ccgcgacgtc cctggccttc    840

accctccacc tgctcgcccg gcatccggag gaacaggtcc tggtacggga ggagatcgac    900

gccgtactgg gggaccggga gccggaagcc gccgacctgg agcggttgcc gcggctgacg    960

atggccctca aggaggccat gcggctgtac ccggcggcgc ccgtggtgag ccggcgcggc   1020

gtcgcggcca ccgagatcgg cggccaccgg ataccggacg gcgccgatgt gatcgtctcg   1080

ccgtgggtga cccaccggca ccccggcctg tgggaggacc cggagcgctt cgatccgcgg   1140

cggttcaccc cggagcggga ggcggcgcgc caccgctacg cgtggttccc gttcggcggc   1200

ggcccgcggg cgtgcatcgg gcagcacttc tcgatgctgg agtcggtgct ggcggcagcg   1260

gtactgctgc gctcgtacga gctgacggcg gtcgaccggg aggtgccgct caccgcgggc   1320

atcaccttgc aggcggcggg cccggcgcgg gtgcggctga ggggagtggg ctaa         1374
```

<210> SEQ ID NO 24
<211> LENGTH: 457
<212> TYPE: PRT
<213> ORGANISM: Streptomyces rimosus

<400> SEQUENCE: 24

Met Thr Leu Thr Thr Arg Ser Gly Pro Ala Ile Pro Gly Pro Arg Gly
1 5 10 15

Val Pro Phe Leu Gly Ser Met Phe Asp Leu Arg Arg Ser Thr Leu Asp
20 25 30

Thr Phe Ala Arg Ala Arg Arg Asp His Gly Asp Leu Val Arg Phe Thr
35 40 45

Ala Gly Pro Pro Gly Leu Arg Ser Val Phe Tyr Gly Val Phe Ser Pro
50 55 60

Glu Gly Ser Gln Arg Ile Leu Ala Ser Glu Ala Ala Asn Phe Arg Lys
65 70 75 80

Asp His Pro Phe Tyr Glu Glu Val Arg Gln Ser Phe Gly Asn Gly Leu
85 90 95

Leu Thr Ser Gln Asp Asp Asp Tyr Leu Arg Gln Arg Arg Ile Val Arg
100 105 110

Pro Leu Phe Thr Lys Arg Arg Val Asp Gly Tyr Ala Ser Ala Val Ala
115 120 125

Ala Asp Ala Gln Ala Val Ala Glu Arg Trp Arg Thr Pro Pro Gly Gly
130 135 140

Thr Val Asp Leu Val Gly Glu Met Asn Arg Leu Ala Leu Arg Thr Val
145 150 155 160

Ser Arg Ile Leu Phe Gly Thr Asp Val Glu Ala Ala Val Ala Thr Val
165 170 175

His Arg Cys Phe Pro Val Ile Asn Ser Tyr Val Val Arg Arg Gly Phe
180 185 190

Ser Pro Arg Asn Pro Pro Arg His Trp Pro Thr Pro Ala Asn Arg Arg
195 200 205

Ala Ala Ala Ala Thr Ala Glu Leu His Ser Val Cys Asp Arg Ile Val
210 215 220

Ala Gly Arg Gln Thr Ala Gly Ala Leu Glu Asp Gly Ala Asp Leu Leu
225 230 235 240

Ser Leu Leu Thr Arg Ala Gly Asn Ala Ala Asp Gly Gly Leu Asp Ala
245 250 255

Thr Glu Ile Arg Asp Gln Val Leu Val Phe Leu Leu Ala Gly His Glu
260 265 270

Thr Thr Ala Thr Ser Leu Ala Phe Thr Leu His Leu Leu Ala Arg His
275 280 285

Pro Glu Glu Gln Val Leu Val Arg Glu Glu Ile Asp Ala Val Leu Gly
290 295 300

Asp Arg Glu Pro Glu Ala Ala Asp Leu Glu Arg Leu Pro Arg Leu Thr
305 310 315 320

Met Ala Leu Lys Glu Ala Met Arg Leu Tyr Pro Ala Ala Pro Val Val
325 330 335

Ser Arg Arg Gly Val Ala Ala Thr Glu Ile Gly Gly His Arg Ile Pro
340 345 350

Asp Gly Ala Asp Val Ile Val Ser Pro Trp Val Thr His Arg His Pro
355 360 365

Gly Leu Trp Glu Asp Pro Glu Arg Phe Asp Pro Arg Arg Phe Thr Pro
370 375 380

-continued

```
Glu Arg Glu Ala Ala Arg His Arg Tyr Ala Trp Phe Pro Phe Gly Gly
385                 390                 395                 400

Gly Pro Arg Ala Cys Ile Gly Gln His Phe Ser Met Leu Glu Ser Val
                405                 410                 415

Leu Ala Ala Ala Val Leu Leu Arg Ser Tyr Glu Leu Thr Ala Val Asp
            420                 425                 430

Arg Glu Val Pro Leu Thr Ala Gly Ile Thr Leu Gln Ala Ala Gly Pro
        435                 440                 445

Ala Arg Val Arg Leu Arg Gly Val Gly
    450                 455


<210> SEQ ID NO 25
<211> LENGTH: 1540
<212> TYPE: DNA
<213> ORGANISM: Streptomyces rimosus

<400> SEQUENCE: 25

atgacgcaca ccgaaccggc cgcgccggcc acctgcccgg tcacgggagc gacggccggg     60

gccacggaca cgacggattc gaccgggcac ggaacggacc cgctggtcgt cgactttccg    120

ctgcgcgcgc ccggcatacc cttcccgccg cccgaatacg ccgattaccg cgacaagaag    180

gggctggtgc tctcgcacct gcccgacggc aaacgggtgt ggctggtcac ccggcacgag    240

gacgtacgcg ccgtcctgac caacccggcc atcagctcca acccccagca cccgggcttt    300

cccaatgtcg gcgagacgat cggcgtaccc aggcaggacc agatacccgg ctggttcgtg    360

ggaatggact cgcccgaaca cgaccggttc cgcaaggccc tcatcccgga gttcaccgtg    420

cggcgcgtcc gcgcgatgaa acccgcgatc gagcgcacgg tggacgcgca actggacgcg    480

atgctggccg cgggcaacac cgccgacctc gtcgccgact tcaccctgcc cattccctcc    540

ctggtgatct cggcactgct cggcgtgccg cccgccgacc gcgagttctt cgaatccagg    600

acccgcgtcc tggtctcgtt ccgtgcgtac tccgacgagg accgcctggc cgccggcaag    660

gacctcatgc ggtacatcaa ccggctgatc gagatcaaga agaactgggg cggcgacgac    720

atcgtcaccc ggctgctggc caccggcgcc atcggtgccc acgaaatgtc cggcgtactg    780

atgctgctgc tcatcgccgg ccacgagacc acggccaaca acatcgcgct cggtgtggtc    840

accctgctga agaatcccca gtggatcggt gacgaacggg ccgtcgagga aaccctgcgc    900

ttccactcgg tcgccgacct ggtgtccctg cgggtggccg tcgaggacgt ggagatcgcc    960

gggcagcaca tcaaggcggg cgagggcatc gtgccgctgg tcgccgccgc caatcacgac   1020

gaggaactct tcgcgtgccc ccacgcgttc gacccctccc gctccgcccg cggccatgtg   1080

gccttcggct acggcgtaca ccagtgcctg ggcagaacc  tggtacgggt cgagatggag   1140

gtcgcgtacc gcaagctctt cgagcgcatt cccaacctcc ggctcgacgt gcccgaggac   1200

ggactgaaca tcaagtacga cggcgtgctc tacggcctgc acgagctgcc cgtccgctgg   1260

tgacctgacc agagaacccg cgcccgcccg gcggcacgcc tcaccggccg ccgggcggcc   1320

cccatccacc gcaggagaga aacccgacat gcgtatcacc gttgactccg accgctgcgt   1380

cggggcgggc cagtgcgtac tgaacgcgcc cgcggtcttc gaccaggacg acgacgggct   1440

cgtcaccctt ctcgccgagc ccggcgccga ccaggaggcc gccgccaaac tggccggtgc   1500

cctgtgcccg tccggggcca tcaccgtgca cgagggctaa                          1540


<210> SEQ ID NO 26
<211> LENGTH: 420
```

<212> TYPE: PRT
<213> ORGANISM: Streptomyces rimosus

<400> SEQUENCE: 26

```
Met Thr His Thr Glu Pro Ala Ala Pro Ala Thr Cys Pro Val Thr Gly
1               5                   10                  15

Ala Thr Ala Gly Ala Thr Asp Thr Thr Asp Ser Thr Gly His Gly Thr
            20                  25                  30

Asp Pro Leu Val Val Asp Phe Pro Leu Arg Ala Pro Gly Ile Pro Phe
        35                  40                  45

Pro Pro Pro Glu Tyr Ala Asp Tyr Arg Asp Lys Lys Gly Leu Val Leu
    50                  55                  60

Ser His Leu Pro Asp Gly Lys Arg Val Trp Leu Val Thr Arg His Glu
65                  70                  75                  80

Asp Val Arg Ala Val Leu Thr Asn Pro Ala Ile Ser Ser Asn Pro Gln
                85                  90                  95

His Pro Gly Phe Pro Asn Val Gly Glu Thr Ile Gly Val Pro Arg Gln
            100                 105                 110

Asp Gln Ile Pro Gly Trp Phe Val Gly Met Asp Ser Pro Glu His Asp
        115                 120                 125

Arg Phe Arg Lys Ala Leu Ile Pro Glu Phe Thr Val Arg Arg Val Arg
    130                 135                 140

Ala Met Lys Pro Ala Ile Glu Arg Thr Val Asp Ala Gln Leu Asp Ala
145                 150                 155                 160

Met Leu Ala Ala Gly Asn Thr Ala Asp Leu Val Ala Asp Phe Thr Leu
                165                 170                 175

Pro Ile Pro Ser Leu Val Ile Ser Ala Leu Leu Gly Val Pro Pro Ala
            180                 185                 190

Asp Arg Glu Phe Phe Glu Ser Arg Thr Arg Val Leu Val Ser Phe Arg
        195                 200                 205

Ala Tyr Ser Asp Glu Asp Arg Leu Ala Ala Gly Lys Asp Leu Met Arg
    210                 215                 220

Tyr Ile Asn Arg Leu Ile Glu Ile Lys Lys Asn Trp Gly Gly Asp Asp
225                 230                 235                 240

Ile Val Thr Arg Leu Leu Ala Thr Gly Ala Ile Gly Ala His Glu Met
                245                 250                 255

Ser Gly Val Leu Met Leu Leu Leu Ile Ala Gly His Glu Thr Thr Ala
            260                 265                 270

Asn Asn Ile Ala Leu Gly Val Val Thr Leu Leu Lys Asn Pro Gln Trp
        275                 280                 285

Ile Gly Asp Glu Arg Ala Val Glu Glu Thr Leu Arg Phe His Ser Val
    290                 295                 300

Ala Asp Leu Val Ser Leu Arg Val Ala Val Glu Asp Val Glu Ile Ala
305                 310                 315                 320

Gly Gln His Ile Lys Ala Gly Glu Gly Ile Val Pro Leu Val Ala Ala
                325                 330                 335

Ala Asn His Asp Glu Glu Leu Phe Ala Cys Pro His Ala Phe Asp Pro
            340                 345                 350

Ser Arg Ser Ala Arg Gly His Val Ala Phe Gly Tyr Gly Val His Gln
        355                 360                 365

Cys Leu Gly Gln Asn Leu Val Arg Val Glu Met Glu Val Ala Tyr Arg
    370                 375                 380

Lys Leu Phe Glu Arg Ile Pro Asn Leu Arg Leu Asp Val Pro Glu Asp
385                 390                 395                 400
```

Gly Leu Asn Ile Lys Tyr Asp Gly Val Leu Tyr Gly Leu His Glu Leu
405 410 415

Pro Val Arg Trp
420

<210> SEQ ID NO 27
<211> LENGTH: 63
<212> TYPE: PRT
<213> ORGANISM: Streptomyces rimosus

<400> SEQUENCE: 27

Met Arg Ile Thr Val Asp Ser Asp Arg Cys Val Gly Ala Gly Gln Cys
1 5 10 15

Val Leu Asn Ala Pro Ala Val Phe Asp Gln Asp Asp Asp Gly Leu Val
20 25 30

Thr Leu Leu Ala Glu Pro Gly Ala Asp Gln Glu Ala Ala Ala Lys Leu
35 40 45

Ala Gly Ala Leu Cys Pro Ser Gly Ala Ile Thr Val His Glu Gly
50 55 60

<210> SEQ ID NO 28
<211> LENGTH: 1432
<212> TYPE: DNA
<213> ORGANISM: Streptomyces rimosus

<400> SEQUENCE: 28
atgaccgagg cgctgccctt cccgcaggac cggacctgtc cctacgaccc gcccgccggc 60
taccagcccc tgcgcgacag ccgccccctg tcccgcgtga cgctctacga cgggcgcccc 120
gcctgggtgg tgaccgggca cgccgaatcg cgggcgctgc tcaccgaccc gcgcctgtcc 180
gccgaccggc agaatccggc gttcccctcc cccgccccgc gcttcgagac gctgcgcaag 240
gtgcggaccc cgctgctggg cgtcgacgac cccgaacaca acacccagcg ccggatgctg 300
ataccgagct tcagcgtcaa gcgcgccgcc gcgctgcgcc cccgcatcca ggagatcgtg 360
gaccggctgc tggacgccat ggagcagcag ggcccgcccg ccgagctggt gtccgccttc 420
gcgctgccgg tgccgtccat ggtgatctgc gcgctcctcg gcgtcccgta cgccgaccac 480
gagctgttcg agggcctgtc ccggacgctc ctgcagagcg ccgacccgca ggaggtcacc 540
gaggcccgcg acaagctgga ggactacttc accgccctgg tggagcgcaa acggaaggag 600
ccgggcgacg gcctgctgga cgagctgatc gccgagcggc tggactccgg cgagctgggc 660
caccgcgaac tggtccggat ggccatgctg ctgctggtgg ccggccacga gaccacctcc 720
aacatgctgt ccctgggcac cttcacgctg ctggaacacc ccgagcagtt cgccgccctg 780
cgcgccgacc cgtcgctgct cccggccgcg gtcgaggagc tgctgaggtt cctgtccatc 840
gccgacggca tggtgcgggt ggcgaccgag gacatcgaga tcggcggcgt gacgatccgg 900
gcggacgacg gcgtgatctt ctccacctcg gtcgtcaacc gggacggcgc cgcctacgcc 960
tcgccggaca ccctggactg ggagcgctcc gcccgccacc acgtcgcctt cggcttcggc 1020
gtccaccagt gcctgggcca gaacctggcc cgcgcggaga tggagatcgc cttcggggcg 1080
ctcttcgccc gcttccccgg tctgcgcctg gcggtgcccg ccgccgagat acccgtcaaa 1140
cccgcccacg ccctccaggg cctggtcgaa ctgcccgtca cctggtagcg gcggaccgcc 1200
gcccacaccc tgtacccgtc aacggaggag agccaccatg aagatcgaca tcgatacgtc 1260
cgtgtgcatc ggctcgggcc agtgcgtgct gaccgcgccg gggtgttca cccaggacga 1320

```
cgacggtttc agcaccctgc tgcccggccg cgaggacggc acgggcgacc cgctcgtacg   1380

cgaggccgcc cgcgcttgtc cggttcaggc gatcgcggtc acggacgact aa           1432


<210> SEQ ID NO 29
<211> LENGTH: 395
<212> TYPE: PRT
<213> ORGANISM: Streptomyces rimosus

<400> SEQUENCE: 29

Met Thr Glu Ala Leu Pro Phe Pro Gln Asp Arg Thr Cys Pro Tyr Asp
1               5                   10                  15

Pro Pro Ala Gly Tyr Gln Pro Leu Arg Asp Ser Arg Pro Leu Ser Arg
            20                  25                  30

Val Thr Leu Tyr Asp Gly Arg Pro Ala Trp Val Val Thr Gly His Ala
        35                  40                  45

Glu Ser Arg Ala Leu Leu Thr Asp Pro Arg Leu Ser Ala Asp Arg Gln
    50                  55                  60

Asn Pro Ala Phe Pro Ser Pro Ala Pro Arg Phe Glu Thr Leu Arg Lys
65                  70                  75                  80

Val Arg Thr Pro Leu Leu Gly Val Asp Asp Pro Glu His Asn Thr Gln
                85                  90                  95

Arg Arg Met Leu Ile Pro Ser Phe Ser Val Lys Arg Ala Ala Ala Leu
            100                 105                 110

Arg Pro Arg Ile Gln Glu Ile Val Asp Arg Leu Leu Asp Ala Met Glu
        115                 120                 125

Gln Gln Gly Pro Pro Ala Glu Leu Val Ser Ala Phe Ala Leu Pro Val
    130                 135                 140

Pro Ser Met Val Ile Cys Ala Leu Leu Gly Val Pro Tyr Ala Asp His
145                 150                 155                 160

Glu Leu Phe Glu Gly Leu Ser Arg Thr Leu Leu Gln Ser Ala Asp Pro
                165                 170                 175

Gln Glu Val Thr Glu Ala Arg Asp Lys Leu Glu Asp Tyr Phe Thr Ala
            180                 185                 190

Leu Val Glu Arg Lys Arg Lys Glu Pro Gly Asp Gly Leu Leu Asp Glu
        195                 200                 205

Leu Ile Ala Glu Arg Leu Asp Ser Gly Glu Leu Gly His Arg Glu Leu
    210                 215                 220

Val Arg Met Ala Met Leu Leu Leu Val Ala Gly His Glu Thr Thr Ser
225                 230                 235                 240

Asn Met Leu Ser Leu Gly Thr Phe Thr Leu Leu Glu His Pro Glu Gln
                245                 250                 255

Phe Ala Ala Leu Arg Ala Asp Pro Ser Leu Leu Pro Ala Ala Val Glu
            260                 265                 270

Glu Leu Leu Arg Phe Leu Ser Ile Ala Asp Gly Met Val Arg Val Ala
        275                 280                 285

Thr Glu Asp Ile Glu Ile Gly Gly Val Thr Ile Arg Ala Asp Asp Gly
    290                 295                 300

Val Ile Phe Ser Thr Ser Val Val Asn Arg Asp Gly Ala Ala Tyr Ala
305                 310                 315                 320

Ser Pro Asp Thr Leu Asp Trp Glu Arg Ser Ala Arg His His Val Ala
                325                 330                 335

Phe Gly Phe Gly Val His Gln Cys Leu Gly Gln Asn Leu Ala Arg Ala
            340                 345                 350

Glu Met Glu Ile Ala Phe Gly Ala Leu Phe Ala Arg Phe Pro Gly Leu
```

```
        355                 360                 365

Arg Leu Ala Val Pro Ala Ala Glu Ile Pro Val Lys Pro Ala His Ala
    370                 375                 380

Leu Gln Gly Leu Val Glu Leu Pro Val Thr Trp
385                 390                 395


<210> SEQ ID NO 30
<211> LENGTH: 64
<212> TYPE: PRT
<213> ORGANISM: Streptomyces rimosus

<400> SEQUENCE: 30

Met Lys Ile Asp Ile Asp Thr Ser Val Cys Ile Gly Ser Gly Gln Cys
1               5                   10                  15

Val Leu Thr Ala Pro Gly Val Phe Thr Gln Asp Asp Asp Gly Phe Ser
            20                  25                  30

Thr Leu Leu Pro Gly Arg Glu Asp Gly Thr Gly Asp Pro Leu Val Arg
        35                  40                  45

Glu Ala Ala Arg Ala Cys Pro Val Gln Ala Ile Ala Val Thr Asp Asp
    50                  55                  60


<210> SEQ ID NO 31
<211> LENGTH: 1200
<212> TYPE: DNA
<213> ORGANISM: Streptomyces rimosus

<400> SEQUENCE: 31

atgaccgcgg ccgcgcagga actggaaatc gcccgcgcct gcccctactc cccgaatgcg      60

cagcacatcg cattccagca gcagggccgc cccgtcaagg tcaccctggc gaccttgggg     120

ccgggtgcgc cggtctgggc ggtgagcaat cacgccgata tccgcaccat gctcaacgac     180

gcccgattca gcgccgaccg gcagcagcag ggctttccct tccaggtcga cgggcagccg     240

ggcaacttcc gccggacgat gatttccatg gacggggcgg aacaccggga agtccgccgt     300

tccgtgaccg gcgaattcac cctcaagcgc atgaaggccc tgcagccgcg gatccagcag     360

atcgtggacg actgcatcga caccatgctg gccggtccga aacccgctga cctggtcagc     420

gcgctcgcgc tccccgttcc ctcgctggtg atctgtgaac agctcggtgt gccctacgaa     480

ggccacgact tcttccagtc ccggtcccac atgctgttgc tacgcggcgc ttcggcggaa     540

gagcggctgc gcgcgctgga cgaactcatc gattttctcg gcgacctcat caccgagaag     600

gaggccgagc cgaccgacga cctgctcggg cgccagatcg tgaagctgcg cgaggcgggg     660

acgtaccgcc accaggacct ggcgcgcatg gcctttctgc tgctggtcgc cggacacgag     720

accaccgcga acatgatttc gctgggcacc atggccctgc tcgaccgccc cgcggacgcg     780

gacgccctgc gcgcggaccc gagcaagctc ccggtcgcgg tggaggaact cctgcggtac     840

ttcaccatcg ccgagttcat tcccacgcgc gtcgccaccg aggacgtgga actgggcggc     900

agcctcatca aggcgggcga tgtcctcgtg gcgctgtgca atgtggccaa ccgcgacccc     960

tcggtgtttc ccgacggcga cacactggac ctgcaacgcg gagcccgtca ccaactggcg    1020

ttcggcttcg ggctcatca gtgcctgggg cagaatctcg cccgcatgga actggagatc    1080

gtctatgcga cgctgctccg gcggataccg acgctgcgct ccgcgatacc gacccgtgaa    1140

ctgccgttca agcacgacgc ggacatctac ggtatccacg cattcccggt cacctggtaa    1200


<210> SEQ ID NO 32
<211> LENGTH: 399
```

<212> TYPE: PRT
<213> ORGANISM: Streptomyces rimosus

<400> SEQUENCE: 32

```
Met Thr Ala Ala Ala Gln Glu Leu Glu Ile Ala Arg Ala Cys Pro Tyr
1               5                   10                  15

Ser Pro Asn Ala Gln His Ile Ala Phe Gln Gln Gln Gly Arg Pro Val
            20                  25                  30

Lys Val Thr Leu Ala Thr Leu Gly Pro Gly Ala Pro Val Trp Ala Val
        35                  40                  45

Ser Asn His Ala Asp Ile Arg Thr Met Leu Asn Asp Ala Arg Phe Ser
    50                  55                  60

Ala Asp Arg Gln Gln Gln Gly Phe Pro Phe Gln Val Asp Gly Gln Pro
65                  70                  75                  80

Gly Asn Phe Arg Arg Thr Met Ile Ser Met Asp Gly Ala Glu His Arg
                85                  90                  95

Glu Val Arg Arg Ser Val Thr Gly Glu Phe Thr Leu Lys Arg Met Lys
            100                 105                 110

Ala Leu Gln Pro Arg Ile Gln Gln Ile Val Asp Asp Cys Ile Asp Thr
        115                 120                 125

Met Leu Ala Gly Pro Lys Pro Ala Asp Leu Val Ser Ala Leu Ala Leu
    130                 135                 140

Pro Val Pro Ser Leu Val Ile Cys Glu Gln Leu Gly Val Pro Tyr Glu
145                 150                 155                 160

Gly His Asp Phe Phe Gln Ser Arg Ser His Met Leu Leu Leu Arg Gly
                165                 170                 175

Ala Ser Ala Glu Glu Arg Leu Arg Ala Leu Asp Glu Leu Ile Asp Phe
            180                 185                 190

Leu Gly Asp Leu Ile Thr Glu Lys Glu Ala Glu Pro Thr Asp Asp Leu
        195                 200                 205

Leu Gly Arg Gln Ile Val Lys Leu Arg Glu Ala Gly Thr Tyr Arg His
    210                 215                 220

Gln Asp Leu Ala Arg Met Ala Phe Leu Leu Leu Val Ala Gly His Glu
225                 230                 235                 240

Thr Thr Ala Asn Met Ile Ser Leu Gly Thr Met Ala Leu Leu Asp Arg
                245                 250                 255

Pro Ala Asp Ala Asp Ala Leu Arg Ala Asp Pro Ser Lys Leu Pro Val
            260                 265                 270

Ala Val Glu Glu Leu Leu Arg Tyr Phe Thr Ile Ala Glu Phe Ile Pro
        275                 280                 285

Thr Arg Val Ala Thr Glu Asp Val Glu Leu Gly Gly Ser Leu Ile Lys
    290                 295                 300

Ala Gly Asp Val Leu Val Ala Leu Cys Asn Val Ala Asn Arg Asp Pro
305                 310                 315                 320

Ser Val Phe Pro Asp Gly Asp Thr Leu Asp Leu Gln Arg Gly Ala Arg
                325                 330                 335

His Gln Leu Ala Phe Gly Phe Gly Ala His Gln Cys Leu Gly Gln Asn
            340                 345                 350

Leu Ala Arg Met Glu Leu Glu Ile Val Tyr Ala Thr Leu Leu Arg Arg
        355                 360                 365

Ile Pro Thr Leu Arg Ser Ala Ile Pro Thr Arg Glu Leu Pro Phe Lys
    370                 375                 380

His Asp Ala Asp Ile Tyr Gly Ile His Ala Phe Pro Val Thr Trp
385                 390                 395
```

<210> SEQ ID NO 33
<211> LENGTH: 1433
<212> TYPE: DNA
<213> ORGANISM: Streptomyces rimosus

<400> SEQUENCE: 33

```
atgaccgaga cctccaccgc cttcccggcc caagacgctc ctgccttccc cagcgaccgt     60
acctgcccgt acgggctgcc cgagacgtac gcacggttac gcgacagcga ggacgcgctg    120
cgccccgtga ccctcttcga cggccgcacc gcctgggtcg tcaccaagca cgagaccgcc    180
cgcaccctgc tcgccgaccc gcggctctcc tcgaaccgca cccaccccga cttccctctc    240
acctccccgc gcctggcggg cctgcgcgat cgccgccccg ccttcatcag catggacccg    300
cccgagcacg ggccccggcg ccggatgacg atcagcgaat tcaccgtcaa gcgcatcaag    360
ggcatgcgac cggacatcga gcgaatcgtg cacggcttcc tcgacgagat gctcgccgcg    420
ggcccgcccg ccgacctggt cagccggttc gcgctgccgg tgccctccat ggtgatctgc    480
caactgctcg gtgtccccta cgccgaccac gacttcttcc aggacgccag tcggcgcctg    540
gtgcagtcga ccagcgcgga ggaggcgacc ggcgcgcgcg acgacctgga acgctacctg    600
gacgggctga tcaccaccct ggagtccgag cccgggcccg gactcctcgg cgcgctggtc    660
acccggcagc tcgcggacgg cgccatcgac cgcgacgaac tgatctcgaa cgcgctgctg    720
ctgctcgtcg ccggccacga gaccaccgcc tccatgacct ccctgagcgt catcaccctg    780
ctcgaacacc ccgagcagca cgccgccctg cgcgacgatc cgtccctgat cccgggcgcg    840
gtcgaggaac tgctgcgcta cctcgccatc gccgacgtgg cgggcgcccg cgtcgccacc    900
gccgacatcg aagtggacgg acaggtcatc cgggccggcg agggcgtgat cgtcgtccac    960
tccatcgcca accgcgacgc cggggtgttc gagaacccgg acaccttcga cattcaccgc   1020
tcggcccgcc accacctctc cttcggctac ggcgtccacc agtgcctcgg ccagaatctg   1080
gcccgcctcg aactcgaaat catcctgagc gcgctgttcg aacgcatccc cacgctgcgg   1140
ctggccacac cggtcgagcg cttgaccctg cggcccggca gcaccatcca gggcgtcaac   1200
gaactccccg tcacctggtg agcggggcga agggagcgac catgcacgtg accgccgacc   1260
gcgacgtgtg cgtcggtgcc gggatgtgcg ccctgaccgc gcccggcgtc ttcgaccagg   1320
acgacgacgg gctcgtcacc gtcctgacct ccgatatcgg agagaacgac cgggacgccg   1380
tgcgcgaggc cggcatgctg tgcccgtccg gggcccttcg ggtcacggag taa          1433
```

<210> SEQ ID NO 34
<211> LENGTH: 406
<212> TYPE: PRT
<213> ORGANISM: Streptomyces rimosus

<400> SEQUENCE: 34

```
Met Thr Glu Thr Ser Thr Ala Phe Pro Ala Gln Asp Ala Pro Ala Phe
1               5                   10                  15

Pro Ser Asp Arg Thr Cys Pro Tyr Gly Leu Pro Glu Thr Tyr Ala Arg
            20                  25                  30

Leu Arg Asp Ser Glu Asp Ala Leu Arg Pro Val Thr Leu Phe Asp Gly
        35                  40                  45

Arg Thr Ala Trp Val Val Thr Lys His Glu Thr Ala Arg Thr Leu Leu
    50                  55                  60

Ala Asp Pro Arg Leu Ser Ser Asn Arg Thr His Pro Asp Phe Pro Leu
65                  70                  75                  80
```

```
Thr Ser Pro Arg Leu Ala Gly Leu Arg Asp Arg Arg Pro Ala Phe Ile
                85                  90                  95

Ser Met Asp Pro Pro Glu His Gly Pro Arg Arg Arg Met Thr Ile Ser
            100                 105                 110

Glu Phe Thr Val Lys Arg Ile Lys Gly Met Arg Pro Asp Ile Glu Arg
        115                 120                 125

Ile Val His Gly Phe Leu Asp Glu Met Leu Ala Ala Gly Pro Pro Ala
    130                 135                 140

Asp Leu Val Ser Arg Phe Ala Leu Pro Val Pro Ser Met Val Ile Cys
145                 150                 155                 160

Gln Leu Leu Gly Val Pro Tyr Ala Asp His Asp Phe Phe Gln Asp Ala
                165                 170                 175

Ser Arg Arg Leu Val Gln Ser Thr Ser Ala Glu Glu Ala Thr Gly Ala
            180                 185                 190

Arg Asp Asp Leu Glu Arg Tyr Leu Asp Gly Leu Ile Thr Thr Leu Glu
        195                 200                 205

Ser Glu Pro Gly Pro Gly Leu Leu Gly Ala Leu Val Thr Arg Gln Leu
    210                 215                 220

Ala Asp Gly Ala Ile Asp Arg Asp Glu Leu Ile Ser Asn Ala Leu Leu
225                 230                 235                 240

Leu Leu Val Ala Gly His Glu Thr Thr Ala Ser Met Thr Ser Leu Ser
                245                 250                 255

Val Ile Thr Leu Leu Glu His Pro Glu Gln His Ala Ala Leu Arg Asp
            260                 265                 270

Asp Pro Ser Leu Ile Pro Gly Ala Val Glu Glu Leu Leu Arg Tyr Leu
        275                 280                 285

Ala Ile Ala Asp Val Ala Gly Ala Arg Val Ala Thr Ala Asp Ile Glu
    290                 295                 300

Val Asp Gly Gln Val Ile Arg Ala Gly Glu Gly Val Ile Val Val His
305                 310                 315                 320

Ser Ile Ala Asn Arg Asp Ala Gly Val Phe Glu Asn Pro Asp Thr Phe
                325                 330                 335

Asp Ile His Arg Ser Ala Arg His His Leu Ser Phe Gly Tyr Gly Val
            340                 345                 350

His Gln Cys Leu Gly Gln Asn Leu Ala Arg Leu Glu Leu Glu Ile Ile
        355                 360                 365

Leu Ser Ala Leu Phe Glu Arg Ile Pro Thr Leu Arg Leu Ala Thr Pro
    370                 375                 380

Val Glu Arg Leu Thr Leu Arg Pro Gly Ser Thr Ile Gln Gly Val Asn
385                 390                 395                 400

Glu Leu Pro Val Thr Trp
                405
```

<210> SEQ ID NO 35
<211> LENGTH: 63
<212> TYPE: PRT
<213> ORGANISM: Streptomyces rimosus

<400> SEQUENCE: 35

```
Met His Val Thr Ala Asp Arg Asp Val Cys Val Gly Ala Gly Met Cys
1               5                   10                  15

Ala Leu Thr Ala Pro Gly Val Phe Asp Gln Asp Asp Asp Gly Leu Val
            20                  25                  30

Thr Val Leu Thr Ser Asp Ile Gly Glu Asn Asp Arg Asp Ala Val Arg
```

```
        35                  40                  45

Glu Ala Gly Met Leu Cys Pro Ser Gly Ala Leu Arg Val Thr Glu
    50                  55                  60
```

<210> SEQ ID NO 36
<211> LENGTH: 1356
<212> TYPE: DNA
<213> ORGANISM: Streptomyces rimosus

<400> SEQUENCE: 36

```
atggctgcac acgccgatga gccgatccgc ctggcggtgg gggaactggc acggtttctc      60
ggcgcggacg tcgacgaccc cgcctttctg accgatcctc acagatgtct gacgcccggg     120
atacgcgaga aatccgtgca ccggctgccc ggaggcgccc tggccgttct cggttacacg     180
gcgtgcgccg aggtgctgcg tgatacacgg ttcggccacg gtgcccgcga actgtacgag     240
accaccctgc tggggctgcc ggcccggtct tttctccaac tggacgcacc ggggcacacc     300
cggctgcgcg gccaggtcgc gcggcatttc accgcacggc gagtacgggc cttggccgag     360
aacgtcgggt attacagcac tgctctcgta cgggagcacg cgggccgccc gggggatttc     420
gtggcggatt tcgccgagcc gctggcgatg tcggtcatca gcgacgtact gggcgtgccg     480
cccgaggatc gccccgcctt ccaccgtgac gcccggctgg tcgtccgcgg actggaccag     540
ccggcccgcg ccatggacga acgggccgtc gcccaggcgc ggttccgctt cgtacggttc     600
ttccgccgcc gggcgcaggc gcgccgccag gccgggacgc ggcaccgggc gccccgggac     660
ggcctgctgg acgccttgtc gcaccggccg gacggcagcc cggccgacat ccgcgagctg     720
gtcaccacgt gcagcctgct gctgagcgcc ggatacgaca ccacggtcag cctgctgtcg     780
cacgcggtgg cggaactggg cggcgcaccg tccgggcagg ggtgggcgct ggcccgggac     840
ccgcagacgg tgggcgcggt cgtggaggag gtgctgcgtc tgcactctcc cgtgcagatc     900
gctccgcgcg ccgcggtgcg tgacgcggcc ctggacgggc tgccggtggc ccgcggcacg     960
atcgtgctgc ccctgctgcc ggcggccaac cgggacccgg acatcttcga cagcccgcac    1020
accttccggc cccggcgcta tctcgccccg gcagctcaag gccgttcgac agcaaggcat    1080
ttggcgttcg gagcgggcgc gcatttctgt ctgggggcgg ccctggcccg gctgaccgcc    1140
cacagcgcgc tggctgttct ggccgcctgc ccgcccagac cgcgcgacgc gccccgtacg    1200
tacagcgaag gcgtcgtcgt acgcggcctg cgcagtctgc cggtcacctg gccgcaccgg    1260
cccgcggaac ggcccccgca ccctccggcc gacggcgcgg ccgcgtacgt cgagccgtcg    1320
tgccccatcc cccacgcgca aaggagcgtc acataa                              1356
```

<210> SEQ ID NO 37
<211> LENGTH: 451
<212> TYPE: PRT
<213> ORGANISM: Streptomyces rimosus

<400> SEQUENCE: 37

```
Met Ala Ala His Ala Asp Glu Pro Ile Arg Leu Ala Val Gly Glu Leu
1               5                   10                  15

Ala Arg Phe Leu Gly Ala Asp Val Asp Asp Pro Ala Phe Leu Thr Asp
            20                  25                  30

Pro His Arg Cys Leu Thr Pro Gly Ile Arg Glu Lys Ser Val His Arg
        35                  40                  45

Leu Pro Gly Gly Ala Leu Ala Val Leu Gly Tyr Thr Ala Cys Ala Glu
    50                  55                  60
```

```
Val Leu Arg Asp Thr Arg Phe Gly His Gly Ala Arg Glu Leu Tyr Glu
65                  70                  75                  80

Thr Thr Leu Leu Gly Leu Pro Ala Arg Ser Phe Leu Gln Leu Asp Ala
                85                  90                  95

Pro Gly His Thr Arg Leu Arg Gly Gln Val Ala Arg His Phe Thr Ala
            100                 105                 110

Arg Arg Val Arg Ala Leu Ala Glu Asn Val Gly Tyr Tyr Ser Thr Ala
        115                 120                 125

Leu Val Arg Glu His Ala Gly Arg Pro Gly Asp Phe Val Ala Asp Phe
    130                 135                 140

Ala Glu Pro Leu Ala Met Ser Val Ile Ser Asp Val Leu Gly Val Pro
145                 150                 155                 160

Pro Glu Asp Arg Pro Ala Phe His Arg Asp Ala Arg Leu Val Val Arg
                165                 170                 175

Gly Leu Asp Gln Pro Ala Arg Ala Met Asp Glu Arg Ala Val Ala Gln
            180                 185                 190

Ala Arg Phe Arg Phe Val Arg Phe Phe Arg Arg Arg Ala Gln Ala Arg
        195                 200                 205

Arg Gln Ala Gly Thr Arg His Arg Ala Pro Arg Asp Gly Leu Leu Asp
    210                 215                 220

Ala Leu Ser His Arg Pro Asp Gly Ser Pro Ala Asp Ile Arg Glu Leu
225                 230                 235                 240

Val Thr Thr Cys Ser Leu Leu Leu Ser Ala Gly Tyr Asp Thr Thr Val
                245                 250                 255

Ser Leu Leu Ser His Ala Val Ala Glu Leu Gly Gly Ala Pro Ser Gly
            260                 265                 270

Gln Gly Trp Ala Leu Ala Arg Asp Pro Gln Thr Val Gly Ala Val Val
        275                 280                 285

Glu Glu Val Leu Arg Leu His Ser Pro Val Gln Ile Ala Pro Arg Ala
    290                 295                 300

Ala Val Arg Asp Ala Ala Leu Asp Gly Leu Pro Val Ala Arg Gly Thr
305                 310                 315                 320

Ile Val Leu Pro Leu Leu Pro Ala Ala Asn Arg Asp Pro Asp Ile Phe
                325                 330                 335

Asp Ser Pro His Thr Phe Arg Pro Arg Arg Tyr Leu Ala Pro Ala Ala
            340                 345                 350

Gln Gly Arg Ser Thr Ala Arg His Leu Ala Phe Gly Ala Gly Ala His
        355                 360                 365

Phe Cys Leu Gly Ala Ala Leu Ala Arg Leu Thr Ala His Ser Ala Leu
    370                 375                 380

Ala Val Leu Ala Ala Cys Pro Pro Arg Pro Arg Asp Ala Pro Arg Thr
385                 390                 395                 400

Tyr Ser Glu Gly Val Val Val Arg Gly Leu Arg Ser Leu Pro Val Thr
                405                 410                 415

Trp Pro His Arg Pro Ala Glu Arg Pro Pro His Pro Pro Ala Asp Gly
            420                 425                 430

Ala Ala Ala Tyr Val Glu Pro Ser Cys Pro Ile Pro His Ala Gln Arg
        435                 440                 445

Ser Val Thr
    450
```

<210> SEQ ID NO 38
<211> LENGTH: 1341
<212> TYPE: DNA

<213> ORGANISM: Streptomyces rimosus

<400> SEQUENCE: 38
atgccgggcg ccttgcccct cgtcgggcac gcgcccgcgc tcattcgtga tcccttcggc 60
ttcttcctgt cgctgcggga ccacgccgac gaccgcggcc tggtccgcat ccggctcggc 120
tcgatgcccg tctacatggc caccacccct gagcggctgc acgaggtcct ggtggacaag 180
gggcggtggt tcgagaaggg ccggttcttc cagcgcctca agcggctggc cggcgagggg 240
ctgagcaccg cggacgggga gctgcacaaa cgtaaccgcc gcttcctcgc gccccttttc 300
ggcgcgcagc gcatcaagga ctactccctg gtcatgagcc gcaatgcccg gcgcctgtcc 360
cagtcctggc agccggatca gcaggtggac atctacaagg aggccgccgc ttattccatc 420
gactccatcg ccatgtcgct gttcagtaca gacgtcggaa cgccggcggt ggaaacgatc 480
cgtaccgaac tgccggtgct gctggacatg ctcctcaagc gcgctgcctc accgaagatc 540
ctggatcgcc tgccggtacg ctacaaccgc gttttcgacc gggcgtccgc gcagttgacc 600
ggggtgatcg accaggtcat caccaccgca cacgccggcg gccacgccga ggagcacgac 660
gacctgctcg cgcagctgct gcgggcgcag gtccacgacg acgttccggt ccgcctcagt 720
gacgttcaga tccgcgacga ggtggccacg ctgctgttcg ccggggccga gaccacggcg 780
tcgaccctgg cctgggcctg gcactacctg gcgcaccacc ccgaggtcga ccggcaggtg 840
gtggacgagg tcctggaggt cgtgggcccc gaccgcgcgg tgaccatcga agacgtcccc 900
cggctgaccg tgatccgccg ggtgctggac gaggtgatcc gcctgcacgg tgtcacgttc 960
ctgatgcgcc gcagcaccgc gccggtgacc ctcgccgatg tcacgctgcc cgcgggcacc 1020
gaggtggcgt tcagcatgta cgccatccac cgtgatcccg aggctttcga ggaccccccac 1080 accttcaacc cggaccggtg gctggacccc ggggccaaac ggtcgttcat gcccttcggc 1140
ggcggcaacc gcaagtgcat cggcgatcag ttcgccctgg ccgagaccac catcgccgtc 1200
gcggaggtgc tgcgcgactg gcgcatgacc cccgccggcg gccacactcc gcagcaggtg 1260
atctccgctg tcgcccggcc cgaccgggta cccatgaccg tacggccgcg taaccccgca 1320
cccagccggc cgagcaacta a 1341

<210> SEQ ID NO 39
<211> LENGTH: 446
<212> TYPE: PRT
<213> ORGANISM: Streptomyces rimosus

<400> SEQUENCE: 39

Met Pro Gly Ala Leu Pro Leu Val Gly His Ala Pro Ala Leu Ile Arg
1 5 10 15

Asp Pro Phe Gly Phe Phe Leu Ser Leu Arg Asp His Ala Asp Asp Arg
20 25 30

Gly Leu Val Arg Ile Arg Leu Gly Ser Met Pro Val Tyr Met Ala Thr
35 40 45

Thr Pro Glu Arg Leu His Glu Val Leu Val Asp Lys Gly Arg Trp Phe
50 55 60

Glu Lys Gly Arg Phe Phe Gln Arg Leu Lys Arg Leu Ala Gly Glu Gly
65 70 75 80

Leu Ser Thr Ala Asp Gly Glu Leu His Lys Arg Asn Arg Arg Phe Leu
85 90 95

Ala Pro Leu Phe Gly Ala Gln Arg Ile Lys Asp Tyr Ser Leu Val Met
100 105 110

-continued

```
Ser Arg Asn Ala Arg Arg Leu Ser Gln Ser Trp Gln Pro Asp Gln Gln
        115                 120                 125

Val Asp Ile Tyr Lys Glu Ala Ala Ala Tyr Ser Ile Asp Ser Ile Ala
    130                 135                 140

Met Ser Leu Phe Ser Thr Asp Val Gly Thr Pro Ala Val Glu Thr Ile
145                 150                 155                 160

Arg Thr Glu Leu Pro Val Leu Leu Asp Met Leu Leu Lys Arg Ala Ala
                165                 170                 175

Ser Pro Lys Ile Leu Asp Arg Leu Pro Val Arg Tyr Asn Arg Val Phe
            180                 185                 190

Asp Arg Ala Ser Ala Gln Leu Thr Gly Val Ile Asp Gln Val Ile Thr
        195                 200                 205

Thr Ala His Ala Gly Gly His Ala Glu Glu His Asp Asp Leu Leu Ala
    210                 215                 220

Gln Leu Leu Arg Ala Gln Val His Asp Asp Val Pro Val Arg Leu Ser
225                 230                 235                 240

Asp Val Gln Ile Arg Asp Glu Val Ala Thr Leu Leu Phe Ala Gly Ala
                245                 250                 255

Glu Thr Thr Ala Ser Thr Leu Ala Trp Ala Trp His Tyr Leu Ala His
            260                 265                 270

His Pro Glu Val Asp Arg Gln Val Val Asp Glu Val Leu Glu Val Val
        275                 280                 285

Gly Pro Asp Arg Ala Val Thr Ile Glu Asp Val Pro Arg Leu Thr Val
    290                 295                 300

Ile Arg Arg Val Leu Asp Glu Val Ile Arg Leu His Gly Val Thr Phe
305                 310                 315                 320

Leu Met Arg Arg Ser Thr Ala Pro Val Thr Leu Ala Asp Val Thr Leu
                325                 330                 335

Pro Ala Gly Thr Glu Val Ala Phe Ser Met Tyr Ala Ile His Arg Asp
            340                 345                 350

Pro Glu Ala Phe Glu Asp Pro His Thr Phe Asn Pro Asp Arg Trp Leu
        355                 360                 365

Asp Pro Gly Ala Lys Arg Ser Phe Met Pro Phe Gly Gly Gly Asn Arg
    370                 375                 380

Lys Cys Ile Gly Asp Gln Phe Ala Leu Ala Glu Thr Thr Ile Ala Val
385                 390                 395                 400

Ala Glu Val Leu Arg Asp Trp Arg Met Thr Pro Ala Gly Gly His Thr
                405                 410                 415

Pro Gln Gln Val Ile Ser Ala Val Ala Arg Pro Asp Arg Val Pro Met
            420                 425                 430

Thr Val Arg Pro Arg Asn Pro Ala Pro Ser Arg Pro Ser Asn
        435                 440                 445
```

<210> SEQ ID NO 40
<211> LENGTH: 1194
<212> TYPE: DNA
<213> ORGANISM: Streptomyces rimosus

<400> SEQUENCE: 40

```
atgccggtcc agctccccgg cggcatcccc ggccacgccg tgacccgcca ccacgccctg      60

cgcgacttcc tcacccaccc ggaagtggcc aaggacgcct gccacttcgc cgcgctgcgc     120

gagggccgca tcccgcccgg ctggccgctc accaccttcg cgaccgtgga cgggatgacg     180

acggccgacg gcgcggacca ccggcggctg cgggaaccgg ccgtcaaggc gctctcgccc     240
```

-continued

```
cggcgggtgg cggcgctgcg gccgcgggtg gagcggctga ccgccgagct gctcgacggg    300

ctgcccgccc tggccgcgcg gggcggcggg acggtcgatc tccggcacgc cttcgcctat    360

ccgctgccca tgcgggtgat cagtgaactc atcggcgtgg acgaggagtt ccgggaccgg    420

ctgcaccagc tgtccgggct ggtcgtgagc accgtcatcg acccggaggc ggcgctggcg    480

gccaaccggg agctggtcgg ggtcctcggg caggtcgtgg cggcccgccg cgcggcgccg    540

ggcgacgacc tgaccagcgc gctcatcgcg gcctgtgacg aggcggacgc ccggctgagc    600

gaacgggagc tgatcggcac cctgttgctg atgatcgccg ccgggcacca gaccaccctc    660

gacttgatca ccaacgccgt acgggccctc tgcgcccacc gcgaccagct ggacctggtc    720

cgcgcggggc gggcggactg ggcggacgtg gtcgaggaga cgctgcgcca cgacagcccg    780

gtggcccact tcccgttccg ctacccgacc cgggacctgg acgtcggcgg cacggtgatc    840

ccccggggga cgccggtgct cgcctcgtac gcggcggccg ggcgcgaccc ggaggcgtac    900

gggccggacg cggaccgctt cgacgtgacg cgacggcccg ccgtccggca cctgtccttc    960

gggcacgggc cgcatgtctg tccgggcgca ccgctggccc gcttggaggc gcggatcgcc   1020

ctgcgcgcgc tgttcacccg cttccctgat ctggccctgg ccgtaccgga ggcggacctg   1080

cggccgctgc ccacgttcgt gggcaacagc gtcgcggagc ttccggtacg gccgggtcgg   1140

gacgtcggga cggccggtca ggacgcgtcg gccaccagcc ccggcgccgg gtaa         1194
```

<210> SEQ ID NO 41
<211> LENGTH: 397
<212> TYPE: PRT
<213> ORGANISM: Streptomyces rimosus

<400> SEQUENCE: 41

```
Met Pro Val Gln Leu Pro Gly Gly Ile Pro Gly His Ala Val Thr Arg
1               5                   10                  15

His His Ala Leu Arg Asp Phe Leu Thr His Pro Glu Val Ala Lys Asp
            20                  25                  30

Ala Cys His Phe Ala Ala Leu Arg Glu Gly Arg Ile Pro Pro Gly Trp
        35                  40                  45

Pro Leu Thr Thr Phe Ala Thr Val Asp Gly Met Thr Thr Ala Asp Gly
    50                  55                  60

Ala Asp His Arg Arg Leu Arg Glu Pro Ala Val Lys Ala Leu Ser Pro
65                  70                  75                  80

Arg Arg Val Ala Ala Leu Arg Pro Arg Val Glu Arg Leu Thr Ala Glu
                85                  90                  95

Leu Leu Asp Gly Leu Pro Ala Leu Ala Ala Arg Gly Gly Gly Thr Val
            100                 105                 110

Asp Leu Arg His Ala Phe Ala Tyr Pro Leu Pro Met Arg Val Ile Ser
        115                 120                 125

Glu Leu Ile Gly Val Asp Glu Glu Phe Arg Asp Arg Leu His Gln Leu
    130                 135                 140

Ser Gly Leu Val Val Ser Thr Val Ile Asp Pro Glu Ala Ala Leu Ala
145                 150                 155                 160

Ala Asn Arg Glu Leu Val Gly Val Leu Gly Gln Val Val Ala Ala Arg
                165                 170                 175

Arg Ala Ala Pro Gly Asp Asp Leu Thr Ser Ala Leu Ile Ala Ala Cys
            180                 185                 190

Asp Glu Ala Asp Ala Arg Leu Ser Glu Arg Glu Leu Ile Gly Thr Leu
        195                 200                 205
```

```
Leu Leu Met Ile Ala Ala Gly His Gln Thr Thr Leu Asp Leu Ile Thr
    210                 215                 220

Asn Ala Val Arg Ala Leu Cys Ala His Arg Asp Gln Leu Asp Leu Val
225                 230                 235                 240

Arg Ala Gly Arg Ala Asp Trp Ala Asp Val Val Glu Glu Thr Leu Arg
                245                 250                 255

His Asp Ser Pro Val Ala His Phe Pro Phe Arg Tyr Pro Thr Arg Asp
            260                 265                 270

Leu Asp Val Gly Gly Thr Val Ile Pro Arg Gly Thr Pro Val Leu Ala
        275                 280                 285

Ser Tyr Ala Ala Ala Gly Arg Asp Pro Glu Ala Tyr Gly Pro Asp Ala
290                 295                 300

Asp Arg Phe Asp Val Thr Arg Arg Pro Ala Val Arg His Leu Ser Phe
305                 310                 315                 320

Gly His Gly Pro His Val Cys Pro Gly Ala Pro Leu Ala Arg Leu Glu
                325                 330                 335

Ala Arg Ile Ala Leu Arg Ala Leu Phe Thr Arg Phe Pro Asp Leu Ala
            340                 345                 350

Leu Ala Val Pro Glu Ala Asp Leu Arg Pro Leu Pro Thr Phe Val Gly
        355                 360                 365

Asn Ser Val Ala Glu Leu Pro Val Arg Pro Gly Arg Asp Val Gly Thr
370                 375                 380

Ala Gly Gln Asp Ala Ser Ala Thr Ser Pro Gly Ala Gly
385                 390                 395
```

```
<210> SEQ ID NO 42
<211> LENGTH: 1224
<212> TYPE: DNA
<213> ORGANISM: Streptomyces rimosus

<400> SEQUENCE: 42

atgacgaccg ttcccgatct tcccgacgcc acagaggcgc tggagcactt ccccttcgac      60

gacggccgtg gcatcgaggt ccacgagcgg ttccgggagc tgcgggagcg cgcggggctg     120

ctccgggtgc ggctcgacta cggtgaaccc acctggctgg tcacccgtta cgcggacgcc     180

cggctggtgc tgggcgacgc gcggttcagc cgtgccatgt cggtcggccg ggacttcccg     240

cgccaggagg aagcgacgga actggccggg ctgatcacca tggacgcccc cgaacacacc     300

cggctgcgca cactgttggt caaagccctc agcaaatccc gtatcgacgc gcagcgcccg     360

acggtgcgcg cgacggcgga cgcgctgctg tcgtcggcga tggacgccgg gccgggcatg     420

gacatcgtgg tggactacgc gcagcagatg agcgtgctgt ccatctgcga cctgctcggc     480

gtgccggcct cggaccggga ggcgttcgag tcgaccagcg cggcactgct ccccggcagc     540

gccgtcggcg ccgaggacat gatgcggcgg ttcggtgagc tgcgcgcctg caccgagcgg     600

ctcatcgccg agcgccgggc ccgcccccgc gacgacctga tgtcggcgat gatccaggcc     660

cgggacgagg aggaccggct caccgacgcc gagctgatcg agctggtcgt cagcatgctg     720

ctggccaggt tcgaggcgat catcacccag atcccgaact gcgtctacgt tctcacgcgg     780

ggcgaccggg cgctctggaa ccggctgcgt gcgaatccgg ccgagctgcc cgcggcggtc     840

gaggagctgc tgcgcaacaa cgcctccgcc ggcgcgggcc tgttcgtccg ctatgcgcgg     900

gaggatgtca acgtcggcgg cacgctggtg cgcgcgggcg aagccctgac catcgccgtc     960

gagtcggcca accacgaccc ggcccggttc gaggaccccg acgcgatcga tttcacccgg    1020

ccacccggcg ggcacctcac cttcggttat ggcgcgcact actgcgtcgg cgcccagctc    1080
```

gggcgcatcg acctccagga agggctgcgg gtgctgctca ccagggcccc ggagctgacc 1140
gtccgcgacc tcacgtggag agtacggccg cacatccggg gaccggtggc gatgcgcgtg 1200
acctggcagg gcgacccgga ataa 1224

<210> SEQ ID NO 43
<211> LENGTH: 407
<212> TYPE: PRT
<213> ORGANISM: Streptomyces rimosus

<400> SEQUENCE: 43

```
Met Thr Thr Val Pro Asp Leu Pro Asp Ala Thr Glu Ala Leu Glu His
1               5                   10                  15

Phe Pro Phe Asp Asp Gly Arg Gly Ile Glu Val His Glu Arg Phe Arg
            20                  25                  30

Glu Leu Arg Glu Arg Ala Gly Leu Leu Arg Val Arg Leu Asp Tyr Gly
        35                  40                  45

Glu Pro Thr Trp Leu Val Thr Arg Tyr Ala Asp Ala Arg Leu Val Leu
    50                  55                  60

Gly Asp Ala Arg Phe Ser Arg Ala Met Ser Val Gly Arg Asp Phe Pro
65                  70                  75                  80

Arg Gln Glu Glu Ala Thr Glu Leu Ala Gly Leu Ile Thr Met Asp Ala
                85                  90                  95

Pro Glu His Thr Arg Leu Arg Thr Leu Leu Val Lys Ala Leu Ser Lys
            100                 105                 110

Ser Arg Ile Asp Ala Gln Arg Pro Thr Val Arg Ala Thr Ala Asp Ala
        115                 120                 125

Leu Leu Ser Ser Ala Met Asp Ala Gly Pro Gly Met Asp Ile Val Val
    130                 135                 140

Asp Tyr Ala Gln Gln Met Ser Val Leu Ser Ile Cys Asp Leu Leu Gly
145                 150                 155                 160

Val Pro Ala Ser Asp Arg Glu Ala Phe Glu Ser Thr Ser Ala Ala Leu
                165                 170                 175

Leu Pro Gly Ser Ala Val Gly Ala Glu Asp Met Met Arg Arg Phe Gly
            180                 185                 190

Glu Leu Arg Ala Cys Thr Glu Arg Leu Ile Ala Glu Arg Arg Ala Arg
        195                 200                 205

Pro Arg Asp Asp Leu Met Ser Ala Met Ile Gln Ala Arg Asp Glu Glu
    210                 215                 220

Asp Arg Leu Thr Asp Ala Glu Leu Ile Glu Leu Val Val Ser Met Leu
225                 230                 235                 240

Leu Ala Arg Phe Glu Ala Ile Ile Thr Gln Ile Pro Asn Cys Val Tyr
                245                 250                 255

Val Leu Thr Arg Gly Asp Arg Ala Leu Trp Asn Arg Leu Arg Ala Asn
            260                 265                 270

Pro Ala Glu Leu Pro Ala Ala Val Glu Glu Leu Leu Arg Asn Asn Ala
        275                 280                 285

Ser Ala Gly Ala Gly Leu Phe Val Arg Tyr Ala Arg Glu Asp Val Asn
    290                 295                 300

Val Gly Gly Thr Leu Val Arg Ala Gly Glu Ala Leu Thr Ile Ala Val
305                 310                 315                 320

Glu Ser Ala Asn His Asp Pro Ala Arg Phe Glu Asp Pro Asp Ala Ile
                325                 330                 335

Asp Phe Thr Arg Pro Pro Gly Gly His Leu Thr Phe Gly Tyr Gly Ala
```

```
            340                 345                 350

His Tyr Cys Val Gly Ala Gln Leu Gly Arg Ile Asp Leu Gln Glu Gly
        355                 360                 365

Leu Arg Val Leu Leu Thr Arg Ala Pro Glu Leu Thr Val Arg Asp Leu
    370                 375                 380

Thr Trp Arg Val Arg Pro His Ile Arg Gly Pro Val Ala Met Arg Val
385                 390                 395                 400

Thr Trp Gln Gly Asp Pro Glu
                405


<210> SEQ ID NO 44
<211> LENGTH: 1224
<212> TYPE: DNA
<213> ORGANISM: Streptomyces rimosus

<400> SEQUENCE: 44

atgcagaaca ccgccgagac cggccccgac gacctcattg acgtgacgca gcttctggac     60

gatccgcacg ccgggtacgc ggtgttgcgg gaggcggggc ccgtccatcg gattgccggg    120

ccggacgggc agcccgcgtg gctggtgacg cggtacgagg atgtgcggcg gtgtctgtcc    180

gatccgcggc tttccctgga caagcggaac gcgcggggcg gctatcgcgg gttcgcgctg    240

ccgcccgcgc tggacgcgaa tctgctcaac atggatccgc cggaccacac ccgggtgcgc    300

cggctggtgg ccaaggcatt cacgcccgcg cgggtcgaga agctgcggga gcccgtacgg    360

cggctggcgg acgggttgct ggacgcggtc gcggacgccg ggcgggccga cctgatggag    420

tgttacgccg gtccgctgcc catcatcgtc atctgcgacc tgctgggcgt accggaggac    480

gaccggccgg acttccgggc ctggacggac gcgctgatca cgcccgaccc ggcccggccg    540

gagcgggcga aggaggccgt cggggcgatg atgcgctact acacggggct gatcacggcc    600

aagcgggccg cgccggggga cgatctgctc tccgacctga tcctggtgcg ggacggcgcg    660

gcggcggagg gtggcgcggg ggaccggctc ggtgaggacg agctgacctc gttggcgttc    720

ctcctgctct tcgccggtta cgagaacacc gttcacctca tcggtaactc agtcctcgcc    780

ctgctcgacc accccgaaca cctcatggcg ttgcgtacga atccagccga actgtcggcg    840

gccgtggaag agttcgcacg ctatgacgga ccggcctcgc tggccatccg ccggttcccc    900

ctggaggacg tggaaatcgg cggcgtacgg gtgcccgcgg gcgagagtgt gctgctctcc    960

cttgcctcgg cgaaccgcga cccgcaccgc ttcgccgacc ccgggacgct cgatccgggc   1020

cgcgacgcca cgggtcagct gatgttcggg cacggcatcc actactgcct cggcgcggcc   1080

ctggcgcgcc tgcagaccga gaccgcgctg accgctctca tcagccgttt tcccgggttg   1140

cggctggatg tgccacggtc ggaactgcgc caccgccgca ccctgcgggc acgtggcttg   1200

atctcgctcc ccgtcgcctg gtaa                                          1224


<210> SEQ ID NO 45
<211> LENGTH: 407
<212> TYPE: PRT
<213> ORGANISM: Streptomyces rimosus

<400> SEQUENCE: 45

Met Gln Asn Thr Ala Glu Thr Gly Pro Asp Asp Leu Ile Asp Val Thr
1               5                   10                  15

Gln Leu Leu Asp Asp Pro His Ala Gly Tyr Ala Val Leu Arg Glu Ala
            20                  25                  30

Gly Pro Val His Arg Ile Ala Gly Pro Asp Gly Gln Pro Ala Trp Leu
```

```
        35                  40                  45

Val Thr Arg Tyr Glu Asp Val Arg Arg Cys Leu Ser Asp Pro Arg Leu
    50                  55                  60

Ser Leu Asp Lys Arg Asn Ala Arg Gly Gly Tyr Arg Gly Phe Ala Leu
65                  70                  75                  80

Pro Pro Ala Leu Asp Ala Asn Leu Leu Asn Met Asp Pro Pro Asp His
                85                  90                  95

Thr Arg Val Arg Arg Leu Val Ala Lys Ala Phe Thr Pro Ala Arg Val
            100                 105                 110

Glu Lys Leu Arg Glu Pro Val Arg Arg Leu Ala Asp Gly Leu Leu Asp
        115                 120                 125

Ala Val Ala Asp Ala Gly Arg Ala Asp Leu Met Glu Cys Tyr Ala Gly
    130                 135                 140

Pro Leu Pro Ile Ile Val Ile Cys Asp Leu Leu Gly Val Pro Glu Asp
145                 150                 155                 160

Asp Arg Pro Asp Phe Arg Ala Trp Thr Asp Ala Leu Ile Thr Pro Asp
                165                 170                 175

Pro Ala Arg Pro Glu Arg Ala Lys Glu Ala Val Gly Ala Met Met Arg
            180                 185                 190

Tyr Tyr Thr Gly Leu Ile Thr Ala Lys Arg Ala Ala Pro Gly Asp Asp
        195                 200                 205

Leu Leu Ser Asp Leu Ile Leu Val Arg Asp Gly Ala Ala Ala Glu Gly
    210                 215                 220

Gly Ala Gly Asp Arg Leu Gly Glu Asp Glu Leu Thr Ser Leu Ala Phe
225                 230                 235                 240

Leu Leu Leu Phe Ala Gly Tyr Glu Asn Thr Val His Leu Ile Gly Asn
                245                 250                 255

Ser Val Leu Ala Leu Leu Asp His Pro Glu His Leu Met Ala Leu Arg
            260                 265                 270

Thr Asn Pro Ala Glu Leu Ser Ala Ala Val Glu Glu Phe Ala Arg Tyr
        275                 280                 285

Asp Gly Pro Ala Ser Leu Ala Ile Arg Arg Phe Pro Leu Glu Asp Val
    290                 295                 300

Glu Ile Gly Gly Val Arg Val Pro Ala Gly Glu Ser Val Leu Leu Ser
305                 310                 315                 320

Leu Ala Ser Ala Asn Arg Asp Pro His Arg Phe Ala Asp Pro Gly Thr
                325                 330                 335

Leu Asp Pro Gly Arg Asp Ala Thr Gly Gln Leu Met Phe Gly His Gly
            340                 345                 350

Ile His Tyr Cys Leu Gly Ala Ala Leu Ala Arg Leu Gln Thr Glu Thr
        355                 360                 365

Ala Leu Thr Ala Leu Ile Ser Arg Phe Pro Gly Leu Arg Leu Asp Val
    370                 375                 380

Pro Arg Ser Glu Leu Arg His Arg Arg Thr Leu Arg Ala Arg Gly Leu
385                 390                 395                 400

Ile Ser Leu Pro Val Ala Trp
                405
```

<210> SEQ ID NO 46
<211> LENGTH: 1212
<212> TYPE: DNA
<213> ORGANISM: Streptomyces rimosus

<400> SEQUENCE: 46

-continued

```
atgccggaaa tcatcgacct gggcgcgtac ggcccggact tcgtcgccga cccgcatccg      60
tactacgcca agctgcgcgc ccagggcccg gtccaccggg tccgcgcccc ggagatggag     120
ccggagttcc cgcaggcctg gctgatcgtc ggatacgacg aagcgcgggc cgtgctggcc     180
gacaaccgct tcgccaagga ctggtcccgg gcgaacggct ccctcgccga cagcgaggtc     240
ctggccgagt ggcagctgat gaacatgctc gacgccgacc cgccgcagca cacccggctg     300
cgcaagctgg tggcccggga gttcaccacc cgccgcgtcg aggcgctgcg cccgcgcgtc     360
cagcagatca ccgacgagct gctggacgcc atgctggccg ccccggacgg ccgcgccgac     420
ctcgtggagg cgctcgcctt cccgctcccg atgaccgtca tctgcgaact cctcggcgtg     480
cccgacatcg agcgggacac cttccgcgcc tggtccaacg aactggtctc gccgaccgac     540
aacgaggcga cgatgaccgc cgcccgcgag atggccgcct atctggacgg cctgatcgaa     600
agcaagcgga gctcgccggg cgaggacctg ctgagcgcgc tggtgcgcac gagcgatgag     660
gacggcgacc agctctcccg gcaggaactg ctcggcatgg ccttcctcct gctcgtggcc     720
ggccacgaaa ccaccgtcaa cctgatctcc aacggcgtac gggccctgct ccagcacccc     780
gcgcaactgg ccgcactgcg cgccgatccc tcgcttctcg acaacgccgt cgaggagatg     840
ctgcgctacg acggccccgt ggagaccgcc acctggcgct tcaccgccga gcccgtcggg     900
atcggcggcg tggagatccc ggccggtgag atcgtcctcg tcggcctggc cggggcggac     960
cgcgacccgg agcgcttcga ggcccccgac accttcgaca tcacccgcga gacccgcggc    1020
cacgtcgcct tcggccacgg cattcacttc tgcctcggcg ccccactggc ccgcgtcgag    1080
ggccgtatcg cggtgcgcac tctcctggac cgctgcccgg acctggccct ggacaccgct    1140
cccgaggcgc tgacctggcg cgcgggcatg acgatacgag ggccccagca cctgccggtg    1200
cggtggcggt aa                                                        1212
```

```
<210> SEQ ID NO 47
<211> LENGTH: 403
<212> TYPE: PRT
<213> ORGANISM: Streptomyces rimosus

<400> SEQUENCE: 47

Met Pro Glu Ile Ile Asp Leu Gly Ala Tyr Gly Pro Asp Phe Val Ala
1               5                   10                  15

Asp Pro His Pro Tyr Tyr Ala Lys Leu Arg Ala Gln Gly Pro Val His
            20                  25                  30

Arg Val Arg Ala Pro Glu Met Glu Pro Glu Phe Pro Gln Ala Trp Leu
        35                  40                  45

Ile Val Gly Tyr Asp Glu Ala Arg Ala Val Leu Ala Asp Asn Arg Phe
    50                  55                  60

Ala Lys Asp Trp Ser Arg Ala Asn Gly Ser Leu Ala Asp Ser Glu Val
65                  70                  75                  80

Leu Ala Glu Trp Gln Leu Met Asn Met Leu Asp Ala Asp Pro Pro Gln
                85                  90                  95

His Thr Arg Leu Arg Lys Leu Val Ala Arg Glu Phe Thr Thr Arg Arg
            100                 105                 110

Val Glu Ala Leu Arg Pro Arg Val Gln Gln Ile Thr Asp Glu Leu Leu
        115                 120                 125

Asp Ala Met Leu Ala Ala Pro Asp Gly Arg Ala Asp Leu Val Glu Ala
    130                 135                 140

Leu Ala Phe Pro Leu Pro Met Thr Val Ile Cys Glu Leu Leu Gly Val
145                 150                 155                 160
```

```
Pro Asp Ile Glu Arg Asp Thr Phe Arg Ala Trp Ser Asn Glu Leu Val
                165                 170                 175

Ser Pro Thr Asp Asn Glu Ala Thr Met Thr Ala Ala Arg Glu Met Ala
            180                 185                 190

Ala Tyr Leu Asp Gly Leu Ile Glu Ser Lys Arg Ser Ser Pro Gly Glu
        195                 200                 205

Asp Leu Leu Ser Ala Leu Val Arg Thr Ser Asp Glu Asp Gly Asp Gln
    210                 215                 220

Leu Ser Arg Gln Glu Leu Leu Gly Met Ala Phe Leu Leu Leu Val Ala
225                 230                 235                 240

Gly His Glu Thr Thr Val Asn Leu Ile Ser Asn Gly Val Arg Ala Leu
                245                 250                 255

Leu Gln His Pro Ala Gln Leu Ala Ala Leu Arg Ala Asp Pro Ser Leu
            260                 265                 270

Leu Asp Asn Ala Val Glu Glu Met Leu Arg Tyr Asp Gly Pro Val Glu
        275                 280                 285

Thr Ala Thr Trp Arg Phe Thr Ala Glu Pro Val Gly Ile Gly Gly Val
    290                 295                 300

Glu Ile Pro Ala Gly Glu Ile Val Leu Val Gly Leu Ala Gly Ala Asp
305                 310                 315                 320

Arg Asp Pro Glu Arg Phe Glu Ala Pro Asp Thr Phe Asp Ile Thr Arg
                325                 330                 335

Glu Thr Arg Gly His Val Ala Phe Gly His Gly Ile His Phe Cys Leu
            340                 345                 350

Gly Ala Pro Leu Ala Arg Val Glu Gly Arg Ile Ala Val Arg Thr Leu
        355                 360                 365

Leu Asp Arg Cys Pro Asp Leu Ala Leu Asp Thr Ala Pro Glu Ala Leu
    370                 375                 380

Thr Trp Arg Ala Gly Met Thr Ile Arg Gly Pro Gln His Leu Pro Val
385                 390                 395                 400

Arg Trp Arg
```

<210> SEQ ID NO 48
<211> LENGTH: 1263
<212> TYPE: DNA
<213> ORGANISM: Streptomyces rimosus

<400> SEQUENCE: 48

```
atgtcagtgc cgagccgccc gccggccacc gtgctcgaca acccgctgca cgccctgctc      60

gaccgggagg tgctcgcgaa cccctacccg ctgttcgagc ggtggcggga gcaaggtccg     120

atgtggacgt cggacggttc cctgctgctg agcgaccacg ccagttgtct ggcggtgctc     180

aagagccacc cgaccatggg cagtgacacg ttcaacgcgc cggggatgcg ggaactcttc     240

ggcgaccgcg gcgacgagcc ggtgctcaac tcgatcttct tcatggacga tcccggacac     300

gggcggcagc ggaacctggt cagcaaggca ttcacaccac ggatcaccgc gcgcttcgag     360

ccgtggatcc gcgagatcgt ggacgaactg cttcgcgact gcctggccga cggcgagttc     420

gacggcgtgc aggacctggc cgcggtgctc tcgctgcggg tcatcgcgac gctcctgggc     480

atcccgcgcg aggacatccc gatgctgcgg gagtggtcca gcgacatggc gctgtccacg     540

gagctgccca cgctggtggc cagcttccac tccaccgcga tgttcgaccg cgaggaactc     600

gtccgcatca tccgtaccac caccgaactg cacggctact tcgcgaacct catccacaag     660

cgccgccgca accccggcga ggacctcatc tccagtctga tctccacgca ggagaacggg     720
```

cgcggactga gccggcgtga ggtgacgaac gtcgtggtga ccgtgttcac cgcggcccac 780
gagtccacca cgaacctgat caccaacggc ctgctcgcga tgtcgcgcca cccggagcag 840
ttccagctgc tccggcagaa cccggcgatc gtcggcgacg tggtcggcga ggcgctgcgc 900
tacgactgcc cgatcatgct gaccggccgg gtcgcgctgc ggtccgaccg gatcaacggc 960
atcgacatcc ccgagggctc ggtggtcacc ctggtcctcg cgtccggcaa cagggacgag 1020
cgggtgcacc cgaaggcgga tcggttcatc gcggaccgga agccggccgt gatgaacctc 1080
gccttcggcg ccggcgcgca cttctgcctc ggtagcagtc tggcccggct ggaggcggag 1140
atcgtgttcg gtgagctggc tcgccggctg cgcggctttc acgtgcacga ggactcactg 1200
agctatcgca ggcacgtggt cgtccgcggc ctcgacaccg aacggatcac tttccaactc 1260
taa 1263

<210> SEQ ID NO 49
<211> LENGTH: 420
<212> TYPE: PRT
<213> ORGANISM: Streptomyces rimosus

<400> SEQUENCE: 49

Met Ser Val Pro Ser Arg Pro Pro Ala Thr Val Leu Asp Asn Pro Leu
1 5 10 15

His Ala Leu Leu Asp Arg Glu Val Leu Ala Asn Pro Tyr Pro Leu Phe
20 25 30

Glu Arg Trp Arg Glu Gln Gly Pro Met Trp Thr Ser Asp Gly Ser Leu
35 40 45

Leu Leu Ser Asp His Ala Ser Cys Leu Ala Val Leu Lys Ser His Pro
50 55 60

Thr Met Gly Ser Asp Thr Phe Asn Ala Pro Gly Met Arg Glu Leu Phe
65 70 75 80

Gly Asp Arg Gly Asp Glu Pro Val Leu Asn Ser Ile Phe Phe Met Asp
85 90 95

Asp Pro Gly His Gly Arg Gln Arg Asn Leu Val Ser Lys Ala Phe Thr
100 105 110

Pro Arg Ile Thr Ala Arg Phe Glu Pro Trp Ile Arg Glu Ile Val Asp
115 120 125

Glu Leu Leu Arg Asp Cys Leu Ala Asp Gly Glu Phe Asp Gly Val Gln
130 135 140

Asp Leu Ala Ala Val Leu Ser Leu Arg Val Ile Ala Thr Leu Leu Gly
145 150 155 160

Ile Pro Arg Glu Asp Ile Pro Met Leu Arg Glu Trp Ser Ser Asp Met
165 170 175

Ala Leu Ser Thr Glu Leu Pro Thr Leu Val Ala Ser Phe His Ser Thr
180 185 190

Ala Met Phe Asp Arg Glu Glu Leu Val Arg Ile Ile Arg Thr Thr Thr
195 200 205

Glu Leu His Gly Tyr Phe Ala Asn Leu Ile His Lys Arg Arg Arg Asn
210 215 220

Pro Gly Glu Asp Leu Ile Ser Ser Leu Ile Ser Thr Gln Glu Asn Gly
225 230 235 240

Arg Gly Leu Ser Arg Arg Glu Val Thr Asn Val Val Val Thr Val Phe
245 250 255

Thr Ala Ala His Glu Ser Thr Thr Asn Leu Ile Thr Asn Gly Leu Leu
260 265 270

```
Ala Met Ser Arg His Pro Glu Gln Phe Gln Leu Leu Arg Gln Asn Pro
        275                 280                 285

Ala Ile Val Gly Asp Val Val Gly Glu Ala Leu Arg Tyr Asp Cys Pro
    290                 295                 300

Ile Met Leu Thr Gly Arg Val Ala Leu Arg Ser Asp Arg Ile Asn Gly
305                 310                 315                 320

Ile Asp Ile Pro Glu Gly Ser Val Val Thr Leu Val Leu Ala Ser Gly
                325                 330                 335

Asn Arg Asp Glu Arg Val His Pro Lys Ala Asp Arg Phe Ile Ala Asp
            340                 345                 350

Arg Lys Pro Ala Val Met Asn Leu Ala Phe Gly Ala Gly Ala His Phe
        355                 360                 365

Cys Leu Gly Ser Ser Leu Ala Arg Leu Glu Ala Glu Ile Val Phe Gly
    370                 375                 380

Glu Leu Ala Arg Arg Leu Arg Gly Phe His Val His Glu Asp Ser Leu
385                 390                 395                 400

Ser Tyr Arg Arg His Val Val Val Arg Gly Leu Asp Thr Glu Arg Ile
                405                 410                 415

Thr Phe Gln Leu
            420


<210> SEQ ID NO 50
<211> LENGTH: 1365
<212> TYPE: DNA
<213> ORGANISM: Streptomyces rimosus

<400> SEQUENCE: 50

atgaccacat cgcccaccga gtccaccacg gccaccccgc ccgactccac caccgcctcc      60

gcccccggca ccccgccgga cgccctgccg tcctacgtcg gcctgcaccc gggcgagccg     120

aacgtgatgg agccggagct gctcaacgac ccgtacgccg gttacgggaa gctgcgcgaa     180

cagggcgccc tggtgcgcgg ccggtttctc gacgactcgc ccgtctggct cgtgacccgc     240

ttcgacgtgg tacgcgaggt catgcgcgac ccgcggttca tcaacaaccc gtcccgcctg     300

cccggccgca cggagaagga cccgcgcgcc cagctgatcg agctgttcgg catccccgac     360

cacatggccc ggtacctggt ggacaccatc ctcaccagcg acccgccgga ccacacccgg     420

ctgcggcgcc tggtctcgcg ggccttcacc gcccgccgca tccaggacct gcggccgcgg     480

gtggaggcga tcaccgacga gctgctggac cggttgccgg cccacgcgca ggacggcgtc     540

gtcgacctcg tcgagcactt cgcgtacccg ctgcccatca ccgtgatctg cgaactggtc     600

ggcatcgacg aggaggaccg gccgctgtgg cggcagttcg gcgccgacct cacctccctg     660

gagccgaagc ggatcggcgc cacggtaccg gccatggtcg agcacatcca caaggtgatc     720

ggcgagcgcc aatcggccct gcgggacgac ctgctcagcg cgctcatccg ggcccgggac     780

gacgacggcg gccggctgag cgagaccgag atggtcacca tggtcctcac gctggtactg     840

gccggccacg agaccaccgc ccacctcatc agcaacggca ccctcgccct gctcacccac     900

cccgaccagc ggcgcctgct caccgaggac ccgggcctgc tcccccgcgc ggtccacgag     960

ctgatgcgct ggtgcgggcc gatccaggcc acccagctgc ggtacgcctc cgaggacgtc    1020

gaggtggccg gcacccaggt ccacaagggc gacgccctga tgttcagcct cgtggcggcc    1080

aaccacgacc cgcgccacta caccgagccg gaaaaactcg acctgacacg ccagccggcg    1140

ggccgcgccg aggaccacgt cggcttcgga cacggcatgc actactgcct gggcgcctca    1200
```

-continued

```
ctcgcccggc aggaaggcga agtcgccttc ggcaagctgc tcgcacgcta tccggaggtg   1260

gcactcgccc tgccccatga gcagctggag gagcaagagc gcatacgcca gcccgggtcc   1320

tggcgactgc ggcggctgcc gttgcggctg cgtccggagg actaa                   1365


<210> SEQ ID NO 51
<211> LENGTH: 454
<212> TYPE: PRT
<213> ORGANISM: Streptomyces rimosus

<400> SEQUENCE: 51

Met Thr Thr Ser Pro Thr Glu Ser Thr Thr Ala Thr Pro Pro Asp Ser
1               5                   10                  15

Thr Thr Ala Ser Ala Pro Gly Thr Pro Pro Asp Ala Leu Pro Ser Tyr
            20                  25                  30

Val Gly Leu His Pro Gly Glu Pro Asn Val Met Glu Pro Glu Leu Leu
        35                  40                  45

Asn Asp Pro Tyr Ala Gly Tyr Gly Lys Leu Arg Glu Gln Gly Ala Leu
    50                  55                  60

Val Arg Gly Arg Phe Leu Asp Asp Ser Pro Val Trp Leu Val Thr Arg
65                  70                  75                  80

Phe Asp Val Val Arg Glu Val Met Arg Asp Pro Arg Phe Ile Asn Asn
                85                  90                  95

Pro Ser Arg Leu Pro Gly Arg Thr Glu Lys Asp Pro Arg Ala Gln Leu
            100                 105                 110

Ile Glu Leu Phe Gly Ile Pro Asp His Met Ala Arg Tyr Leu Val Asp
        115                 120                 125

Thr Ile Leu Thr Ser Asp Pro Pro Asp His Thr Arg Leu Arg Arg Leu
    130                 135                 140

Val Ser Arg Ala Phe Thr Ala Arg Arg Ile Gln Asp Leu Arg Pro Arg
145                 150                 155                 160

Val Glu Ala Ile Thr Asp Glu Leu Leu Asp Arg Leu Pro Ala His Ala
                165                 170                 175

Gln Asp Gly Val Val Asp Leu Val Glu His Phe Ala Tyr Pro Leu Pro
            180                 185                 190

Ile Thr Val Ile Cys Glu Leu Val Gly Ile Asp Glu Glu Asp Arg Pro
        195                 200                 205

Leu Trp Arg Gln Phe Gly Ala Asp Leu Thr Ser Leu Glu Pro Lys Arg
    210                 215                 220

Ile Gly Ala Thr Val Pro Ala Met Val Glu His Ile His Lys Val Ile
225                 230                 235                 240

Gly Glu Arg Gln Ser Ala Leu Arg Asp Asp Leu Leu Ser Ala Leu Ile
                245                 250                 255

Arg Ala Arg Asp Asp Asp Gly Gly Arg Leu Ser Glu Thr Glu Met Val
            260                 265                 270

Thr Met Val Leu Thr Leu Val Leu Ala Gly His Glu Thr Thr Ala His
        275                 280                 285

Leu Ile Ser Asn Gly Thr Leu Ala Leu Leu Thr His Pro Asp Gln Arg
    290                 295                 300

Arg Leu Leu Thr Glu Asp Pro Gly Leu Leu Pro Arg Ala Val His Glu
305                 310                 315                 320

Leu Met Arg Trp Cys Gly Pro Ile Gln Ala Thr Gln Leu Arg Tyr Ala
                325                 330                 335

Ser Glu Asp Val Glu Val Ala Gly Thr Gln Val His Lys Gly Asp Ala
            340                 345                 350
```

-continued

Leu Met Phe Ser Leu Val Ala Ala Asn His Asp Pro Arg His Tyr Thr
355 360 365

Glu Pro Glu Lys Leu Asp Leu Thr Arg Gln Pro Ala Gly Arg Ala Glu
370 375 380

Asp His Val Gly Phe Gly His Gly Met His Tyr Cys Leu Gly Ala Ser
385 390 395 400

Leu Ala Arg Gln Glu Gly Glu Val Ala Phe Gly Lys Leu Leu Ala Arg
405 410 415

Tyr Pro Glu Val Ala Leu Ala Leu Pro His Glu Gln Leu Glu Glu Gln
420 425 430

Glu Arg Ile Arg Gln Pro Gly Ser Trp Arg Leu Arg Arg Leu Pro Leu
435 440 445

Arg Leu Arg Pro Glu Asp
450

<210> SEQ ID NO 52
<211> LENGTH: 1245
<212> TYPE: DNA
<213> ORGANISM: Streptomyces rimosus

<400> SEQUENCE: 52
atgaccgccg agaaccacac cgcgcagccc caggcgcccg cgcccgacgg gatcccgtac 60
gacgagcccc ttccgcacta ccccttcagc accaaggggg accggctcgc cccgaactc 120 gacgagctgc gcagccgctg ccccgtggcc cgggtcagca ccaactccgg tgaacaggcg 180
tggctggtga ccgactacgg gctcgcccag cacgtactgc gggaccgcgc cttcgcccgc 240
tccgtgctgg gcgaggcgga cagccccgcc caggacgccc cgatcctcgc gcccgaactg 300
ctcgacgcca tgaaccacct ccagcaggcc gggctgcgtg ccgaagtgct ccgctcgctc 360
ggccgcgacc agcccgacct gcccgccgac tgggtcgcgc gggtcaccgg cgaagggctg 420
gacgcgatga tccgcgaagg cgcccccggc gacctccagc gccacttcgc tgagtgggtc 480
gccgcccagt gcatgtgccg cctcctcggc gtgcccttcg aggaccatgc ctggctcgcc 540
gtacgggcgg acctggacct gaccatggtc acccccaccc ccgaggaact cgcccgcaac 600
tgggaggaga tccgcgccta catggccgcg cacatgacgg cccgccgccc cggcgagccc 660
cgaggcctcg tggaccgcct cgccgacctc aacgccgcgc accaagggct gacggagcgg 720
cagctgtcga acatcgtgtc cgtcctcttc gtcagcggct acgaggactt cgcgagcttc 780
ctgggcgtcg cggcctacaa cctgctccag cacccggaga ccatcagcgc ggtgcgcgcc 840
gagccggaga ccatgccgca gtgcgtggag gagctgctgc ggtgcagcgt cgtgctgggc 900
aacgcgattc cccgctttgt caccgccgac gcgcggatcg gcccgtccca ggtcaaaaag 960
ggcgacatgg tcctgctctc cctggacgcg gtcaactacg actcgaccgc gttccccgac 1020
cccaagacct tcgaccccac ccgctcaccc aacccccacc tgcgcttcgg ctacggccgc 1080
caccactgcc ccggcgccca cctggtccgc cgccagtccg aggtcgcctt ccgcgtcctc 1140
ctcgaccgcc tgcccggcat ccacctggtg gtgccgccgc aagaggttcc ctggcacccg 1200
aaccgcatgg cgatcatggc ggcggagatt ccggtggcgt ggtaa 1245

<210> SEQ ID NO 53
<211> LENGTH: 414
<212> TYPE: PRT
<213> ORGANISM: Streptomyces rimosus

<400> SEQUENCE: 53

-continued

```
Met Thr Ala Glu Asn His Thr Ala Gln Pro Gln Ala Pro Ala Pro Asp
1               5                   10                  15

Gly Ile Pro Tyr Asp Glu Pro Leu Pro His Tyr Pro Phe Ser Thr Lys
            20                  25                  30

Gly Asp Arg Leu Ala Pro Glu Leu Asp Glu Leu Arg Ser Arg Cys Pro
        35                  40                  45

Val Ala Arg Val Ser Thr Asn Ser Gly Glu Gln Ala Trp Leu Val Thr
    50                  55                  60

Asp Tyr Gly Leu Ala Gln His Val Leu Arg Asp Arg Ala Phe Ala Arg
65                  70                  75                  80

Ser Val Leu Gly Glu Ala Asp Ser Pro Ala Gln Asp Ala Pro Ile Leu
                85                  90                  95

Ala Pro Glu Leu Leu Asp Ala Met Asn His Leu Gln Gln Ala Gly Leu
            100                 105                 110

Arg Ala Glu Val Leu Arg Ser Leu Gly Arg Asp Gln Pro Asp Leu Pro
        115                 120                 125

Ala Asp Trp Val Ala Arg Val Thr Gly Glu Gly Leu Asp Ala Met Ile
    130                 135                 140

Arg Glu Gly Ala Pro Gly Asp Leu Gln Arg His Phe Ala Glu Trp Val
145                 150                 155                 160

Ala Ala Gln Cys Met Cys Arg Leu Leu Gly Val Pro Phe Glu Asp His
                165                 170                 175

Ala Trp Leu Ala Val Arg Ala Asp Leu Asp Leu Thr Met Val Thr Pro
            180                 185                 190

Thr Pro Glu Glu Leu Ala Arg Asn Trp Glu Glu Ile Arg Ala Tyr Met
        195                 200                 205

Ala Ala His Met Thr Ala Arg Arg Pro Gly Glu Pro Arg Gly Leu Val
    210                 215                 220

Asp Arg Leu Ala Asp Leu Asn Ala Ala His Gln Gly Leu Thr Glu Arg
225                 230                 235                 240

Gln Leu Ser Asn Ile Val Ser Val Leu Phe Val Ser Gly Tyr Glu Asp
                245                 250                 255

Phe Ala Ser Phe Leu Gly Val Ala Ala Tyr Asn Leu Leu Gln His Pro
            260                 265                 270

Glu Thr Ile Ser Ala Val Arg Ala Glu Pro Glu Thr Met Pro Gln Cys
        275                 280                 285

Val Glu Glu Leu Leu Arg Cys Ser Val Val Leu Gly Asn Ala Ile Pro
    290                 295                 300

Arg Phe Val Thr Ala Asp Ala Arg Ile Gly Pro Ser Gln Val Lys Lys
305                 310                 315                 320

Gly Asp Met Val Leu Leu Ser Leu Asp Ala Val Asn Tyr Asp Ser Thr
                325                 330                 335

Ala Phe Pro Asp Pro Lys Thr Phe Asp Pro Thr Arg Ser Pro Asn Pro
            340                 345                 350

His Leu Arg Phe Gly Tyr Gly Arg His His Cys Pro Gly Ala His Leu
        355                 360                 365

Val Arg Arg Gln Ser Glu Val Ala Phe Arg Val Leu Leu Asp Arg Leu
    370                 375                 380

Pro Gly Ile His Leu Val Val Pro Pro Gln Glu Val Pro Trp His Pro
385                 390                 395                 400

Asn Arg Met Ala Ile Met Ala Ala Glu Ile Pro Val Ala Trp
                405                 410
```

<210> SEQ ID NO 54
<211> LENGTH: 1215
<212> TYPE: DNA
<213> ORGANISM: Streptomyces rimosus

<400> SEQUENCE: 54

```
atgccgcagg acacctcccg ccggttcgag cgagcgccca gggccgcctt cggccccgac     60
gcccacaccc gcgagctgca cgggaaagca ccggtcagca aagtcgacat gggcccgata    120
cccgactcgg acgccggccg cgccacggtc tggctggtca cgggctacca cgaggtacgc    180
caggtcctcg gcgaccacgt acggttcggc aacggcttcg cctccggccc ggtgtacggg    240
accgcgagcc gcttccggcc cccggaggtc gtcgggcacc tgatggacta cgacccgccg    300
gagcacaccc ggctgcgccg gatgctgacc ccggcgttca cggtccggcg gatgcggcag    360
ctggagcccc gtatcgaaga ggtcgtggcg cgctgcctgg acggcgtggc gaaggccggg    420
cagcccgccg acctggtgga acggttcgcc cgcccggtgt cgggcgaggc gctgtgcgaa    480
ctgctcgggg tgccgcgcga cgaccgtacg gacttcgtgc gccgcgtcca gtggcagctg    540
gagcaggacc ggccgcgcag gcagcgggcc gacgcgggcg agtcctacct gcgctacctc    600
ggcgcgatgg tgcgccgccg tcgcaaggac cccgacgaca gcttcatcgg cacgctcgta    660
cgcgagcacg gcgacagcat caccgacgag gaactgcgcg gcgtctgcgg cctgatgatg    720
ctcgccgggc tcgacaacgt ctccggcatg atcagcctgg gcatcctcgt cctgctccag    780
caccccgacc agctcgccgc gctgcacgcc ggcaccgcgt ccgcggaccg cgtggtcgac    840
gagctgctgc gctacctgtc ggtggcgcac gcaccgcagc ggcggatcgc cctggcggac    900
gtcaccgtcg cgggccaggt gatcaaaaag ggggagcagg tcctgtgctc cctccagatg    960
gccaaccgcg acccggcctt cctcccgcac cccgaccgct tcgacgccac ccgcgacccc   1020
gcgccccacg tcgccttcgg ccatggcatc caccactgca tcggcgccgc gatgtccagg   1080
atggaactgc gcatcgccta ccgcgccctg tggcaccgct tccccggact gcggctggcc   1140
gtccccgtgg aggagatcgc gtatcggacc aatgcggtgg cggacggggt ggtgaggctg   1200
cctgtggtgt ggtaa                                                    1215
```

<210> SEQ ID NO 55
<211> LENGTH: 404
<212> TYPE: PRT
<213> ORGANISM: Streptomyces rimosus

<400> SEQUENCE: 55

```
Met Pro Gln Asp Thr Ser Arg Arg Phe Glu Arg Ala Pro Arg Ala Ala
1               5                   10                  15

Phe Gly Pro Asp Ala His Thr Arg Glu Leu His Gly Lys Ala Pro Val
            20                  25                  30

Ser Lys Val Asp Met Gly Pro Ile Pro Asp Ser Asp Ala Gly Arg Ala
        35                  40                  45

Thr Val Trp Leu Val Thr Gly Tyr His Glu Val Arg Gln Val Leu Gly
    50                  55                  60

Asp His Val Arg Phe Gly Asn Gly Phe Ala Ser Gly Pro Val Tyr Gly
65                  70                  75                  80

Thr Ala Ser Arg Phe Arg Pro Pro Glu Val Val Gly His Leu Met Asp
                85                  90                  95

Tyr Asp Pro Pro Glu His Thr Arg Leu Arg Arg Met Leu Thr Pro Ala
            100                 105                 110
```

-continued

```
Phe Thr Val Arg Arg Met Arg Gln Leu Glu Pro Arg Ile Glu Glu Val
        115                 120                 125

Val Ala Arg Cys Leu Asp Gly Val Ala Lys Ala Gly Gln Pro Ala Asp
    130                 135                 140

Leu Val Glu Arg Phe Ala Arg Pro Val Ser Gly Glu Ala Leu Cys Glu
145                 150                 155                 160

Leu Leu Gly Val Pro Arg Asp Asp Arg Thr Asp Phe Val Arg Arg Val
                165                 170                 175

Gln Trp Gln Leu Glu Gln Asp Arg Pro Arg Arg Gln Arg Ala Asp Ala
            180                 185                 190

Gly Glu Ser Tyr Leu Arg Tyr Leu Gly Ala Met Val Arg Arg Arg Arg
        195                 200                 205

Lys Asp Pro Asp Asp Ser Phe Ile Gly Thr Leu Val Arg Glu His Gly
    210                 215                 220

Asp Ser Ile Thr Asp Glu Glu Leu Arg Gly Val Cys Gly Leu Met Met
225                 230                 235                 240

Leu Ala Gly Leu Asp Asn Val Ser Gly Met Ile Ser Leu Gly Ile Leu
                245                 250                 255

Val Leu Leu Gln His Pro Asp Gln Leu Ala Ala Leu His Ala Gly Thr
            260                 265                 270

Ala Ser Ala Asp Arg Val Val Asp Glu Leu Leu Arg Tyr Leu Ser Val
        275                 280                 285

Ala His Ala Pro Gln Arg Arg Ile Ala Leu Ala Asp Val Thr Val Ala
    290                 295                 300

Gly Gln Val Ile Lys Lys Gly Glu Gln Val Leu Cys Ser Leu Gln Met
305                 310                 315                 320

Ala Asn Arg Asp Pro Ala Phe Leu Pro His Pro Asp Arg Phe Asp Ala
                325                 330                 335

Thr Arg Asp Pro Ala Pro His Val Ala Phe Gly His Gly Ile His His
            340                 345                 350

Cys Ile Gly Ala Ala Met Ser Arg Met Glu Leu Arg Ile Ala Tyr Arg
        355                 360                 365

Ala Leu Trp His Arg Phe Pro Gly Leu Arg Leu Ala Val Pro Val Glu
    370                 375                 380

Glu Ile Ala Tyr Arg Thr Asn Ala Val Ala Asp Gly Val Val Arg Leu
385                 390                 395                 400

Pro Val Val Trp


<210> SEQ ID NO 56
<211> LENGTH: 1254
<212> TYPE: DNA
<213> ORGANISM: Streptomyces rimosus

<400> SEQUENCE: 56

atggatgagt cgcccgtctt cgtcctggat cccgcaggcc gtgaccggca cggtgaggac      60

gcccggttgc gcgcccgtgg cccgctcacc cgggtggacg tgctcggcgt cgaagcctgg     120

gcggtctccg accctgttct gctgcgtcgg ctcctcatgg acccgcgcgt ctccaaggat     180

gcccgccgtc actggcctgc ctatcccggc cggatcgcgg gggtctggcc gctggagctg     240

tgggtggcgg tggacaacat gttcaccgcc tacggtgacg aacaccgtcg gctccgccgc     300

atcatcagcc aggtcttcac cgcgcggcac gtcaacgccc tggcacccgt catcgaacgc     360

atcgccggag agctgctcga cggccttgct gccacaccgc ccggtacgcc ggtggacctg     420

cgtgaacgct tcgcgtcgcc gttgccgatc agggtcgtca gccacttggt gggcctgtcc     480
```

```
gaagcggacg ggccacgctt ccgccgtacc gtcgacaagg tcttctccac cagtctggac    540

ccggtggagg caggcgccaa cgtcgctgaa ctgtacgcgc tgctgaccgg cctggtcgcc    600

gcgaaacggg ccgagcccgg cgacgacctg gcctccaagc tcatcaccgc gcgggacagt    660

gagggcgacg gatcacgtct caccgagacc gaactgatcg acactctcct cctggtgatc    720

aacgccgggt tcgagaccac cgtcaacctg atcgaccaag ccgtcacggc cttgctcacc    780

caccccggcc ggctcgccct cgcgcgagcg ggccgcgtcg gctggcagga cgtcgtggag    840

gagacgctgc gctgggaggc cccggtaccg tacctgccca tgcgctacgc ggtggaggac    900

atcccgctgc ccggccacgg cccgacgatc cgcaaagggg acgcgatcct cgcctcgtac    960

ggcgccgcca accggcaccc ggacctccac ggtcccaccg ccgatcagtt cgaccccgcc   1020

aggacggaca aatcccacct ctccttcgga cacggagtgc acgcctgcct gggtgccgca   1080

ctcgcccggc tggaaggcac gatcgccctg cgcggcctct tcgaacgctt ccccgatctc   1140

gctctcgccg tcccggcaca ccggctgcgc cccctgccga gcttcgtctc caacggccac   1200

cgcgaactac cggttgtgct ccgctccgcg ccggccgggg aagcaggggg ataa         1254
```

<210> SEQ ID NO 57
<211> LENGTH: 417
<212> TYPE: PRT
<213> ORGANISM: Streptomyces rimosus

<400> SEQUENCE: 57

```
Met Asp Glu Ser Pro Val Phe Val Leu Asp Pro Ala Gly Arg Asp Arg
1               5                   10                  15

His Gly Glu Asp Ala Arg Leu Arg Ala Arg Gly Pro Leu Thr Arg Val
            20                  25                  30

Asp Val Leu Gly Val Glu Ala Trp Ala Val Ser Asp Pro Val Leu Leu
        35                  40                  45

Arg Arg Leu Leu Met Asp Pro Arg Val Ser Lys Asp Ala Arg Arg His
    50                  55                  60

Trp Pro Ala Tyr Pro Gly Arg Ile Ala Gly Val Trp Pro Leu Glu Leu
65                  70                  75                  80

Trp Val Ala Val Asp Asn Met Phe Thr Ala Tyr Gly Asp Glu His Arg
                85                  90                  95

Arg Leu Arg Arg Ile Ile Ser Gln Val Phe Thr Ala Arg His Val Asn
            100                 105                 110

Ala Leu Ala Pro Val Ile Glu Arg Ile Ala Gly Glu Leu Leu Asp Gly
        115                 120                 125

Leu Ala Ala Thr Pro Pro Gly Thr Pro Val Asp Leu Arg Glu Arg Phe
    130                 135                 140

Ala Ser Pro Leu Pro Ile Arg Val Val Ser His Leu Val Gly Leu Ser
145                 150                 155                 160

Glu Ala Asp Gly Pro Arg Phe Arg Arg Thr Val Asp Lys Val Phe Ser
                165                 170                 175

Thr Ser Leu Asp Pro Val Glu Ala Gly Ala Asn Val Ala Glu Leu Tyr
            180                 185                 190

Ala Leu Leu Thr Gly Leu Val Ala Ala Lys Arg Ala Glu Pro Gly Asp
        195                 200                 205

Asp Leu Ala Ser Lys Leu Ile Thr Ala Arg Asp Ser Glu Gly Asp Gly
    210                 215                 220

Ser Arg Leu Thr Glu Thr Glu Leu Ile Asp Thr Leu Leu Leu Val Ile
225                 230                 235                 240
```

```
Asn Ala Gly Phe Glu Thr Thr Val Asn Leu Ile Asp Gln Ala Val Thr
                245                 250                 255

Ala Leu Leu Thr His Pro Gly Arg Leu Ala Leu Ala Arg Ala Gly Arg
            260                 265                 270

Val Gly Trp Gln Asp Val Val Glu Glu Thr Leu Arg Trp Glu Ala Pro
        275                 280                 285

Val Pro Tyr Leu Pro Met Arg Tyr Ala Val Glu Asp Ile Pro Leu Pro
    290                 295                 300

Gly His Gly Pro Thr Ile Arg Lys Gly Asp Ala Ile Leu Ala Ser Tyr
305                 310                 315                 320

Gly Ala Ala Asn Arg His Pro Asp Leu His Gly Pro Thr Ala Asp Gln
                325                 330                 335

Phe Asp Pro Ala Arg Thr Asp Lys Ser His Leu Ser Phe Gly His Gly
            340                 345                 350

Val His Ala Cys Leu Gly Ala Ala Leu Ala Arg Leu Glu Gly Thr Ile
        355                 360                 365

Ala Leu Arg Gly Leu Phe Glu Arg Phe Pro Asp Leu Ala Leu Ala Val
    370                 375                 380

Pro Ala His Arg Leu Arg Pro Leu Pro Ser Phe Val Ser Asn Gly His
385                 390                 395                 400

Arg Glu Leu Pro Val Val Leu Arg Ser Ala Pro Ala Gly Glu Ala Gly
                405                 410                 415

Gly
```

<210> SEQ ID NO 58
<211> LENGTH: 1377
<212> TYPE: DNA
<213> ORGANISM: Streptomyces rimosus

<400> SEQUENCE: 58

```
atggagactg ccccgctccg ccccgtaccc ggcccgcgcg gcctgccgtg gctcggaaac     60

ctgcccgcct tcggcaagga cccgctggcg ttcctgaccc ggctgcggga cgccggcgac    120

gccgtgacgt ggtccctcgg cccgcggcgc agcctgttcc tctcccaccc gcagcacatc    180

gccgaattcc tcggctcccg gggcggcgcc tacgacgtcc tgcgaatcgg ctgggccatg    240

caccagctcg tcggcgagag cgtcctgctc accgcggggg ccgagtggcg ccgcaagcgc    300

ggcatggtcc agccgaccgt ccgcccgcgc caggtccgcc gcttcgcccg gaccatggtc    360

gacagcgccc tcgcggcggt cggcggctgg cgcgacggcg accgcttcga cctgcggcgg    420

gagatgacgc tcatcactca gcgcatcgtg ctccgtacgc tgttcggcaa cgacctcggg    480

gaccggaccc aggccctcgg cgaggcgatg gcgacggccg aacgcgcggt cgccaccgag    540

atccgcggcc tgcctctgat cctcccgcca tgggtgccgc tgccctaccg ccggcgtcat    600

ctcggcgccg tcgccaccat cgacgccgag atgcggcggc tgatcgacgc ccggcgggcc    660

ggggcggacg gcggggacgg tgccggtgcg gacggcggcc agggcggcga tctgctgacc    720

cggctgctcg cggcgcggga cgaggaaggg cgcccgctgt ccgccaaaga ggtccaggac    780

gaggcggtga cgctctgggc ggccggtcac gagacgacct ccaccgcgtt gacgtggacc    840

tggtacctgc tgtcccggtc gcccgaggcg cgggcccggc tggacgacga ggtcgaccgc    900

gtcctgggcg gccgcccacc caccgaggag gactacgaac ggctggtctg gacccggcag    960

atcgtcaagg agagcctgcg gatgtatccg ccggtctggc tcgtccccgc cgtggccaag   1020

gagggcgtcg tcctgggcgg ccgcgccatt cccgccggta cgacggtgtg gtgcagccag   1080
```

```
tggacggtcc accgggaccc gcgctggttc cgcgaccccc aggtgttccg ccctgaacgc   1140

tgggacgccg acgctcccga cgtcatcccc gaacacgctt ggttcccgtt cggcggcggc   1200

tcccgcggct gtatcggcgc ccggttcgcc cagatggagg cggctttgct catcgccgcc   1260

gtggcgcagc gcttccacct ggacgtgacg ccgaaggagg cgacgccgcg catgggcatg   1320

gtcattcagc cggccgtgcc gctgatcgcc acggtgcgcg ctcgttcgcg tccgtaa      1377


<210> SEQ ID NO 59
<211> LENGTH: 458
<212> TYPE: PRT
<213> ORGANISM: Streptomyces rimosus

<400> SEQUENCE: 59

Met Glu Thr Ala Pro Leu Arg Pro Val Pro Gly Pro Arg Gly Leu Pro
1               5                   10                  15

Trp Leu Gly Asn Leu Pro Ala Phe Gly Lys Asp Pro Leu Ala Phe Leu
            20                  25                  30

Thr Arg Leu Arg Asp Ala Gly Asp Ala Val Thr Trp Ser Leu Gly Pro
        35                  40                  45

Arg Arg Ser Leu Phe Leu Ser His Pro Gln His Ile Ala Glu Phe Leu
    50                  55                  60

Gly Ser Arg Gly Gly Ala Tyr Asp Val Leu Arg Ile Gly Trp Ala Met
65                  70                  75                  80

His Gln Leu Val Gly Glu Ser Val Leu Leu Thr Ala Gly Ala Glu Trp
                85                  90                  95

Arg Arg Lys Arg Gly Met Val Gln Pro Thr Val Arg Pro Arg Gln Val
            100                 105                 110

Arg Arg Phe Ala Arg Thr Met Val Asp Ser Ala Leu Ala Ala Val Gly
        115                 120                 125

Gly Trp Arg Asp Gly Asp Arg Phe Asp Leu Arg Arg Glu Met Thr Leu
    130                 135                 140

Ile Thr Gln Arg Ile Val Leu Arg Thr Leu Phe Gly Asn Asp Leu Gly
145                 150                 155                 160

Asp Arg Thr Gln Ala Leu Gly Glu Ala Met Ala Thr Ala Glu Arg Ala
                165                 170                 175

Val Ala Thr Glu Ile Arg Gly Leu Pro Leu Ile Leu Pro Pro Trp Val
            180                 185                 190

Pro Leu Pro Tyr Arg Arg Arg His Leu Gly Ala Val Ala Thr Ile Asp
        195                 200                 205

Ala Glu Met Arg Arg Leu Ile Asp Ala Arg Arg Ala Gly Ala Asp Gly
    210                 215                 220

Gly Asp Gly Ala Gly Ala Asp Gly Gly Gln Gly Gly Asp Leu Leu Thr
225                 230                 235                 240

Arg Leu Leu Ala Ala Arg Asp Glu Glu Gly Arg Pro Leu Ser Ala Lys
                245                 250                 255

Glu Val Gln Asp Glu Ala Val Thr Leu Trp Ala Ala Gly His Glu Thr
            260                 265                 270

Thr Ser Thr Ala Leu Thr Trp Thr Trp Tyr Leu Leu Ser Arg Ser Pro
        275                 280                 285

Glu Ala Arg Ala Arg Leu Asp Asp Glu Val Asp Arg Val Leu Gly Gly
    290                 295                 300

Arg Pro Pro Thr Glu Glu Asp Tyr Glu Arg Leu Val Trp Thr Arg Gln
305                 310                 315                 320
```

-continued

```
Ile Val Lys Glu Ser Leu Arg Met Tyr Pro Pro Val Trp Leu Val Pro
                325                 330                 335

Ala Val Ala Lys Glu Gly Val Val Leu Gly Gly Arg Ala Ile Pro Ala
            340                 345                 350

Gly Thr Thr Val Trp Cys Ser Gln Trp Thr Val His Arg Asp Pro Arg
        355                 360                 365

Trp Phe Arg Asp Pro Gln Val Phe Arg Pro Glu Arg Trp Asp Ala Asp
    370                 375                 380

Ala Pro Asp Val Ile Pro Glu His Ala Trp Phe Pro Phe Gly Gly Gly
385                 390                 395                 400

Ser Arg Gly Cys Ile Gly Ala Arg Phe Ala Gln Met Glu Ala Ala Leu
                405                 410                 415

Leu Ile Ala Ala Val Ala Gln Arg Phe His Leu Asp Val Thr Pro Lys
            420                 425                 430

Glu Ala Thr Pro Arg Met Gly Met Val Ile Gln Pro Ala Val Pro Leu
        435                 440                 445

Ile Ala Thr Val Arg Ala Arg Ser Arg Pro
    450                 455
```

<210> SEQ ID NO 60
<211> LENGTH: 1350
<212> TYPE: DNA
<213> ORGANISM: Streptomyces rimosus

<400> SEQUENCE: 60

```
atgcgcgatc cggtccgcta cttcgagacg ttgcgccggc gctacggtcc ggtgttccgt      60

atgaaattgc tcggcttccc gccccaggtc gtggtctcga ccgcggagct ggccgcggag     120

atctaccgta tggacggcga cggcaaccgc gccggagcgc tgcgcgcggg gtacgtgccg     180

tgggtcggac agcactcgct gctcaccaac gacggcgagg aatggtggcg ccaccgcaag     240

ctgctcagcc ccaccctgca cggcaggtcc atcgcgaact atcccgagct gatcgccgag     300

atcgccgcga aggacatcgg gacgtggccg ctcggcaggc cgttcaccct gcgcgagcac     360

atgcaggcca tcaccctgga ggtcatcctg cggctggtct tcggggtccg ggacaccgag     420

caggggggccc ggttacgggc cggtctcatc gacctgtcca aggccaccgg ctccgccgcc     480

ctgttcctga cgcccgcccg gctgcgggcc tgggcgcaac ggtctccgct ggcgatgcgc     540

ctgccgttcc tgccgacgac ccgcgccgcg caggccgtcg agacggtgga ccacatcctg     600

ttcgccgaga tcgcccggcg ccgggccgag gaggacgcgg acgccgacga cgtcctgggg     660

cggctgctcc gcgcccggga cgaccagggc cgcccgctca gcgaccagga gatccgcgac     720

gaactgctca ccctgctgga ggccggcctg gagaccacgg cgaccggcct gtcatggacc     780

ttcgagcggc tgatgcgcaa tccgcgggtg ctcgcgcggc tccaggagga ggtggagcag     840

ggcgaggacg acacctacct cgacgcggtc gtcaaggagg cgctgcggtc ccgtccggtg     900

atcttcggca tggggcggct gctggacaag ccgttgcggg tcggtgggtt cgaggtgccg     960

gccggctggg tggccatccc gatgttctcg ctgatcctcc aggaccgtgc ggtgtacccg    1020

gacgccgggg agttccggcc ggaacgcttc ctcggtgagg gcgccaaggc ggcgcagaag    1080

tcgttcctgc cgttcggcgg cggccgccgt tactgcgtcg gcgcccaact cgccacgctg    1140

gagatgaaga tcatcactcg cgaggtgctc cggcacgtcc atctggcccc cgccgacccc    1200

gcgccggagg cccagcgcat gtggcacgcc accctcatcc ccggcaagca ggtcgtcgcg    1260

gtggcccgca agcaaccgcc gaagcggcgg gcgccggtcc aggaggcgaa gtgccccgta    1320
```

```
catccggctc tttcggacga cgcggggtaa                                    1350


<210> SEQ ID NO 61
<211> LENGTH: 449
<212> TYPE: PRT
<213> ORGANISM: Streptomyces rimosus

<400> SEQUENCE: 61

Met Arg Asp Pro Val Arg Tyr Phe Glu Thr Leu Arg Arg Arg Tyr Gly
1               5                   10                  15

Pro Val Phe Arg Met Lys Leu Leu Gly Phe Pro Pro Gln Val Val Val
            20                  25                  30

Ser Thr Ala Glu Leu Ala Ala Glu Ile Tyr Arg Met Asp Gly Asp Gly
        35                  40                  45

Asn Arg Ala Gly Ala Leu Arg Ala Gly Tyr Val Pro Trp Val Gly Gln
    50                  55                  60

His Ser Leu Leu Thr Asn Asp Gly Glu Glu Trp Trp Arg His Arg Lys
65                  70                  75                  80

Leu Leu Ser Pro Thr Leu His Gly Arg Ser Ile Ala Asn Tyr Pro Glu
                85                  90                  95

Leu Ile Ala Glu Ile Ala Ala Lys Asp Ile Gly Thr Trp Pro Leu Gly
            100                 105                 110

Arg Pro Phe Thr Leu Arg Glu His Met Gln Ala Ile Thr Leu Glu Val
        115                 120                 125

Ile Leu Arg Leu Val Phe Gly Val Arg Asp Thr Glu Gln Gly Ala Arg
    130                 135                 140

Leu Arg Ala Gly Leu Ile Asp Leu Ser Lys Ala Thr Gly Ser Ala Ala
145                 150                 155                 160

Leu Phe Leu Thr Pro Ala Arg Leu Arg Ala Trp Ala Gln Arg Ser Pro
                165                 170                 175

Leu Ala Met Arg Leu Pro Phe Leu Pro Thr Thr Arg Ala Ala Gln Ala
            180                 185                 190

Val Glu Thr Val Asp His Ile Leu Phe Ala Glu Ile Ala Arg Arg Arg
        195                 200                 205

Ala Glu Glu Asp Ala Asp Ala Asp Asp Val Leu Gly Arg Leu Leu Arg
    210                 215                 220

Ala Arg Asp Asp Gln Gly Arg Pro Leu Ser Asp Gln Glu Ile Arg Asp
225                 230                 235                 240

Glu Leu Leu Thr Leu Leu Glu Ala Gly Leu Glu Thr Thr Ala Thr Gly
                245                 250                 255

Leu Ser Trp Thr Phe Glu Arg Leu Met Arg Asn Pro Arg Val Leu Ala
            260                 265                 270

Arg Leu Gln Glu Glu Val Glu Gln Gly Glu Asp Asp Thr Tyr Leu Asp
        275                 280                 285

Ala Val Val Lys Glu Ala Leu Arg Ser Arg Pro Val Ile Phe Gly Met
    290                 295                 300

Gly Arg Leu Leu Asp Lys Pro Leu Arg Val Gly Gly Phe Glu Val Pro
305                 310                 315                 320

Ala Gly Trp Val Ala Ile Pro Met Phe Ser Leu Ile Leu Gln Asp Arg
                325                 330                 335

Ala Val Tyr Pro Asp Ala Gly Glu Phe Arg Pro Glu Arg Phe Leu Gly
            340                 345                 350

Glu Gly Ala Lys Ala Ala Gln Lys Ser Phe Leu Pro Phe Gly Gly Gly
        355                 360                 365
```

```
Arg Arg Tyr Cys Val Gly Ala Gln Leu Ala Thr Leu Glu Met Lys Ile
    370                 375                 380

Ile Thr Arg Glu Val Leu Arg His Val His Leu Ala Pro Ala Asp Pro
385                 390                 395                 400

Ala Pro Glu Ala Gln Arg Met Trp His Ala Thr Leu Ile Pro Gly Lys
                405                 410                 415

Gln Val Val Ala Val Ala Arg Lys Gln Pro Pro Lys Arg Arg Ala Pro
            420                 425                 430

Val Gln Glu Ala Lys Cys Pro Val His Pro Ala Leu Ser Asp Asp Ala
        435                 440                 445

Gly
```

<210> SEQ ID NO 62
<211> LENGTH: 1269
<212> TYPE: DNA
<213> ORGANISM: Streptomyces rimosus

<400> SEQUENCE: 62

```
atgttcacac cccgcacgta cgccaccgcg gtcccgtacg aactcttcag ggaactgcgg     60

gcgacccggc cggtgtgctg gatcgaggaa ccggcggtcg acggctggcc cgccgggccc    120

ggctactggg ccgtgctgcg gcacgccgac gtcaaacacg tcctgcgtac ccccgagatc    180

tactcctcgt acctgggcgc gacccagatc cgcgaccccg acaccgagga ggacctcgcg    240

ttcgtccggg cgatgatgct caaccaggac cctccggacc acgcgcgcat ccggcgtgtc    300

gtcgccgcgg ccttcacccc gcgcgcggta cgggaactgg cggacgtcat cgacgcgcgg    360

gcacgggagc tggtggcgga ggtggcacgg gcgggcgagg cggacttcgt gaccgtggcc    420

gccgacctgc cggtgtggac gctggcgcac gtcatgggcg tcccggagga ggaccggcag    480

ctgctcttcg actggtcgaa ccgcgtcatc ggctaccagg acgacgcgta cgccacctcc    540

agcactgccg accccgcccg cctcagcccg atgggacggg ccgccctgcg ccaccggccc    600

gcaccggcgc tccgcccgga cggacgcccg gtcaacccgc gctcgcgccg cgcactggcc    660

gacatgttcg cgtacgccca cgcgctggcc gagcacccgc gccccggcac cgtgatggcc    720

cacctacggg aaggcggcct gacccgcgcc gagttcgaga acacgttctt cctcttcgcc    780

gtggccggca acgaaaccct gcgcaacggc atcccgggcg gcctgctcac cctcctccag    840

cacccggacc agttcgcccg cctccgccgg gaaccggacc tgaccgacag cgcggtggag    900

gaaatgctgc gctactggcc cccggtgatc gacttccgcc gcaccgccac ccgcgacacc    960

gaactcgccg gacagcacat ccgccgcggc gacaaggtcg tcgtctacca cgcctccgcc   1020

aaccgcgacg aaaccgtctt ccccaccccc gaccacttca acatcacccg cacccccaac   1080

gaccacctca gcttcggctt cggcccacac ttctgcctgg gcagccacct cgcccgcctc   1140

cagatgcggg cggtactccg gcatgtgctg gagcggctgc cgggggtgga gctggcgggg   1200

gagccggtgc ggttggtttc caactttcag aacgggttgc ggcggttgcc ggtgcgggtg   1260

ggggcgtaa                                                           1269
```

<210> SEQ ID NO 63
<211> LENGTH: 422
<212> TYPE: PRT
<213> ORGANISM: Streptomyces rimosus

<400> SEQUENCE: 63

```
Met Phe Thr Pro Arg Thr Tyr Ala Thr Ala Val Pro Tyr Glu Leu Phe
1               5                   10                  15
```

-continued

```
Arg Glu Leu Arg Ala Thr Arg Pro Val Cys Trp Ile Glu Glu Pro Ala
            20                  25                  30

Val Asp Gly Trp Pro Ala Gly Pro Gly Tyr Trp Ala Val Leu Arg His
        35                  40                  45

Ala Asp Val Lys His Val Leu Arg Thr Pro Glu Ile Tyr Ser Ser Tyr
    50                  55                  60

Leu Gly Ala Thr Gln Ile Arg Asp Pro Asp Thr Glu Glu Asp Leu Ala
65                  70                  75                  80

Phe Val Arg Ala Met Met Leu Asn Gln Asp Pro Pro Asp His Ala Arg
                85                  90                  95

Ile Arg Arg Val Val Ala Ala Ala Phe Thr Pro Arg Ala Val Arg Glu
            100                 105                 110

Leu Ala Asp Val Ile Asp Ala Arg Ala Arg Glu Leu Val Ala Glu Val
        115                 120                 125

Ala Arg Ala Gly Glu Ala Asp Phe Val Thr Val Ala Ala Asp Leu Pro
    130                 135                 140

Val Trp Thr Leu Ala His Val Met Gly Val Pro Glu Glu Asp Arg Gln
145                 150                 155                 160

Leu Leu Phe Asp Trp Ser Asn Arg Val Ile Gly Tyr Gln Asp Asp Ala
                165                 170                 175

Tyr Ala Thr Ser Ser Thr Ala Asp Pro Ala Arg Leu Ser Pro Met Gly
            180                 185                 190

Arg Ala Ala Leu Arg His Arg Pro Ala Pro Ala Leu Arg Pro Asp Gly
        195                 200                 205

Arg Pro Val Asn Pro Arg Ser Arg Arg Ala Leu Ala Asp Met Phe Ala
    210                 215                 220

Tyr Ala His Ala Leu Ala Glu His Pro Arg Pro Gly Thr Val Met Ala
225                 230                 235                 240

His Leu Arg Glu Gly Gly Leu Thr Arg Ala Glu Phe Glu Asn Thr Phe
                245                 250                 255

Phe Leu Phe Ala Val Ala Gly Asn Glu Thr Leu Arg Asn Gly Ile Pro
            260                 265                 270

Gly Gly Leu Leu Thr Leu Leu Gln His Pro Asp Gln Phe Ala Arg Leu
        275                 280                 285

Arg Arg Glu Pro Asp Leu Thr Asp Ser Ala Val Glu Glu Met Leu Arg
    290                 295                 300

Tyr Trp Pro Pro Val Ile Asp Phe Arg Arg Thr Ala Thr Arg Asp Thr
305                 310                 315                 320

Glu Leu Ala Gly Gln His Ile Arg Arg Gly Asp Lys Val Val Val Tyr
                325                 330                 335

His Ala Ser Ala Asn Arg Asp Glu Thr Val Phe Pro Thr Pro Asp His
            340                 345                 350

Phe Asn Ile Thr Arg Thr Pro Asn Asp His Leu Ser Phe Gly Phe Gly
        355                 360                 365

Pro His Phe Cys Leu Gly Ser His Leu Ala Arg Leu Gln Met Arg Ala
    370                 375                 380

Val Leu Arg His Val Leu Glu Arg Leu Pro Gly Val Glu Leu Ala Gly
385                 390                 395                 400

Glu Pro Val Arg Leu Val Ser Asn Phe Gln Asn Gly Leu Arg Arg Leu
                405                 410                 415

Pro Val Arg Val Gly Ala
            420
```

<210> SEQ ID NO 64
<211> LENGTH: 1227
<212> TYPE: DNA
<213> ORGANISM: Streptomyces rimosus

<400> SEQUENCE: 64

```
atgaccacgg acgacgacga agaagaggat cagcggatgc ccgagacacc cgagattccc     60

gcgcactacc ggcgggaccg cttcgacccg gtacccgaac tcgtccggat ggccagggag    120

acgccgctgg tcgagaccga cgtcacgatc ggtccctccg agcaggtggg ctgggtggcc    180

accgggcacg ccgaggtgcg ggcggtgctg gccgacgcgg agcggttcag cacccgcccg    240

cccgccgaca gcgaggagga cgccgagagc ctggtccagg ccgggaacct gctccagtac    300

gacccgcccg accacacccg gctgcgcaag ctgctcacgc cggagtacac ggtgcgcaag    360

atgcgccgcc tggagccccg catcgaggag atcgtccagg actgcctgga caccatggag    420

cgcgtcggcc gcccggccga cctcgtacgc tacttcgcct ggccgatccc gggcctcgcc    480

agctgcgaac tgctcggcgt cccccgcgac gaccagacgg aactggcgcg ctacctggac    540

atcacccggg acgtgggccg cagccaggaa cagcagctgg ccgccgggaa ggcgtactgg    600

gcgtacatgg gccagctcgc cgagcgccgc cgccgcaacc ccggcgacga catgctcggc    660

agtctcgtcc gcgaacaggg cgcggccgtc tccgacgcgg aactggcggg catcggcgcg    720

acggtgatgg ccgccggctt cgaacaggtc gccagcatcc tggggctggg caccctgctg    780

ctgctggaac accccgacca gctcgccctg tggcgcgaac agcccgaact gaccgaccgc    840

gcggtcgagg aagtgctgcg ctacctcacg gtcatccaca ccgcctcgcc ccgtacggca    900

ctggtggacg tgacgatcgg cgggcagacc atcaaggccg gggagagcgt ggcctgttcg    960

ctgctggccg ccaaccgcgt accggccccc ggtgagcccg ccgaccgctt cgacatcacc   1020

cgtgagccgg ccacccacat ggccttcggc cacggcatcc accactgcct cggcgccccg   1080

ctggcccgga tggaactgcg catcgccttc ccggccctgc tgcgccgctt cccggacctg   1140

cggctcgccg tgccgcacga gcgggtccgg ttccggcccg cccggtcccg ccagtacgcc   1200

ctggaatcgt tgcccgtcgc atggtaa                                       1227
```

<210> SEQ ID NO 65
<211> LENGTH: 408
<212> TYPE: PRT
<213> ORGANISM: Streptomyces rimosus

<400> SEQUENCE: 65

```
Met Thr Thr Asp Asp Asp Glu Glu Glu Asp Gln Arg Met Pro Glu Thr
1               5                   10                  15

Pro Glu Ile Pro Ala His Tyr Arg Arg Asp Arg Phe Asp Pro Val Pro
            20                  25                  30

Glu Leu Val Arg Met Ala Arg Glu Thr Pro Leu Val Glu Thr Asp Val
        35                  40                  45

Thr Ile Gly Pro Ser Glu Gln Val Gly Trp Val Ala Thr Gly His Ala
    50                  55                  60

Glu Val Arg Ala Val Leu Ala Asp Ala Glu Arg Phe Ser Thr Arg Pro
65                  70                  75                  80

Pro Ala Asp Ser Glu Glu Asp Ala Glu Ser Leu Val Gln Ala Gly Asn
                85                  90                  95

Leu Leu Gln Tyr Asp Pro Pro Asp His Thr Arg Leu Arg Lys Leu Leu
            100                 105                 110
```

```
Thr Pro Glu Tyr Thr Val Arg Lys Met Arg Arg Leu Glu Pro Arg Ile
        115                 120                 125

Glu Glu Ile Val Gln Asp Cys Leu Asp Thr Met Glu Arg Val Gly Arg
    130                 135                 140

Pro Ala Asp Leu Val Arg Tyr Phe Ala Trp Pro Ile Pro Gly Leu Ala
145                 150                 155                 160

Ser Cys Glu Leu Leu Gly Val Pro Arg Asp Asp Gln Thr Glu Leu Ala
                165                 170                 175

Arg Tyr Leu Asp Ile Thr Arg Asp Val Gly Arg Ser Gln Glu Gln Gln
            180                 185                 190

Leu Ala Ala Gly Lys Ala Tyr Trp Ala Tyr Met Gly Gln Leu Ala Glu
        195                 200                 205

Arg Arg Arg Arg Asn Pro Gly Asp Asp Met Leu Gly Ser Leu Val Arg
    210                 215                 220

Glu Gln Gly Ala Ala Val Ser Asp Ala Glu Leu Ala Gly Ile Gly Ala
225                 230                 235                 240

Thr Val Met Ala Ala Gly Phe Glu Gln Val Ala Ser Ile Leu Gly Leu
                245                 250                 255

Gly Thr Leu Leu Leu Leu Glu His Pro Asp Gln Leu Ala Leu Trp Arg
            260                 265                 270

Glu Gln Pro Glu Leu Thr Asp Arg Ala Val Glu Glu Val Leu Arg Tyr
        275                 280                 285

Leu Thr Val Ile His Thr Ala Ser Pro Arg Thr Ala Leu Val Asp Val
    290                 295                 300

Thr Ile Gly Gly Gln Thr Ile Lys Ala Gly Glu Ser Val Ala Cys Ser
305                 310                 315                 320

Leu Leu Ala Ala Asn Arg Val Pro Ala Pro Gly Glu Pro Ala Asp Arg
                325                 330                 335

Phe Asp Ile Thr Arg Glu Pro Ala Thr His Met Ala Phe Gly His Gly
            340                 345                 350

Ile His His Cys Leu Gly Ala Pro Leu Ala Arg Met Glu Leu Arg Ile
        355                 360                 365

Ala Phe Pro Ala Leu Leu Arg Arg Phe Pro Asp Leu Arg Leu Ala Val
    370                 375                 380

Pro His Glu Arg Val Arg Phe Arg Pro Ala Arg Ser Arg Gln Tyr Ala
385                 390                 395                 400

Leu Glu Ser Leu Pro Val Ala Trp
                405
```

<210> SEQ ID NO 66
<211> LENGTH: 1179
<212> TYPE: DNA
<213> ORGANISM: Streptomyces rimosus

<400> SEQUENCE: 66

```
atgttgatgc cgctgcggcg tcaggggctg gacccggtgg gcgagctggc gacggtgcgc      60

gagcaggagc ccatctccaa gctgccggtg ccgatcgccg ccaatgtgtg gctcgtcacc     120

gggtacgacg aggtcaaggc ggtactgggc aaggccaacg ccttcagctc ggacttcacc     180

aacctcatcg gccaggccgg tgccagcacc gaccagaacc ccggcggcct cggattcgcc     240

gacccgccgg tgcacacccg gctgcgccgt ctgctgaccc ccgaattcac catgcgccgg     300

ctcgggcggc tcacgccccg tatccacgag atcgtggagg agcggctgga cgccatggag     360

aaggccggca gctccggcga gccggtcgac atcgtggaaa cctttgcgct gccgattccg     420
```

-continued

```
tccttggtca tttgcgaact gctcggtgtg ccgtacgagg accgcgcgga cttcgagcgg    480

ctgagcgccg cgcgcttcga cctcttcagc ggcgccaacg cgtccttcgg cgccatatcg    540

gaatcgctcg cctatttccg tgaggtggtc aagaagcagc ggcagaaccc gggcgacggc    600

ctgctcggca tgatcgtcaa ggaacacggc gactcggtca gcgacgagga gctggcgggc    660

ctggccgacg gcgtgctgac cggcggcttc gagaccaccg cgagcatgct ggcgctgggc    720

gccctggtcc tcctccagga ccccgagcac ttcgccgccc tcaaggacgg cgacgaggcg    780

gccgagcgct acgtcgagga gctgctgcgc tacctcaccg tcgtccaggt cgccttcccc    840

cgcttcgcgc gcgaggacat ggagatcgcc ggtgtgccga tcgccaaggg cgacgtggtg    900

ctgtgctcgc tcagcggcgc cgaccgggac ggcaagctcg gtcccgacat ggagcgcttc    960

gacccgtccc gcaacgttcc ctcgcacctg gccttcggct acggcataca ccgctgcgtc   1020

ggcgccgagc tggcccgtat ggagctgcgc gccgcctacc ccgcgctggt acggcggttc   1080

ccgaacatgc ggctcgcggt ggagccggac gcgctggaat tccgcaagct gtcgatcgtg   1140

tacggaatcg agtcgctgcc ggtgcacctc ggcggctaa                          1179
```

<210> SEQ ID NO 67
<211> LENGTH: 392
<212> TYPE: PRT
<213> ORGANISM: Streptomyces rimosus

<400> SEQUENCE: 67

```
Met Leu Met Pro Leu Arg Arg Gln Gly Leu Asp Pro Val Gly Glu Leu
1               5                   10                  15

Ala Thr Val Arg Glu Gln Glu Pro Ile Ser Lys Leu Pro Val Pro Ile
            20                  25                  30

Ala Ala Asn Val Trp Leu Val Thr Gly Tyr Asp Glu Val Lys Ala Val
        35                  40                  45

Leu Gly Lys Ala Asn Ala Phe Ser Ser Asp Phe Thr Asn Leu Ile Gly
    50                  55                  60

Gln Ala Gly Ala Ser Thr Asp Gln Asn Pro Gly Gly Leu Gly Phe Ala
65                  70                  75                  80

Asp Pro Pro Val His Thr Arg Leu Arg Arg Leu Leu Thr Pro Glu Phe
                85                  90                  95

Thr Met Arg Arg Leu Gly Arg Leu Thr Pro Arg Ile His Glu Ile Val
            100                 105                 110

Glu Glu Arg Leu Asp Ala Met Glu Lys Ala Gly Ser Ser Gly Glu Pro
        115                 120                 125

Val Asp Ile Val Glu Thr Phe Ala Leu Pro Ile Pro Ser Leu Val Ile
    130                 135                 140

Cys Glu Leu Leu Gly Val Pro Tyr Glu Asp Arg Ala Asp Phe Glu Arg
145                 150                 155                 160

Leu Ser Ala Ala Arg Phe Asp Leu Phe Ser Gly Ala Asn Ala Ser Phe
                165                 170                 175

Gly Ala Ile Ser Glu Ser Leu Ala Tyr Phe Arg Glu Val Val Lys Lys
            180                 185                 190

Gln Arg Gln Asn Pro Gly Asp Gly Leu Leu Gly Met Ile Val Lys Glu
        195                 200                 205

His Gly Asp Ser Val Ser Asp Glu Glu Leu Ala Gly Leu Ala Asp Gly
    210                 215                 220

Val Leu Thr Gly Gly Phe Glu Thr Thr Ala Ser Met Leu Ala Leu Gly
225                 230                 235                 240
```

-continued

```
Ala Leu Val Leu Leu Gln Asp Pro Glu His Phe Ala Ala Leu Lys Asp
                245                 250                 255

Gly Asp Glu Ala Ala Glu Arg Tyr Val Glu Glu Leu Leu Arg Tyr Leu
            260                 265                 270

Thr Val Val Gln Val Ala Phe Pro Arg Phe Ala Arg Glu Asp Met Glu
        275                 280                 285

Ile Ala Gly Val Pro Ile Ala Lys Gly Asp Val Val Leu Cys Ser Leu
    290                 295                 300

Ser Gly Ala Asp Arg Asp Gly Lys Leu Gly Pro Asp Met Glu Arg Phe
305                 310                 315                 320

Asp Pro Ser Arg Asn Val Pro Ser His Leu Ala Phe Gly Tyr Gly Ile
                325                 330                 335

His Arg Cys Val Gly Ala Glu Leu Ala Arg Met Glu Leu Arg Ala Ala
            340                 345                 350

Tyr Pro Ala Leu Val Arg Arg Phe Pro Asn Met Arg Leu Ala Val Glu
        355                 360                 365

Pro Asp Ala Leu Glu Phe Arg Lys Leu Ser Ile Val Tyr Gly Ile Glu
    370                 375                 380

Ser Leu Pro Val His Leu Gly Gly
385                 390
```

<210> SEQ ID NO 68
<211> LENGTH: 1035
<212> TYPE: DNA
<213> ORGANISM: Streptomyces rimosus

<400> SEQUENCE: 68

```
atgctcggcg acgcccggtt cagctccgac cgctcgcacc cggacttccc gtggatgcgc     60

gtcggcgaga ccgttttccc cggcttcagg ccctcgctga tcgagatgga cccgcccgag    120

cacggccccg cccgtcgtgc ggtcgccggc gagttcacca tccaccgcat gcgggagctg    180

cgccccaaga ttcagcgcat tgttgacggt ctgctcgacg atgtgctggc cggtgccaag    240

cccgccgacc tggtgtccgc gctggccgtg ccgctgtccg gtctggtgct gtgtgagctg    300

ctcgggatcc cgaccggtta ccgggaggag ctcaccacca acaccgcggt gttggtggcc    360

cacgactccg ctgatgcgga tcgcgccgag tccttccgct ccctgagcga gtatttcgac    420

gcgctgtgtg ccacgaagat gaccgagcgg cccggggacc tgctgggcag gctggcgggc    480

caccggctct tcagcggtga cgagagtcgc tgggccatgg tcgaactgtg catactcctg    540

gtcgtcgcgg gcctggagac caccgccacg atgaccgcac tcggaatcct ggctctcctc    600

gaacaccccg gccagctcgc cctcctcacc gccgacccgg gcctgacccc gggagcggtg    660

gatgaattgc tgaggttctt ctccattgcc gagctgtccc tgatgcgccg cgccacggcg    720

gacgttgaga tcggcggcac tctggtacgt acgggtgagg gcgtcgccgc cctgtccgcc    780

gccgccaacc gcgaccccgc ggtcttcgcc gacccggaca cgttcgatgt caccagggac    840

aaccgcaggc atctggcttt cggttcggga ccgcaccagt gcctcggcaa gaacctggcc    900

cggatggagc tgcgcatcgt tctcgatacc ctgttccggc gcatccccac tctccgcctg    960

gccacgccac gcgacgaatt gcgcttcgtc aacggctccg ggttctcggt atcggcactc   1020

ccggtcactt ggtaa                                                    1035
```

<210> SEQ ID NO 69
<211> LENGTH: 344
<212> TYPE: PRT
<213> ORGANISM: Streptomyces rimosus

<400> SEQUENCE: 69

Met Leu Gly Asp Ala Arg Phe Ser Ser Asp Arg Ser His Pro Asp Phe
1               5                   10                  15

Pro Trp Met Arg Val Gly Glu Thr Val Phe Pro Gly Phe Arg Pro Ser
            20                  25                  30

Leu Ile Glu Met Asp Pro Pro Glu His Gly Pro Ala Arg Arg Ala Val
        35                  40                  45

Ala Gly Glu Phe Thr Ile His Arg Met Arg Glu Leu Arg Pro Lys Ile
    50                  55                  60

Gln Arg Ile Val Asp Gly Leu Leu Asp Asp Val Leu Ala Gly Ala Lys
65                  70                  75                  80

Pro Ala Asp Leu Val Ser Ala Leu Ala Val Pro Leu Ser Gly Leu Val
                85                  90                  95

Leu Cys Glu Leu Leu Gly Ile Pro Thr Gly Tyr Arg Glu Glu Leu Thr
            100                 105                 110

Thr Asn Thr Ala Val Leu Val Ala His Asp Ser Ala Asp Ala Asp Arg
        115                 120                 125

Ala Glu Ser Phe Arg Ser Leu Ser Glu Tyr Phe Asp Ala Leu Cys Ala
    130                 135                 140

Thr Lys Met Thr Glu Arg Pro Gly Asp Leu Leu Gly Arg Leu Ala Gly
145                 150                 155                 160

His Arg Leu Phe Ser Gly Asp Glu Ser Arg Trp Ala Met Val Glu Leu
                165                 170                 175

Cys Ile Leu Leu Val Val Ala Gly Leu Glu Thr Thr Ala Thr Met Thr
            180                 185                 190

Ala Leu Gly Ile Leu Ala Leu Leu Glu His Pro Gly Gln Leu Ala Leu
        195                 200                 205

Leu Thr Ala Asp Pro Gly Leu Thr Pro Gly Ala Val Asp Glu Leu Leu
    210                 215                 220

Arg Phe Phe Ser Ile Ala Glu Leu Ser Leu Met Arg Arg Ala Thr Ala
225                 230                 235                 240

Asp Val Glu Ile Gly Gly Thr Leu Val Arg Thr Gly Glu Gly Val Ala
                245                 250                 255

Ala Leu Ser Ala Ala Ala Asn Arg Asp Pro Ala Val Phe Ala Asp Pro
            260                 265                 270

Asp Thr Phe Asp Val Thr Arg Asp Asn Arg Arg His Leu Ala Phe Gly
        275                 280                 285

Ser Gly Pro His Gln Cys Leu Gly Lys Asn Leu Ala Arg Met Glu Leu
    290                 295                 300

Arg Ile Val Leu Asp Thr Leu Phe Arg Arg Ile Pro Thr Leu Arg Leu
305                 310                 315                 320

Ala Thr Pro Arg Asp Glu Leu Arg Phe Val Asn Gly Ser Gly Phe Ser
                325                 330                 335

Val Ser Ala Leu Pro Val Thr Trp
            340

<210> SEQ ID NO 70
<211> LENGTH: 1194
<212> TYPE: DNA
<213> ORGANISM: Streptomyces rimosus

<400> SEQUENCE: 70
atggacacac accccgaacc catcgattac ccttttttccg agccgtccgg gctcaccgtc      60

```
gatccggaat acgaggactg ccgcagccgc cccggcctga cgtggatccg gccgccgtac    120

ggtgaccacg cctggctggt gacgcgctac gcggacatcc gcttcgtcct gcgggaccgg    180

cggttcgtcc gcacgccccc gccgggcagc gacgaggcgc ggctgacccc gctgccgctg    240

caggacagca tcctgaacac cgatccgccc cagcagcccc gcctgcgcaa ggccctcgcc    300

cagggcctca agttcaacgc cgagcacgtc cgtgagctgg aggaactggc caccggggag    360

gcgcggcggc tgctggcccg ctgcacggcg gagccgcccc cggccgatct ggccgccgcg    420

tacaccaagc cgctcaccgt ggccatcctc tgcccgctga tcggcatccc cgaagaggac    480

ctggcggtct tcctcgactg gttcgagggg ttcgcgggca ccggcctgcc cgccgacgtg    540

gtggagtcgc gtatcgagga gatctcccgc tacacggccc ggctcatcgc cgaccgccgg    600

cagcggccgc gggaggacct ggtcagccgc ctggtggccc ggctgggcca ggacgacggg    660

ctgtcgatgg aggagctggg cgagctggtc aacgacatcc tgctcgccgt cgacaacgtc    720

accacccagc tcaccaacgc ctgttacgtg ctgctctcct cccccgccca cttccgggag    780

ctggcggccg acccggacct gctgccgcgg gcggccgacg agctgctgcg ctacgcgccg    840

ttcccctcgc acgtcacctt cgcccggtac gccaccgagg acgtggaggt cggcggcacc    900

ctcgtacggg ccggtgagca ggtgctgccc gcgctgccgg ccggcaacca cgacccgcgg    960

atgttcgccg agccggagcg gctggacttc caccgcggcg gcaacccgca tctgtccttc   1020

ggccacggca cccatcactg catggggccg ccgctggtgc ggatgctggt gaaggtggcc   1080

gtggccgccc tgctcggcca ccccggcctg cggctggccg cgccggacga ggagctgccg   1140

tggcgcgccg acctgatcat ccggcggatc gaggagctgc cggtcacctg gtaa         1194
```

<210> SEQ ID NO 71
<211> LENGTH: 397
<212> TYPE: PRT
<213> ORGANISM: Streptomyces rimosus

<400> SEQUENCE: 71

```
Met Asp Thr His Pro Glu Pro Ile Asp Tyr Pro Phe Ser Glu Pro Ser
1               5                   10                  15

Gly Leu Thr Val Asp Pro Glu Tyr Glu Asp Cys Arg Ser Arg Pro Gly
            20                  25                  30

Leu Thr Trp Ile Arg Pro Pro Tyr Gly Asp His Ala Trp Leu Val Thr
        35                  40                  45

Arg Tyr Ala Asp Ile Arg Phe Val Leu Arg Asp Arg Arg Phe Val Arg
    50                  55                  60

Thr Pro Pro Pro Gly Ser Asp Glu Ala Arg Leu Thr Pro Leu Pro Leu
65                  70                  75                  80

Gln Asp Ser Ile Leu Asn Thr Asp Pro Pro Gln Gln Pro Arg Leu Arg
                85                  90                  95

Lys Ala Leu Ala Gln Gly Leu Lys Phe Asn Ala Glu His Val Arg Glu
            100                 105                 110

Leu Glu Glu Leu Ala Thr Gly Glu Ala Arg Arg Leu Leu Ala Arg Cys
        115                 120                 125

Thr Ala Glu Pro Pro Pro Ala Asp Leu Ala Ala Ala Tyr Thr Lys Pro
    130                 135                 140

Leu Thr Val Ala Ile Leu Cys Pro Leu Ile Gly Ile Pro Glu Glu Asp
145                 150                 155                 160

Leu Ala Val Phe Leu Asp Trp Phe Glu Gly Phe Ala Gly Thr Gly Leu
                165                 170                 175
```

-continued

```
Pro Ala Asp Val Val Glu Ser Arg Ile Glu Glu Ile Ser Arg Tyr Thr
            180                 185                 190

Ala Arg Leu Ile Ala Asp Arg Arg Gln Arg Pro Arg Glu Asp Leu Val
        195                 200                 205

Ser Arg Leu Val Ala Arg Leu Gly Gln Asp Asp Gly Leu Ser Met Glu
    210                 215                 220

Glu Leu Gly Glu Leu Val Asn Asp Ile Leu Leu Ala Val Asp Asn Val
225                 230                 235                 240

Thr Thr Gln Leu Thr Asn Ala Cys Tyr Val Leu Leu Ser Ser Pro Ala
                245                 250                 255

His Phe Arg Glu Leu Ala Ala Asp Pro Asp Leu Leu Pro Arg Ala Ala
            260                 265                 270

Asp Glu Leu Leu Arg Tyr Ala Pro Phe Pro Ser His Val Thr Phe Ala
        275                 280                 285

Arg Tyr Ala Thr Glu Asp Val Glu Val Gly Gly Thr Leu Val Arg Ala
    290                 295                 300

Gly Glu Gln Val Leu Pro Ala Leu Pro Ala Gly Asn His Asp Pro Arg
305                 310                 315                 320

Met Phe Ala Glu Pro Glu Arg Leu Asp Phe His Arg Gly Gly Asn Pro
                325                 330                 335

His Leu Ser Phe Gly His Gly Thr His His Cys Met Gly Pro Pro Leu
            340                 345                 350

Val Arg Met Leu Val Lys Val Ala Val Ala Ala Leu Leu Gly His Pro
        355                 360                 365

Gly Leu Arg Leu Ala Ala Pro Asp Glu Glu Leu Pro Trp Arg Ala Asp
    370                 375                 380

Leu Ile Ile Arg Arg Ile Glu Glu Leu Pro Val Thr Trp
385                 390                 395
```

<210> SEQ ID NO 72
<211> LENGTH: 1230
<212> TYPE: DNA
<213> ORGANISM: Streptomyces rimosus

<400> SEQUENCE: 72

```
atgacgcagc cggacaccag gacgaaccag ccggacaccg ggccgggccg gcccgagcag      60

atacccgccc acctgcggcg ggaccgtttc gacccggttc ccgaactccg gcggcaggtc     120

cgggaggcgc cgctcgtggt ggccgacgtc gaattcgggc tcttcggccg ggtgaagtgg     180

gtggccaccg gcgaggccga aatccgggag gtgctgggcg acctgaaacg tttcagctcc     240

cggctgcccg acgacggcca ggacacgtcc ggggcccgcg ccgcacccgg caacctcctg     300

cagtgcgacc cacccgacca cacccgcctc cggcgcatgg tggcaccgga attcacggcg     360

cggcggaccc ggcggctgga accgcgcatc accgcgatcg tcgaagagtg cctggacatc     420

atggagcgcg tcggaccgcc gaccgacttc atgcgaaact tcgcctggcc cgtggcaggg     480

ctgatcacct gcgagctgct gggcattccc cgcgacgacc gggcggaact gtcccgctat     540

ctcgacatcg cccaggacga atccgcgccc ccggaacagc agacggccgt cggcaaggcg     600

tactgggcct atatggtgcg gctcgccaaa cggcagcgcc gcagccccgg cgacggcctc     660

ttcggccacg tggtgcgcga gcacggcgcg gacatcggcg acgacgaact ggcgggtgtc     720

ggcgcgacct tcgtctccga cggcttcctc caggtctcca gcatgctggg gctgggcgcg     780

ctggcgctgc tggaccaccc cggccagctg cggctgctgc gggaacggcc ggagctgatc     840

gaccgggccg tggaagaact gctgcgctac gtcaccgtca tccacaccgt ctcgccccgc     900
```

```
accgccctgg aggacgtgac catcgggaac caggtgatca aggcgggcga gatggtcgcc    960

tgctcgctgt tcgccgtcaa ccgggcgcag ggcggaccgg gggcggacgc gttcgacatc   1020

acccgcgagt ccgccccgca cctggccttc ggccacggca tgcaccactg cgtcgccgcg   1080

ccgctggtca agctggagat gcgcatcgcc tacccggcac tgctgcgccg gttccccggg   1140

ctgcggcccg cggtggcgcc ggacggcatc cgcttccggt ccgcgcagac gcggcagttc   1200

agcctggacg cgctgcccgt cgcctggtaa                                    1230


<210> SEQ ID NO 73
<211> LENGTH: 409
<212> TYPE: PRT
<213> ORGANISM: Streptomyces rimosus

<400> SEQUENCE: 73

Met Thr Gln Pro Asp Thr Arg Thr Asn Gln Pro Asp Thr Gly Pro Gly
1               5                   10                  15

Arg Pro Glu Gln Ile Pro Ala His Leu Arg Arg Asp Arg Phe Asp Pro
            20                  25                  30

Val Pro Glu Leu Arg Arg Gln Val Arg Glu Ala Pro Leu Val Val Ala
        35                  40                  45

Asp Val Glu Phe Gly Leu Phe Gly Arg Val Lys Trp Val Ala Thr Gly
    50                  55                  60

Glu Ala Glu Ile Arg Glu Val Leu Gly Asp Leu Lys Arg Phe Ser Ser
65                  70                  75                  80

Arg Leu Pro Asp Asp Gly Gln Asp Thr Ser Gly Ala Arg Ala Ala Pro
                85                  90                  95

Gly Asn Leu Leu Gln Cys Asp Pro Pro Asp His Thr Arg Leu Arg Arg
            100                 105                 110

Met Val Ala Pro Glu Phe Thr Ala Arg Arg Thr Arg Arg Leu Glu Pro
        115                 120                 125

Arg Ile Thr Ala Ile Val Glu Glu Cys Leu Asp Ile Met Glu Arg Val
    130                 135                 140

Gly Pro Pro Thr Asp Phe Met Arg Asn Phe Ala Trp Pro Val Ala Gly
145                 150                 155                 160

Leu Ile Thr Cys Glu Leu Leu Gly Ile Pro Arg Asp Asp Arg Ala Glu
                165                 170                 175

Leu Ser Arg Tyr Leu Asp Ile Ala Gln Asp Glu Ser Ala Pro Pro Glu
            180                 185                 190

Gln Gln Thr Ala Val Gly Lys Ala Tyr Trp Ala Tyr Met Val Arg Leu
        195                 200                 205

Ala Lys Arg Gln Arg Arg Ser Pro Gly Asp Gly Leu Phe Gly His Val
    210                 215                 220

Val Arg Glu His Gly Ala Asp Ile Gly Asp Asp Glu Leu Ala Gly Val
225                 230                 235                 240

Gly Ala Thr Phe Val Ser Asp Gly Phe Leu Gln Val Ser Ser Met Leu
                245                 250                 255

Gly Leu Gly Ala Leu Ala Leu Leu Asp His Pro Gly Gln Leu Arg Leu
            260                 265                 270

Leu Arg Glu Arg Pro Glu Leu Ile Asp Arg Ala Val Glu Glu Leu Leu
        275                 280                 285

Arg Tyr Val Thr Val Ile His Thr Val Ser Pro Arg Thr Ala Leu Glu
    290                 295                 300

Asp Val Thr Ile Gly Asn Gln Val Ile Lys Ala Gly Glu Met Val Ala
```

```
305                 310                 315                 320

Cys Ser Leu Phe Ala Val Asn Arg Ala Gln Gly Gly Pro Gly Ala Asp
                325                 330                 335

Ala Phe Asp Ile Thr Arg Glu Ser Ala Pro His Leu Ala Phe Gly His
            340                 345                 350

Gly Met His His Cys Val Ala Ala Pro Leu Val Lys Leu Glu Met Arg
        355                 360                 365

Ile Ala Tyr Pro Ala Leu Leu Arg Arg Phe Pro Gly Leu Arg Pro Ala
    370                 375                 380

Val Ala Pro Asp Gly Ile Arg Phe Arg Ser Ala Gln Thr Arg Gln Phe
385                 390                 395                 400

Ser Leu Asp Ala Leu Pro Val Ala Trp
                405
```

<210> SEQ ID NO 74
<211> LENGTH: 1278
<212> TYPE: DNA
<213> ORGANISM: Streptomyces rimosus

<400> SEQUENCE: 74

```
atgccggacg ccggacgtct ccctcgatac cctttcgcct tccggggcga ccagctcgcg     60

cccgagctgg ccgcatcggt ggtccaccgc ccgatccagc gcgtacggac caacaccggt    120

accgacgcct ggctggtgac cggccacgag ctggtgcgct cggtgctccg ggaccgccgc    180

ttcagcctca ccctcacctc cgacccctgg atgccccggc aggaccccct catcccaccg    240

ctctcggtca ccgacatccg cacccagtgc gagaacgcgg gcctcctcca ggacctcttc    300

caaggcgtgg gaccgcacca gcggtacctg acaccgggcc gcgtccggga gatcgccgac    360

gggctgctgg acaccttcct ggccggagag caacccggcg acctgatgga cgggttcatc    420

atgccgctct cccgcgcgct caccatggaa ctgctgggcc tggacccgga aggctgcccg    480

gacaacgccg aaatcttcaa catcttccgt accggcccgg aaagcatgca gggcgtgccg    540

gagagctgga acctggccct tacgtggatg ctcggacggc ttcccgggct gcgcgcgtcc    600

ggcgcagggc tgctgggccg cctcatcacc ctcagcgacg cgtccggcgt actgagcgag    660

gaggaggtcg ccgacctctt cgtcttcctc ctcatctccc agttcggcaa ccccgccacc    720

ttcctcggcg cggcgaccgt ggggctgatg cagcacccgg aggtgacggc ccggctgcgg    780

aaggaccccg ggctgctgcc acgggccgtc gacgagctgc tgcgctggac ggtcttcctg    840

ggcgacgcac tgccccgcaa cgcgcgcgag gacgtgctgc tggacggcgt tctcgtacgg    900

gagggcgacc tcgtgctggt gtccaccgac gcggccaacc gcgacccgcg ggtcttcccc    960

gacccgcacc gcctcgacat cgaccgggag cccggcccgc acctgcggtt cagcgacgcg   1020

cggcaccgct gtccgggcgg cccggtctcc cgcatgcagg ccgcggagac gctgcgcgta   1080

ctgctggggc ggaccgccga tctgcgcctg gccgtgcccg ccgacgagat cgaatggcac   1140

cgctactacg cggtcacact gccggtggcg gtgccggtca actggacgct ccccggagcg   1200

gccactcccg ggaccggcga cggtaagccc cgcggagcgg ccgttcccag gcccgatggc   1260

gggacgctca ctccgtaa                                                 1278
```

<210> SEQ ID NO 75
<211> LENGTH: 425
<212> TYPE: PRT
<213> ORGANISM: Streptomyces rimosus

<400> SEQUENCE: 75

-continued

```
Met Pro Asp Ala Gly Arg Leu Pro Arg Tyr Pro Phe Ala Phe Arg Gly
1               5                   10                  15

Asp Gln Leu Ala Pro Glu Leu Ala Ala Ser Val Val His Arg Pro Ile
            20                  25                  30

Gln Arg Val Arg Thr Asn Thr Gly Thr Asp Ala Trp Leu Val Thr Gly
        35                  40                  45

His Glu Leu Val Arg Ser Val Leu Arg Asp Arg Arg Phe Ser Leu Thr
    50                  55                  60

Leu Thr Ser Asp Pro Trp Met Pro Arg Gln Asp Pro Leu Ile Pro Pro
65                  70                  75                  80

Leu Ser Val Thr Asp Ile Arg Thr Gln Cys Glu Asn Ala Gly Leu Leu
                85                  90                  95

Gln Asp Leu Phe Gln Gly Val Gly Pro His Gln Arg Tyr Leu Thr Pro
            100                 105                 110

Gly Arg Val Arg Glu Ile Ala Asp Gly Leu Leu Asp Thr Phe Leu Ala
        115                 120                 125

Gly Glu Gln Pro Gly Asp Leu Met Asp Gly Phe Ile Met Pro Leu Ser
    130                 135                 140

Arg Ala Leu Thr Met Glu Leu Leu Gly Leu Asp Pro Glu Gly Cys Pro
145                 150                 155                 160

Asp Asn Ala Glu Ile Phe Asn Ile Phe Arg Thr Gly Pro Glu Ser Met
                165                 170                 175

Gln Gly Val Pro Glu Ser Trp Asn Leu Ala Leu Thr Trp Met Leu Gly
            180                 185                 190

Arg Leu Pro Gly Leu Arg Ala Ser Gly Ala Gly Leu Leu Gly Arg Leu
        195                 200                 205

Ile Thr Leu Ser Asp Ala Ser Gly Val Leu Ser Glu Glu Glu Val Ala
    210                 215                 220

Asp Leu Phe Val Phe Leu Leu Ile Ser Gln Phe Gly Asn Pro Ala Thr
225                 230                 235                 240

Phe Leu Gly Ala Ala Thr Val Gly Leu Met Gln His Pro Glu Val Thr
                245                 250                 255

Ala Arg Leu Arg Lys Asp Pro Gly Leu Leu Pro Arg Ala Val Asp Glu
            260                 265                 270

Leu Leu Arg Trp Thr Val Phe Leu Gly Asp Ala Leu Pro Arg Asn Ala
        275                 280                 285

Arg Glu Asp Val Leu Leu Asp Gly Val Leu Val Arg Glu Gly Asp Leu
    290                 295                 300

Val Leu Val Ser Thr Asp Ala Ala Asn Arg Asp Pro Arg Val Phe Pro
305                 310                 315                 320

Asp Pro His Arg Leu Asp Ile Asp Arg Glu Pro Gly Pro His Leu Arg
                325                 330                 335

Phe Ser Asp Gly Arg His Arg Cys Pro Gly Gly Pro Val Ser Arg Met
            340                 345                 350

Gln Ala Ala Glu Thr Leu Arg Val Leu Leu Gly Arg Thr Ala Asp Leu
        355                 360                 365

Arg Leu Ala Val Pro Ala Asp Glu Ile Glu Trp His Arg Tyr Tyr Ala
    370                 375                 380

Val Thr Leu Pro Val Ala Val Pro Val Asn Trp Thr Leu Pro Gly Ala
385                 390                 395                 400

Ala Thr Pro Gly Thr Gly Asp Gly Lys Pro Arg Gly Ala Ala Val Pro
                405                 410                 415
```

-continued

```
Arg Pro Asp Gly Gly Thr Leu Thr Pro
            420                 425


<210> SEQ ID NO 76
<211> LENGTH: 1188
<212> TYPE: DNA
<213> ORGANISM: Streptomyces rimosus

<400> SEQUENCE: 76

atggagtcac cggagttctt ccgcgacccg tacccgctgc tcgccgcgct gcgcgagcgc      60

ggtcccgtcc agcaggtacg gtccgggccg cacggcgcga cgtggctcgt caccggctgg     120

gccgaggccc gtacggcgct ggcggagccc cggctctcca aggacaccac ccgctacttc     180

gccgacaagc cgtccaagcg caacctggcg cccgccgtca gcgccaccat gctggccacc     240

gacccgccgg accacacccg gctgcgccgg ctggccgtca aggcgttcac gccggcggcg     300

gtggcccgcc tggagccgcg ggtggcggag atcgcggacg gtctgctgga ccggatggcc     360

gacggcggcg attcggccga tctcgtcgag gacttcgccg taccgctgcc catcgaggtc     420

atcggcgacc tgctcggcgt tccccgcgag gaccgcccgg cgctgcgccg ctggtccaac     480

gacctcttcg cggccggcgc gccggacagc atcgacgcgg cctcgcacgc catcagcgac     540

tacatgacgg agctgatcgc gaagaagcgc gccgaaggta ccggggccga tctgctcacc     600

gagctgatcg ccgcgcgcga cgagggcgac cggctcagcg agttcgaact ggtctcgctg     660

gccgtcctgc tggtcgtcgc cgggcacgag acgaccacca acctgatcgg caacggcgcg     720

ctcgcgctcc tccgggacga cgcgctccgt acccgcctgc ggcaggaccc ggcgctcatc     780

ccggacgccg tggaggaact gctccgctat gactccccga tcaccacggc cacgttccgg     840

tacgcggccg aaccgctcac cctcggcggc gccgagatcg cggcgggcga tgtcgtcctg     900

gtctccccgg gcgccgccaa ccgtgacccg gcccggttcc ccgacccgga cacggtcacc     960

cccggccgtt ccgccggcca tctctccttc ggccacggtc cgcaccactg cctgggcgcg    1020

cccctggccc gcctggaagc ccgtatcgcc ttccgagcgc tgctcacccg cttccccggc    1080

ctgcggctgg ccgtcccgcc cggcgaactc ccgtggcgcc acacccgcct gatgcgcggt    1140

ctgtcgcacc tcccggtcac ctggtccgca caggtcacgg attgttaa                1188


<210> SEQ ID NO 77
<211> LENGTH: 395
<212> TYPE: PRT
<213> ORGANISM: Streptomyces rimosus

<400> SEQUENCE: 77

Met Glu Ser Pro Glu Phe Phe Arg Asp Pro Tyr Pro Leu Leu Ala Ala
1               5                   10                  15

Leu Arg Glu Arg Gly Pro Val Gln Gln Val Arg Ser Gly Pro His Gly
            20                  25                  30

Ala Thr Trp Leu Val Thr Gly Trp Ala Glu Ala Arg Thr Ala Leu Ala
        35                  40                  45

Glu Pro Arg Leu Ser Lys Asp Thr Thr Arg Tyr Phe Ala Asp Lys Pro
    50                  55                  60

Ser Lys Arg Asn Leu Ala Pro Ala Val Ser Ala Thr Met Leu Ala Thr
65                  70                  75                  80

Asp Pro Pro Asp His Thr Arg Leu Arg Arg Leu Ala Val Lys Ala Phe
                85                  90                  95

Thr Pro Ala Ala Val Ala Arg Leu Glu Pro Arg Val Ala Glu Ile Ala
            100                 105                 110
```

```
Asp Gly Leu Leu Asp Arg Met Ala Asp Gly Gly Asp Ser Ala Asp Leu
        115                 120                 125

Val Glu Asp Phe Ala Val Pro Leu Pro Ile Glu Val Ile Gly Asp Leu
    130                 135                 140

Leu Gly Val Pro Arg Glu Asp Arg Pro Ala Leu Arg Arg Trp Ser Asn
145                 150                 155                 160

Asp Leu Phe Ala Ala Gly Ala Pro Asp Ser Ile Asp Ala Ala Ser His
                165                 170                 175

Ala Ile Ser Asp Tyr Met Thr Glu Leu Ile Ala Lys Lys Arg Ala Glu
            180                 185                 190

Gly Thr Gly Ala Asp Leu Leu Thr Glu Leu Ile Ala Ala Arg Asp Glu
        195                 200                 205

Gly Asp Arg Leu Ser Glu Phe Glu Leu Val Ser Leu Ala Val Leu Leu
    210                 215                 220

Val Val Ala Gly His Glu Thr Thr Thr Asn Leu Ile Gly Asn Gly Ala
225                 230                 235                 240

Leu Ala Leu Leu Arg Asp Asp Ala Leu Arg Thr Arg Leu Arg Gln Asp
                245                 250                 255

Pro Ala Leu Ile Pro Asp Ala Val Glu Glu Leu Leu Arg Tyr Asp Ser
            260                 265                 270

Pro Ile Thr Thr Ala Thr Phe Arg Tyr Ala Ala Glu Pro Leu Thr Leu
        275                 280                 285

Gly Gly Ala Glu Ile Ala Ala Gly Asp Val Val Leu Val Ser Pro Gly
    290                 295                 300

Ala Ala Asn Arg Asp Pro Ala Arg Phe Pro Asp Pro Asp Thr Val Thr
305                 310                 315                 320

Pro Gly Arg Ser Ala Gly His Leu Ser Phe Gly His Gly Pro His His
                325                 330                 335

Cys Leu Gly Ala Pro Leu Ala Arg Leu Glu Ala Arg Ile Ala Phe Arg
            340                 345                 350

Ala Leu Leu Thr Arg Phe Pro Gly Leu Arg Leu Ala Val Pro Pro Gly
        355                 360                 365

Glu Leu Pro Trp Arg His Thr Arg Leu Met Arg Gly Leu Ser His Leu
    370                 375                 380

Pro Val Thr Trp Ser Ala Gln Val Thr Asp Cys
385                 390                 395
```

<210> SEQ ID NO 78
<211> LENGTH: 1209
<212> TYPE: DNA
<213> ORGANISM: Streptomyces rimosus

<400> SEQUENCE: 78

```
atgaagtcgt ccgcgacgcg gtccggggcc ggcggacacg cccgtacccc gtgcgatgcc      60

gcggcccgcg cccactccag cggcccgctg gatctcttgc gcgccgagtt cgacggcgtg     120

cacgacgtgt ggcgctcggc ctcgggaatg gtgtacgtgg ccggcccgga ggcggcgcgg     180

gcggtgctgg gcaaccggcc ggccatcgtg gccgagacgt ccgacttcta ccggacccgg     240

cacggcgtct tcgggccgcg ggccgcgcag gcggagatcg gccgtgcggc ccgcgccctg     300

atgcaccacc acctcgacgc ccggcggtcg cagctgcccc ggctgatcca cgagcgcctc     360

gcgccccgca gttcctggcc ggacgcgggg aacctgctgg tccacgagca cctggcggat     420

gtcctgctgc acccgggcgc gccgatctcc ctgcgtacga cggtcggcaa ggtcgtcacc     480
```

-continued

```
cgcgccgtgc tggcgggtgc ccgcaggcgc cacgcaccgc cgtccaggct cctcctccgc    540

caccgcgcgt ccgccgcgct gcaggccgag atacgcgccc ggcagcaccg gcgacagcac    600

cacggcggca gcgccggccc ccgcgacctg ctcgatgtcg tggtggacgg ctgcggtccc    660

gcgacggcat ccgacgatct cgccgaggtc tacctgtctt tcctgttcgc cgcggtgggc    720

tccatcggct tcgccctcgg atggtcggtc caccttctcg gcacccatcc cggctgcccg    780

gcggcaccgg accggatcgt gcgcgaggcc ctgcgcctgt ggccggtggc ctggctgttc    840

gcccgtacgc cgctgcgggc cgtggagctc ggcgggatga cggtgacacc cgaggaccag    900

ctcgccgtgt gcacctacct ggtgcaccgg catcccgcgt actgggagcg acccgacgag    960

ttcctcccgc agcgctgggc ggcacccgtc tcccgggccg cctacctccc cttcgggcac   1020

gggccgcaca cctgcgccgg agcgaccgtc accctgcaac tcctcaagga catcgtcggc   1080

ctgctcatcc atgactggcg gctgtcggtc atccacgacg gcggcggtcc tcaggtgggc   1140

ccggcgctgg ctccgccgcg cttcaccgcg gtgctgagcc cacgtgccaa cagctccgga   1200

aggaggtaa                                                           1209
```

```
<210> SEQ ID NO 79
<211> LENGTH: 402
<212> TYPE: PRT
<213> ORGANISM: Streptomyces rimosus

<400> SEQUENCE: 79

Met Lys Ser Ser Ala Thr Arg Ser Gly Ala Gly Gly His Ala Arg Thr
1               5                   10                  15

Pro Cys Asp Ala Ala Ala Arg Ala His Ser Ser Gly Pro Leu Asp Leu
            20                  25                  30

Leu Arg Ala Glu Phe Asp Gly Val His Asp Val Trp Arg Ser Ala Ser
        35                  40                  45

Gly Met Val Tyr Val Ala Gly Pro Glu Ala Ala Arg Ala Val Leu Gly
    50                  55                  60

Asn Arg Pro Ala Ile Val Ala Glu Thr Ser Asp Phe Tyr Arg Thr Arg
65                  70                  75                  80

His Gly Val Phe Gly Pro Arg Ala Ala Gln Ala Glu Ile Gly Arg Ala
                85                  90                  95

Ala Arg Ala Leu Met His His His Leu Asp Ala Arg Arg Ser Gln Leu
            100                 105                 110

Pro Arg Leu Ile His Glu Arg Leu Ala Pro Arg Ser Ser Trp Pro Asp
        115                 120                 125

Ala Gly Asn Leu Leu Val His Glu His Leu Ala Asp Val Leu Leu His
    130                 135                 140

Pro Gly Ala Pro Ile Ser Leu Arg Thr Thr Val Gly Lys Val Val Thr
145                 150                 155                 160

Arg Ala Val Leu Ala Gly Ala Arg Arg Arg His Ala Pro Pro Ser Arg
                165                 170                 175

Leu Leu Leu Arg His Arg Ala Ser Ala Ala Leu Gln Ala Glu Ile Arg
            180                 185                 190

Ala Arg Gln His Arg Arg Gln His His Gly Gly Ser Ala Gly Pro Arg
        195                 200                 205

Asp Leu Leu Asp Val Val Val Asp Gly Cys Gly Pro Ala Thr Ala Ser
    210                 215                 220

Asp Asp Leu Ala Glu Val Tyr Leu Ser Phe Leu Phe Ala Ala Val Gly
225                 230                 235                 240
```

```
Ser Ile Gly Phe Ala Leu Gly Trp Ser Val His Leu Leu Gly Thr His
                245                 250                 255

Pro Gly Cys Pro Ala Ala Pro Asp Arg Ile Val Arg Glu Ala Leu Arg
            260                 265                 270

Leu Trp Pro Val Ala Trp Leu Phe Ala Arg Thr Pro Leu Arg Ala Val
        275                 280                 285

Glu Leu Gly Gly Met Thr Val Thr Pro Glu Asp Gln Leu Ala Val Cys
    290                 295                 300

Thr Tyr Leu Val His Arg His Pro Ala Tyr Trp Glu Arg Pro Asp Glu
305                 310                 315                 320

Phe Leu Pro Gln Arg Trp Ala Ala Pro Val Ser Arg Ala Ala Tyr Leu
                325                 330                 335

Pro Phe Gly His Gly Pro His Thr Cys Ala Gly Ala Thr Val Thr Leu
            340                 345                 350

Gln Leu Leu Lys Asp Ile Val Gly Leu Leu Ile His Asp Trp Arg Leu
        355                 360                 365

Ser Val Ile His Asp Gly Gly Gly Pro Gln Val Gly Pro Ala Leu Ala
    370                 375                 380

Pro Pro Arg Phe Thr Ala Val Leu Ser Pro Arg Ala Asn Ser Ser Gly
385                 390                 395                 400

Arg Arg


<210> SEQ ID NO 80
<211> LENGTH: 1434
<212> TYPE: DNA
<213> ORGANISM: Streptomyces rimosus

<400> SEQUENCE: 80

atgcgcccac cccgcctacc cgaaccgctc cccctctacg gggaggacta caagcgcgac      60

ccgtaccccc tgtacgccga gctgcgcgag cgcggccccg tccaccgggt caggttcccg     120

agcggcgtgc acgcctggct cgtcaccgga tacgaggccg ctcaccgggc gctgaacgat     180

ccccggctgg gcaagcacca ctcccgcggc aacgccgcct ggcgcgcccg tgcctcgatc     240

atgcccgagc cgcagcattc gcggctccag gtccacctgc tgcaccagga cccgcccccgg    300

cacaccgcca tgcggcgcct gatcaccgac gccttcgcac ccaggcggat cgccggactc     360

cggccgcggt tcgagcgctt ggcggaggcg ctgttggatg aactgccgcc cgcagggccg     420

agcggcgaag gcggtccgga gcggggcgcc cgcgccgacc tggtcgcctc gttcgcggcg     480

cgcttcccct tcctcgtgct cgccgaggtc atcggcctgc cggacgcgtt caccgcgcgc     540

ttcgaccgcg actggggcaa ggtcgtccag cccgtcggcc cggacgatcc cggccgtccg     600

gcgtacgagg cccggctgcg cggcttgcag ggctatatcg ccgacctcgt acaacacaag     660

cggcgggaac gcggcaccga cctgctctcc cgtctggtca ccgcccgcga cgccggggaa     720

ctggacgatg ccgagctgga ctccatgatc ttccaactcc tcgtcgccgg acaggaaccc     780

gtcaccaacc agatcaccac agcgctgacc gccctgctcc ggcacccgga acacctcgcg     840

cggctgcgcg acgaccccgc gctcctcccc cgcgcggtgg aggaactgct ccgctacgac     900

agtgctttcg agctgacgac ctggcggttc ctcgcggcgg acgcggacgt gtcgggcacg     960

cggattccgg ccggcgactc cgtgatcgtc tcgctgtgcg cggccaaccg cgaccccgcc    1020

cgcttccccg cccccgacac gctcgacttc gaccgtacgc ccaacccgca tctcgccttc    1080

ggccacggca tccacttctg cccgggcgcc acgctcgccc gtaccgaact gcacatcgct    1140

ctggaaacgc tgctccgccg cctgccgggc ctgcgcctgg ccgtgccgga tgccgacttg    1200
```

```
aggtggatac cggcggtgct ggcgcgcggg gtggatgagc ttccggtctc gtacggggcg   1260

gttggcgggg ctgcgggcag cgatggcggg gtgggtacag aaccggccgg atcgggtaca   1320

gaaccggccg gtactcctgc gggcagaggc ggcgggtcgg gtacagaacc cgccggaccg   1380

cctccgtacg cctgcccctt cagcggctct gccggagagg ccgccacccg ataa         1434


<210> SEQ ID NO 81
<211> LENGTH: 477
<212> TYPE: PRT
<213> ORGANISM: Streptomyces rimosus

<400> SEQUENCE: 81

Met Arg Pro Pro Arg Leu Pro Glu Pro Leu Pro Leu Tyr Gly Glu Asp
1               5                   10                  15

Tyr Lys Arg Asp Pro Tyr Pro Leu Tyr Ala Glu Leu Arg Glu Arg Gly
            20                  25                  30

Pro Val His Arg Val Arg Phe Pro Ser Gly Val His Ala Trp Leu Val
        35                  40                  45

Thr Gly Tyr Glu Ala Ala His Arg Ala Leu Asn Asp Pro Arg Leu Gly
    50                  55                  60

Lys His His Ser Arg Gly Asn Ala Ala Trp Arg Ala Arg Ala Ser Ile
65                  70                  75                  80

Met Pro Glu Pro Gln His Ser Arg Leu Gln Val His Leu Leu His Gln
                85                  90                  95

Asp Pro Pro Arg His Thr Ala Met Arg Arg Leu Ile Thr Asp Ala Phe
            100                 105                 110

Ala Pro Arg Arg Ile Ala Gly Leu Arg Pro Arg Phe Glu Arg Leu Ala
        115                 120                 125

Glu Ala Leu Leu Asp Glu Leu Pro Pro Ala Gly Pro Ser Gly Glu Gly
    130                 135                 140

Gly Pro Glu Arg Gly Ala Arg Ala Asp Leu Val Ala Ser Phe Ala Ala
145                 150                 155                 160

Arg Phe Pro Phe Leu Val Leu Ala Glu Val Ile Gly Leu Pro Asp Ala
                165                 170                 175

Phe Thr Ala Arg Phe Asp Arg Asp Trp Gly Lys Val Val Gln Pro Val
            180                 185                 190

Gly Pro Asp Asp Pro Gly Arg Pro Ala Tyr Glu Ala Arg Leu Arg Gly
        195                 200                 205

Leu Gln Gly Tyr Ile Ala Asp Leu Val Gln His Lys Arg Arg Glu Arg
    210                 215                 220

Gly Thr Asp Leu Leu Ser Arg Leu Val Thr Ala Arg Asp Ala Gly Glu
225                 230                 235                 240

Leu Asp Asp Ala Glu Leu Asp Ser Met Ile Phe Gln Leu Leu Val Ala
                245                 250                 255

Gly Gln Glu Pro Val Thr Asn Gln Ile Thr Thr Ala Leu Thr Ala Leu
            260                 265                 270

Leu Arg His Pro Glu His Leu Ala Arg Leu Arg Asp Asp Pro Ala Leu
        275                 280                 285

Leu Pro Arg Ala Val Glu Glu Leu Leu Arg Tyr Asp Ser Ala Phe Glu
    290                 295                 300

Leu Thr Thr Trp Arg Phe Leu Ala Ala Asp Ala Asp Val Ser Gly Thr
305                 310                 315                 320

Arg Ile Pro Ala Gly Asp Ser Val Ile Val Ser Leu Cys Ala Ala Asn
                325                 330                 335
```

```
Arg Asp Pro Ala Arg Phe Pro Ala Pro Asp Thr Leu Asp Phe Asp Arg
            340                 345                 350

Thr Pro Asn Pro His Leu Ala Phe Gly His Gly Ile His Phe Cys Pro
        355                 360                 365

Gly Ala Thr Leu Ala Arg Thr Glu Leu His Ile Ala Leu Glu Thr Leu
    370                 375                 380

Leu Arg Arg Leu Pro Gly Leu Arg Leu Ala Val Pro Asp Ala Asp Leu
385                 390                 395                 400

Arg Trp Ile Pro Ala Val Leu Ala Arg Gly Val Asp Glu Leu Pro Val
                405                 410                 415

Ser Tyr Gly Ala Val Gly Gly Ala Ala Gly Ser Asp Gly Gly Val Gly
            420                 425                 430

Thr Glu Pro Ala Gly Ser Gly Thr Glu Pro Ala Gly Thr Pro Ala Gly
        435                 440                 445

Arg Gly Gly Gly Ser Gly Thr Glu Pro Ala Gly Pro Pro Pro Tyr Ala
    450                 455                 460

Cys Pro Phe Ser Gly Ser Ala Gly Glu Ala Ala Thr Arg
465                 470                 475


<210> SEQ ID NO 82
<211> LENGTH: 1218
<212> TYPE: DNA
<213> ORGANISM: Streptomyces rimosus

<400> SEQUENCE: 82

atggaaggag tccaggcagt cttcgatccc tggtcgccgg atttcgtcgc cgacccgtat      60

cccgcctacg ccgagctgcg cgcccgcggc cgggtgcact atttcgcgcc ctccaaccag     120

tggctcgtcc cgcgccacgc ggacgtcgcg gcgctgctcc gcgaccgccg gctgggccgt     180

acgtaccggc accgcttcac gcacgaggag ttcggccgta ccgctccgcc acccgagcac     240

gagccgttcc acgtgctcaa cgacaacggc atgctcgacc tggaggcgcc cgcccacacc     300

cgcatccgcc gtctggtctc gaaggcgttc accgcccgta cggtcgagcg gctgcggccc     360

tacgtcgaag ccctggcgga ccggctggcc gcggatctgg tcgcggacgg cggcggggac     420

ctggtggcgc gggtcgcgga gccgctgccc gtcgcggtga tcgccgaaat gctcggcatc     480

cccgaggccg accggcatgc gctgcgcccc tggtcggccg ccatctgcgg catgtacgag     540

ctgaacccgc cggaggagac ggcccggcgc gcggtggccg cttcgctgga attctccggc     600

tacctgcggg aattgatcgc cgctcggcgc agtgcgccgg gggacgacct gatctccggg     660

ctgatcgccg cgtacgacga gggcgagtcg ctgagcgaac aggagatgat ctcgacctgt     720

gtcctgctgc tgaacgcggg ccacgaggcc actgtcaacg cgacggccaa cggctggtac     780

gcgctcttcc gccacccgga gcagttggcg gccctgcgcg cggccccggc cgcgctgctg     840

cccaccgccg tggaggagtt gctgcgccac gacacgccgc tccagctctt cgaacgctgg     900

gtgctggacg acatcgagat cggcggtacg gtcgtgccgc gcggcagcga gatcgcgcta     960

ctcttcggct cggccaacca cgacccggca gccttcgacc accccgaacg gctcgacctc    1020

gcccgtaagg acaacccgca catctccttc agcgccggta tccactactg catcggcgcg    1080

cccctggccc gtatcgaact ggccgcctcg ctggcggcgt tgctccgccg ggcccctgac    1140

ctgcgcctgg ccgccactcc ggaacgcaag ccgaacttcg tgatccgagg actgcgcgag    1200

ctgctggtcg cggtgtaa                                                  1218
```

-continued

<210> SEQ ID NO 83
<211> LENGTH: 405
<212> TYPE: PRT
<213> ORGANISM: Streptomyces rimosus

<400> SEQUENCE: 83

```
Met Glu Gly Val Gln Ala Val Phe Asp Pro Trp Ser Pro Asp Phe Val
1               5                   10                  15

Ala Asp Pro Tyr Pro Ala Tyr Ala Glu Leu Arg Ala Arg Gly Arg Val
            20                  25                  30

His Tyr Phe Ala Pro Ser Asn Gln Trp Leu Val Pro Arg His Ala Asp
        35                  40                  45

Val Ala Ala Leu Leu Arg Asp Arg Arg Leu Gly Arg Thr Tyr Arg His
    50                  55                  60

Arg Phe Thr His Glu Glu Phe Gly Arg Thr Ala Pro Pro Pro Glu His
65                  70                  75                  80

Glu Pro Phe His Val Leu Asn Asp Asn Gly Met Leu Asp Leu Glu Ala
                85                  90                  95

Pro Ala His Thr Arg Ile Arg Arg Leu Val Ser Lys Ala Phe Thr Ala
            100                 105                 110

Arg Thr Val Glu Arg Leu Arg Pro Tyr Val Glu Ala Leu Ala Asp Arg
        115                 120                 125

Leu Ala Ala Asp Leu Val Ala Asp Gly Gly Gly Asp Leu Val Ala Arg
    130                 135                 140

Val Ala Glu Pro Leu Pro Val Ala Val Ile Ala Glu Met Leu Gly Ile
145                 150                 155                 160

Pro Glu Ala Asp Arg His Ala Leu Arg Pro Trp Ser Ala Ala Ile Cys
                165                 170                 175

Gly Met Tyr Glu Leu Asn Pro Pro Glu Glu Thr Ala Arg Arg Ala Val
            180                 185                 190

Ala Ala Ser Leu Glu Phe Ser Gly Tyr Leu Arg Glu Leu Ile Ala Ala
        195                 200                 205

Arg Arg Ser Ala Pro Gly Asp Asp Leu Ile Ser Gly Leu Ile Ala Ala
    210                 215                 220

Tyr Asp Glu Gly Glu Ser Leu Ser Glu Gln Glu Met Ile Ser Thr Cys
225                 230                 235                 240

Val Leu Leu Leu Asn Ala Gly His Glu Ala Thr Val Asn Ala Thr Ala
                245                 250                 255

Asn Gly Trp Tyr Ala Leu Phe Arg His Pro Glu Gln Leu Ala Ala Leu
            260                 265                 270

Arg Ala Ala Pro Ala Ala Leu Leu Pro Thr Ala Val Glu Glu Leu Leu
        275                 280                 285

Arg His Asp Thr Pro Leu Gln Leu Phe Glu Arg Trp Val Leu Asp Asp
    290                 295                 300

Ile Glu Ile Gly Gly Thr Val Val Pro Arg Gly Ser Glu Ile Ala Leu
305                 310                 315                 320

Leu Phe Gly Ser Ala Asn His Asp Pro Ala Ala Phe Asp His Pro Glu
                325                 330                 335

Arg Leu Asp Leu Ala Arg Lys Asp Asn Pro His Ile Ser Phe Ser Ala
            340                 345                 350

Gly Ile His Tyr Cys Ile Gly Ala Pro Leu Ala Arg Ile Glu Leu Ala
        355                 360                 365

Ala Ser Leu Ala Ala Leu Leu Arg Arg Ala Pro Asp Leu Arg Leu Ala
    370                 375                 380
```

-continued

```
Ala Thr Pro Glu Arg Lys Pro Asn Phe Val Ile Arg Gly Leu Arg Glu
385                 390                 395                 400

Leu Leu Val Ala Val
                405


<210> SEQ ID NO 84
<211> LENGTH: 2846
<212> TYPE: DNA
<213> ORGANISM: Streptomyces rimosus

<400> SEQUENCE: 84

atgcagatcg tcgtggacct cacccgctgt caggcgtacg cgcaatgcgt cttcctcgcg      60

ccggaggtct tccggctgcc cagggaggag agcctgctgt accgcccgga cgttcccgag     120

gaccagatgg agcgcgtgcg ccaggccgcg gcggcgtgcc cggtgcaggc gatcctgatg     180

ggagaggcgg tgagtcccgg tgcccggtga cctgcgggac ggccggatcg tcatcgtcgg     240

cgcgtcgctg gccggactgc gcgccgcgga gacgctgcgc gacgagggct tcaccggttc     300

gctgaccgtg ctgggcgagg agccgtggcc gccgtacgac aggccgccgc tgaccaagca     360

ggtgctcctc ggcaccgcgg ccccggagag caccgggctg ccgatgcgcc gggacgtgga     420

cgccgactgg cggctcgggg tacgcgccga cgggctcgat ccgatcggca agcgtgtgct     480

gctggccggc ggcgaggcgc tgccgtacga ccggctgctg atcgccaccg gtacccgggc     540

gcgcccctgg ccccacccgg aacaggccgc tctggacggg gtactggccg tgcgtacccg     600

cgacgacgcc gcgcatctgg ccgaccggct ggccgccggt ccgcgccggg tgctggtcat     660

cggcggcggc ttcaccggct cggagatcgc ctcggcctgc cgggaacggg acatcgaggt     720

cacggtcgcc gaacgcggcc ccggaccgct ggtgggcgcg ctcggcggca cgttggcgaa     780

gctcgccgcc ggcctgcaac gggcccacgg cgtggacctg cgctgcggcg tgacggtcac     840

cgcactgcgc ggggacgaca agggccgctt caccggggcg gatctctccg acggcagccg     900

catcgacgcg gacgtgtgcg tcatcgcgtt gggcgcggtg cgcaacgtcg aatggctggc     960

ggactccggg ctggcggcgg gcccccacgg agtcgcctgc gacgccggat gccgtgcctt    1020

cacccggtac gggatcgtca ccgacgacgt cttcgtggcc ggtgacgtct cccgcttccc    1080

gcatccgctc ttcgactacc agatgctctc cctggaacat tggggcaacg cggtcgccca    1140

ggccgaggtg gcggcccaca acatggtcag cccggggccg ctgcgccgtc cgcacctcgg    1200

cgttccggtg ttctggtcga accacttcgg gatcagcatc aagtccgtgg gcgtccccac    1260

cttctccgac caggtggtcg tcgcccaagg ctcggtggcc gaacgccggc tggcggcggt    1320

ctacggctac cagggccgcg tcaccgccgc ggtcaccgtc gacatgggca agtggctgga    1380

gcactaccag cgactgatcg agaccgccgc cccgttcccg cccgctcccg gcgcggccga    1440

cggccacccg ctgatcagcg aactcccggt gccctccgac gtaccggacc ccgcggggct    1500

ctcccacggc cccaccgtcg cgctcaccgg tcatctgccg gaccgccggc tcaccgtgcg    1560

gcattccggc acctgactcc tcagctctgt tgtcagtccc tcccgtccga ggagccgtca    1620

tggccgtcga caccctgctg gagcggatca ccgactacgc cagccgtccc gacccctacc    1680

cgctgtacgc ggagctgcgc gaggcgggcg tggcgcggca gacggacggc agctacctga    1740

tcggcgggta tcacgacatc gtcgcgttgc tgcacgaccc gcggctcagt tccgaccgcc    1800

gcaaccgcgc cgcgccctac cacggtctgc gcgaggacga ggagacgctg gtccccttcc    1860

tccggctcga cgaccccgag caccaccggc tgcgcgcgct ggccatgcgg ccgttcgggc    1920

caccgcacag cccgggccgg gtcgacgcga tgcgcggtga aatcgcccgt atcacccggg    1980
```

```
aactggccga ggcgttccgc ggccgtacgc acctcgacct cgtcgacgac ttcgcctacc   2040

cgctgcccgt caccgtgatc tgccggctgc tcggcgtccc gcgcgaggac gagccggtct   2100

tccgtgactg gtccaccacg atcatcgacg ccttcgacgt ccggtccggc gaggacgccg   2160

acaagcgtca acgggccggt gcccaggccc gcacggagat gggccgctac ctggtggacc   2220

tcgccgagcg gcgccgcgga cagccggacg acaccatgct ctccgcgttc gtcaacgccc   2280

cggccgcgga cggcgtgctc atccgcgagg aactggcggc caccgcagtc ctgttgctgg   2340

tcgccggaca cgagaccacc gtcaacctga tcaccaacgg cgtactcacc ctgctgcgcc   2400

accccgacca gctggaccga ctcctgcggg agccgcagct gatgcccacg gcggtggagg   2460

aactgctgcg ctacgagcca cccgtacacc tgctacaacg cgtacccctc gcccacatag   2520

acgtcgcggg cacaaccctc cccaagggcg tgccggtggt actcgccgtg gcctcgggca   2580

gccgcgaccc caggcgcttc cagaaccccg accggttcga ccccacccgc caggacaacc   2640

agcacctcgg cttcggcagc ggcatccacc tctgctacgg cgcccccctc gcccgcatag   2700

aagcccaaac cgccctcacg gcactcctgc cccacctcag cacagcaacg ctcaccgaag   2760

acccaccccc ttaccgccac agcgccctcc tgcgcggtcc tcggcacctg cccctcgatt   2820

tggcgtcgcc tcgaaataaa gggtaa                                         2846
```

<210> SEQ ID NO 85
<211> LENGTH: 408
<212> TYPE: PRT
<213> ORGANISM: Streptomyces rimosus

<400> SEQUENCE: 85

```
Met Ala Val Asp Thr Leu Leu Glu Arg Ile Thr Asp Tyr Ala Ser Arg
1               5                   10                  15

Pro Asp Pro Tyr Pro Leu Tyr Ala Glu Leu Arg Glu Ala Gly Val Ala
            20                  25                  30

Arg Gln Thr Asp Gly Ser Tyr Leu Ile Gly Gly Tyr His Asp Ile Val
        35                  40                  45

Ala Leu Leu His Asp Pro Arg Leu Ser Ser Asp Arg Arg Asn Arg Ala
    50                  55                  60

Ala Pro Tyr His Gly Leu Arg Glu Asp Glu Glu Thr Leu Val Pro Phe
65                  70                  75                  80

Leu Arg Leu Asp Asp Pro Glu His His Arg Leu Arg Ala Leu Ala Met
                85                  90                  95

Arg Pro Phe Gly Pro Pro His Ser Pro Gly Arg Val Asp Ala Met Arg
            100                 105                 110

Gly Glu Ile Ala Arg Ile Thr Arg Glu Leu Ala Glu Ala Phe Arg Gly
        115                 120                 125

Arg Thr His Leu Asp Leu Val Asp Asp Phe Ala Tyr Pro Leu Pro Val
    130                 135                 140

Thr Val Ile Cys Arg Leu Leu Gly Val Pro Arg Glu Asp Glu Pro Val
145                 150                 155                 160

Phe Arg Asp Trp Ser Thr Thr Ile Ile Asp Ala Phe Asp Val Arg Ser
                165                 170                 175

Gly Glu Asp Ala Asp Lys Arg Gln Arg Ala Gly Ala Gln Ala Arg Thr
            180                 185                 190

Glu Met Gly Arg Tyr Leu Val Asp Leu Ala Glu Arg Arg Arg Gly Gln
        195                 200                 205

Pro Asp Asp Thr Met Leu Ser Ala Phe Val Asn Ala Pro Ala Ala Asp
```

```
    210                 215                 220

Gly Val Leu Ile Arg Glu Glu Leu Ala Ala Thr Ala Val Leu Leu Leu
225                 230                 235                 240

Val Ala Gly His Glu Thr Thr Val Asn Leu Ile Thr Asn Gly Val Leu
                245                 250                 255

Thr Leu Leu Arg His Pro Asp Gln Leu Asp Arg Leu Leu Arg Glu Pro
            260                 265                 270

Gln Leu Met Pro Thr Ala Val Glu Glu Leu Leu Arg Tyr Glu Pro Pro
        275                 280                 285

Val His Leu Leu Gln Arg Val Pro Leu Ala His Ile Asp Val Ala Gly
    290                 295                 300

Thr Thr Leu Pro Lys Gly Val Pro Val Val Leu Ala Val Ala Ser Gly
305                 310                 315                 320

Ser Arg Asp Pro Arg Arg Phe Gln Asn Pro Asp Arg Phe Asp Pro Thr
                325                 330                 335

Arg Gln Asp Asn Gln His Leu Gly Phe Gly Ser Gly Ile His Leu Cys
            340                 345                 350

Tyr Gly Ala Pro Leu Ala Arg Ile Glu Ala Gln Thr Ala Leu Thr Ala
        355                 360                 365

Leu Leu Pro His Leu Ser Thr Ala Thr Leu Thr Glu Asp Pro Pro Pro
    370                 375                 380

Tyr Arg His Ser Ala Leu Leu Arg Gly Pro Arg His Leu Pro Leu Asp
385                 390                 395                 400

Leu Ala Ser Pro Arg Asn Lys Gly
                405


<210> SEQ ID NO 86
<211> LENGTH: 69
<212> TYPE: PRT
<213> ORGANISM: Streptomyces rimosus

<400> SEQUENCE: 86

Met Gln Ile Val Val Asp Leu Thr Arg Cys Gln Ala Tyr Ala Gln Cys
1               5                   10                  15

Val Phe Leu Ala Pro Glu Val Phe Arg Leu Pro Arg Glu Glu Ser Leu
            20                  25                  30

Leu Tyr Arg Pro Asp Val Pro Glu Asp Gln Met Glu Arg Val Arg Gln
        35                  40                  45

Ala Ala Ala Ala Cys Pro Val Gln Ala Ile Leu Met Gly Glu Ala Val
    50                  55                  60

Ser Pro Gly Ala Arg
65


<210> SEQ ID NO 87
<211> LENGTH: 458
<212> TYPE: PRT
<213> ORGANISM: Streptomyces rimosus

<400> SEQUENCE: 87

Val Pro Gly Asp Leu Arg Asp Gly Arg Ile Val Ile Val Gly Ala Ser
1               5                   10                  15

Leu Ala Gly Leu Arg Ala Ala Glu Thr Leu Arg Asp Glu Gly Phe Thr
            20                  25                  30

Gly Ser Leu Thr Val Leu Gly Glu Glu Pro Trp Pro Pro Tyr Asp Arg
        35                  40                  45

Pro Pro Leu Thr Lys Gln Val Leu Leu Gly Thr Ala Ala Pro Glu Ser
```

-continued

```
    50                  55                  60

Thr Gly Leu Pro Met Arg Arg Asp Val Asp Ala Asp Trp Arg Leu Gly
65                  70                  75                  80

Val Arg Ala Asp Gly Leu Asp Pro Ile Gly Lys Arg Val Leu Leu Ala
                85                  90                  95

Gly Gly Glu Ala Leu Pro Tyr Asp Arg Leu Leu Ile Ala Thr Gly Thr
            100                 105                 110

Arg Ala Arg Pro Trp Pro His Pro Glu Gln Ala Ala Leu Asp Gly Val
        115                 120                 125

Leu Ala Val Arg Thr Arg Asp Asp Ala Ala His Leu Ala Asp Arg Leu
    130                 135                 140

Ala Ala Gly Pro Arg Arg Val Leu Val Ile Gly Gly Gly Phe Thr Gly
145                 150                 155                 160

Ser Glu Ile Ala Ser Ala Cys Arg Glu Arg Asp Ile Glu Val Thr Val
                165                 170                 175

Ala Glu Arg Gly Pro Gly Pro Leu Val Gly Ala Leu Gly Gly Thr Leu
            180                 185                 190

Ala Lys Leu Ala Ala Gly Leu Gln Arg Ala His Gly Val Asp Leu Arg
        195                 200                 205

Cys Gly Val Thr Val Thr Ala Leu Arg Gly Asp Asp Lys Gly Arg Phe
    210                 215                 220

Thr Gly Ala Asp Leu Ser Asp Gly Ser Arg Ile Asp Ala Asp Val Cys
225                 230                 235                 240

Val Ile Ala Leu Gly Ala Val Arg Asn Val Glu Trp Leu Ala Asp Ser
                245                 250                 255

Gly Leu Ala Ala Gly Pro His Gly Val Ala Cys Asp Ala Gly Cys Arg
            260                 265                 270

Ala Phe Thr Arg Tyr Gly Ile Val Thr Asp Asp Val Phe Val Ala Gly
        275                 280                 285

Asp Val Ser Arg Phe Pro His Pro Leu Phe Asp Tyr Gln Met Leu Ser
    290                 295                 300

Leu Glu His Trp Gly Asn Ala Val Ala Gln Ala Glu Val Ala Ala His
305                 310                 315                 320

Asn Met Val Ser Pro Gly Pro Leu Arg Arg Pro His Leu Gly Val Pro
                325                 330                 335

Val Phe Trp Ser Asn His Phe Gly Ile Ser Ile Lys Ser Val Gly Val
            340                 345                 350

Pro Thr Phe Ser Asp Gln Val Val Val Ala Gln Gly Ser Val Ala Glu
        355                 360                 365

Arg Arg Leu Ala Ala Val Tyr Gly Tyr Gln Gly Arg Val Thr Ala Ala
    370                 375                 380

Val Thr Val Asp Met Gly Lys Trp Leu Glu His Tyr Gln Arg Leu Ile
385                 390                 395                 400

Glu Thr Ala Ala Pro Phe Pro Pro Ala Pro Gly Ala Ala Asp Gly His
                405                 410                 415

Pro Leu Ile Ser Glu Leu Pro Val Pro Ser Asp Val Pro Asp Pro Ala
            420                 425                 430

Gly Leu Ser His Gly Pro Thr Val Ala Leu Thr Gly His Leu Pro Asp
        435                 440                 445

Arg Arg Leu Thr Val Arg His Ser Gly Thr
    450                 455
```

<210> SEQ ID NO 88

<211> LENGTH: 1272
<212> TYPE: DNA
<213> ORGANISM: Streptomyces rimosus

<400> SEQUENCE: 88
atgtccggcc acggaccggc ggccgtcccg ccctgtccgg aactgttcac gtgggagttc 60
gccgccgacc cgtacccggc gtacgcctgg ctgcgcgagc acgcgcccgt acaccgcacc 120
cggctgccca gcggtgtcga agcctggctg gtgacccggt acgcggacgc gcggcaggcg 180
ctcgccgaca cccggctgtc gaagaacccg gtgcaccaca gcgaggccgc gcacggcaag 240
ggcaaggtcg gcatccccgg cgagcggggc gccaacctga tgacgcacct gctcaacatc 300
gacccaccgg accacacccg gctgcgccgc ctggtctcca aagccttcac cccgcgccgc 360
atcgcccggt tcgcgccgcg cgtacaggaa ctgaccgacg cgctgatcga ctccttcgcg 420
gagcgcggcg aggccgatct catccacgag ttcgccttcc cgctccccat ctacgccatc 480
tgcgatctgc tcggtgtccc gcgcgaggac caggacgact tccgcgactg ggccgggatg 540
atgatccggc acggcggcgg gccgcgcggc ggcgtcgccc ggtcggtgaa gaagatgcgc 600
ggctacctcg ccgagctgat ccaccgcaag cgcgaggccc tgggggagga aggggccgac 660
gacctcatct ccggcctgat ccgcgcctcc gaccacggcg agcacctgac ggagaacgag 720
gccgccgcga tggccttcat cctgctgttc gcgggcttcg agaccaccgt caatctcatc 780
ggcaacggcg tgtaccagct gctgcgccac cctgaccagc gcgcactgct ccagaaggcc 840
gctgcggcgg gcgatacgga gctgctcgcc gccggggtcg aggagctgct gcgctacgac 900
ggcccggtcg agctggccac ctggcgcttc gcgacccggg acctgaccct gggcgggcag 960
cgcatcgccg agggagatcc ggtcctggtc gtgctcgccg ccgccgaccg cgacccgcgg 1020
cgcttcgcgg aaccggacgt actggacctg cgccgccgcg acaatcagca cctcggatac 1080
ggccacggca tccactactg cctgggcgcg ccgctggccc gtctcgaagg ccaggccgcc 1140
atcgccacgc tgctgacccg gctgccggac ctggcactcg ccgccgaccc ggacgatctg 1200
cggtggcgcg gcgggctgat catgcgaggg ctgcgggccc tgccggtgga gttcacgccc 1260
gtacggaagt aa 1272

<210> SEQ ID NO 89
<211> LENGTH: 423
<212> TYPE: PRT
<213> ORGANISM: Streptomyces rimosus

<400> SEQUENCE: 89

Met Ser Gly His Gly Pro Ala Ala Val Pro Pro Cys Pro Glu Leu Phe
1 5 10 15

Thr Trp Glu Phe Ala Ala Asp Pro Tyr Pro Ala Tyr Ala Trp Leu Arg
20 25 30

Glu His Ala Pro Val His Arg Thr Arg Leu Pro Ser Gly Val Glu Ala
35 40 45

Trp Leu Val Thr Arg Tyr Ala Asp Ala Arg Gln Ala Leu Ala Asp Thr
50 55 60

Arg Leu Ser Lys Asn Pro Val His His Ser Glu Ala Ala His Gly Lys
65 70 75 80

Gly Lys Val Gly Ile Pro Gly Glu Arg Gly Ala Asn Leu Met Thr His
85 90 95

Leu Leu Asn Ile Asp Pro Pro Asp His Thr Arg Leu Arg Arg Leu Val
100 105 110

```
Ser Lys Ala Phe Thr Pro Arg Arg Ile Ala Arg Phe Ala Pro Arg Val
        115                 120                 125

Gln Glu Leu Thr Asp Ala Leu Ile Asp Ser Phe Ala Glu Arg Gly Glu
    130                 135                 140

Ala Asp Leu Ile His Glu Phe Ala Phe Pro Leu Pro Ile Tyr Ala Ile
145                 150                 155                 160

Cys Asp Leu Leu Gly Val Pro Arg Glu Asp Gln Asp Asp Phe Arg Asp
                165                 170                 175

Trp Ala Gly Met Met Ile Arg His Gly Gly Gly Pro Arg Gly Gly Val
            180                 185                 190

Ala Arg Ser Val Lys Lys Met Arg Gly Tyr Leu Ala Glu Leu Ile His
        195                 200                 205

Arg Lys Arg Glu Ala Leu Gly Glu Glu Gly Ala Asp Asp Leu Ile Ser
    210                 215                 220

Gly Leu Ile Arg Ala Ser Asp His Gly Glu His Leu Thr Glu Asn Glu
225                 230                 235                 240

Ala Ala Ala Met Ala Phe Ile Leu Leu Phe Ala Gly Phe Glu Thr Thr
                245                 250                 255

Val Asn Leu Ile Gly Asn Gly Val Tyr Gln Leu Leu Arg His Pro Asp
            260                 265                 270

Gln Arg Ala Leu Leu Gln Lys Ala Ala Ala Ala Gly Asp Thr Glu Leu
        275                 280                 285

Leu Ala Ala Gly Val Glu Glu Leu Leu Arg Tyr Asp Gly Pro Val Glu
    290                 295                 300

Leu Ala Thr Trp Arg Phe Ala Thr Arg Asp Leu Thr Leu Gly Gly Gln
305                 310                 315                 320

Arg Ile Ala Glu Gly Asp Pro Val Leu Val Val Leu Ala Ala Ala Asp
                325                 330                 335

Arg Asp Pro Arg Arg Phe Ala Glu Pro Asp Val Leu Asp Leu Arg Arg
            340                 345                 350

Arg Asp Asn Gln His Leu Gly Tyr Gly His Gly Ile His Tyr Cys Leu
        355                 360                 365

Gly Ala Pro Leu Ala Arg Leu Glu Gly Gln Ala Ala Ile Ala Thr Leu
    370                 375                 380

Leu Thr Arg Leu Pro Asp Leu Ala Leu Ala Ala Asp Pro Asp Asp Leu
385                 390                 395                 400

Arg Trp Arg Gly Gly Leu Ile Met Arg Gly Leu Arg Ala Leu Pro Val
                405                 410                 415

Glu Phe Thr Pro Val Arg Lys
            420
```

<210> SEQ ID NO 90
<211> LENGTH: 1233
<212> TYPE: DNA
<213> ORGANISM: Streptomyces rimosus

<400> SEQUENCE: 90

```
atgccatgcc ccgcgctgcc cgacgggttc gacttcaccg accccgacgt ctaccagagc      60

cgtgtaccgc tgcccgagtt cgcgcggctg cggcgtacca cccccgtctg gtggaacgcc     120

cagccgcacg gcatcgccgg gttcggcgac gacgggtact gggtggtgac ccgccacgag     180

gacgtcaagg aggtctccac ccggccggag gtcttctcgg cgagcaccaa cacctcgatc     240

atccggttca acgcggccat gacccgcgac cggatcgacg tccagaagct gatcatgctg     300

aacatggacc cgccggagca cacccgggtc cgccagatcg tccagcgcgg cttcacgccc     360
```

```
cgcgccatcc gcgccctgga ggacgcgctg cgcacccgcg cgcggaccat cgtcgccgag    420

gcgcggcgca aggagtccgg cgacttcgtc accgatgtcg cctgtgaact gcccctccag    480

gccatcgccg agctgatcgg catcccccag gacgaccggg cccggatctt cgactggtcg    540

aacaagatgg tcgcgtacga cgatcccgag ctggccatca ccgaggaggt cggcaacacc    600

gcggcggcgg agctgatctc gtacgcgatg aacctggccg cggaccgcaa ggagtgcccc    660

gcccaggaca tcgtcagccg gctcgtcgcg gcggaggacg agggcaacct cgcgtccgac    720

gagttcgggt tcttcgtcct gctgctggcc gtcgcgggca acgagaccac gcgcaacgcg    780

atcacgcacg gcatgcacgc gttcctgacg caccccgacc agtgggagct gtacaagcgc    840

gagcggccga gcaccacggc cgaggagatc gtgcgctggg cgacgcccgt cgtctccttc    900

cagcgcacgg ccacccagga caccaccctg ggcggcgcgc ggatcgaaaa ggggcagcgc    960

gtcggcctct tctacgcctc cgccaaccac gaccccgagg tcttcgcgca cccggagacg   1020

ttcgacatca cccgcgaccc caacccccat ctgggcttcg gcgggggcgg cccgcacttc   1080

tgcctcggca agtcgctcgc cgtcctggag atcgacctga tcttccaggc catcgccgac   1140

gccatgccgg acatcgccct cgtgggcacc ccgcgccggc tgcggtcggc gtggctcaac   1200

ggggtgaagg agctgcgggt ccggtacgtg taa                                1233
```

<210> SEQ ID NO 91
<211> LENGTH: 410
<212> TYPE: PRT
<213> ORGANISM: Streptomyces rimosus

<400> SEQUENCE: 91

```
Met Pro Cys Pro Ala Leu Pro Asp Gly Phe Asp Phe Thr Asp Pro Asp
1               5                   10                  15

Val Tyr Gln Ser Arg Val Pro Leu Pro Glu Phe Ala Arg Leu Arg Arg
            20                  25                  30

Thr Thr Pro Val Trp Trp Asn Ala Gln Pro His Gly Ile Ala Gly Phe
        35                  40                  45

Gly Asp Asp Gly Tyr Trp Val Val Thr Arg His Glu Asp Val Lys Glu
    50                  55                  60

Val Ser Thr Arg Pro Glu Val Phe Ser Ala Ser Thr Asn Thr Ser Ile
65                  70                  75                  80

Ile Arg Phe Asn Ala Ala Met Thr Arg Asp Arg Ile Asp Val Gln Lys
                85                  90                  95

Leu Ile Met Leu Asn Met Asp Pro Pro Glu His Thr Arg Val Arg Gln
            100                 105                 110

Ile Val Gln Arg Gly Phe Thr Pro Arg Ala Ile Arg Ala Leu Glu Asp
        115                 120                 125

Ala Leu Arg Thr Arg Ala Arg Thr Ile Val Ala Glu Ala Arg Arg Lys
    130                 135                 140

Glu Ser Gly Asp Phe Val Thr Asp Val Ala Cys Glu Leu Pro Leu Gln
145                 150                 155                 160

Ala Ile Ala Glu Leu Ile Gly Ile Pro Gln Asp Asp Arg Ala Arg Ile
                165                 170                 175

Phe Asp Trp Ser Asn Lys Met Val Ala Tyr Asp Asp Pro Glu Leu Ala
            180                 185                 190

Ile Thr Glu Glu Val Gly Asn Thr Ala Ala Ala Glu Leu Ile Ser Tyr
        195                 200                 205

Ala Met Asn Leu Ala Ala Asp Arg Lys Glu Cys Pro Ala Gln Asp Ile
```

```
    210                 215                 220

Val Ser Arg Leu Val Ala Ala Glu Asp Glu Gly Asn Leu Ala Ser Asp
225                 230                 235                 240

Glu Phe Gly Phe Phe Val Leu Leu Leu Ala Val Ala Gly Asn Glu Thr
                245                 250                 255

Thr Arg Asn Ala Ile Thr His Gly Met His Ala Phe Leu Thr His Pro
            260                 265                 270

Asp Gln Trp Glu Leu Tyr Lys Arg Glu Arg Pro Ser Thr Thr Ala Glu
        275                 280                 285

Glu Ile Val Arg Trp Ala Thr Pro Val Val Ser Phe Gln Arg Thr Ala
    290                 295                 300

Thr Gln Asp Thr Thr Leu Gly Gly Ala Arg Ile Glu Lys Gly Gln Arg
305                 310                 315                 320

Val Gly Leu Phe Tyr Ala Ser Ala Asn His Asp Pro Glu Val Phe Ala
                325                 330                 335

His Pro Glu Thr Phe Asp Ile Thr Arg Asp Pro Asn Pro His Leu Gly
            340                 345                 350

Phe Gly Gly Gly Gly Pro His Phe Cys Leu Gly Lys Ser Leu Ala Val
        355                 360                 365

Leu Glu Ile Asp Leu Ile Phe Gln Ala Ile Ala Asp Ala Met Pro Asp
    370                 375                 380

Ile Ala Leu Val Gly Thr Pro Arg Arg Leu Arg Ser Ala Trp Leu Asn
385                 390                 395                 400

Gly Val Lys Glu Leu Arg Val Arg Tyr Val
                405                 410
```

<210> SEQ ID NO 92
<211> LENGTH: 1230
<212> TYPE: DNA
<213> ORGANISM: Streptomyces rimosus

<400> SEQUENCE: 92

```
atggacgcgc gggtccgcca cagccccgag gccgagcgca tcgacacccg cggcgaaccg     60

ccggtgtggc gcgcggagct gcccgacggc tccaccgcct gggtcgcgtc cgggtacgac    120

gccgcgcgcc aggtgctgac ggactccggc ttcgcgaaac cggccgtccg gggcggcgag    180

cgctggacgg actatctggc cttcaccggc aaggaggtca ccgacagcat cgtgcgcagc    240

atgctcaaca ccgacggcga cctgcaccgg cagctgcgcg aactgggcgc gtcggcgttc    300

acgcccgagc gggtgcggga gaccgccgac cgcgcggaaa cgctcgccga gaccctgctc    360

gacgagatcg cgggacgcgg ccgcgccgac ctcgtccacg aattcgccca ccccttcgcc    420

gtccgggcca tcaccgaaca cctcggctat ccgcccgatt tcatccggcg cgccctggag    480

ctgcggcgct ggggcccgtc cccgctgttc gatccccccg gctccccgga ccgcgcgcgc    540

tacgccgccg accgcacggc catgagcgag ctgctgcacg acctggtggc cttccggcgc    600

ggcagccccg ggcccgacgc cgtcagcggg atgatcgcgc gcgccgacgc cgcgggcctg    660

gacgaagggc agctgacctc caccctcttc ctgctgctcg tctccgccta cgaaccggtc    720

gccgacttcc tcacgtcgag cctgtactcc ctctggcacc gccccgacct gctcgccgac    780

cccgcccggg tggccgacgg cctcggcgag ctgctgcgct acacctcccc gctggccgcc    840

accatgccgc gcttcgccac ccgcccgatg gagctgtacg gcgccgagct ggcgccgggg    900

gacgcggtga tcgtgcacct ggccctcgcc aaccgcgacc cgcgccgctt caccgccccc    960

aaccgcctcg acctcgaccg ggaaaccggc caggacctgg tcttcgcgca cggcccgcac   1020
```

```
ttctgcctcg gcagccagtt cgcggtccgg ctgtgccgta cggccctcgg cgccgtgctg   1080

cgccgcctgc ccggactcgc cgccgcccgg ccgctcgaca cactgccctg gcagcgcggc   1140

tccacgggcg gcatcaccca tctgcacgtc accgcgggcc tgacggagct gcccgtcacc   1200

ttccagcccc ggcacgcggt ggtctcctaa                                    1230
```

<210> SEQ ID NO 93
<211> LENGTH: 409
<212> TYPE: PRT
<213> ORGANISM: Streptomyces rimosus

<400> SEQUENCE: 93

```
Met Asp Ala Arg Val Arg His Ser Pro Glu Ala Glu Arg Ile Asp Thr
1               5                   10                  15

Arg Gly Glu Pro Pro Val Trp Arg Ala Glu Leu Pro Asp Gly Ser Thr
            20                  25                  30

Ala Trp Val Ala Ser Gly Tyr Asp Ala Ala Arg Gln Val Leu Thr Asp
        35                  40                  45

Ser Gly Phe Ala Lys Pro Ala Val Arg Gly Gly Glu Arg Trp Thr Asp
    50                  55                  60

Tyr Leu Ala Phe Thr Gly Lys Glu Val Thr Asp Ser Ile Val Arg Ser
65                  70                  75                  80

Met Leu Asn Thr Asp Gly Asp Leu His Arg Gln Leu Arg Glu Leu Gly
                85                  90                  95

Ala Ser Ala Phe Thr Pro Glu Arg Val Arg Glu Thr Ala Asp Arg Ala
            100                 105                 110

Glu Thr Leu Ala Glu Thr Leu Leu Asp Glu Ile Ala Gly Arg Gly Arg
        115                 120                 125

Ala Asp Leu Val His Glu Phe Ala His Pro Phe Ala Val Arg Ala Ile
    130                 135                 140

Thr Glu His Leu Gly Tyr Pro Pro Asp Phe Ile Arg Arg Ala Leu Glu
145                 150                 155                 160

Leu Arg Arg Trp Gly Pro Ser Pro Leu Phe Asp Pro Pro Gly Ser Pro
                165                 170                 175

Asp Arg Ala Arg Tyr Ala Ala Asp Arg Thr Ala Met Ser Glu Leu Leu
            180                 185                 190

His Asp Leu Val Ala Phe Arg Arg Gly Ser Pro Gly Pro Asp Ala Val
        195                 200                 205

Ser Gly Met Ile Ala Arg Ala Asp Ala Ala Gly Leu Asp Glu Gly Gln
    210                 215                 220

Leu Thr Ser Thr Leu Phe Leu Leu Leu Val Ser Ala Tyr Glu Pro Val
225                 230                 235                 240

Ala Asp Phe Leu Thr Ser Ser Leu Tyr Ser Leu Trp His Arg Pro Asp
                245                 250                 255

Leu Leu Ala Asp Pro Ala Arg Val Ala Asp Gly Leu Gly Glu Leu Leu
            260                 265                 270

Arg Tyr Thr Ser Pro Leu Ala Ala Thr Met Pro Arg Phe Ala Thr Arg
        275                 280                 285

Pro Met Glu Leu Tyr Gly Ala Glu Leu Ala Pro Gly Asp Ala Val Ile
    290                 295                 300

Val His Leu Ala Leu Ala Asn Arg Asp Pro Arg Arg Phe Thr Ala Pro
305                 310                 315                 320

Asn Arg Leu Asp Leu Asp Arg Glu Thr Gly Gln Asp Leu Val Phe Ala
                325                 330                 335
```

His Gly Pro His Phe Cys Leu Gly Ser Gln Phe Ala Val Arg Leu Cys
340 345 350

Arg Thr Ala Leu Gly Ala Val Leu Arg Arg Leu Pro Gly Leu Ala Ala
355 360 365

Ala Arg Pro Leu Asp Thr Leu Pro Trp Gln Arg Gly Ser Thr Gly Gly
370 375 380

Ile Thr His Leu His Val Thr Ala Gly Leu Thr Glu Leu Pro Val Thr
385 390 395 400

Phe Gln Pro Arg His Ala Val Val Ser
405

<210> SEQ ID NO 94
<211> LENGTH: 1518
<212> TYPE: DNA
<213> ORGANISM: Streptomyces rimosus

<400> SEQUENCE: 94
atgggtatac gtggtgcggc gggcgtccgc gcggcccgcg gtcccgcccc gcacagctgg 60
accgtgtcga cggcacccgg cggcgtaccg ctgctgggac acgcgctccc gctgtggcgg 120
cgcccgctgg acttcctcgc ctcgctgccc gcgcacggcg acctggtcgc gatccgcctc 180
ggaccgcagc gcgtgtggct cgcctgcgac ccggcgctgg tgcagcagat cctcatggac 240
ccgcgcacgt acgacaaggg cggtccgctc tacgacacca tgcgcatggt gctcggcaac 300
gggctggtca cctgcaccca ggacgtgcac cgcaggcagc gccggctggc ccagccctgc 360
ttccgcccgt cccggatcgc cgactacgcg caggtgatga gcgccgagat cgacgccgcc 420
gtcggaaagt ggcggcccgg acagacgctg gacgtcaccg acgcgatgat ggacctctcg 480
gcccgggtca ccaccggcgt gctgatgtcc acgtccctcg acccgggcct cgccgccgag 540
gtacgcgcct gcctgtcgac cgtcatgcgc ggcgtcctgc tgcgcgcggt cgtcccgctc 600
ggcccgctct acagactccc cacgcccggc aaccgccgct tcgaccgggc tctcgcccgg 660
ctgcaccaca tcatcgacgg gatcatcgcc gaacgccgcg gcagcaccgc ccggcacggc 720
gacctgctcg acaccctcct gggagccacg gacgacgccc ccggaccgga cggccgcgcc 780
gtacccgaag gccttgccca ggactgcccc cacgccaccg ccgcgcccac cccccaggag 840
gcaccccacg atcaggaacc gctcaccgac caagaggcgc acgaccagtt gatgaccttc 900
ctcgtggccg gcatcgagac caccgcgctg gccctcgcct ggacgctcca cctcctggcg 960
gcccaccccg aggaagaacg ccggctgcac gccgaggtgg actccgtgct cgccggccgg 1020
ccgcccgcgc cggacgatct gccccggctc ggccacgccc ggcgcgtggt caccgaagcc 1080
ctgcgcatgt acccgccggg ctgggccctg acccgggtga ccaccaccga gaccacgctg 1140
gccggccacc ggctggcacc gggaagcacc gtcctgtaca gcgcgtacgt gctccaccag 1200
gacccggtgg ccttccccga cccccagcgt ttcgaccccg accgatggtt gccggaacgg 1260
gcagggggcg ttccgggcgg tgcgatgctc ccgttcgccg ccggcaaccg caagtgcatc 1320
ggcgaccact tcgcgatgac cgaagccgtg ctcgtccttg ccgccatcgc cgcgcgctgg 1380
cgcctgcgcc cgccgtcccc caggaccgta cgaccggtcc cggcggccgt gctgagcccg 1440
ggcccgctgc ccatggtctg cgcctcacgc cgcggaccgg acggcccagc gccggccgtg 1500
ccatctgaag caccgtaa 1518

<210> SEQ ID NO 95
<211> LENGTH: 505

<212> TYPE: PRT
<213> ORGANISM: Streptomyces rimosus

<400> SEQUENCE: 95

Met Gly Ile Arg Gly Ala Ala Gly Val Arg Ala Ala Arg Gly Pro Ala
1 5 10 15

Pro His Ser Trp Thr Val Ser Thr Ala Pro Gly Gly Val Pro Leu Leu
20 25 30

Gly His Ala Leu Pro Leu Trp Arg Arg Pro Leu Asp Phe Leu Ala Ser
35 40 45

Leu Pro Ala His Gly Asp Leu Val Ala Ile Arg Leu Gly Pro Gln Arg
50 55 60

Val Trp Leu Ala Cys Asp Pro Ala Leu Val Gln Gln Ile Leu Met Asp
65 70 75 80

Pro Arg Thr Tyr Asp Lys Gly Gly Pro Leu Tyr Asp Thr Met Arg Met
85 90 95

Val Leu Gly Asn Gly Leu Val Thr Cys Thr Gln Asp Val His Arg Arg
100 105 110

Gln Arg Arg Leu Ala Gln Pro Cys Phe Arg Pro Ser Arg Ile Ala Asp
115 120 125

Tyr Ala Gln Val Met Ser Ala Glu Ile Asp Ala Ala Val Gly Lys Trp
130 135 140

Arg Pro Gly Gln Thr Leu Asp Val Thr Asp Ala Met Met Asp Leu Ser
145 150 155 160

Ala Arg Val Thr Thr Gly Val Leu Met Ser Thr Ser Leu Asp Pro Gly
165 170 175

Leu Ala Ala Glu Val Arg Ala Cys Leu Ser Thr Val Met Arg Gly Val
180 185 190

Leu Leu Arg Ala Val Val Pro Leu Gly Pro Leu Tyr Arg Leu Pro Thr
195 200 205

Pro Gly Asn Arg Arg Phe Asp Arg Ala Leu Ala Arg Leu His His Ile
210 215 220

Ile Asp Gly Ile Ile Ala Glu Arg Arg Gly Ser Thr Ala Arg His Gly
225 230 235 240

Asp Leu Leu Asp Thr Leu Leu Gly Ala Thr Asp Asp Ala Pro Gly Pro
245 250 255

Asp Gly Arg Ala Val Pro Glu Gly Leu Ala Gln Asp Cys Pro His Ala
260 265 270

Thr Ala Ala Pro Thr Pro Gln Glu Ala Pro His Asp Gln Glu Pro Leu
275 280 285

Thr Asp Gln Glu Ala His Asp Gln Leu Met Thr Phe Leu Val Ala Gly
290 295 300

Ile Glu Thr Thr Ala Leu Ala Leu Ala Trp Thr Leu His Leu Leu Ala
305 310 315 320

Ala His Pro Glu Glu Glu Arg Arg Leu His Ala Glu Val Asp Ser Val
325 330 335

Leu Ala Gly Arg Pro Pro Ala Pro Asp Asp Leu Pro Arg Leu Gly His
340 345 350

Ala Arg Arg Val Val Thr Glu Ala Leu Arg Met Tyr Pro Pro Gly Trp
355 360 365

Ala Leu Thr Arg Val Thr Thr Thr Glu Thr Thr Leu Ala Gly His Arg
370 375 380

Leu Ala Pro Gly Ser Thr Val Leu Tyr Ser Ala Tyr Val Leu His Gln
385 390 395 400

-continued

```
Asp Pro Val Ala Phe Pro Asp Pro Gln Arg Phe Asp Pro Asp Arg Trp
                405                 410                 415

Leu Pro Glu Arg Ala Gly Gly Val Pro Gly Gly Ala Met Leu Pro Phe
            420                 425                 430

Ala Ala Gly Asn Arg Lys Cys Ile Gly Asp His Phe Ala Met Thr Glu
        435                 440                 445

Ala Val Leu Val Leu Ala Ala Ile Ala Ala Arg Trp Arg Leu Arg Pro
    450                 455                 460

Pro Ser Pro Arg Thr Val Arg Pro Val Pro Ala Ala Val Leu Ser Pro
465                 470                 475                 480

Gly Pro Leu Pro Met Val Cys Ala Ser Arg Arg Gly Pro Asp Gly Pro
                485                 490                 495

Ala Pro Ala Val Pro Ser Glu Ala Pro
            500                 505


<210> SEQ ID NO 96
<211> LENGTH: 1341
<212> TYPE: DNA
<213> ORGANISM: Streptomyces rimosus

<400> SEQUENCE: 96

atgggtacgc acattcctgg acccgaaccc cggccggacg gcggggtgga tgctgtcgcg     60

gcggcgggtg ggctgcaccg gtatcagttg tggctgcatg ccgagtacgg gcccgtggtg    120

cggttccagc tgccgggggc ggagacggcc gtttcggtgg cggatccggt gctgctggag    180

gccacggcgc acatcgacaa gcggccggag cggttgttcg agtttctggc accgctgtgc    240

gaggcgggca atctgcaggt gttgccggcc gaggagcaca ccccgtggcg tcgggtgctg    300

ttgtcggtgc tggccgggcg gccgtcgcac gaacggcact tcgagcggtt caccgagctg    360

acgacgtccc tcgcggaccg gtgggccggg cagggcgaac aggaaccggt cgcgttgcag    420

aaggaactga ccgcactgtc gttgcggatg atcggtgcgt acgcgctggg gggcgacgcg    480

gcggatccgg agaaggtcat cgcggccttc gaggaggtgc tcaccgagta tctggggcgg    540

ctctaccagg tgcccgtgcc gggtacggag gaggagcgcg cccggcgggc ggagcaggcc    600

ctcgcgtatc tgcgggcgac cgtcgaccgg gtgctgacgg cgcaccgccc tgacagccgt    660

acggaccgga gcgatctgat cggggccctc gtggcggccg gtgaggaccc ggcgcggatc    720

cgtgacacgg tgatggtggc gatgctggcc gcgcaccaca cgacgggcgt ggccgtgtcg    780

tggaccctgc acctgctggg acgccacccc gaggtggccg aacgcgtcgc cggggagctg    840

gaccgcgtgc tcggcgaccg tgcggtgccc gggtacgccg atctgcggcg cctgacgtat    900

ctggacatgg tcctgaagga gtcgatgcgg ctgttcccgc ccggtccgta cggtgcacgg    960

gagacgaccg aggcgctggt cctgggcgcg tacgaggttc cggccgggac ggtgatcttc   1020

tatccgttct gggccgtcca tctgaacccc gatcactggc ccgagcccga gaggttcgtg   1080

cccgagcggt tccttccgga agaggtggcc aagcgtccga ggctggcgta catcccgttc   1140

ggcctcgggc cgcgcagctg tgagggcgcc ggtctggcca cggtcgaggc gcaactggtc   1200

ctggccgtac tgctcaagcg cttccggttc cggcctgtgc cagggcatga ggtgacgccg   1260

atcgagcggt tcgtgctgtg ggcggccgat gacatccgga tgttcgtgag tcggcgggag   1320

gtgggggcgg ggagcccgta a                                             1341


<210> SEQ ID NO 97
<211> LENGTH: 446
```

<212> TYPE: PRT
<213> ORGANISM: Streptomyces rimosus

<400> SEQUENCE: 97

```
Met Gly Thr His Ile Pro Gly Pro Glu Pro Arg Pro Asp Gly Gly Val
1               5                   10                  15

Asp Ala Val Ala Ala Ala Gly Gly Leu His Arg Tyr Gln Leu Trp Leu
            20                  25                  30

His Ala Glu Tyr Gly Pro Val Val Arg Phe Gln Leu Pro Gly Ala Glu
        35                  40                  45

Thr Ala Val Ser Val Ala Asp Pro Val Leu Leu Glu Ala Thr Ala His
    50                  55                  60

Ile Asp Lys Arg Pro Glu Arg Leu Phe Glu Phe Leu Ala Pro Leu Cys
65                  70                  75                  80

Glu Ala Gly Asn Leu Gln Val Leu Pro Ala Glu Glu His Thr Pro Trp
                85                  90                  95

Arg Arg Val Leu Leu Ser Val Leu Ala Gly Arg Pro Ser His Glu Arg
            100                 105                 110

His Phe Glu Arg Phe Thr Glu Leu Thr Thr Ser Leu Ala Asp Arg Trp
        115                 120                 125

Ala Gly Gln Gly Glu Gln Glu Pro Val Ala Leu Gln Lys Glu Leu Thr
    130                 135                 140

Ala Leu Ser Leu Arg Met Ile Gly Ala Tyr Ala Leu Gly Gly Asp Ala
145                 150                 155                 160

Ala Asp Pro Glu Lys Val Ile Ala Ala Phe Glu Glu Val Leu Thr Glu
                165                 170                 175

Tyr Leu Gly Arg Leu Tyr Gln Val Pro Val Pro Gly Thr Glu Glu Glu
            180                 185                 190

Arg Ala Arg Arg Ala Glu Gln Ala Leu Ala Tyr Leu Arg Ala Thr Val
        195                 200                 205

Asp Arg Val Leu Thr Ala His Arg Pro Asp Ser Arg Thr Asp Arg Ser
    210                 215                 220

Asp Leu Ile Gly Ala Leu Val Ala Ala Gly Glu Asp Pro Ala Arg Ile
225                 230                 235                 240

Arg Asp Thr Val Met Val Ala Met Leu Ala Ala His His Thr Thr Gly
                245                 250                 255

Val Ala Val Ser Trp Thr Leu His Leu Leu Gly Arg His Pro Glu Val
            260                 265                 270

Ala Glu Arg Val Ala Gly Glu Leu Asp Arg Val Leu Gly Asp Arg Ala
        275                 280                 285

Val Pro Gly Tyr Ala Asp Leu Arg Arg Leu Thr Tyr Leu Asp Met Val
    290                 295                 300

Leu Lys Glu Ser Met Arg Leu Phe Pro Pro Gly Pro Tyr Gly Ala Arg
305                 310                 315                 320

Glu Thr Thr Glu Ala Leu Val Leu Gly Ala Tyr Glu Val Pro Ala Gly
                325                 330                 335

Thr Val Ile Phe Tyr Pro Phe Trp Ala Val His Leu Asn Pro Asp His
            340                 345                 350

Trp Pro Glu Pro Glu Arg Phe Val Pro Glu Arg Phe Leu Pro Glu Glu
        355                 360                 365

Val Ala Lys Arg Pro Arg Leu Ala Tyr Ile Pro Phe Gly Leu Gly Pro
    370                 375                 380

Arg Ser Cys Glu Gly Ala Gly Leu Ala Thr Val Glu Ala Gln Leu Val
385                 390                 395                 400
```

Leu Ala Val Leu Leu Lys Arg Phe Arg Phe Arg Pro Val Pro Gly His
405 410 415

Glu Val Thr Pro Ile Glu Arg Phe Val Leu Trp Ala Ala Asp Asp Ile
420 425 430

Arg Met Phe Val Ser Arg Arg Glu Val Gly Ala Gly Ser Pro
435 440 445

<210> SEQ ID NO 98
<211> LENGTH: 1224
<212> TYPE: DNA
<213> ORGANISM: Streptomyces rimosus

<400> SEQUENCE: 98
atgaccaccc cccagcaccc cgacgacttc ctgcgtctcc tgcgaatgcg cagcgcggcc 60
gaggacggga tcttccgggt cgacgaggaa cggctcgccg tgttcgatcc ggaagcggcc 120
cgccggatca gcgccgcgaa ctggcaccgg ttcgtcatgc acgaccgcct ggtcgacatg 180
gtgcggcggc gccggagtcc cgaggtgcgg tggagccagg tacggtccgc ctggctcacc 240
cagctgcacg cgctggccac gccggaacag cacggccggc tgatcgagcg catggcacag 300
atcatggacg cgcggctcgg ccgggacgtg gatctcacca tgctcagcca ggacgtggcc 360
gtgcggtcgc tgctgccgct cgcgctgtcg ggcctcacca ccggcgaggc ggatctcgtc 420
cgccgggacc tggagatgaa gctgctgcgg ctggtctcgc ccgacccggg cagcacctgg 480
caccacctgc ggttcgtcgc ggtccagata cggtcgggac tggtcgtgcg ccgggtcctg 540
cgccaacgcg cccgcgggcg ccggggccgc gagccggacc tcgccgaccc gatcgtcgac 600
ctgctgcccg cactcggcat ggaccgcgcc ctggacgtgg tgacggccgt cctcaccgcc 660
atcggcggcc cgccgggcac ggccgccgcg agcgtgctgt acgagttcgc ccgccgcccc 720
gagtggcagc ggcggctcgc cgatgagctg ggcgccgtcg accccgtcgc gttccgtacg 780
gcaccgccgg acgcggcccc ggtgacccac cgcttcgtca aggaagtgct gcgcctgtgg 840
agtccgccgc tgctgctggt acgacgctcc acggtcccgt tcgacctcgg gaagacacgc 900
ctggcgccgg gcgactggta cttgctgagc ccgcacatga tccatcgcga tgaccgcgtc 960
tggaaacggc ccgacctctt cgacccggac cgatttctgc ccggtgcgcc ccacggcccg 1020
gcggaccgca cgtgctacgt gccgttcggc tgggcgccca agaagtgcat cggcgcgaac 1080
atcgccatcg tccagctgat ggccctgtgc cacctgctgt gcacccggta ccgcctgacc 1140
gtgcaccggc cggacgaggt cacgatggcc ttgcgtttcg ctccggtacc ggagaacttc 1200
cggggggagc tggccttccg gtaa 1224

<210> SEQ ID NO 99
<211> LENGTH: 407
<212> TYPE: PRT
<213> ORGANISM: Streptomyces rimosus

<400> SEQUENCE: 99

Met Thr Thr Pro Gln His Pro Asp Asp Phe Leu Arg Leu Leu Arg Met
1 5 10 15

Arg Ser Ala Ala Glu Asp Gly Ile Phe Arg Val Asp Glu Glu Arg Leu
20 25 30

Ala Val Phe Asp Pro Glu Ala Ala Arg Arg Ile Ser Ala Ala Asn Trp
35 40 45

His Arg Phe Val Met His Asp Arg Leu Val Asp Met Val Arg Arg Arg
50 55 60

```
Arg Ser Pro Glu Val Arg Trp Ser Gln Val Arg Ser Ala Trp Leu Thr
65                  70                  75                  80

Gln Leu His Ala Leu Ala Thr Pro Glu Gln His Gly Arg Leu Ile Glu
                85                  90                  95

Arg Met Ala Gln Ile Met Asp Ala Arg Leu Gly Arg Asp Val Asp Leu
            100                 105                 110

Thr Met Leu Ser Gln Asp Val Ala Val Arg Ser Leu Leu Pro Leu Ala
        115                 120                 125

Leu Ser Gly Leu Thr Thr Gly Glu Ala Asp Leu Val Arg Arg Asp Leu
    130                 135                 140

Glu Met Lys Leu Leu Arg Leu Val Ser Pro Asp Pro Gly Ser Thr Trp
145                 150                 155                 160

His His Leu Arg Phe Val Ala Val Gln Ile Arg Ser Gly Leu Val Val
                165                 170                 175

Arg Arg Val Leu Arg Gln Arg Ala Arg Gly Arg Arg Gly Arg Glu Pro
            180                 185                 190

Asp Leu Ala Asp Pro Ile Val Asp Leu Leu Pro Ala Leu Gly Met Asp
        195                 200                 205

Arg Ala Leu Asp Val Val Thr Ala Val Leu Thr Ala Ile Gly Gly Pro
    210                 215                 220

Pro Gly Thr Ala Ala Ala Ser Val Leu Tyr Glu Phe Ala Arg Arg Pro
225                 230                 235                 240

Glu Trp Gln Arg Arg Leu Ala Asp Glu Leu Gly Ala Val Asp Pro Val
                245                 250                 255

Ala Phe Arg Thr Ala Pro Pro Asp Ala Ala Pro Val Thr His Arg Phe
            260                 265                 270

Val Lys Glu Val Leu Arg Leu Trp Ser Pro Pro Leu Leu Leu Val Arg
        275                 280                 285

Arg Ser Thr Val Pro Phe Asp Leu Gly Lys Thr Arg Leu Ala Pro Gly
    290                 295                 300

Asp Trp Tyr Leu Leu Ser Pro His Met Ile His Arg Asp Asp Arg Val
305                 310                 315                 320

Trp Lys Arg Pro Asp Leu Phe Asp Pro Asp Arg Phe Leu Pro Gly Ala
                325                 330                 335

Pro His Gly Pro Ala Asp Arg Thr Cys Tyr Val Pro Phe Gly Trp Ala
            340                 345                 350

Pro Lys Lys Cys Ile Gly Ala Asn Ile Ala Ile Val Gln Leu Met Ala
        355                 360                 365

Leu Cys His Leu Leu Cys Thr Arg Tyr Arg Leu Thr Val His Arg Pro
    370                 375                 380

Asp Glu Val Thr Met Ala Leu Arg Phe Ala Pro Val Pro Glu Asn Phe
385                 390                 395                 400

Arg Gly Glu Leu Ala Phe Arg
                405
```

<210> SEQ ID NO 100
<211> LENGTH: 1467
<212> TYPE: DNA
<213> ORGANISM: Streptomyces rimosus

<400> SEQUENCE: 100

```
atgactttcc cttttcccga acagcccggc accacgtggg ccgccacgcc gcctccggag      60

tgcccggcac acgcccggcc cggcgccgcc gacgggctgg cgcggctctt cggccccgag     120
```

```
gcggccgccg accccatggg cctgtacgag cgcctgcgcg cccggcacgg ggccgtcgcg    180

cccgtcctgc tggacggcga cctgcccgcc tggctcgtcc tcggctaccg agagatcctg    240

gaggtcgccg gtacgcccgc ccgtttcagc cgcgattcgc gcaactggcg ctggttcagg    300

gaggggcggg tcccgccgga ctcgccgctg ctcccgatga tcgcctggca gccggtgtgc    360

ctgttcctgg acggggagga gcgcaaccgg ctgcgcctgg ccgtcaccga cagcctggac    420

cgcttcaacc gccggggcat ccggcggcac atcacccgct tcacccacca gctggtggac    480

ggcttcatcg agcgcgggga ggcggacctg gccgaggagt tctgcgaaca cctgcccatg    540

ctcgtgctga cccagctcct gggcatgccg gacgagtacg ggccccggct ggtcgcggcc    600

agccgggaca tggtggcggg caccgcgacc tcggtggcca gcaacgcgtt catcgtggac    660

accctcatgg agctggtacg gagcaagcac accacccgcg ggcacgacat cacgtcctgg    720

ctgatcgacc actcctcccg gctgaccgac gaggaggtgt ggaaccacct gcgggtcgtc    780

ctgatcgccg cgaacgagac caccgtcaac ctcctcaaga gcacgctgcg gatggtgctg    840

accgaccccc ggtgccacgc gtcgctggcc ggcgggcaga tgacgctgcc cgacgtggtg    900

gagcaggtgc tgtggagcga accgccgctg atgaccatcc ccggccgctg ggccgcggtg    960

gacacggagg tcggcggcca gaagatcgag gcgggggaca tgctgctgct cagcctggcc   1020

gccgggaacc acgatccggc cgtccggccg gacccgtcga tcccgctgca cggcaaccgc   1080

tcgcacctcg ccttcagcag cggcccgcag gagtgccccg gccagaacat cggccgcgcc   1140

atcgccgaca ccggcatcga cacgctgatg gcacggctgc ccgacgtacg gctgcgcatc   1200

cccgaggagg agctgcgctg gacgtcgggc tggatgacgc gccatctgac cagccttccg   1260

gtgacgttca gcgcctcccg gcccgcgcac tccggcgcga ccgccggtac ggccttcgaa   1320

cgcccgccgg gcaccacccc gcacgacggc tccctgcccg cggccgagcc cccggccacg   1380

cccccgcccg gcccgcctcc ggcggctccc gtgcccaggg ggcgtacgtc ctggtgggcc   1440

gcgttgaagg cttggctgcg cggctaa                                       1467
```

<210> SEQ ID NO 101
<211> LENGTH: 488
<212> TYPE: PRT
<213> ORGANISM: Streptomyces rimosus

<400> SEQUENCE: 101

```
Met Thr Phe Pro Phe Pro Glu Gln Pro Gly Thr Thr Trp Ala Ala Thr
1               5                   10                  15

Pro Pro Pro Glu Cys Pro Ala His Ala Arg Pro Gly Ala Ala Asp Gly
            20                  25                  30

Leu Ala Arg Leu Phe Gly Pro Glu Ala Ala Ala Asp Pro Met Gly Leu
        35                  40                  45

Tyr Glu Arg Leu Arg Ala Arg His Gly Ala Val Ala Pro Val Leu Leu
    50                  55                  60

Asp Gly Asp Leu Pro Ala Trp Leu Val Leu Gly Tyr Arg Glu Ile Leu
65                  70                  75                  80

Glu Val Ala Gly Thr Pro Ala Arg Phe Ser Arg Asp Ser Arg Asn Trp
                85                  90                  95

Arg Trp Phe Arg Glu Gly Arg Val Pro Pro Asp Ser Pro Leu Leu Pro
            100                 105                 110

Met Ile Ala Trp Gln Pro Val Cys Leu Phe Leu Asp Gly Glu Glu Arg
        115                 120                 125

Asn Arg Leu Arg Leu Ala Val Thr Asp Ser Leu Asp Arg Phe Asn Arg
```

-continued

```
    130                 135                 140

Arg Gly Ile Arg Arg His Ile Thr Arg Phe Thr His Gln Leu Val Asp
145                 150                 155                 160

Gly Phe Ile Glu Arg Gly Glu Ala Asp Leu Ala Glu Glu Phe Cys Glu
                165                 170                 175

His Leu Pro Met Leu Val Leu Thr Gln Leu Leu Gly Met Pro Asp Glu
            180                 185                 190

Tyr Gly Pro Arg Leu Val Ala Ala Ser Arg Asp Met Val Ala Gly Thr
        195                 200                 205

Ala Thr Ser Val Ala Ser Asn Ala Phe Ile Val Asp Thr Leu Met Glu
    210                 215                 220

Leu Val Arg Ser Lys His Thr Thr Arg Gly His Asp Ile Thr Ser Trp
225                 230                 235                 240

Leu Ile Asp His Ser Ser Arg Leu Thr Asp Glu Glu Val Trp Asn His
                245                 250                 255

Leu Arg Val Val Leu Ile Ala Ala Asn Glu Thr Thr Val Asn Leu Leu
            260                 265                 270

Lys Ser Thr Leu Arg Met Val Leu Thr Asp Pro Arg Cys His Ala Ser
        275                 280                 285

Leu Ala Gly Gly Gln Met Thr Leu Pro Asp Val Val Glu Gln Val Leu
    290                 295                 300

Trp Ser Glu Pro Pro Leu Met Thr Ile Pro Gly Arg Trp Ala Ala Val
305                 310                 315                 320

Asp Thr Glu Val Gly Gly Gln Lys Ile Glu Ala Gly Asp Met Leu Leu
                325                 330                 335

Leu Ser Leu Ala Ala Gly Asn His Asp Pro Ala Val Arg Pro Asp Pro
            340                 345                 350

Ser Ile Pro Leu His Gly Asn Arg Ser His Leu Ala Phe Ser Ser Gly
        355                 360                 365

Pro Gln Glu Cys Pro Gly Gln Asn Ile Gly Arg Ala Ile Ala Asp Thr
    370                 375                 380

Gly Ile Asp Thr Leu Met Ala Arg Leu Pro Asp Val Arg Leu Arg Ile
385                 390                 395                 400

Pro Glu Glu Glu Leu Arg Trp Thr Ser Gly Trp Met Thr Arg His Leu
                405                 410                 415

Thr Ser Leu Pro Val Thr Phe Ser Ala Ser Arg Pro Ala His Ser Gly
            420                 425                 430

Ala Thr Ala Gly Thr Ala Phe Glu Arg Pro Pro Gly Thr Thr Pro His
        435                 440                 445

Asp Gly Ser Leu Pro Ala Ala Glu Pro Pro Ala Thr Pro Pro Pro Gly
    450                 455                 460

Pro Pro Pro Ala Ala Pro Val Pro Arg Gly Arg Thr Ser Trp Trp Ala
465                 470                 475                 480

Ala Leu Lys Ala Trp Leu Arg Gly
                485


<210> SEQ ID NO 102
<211> LENGTH: 1227
<212> TYPE: DNA
<213> ORGANISM: Streptomyces rimosus

<400> SEQUENCE: 102

atgctggaac agctgcgcag gcagtacggg gacgtcgcac cggtcctcgt ccccggcgac      60

atcccggcct acctggtcct gggatacaac gcgacacgcg atgtcatgca gagcaactcc     120
```

-continued

```
cgcgtggtct gcgactcccg ccgcggccgt gtctaccagg acggccggat cccggcggac    180

cacccccctgg cgccgatgac cgcgtaccag ccggtcgtgg cgttcgagga cggcgtgccc    240

cacgcccgcc tgcgcagcgc cgtggtcgac agcctggact tcaaccggca ctccctgcgc    300

cgctacatcg gccggtacgc caaccgcctc atcgactgcg tcgcctcccg cggcaccgcc    360

gacctggtca gcgagtacgc cgcgcagctg ccggccctcg tgatggcctg gatgtacggc    420

atgcccgagg aggagagccc cgccctggtg gccgcggtac gggacctgac cagcggcaac    480

gagcgggccg ccgagggcaa cgcgttcgtc acccgcacga tggaggaact cgtccggcgc    540

aggcgggccg gcgagggcgc cgacaacacc atcggcggcc gggacttcgt cagccgtctc    600

ctggaccacg aggcgggcct cagcgatcag gaggtcgtcg agcacctgcg catgatcttc    660

gtcgccggct acacgccgac ggtcgcgctg atcgcaaaca cgctgctggt gctgctgacc    720

cagcgtcagt tcagccgtga cctgaccagc ggccagatga cgctgcccga ggccctggaa    780

cgcgtgctct gggaccaccc gccgatcggg ctgctgccca cccgctgggc ggccggggac    840

atgaccatcg ccggccagca gatcaaggcc ggagacatga tcatcctggg gatcgaggct    900

gccaacgcgg accccgccgc ccgggaaccc ggacgccccg tagtccacaa ttcgggacac    960

ctcgccttct ccaccggccc ccacgagtgt cccggccgcg acatcggaca ggccatcgcg   1020

gagaccggca tcgacatcct gctgagcacg ctcagggacc tggaactggc ggtgcccgag   1080

gcagagctgc agtggcagtc ggcttgggtc tcgcgtcgcc tgctgtcctt gccggtgacg   1140

ttcactccgc cgcgggtcag gggggtgcgg gctccgcagc cggaggctgc tgtggcggga   1200

gtgggtaggt cggttggtac tgcctaa                                        1227
```

```
<210> SEQ ID NO 103
<211> LENGTH: 408
<212> TYPE: PRT
<213> ORGANISM: Streptomyces rimosus

<400> SEQUENCE: 103

Met Leu Glu Gln Leu Arg Arg Gln Tyr Gly Asp Val Ala Pro Val Leu
1               5                   10                  15

Val Pro Gly Asp Ile Pro Ala Tyr Leu Val Leu Gly Tyr Asn Ala Thr
            20                  25                  30

Arg Asp Val Met Gln Ser Asn Ser Arg Val Val Cys Asp Ser Arg Arg
        35                  40                  45

Gly Arg Val Tyr Gln Asp Gly Arg Ile Pro Ala Asp His Pro Leu Ala
    50                  55                  60

Pro Met Thr Ala Tyr Gln Pro Val Val Ala Phe Glu Asp Gly Val Pro
65                  70                  75                  80

His Ala Arg Leu Arg Ser Ala Val Val Asp Ser Leu Asp Phe Asn Arg
                85                  90                  95

His Ser Leu Arg Arg Tyr Ile Gly Arg Tyr Ala Asn Arg Leu Ile Asp
            100                 105                 110

Cys Val Ala Ser Arg Gly Thr Ala Asp Leu Val Ser Glu Tyr Ala Ala
        115                 120                 125

Gln Leu Pro Ala Leu Val Met Ala Trp Met Tyr Gly Met Pro Glu Glu
    130                 135                 140

Glu Ser Pro Ala Leu Val Ala Ala Val Arg Asp Leu Thr Ser Gly Asn
145                 150                 155                 160

Glu Arg Ala Ala Glu Gly Asn Ala Phe Val Thr Arg Thr Met Glu Glu
                165                 170                 175
```

```
Leu Val Arg Arg Arg Arg Ala Gly Glu Gly Ala Asp Asn Thr Ile Gly
            180                 185                 190

Gly Arg Asp Phe Val Ser Arg Leu Leu Asp His Glu Ala Gly Leu Ser
        195                 200                 205

Asp Gln Glu Val Val Glu His Leu Arg Met Ile Phe Val Ala Gly Tyr
    210                 215                 220

Thr Pro Thr Val Ala Leu Ile Ala Asn Thr Leu Leu Val Leu Leu Thr
225                 230                 235                 240

Gln Arg Gln Phe Ser Arg Asp Leu Thr Ser Gly Gln Met Thr Leu Pro
                245                 250                 255

Glu Ala Leu Glu Arg Val Leu Trp Asp His Pro Pro Ile Gly Leu Leu
            260                 265                 270

Pro Thr Arg Trp Ala Ala Gly Asp Met Thr Ile Ala Gly Gln Gln Ile
        275                 280                 285

Lys Ala Gly Asp Met Ile Ile Leu Gly Ile Glu Ala Ala Asn Ala Asp
    290                 295                 300

Pro Ala Ala Arg Glu Pro Gly Arg Pro Val Val His Asn Ser Gly His
305                 310                 315                 320

Leu Ala Phe Ser Thr Gly Pro His Glu Cys Pro Gly Arg Asp Ile Gly
                325                 330                 335

Gln Ala Ile Ala Glu Thr Gly Ile Asp Ile Leu Leu Ser Thr Leu Arg
            340                 345                 350

Asp Leu Glu Leu Ala Val Pro Glu Ala Glu Leu Gln Trp Gln Ser Ala
        355                 360                 365

Trp Val Ser Arg Arg Leu Leu Ser Leu Pro Val Thr Phe Thr Pro Pro
    370                 375                 380

Arg Val Arg Gly Val Arg Ala Pro Gln Pro Glu Ala Ala Val Ala Gly
385                 390                 395                 400

Val Gly Arg Ser Val Gly Thr Ala
                405


<210> SEQ ID NO 104
<211> LENGTH: 1425
<212> TYPE: DNA
<213> ORGANISM: Streptomyces rimosus

<400> SEQUENCE: 104

atgaacaccc tccgcaccgc caagctgctc gccgccgcgg ccggtctcct ctccgtcccg      60

tactggctgc cgcgctccgt cgtcgccgcc cgcgtcgcgc tcttcgcgcg gatcaacggc     120

gacgagggca tcgccttccc gagcgccgac gtccccgccg accgcttcca ggagatctac     180

tcccaccccg ccgccaacgg ccgcagccgg ggcgccgccc tctcggacct cttctggtac     240

tggctggcgc ccggccccga ggtgcaccag gagcacctgg aggacggccc gcgctacgac     300

gaggtcgccc gtaccaccct cgccgtgctg ggcggtccca gccgcgagct gtccgccgcg     360

gtggcccgcc gtaccgccgc cgtgctcgac gaactggtca ccggccgggc cgagttggtc     420

cggctgcgcg acctgatgat gccggtgtgg gcggagttct tctacggact cgtgttccgc     480

gaaccgtgcc cgccgtacgt ccggcgcctg atcgtggaca acgccgccga cgtggtcaac     540

tccctgaagt gcacccggct ccgccacccg gcccgccgcg cccgcctcac ccgccacctg     600

cggcagcgca tcgccgccgg gaccgtaccg ccgcaccacc tgccgggctc cctcacgccc     660

gacgagcagg cgtactacct ccagggcacc ttcttcaaca cggccatcgt ccagatgtcc     720

gaggccatgg cccacctgct gctggtcctc gcccagcacc cggaggcgca gcgcaggctc     780
```

```
gccgccggac cggacgacga ccggtacttc tccaacgtcc tcaacgagac gctgcggctc    840

tacccgctct tcggcgtcgc ccaccgcatc agcacggacg acatcccgct cggccccggc    900

acggccatcc ccgccggctc cgtcctgtgc ttcaactacc ccgactacca cgccaccggc    960

tacaccgacc ccgaggtctt cgaccccgcc cgctgggacc gcctggtggc caaggagcag   1020

caccacatcc cgttcggcgt cgccgccaac cggccgtgcc cggcctggcg gctcgccccg   1080

ctggccatgc acgccgcgac ccgcgaggtg ctgcgccgct tcaccctcca ctccaccgtc   1140

gcccacaccc gctccatccc gcaccgcgcc ccctgcctgc tggtccggcg cgaccgtccg   1200

ctgccgaagc accggctgct cgccgcccgg gtcttcctga gggtgcgcga ccggtgggag   1260

gacgtgtggc gcagctgcgt ccagctcgtc ctcggtacgt ggatggtgct cgacgcccgc   1320

cgcctgcgcc cggccgagcg ctacttcgcc acccacgaca cgcagggcgt cccgctgccg   1380

ggcaccgccc ccgccccggc gcgctgtccg tacccgcacg cctaa                   1425
```

<210> SEQ ID NO 105
<211> LENGTH: 474
<212> TYPE: PRT
<213> ORGANISM: Streptomyces rimosus

<400> SEQUENCE: 105

```
Met Asn Thr Leu Arg Thr Ala Lys Leu Leu Ala Ala Ala Ala Gly Leu
1               5                   10                  15

Leu Ser Val Pro Tyr Trp Leu Pro Arg Ser Val Val Ala Ala Arg Val
            20                  25                  30

Ala Leu Phe Ala Arg Ile Asn Gly Asp Glu Gly Ile Ala Phe Pro Ser
        35                  40                  45

Ala Asp Val Pro Ala Asp Arg Phe Gln Glu Ile Tyr Ser His Pro Ala
    50                  55                  60

Ala Asn Gly Arg Ser Arg Gly Ala Ala Leu Ser Asp Leu Phe Trp Tyr
65                  70                  75                  80

Trp Leu Ala Pro Gly Pro Glu Val His Gln Glu His Leu Glu Asp Gly
                85                  90                  95

Pro Arg Tyr Asp Glu Val Ala Arg Thr Thr Leu Ala Val Leu Gly Gly
            100                 105                 110

Pro Ser Arg Glu Leu Ser Ala Ala Val Ala Arg Arg Thr Ala Ala Val
        115                 120                 125

Leu Asp Glu Leu Val Thr Gly Arg Ala Glu Leu Val Arg Leu Arg Asp
    130                 135                 140

Leu Met Met Pro Val Trp Ala Glu Phe Phe Tyr Gly Leu Val Phe Arg
145                 150                 155                 160

Glu Pro Cys Pro Pro Tyr Val Arg Arg Leu Ile Val Asp Asn Ala Ala
                165                 170                 175

Asp Val Val Asn Ser Leu Lys Cys Thr Arg Leu Arg His Pro Ala Arg
            180                 185                 190

Arg Ala Arg Leu Thr Arg His Leu Arg Gln Arg Ile Ala Ala Gly Thr
        195                 200                 205

Val Pro Pro His His Leu Pro Gly Ser Leu Thr Pro Asp Glu Gln Ala
    210                 215                 220

Tyr Tyr Leu Gln Gly Thr Phe Phe Asn Thr Ala Ile Val Gln Met Ser
225                 230                 235                 240

Glu Ala Met Ala His Leu Leu Leu Val Leu Ala Gln His Pro Glu Ala
                245                 250                 255
```

-continued

```
Gln Arg Arg Leu Ala Ala Gly Pro Asp Asp Asp Arg Tyr Phe Ser Asn
            260                 265                 270

Val Leu Asn Glu Thr Leu Arg Leu Tyr Pro Leu Phe Gly Val Ala His
        275                 280                 285

Arg Ile Ser Thr Asp Asp Ile Pro Leu Gly Pro Gly Thr Ala Ile Pro
    290                 295                 300

Ala Gly Ser Val Leu Cys Phe Asn Tyr Pro Asp Tyr His Ala Thr Gly
305                 310                 315                 320

Tyr Thr Asp Pro Glu Val Phe Asp Pro Ala Arg Trp Asp Arg Leu Val
                325                 330                 335

Ala Lys Glu Gln His His Ile Pro Phe Gly Val Ala Ala Asn Arg Pro
            340                 345                 350

Cys Pro Ala Trp Arg Leu Ala Pro Leu Ala Met His Ala Ala Thr Arg
        355                 360                 365

Glu Val Leu Arg Arg Phe Thr Leu His Ser Thr Val Ala His Thr Arg
    370                 375                 380

Ser Ile Pro His Arg Ala Pro Cys Leu Leu Val Arg Arg Asp Arg Pro
385                 390                 395                 400

Leu Pro Lys His Arg Leu Leu Ala Ala Arg Val Phe Leu Arg Val Arg
                405                 410                 415

Asp Arg Trp Glu Asp Val Trp Arg Ser Cys Val Gln Leu Val Leu Gly
            420                 425                 430

Thr Trp Met Val Leu Asp Ala Arg Arg Leu Arg Pro Ala Glu Arg Tyr
        435                 440                 445

Phe Ala Thr His Asp Thr Gln Gly Val Pro Leu Pro Gly Thr Ala Pro
    450                 455                 460

Ala Pro Ala Arg Cys Pro Tyr Pro His Ala
465                 470
```

<210> SEQ ID NO 106
<211> LENGTH: 1056
<212> TYPE: DNA
<213> ORGANISM: Streptomyces rimosus

<400> SEQUENCE: 106

```
atgcgtacgt acggtacgga acggagcgac cgggtcacgg tcttcacgcc gcggctcggc      60

cggctcctca gtgagcaccg cggcgcggac gtcttccggc tggaggccga cacggtcggc     120

gtcgccggac ccgggctgat cgacgccgtg ctgcgcagca gaccggccaa cgcggccgaa     180

cggcccactt tcaaacccct acagggccgg cccatcagcc gccccgaatc ctccgcggtc     240

atgcgggccg tttccctgga cgtgcgcgcg gcactggaaa agcccgacgg gaaaggcggc     300

ccggcggccg atctgtcggg ggaatggccg cgggtggcac acctttatct gcgggacctg     360

gttttcgggt ccgatccgat gcggctgcgc gtactcgtgg accgcaagct ggaatggacg     420

cccaaactga cgtggaccgt gatcgcggcg ggcgcggcgc tgccgggctg cccgggggcc     480

ggtgcgccgg tgtcccggct ggcgggtctc gccgccgccg cggccggtta cggggaccgg     540

cggtacgcga tgggcctgta ccggcgggcg gcggcaccgg tgtgcttcac cgtgtccacg     600

ctggtcgcca acgccctctg gctcgggtcg cccttcgagg accacatacc gaaccgtcac     660

atcctgtacg agtcgatgcg gctgctgccg ccttcgtgga acctcctgcg cgtggcgtca     720

ccggagttcg cggccctcga cgaccggatc ggcgcgggcg acgacgtcct gctgctgccg     780

ctgctcagcc accgcgatcc gcggctgtgg gacgcgccgg acgcgttccg gcccgagcgc     840

tgggcggccc tcgacgccga cgaccagccc ggctacctgc ccttcgggca cgcgaacgag     900
```

cggtgctggg ggcggcacat ggtcatgccg ctggccgaac ggctgctgga cctggtgcgg 960
gaacagggcc tggcggtgag cccggagcag aagtccgccg aggtgccgct ggccgggctg 1020
ctcggggtgt cgcgggtgtc ggtcgtacgg cgctaa 1056

<210> SEQ ID NO 107
<211> LENGTH: 351
<212> TYPE: PRT
<213> ORGANISM: Streptomyces rimosus

<400> SEQUENCE: 107

Met Arg Thr Tyr Gly Thr Glu Arg Ser Asp Arg Val Thr Val Phe Thr
1 5 10 15

Pro Arg Leu Gly Arg Leu Leu Ser Glu His Arg Gly Ala Asp Val Phe
20 25 30

Arg Leu Glu Ala Asp Thr Val Gly Val Ala Gly Pro Gly Leu Ile Asp
35 40 45

Ala Val Leu Arg Ser Arg Pro Ala Asn Ala Ala Glu Arg Pro Thr Phe
50 55 60

Lys Pro Leu Gln Gly Arg Pro Ile Ser Arg Pro Glu Ser Ser Ala Val
65 70 75 80

Met Arg Ala Val Ser Leu Asp Val Arg Ala Ala Leu Glu Lys Pro Asp
85 90 95

Gly Lys Gly Gly Pro Ala Ala Asp Leu Ser Gly Glu Trp Pro Arg Val
100 105 110

Ala His Leu Tyr Leu Arg Asp Leu Val Phe Gly Ser Asp Pro Met Arg
115 120 125

Leu Arg Val Leu Val Asp Arg Lys Leu Glu Trp Thr Pro Lys Leu Thr
130 135 140

Trp Thr Val Ile Ala Ala Gly Ala Ala Leu Pro Gly Cys Pro Gly Ala
145 150 155 160

Gly Ala Pro Val Ser Arg Leu Ala Gly Leu Ala Ala Ala Ala Ala Gly
165 170 175

Tyr Gly Asp Arg Arg Tyr Ala Met Gly Leu Tyr Arg Arg Ala Ala Ala
180 185 190

Pro Val Cys Phe Thr Val Ser Thr Leu Val Ala Asn Ala Leu Trp Leu
195 200 205

Gly Ser Pro Phe Glu Asp His Ile Pro Asn Arg His Ile Leu Tyr Glu
210 215 220

Ser Met Arg Leu Leu Pro Pro Ser Trp Asn Leu Leu Arg Val Ala Ser
225 230 235 240

Pro Glu Phe Ala Ala Leu Asp Asp Arg Ile Gly Ala Gly Asp Asp Val
245 250 255

Leu Leu Leu Pro Leu Leu Ser His Arg Asp Pro Arg Leu Trp Asp Ala
260 265 270

Pro Asp Ala Phe Arg Pro Glu Arg Trp Ala Ala Leu Asp Ala Asp Asp
275 280 285

Gln Pro Gly Tyr Leu Pro Phe Gly His Ala Asn Glu Arg Cys Trp Gly
290 295 300

Arg His Met Val Met Pro Leu Ala Glu Arg Leu Leu Asp Leu Val Arg
305 310 315 320

Glu Gln Gly Leu Ala Val Ser Pro Glu Gln Lys Ser Ala Glu Val Pro
325 330 335

Leu Ala Gly Leu Leu Gly Val Ser Arg Val Ser Val Val Arg Arg 340 345 350

<210> SEQ ID NO 108
<211> LENGTH: 1412
<212> TYPE: DNA
<213> ORGANISM: Streptomyces rimosus

<400> SEQUENCE: 108
atgaccacag ccgacacgat gccccttgcc tacccgttca acgacgccga cggactggct 60
ctgtccgaga cctacgaaca ggtccgcgac cggcccggac tgctccgggt acagatggcg 120
tacggcgaac cggcctggct cgccacccgc tacgccgacg cccggctggt cctcggcgac 180
cggcgcttca gccgcgcgga agggctcgaa cgcgacgagc cgcggcagtc ggagggccag 240
cgggacagcg ggatactgag catggacccg cccgaccaca cccggctgcg caccctggtc 300
gccaaggcgt tcaccgtgca ccaggtggag aaactccggc cgtgggtgcg cgagttgaca 360
cacggcctga tcgacgagct ggaggccgcg ggcccgcccg tggacctcgt ggaccgctac 420
gcgctgccca tcccggtcgc ggtgatctgc cggatgctcg gcgtaccgga agaggaccgg 480
cccaagttcc gtacgtggag cgacgccgca ctgtccacca gctcgctgac ggccgaggag 540
ttcgaggcca accgcgagga actgcgcgcc tacatggcga agttgatcga ggatcaccgc 600
acgacgccgc gggacgacct gatgacgcgg ctgatcgagg cccgggacgt cggcgaccgg 660
ctctccgagc tggagctgat cgacctgtgc gtcggcatcc tggtcgccgg acacgagaca 720
acggccaccc agatccccaa cttcgtcctg tcgctgctgg accacccggg cgagctggag 780
cggctgcgcg ccgaacccgc gctgatcaag agcgccgtcg aggaactgct gcgcttcgta 840
ccgctcggca gcggcgcggg cttcccgcgc tacgccaccg aggacatcga ggtgggcggc 900
acactcgtcc gtgcgggtga accggtactg gtcgccgtcg gcgcggccaa ccgggacgcg 960
ctgcgcttcg acgagccggg caccctcaac atcacccgcg acggcaacca gcacctcggc 1020
ttcggacacg gcgtgcacca ctgcctcggc gcgccgctgg cccggctgga actccaggag 1080
gcgctgatcg ccctgatcac ccggttcccg aagctgcatg tggccgggga cgtggtgtgg 1140
aaggaccaga tgctggtccg cggcccgcgc gtgatgccgg tggggtggtg agccggatga 1200
cgtggaaagc ggcgatcgac ggacagcagt gcatggcgtc cggcatgtgc gcgggcatcg 1260
ccccggacct cttcgtcctg gacggcccgc acgcccgacc gctccaggag gagatccccg 1320
aggacgaggc cgcgctcgac gcggcggact cctgccccgc catggcgatc ctgatccggg 1380
acggggagaa ggtggtgggg ccgcggccct aa 1412

<210> SEQ ID NO 109
<211> LENGTH: 396
<212> TYPE: PRT
<213> ORGANISM: Streptomyces rimosus

<400> SEQUENCE: 109

Met Thr Thr Ala Asp Thr Met Pro Leu Ala Tyr Pro Phe Asn Asp Ala
1 5 10 15

Asp Gly Leu Ala Leu Ser Glu Thr Tyr Glu Gln Val Arg Asp Arg Pro
20 25 30

Gly Leu Leu Arg Val Gln Met Ala Tyr Gly Glu Pro Ala Trp Leu Ala
35 40 45

Thr Arg Tyr Ala Asp Ala Arg Leu Val Leu Gly Asp Arg Arg Phe Ser
50 55 60

Arg Ala Glu Gly Leu Glu Arg Asp Glu Pro Arg Gln Ser Glu Gly Gln

```
65                  70                  75                  80

Arg Asp Ser Gly Ile Leu Ser Met Asp Pro Pro Asp His Thr Arg Leu
                85                  90                  95

Arg Thr Leu Val Ala Lys Ala Phe Thr Val His Gln Val Glu Lys Leu
            100                 105                 110

Arg Pro Trp Val Arg Glu Leu Thr His Gly Leu Ile Asp Glu Leu Glu
        115                 120                 125

Ala Ala Gly Pro Pro Val Asp Leu Val Asp Arg Tyr Ala Leu Pro Ile
    130                 135                 140

Pro Val Ala Val Ile Cys Arg Met Leu Gly Val Pro Glu Glu Asp Arg
145                 150                 155                 160

Pro Lys Phe Arg Thr Trp Ser Asp Ala Ala Leu Ser Thr Ser Ser Leu
                165                 170                 175

Thr Ala Glu Glu Phe Glu Ala Asn Arg Glu Glu Leu Arg Ala Tyr Met
            180                 185                 190

Ala Lys Leu Ile Glu Asp His Arg Thr Thr Pro Arg Asp Asp Leu Met
        195                 200                 205

Thr Arg Leu Ile Glu Ala Arg Asp Val Gly Asp Arg Leu Ser Glu Leu
    210                 215                 220

Glu Leu Ile Asp Leu Cys Val Gly Ile Leu Val Ala Gly His Glu Thr
225                 230                 235                 240

Thr Ala Thr Gln Ile Pro Asn Phe Val Leu Ser Leu Leu Asp His Pro
                245                 250                 255

Gly Glu Leu Glu Arg Leu Arg Ala Glu Pro Ala Leu Ile Lys Ser Ala
            260                 265                 270

Val Glu Glu Leu Leu Arg Phe Val Pro Leu Gly Ser Gly Ala Gly Phe
        275                 280                 285

Pro Arg Tyr Ala Thr Glu Asp Ile Glu Val Gly Gly Thr Leu Val Arg
    290                 295                 300

Ala Gly Glu Pro Val Leu Val Ala Val Gly Ala Ala Asn Arg Asp Ala
305                 310                 315                 320

Leu Arg Phe Asp Glu Pro Gly Thr Leu Asn Ile Thr Arg Asp Gly Asn
                325                 330                 335

Gln His Leu Gly Phe Gly His Gly Val His His Cys Leu Gly Ala Pro
            340                 345                 350

Leu Ala Arg Leu Glu Leu Gln Glu Ala Leu Ile Ala Leu Ile Thr Arg
        355                 360                 365

Phe Pro Lys Leu His Val Ala Gly Asp Val Val Trp Lys Asp Gln Met
    370                 375                 380

Leu Val Arg Gly Pro Arg Val Met Pro Val Gly Trp
385                 390                 395


<210> SEQ ID NO 110
<211> LENGTH: 71
<212> TYPE: PRT
<213> ORGANISM: Streptomyces rimosus

<400> SEQUENCE: 110

Met Thr Trp Lys Ala Ala Ile Asp Gly Gln Gln Cys Met Ala Ser Gly
1               5                   10                  15

Met Cys Ala Gly Ile Ala Pro Asp Leu Phe Val Leu Asp Gly Pro His
            20                  25                  30

Ala Arg Pro Leu Gln Glu Glu Ile Pro Glu Asp Glu Ala Ala Leu Asp
        35                  40                  45
```

```
Ala Ala Asp Ser Cys Pro Ala Met Ala Ile Leu Ile Arg Asp Gly Glu
    50                  55                  60

Lys Val Val Gly Pro Arg Pro
65                  70


<210> SEQ ID NO 111
<211> LENGTH: 1095
<212> TYPE: DNA
<213> ORGANISM: Streptomyces rimosus

<400> SEQUENCE: 111

atggcgtggc tccaggacgc ggacgcgccc agttggttcg tgagccggta cgacgacgtc      60

cgtgcggtga tcggggatcc acggctggtc aggccgagtg tcaacggctg gtccttcatg     120

ccggagcagg accggccgga cggcatggaa ctgatcacga tgatggagat ggagggcccg     180

cggcacacgg cgctgcgcag ggccctgtcc ggggcgttca gcgcacggtc cgtacggcgc     240

cgtctgccgc gtatccgccg gagcgccgag cggctgctgg acgagttcgc cgacggcggc     300

gcacccggcg atctgatcgc cggttacacc gagccctttc cgctgctggt ggtgtgcgaa     360

tcggtgggca tcccgtacga ggaccgcgac tactacctgc ccatggcgga cgcggctctg     420

ggggcgctgc tcaccgtgga ggaggcgcgg cgggtcacgc cgctgctacg ggactacgtc     480

cggtcactga tcgtccaacg gcggcgggcg cccgcggacg acatcctcgg cgacctggtc     540

cgcaggtgtg accggggcga gctggacgag gagagcgtgc tcagcttcgg gctgtcgatg     600

ctcgtcgccg gttaccgcac gacgaccatg ttcctgtccg acgccgtcct ggcgctgctg     660

gccgatccgg accagtacgt ccggctgcgc gacgaccgcg gcctgctgcc cggcgcggtg     720

gaggagttcc tgcgctacgt cccggcgatg aacggggtgg tggtgctgca ggccaccgag     780

gacttcgaac tgggcgggca gacgatccgg gcgggggacg cggtcctgcc ggcactggcc     840

tccgccaacc gcgacgagac cgtgttcgat gagcccgaac ggctcgatgt gtgccggcgg     900

ccgaacccgc acatcgcgtt cggccggggc ccgcacaact gcatcggcgc ccacctggcg     960

cgggcggagc tgaccgtggg cctggaaacg ctcctggacc gtttcccgca cctgcgcctg    1020

gccgagggac acagccccac ctgggacgac gcctccccgt ccaagtcgcc tctcaccctt    1080

ccggtcagct ggtaa                                                     1095


<210> SEQ ID NO 112
<211> LENGTH: 364
<212> TYPE: PRT
<213> ORGANISM: Streptomyces rimosus

<400> SEQUENCE: 112

Met Ala Trp Leu Gln Asp Ala Asp Ala Pro Ser Trp Phe Val Ser Arg
1               5                   10                  15

Tyr Asp Asp Val Arg Ala Val Ile Gly Asp Pro Arg Leu Val Arg Pro
            20                  25                  30

Ser Val Asn Gly Trp Ser Phe Met Pro Glu Gln Asp Arg Pro Asp Gly
        35                  40                  45

Met Glu Leu Ile Thr Met Met Glu Met Glu Gly Pro Arg His Thr Ala
    50                  55                  60

Leu Arg Arg Ala Leu Ser Gly Ala Phe Ser Ala Arg Ser Val Arg Arg
65                  70                  75                  80

Arg Leu Pro Arg Ile Arg Arg Ser Ala Glu Arg Leu Leu Asp Glu Phe
                85                  90                  95

Ala Asp Gly Gly Ala Pro Gly Asp Leu Ile Ala Gly Tyr Thr Glu Pro
```

100 105 110

Phe Pro Leu Leu Val Val Cys Glu Ser Val Gly Ile Pro Tyr Glu Asp
115 120 125

Arg Asp Tyr Tyr Leu Pro Met Ala Asp Ala Ala Leu Gly Ala Leu Leu
130 135 140

Thr Val Glu Glu Ala Arg Arg Val Thr Pro Leu Leu Arg Asp Tyr Val
145 150 155 160

Arg Ser Leu Ile Val Gln Arg Arg Arg Ala Pro Ala Asp Asp Ile Leu
165 170 175

Gly Asp Leu Val Arg Arg Cys Asp Arg Gly Glu Leu Asp Glu Glu Ser
180 185 190

Val Leu Ser Phe Gly Leu Ser Met Leu Val Ala Gly Tyr Arg Thr Thr
195 200 205

Thr Met Phe Leu Ser Asp Ala Val Leu Ala Leu Leu Ala Asp Pro Asp
210 215 220

Gln Tyr Val Arg Leu Arg Asp Asp Arg Gly Leu Leu Pro Gly Ala Val
225 230 235 240

Glu Glu Phe Leu Arg Tyr Val Pro Ala Met Asn Gly Val Val Val Leu
245 250 255

Gln Ala Thr Glu Asp Phe Glu Leu Gly Gly Gln Thr Ile Arg Ala Gly
260 265 270

Asp Ala Val Leu Pro Ala Leu Ala Ser Ala Asn Arg Asp Glu Thr Val
275 280 285

Phe Asp Glu Pro Glu Arg Leu Asp Val Cys Arg Arg Pro Asn Pro His
290 295 300

Ile Ala Phe Gly Arg Gly Pro His Asn Cys Ile Gly Ala His Leu Ala
305 310 315 320

Arg Ala Glu Leu Thr Val Gly Leu Glu Thr Leu Leu Asp Arg Phe Pro
325 330 335

His Leu Arg Leu Ala Glu Gly His Ser Pro Thr Trp Asp Asp Ala Ser
340 345 350

Pro Ser Lys Ser Pro Leu Thr Leu Pro Val Ser Trp
355 360

<210> SEQ ID NO 113
<211> LENGTH: 1215
<212> TYPE: DNA
<213> ORGANISM: Streptomyces rimosus

<400> SEQUENCE: 113
atgagccacc ccgaagccct cataccggtc ccggaggtcg agcccggtac cgcggggccg 60
ccgtgcgcct acgcccggct gcggaccgag gcgcccgtgg tcaaggcgca gctgcccaac 120
ggcgagacgg gctggctgat cagccgctac gaggacgccc gcgccgcgtt cgccgacccc 180
cggctcgtac ggccgctgct gtcggcctgg ccgcccccgcg agggaagcga cgcccccgccg 240 ccgtgcctgc ccaccttcct ggagatgacc ggcgcccacc acgaacgcgt gcgccgcacc 300
gtactgccgc tgttcggcag gcggcggctc gccttcatgg agccccgcgt ccgggcgatg 360
gcggaggaac tcctcgacac gatggtggcc ggggccgacg ggggagtggc ggatctcgtc 420
gcctcctacg ccgagccgct gccgctgcgg gtgctgtgcg cgaccgtcgg cctgccgtac 480
gaggaccgcg agacctacct gccgcacacc ctcgcgctcc tgggcgcgtc cggcctcacg 540
atggaggagg tactcgcggc cctgtacgcg ctgcaggact atgcggacga cctcatctcc 600
cgtaaggaga agacggacgg cgaggacgag gactacatcc ggctgctgct ggcggaggca 660

```
cgccggccgg acagcgagat cacccgcgac gacgtcgtca gcttcgtcgt caccatgctg    720

atggccggct acaagaccaa catccagcac accggcaacg ccctgctcgc gctgctcacc    780

caccccgagc agctgaaggc gctgcgcgag gcgcccgagc ggaccggcgc cgcggtggag    840

gaactgctgc ggtacgtccc gctgatgaac gccatcaaca tcctcgtcgc caccgaggac    900

ttcaccctcc acgggcagaa catcagggcc ggggacgcgg tcgtgcccgt accggcgtcc    960

gccaaccgcg acccggacgc cttcgccgaa cccgaccgcc tcgacctgac gcggactccg   1020

aacgcgcaca tcgcgttcgg gcacggcccc cacgcctgca ccggcggcca cctgacccgt   1080

atgcagctcg gtatcgccat ccaggtactg ctggaacggc tgcccggcat cgaactggcc   1140

gtcgcggcgg acaccatccc ctgggacgag tccactccac tgcgcgcacc ggcccggctc   1200

cccgtgcgct ggtaa                                                    1215


<210> SEQ ID NO 114
<211> LENGTH: 404
<212> TYPE: PRT
<213> ORGANISM: Streptomyces rimosus

<400> SEQUENCE: 114

Met Ser His Pro Glu Ala Leu Ile Pro Val Pro Glu Val Glu Pro Gly
1               5                   10                  15

Thr Ala Gly Pro Pro Cys Ala Tyr Ala Arg Leu Arg Thr Glu Ala Pro
            20                  25                  30

Val Val Lys Ala Gln Leu Pro Asn Gly Glu Thr Gly Trp Leu Ile Ser
        35                  40                  45

Arg Tyr Glu Asp Ala Arg Ala Ala Phe Ala Asp Pro Arg Leu Val Arg
    50                  55                  60

Pro Leu Leu Ser Ala Trp Pro Pro Arg Glu Gly Ser Asp Ala Pro Pro
65                  70                  75                  80

Pro Cys Leu Pro Thr Phe Leu Glu Met Thr Gly Ala His His Glu Arg
                85                  90                  95

Val Arg Arg Thr Val Leu Pro Leu Phe Gly Arg Arg Arg Leu Ala Phe
            100                 105                 110

Met Glu Pro Arg Val Arg Ala Met Ala Glu Glu Leu Leu Asp Thr Met
        115                 120                 125

Val Ala Gly Ala Asp Gly Gly Val Ala Asp Leu Val Ala Ser Tyr Ala
    130                 135                 140

Glu Pro Leu Pro Leu Arg Val Leu Cys Ala Thr Val Gly Leu Pro Tyr
145                 150                 155                 160

Glu Asp Arg Glu Thr Tyr Leu Pro His Thr Leu Ala Leu Leu Gly Ala
                165                 170                 175

Ser Gly Leu Thr Met Glu Glu Val Leu Ala Ala Leu Tyr Ala Leu Gln
            180                 185                 190

Asp Tyr Ala Asp Asp Leu Ile Ser Arg Lys Glu Lys Thr Asp Gly Glu
        195                 200                 205

Asp Glu Asp Tyr Ile Arg Leu Leu Leu Ala Glu Ala Arg Arg Pro Asp
    210                 215                 220

Ser Glu Ile Thr Arg Asp Asp Val Val Ser Phe Val Val Thr Met Leu
225                 230                 235                 240

Met Ala Gly Tyr Lys Thr Asn Ile Gln His Thr Gly Asn Ala Leu Leu
                245                 250                 255

Ala Leu Leu Thr His Pro Glu Gln Leu Lys Ala Leu Arg Glu Ala Pro
            260                 265                 270
```

Glu Arg Thr Gly Ala Ala Val Glu Glu Leu Leu Arg Tyr Val Pro Leu
        275                 280                 285

Met Asn Ala Ile Asn Ile Leu Val Ala Thr Glu Asp Phe Thr Leu His
    290                 295                 300

Gly Gln Asn Ile Arg Ala Gly Asp Ala Val Val Pro Val Pro Ala Ser
305                 310                 315                 320

Ala Asn Arg Asp Pro Asp Ala Phe Ala Glu Pro Asp Arg Leu Asp Leu
                325                 330                 335

Thr Arg Thr Pro Asn Ala His Ile Ala Phe Gly His Gly Pro His Ala
            340                 345                 350

Cys Thr Gly Gly His Leu Thr Arg Met Gln Leu Gly Ile Ala Ile Gln
        355                 360                 365

Val Leu Leu Glu Arg Leu Pro Gly Ile Glu Leu Ala Val Ala Ala Asp
    370                 375                 380

Thr Ile Pro Trp Asp Glu Ser Thr Pro Leu Arg Ala Pro Ala Arg Leu
385                 390                 395                 400

Pro Val Arg Trp

<210> SEQ ID NO 115
<211> LENGTH: 915
<212> TYPE: DNA
<213> ORGANISM: Streptomyces rimosus

<400> SEQUENCE: 115
atgggcccgg gcgcgctcac cgacccggac tgggtggtgc cgccggtgcc ccaggacgta      60
ccggagggcg ggatggcctg gctgcgggcg cgggtcgccc gcttcagcag cggggaggcg     120
cacgtacggc gccgggcgct ggcggtcggc ccgctcggcg ggggagacgc ggccgacgcg     180
ctgcgcgaca ccgcccgcgt acggacgcaa gcgctgctgg acggggcggg ggtggggccg     240
ggatcggggc cggggacggt ggacgtgatg gcgctggtgg cgcgcgtcgt gcccgtcgaa     300
gtgcttgccg atttcgtcgg gctgccggtc acggcggaga cggccgggct ggtcgggcac     360
gtcgcccgcg cgtaccacgc acacggcgag accgtcccgg ccgccgaccg cgccctcgcc     420
cggctcgtaa cggtgtgcgg cggtacgtgg gacgaggcca cggcggcccg catcgggctg     480
ctggtgcagg cgtacgacgc gacggcgggg ctgatcggca acgcggcgca tcggatgctg     540
tcctgcgata caggcgatac ggggagtgcg agcggtacgg gggatacgcc ggagggctcc     600
gccgagtctg ccgccgatgt cgtcaccgcc tcgctcgacc ggacgctgag cgccgaccca     660
cccgtacggg gcaccctccg cgcccctgcg aacggcggtg atccagtacg gatcgccctg     720
ctcacggacg acggatcgct cgccttcggt gccggcccgc acgcctgccc cgggcgcgcc     780
cacgcccggg cgctcgcggc cggagtgctg gacgcgctgc tcgggcgcgg ctgccgcctc     840
gtccggccgg acctcgcgta cgagccgtcc ccgaacctgc gggtgccggt gcggctggag     900
gtgacgtgca cataa                                                      915

<210> SEQ ID NO 116
<211> LENGTH: 304
<212> TYPE: PRT
<213> ORGANISM: Streptomyces rimosus

<400> SEQUENCE: 116

Met Gly Pro Gly Ala Leu Thr Asp Pro Asp Trp Val Val Pro Pro Val
1               5                   10                  15

Pro Gln Asp Val Pro Glu Gly Gly Met Ala Trp Leu Arg Ala Arg Val

```
            20                  25                  30

Ala Arg Phe Ser Ser Gly Glu Ala His Val Arg Arg Arg Ala Leu Ala
        35                  40                  45

Val Gly Pro Leu Gly Gly Gly Asp Ala Ala Asp Ala Leu Arg Asp Thr
    50                  55                  60

Ala Arg Val Arg Thr Gln Ala Leu Leu Asp Gly Ala Gly Val Gly Pro
65                  70                  75                  80

Gly Ser Gly Pro Gly Thr Val Asp Val Met Ala Leu Val Ala Arg Val
                85                  90                  95

Val Pro Val Glu Val Leu Ala Asp Phe Val Gly Leu Pro Val Thr Ala
            100                 105                 110

Glu Thr Ala Gly Leu Val Gly His Val Ala Arg Ala Tyr His Ala His
        115                 120                 125

Gly Glu Thr Val Pro Ala Ala Asp Arg Ala Leu Ala Arg Leu Val Thr
    130                 135                 140

Val Cys Gly Gly Thr Trp Asp Glu Ala Thr Ala Ala Arg Ile Gly Leu
145                 150                 155                 160

Leu Val Gln Ala Tyr Asp Ala Thr Ala Gly Leu Ile Gly Asn Ala Ala
                165                 170                 175

His Arg Met Leu Ser Cys Asp Thr Gly Asp Thr Gly Ser Ala Ser Gly
            180                 185                 190

Thr Gly Asp Thr Pro Glu Gly Ser Ala Glu Ser Ala Ala Asp Val Val
        195                 200                 205

Thr Ala Ser Leu Asp Arg Thr Leu Ser Ala Asp Pro Pro Val Arg Gly
    210                 215                 220

Thr Leu Arg Ala Pro Ala Asn Gly Gly Asp Pro Val Arg Ile Ala Leu
225                 230                 235                 240

Leu Thr Asp Asp Gly Ser Leu Ala Phe Gly Ala Gly Pro His Ala Cys
                245                 250                 255

Pro Gly Arg Ala His Ala Arg Ala Leu Ala Ala Gly Val Leu Asp Ala
            260                 265                 270

Leu Leu Gly Arg Gly Cys Arg Leu Val Arg Pro Asp Leu Ala Tyr Glu
        275                 280                 285

Pro Ser Pro Asn Leu Arg Val Pro Val Arg Leu Glu Val Thr Cys Thr
    290                 295                 300
```

<210> SEQ ID NO 117
<211> LENGTH: 1146
<212> TYPE: DNA
<213> ORGANISM: Streptomyces rimosus

<400> SEQUENCE: 117

```
atggacaatc cctaccccct gtaccggcgg ctgcgcgaaa cctcccccgt tctgtgggat      60

cccgtacgcc atcactggac cgtcacccgc caccaggaag tcacccaggc actgcgctcc     120

ccggccctgc acgccgtacc ccgccgcctc ggcccccgca caccccccac cctgcgcctg     180

ctcaacagcg ccatgctcga ctccgatccg cccgagcaca cccgccgccg tcgcgtcttc     240

acccaagcct tcaccccgcg cctgaccgca gacctcgcac ccgccatcac ccaccgcgtc     300

gacgccctcc tcgaccgcgt gcacgaaagc ggccacatgg acctcatcga agacctggcc     360

actccactgc ccctgcacgt catcggccag ctgctcggca tacccccgca agaccgcccc     420

cgcctgcacg ccggagcccg cggctacgcc cgactgtggg gcggcgacga caccgaccag     480

accaccatcg gccaagccgt caccgacatc accagagcca tcgaccactg ccgcgagctg     540
```

```
atcacccagc gtcgcaacgc tccccgctcc gacctgatca gccgtctggc ctcaccagcc    600

ggccgggcgg gctcgctcag cgacggcgaa ctggccgcca acctcttcat ggtcttcacc    660

gcaggccact acacgaccac cgacttcctg ggaaactccg tcctcgcact ggcacaccac    720

ccgcaccagt ggcaacaact gtgcacggac ccggcactgg cctcctcggc cgtcaccgaa    780

ctgctgcgct acgaagcccc cgtccagttc gtcatccgcc tggccgcaca agacctcacc    840

ctcgccggcc agcgcatcac agccggccag ctcgtcgtcc ttctgctcgc cgcagcgaac    900

cgcgacccac gggccttccc cgaccccgac cgcctcgacc tcacacgcac tcccaaccac    960

cacctcaccc tcggcttcgg catccactcc tgcctgggca ccgccctggc ccggctccaa   1020

ggcgagatca ccctgagccg cctggccgcc cgcatgcccc gtctccgccc ggccggcgac   1080

accatccgct ggaagaccac caccggactc cgcggacctc tccgtctatc cgtccactgg   1140

gactaa                                                              1146
```

```
<210> SEQ ID NO 118
<211> LENGTH: 381
<212> TYPE: PRT
<213> ORGANISM: Streptomyces rimosus

<400> SEQUENCE: 118

Met Asp Asn Pro Tyr Pro Leu Tyr Arg Arg Leu Arg Glu Thr Ser Pro
1               5                   10                  15

Val Leu Trp Asp Pro Val Arg His His Trp Thr Val Thr Arg His Gln
            20                  25                  30

Glu Val Thr Gln Ala Leu Arg Ser Pro Ala Leu His Ala Val Pro Arg
        35                  40                  45

Arg Leu Gly Pro Arg Thr Pro Pro Thr Leu Arg Leu Leu Asn Ser Ala
    50                  55                  60

Met Leu Asp Ser Asp Pro Pro Glu His Thr Arg Arg Arg Arg Val Phe
65                  70                  75                  80

Thr Gln Ala Phe Thr Pro Arg Leu Thr Ala Asp Leu Ala Pro Ala Ile
                85                  90                  95

Thr His Arg Val Asp Ala Leu Leu Asp Arg Val His Glu Ser Gly His
            100                 105                 110

Met Asp Leu Ile Glu Asp Leu Ala Thr Pro Leu Pro Leu His Val Ile
        115                 120                 125

Gly Gln Leu Leu Gly Ile Pro Pro Gln Asp Arg Pro Arg Leu His Ala
    130                 135                 140

Gly Ala Arg Gly Tyr Ala Arg Leu Trp Gly Gly Asp Asp Thr Asp Gln
145                 150                 155                 160

Thr Thr Ile Gly Gln Ala Val Thr Asp Ile Thr Arg Ala Ile Asp His
                165                 170                 175

Cys Arg Glu Leu Ile Thr Gln Arg Arg Asn Ala Pro Arg Ser Asp Leu
            180                 185                 190

Ile Ser Arg Leu Ala Ser Pro Ala Gly Arg Ala Gly Ser Leu Ser Asp
        195                 200                 205

Gly Glu Leu Ala Ala Asn Leu Phe Met Val Phe Thr Ala Gly His Tyr
    210                 215                 220

Thr Thr Thr Asp Phe Leu Gly Asn Ser Val Leu Ala Leu Ala His His
225                 230                 235                 240

Pro His Gln Trp Gln Gln Leu Cys Thr Asp Pro Ala Leu Ala Ser Ser
                245                 250                 255

Ala Val Thr Glu Leu Leu Arg Tyr Glu Ala Pro Val Gln Phe Val Ile
```

```
        260                 265                 270

Arg Leu Ala Ala Gln Asp Leu Thr Leu Ala Gly Gln Arg Ile Thr Ala
        275                 280                 285

Gly Gln Leu Val Val Leu Leu Leu Ala Ala Ala Asn Arg Asp Pro Arg
    290                 295                 300

Ala Phe Pro Asp Pro Asp Arg Leu Asp Leu Thr Arg Thr Pro Asn His
305                 310                 315                 320

His Leu Thr Leu Gly Phe Gly Ile His Ser Cys Leu Gly Thr Ala Leu
                325                 330                 335

Ala Arg Leu Gln Gly Glu Ile Thr Leu Ser Arg Leu Ala Ala Arg Met
            340                 345                 350

Pro Arg Leu Arg Pro Ala Gly Asp Thr Ile Arg Trp Lys Thr Thr Thr
        355                 360                 365

Gly Leu Arg Gly Pro Leu Arg Leu Ser Val His Trp Asp
    370                 375                 380


<210> SEQ ID NO 119
<211> LENGTH: 57
<212> TYPE: DNA
<213> ORGANISM: Artificial Sequence
<220> FEATURE:
<223> OTHER INFORMATION: Primer Sequence

<400> SEQUENCE: 119

attttgttta actttaagaa ggagatatac atatgaccga gacgatcccg ttcgaag        57


<210> SEQ ID NO 120
<211> LENGTH: 60
<212> TYPE: DNA
<213> ORGANISM: Artificial Sequence
<220> FEATURE:
<223> OTHER INFORMATION: Primer Sequence

<400> SEQUENCE: 120

gtggtggtgg tggtggtgct cgagtgcggc cgctaattac cccgtcacat agacatcctc     60


<210> SEQ ID NO 121
<211> LENGTH: 57
<212> TYPE: DNA
<213> ORGANISM: Artificial Sequence
<220> FEATURE:
<223> OTHER INFORMATION: Primer Sequence

<400> SEQUENCE: 121

attttgttta actttaagaa ggagatatac atatgaccgg cgtatccgcc cgcgaac        57


<210> SEQ ID NO 122
<211> LENGTH: 68
<212> TYPE: DNA
<213> ORGANISM: Artificial Sequence
<220> FEATURE:
<223> OTHER INFORMATION: Primer Sequence

<400> SEQUENCE: 122

cgatccgcac tcacccgcat ggtcatgaat tctgtttcct ataattacca ggcgaccggc     60

agggattc                                                              68


<210> SEQ ID NO 123
<211> LENGTH: 59
<212> TYPE: DNA
<213> ORGANISM: Artificial Sequence
<220> FEATURE:
```

<223> OTHER INFORMATION: Primer Sequence

<400> SEQUENCE: 123
attttgttta actttaagaa ggagatatac atatgccgga cgagtcccag caccagttc 59

<210> SEQ ID NO 124
<211> LENGTH: 62
<212> TYPE: DNA
<213> ORGANISM: Artificial Sequence
<220> FEATURE:
<223> OTHER INFORMATION: Primer Sequence

<400> SEQUENCE: 124
ctacccgcag agggcggggc ataagcttcc tattacgtac ccgggccgtc cgcctcccgc 60
tc 62

<210> SEQ ID NO 125
<211> LENGTH: 58
<212> TYPE: DNA
<213> ORGANISM: Artificial Sequence
<220> FEATURE:
<223> OTHER INFORMATION: Primer Sequence

<400> SEQUENCE: 125
attttgttta actttaagaa ggagatatac atatggcgag ccgtacccgt atcgatac 58

<210> SEQ ID NO 126
<211> LENGTH: 71
<212> TYPE: DNA
<213> ORGANISM: Artificial Sequence
<220> FEATURE:
<223> OTHER INFORMATION: Primer Sequence

<400> SEQUENCE: 126
cgatccgcac tcacccgcat ggtcatgaat tctgtttcct ataattagcc gcgcggggtg 60
agcgccagat c 71

<210> SEQ ID NO 127
<211> LENGTH: 59
<212> TYPE: DNA
<213> ORGANISM: Artificial Sequence
<220> FEATURE:
<223> OTHER INFORMATION: Primer Sequence

<400> SEQUENCE: 127
attttgttta actttaagaa ggagatatac atatgtcgta caacccgacg gcccccgac 59

<210> SEQ ID NO 128
<211> LENGTH: 57
<212> TYPE: DNA
<213> ORGANISM: Artificial Sequence
<220> FEATURE:
<223> OTHER INFORMATION: Primer Sequence

<400> SEQUENCE: 128
ctacccgcag agggcggggc ataagcttcc tattacgggt ccgtgggttc cggggag 57

<210> SEQ ID NO 129
<211> LENGTH: 54
<212> TYPE: DNA
<213> ORGANISM: Artificial Sequence
<220> FEATURE:
<223> OTHER INFORMATION: Primer Sequence

<400> SEQUENCE: 129
attttgttta actttaagaa ggagatatac atatgagcga cccggccgcg gtac 54

<210> SEQ ID NO 130
<211> LENGTH: 68
<212> TYPE: DNA
<213> ORGANISM: Artificial Sequence
<220> FEATURE:
<223> OTHER INFORMATION: Primer Sequence

<400> SEQUENCE: 130
cgatccgcac tcacccgcat ggtcatgaat tctgtttcct ataattacga caggagcagg 60
ggcagctc 68

<210> SEQ ID NO 131
<211> LENGTH: 70
<212> TYPE: DNA
<213> ORGANISM: Artificial Sequence
<220> FEATURE:
<223> OTHER INFORMATION: Primer Sequence

<400> SEQUENCE: 131
attttgttta actttaagaa ggagatatac atatggacat cgatggcgcg gagcccggcg 60
gcggcccttc 70

<210> SEQ ID NO 132
<211> LENGTH: 71
<212> TYPE: DNA
<213> ORGANISM: Artificial Sequence
<220> FEATURE:
<223> OTHER INFORMATION: Primer Sequence

<400> SEQUENCE: 132
cgatccgcac tcacccgcat ggtcatgaat tctgtttcct ataattatga accgccgggc 60
gggccgagga c 71

<210> SEQ ID NO 133
<211> LENGTH: 54
<212> TYPE: DNA
<213> ORGANISM: Artificial Sequence
<220> FEATURE:
<223> OTHER INFORMATION: Primer Sequence

<400> SEQUENCE: 133
attttgttta actttaagaa ggagatatac atatggctga gtccacccac actg 54

<210> SEQ ID NO 134
<211> LENGTH: 70
<212> TYPE: DNA
<213> ORGANISM: Artificial Sequence
<220> FEATURE:
<223> OTHER INFORMATION: Primer Sequence

<400> SEQUENCE: 134
cgatccgcac tcacccgcat ggtcatgaat tctgtttcct ataattacac atcccaggcg 60
accggaagac 70

<210> SEQ ID NO 135
<211> LENGTH: 61
<212> TYPE: DNA
<213> ORGANISM: Artificial Sequence
<220> FEATURE:
<223> OTHER INFORMATION: Primer Sequence

<400> SEQUENCE: 135
attttgttta actttaagaa ggagatatac atatgacccc ctctcccgct tcccccgcca 60
c 61

<210> SEQ ID NO 136
<211> LENGTH: 68
<212> TYPE: DNA
<213> ORGANISM: Artificial Sequence
<220> FEATURE:
<223> OTHER INFORMATION: Primer Sequence

<400> SEQUENCE: 136
gtggtggtgg tggtggtgct cgagtgcggc cgctaattac gcgcgggcgt tgtgcagccc 60
ctcgcgag 68

<210> SEQ ID NO 137
<211> LENGTH: 63
<212> TYPE: DNA
<213> ORGANISM: Artificial Sequence
<220> FEATURE:
<223> OTHER INFORMATION: Primer Sequence

<400> SEQUENCE: 137
attttgttta actttaagaa ggagatatac atatgaccct caccacacga tccggcccgg 60
cga 63

<210> SEQ ID NO 138
<211> LENGTH: 89
<212> TYPE: DNA
<213> ORGANISM: Artificial Sequence
<220> FEATURE:
<223> OTHER INFORMATION: Primer Sequence

<400> SEQUENCE: 138
cgatccgcac tcacccgcat ggtcatgaat tctgtttcct ataattagcc cactcccctc 60
agccgcaccc gcgccgggcc cgccgcctg 89

<210> SEQ ID NO 139
<211> LENGTH: 67
<212> TYPE: DNA
<213> ORGANISM: Artificial Sequence
<220> FEATURE:
<223> OTHER INFORMATION: Primer Sequence

<400> SEQUENCE: 139
attttgttta actttaagaa ggagatatac atatgacgca caccgaaccg gccgcgccgg 60
ccacctg 67

<210> SEQ ID NO 140
<211> LENGTH: 63
<212> TYPE: DNA
<213> ORGANISM: Artificial Sequence
<220> FEATURE:
<223> OTHER INFORMATION: Primer Sequence

<400> SEQUENCE: 140
ctacccgcag agggcggggc ataagcttcc tattagccct cgtgcacggt gatggccccg 60
gac 63

<210> SEQ ID NO 141
<211> LENGTH: 59

<212> TYPE: DNA
<213> ORGANISM: Artificial Sequence
<220> FEATURE:
<223> OTHER INFORMATION: Primer Sequence

<400> SEQUENCE: 141
attttgttta actttaagaa ggagatatac atatgaccga ggcgctgccc ttcccgcag 59

<210> SEQ ID NO 142
<211> LENGTH: 62
<212> TYPE: DNA
<213> ORGANISM: Artificial Sequence
<220> FEATURE:
<223> OTHER INFORMATION: Primer Sequence

<400> SEQUENCE: 142
ctacccgcag agggcggggc ataagcttcc tattagtcgt ccgtgaccgc gatcgcctga 60
ac 62

<210> SEQ ID NO 143
<211> LENGTH: 62
<212> TYPE: DNA
<213> ORGANISM: Artificial Sequence
<220> FEATURE:
<223> OTHER INFORMATION: Primer Sequence

<400> SEQUENCE: 143
attttgttta actttaagaa ggagatatac atatgaccgc ggccgcgcag gaactggaaa 60
tc 62

<210> SEQ ID NO 144
<211> LENGTH: 73
<212> TYPE: DNA
<213> ORGANISM: Artificial Sequence
<220> FEATURE:
<223> OTHER INFORMATION: Primer Sequence

<400> SEQUENCE: 144
cgatccgcac tcacccgcat ggtcatgaat tctgtttcct ataattacca ggtgaccggg 60
aatgcgtgga tac 73

<210> SEQ ID NO 145
<211> LENGTH: 68
<212> TYPE: DNA
<213> ORGANISM: Artificial Sequence
<220> FEATURE:
<223> OTHER INFORMATION: Primer Sequence

<400> SEQUENCE: 145
attttgttta actttaagaa ggagatatac atatgaccga gacctccacc gccttcccgg 60
cccaagac 68

<210> SEQ ID NO 146
<211> LENGTH: 72
<212> TYPE: DNA
<213> ORGANISM: Artificial Sequence
<220> FEATURE:
<223> OTHER INFORMATION: Primer Sequence

<400> SEQUENCE: 146
ctacccgcag agggcggggc ataagcttcc tattactccg tgacccgaag ggccccggac 60
gggcacagca tg 72

<210> SEQ ID NO 147
<211> LENGTH: 59
<212> TYPE: DNA
<213> ORGANISM: Artificial Sequence
<220> FEATURE:
<223> OTHER INFORMATION: Primer Sequence

<400> SEQUENCE: 147
attttgttta actttaagaa ggagatatac atatggctgc acacgccgat gagccgatc 59

<210> SEQ ID NO 148
<211> LENGTH: 75
<212> TYPE: DNA
<213> ORGANISM: Artificial Sequence
<220> FEATURE:
<223> OTHER INFORMATION: Primer Sequence

<400> SEQUENCE: 148
cgatccgcac tcacccgcat ggtcatgaat tctgtttcct ataattatgt gacgctcctt 60
tgcgcgtggg ggatg 75

<210> SEQ ID NO 149
<211> LENGTH: 62
<212> TYPE: DNA
<213> ORGANISM: Artificial Sequence
<220> FEATURE:
<223> OTHER INFORMATION: Primer Sequence

<400> SEQUENCE: 149
attttgttta actttaagaa ggagatatac atatgccggg cgccttgccc ctcgtcgggc 60
ac 62

<210> SEQ ID NO 150
<211> LENGTH: 76
<212> TYPE: DNA
<213> ORGANISM: Artificial Sequence
<220> FEATURE:
<223> OTHER INFORMATION: Primer Sequence

<400> SEQUENCE: 150
cgatccgcac tcacccgcat ggtcatgaat tctgtttcct ataattagtt gctcggccgg 60
ctgggtgcgg ggttac 76

<210> SEQ ID NO 151
<211> LENGTH: 59
<212> TYPE: DNA
<213> ORGANISM: Artificial Sequence
<220> FEATURE:
<223> OTHER INFORMATION: Primer Sequence

<400> SEQUENCE: 151
attttgttta actttaagaa ggagatatac atatgccggt ccagctcccc ggcggcatc 59

<210> SEQ ID NO 152
<211> LENGTH: 72
<212> TYPE: DNA
<213> ORGANISM: Artificial Sequence
<220> FEATURE:
<223> OTHER INFORMATION: Primer Sequence

<400> SEQUENCE: 152
cgatccgcac tcacccgcat ggtcatgaat tctgtttcct ataattaccc ggcgccgggg 60
ctggtggccg ac 72

<210> SEQ ID NO 153
<211> LENGTH: 66
<212> TYPE: DNA
<213> ORGANISM: Artificial Sequence
<220> FEATURE:
<223> OTHER INFORMATION: Primer Sequence

<400> SEQUENCE: 153
attttgttta actttaagaa ggagatatac atatgacgac cgttcccgat cttcccgacg 60
ccacag 66

<210> SEQ ID NO 154
<211> LENGTH: 71
<212> TYPE: DNA
<213> ORGANISM: Artificial Sequence
<220> FEATURE:
<223> OTHER INFORMATION: Primer Sequence

<400> SEQUENCE: 154
cgatccgcac tcacccgcat ggtcatgaat tctgtttcct ataattattc cgggtcgccc 60
tgccaggtca c 71

<210> SEQ ID NO 155
<211> LENGTH: 62
<212> TYPE: DNA
<213> ORGANISM: Artificial Sequence
<220> FEATURE:
<223> OTHER INFORMATION: Primer Sequence

<400> SEQUENCE: 155
attttgttta actttaagaa ggagatatac atatgcagaa caccgccgag accggccccg 60
ac 62

<210> SEQ ID NO 156
<211> LENGTH: 72
<212> TYPE: DNA
<213> ORGANISM: Artificial Sequence
<220> FEATURE:
<223> OTHER INFORMATION: Primer Sequence

<400> SEQUENCE: 156
cgatccgcac tcacccgcat ggtcatgaat tctgtttcct ataattacca ggcgacgggg 60
agcgagatca ag 72

<210> SEQ ID NO 157
<211> LENGTH: 53
<212> TYPE: DNA
<213> ORGANISM: Artificial Sequence
<220> FEATURE:
<223> OTHER INFORMATION: Primer Sequence

<400> SEQUENCE: 157
attttgttta actttaagaa ggagatatac atatgccgga aatcatcgac ctg 53

<210> SEQ ID NO 158
<211> LENGTH: 68
<212> TYPE: DNA
<213> ORGANISM: Artificial Sequence
<220> FEATURE:
<223> OTHER INFORMATION: Primer Sequence

<400> SEQUENCE: 158

-continued cgatccgcac tcacccgcat ggtcatgaat tctgtttcct ataattaccg ccaccgcacc 60
ggcaggtg 68

<210> SEQ ID NO 159
<211> LENGTH: 61
<212> TYPE: DNA
<213> ORGANISM: Artificial Sequence
<220> FEATURE:
<223> OTHER INFORMATION: Primer Sequence

<400> SEQUENCE: 159
attttgttta actttaagaa ggagatatac atatgtcagt gccgagccgc ccgccggcca 60
c 61

<210> SEQ ID NO 160
<211> LENGTH: 72
<212> TYPE: DNA
<213> ORGANISM: Artificial Sequence
<220> FEATURE:
<223> OTHER INFORMATION: Primer Sequence

<400> SEQUENCE: 160
cgatccgcac tcacccgcat ggtcatgaat tctgtttcct ataattagag ttggaaagtg 60
atccgttcgg tg 72

<210> SEQ ID NO 161
<211> LENGTH: 58
<212> TYPE: DNA
<213> ORGANISM: Artificial Sequence
<220> FEATURE:
<223> OTHER INFORMATION: Primer Sequence

<400> SEQUENCE: 161
attttgttta actttaagaa ggagatatac atatgaccac atcgcccacc gagtccac 58

<210> SEQ ID NO 162
<211> LENGTH: 74
<212> TYPE: DNA
<213> ORGANISM: Artificial Sequence
<220> FEATURE:
<223> OTHER INFORMATION: Primer Sequence

<400> SEQUENCE: 162
cgatccgcac tcacccgcat ggtcatgaat tctgtttcct ataattagtc ctccggacgc 60
agccgcaacg gcag 74

<210> SEQ ID NO 163
<211> LENGTH: 59
<212> TYPE: DNA
<213> ORGANISM: Artificial Sequence
<220> FEATURE:
<223> OTHER INFORMATION: Primer Sequence

<400> SEQUENCE: 163
attttgttta actttaagaa ggagatatac atatgaccgc cgagaaccac accgcgcag 59

<210> SEQ ID NO 164
<211> LENGTH: 75
<212> TYPE: DNA
<213> ORGANISM: Artificial Sequence
<220> FEATURE:
<223> OTHER INFORMATION: Primer Sequence

<400> SEQUENCE: 164
cgatccgcac tcacccgcat ggtcatgaat tctgtttcct ataattacca cgccaccgga 60
atctccgccg ccatg 75

<210> SEQ ID NO 165
<211> LENGTH: 59
<212> TYPE: DNA
<213> ORGANISM: Artificial Sequence
<220> FEATURE:
<223> OTHER INFORMATION: Primer Sequence

<400> SEQUENCE: 165
attttgttta actttaagaa ggagatatac atatgccgca ggacacctcc cgccggttc 59

<210> SEQ ID NO 166
<211> LENGTH: 71
<212> TYPE: DNA
<213> ORGANISM: Artificial Sequence
<220> FEATURE:
<223> OTHER INFORMATION: Primer Sequence

<400> SEQUENCE: 166
cgatccgcac tcacccgcat ggtcatgaat tctgtttcct ataattacca caccacaggc 60
agcctcacca c 71

<210> SEQ ID NO 167
<211> LENGTH: 63
<212> TYPE: DNA
<213> ORGANISM: Artificial Sequence
<220> FEATURE:
<223> OTHER INFORMATION: Primer Sequence

<400> SEQUENCE: 167
attttgttta actttaagaa ggagatatac atatggatga gtcgcccgtc ttcgtcctgg 60
atc 63

<210> SEQ ID NO 168
<211> LENGTH: 80
<212> TYPE: DNA
<213> ORGANISM: Artificial Sequence
<220> FEATURE:
<223> OTHER INFORMATION: Primer Sequence

<400> SEQUENCE: 168
cgatccgcac tcacccgcat ggtcatgaat tctgtttcct ataattatcc ccctgcttcc 60
ccggccggcg cggagcggag 80

<210> SEQ ID NO 169
<211> LENGTH: 60
<212> TYPE: DNA
<213> ORGANISM: Artificial Sequence
<220> FEATURE:
<223> OTHER INFORMATION: Primer Sequence

<400> SEQUENCE: 169
attttgttta actttaagaa ggagatatac atatggagac tgccccgctc cgccccgtac 60

<210> SEQ ID NO 170
<211> LENGTH: 72
<212> TYPE: DNA
<213> ORGANISM: Artificial Sequence
<220> FEATURE:
<223> OTHER INFORMATION: Primer Sequence

<400> SEQUENCE: 170
cgatccgcac tcacccgcat ggtcatgaat tctgtttcct ataattacgg acgcgaacga 60
gcgcgcaccg tg 72

<210> SEQ ID NO 171
<211> LENGTH: 61
<212> TYPE: DNA
<213> ORGANISM: Artificial Sequence
<220> FEATURE:
<223> OTHER INFORMATION: Primer Sequence

<400> SEQUENCE: 171
attttgttta actttaagaa ggagatatac atatgcgcga tccggtccgc tacttcgaga 60
c 61

<210> SEQ ID NO 172
<211> LENGTH: 74
<212> TYPE: DNA
<213> ORGANISM: Artificial Sequence
<220> FEATURE:
<223> OTHER INFORMATION: Primer Sequence

<400> SEQUENCE: 172
cgatccgcac tcacccgcat ggtcatgaat tctgtttcct ataattaccc cgcgtcgtcc 60
gaaagagccg gatg 74

<210> SEQ ID NO 173
<211> LENGTH: 58
<212> TYPE: DNA
<213> ORGANISM: Artificial Sequence
<220> FEATURE:
<223> OTHER INFORMATION: Primer Sequence

<400> SEQUENCE: 173
attttgttta actttaagaa ggagatatac atatgttcac accccgcacg tacgccac 58

<210> SEQ ID NO 174
<211> LENGTH: 78
<212> TYPE: DNA
<213> ORGANISM: Artificial Sequence
<220> FEATURE:
<223> OTHER INFORMATION: Primer Sequence

<400> SEQUENCE: 174
cgatccgcac tcacccgcat ggtcatgaat tctgtttcct ataattacgc ccccacccgc 60
accggcaacc gccgcaac 78

<210> SEQ ID NO 175
<211> LENGTH: 65
<212> TYPE: DNA
<213> ORGANISM: Artificial Sequence
<220> FEATURE:
<223> OTHER INFORMATION: Primer Sequence

<400> SEQUENCE: 175
attttgttta actttaagaa ggagatatac atatgaccac ggacgacgac gaagaagagg 60
atcag 65

<210> SEQ ID NO 176
<211> LENGTH: 71
<212> TYPE: DNA
<213> ORGANISM: Artificial Sequence
<220> FEATURE:
<223> OTHER INFORMATION: Primer Sequence

<400> SEQUENCE: 176
cgatccgcac tcacccgcat ggtcatgaat tctgtttcct ataattacca tgcgacgggc 60
aacgattcca g 71

<210> SEQ ID NO 177
<211> LENGTH: 62
<212> TYPE: DNA
<213> ORGANISM: Artificial Sequence
<220> FEATURE:
<223> OTHER INFORMATION: Primer Sequence

<400> SEQUENCE: 177
attttgttta actttaagaa ggagatatac atatgttgat gccgctgcgg cgtcaggggc 60
tg 62

<210> SEQ ID NO 178
<211> LENGTH: 72
<212> TYPE: DNA
<213> ORGANISM: Artificial Sequence
<220> FEATURE:
<223> OTHER INFORMATION: Primer Sequence

<400> SEQUENCE: 178
cgatccgcac tcacccgcat ggtcatgaat tctgtttcct ataattagcc gccgaggtgc 60
accggcagcg ac 72

<210> SEQ ID NO 179
<211> LENGTH: 58
<212> TYPE: DNA
<213> ORGANISM: Artificial Sequence
<220> FEATURE:
<223> OTHER INFORMATION: Primer Sequence

<400> SEQUENCE: 179
attttgttta actttaagaa ggagatatac atatgctcgg cgacgcccgg ttcagctc 58

<210> SEQ ID NO 180
<211> LENGTH: 71
<212> TYPE: DNA
<213> ORGANISM: Artificial Sequence
<220> FEATURE:
<223> OTHER INFORMATION: Primer Sequence

<400> SEQUENCE: 180
cgatccgcac tcacccgcat ggtcatgaat tctgtttcct ataattacca agtgaccggg 60
agtgccgata c 71

<210> SEQ ID NO 181
<211> LENGTH: 62
<212> TYPE: DNA
<213> ORGANISM: Artificial Sequence
<220> FEATURE:
<223> OTHER INFORMATION: Primer Sequence

<400> SEQUENCE: 181
attttgttta actttaagaa ggagatatac atatggacac acaccccgaa cccatcgatt 60
ac 62

<210> SEQ ID NO 182

<211> LENGTH: 72
<212> TYPE: DNA
<213> ORGANISM: Artificial Sequence
<220> FEATURE:
<223> OTHER INFORMATION: Primer Sequence

<400> SEQUENCE: 182
cgatccgcac tcacccgcat ggtcatgaat tctgtttcct ataattacca ggtgaccggc 60
agctcctcga tc 72

<210> SEQ ID NO 183
<211> LENGTH: 59
<212> TYPE: DNA
<213> ORGANISM: Artificial Sequence
<220> FEATURE:
<223> OTHER INFORMATION: Primer Sequence

<400> SEQUENCE: 183
attttgttta actttaagaa ggagatatac atatgacgca gccggacacc aggacgaac 59

<210> SEQ ID NO 184
<211> LENGTH: 71
<212> TYPE: DNA
<213> ORGANISM: Artificial Sequence
<220> FEATURE:
<223> OTHER INFORMATION: Primer Sequence

<400> SEQUENCE: 184
cgatccgcac tcacccgcat ggtcatgaat tctgtttcct ataattacca ggcgacgggc 60
agcgcgtcca g 71

<210> SEQ ID NO 185
<211> LENGTH: 57
<212> TYPE: DNA
<213> ORGANISM: Artificial Sequence
<220> FEATURE:
<223> OTHER INFORMATION: Primer Sequence

<400> SEQUENCE: 185
attttgttta actttaagaa ggagatatac atatgccgga cgccggacgt ctccctc 57

<210> SEQ ID NO 186
<211> LENGTH: 75
<212> TYPE: DNA
<213> ORGANISM: Artificial Sequence
<220> FEATURE:
<223> OTHER INFORMATION: Primer Sequence

<400> SEQUENCE: 186
cgatccgcac tcacccgcat ggtcatgaat tctgtttcct ataattacgg agtgagcgtc 60
ccgccatcgg gcctg 75

<210> SEQ ID NO 187
<211> LENGTH: 59
<212> TYPE: DNA
<213> ORGANISM: Artificial Sequence
<220> FEATURE:
<223> OTHER INFORMATION: Primer Sequence

<400> SEQUENCE: 187
attttgttta actttaagaa ggagatatac atatggagtc accggagttc ttccgcgac 59

<210> SEQ ID NO 188
<211> LENGTH: 72

<212> TYPE: DNA
<213> ORGANISM: Artificial Sequence
<220> FEATURE:
<223> OTHER INFORMATION: Primer Sequence

<400> SEQUENCE: 188
cgatccgcac tcacccgcat ggtcatgaat tctgtttcct ataattaaca atccgtgacc 60
tgtgcggacc ag 72

<210> SEQ ID NO 189
<211> LENGTH: 69
<212> TYPE: DNA
<213> ORGANISM: Artificial Sequence
<220> FEATURE:
<223> OTHER INFORMATION: Primer Sequence

<400> SEQUENCE: 189
attttgttta actttaagaa ggagatatac atatgaagtc gtccgcgacg cggtccgggg 60
ccggcggac 69

<210> SEQ ID NO 190
<211> LENGTH: 73
<212> TYPE: DNA
<213> ORGANISM: Artificial Sequence
<220> FEATURE:
<223> OTHER INFORMATION: Primer Sequence

<400> SEQUENCE: 190
cgatccgcac tcacccgcat ggtcatgaat tctgtttcct ataattacct ccttccggag 60
ctgttggcac gtg 73

<210> SEQ ID NO 191
<211> LENGTH: 57
<212> TYPE: DNA
<213> ORGANISM: Artificial Sequence
<220> FEATURE:
<223> OTHER INFORMATION: Primer Sequence

<400> SEQUENCE: 191
attttgttta actttaagaa ggagatatac atatgcgccc accccgccta cccgaac 57

<210> SEQ ID NO 192
<211> LENGTH: 70
<212> TYPE: DNA
<213> ORGANISM: Artificial Sequence
<220> FEATURE:
<223> OTHER INFORMATION: Primer Sequence

<400> SEQUENCE: 192
cgatccgcac tcacccgcat ggtcatgaat tctgtttcct ataattatcg ggtggcggcc 60
tctccggcag 70

<210> SEQ ID NO 193
<211> LENGTH: 56
<212> TYPE: DNA
<213> ORGANISM: Artificial Sequence
<220> FEATURE:
<223> OTHER INFORMATION: Primer Sequence

<400> SEQUENCE: 193
attttgttta actttaagaa ggagatatac atatggaagg agtccaggca gtcttc 56

<210> SEQ ID NO 194

<211> LENGTH: 71
<212> TYPE: DNA
<213> ORGANISM: Artificial Sequence
<220> FEATURE:
<223> OTHER INFORMATION: Primer Sequence

<400> SEQUENCE: 194
cgatccgcac tcacccgcat ggtcatgaat tctgtttcct ataattacac cgcgaccagc 60
agctcgcgca g 71

<210> SEQ ID NO 195
<211> LENGTH: 55
<212> TYPE: DNA
<213> ORGANISM: Artificial Sequence
<220> FEATURE:
<223> OTHER INFORMATION: Primer Sequence

<400> SEQUENCE: 195
attttgttta actttaagaa ggagatatac atatgcagat cgtcgtggac ctcac 55

<210> SEQ ID NO 196
<211> LENGTH: 66
<212> TYPE: DNA
<213> ORGANISM: Artificial Sequence
<220> FEATURE:
<223> OTHER INFORMATION: Primer Sequence

<400> SEQUENCE: 196
gtggtggtgg tggtggtgct cgagtgcggc cgctaattac cctttatttc gaggcgacgc 60
caaatc 66

<210> SEQ ID NO 197
<211> LENGTH: 59
<212> TYPE: DNA
<213> ORGANISM: Artificial Sequence
<220> FEATURE:
<223> OTHER INFORMATION: Primer Sequence

<400> SEQUENCE: 197
attttgttta actttaagaa ggagatatac atatgtccgg ccacggaccg gcggccgtc 59

<210> SEQ ID NO 198
<211> LENGTH: 71
<212> TYPE: DNA
<213> ORGANISM: Artificial Sequence
<220> FEATURE:
<223> OTHER INFORMATION: Primer Sequence

<400> SEQUENCE: 198
cgatccgcac tcacccgcat ggtcatgaat tctgtttcct ataattactt ccgtacgggc 60
gtgaactcca c 71

<210> SEQ ID NO 199
<211> LENGTH: 56
<212> TYPE: DNA
<213> ORGANISM: Artificial Sequence
<220> FEATURE:
<223> OTHER INFORMATION: Primer Sequence

<400> SEQUENCE: 199
attttgttta actttaagaa ggagatatac atatgccatg ccccgcgctg cccgac 56

<210> SEQ ID NO 200
<211> LENGTH: 72

<212> TYPE: DNA
<213> ORGANISM: Artificial Sequence
<220> FEATURE:
<223> OTHER INFORMATION: Primer Sequence

<400> SEQUENCE: 200
cgatccgcac tcacccgcat ggtcatgaat tctgtttcct ataattacac gtaccggacc 60
cgcagctcct tc 72

<210> SEQ ID NO 201
<211> LENGTH: 62
<212> TYPE: DNA
<213> ORGANISM: Artificial Sequence
<220> FEATURE:
<223> OTHER INFORMATION: Primer Sequence

<400> SEQUENCE: 201
attttgttta actttaagaa ggagatatac atatggacgc gcgggtccgc cacagccccg 60
ag 62

<210> SEQ ID NO 202
<211> LENGTH: 71
<212> TYPE: DNA
<213> ORGANISM: Artificial Sequence
<220> FEATURE:
<223> OTHER INFORMATION: Primer Sequence

<400> SEQUENCE: 202
cgatccgcac tcacccgcat ggtcatgaat tctgtttcct ataattagga gaccaccgcg 60
tgccggggct g 71

<210> SEQ ID NO 203
<211> LENGTH: 75
<212> TYPE: DNA
<213> ORGANISM: Artificial Sequence
<220> FEATURE:
<223> OTHER INFORMATION: Primer Sequence

<400> SEQUENCE: 203
attttgttta actttaagaa ggagatatac atatgggtat acgtggtgcg gcgggcgtcc 60
gcgcggcccg cggtc 75

<210> SEQ ID NO 204
<211> LENGTH: 83
<212> TYPE: DNA
<213> ORGANISM: Artificial Sequence
<220> FEATURE:
<223> OTHER INFORMATION: Primer Sequence

<400> SEQUENCE: 204
cgatccgcac tcacccgcat ggtcatgaat tctgtttcct ataattacgg tgcttcagat 60
ggcacggccg gcgctgggcc gtc 83

<210> SEQ ID NO 205
<211> LENGTH: 60
<212> TYPE: DNA
<213> ORGANISM: Artificial Sequence
<220> FEATURE:
<223> OTHER INFORMATION: Primer Sequence

<400> SEQUENCE: 205
attttgttta actttaagaa ggagatatac atatgggtac gcacattcct ggacccgaac 60

<210> SEQ ID NO 206
<211> LENGTH: 76
<212> TYPE: DNA
<213> ORGANISM: Artificial Sequence
<220> FEATURE:
<223> OTHER INFORMATION: Primer Sequence

<400> SEQUENCE: 206
cgatccgcac tcacccgcat ggtcatgaat tctgtttcct ataattacgg gctccccgcc 60
cccacctccc gccgac 76

<210> SEQ ID NO 207
<211> LENGTH: 59
<212> TYPE: DNA
<213> ORGANISM: Artificial Sequence
<220> FEATURE:
<223> OTHER INFORMATION: Primer Sequence

<400> SEQUENCE: 207
attttgttta actttaagaa ggagatatac atatgaccac cccccagcac cccgacgac 59

<210> SEQ ID NO 208
<211> LENGTH: 72
<212> TYPE: DNA
<213> ORGANISM: Artificial Sequence
<220> FEATURE:
<223> OTHER INFORMATION: Primer Sequence

<400> SEQUENCE: 208
cgatccgcac tcacccgcat ggtcatgaat tctgtttcct ataattaccg gaaggccagc 60
tccccccgga ag 72

<210> SEQ ID NO 209
<211> LENGTH: 64
<212> TYPE: DNA
<213> ORGANISM: Artificial Sequence
<220> FEATURE:
<223> OTHER INFORMATION: Primer Sequence

<400> SEQUENCE: 209
attttgttta actttaagaa ggagatatac atatgacttt cccttttccc gaacagcccg 60
gcac 64

<210> SEQ ID NO 210
<211> LENGTH: 78
<212> TYPE: DNA
<213> ORGANISM: Artificial Sequence
<220> FEATURE:
<223> OTHER INFORMATION: Primer Sequence

<400> SEQUENCE: 210
cgatccgcac tcacccgcat ggtcatgaat tctgtttcct ataattagcc gcgcagccaa 60
gccttcaacg cggcccac 78

<210> SEQ ID NO 211
<211> LENGTH: 59
<212> TYPE: DNA
<213> ORGANISM: Artificial Sequence
<220> FEATURE:
<223> OTHER INFORMATION: Primer Sequence

<400> SEQUENCE: 211
attttgttta actttaagaa ggagatatac atatgctgga acagctgcgc aggcagtac 59

<210> SEQ ID NO 212
<211> LENGTH: 73
<212> TYPE: DNA
<213> ORGANISM: Artificial Sequence
<220> FEATURE:
<223> OTHER INFORMATION: Primer Sequence

<400> SEQUENCE: 212
cgatccgcac tcacccgcat ggtcatgaat tctgtttcct ataattaggc agtaccaacc 60
gacctaccca ctc 73

<210> SEQ ID NO 213
<211> LENGTH: 62
<212> TYPE: DNA
<213> ORGANISM: Artificial Sequence
<220> FEATURE:
<223> OTHER INFORMATION: Primer Sequence

<400> SEQUENCE: 213
attttgttta actttaagaa ggagatatac atatgaacac cctccgcacc gccaagctgc 60
tc 62

<210> SEQ ID NO 214
<211> LENGTH: 95
<212> TYPE: DNA
<213> ORGANISM: Artificial Sequence
<220> FEATURE:
<223> OTHER INFORMATION: Primer Sequence

<400> SEQUENCE: 214
cgatccgcac tcacccgcat ggtcatgaat tctgtttcct ataattaggc gtgcgggtac 60
ggacagcgcg ccggggcggg ggcggtgccc ggcag 95

<210> SEQ ID NO 215
<211> LENGTH: 58
<212> TYPE: DNA
<213> ORGANISM: Artificial Sequence
<220> FEATURE:
<223> OTHER INFORMATION: Primer Sequence

<400> SEQUENCE: 215
attttgttta actttaagaa ggagatatac atatgcgtac gtacggtacg gaacggag 58

<210> SEQ ID NO 216
<211> LENGTH: 72
<212> TYPE: DNA
<213> ORGANISM: Artificial Sequence
<220> FEATURE:
<223> OTHER INFORMATION: Primer Sequence

<400> SEQUENCE: 216
cgatccgcac tcacccgcat ggtcatgaat tctgtttcct ataattagcg ccgtacgacc 60
gacacccgcg ac 72

<210> SEQ ID NO 217
<211> LENGTH: 71
<212> TYPE: DNA
<213> ORGANISM: Artificial Sequence
<220> FEATURE:
<223> OTHER INFORMATION: Primer Sequence

<400> SEQUENCE: 217
attttgttta actttaagaa ggagatatac atatgaccac agccgacacg atgcccccttg 60 cctacccgtt c 71

<210> SEQ ID NO 218
<211> LENGTH: 65
<212> TYPE: DNA
<213> ORGANISM: Artificial Sequence
<220> FEATURE:
<223> OTHER INFORMATION: Primer Sequence

<400> SEQUENCE: 218
ctacccgcag agggcggggc ataagcttcc tattagggcc gcggccccac caccttctcc 60
ccgtc 65

<210> SEQ ID NO 219
<211> LENGTH: 56
<212> TYPE: DNA
<213> ORGANISM: Artificial Sequence
<220> FEATURE:
<223> OTHER INFORMATION: Primer Sequence

<400> SEQUENCE: 219
attttgttta actttaagaa ggagatatac atatggcgtg gctccaggac gcggac 56

<210> SEQ ID NO 220
<211> LENGTH: 68
<212> TYPE: DNA
<213> ORGANISM: Artificial Sequence
<220> FEATURE:
<223> OTHER INFORMATION: Primer Sequence

<400> SEQUENCE: 220
cgatccgcac tcacccgcat ggtcatgaat tctgtttcct ataattacca gctgaccgga 60
agggtgag 68

<210> SEQ ID NO 221
<211> LENGTH: 57
<212> TYPE: DNA
<213> ORGANISM: Artificial Sequence
<220> FEATURE:
<223> OTHER INFORMATION: Primer Sequence

<400> SEQUENCE: 221
attttgttta actttaagaa ggagatatac atatgagcca ccccgaagcc ctcatac 57

<210> SEQ ID NO 222
<211> LENGTH: 73
<212> TYPE: DNA
<213> ORGANISM: Artificial Sequence
<220> FEATURE:
<223> OTHER INFORMATION: Primer Sequence

<400> SEQUENCE: 222
cgatccgcac tcacccgcat ggtcatgaat tctgtttcct ataattacca gcgcacgggg 60
agccgggccg gtg 73

<210> SEQ ID NO 223
<211> LENGTH: 56
<212> TYPE: DNA
<213> ORGANISM: Artificial Sequence
<220> FEATURE:
<223> OTHER INFORMATION: Primer Sequence

<400> SEQUENCE: 223
attttgttta actttaagaa ggagatatac atatgggccc gggcgcgctc accgac 56

<210> SEQ ID NO 224
<211> LENGTH: 71
<212> TYPE: DNA
<213> ORGANISM: Artificial Sequence
<220> FEATURE:
<223> OTHER INFORMATION: Primer Sequence

<400> SEQUENCE: 224
cgatccgcac tcacccgcat ggtcatgaat tctgtttcct ataattatgt gcacgtcacc 60
tccagccgca c 71

<210> SEQ ID NO 225
<211> LENGTH: 56
<212> TYPE: DNA
<213> ORGANISM: Artificial Sequence
<220> FEATURE:
<223> OTHER INFORMATION: Primer Sequence

<400> SEQUENCE: 225
attttgttta actttaagaa ggagatatac atatggacaa tccctacccc ctgtac 56

<210> SEQ ID NO 226
<211> LENGTH: 67
<212> TYPE: DNA
<213> ORGANISM: Artificial Sequence
<220> FEATURE:
<223> OTHER INFORMATION: Primer Sequence

<400> SEQUENCE: 226
cgatccgcac tcacccgcat ggtcatgaat tctgtttcct ataattagtc ccagtggacg 60
gatagac 67

<210> SEQ ID NO 227
<211> LENGTH: 53
<212> TYPE: DNA
<213> ORGANISM: Artificial Sequence
<220> FEATURE:
<223> OTHER INFORMATION: Primer Sequence

<400> SEQUENCE: 227
gggtcctcaa cgacaggagc acgatcatgc cggaaataca ggaacgcacg ctg 53

<210> SEQ ID NO 228
<211> LENGTH: 56
<212> TYPE: DNA
<213> ORGANISM: Artificial Sequence
<220> FEATURE:
<223> OTHER INFORMATION: Primer Sequence

<400> SEQUENCE: 228
ttatcgccgg catggcggcc ccacgggtgc cggggcacaa ctcaatttgc gggtac 56

<210> SEQ ID NO 229
<211> LENGTH: 1451
<212> TYPE: DNA
<213> ORGANISM: Artificial Sequence
<220> FEATURE:
<223> OTHER INFORMATION: Codon-optimised sequence encoding SriC12 and
SriF05

<400> SEQUENCE: 229
catatgaccg aagcactgcc tttcccacaa gaccgcacct gtccgtacga cccaccggct 60
ggctaccagc cgctgagaga tagccgtcca ctgagccgtg ttacgttgta tgatggccgt 120
ccggcgtggg tcgtgacggg ccacgcagag agccgtgcac tgctgacgga cccgcgcttg 180
tcggctgatc gccagaaccc ggcgttcccg tccccggctc cgcgttttga gactctgcgt 240
aaggtccgta ccccgctgct gggcgtggac gatccggagc acaatacgca gcgtcgtatg 300
ttgattccgt ccttcagcgt gaagcgtgca gcagcactgc gcccgcgtat ccaagaaatc 360
gtggatcgcc tgttggacgc tatggaacag caaggtcctc cggcggaact ggtttctgcg 420
ttcgcactgc cggtcccgag catggtcatc tgcgccttgc tgggtgtccc gtacgctgac 480
catgaactgt ttgagggcct gagccgtact ctgctgcaga gcgcagaccc gcaagaggtc 540
accgaagccc gcgataaact ggaagattac tttaccgcac tggtggagcg taagcgcaaa 600
gaaccgggtg acggtctgct ggatgaactg attgcggagc gcctggacag cggcgagctg 660
ggccatcgtg aactggtccg tatggcgatg ctgctgctgg ttgcgggtca tgaaaccacc 720
tccaacatgt tgagcctggg cacgttcacc ctgctggagc acccggagca atttgcggcg 780
ctgcgcgctg atcctagcct gctgccggcg gcagtggaag aattgctgcg tttcctgtct 840
atcgccgacg gcatggttcg tgttgcgacc gaagatatcg agatcggtgg cgttacgatt 900
cgcgcggatg atggtgtgat cttcagcacg agcgtggtta atcgcgacgg tgcggcgtat 960
gcctcaccgg ataccctgga ctgggagcgt agcgcgcgtc accatgtcgc ttttggtttc 1020
ggtgttcacc agtgcctggg tcagaacctg gcccgtgccg agatggaaat tgcatttggt 1080
gcgttattcg cccgttttcc gggtctgcgt cttgcagtgc ctgcggccga gattccggtg 1140
aaaccggcgc acgcgttgca aggtctggtt gagctgccgg tgacctggtg ataacggcgg 1200
accgccgccc acaccctgta cccgtcaacg gaggagagaa aaaatgaaaa ttgacattga 1260
cacgagcgtt tgtatcggta gcggccaatg tgttctgact gccccgggtg tttttaccca 1320
agatgatgat ggtttcagca cgctgctgcc gggtcgcgaa gatggtacgg gcgacccatt 1380
agttcgtgaa gccgcgcgcg cgtgcccggt gcaagcaatc gcggtgaccg acgactaata 1440
ataggaagct t 1451

<210> SEQ ID NO 230
<211> LENGTH: 1188
<212> TYPE: DNA
<213> ORGANISM: Artificial Sequence
<220> FEATURE:
<223> OTHER INFORMATION: R63W mutant of codon-optimised sriC12

<400> SEQUENCE: 230
atgaccgaag cactgccttt cccacaagac cgcacctgtc cgtacgaccc accggctggc 60
taccagccgc tgagagatag ccgtccactg agccgtgtta cgttgtatga tggccgtccg 120
gcgtgggtcg tgacgggcca cgcagagagc cgtgcactgc tgacggaccc gcgcttgtcg 180
gctgattggc agaacccggc gttcccgtcc ccggctccgc gttttgagac tctgcgtaag 240
gtccgtaccc cgctgctggg cgtggacgat ccggagcaca atacgcagcg tcgtatgttg 300
attccgtcct tcagcgtgaa gcgtgcagca gcactgcgcc cgcgtatcca agaaatcgtg 360
gatcgcctgt tggacgctat ggaacagcaa ggtcctccgg cggaactggt ttctgcgttc 420
gcactgccgg tcccgagcat ggtcatctgc gccttgctgg gtgtcccgta cgctgaccat 480
gaactgtttg agggcctgag ccgtactctg ctgcagagcg cagacccgca agaggtcacc 540
gaagcccgcg ataaactgga agattacttt accgcactgg tggagcgtaa gcgcaaagaa 600

```
ccgggtgacg gtctgctgga tgaactgatt gcggagcgcc tggacagcgg cgagctgggc    660

catcgtgaac tggtccgtat ggcgatgctg ctgctggttg cgggtcatga aaccacctcc    720

aacatgttga gcctgggcac gttcaccctg ctggagcacc cggagcaatt tgcggcgctg    780

cgcgctgatc ctagcctgct gccggcggca gtggaagaat tgctgcgttt cctgtctatc    840

gccgacggca tggttcgtgt tgcgaccgaa gatatcgaga tcggtggcgt tacgattcgc    900

gcggatgatg gtgtgatctt cagcacgagc gtggttaatc gcgacggtgc ggcgtatgcc    960

tcaccggata ccctggactg ggagcgtagc gcgcgtcacc atgtcgcttt tggtttcggt   1020

gttcaccagt gcctgggtca gaacctggcc cgtgccgaga tggaaattgc atttggtgcg   1080

ttattcgccc gttttccggg tctgcgtctt gcagtgcctg cggccgagat tccggtgaaa   1140

ccggcgcacg cgttgcaagg tctggttgag ctgccggtga cctggtga                1188
```

```
<210> SEQ ID NO 231
<211> LENGTH: 395
<212> TYPE: PRT
<213> ORGANISM: Artificial Sequence
<220> FEATURE:
<223> OTHER INFORMATION: R63W mutant of SriC12

<400> SEQUENCE: 231

Met Thr Glu Ala Leu Pro Phe Pro Gln Asp Arg Thr Cys Pro Tyr Asp
1               5                   10                  15

Pro Pro Ala Gly Tyr Gln Pro Leu Arg Asp Ser Arg Pro Leu Ser Arg
            20                  25                  30

Val Thr Leu Tyr Asp Gly Arg Pro Ala Trp Val Val Thr Gly His Ala
        35                  40                  45

Glu Ser Arg Ala Leu Leu Thr Asp Pro Arg Leu Ser Ala Asp Trp Gln
    50                  55                  60

Asn Pro Ala Phe Pro Ser Pro Ala Pro Arg Phe Glu Thr Leu Arg Lys
65                  70                  75                  80

Val Arg Thr Pro Leu Leu Gly Val Asp Asp Pro Glu His Asn Thr Gln
                85                  90                  95

Arg Arg Met Leu Ile Pro Ser Phe Ser Val Lys Arg Ala Ala Ala Leu
            100                 105                 110

Arg Pro Arg Ile Gln Glu Ile Val Asp Arg Leu Leu Asp Ala Met Glu
        115                 120                 125

Gln Gln Gly Pro Pro Ala Glu Leu Val Ser Ala Phe Ala Leu Pro Val
    130                 135                 140

Pro Ser Met Val Ile Cys Ala Leu Leu Gly Val Pro Tyr Ala Asp His
145                 150                 155                 160

Glu Leu Phe Glu Gly Leu Ser Arg Thr Leu Leu Gln Ser Ala Asp Pro
                165                 170                 175

Gln Glu Val Thr Glu Ala Arg Asp Lys Leu Glu Asp Tyr Phe Thr Ala
            180                 185                 190

Leu Val Glu Arg Lys Arg Lys Glu Pro Gly Asp Gly Leu Leu Asp Glu
        195                 200                 205

Leu Ile Ala Glu Arg Leu Asp Ser Gly Glu Leu Gly His Arg Glu Leu
    210                 215                 220

Val Arg Met Ala Met Leu Leu Leu Val Ala Gly His Glu Thr Thr Ser
225                 230                 235                 240

Asn Met Leu Ser Leu Gly Thr Phe Thr Leu Leu Glu His Pro Glu Gln
                245                 250                 255

Phe Ala Ala Leu Arg Ala Asp Pro Ser Leu Leu Pro Ala Ala Val Glu
```

```
            260                 265                 270

Glu Leu Leu Arg Phe Leu Ser Ile Ala Asp Gly Met Val Arg Val Ala
        275                 280                 285

Thr Glu Asp Ile Glu Ile Gly Gly Val Thr Ile Arg Ala Asp Asp Gly
    290                 295                 300

Val Ile Phe Ser Thr Ser Val Val Asn Arg Asp Gly Ala Ala Tyr Ala
305                 310                 315                 320

Ser Pro Asp Thr Leu Asp Trp Glu Arg Ser Ala Arg His His Val Ala
                325                 330                 335

Phe Gly Phe Gly Val His Gln Cys Leu Gly Gln Asn Leu Ala Arg Ala
            340                 345                 350

Glu Met Glu Ile Ala Phe Gly Ala Leu Phe Ala Arg Phe Pro Gly Leu
        355                 360                 365

Arg Leu Ala Val Pro Ala Ala Glu Ile Pro Val Lys Pro Ala His Ala
    370                 375                 380

Leu Gln Gly Leu Val Glu Leu Pro Val Thr Trp
385                 390                 395


<210> SEQ ID NO 232
<211> LENGTH: 1188
<212> TYPE: DNA
<213> ORGANISM: Artificial Sequence
<220> FEATURE:
<223> OTHER INFORMATION: R63Y mutant of codon-optimised sriC12

<400> SEQUENCE: 232

atgaccgaag cactgccttt cccacaagac cgcacctgtc cgtacgaccc accggctggc     60

taccagccgc tgagagatag ccgtccactg agccgtgtta cgttgtatga tggccgtccg    120

gcgtgggtcg tgacgggcca cgcagagagc cgtgcactgc tgacggaccc gcgcttgtcg    180

gctgattatc agaacccggc gttcccgtcc ccggctccgc gttttgagac tctgcgtaag    240

gtccgtaccc cgctgctggg cgtggacgat ccggagcaca atacgcagcg tcgtatgttg    300

attccgtcct tcagcgtgaa gcgtgcagca gcactgcgcc cgcgtatcca agaaatcgtg    360

gatcgcctgt tggacgctat ggaacagcaa ggtcctccgg cggaactggt ttctgcgttc    420

gcactgccgg tcccgagcat ggtcatctgc gccttgctgg gtgtcccgta cgctgaccat    480

gaactgtttg agggcctgag ccgtactctg ctgcagagcg cagacccgca agaggtcacc    540

gaagcccgcg ataaactgga agattacttt accgcactgg tggagcgtaa gcgcaaagaa    600

ccgggtgacg gtctgctgga tgaactgatt gcggagcgcc tggacagcgg cgagctgggc    660

catcgtgaac tggtccgtat ggcgatgctg ctgctggttg cgggtcatga aaccacctcc    720

aacatgttga gcctgggcac gttcaccctg ctggagcacc cggagcaatt tgcggcgctg    780

cgcgctgatc ctagcctgct gccggcggca gtggaagaat tgctgcgttt cctgtctatc    840

gccgacggca tggttcgtgt tgcgaccgaa gatatcgaga tcggtggcgt tacgattcgc    900

gcggatgatg gtgtgatctt cagcacgagc gtggttaatc gcgacggtgc ggcgtatgcc    960

tcaccggata ccctggactg ggagcgtagc gcgcgtcacc atgtcgcttt tggtttcggt   1020

gttcaccagt gcctgggtca gaacctggcc cgtgccgaga tggaaattgc atttggtgcg   1080

ttattcgccc gttttccggg tctgcgtctt gcagtgcctg cggccgagat tccggtgaaa   1140

ccggcgcacg cgttgcaagg tctggttgag ctgccggtga cctggtga                1188


<210> SEQ ID NO 233
<211> LENGTH: 395
```

```
<212> TYPE: PRT
<213> ORGANISM: Artificial Sequence
<220> FEATURE:
<223> OTHER INFORMATION: R63Y mutant of SriC12

<400> SEQUENCE: 233

Met Thr Glu Ala Leu Pro Phe Pro Gln Asp Arg Thr Cys Pro Tyr Asp
1               5                   10                  15

Pro Pro Ala Gly Tyr Gln Pro Leu Arg Asp Ser Arg Pro Leu Ser Arg
            20                  25                  30

Val Thr Leu Tyr Asp Gly Arg Pro Ala Trp Val Val Thr Gly His Ala
        35                  40                  45

Glu Ser Arg Ala Leu Leu Thr Asp Pro Arg Leu Ser Ala Asp Tyr Gln
    50                  55                  60

Asn Pro Ala Phe Pro Ser Pro Ala Pro Arg Phe Glu Thr Leu Arg Lys
65                  70                  75                  80

Val Arg Thr Pro Leu Leu Gly Val Asp Asp Pro Glu His Asn Thr Gln
                85                  90                  95

Arg Arg Met Leu Ile Pro Ser Phe Ser Val Lys Arg Ala Ala Ala Leu
            100                 105                 110

Arg Pro Arg Ile Gln Glu Ile Val Asp Arg Leu Leu Asp Ala Met Glu
        115                 120                 125

Gln Gln Gly Pro Pro Ala Glu Leu Val Ser Ala Phe Ala Leu Pro Val
    130                 135                 140

Pro Ser Met Val Ile Cys Ala Leu Leu Gly Val Pro Tyr Ala Asp His
145                 150                 155                 160

Glu Leu Phe Glu Gly Leu Ser Arg Thr Leu Leu Gln Ser Ala Asp Pro
                165                 170                 175

Gln Glu Val Thr Glu Ala Arg Asp Lys Leu Glu Asp Tyr Phe Thr Ala
            180                 185                 190

Leu Val Glu Arg Lys Arg Lys Glu Pro Gly Asp Gly Leu Leu Asp Glu
        195                 200                 205

Leu Ile Ala Glu Arg Leu Asp Ser Gly Glu Leu Gly His Arg Glu Leu
    210                 215                 220

Val Arg Met Ala Met Leu Leu Leu Val Ala Gly His Glu Thr Thr Ser
225                 230                 235                 240

Asn Met Leu Ser Leu Gly Thr Phe Thr Leu Leu Glu His Pro Glu Gln
                245                 250                 255

Phe Ala Ala Leu Arg Ala Asp Pro Ser Leu Leu Pro Ala Ala Val Glu
            260                 265                 270

Glu Leu Leu Arg Phe Leu Ser Ile Ala Asp Gly Met Val Arg Val Ala
        275                 280                 285

Thr Glu Asp Ile Glu Ile Gly Gly Val Thr Ile Arg Ala Asp Asp Gly
    290                 295                 300

Val Ile Phe Ser Thr Ser Val Val Asn Arg Asp Gly Ala Ala Tyr Ala
305                 310                 315                 320

Ser Pro Asp Thr Leu Asp Trp Glu Arg Ser Ala Arg His His Val Ala
                325                 330                 335

Phe Gly Phe Gly Val His Gln Cys Leu Gly Gln Asn Leu Ala Arg Ala
            340                 345                 350

Glu Met Glu Ile Ala Phe Gly Ala Leu Phe Ala Arg Phe Pro Gly Leu
        355                 360                 365

Arg Leu Ala Val Pro Ala Ala Glu Ile Pro Val Lys Pro Ala His Ala
    370                 375                 380
```

Leu Gln Gly Leu Val Glu Leu Pro Val Thr Trp
385 390 395

<210> SEQ ID NO 234
<211> LENGTH: 1188
<212> TYPE: DNA
<213> ORGANISM: Artificial Sequence
<220> FEATURE:
<223> OTHER INFORMATION: L171I mutant of codon-optimised sriC12

<400> SEQUENCE: 234
atgaccgaag cactgccttt cccacaagac cgcacctgtc cgtacgaccc accggctggc 60
taccagccgc tgagagatag ccgtccactg agccgtgtta cgttgtatga tggccgtccg 120
gcgtgggtcg tgacgggcca cgcagagagc cgtgcactgc tgacggaccc gcgcttgtcg 180
gctgatcgcc agaacccggc gttcccgtcc ccggctccgc gttttgagac tctgcgtaag 240
gtccgtaccc cgctgctggg cgtggacgat ccggagcaca atacgcagcg tcgtatgttg 300
attccgtcct tcagcgtgaa gcgtgcagca gcactgcgcc cgcgtatcca agaaatcgtg 360
gatcgcctgt tggacgctat ggaacagcaa ggtcctccgg cggaactggt ttctgcgttc 420
gcactgccgg tcccgagcat ggtcatctgc gccttgctgg gtgtcccgta cgctgaccat 480
gaactgtttg agggcctgag ccgtactctg attcagagcg cagacccgca agaggtcacc 540
gaagcccgcg ataaactgga agattacttt accgcactgg tggagcgtaa gcgcaaagaa 600
ccgggtgacg gtctgctgga tgaactgatt gcggagcgcc tggacagcgg cgagctgggc 660
catcgtgaac tggtccgtat ggcgatgctg ctgctggttg cgggtcatga aaccacctcc 720
aacatgttga gcctgggcac gttcaccctg ctggagcacc cggagcaatt tgcggcgctg 780
cgcgctgatc ctagcctgct gccggcggca gtggaagaat tgctgcgttt cctgtctatc 840
gccgacggca tggttcgtgt tgcgaccgaa gatatcgaga tcggtggcgt tacgattcgc 900
gcggatgatg gtgtgatctt cagcacgagc gtggttaatc gcgacggtgc ggcgtatgcc 960
tcaccggata ccctggactg ggagcgtagc gcgcgtcacc atgtcgcttt tggtttcggt 1020
gttcaccagt gcctgggtca gaacctggcc cgtgccgaga tggaaattgc atttggtgcg 1080
ttattcgccc gttttccggg tctgcgtctt gcagtgcctg cggccgagat tccggtgaaa 1140
ccggcgcacg cgttgcaagg tctggttgag ctgccggtga cctggtga 1188

<210> SEQ ID NO 235
<211> LENGTH: 395
<212> TYPE: PRT
<213> ORGANISM: Artificial Sequence
<220> FEATURE:
<223> OTHER INFORMATION: L171I mutant of SriC12

<400> SEQUENCE: 235

Met Thr Glu Ala Leu Pro Phe Pro Gln Asp Arg Thr Cys Pro Tyr Asp
1 5 10 15

Pro Pro Ala Gly Tyr Gln Pro Leu Arg Asp Ser Arg Pro Leu Ser Arg
20 25 30

Val Thr Leu Tyr Asp Gly Arg Pro Ala Trp Val Val Thr Gly His Ala
35 40 45

Glu Ser Arg Ala Leu Leu Thr Asp Pro Arg Leu Ser Ala Asp Arg Gln
50 55 60

Asn Pro Ala Phe Pro Ser Pro Ala Pro Arg Phe Glu Thr Leu Arg Lys
65 70 75 80

Val Arg Thr Pro Leu Leu Gly Val Asp Asp Pro Glu His Asn Thr Gln

```
                85                  90                  95

Arg Arg Met Leu Ile Pro Ser Phe Ser Val Lys Arg Ala Ala Ala Leu
            100                 105                 110

Arg Pro Arg Ile Gln Glu Ile Val Asp Arg Leu Leu Asp Ala Met Glu
        115                 120                 125

Gln Gln Gly Pro Pro Ala Glu Leu Val Ser Ala Phe Ala Leu Pro Val
    130                 135                 140

Pro Ser Met Val Ile Cys Ala Leu Leu Gly Val Pro Tyr Ala Asp His
145                 150                 155                 160

Glu Leu Phe Glu Gly Leu Ser Arg Thr Leu Ile Gln Ser Ala Asp Pro
                165                 170                 175

Gln Glu Val Thr Glu Ala Arg Asp Lys Leu Glu Asp Tyr Phe Thr Ala
            180                 185                 190

Leu Val Glu Arg Lys Arg Lys Glu Pro Gly Asp Gly Leu Leu Asp Glu
        195                 200                 205

Leu Ile Ala Glu Arg Leu Asp Ser Gly Glu Leu Gly His Arg Glu Leu
    210                 215                 220

Val Arg Met Ala Met Leu Leu Leu Val Ala Gly His Glu Thr Thr Ser
225                 230                 235                 240

Asn Met Leu Ser Leu Gly Thr Phe Thr Leu Leu Glu His Pro Glu Gln
                245                 250                 255

Phe Ala Ala Leu Arg Ala Asp Pro Ser Leu Leu Pro Ala Ala Val Glu
            260                 265                 270

Glu Leu Leu Arg Phe Leu Ser Ile Ala Asp Gly Met Val Arg Val Ala
        275                 280                 285

Thr Glu Asp Ile Glu Ile Gly Gly Val Thr Ile Arg Ala Asp Asp Gly
    290                 295                 300

Val Ile Phe Ser Thr Ser Val Val Asn Arg Asp Gly Ala Ala Tyr Ala
305                 310                 315                 320

Ser Pro Asp Thr Leu Asp Trp Glu Arg Ser Ala Arg His His Val Ala
                325                 330                 335

Phe Gly Phe Gly Val His Gln Cys Leu Gly Gln Asn Leu Ala Arg Ala
            340                 345                 350

Glu Met Glu Ile Ala Phe Gly Ala Leu Phe Ala Arg Phe Pro Gly Leu
        355                 360                 365

Arg Leu Ala Val Pro Ala Ala Glu Ile Pro Val Lys Pro Ala His Ala
    370                 375                 380

Leu Gln Gly Leu Val Glu Leu Pro Val Thr Trp
385                 390                 395
```

<210> SEQ ID NO 236
<211> LENGTH: 1188
<212> TYPE: DNA
<213> ORGANISM: Artificial Sequence
<220> FEATURE:
<223> OTHER INFORMATION: L230I mutant of codon-optimised sriC12

<400> SEQUENCE: 236

```
atgaccgaag cactgccttt cccacaagac cgcacctgtc cgtacgaccc accggctggc      60

taccagccgc tgagagatag ccgtccactg agccgtgtta cgttgtatga tggccgtccg     120

gcgtgggtcg tgacgggcca cgcagagagc cgtgcactgc tgacggaccc gcgcttgtcg     180

gctgatcgcc agaacccggc gttcccgtcc ccggctccgc gttttgagac tctgcgtaag     240

gtccgtaccc cgctgctggg cgtggacgat ccggagcaca atacgcagcg tcgtatgttg     300
```

-continued

```
attccgtcct tcagcgtgaa gcgtgcagca gcactgcgcc cgcgtatcca agaaatcgtg    360

gatcgcctgt tggacgctat ggaacagcaa ggtcctccgg cggaactggt ttctgcgttc    420

gcactgccgg tcccgagcat ggtcatctgc gccttgctgg gtgtcccgta cgctgaccat    480

gaactgtttg agggcctgag ccgtactctg ctgcagagcg cagacccgca agaggtcacc    540

gaagcccgcg ataaactgga agattacttt accgcactgg tggagcgtaa gcgcaaagaa    600

ccgggtgacg gtctgctgga tgaactgatt gcggagcgcc tggacagcgg cgagctgggc    660

catcgtgaac tggtccgtat ggcgatgatt ctgctggttg cgggtcatga aaccacctcc    720

aacatgttga gcctgggcac gttcaccctg ctggagcacc cggagcaatt tgcggcgctg    780

cgcgctgatc ctagcctgct gccggcggca gtggaagaat tgctgcgttt cctgtctatc    840

gccgacggca tggttcgtgt tgcgaccgaa gatatcgaga tcggtggcgt tacgattcgc    900

gcggatgatg gtgtgatctt cagcacgagc gtggttaatc gcgacggtgc ggcgtatgcc    960

tcaccggata ccctggactg ggagcgtagc gcgcgtcacc atgtcgcttt tggtttcggt   1020

gttcaccagt gcctgggtca gaacctggcc cgtgccgaga tggaaattgc atttggtgcg   1080

ttattcgccc gttttccggg tctgcgtctt gcagtgcctg cggccgagat tccggtgaaa   1140

ccggcgcacg cgttgcaagg tctggttgag ctgccggtga cctggtga                1188


<210> SEQ ID NO 237
<211> LENGTH: 395
<212> TYPE: PRT
<213> ORGANISM: Artificial Sequence
<220> FEATURE:
<223> OTHER INFORMATION: L230I mutant of SriC12

<400> SEQUENCE: 237

Met Thr Glu Ala Leu Pro Phe Pro Gln Asp Arg Thr Cys Pro Tyr Asp
1               5                   10                  15

Pro Pro Ala Gly Tyr Gln Pro Leu Arg Asp Ser Arg Pro Leu Ser Arg
            20                  25                  30

Val Thr Leu Tyr Asp Gly Arg Pro Ala Trp Val Val Thr Gly His Ala
        35                  40                  45

Glu Ser Arg Ala Leu Leu Thr Asp Pro Arg Leu Ser Ala Asp Arg Gln
    50                  55                  60

Asn Pro Ala Phe Pro Ser Pro Ala Pro Arg Phe Glu Thr Leu Arg Lys
65                  70                  75                  80

Val Arg Thr Pro Leu Leu Gly Val Asp Asp Pro Glu His Asn Thr Gln
                85                  90                  95

Arg Arg Met Leu Ile Pro Ser Phe Ser Val Lys Arg Ala Ala Ala Leu
            100                 105                 110

Arg Pro Arg Ile Gln Glu Ile Val Asp Arg Leu Leu Asp Ala Met Glu
        115                 120                 125

Gln Gln Gly Pro Pro Ala Glu Leu Val Ser Ala Phe Ala Leu Pro Val
    130                 135                 140

Pro Ser Met Val Ile Cys Ala Leu Leu Gly Val Pro Tyr Ala Asp His
145                 150                 155                 160

Glu Leu Phe Glu Gly Leu Ser Arg Thr Leu Leu Gln Ser Ala Asp Pro
                165                 170                 175

Gln Glu Val Thr Glu Ala Arg Asp Lys Leu Glu Asp Tyr Phe Thr Ala
            180                 185                 190

Leu Val Glu Arg Lys Arg Lys Glu Pro Gly Asp Gly Leu Leu Asp Glu
        195                 200                 205
```

```
Leu Ile Ala Glu Arg Leu Asp Ser Gly Glu Leu Gly His Arg Glu Leu
    210                 215                 220

Val Arg Met Ala Met Ile Leu Leu Val Ala Gly His Glu Thr Thr Ser
225                 230                 235                 240

Asn Met Leu Ser Leu Gly Thr Phe Thr Leu Leu Glu His Pro Glu Gln
                245                 250                 255

Phe Ala Ala Leu Arg Ala Asp Pro Ser Leu Leu Pro Ala Ala Val Glu
            260                 265                 270

Glu Leu Leu Arg Phe Leu Ser Ile Ala Asp Gly Met Val Arg Val Ala
        275                 280                 285

Thr Glu Asp Ile Glu Ile Gly Gly Val Thr Ile Arg Ala Asp Asp Gly
    290                 295                 300

Val Ile Phe Ser Thr Ser Val Val Asn Arg Asp Gly Ala Ala Tyr Ala
305                 310                 315                 320

Ser Pro Asp Thr Leu Asp Trp Glu Arg Ser Ala Arg His His Val Ala
                325                 330                 335

Phe Gly Phe Gly Val His Gln Cys Leu Gly Gln Asn Leu Ala Arg Ala
            340                 345                 350

Glu Met Glu Ile Ala Phe Gly Ala Leu Phe Ala Arg Phe Pro Gly Leu
        355                 360                 365

Arg Leu Ala Val Pro Ala Ala Glu Ile Pro Val Lys Pro Ala His Ala
    370                 375                 380

Leu Gln Gly Leu Val Glu Leu Pro Val Thr Trp
385                 390                 395


<210> SEQ ID NO 238
<211> LENGTH: 23
<212> TYPE: DNA
<213> ORGANISM: Artificial Sequence
<220> FEATURE:
<223> OTHER INFORMATION: Primer Sequence

<400> SEQUENCE: 238

gtcggctgat tggcagaacc cgg                                            23


<210> SEQ ID NO 239
<211> LENGTH: 23
<212> TYPE: DNA
<213> ORGANISM: Artificial Sequence
<220> FEATURE:
<223> OTHER INFORMATION: Primer Sequence

<400> SEQUENCE: 239

ccgggttctg gcgatcagcc gac                                            23


<210> SEQ ID NO 240
<211> LENGTH: 23
<212> TYPE: DNA
<213> ORGANISM: Artificial Sequence
<220> FEATURE:
<223> OTHER INFORMATION: Primer Sequence

<400> SEQUENCE: 240

gtcggctgat tatcagaacc cgg                                            23


<210> SEQ ID NO 241
<211> LENGTH: 23
<212> TYPE: DNA
<213> ORGANISM: Artificial Sequence
<220> FEATURE:
<223> OTHER INFORMATION: Primer Sequence
```

<400> SEQUENCE: 241
ccgggttctg ataatcagcc gac 23

<210> SEQ ID NO 242
<211> LENGTH: 23
<212> TYPE: DNA
<213> ORGANISM: Artificial Sequence
<220> FEATURE:
<223> OTHER INFORMATION: Primer Sequence

<400> SEQUENCE: 242
cccggctccg tattttgaga ctc 23

<210> SEQ ID NO 243
<211> LENGTH: 23
<212> TYPE: DNA
<213> ORGANISM: Artificial Sequence
<220> FEATURE:
<223> OTHER INFORMATION: Primer Sequence

<400> SEQUENCE: 243
gagtctcaaa atacggagcc ggg 23

<210> SEQ ID NO 244
<211> LENGTH: 23
<212> TYPE: DNA
<213> ORGANISM: Artificial Sequence
<220> FEATURE:
<223> OTHER INFORMATION: Primer Sequence

<400> SEQUENCE: 244
ccgtactctg gcgcagagcg cag 23

<210> SEQ ID NO 245
<211> LENGTH: 23
<212> TYPE: DNA
<213> ORGANISM: Artificial Sequence
<220> FEATURE:
<223> OTHER INFORMATION: Primer Sequence

<400> SEQUENCE: 245
ctgcgctctg cgccagagta cgg 23

<210> SEQ ID NO 246
<211> LENGTH: 23
<212> TYPE: DNA
<213> ORGANISM: Artificial Sequence
<220> FEATURE:
<223> OTHER INFORMATION: Primer Sequence

<400> SEQUENCE: 246
ccgtactctg attcagagcg cag 23

<210> SEQ ID NO 247
<211> LENGTH: 23
<212> TYPE: DNA
<213> ORGANISM: Artificial Sequence
<220> FEATURE:
<223> OTHER INFORMATION: Primer Sequence

<400> SEQUENCE: 247
caaccagcag aatcatcgcc ata 23

<210> SEQ ID NO 248

<211> LENGTH: 23
<212> TYPE: DNA
<213> ORGANISM: Artificial Sequence
<220> FEATURE:
<223> OTHER INFORMATION: Primer Sequence

<400> SEQUENCE: 248
tatggcgatg attctgctgg ttg 23

<210> SEQ ID NO 249
<211> LENGTH: 23
<212> TYPE: DNA
<213> ORGANISM: Artificial Sequence
<220> FEATURE:
<223> OTHER INFORMATION: Primer Sequence

<400> SEQUENCE: 249
catgacccgc cagcagcagc agc 23

<210> SEQ ID NO 250
<211> LENGTH: 1188
<212> TYPE: DNA
<213> ORGANISM: Artificial Sequence
<220> FEATURE:
<223> OTHER INFORMATION: R63W R74Y mutant of codon-optimised sriC12

<400> SEQUENCE: 250
atgaccgaag cactgccttt cccacaagac cgcacctgtc cgtacgaccc accggctggc 60
taccagccgc tgagagatag ccgtccactg agccgtgtta cgttgtatga tggccgtccg 120
gcgtgggtcg tgacgggcca cgcagagagc cgtgcactgc tgacggaccc gcgcttgtcg 180
gctgattggc agaacccggc gttcccgtcc ccggctccgt attttgagac tctgcgtaag 240
gtccgtaccc cgctgctggg cgtggacgat ccggagcaca atacgcagcg tcgtatgttg 300
attccgtcct tcagcgtgaa gcgtgcagca gcactgcgcc cgcgtatcca agaaatcgtg 360
gatcgcctgt tggacgctat ggaacagcaa ggtcctccgg cggaactggt ttctgcgttc 420
gcactgccgg tcccgagcat ggtcatctgc gccttgctgg gtgtcccgta cgctgaccat 480
gaactgtttg agggcctgag ccgtactctg ctgcagagcg cagacccgca agaggtcacc 540
gaagcccgcg ataaactgga agattacttt accgcactgg tggagcgtaa gcgcaaagaa 600
ccgggtgacg gtctgctgga tgaactgatt gcggagcgcc tggacagcgg cgagctgggc 660
catcgtgaac tggtccgtat ggcgatgctg ctgctggttg cgggtcatga aaccacctcc 720
aacatgttga gcctgggcac gttcaccctg ctggagcacc cggagcaatt tgcggcgctg 780
cgcgctgatc ctagcctgct gccggcggca gtggaagaat tgctgcgttt cctgtctatc 840
gccgacggca tggttcgtgt tgcgaccgaa gatatcgaga tcggtggcgt tacgattcgc 900
gcggatgatg gtgtgatctt cagcacgagc gtggttaatc gcgacggtgc ggcgtatgcc 960
tcaccggata ccctggactg ggagcgtagc gcgcgtcacc atgtcgcttt tggtttcggt 1020
gttcaccagt gcctgggtca gaacctggcc cgtgccgaga tggaaattgc atttggtgcg 1080
ttattcgccc gttttccggg tctgcgtctt gcagtgcctg cggccgagat tccggtgaaa 1140
ccggcgcacg cgttgcaagg tctggttgag ctgccggtga cctggtga 1188

<210> SEQ ID NO 251
<211> LENGTH: 395
<212> TYPE: PRT
<213> ORGANISM: Artificial Sequence
<220> FEATURE:
<223> OTHER INFORMATION: R63W R74Y mutant of SriC12

<400> SEQUENCE: 251

```
Met Thr Glu Ala Leu Pro Phe Pro Gln Asp Arg Thr Cys Pro Tyr Asp
1               5                   10                  15

Pro Pro Ala Gly Tyr Gln Pro Leu Arg Asp Ser Arg Pro Leu Ser Arg
            20                  25                  30

Val Thr Leu Tyr Asp Gly Arg Pro Ala Trp Val Val Thr Gly His Ala
        35                  40                  45

Glu Ser Arg Ala Leu Leu Thr Asp Pro Arg Leu Ser Ala Asp Trp Gln
    50                  55                  60

Asn Pro Ala Phe Pro Ser Pro Ala Pro Tyr Phe Glu Thr Leu Arg Lys
65                  70                  75                  80

Val Arg Thr Pro Leu Leu Gly Val Asp Asp Pro Glu His Asn Thr Gln
                85                  90                  95

Arg Arg Met Leu Ile Pro Ser Phe Ser Val Lys Arg Ala Ala Ala Leu
            100                 105                 110

Arg Pro Arg Ile Gln Glu Ile Val Asp Arg Leu Leu Asp Ala Met Glu
        115                 120                 125

Gln Gln Gly Pro Pro Ala Glu Leu Val Ser Ala Phe Ala Leu Pro Val
    130                 135                 140

Pro Ser Met Val Ile Cys Ala Leu Leu Gly Val Pro Tyr Ala Asp His
145                 150                 155                 160

Glu Leu Phe Glu Gly Leu Ser Arg Thr Leu Leu Gln Ser Ala Asp Pro
                165                 170                 175

Gln Glu Val Thr Glu Ala Arg Asp Lys Leu Glu Asp Tyr Phe Thr Ala
            180                 185                 190

Leu Val Glu Arg Lys Arg Lys Glu Pro Gly Asp Gly Leu Leu Asp Glu
        195                 200                 205

Leu Ile Ala Glu Arg Leu Asp Ser Gly Glu Leu Gly His Arg Glu Leu
    210                 215                 220

Val Arg Met Ala Met Leu Leu Leu Val Ala Gly His Glu Thr Thr Ser
225                 230                 235                 240

Asn Met Leu Ser Leu Gly Thr Phe Thr Leu Leu Glu His Pro Glu Gln
                245                 250                 255

Phe Ala Ala Leu Arg Ala Asp Pro Ser Leu Leu Pro Ala Ala Val Glu
            260                 265                 270

Glu Leu Leu Arg Phe Leu Ser Ile Ala Asp Gly Met Val Arg Val Ala
        275                 280                 285

Thr Glu Asp Ile Glu Ile Gly Gly Val Thr Ile Arg Ala Asp Asp Gly
    290                 295                 300

Val Ile Phe Ser Thr Ser Val Val Asn Arg Asp Gly Ala Ala Tyr Ala
305                 310                 315                 320

Ser Pro Asp Thr Leu Asp Trp Glu Arg Ser Ala Arg His His Val Ala
                325                 330                 335

Phe Gly Phe Gly Val His Gln Cys Leu Gly Gln Asn Leu Ala Arg Ala
            340                 345                 350

Glu Met Glu Ile Ala Phe Gly Ala Leu Phe Ala Arg Phe Pro Gly Leu
        355                 360                 365

Arg Leu Ala Val Pro Ala Ala Glu Ile Pro Val Lys Pro Ala His Ala
    370                 375                 380

Leu Gln Gly Leu Val Glu Leu Pro Val Thr Trp
385                 390                 395
```

<210> SEQ ID NO 252
<211> LENGTH: 1188
<212> TYPE: DNA
<213> ORGANISM: Artificial Sequence
<220> FEATURE:
<223> OTHER INFORMATION: R63W L171A mutant of codon-optimised sriC12

<400> SEQUENCE: 252

```
atgaccgaag cactgccttt cccacaagac cgcacctgtc cgtacgaccc accggctggc     60

taccagccgc tgagagatag ccgtccactg agccgtgtta cgttgtatga tggccgtccg    120

gcgtgggtcg tgacgggcca cgcagagagc cgtgcactgc tgacggaccc gcgcttgtcg    180

gctgattggc agaacccggc gttcccgtcc ccggctccgc gttttgagac tctgcgtaag    240

gtccgtaccc cgctgctggg cgtggacgat ccggagcaca atacgcagcg tcgtatgttg    300

attccgtcct tcagcgtgaa gcgtgcagca gcactgcgcc cgcgtatcca agaaatcgtg    360

gatcgcctgt tggacgctat ggaacagcaa ggtcctccgg cggaactggt ttctgcgttc    420

gcactgccgg tcccgagcat ggtcatctgc gccttgctgg gtgtcccgta cgctgaccat    480

gaactgtttg agggcctgag ccgtactctg gcgcagagcg cagacccgca agaggtcacc    540

gaagcccgcg ataaactgga agattacttt accgcactgg tggagcgtaa gcgcaaagaa    600

ccgggtgacg gtctgctgga tgaactgatt gcggagcgcc tggacagcgg cgagctgggc    660

catcgtgaac tggtccgtat ggcgatgctg ctgctggttg cgggtcatga aaccacctcc    720

aacatgttga gcctgggcac gttcaccctg ctggagcacc cggagcaatt tgcggcgctg    780

cgcgctgatc ctagcctgct gccggcggca gtggaagaat tgctgcgttt cctgtctatc    840

gccgacggca tggttcgtgt tgcgaccgaa gatatcgaga tcggtggcgt tacgattcgc    900

gcggatgatg gtgtgatctt cagcacgagc gtggttaatc gcgacggtgc ggcgtatgcc    960

tcaccggata ccctggactg ggagcgtagc gcgcgtcacc atgtcgcttt tggtttcggt   1020

gttcaccagt gcctgggtca gaacctggcc cgtgccgaga tggaaattgc atttggtgcg   1080

ttattcgccc gttttccggg tctgcgtctt gcagtgcctg cggccgagat tccggtgaaa   1140

ccggcgcacg cgttgcaagg tctggttgag ctgccggtga cctggtga                 1188
```

<210> SEQ ID NO 253
<211> LENGTH: 395
<212> TYPE: PRT
<213> ORGANISM: Artificial Sequence
<220> FEATURE:
<223> OTHER INFORMATION: R63W L171A mutant of SriC12

<400> SEQUENCE: 253

```
Met Thr Glu Ala Leu Pro Phe Pro Gln Asp Arg Thr Cys Pro Tyr Asp
1               5                   10                  15

Pro Pro Ala Gly Tyr Gln Pro Leu Arg Asp Ser Arg Pro Leu Ser Arg
            20                  25                  30

Val Thr Leu Tyr Asp Gly Arg Pro Ala Trp Val Val Thr Gly His Ala
        35                  40                  45

Glu Ser Arg Ala Leu Leu Thr Asp Pro Arg Leu Ser Ala Asp Trp Gln
    50                  55                  60

Asn Pro Ala Phe Pro Ser Pro Ala Pro Arg Phe Glu Thr Leu Arg Lys
65                  70                  75                  80

Val Arg Thr Pro Leu Leu Gly Val Asp Asp Pro Glu His Asn Thr Gln
                85                  90                  95

Arg Arg Met Leu Ile Pro Ser Phe Ser Val Lys Arg Ala Ala Ala Leu
            100                 105                 110
```

Arg Pro Arg Ile Gln Glu Ile Val Asp Arg Leu Leu Asp Ala Met Glu
115 120 125

Gln Gln Gly Pro Pro Ala Glu Leu Val Ser Ala Phe Ala Leu Pro Val
130 135 140

Pro Ser Met Val Ile Cys Ala Leu Leu Gly Val Pro Tyr Ala Asp His
145 150 155 160

Glu Leu Phe Glu Gly Leu Ser Arg Thr Leu Ala Gln Ser Ala Asp Pro
165 170 175

Gln Glu Val Thr Glu Ala Arg Asp Lys Leu Glu Asp Tyr Phe Thr Ala
180 185 190

Leu Val Glu Arg Lys Arg Lys Glu Pro Gly Asp Gly Leu Leu Asp Glu
195 200 205

Leu Ile Ala Glu Arg Leu Asp Ser Gly Glu Leu Gly His Arg Glu Leu
210 215 220

Val Arg Met Ala Met Leu Leu Leu Val Ala Gly His Glu Thr Thr Ser
225 230 235 240

Asn Met Leu Ser Leu Gly Thr Phe Thr Leu Leu Glu His Pro Glu Gln
245 250 255

Phe Ala Ala Leu Arg Ala Asp Pro Ser Leu Leu Pro Ala Ala Val Glu
260 265 270

Glu Leu Leu Arg Phe Leu Ser Ile Ala Asp Gly Met Val Arg Val Ala
275 280 285

Thr Glu Asp Ile Glu Ile Gly Gly Val Thr Ile Arg Ala Asp Asp Gly
290 295 300

Val Ile Phe Ser Thr Ser Val Val Asn Arg Asp Gly Ala Ala Tyr Ala
305 310 315 320

Ser Pro Asp Thr Leu Asp Trp Glu Arg Ser Ala Arg His His Val Ala
325 330 335

Phe Gly Phe Gly Val His Gln Cys Leu Gly Gln Asn Leu Ala Arg Ala
340 345 350

Glu Met Glu Ile Ala Phe Gly Ala Leu Phe Ala Arg Phe Pro Gly Leu
355 360 365

Arg Leu Ala Val Pro Ala Ala Glu Ile Pro Val Lys Pro Ala His Ala
370 375 380

Leu Gln Gly Leu Val Glu Leu Pro Val Thr Trp
385 390 395

<210> SEQ ID NO 254
<211> LENGTH: 1188
<212> TYPE: DNA
<213> ORGANISM: Artificial Sequence
<220> FEATURE:
<223> OTHER INFORMATION: R74Y L171A R183W mutant of codon-optimised sriC12

<400> SEQUENCE: 254
atgaccgaag cactgccttt cccacaagac cgcacctgtc cgtacgaccc accggctggc 60
taccagccgc tgagagatag ccgtccactg agccgtgtta cgttgtatga tggccgtccg 120
gcgtgggtcg tgacgggcca cgcagagagc cgtgcactgc tgacggaccc gcgcttgtcg 180
gctgatcgcc agaacccggc gttcccgtcc ccggctccgt attttgagac tctgcgtaag 240
gtccgtaccc cgctgctggg cgtggacgat ccggagcaca atacgcagcg tcgtatgttg 300
attccgtcct tcagcgtgaa gcgtgcagca gcactgcgcc cgcgtatcca agaaatcgtg 360
gatcgcctgt tggacgctat ggaacagcaa ggtcctccgg cggaactggt ttctgcgttc 420

```
gcactgccgg tcccgagcat ggtcatctgc gccttgctgg gtgtcccgta cgctgaccat    480

gaactgtttg agggcctgag ccgtactctg gcgcagagcg cagacccgca agaggtcacc    540

gaagcctggg ataaactgga agattacttt accgcactgg tggagcgtaa gcgcaaagaa    600

ccgggtgacg gtctgctgga tgaactgatt gcggagcgcc tggacagcgg cgagctgggc    660

catcgtgaac tggtccgtat ggcgatgctg ctgctggttg cgggtcatga aaccacctcc    720

aacatgttga gcctgggcac gttcaccctg ctggagcacc cggagcaatt tgcggcgctg    780

cgcgctgatc ctagcctgct gccggcggca gtggaagaat tgctgcgttt cctgtctatc    840

gccgacggca tggttcgtgt tgcgaccgaa gatatcgaga tcggtggcgt tacgattcgc    900

gcggatgatg gtgtgatctt cagcacgagc gtggttaatc gcgacggtgc ggcgtatgcc    960

tcaccggata ccctggactg ggagcgtagc gcgcgtcacc atgtcgcttt tggtttcggt   1020

gttcaccagt gcctgggtca gaacctggcc cgtgccgaga tggaaattgc atttggtgcg   1080

ttattcgccc gttttccggg tctgcgtctt gcagtgcctg cggccgagat tccggtgaaa   1140

ccggcgcacg cgttgcaagg tctggttgag ctgccggtga cctggtga                1188
```

```
<210> SEQ ID NO 255
<211> LENGTH: 395
<212> TYPE: PRT
<213> ORGANISM: Artificial Sequence
<220> FEATURE:
<223> OTHER INFORMATION: R74Y L171A R183W mutant of SriC12

<400> SEQUENCE: 255

Met Thr Glu Ala Leu Pro Phe Pro Gln Asp Arg Thr Cys Pro Tyr Asp
1               5                   10                  15

Pro Pro Ala Gly Tyr Gln Pro Leu Arg Asp Ser Arg Pro Leu Ser Arg
            20                  25                  30

Val Thr Leu Tyr Asp Gly Arg Pro Ala Trp Val Val Thr Gly His Ala
        35                  40                  45

Glu Ser Arg Ala Leu Leu Thr Asp Pro Arg Leu Ser Ala Asp Arg Gln
    50                  55                  60

Asn Pro Ala Phe Pro Ser Pro Ala Pro Tyr Phe Glu Thr Leu Arg Lys
65                  70                  75                  80

Val Arg Thr Pro Leu Leu Gly Val Asp Asp Pro Glu His Asn Thr Gln
                85                  90                  95

Arg Arg Met Leu Ile Pro Ser Phe Ser Val Lys Arg Ala Ala Ala Leu
            100                 105                 110

Arg Pro Arg Ile Gln Glu Ile Val Asp Arg Leu Leu Asp Ala Met Glu
        115                 120                 125

Gln Gln Gly Pro Pro Ala Glu Leu Val Ser Ala Phe Ala Leu Pro Val
    130                 135                 140

Pro Ser Met Val Ile Cys Ala Leu Leu Gly Val Pro Tyr Ala Asp His
145                 150                 155                 160

Glu Leu Phe Glu Gly Leu Ser Arg Thr Leu Ala Gln Ser Ala Asp Pro
                165                 170                 175

Gln Glu Val Thr Glu Ala Trp Asp Lys Leu Glu Asp Tyr Phe Thr Ala
            180                 185                 190

Leu Val Glu Arg Lys Arg Lys Glu Pro Gly Asp Gly Leu Leu Asp Glu
        195                 200                 205

Leu Ile Ala Glu Arg Leu Asp Ser Gly Glu Leu Gly His Arg Glu Leu
    210                 215                 220
```

```
Val Arg Met Ala Met Leu Leu Leu Val Ala Gly His Glu Thr Thr Ser
225                 230                 235                 240

Asn Met Leu Ser Leu Gly Thr Phe Thr Leu Leu Glu His Pro Glu Gln
                245                 250                 255

Phe Ala Ala Leu Arg Ala Asp Pro Ser Leu Leu Pro Ala Ala Val Glu
            260                 265                 270

Glu Leu Leu Arg Phe Leu Ser Ile Ala Asp Gly Met Val Arg Val Ala
        275                 280                 285

Thr Glu Asp Ile Glu Ile Gly Gly Val Thr Ile Arg Ala Asp Asp Gly
    290                 295                 300

Val Ile Phe Ser Thr Ser Val Val Asn Arg Asp Gly Ala Ala Tyr Ala
305                 310                 315                 320

Ser Pro Asp Thr Leu Asp Trp Glu Arg Ser Ala Arg His His Val Ala
                325                 330                 335

Phe Gly Phe Gly Val His Gln Cys Leu Gly Gln Asn Leu Ala Arg Ala
            340                 345                 350

Glu Met Glu Ile Ala Phe Gly Ala Leu Phe Ala Arg Phe Pro Gly Leu
        355                 360                 365

Arg Leu Ala Val Pro Ala Ala Glu Ile Pro Val Lys Pro Ala His Ala
    370                 375                 380

Leu Gln Gly Leu Val Glu Leu Pro Val Thr Trp
385                 390                 395


<210> SEQ ID NO 256
<211> LENGTH: 1188
<212> TYPE: DNA
<213> ORGANISM: Artificial Sequence
<220> FEATURE:
<223> OTHER INFORMATION: R63W R74Y L171A mutant of codon-optimised
      sriC12

<400> SEQUENCE: 256

atgaccgaag cactgccttt cccacaagac cgcacctgtc cgtacgaccc accggctggc     60

taccagccgc tgagagatag ccgtccactg agccgtgtta cgttgtatga tggccgtccg    120

gcgtgggtcg tgacgggcca cgcagagagc cgtgcactgc tgacggaccc gcgcttgtcg    180

gctgattggc agaacccggc gttcccgtcc ccggctccgt attttgagac tctgcgtaag    240

gtccgtaccc cgctgctggg cgtggacgat ccggagcaca atacgcagcg tcgtatgttg    300

attccgtcct tcagcgtgaa gcgtgcagca gcactgcgcc cgcgtatcca agaaatcgtg    360

gatcgcctgt tggacgctat ggaacagcaa ggtcctccgg cggaactggt ttctgcgttc    420

gcactgccgg tcccgagcat ggtcatctgc gccttgctgg gtgtcccgta cgctgaccat    480

gaactgtttg agggcctgag ccgtactctg gcgcagagcg cagacccgca agaggtcacc    540

gaagcccgcg ataaactgga agattacttt accgcactgg tggagcgtaa gcgcaaagaa    600

ccgggtgacg gtctgctgga tgaactgatt gcggagcgcc tggacagcgg cgagctgggc    660

catcgtgaac tggtccgtat ggcgatgctg ctgctggttg cgggtcatga aaccacctcc    720

aacatgttga gcctgggcac gttcaccctg ctggagcacc cggagcaatt tgcggcgctg    780

cgcgctgatc ctagcctgct gccggcggca gtggaagaat tgctgcgttt cctgtctatc    840

gccgacggca tggttcgtgt tgcgaccgaa gatatcgaga tcggtggcgt tacgattcgc    900

gcggatgatg gtgtgatctt cagcacgagc gtggttaatc gcgacggtgc ggcgtatgcc    960

tcaccggata ccctggactg ggagcgtagc gcgcgtcacc atgtcgcttt tggtttcggt   1020

gttcaccagt gcctgggtca gaacctggcc cgtgccgaga tggaaattgc atttggtgcg   1080
```

ttattcgccc gttttccggg tctgcgtctt gcagtgcctg cggccgagat tccggtgaaa 1140
ccggcgcacg cgttgcaagg tctggttgag ctgccggtga cctggtga 1188

<210> SEQ ID NO 257
<211> LENGTH: 395
<212> TYPE: PRT
<213> ORGANISM: Artificial Sequence
<220> FEATURE:
<223> OTHER INFORMATION: R63W R74Y L171A mutant of SriC12

<400> SEQUENCE: 257

Met Thr Glu Ala Leu Pro Phe Pro Gln Asp Arg Thr Cys Pro Tyr Asp
1 5 10 15

Pro Pro Ala Gly Tyr Gln Pro Leu Arg Asp Ser Arg Pro Leu Ser Arg
20 25 30

Val Thr Leu Tyr Asp Gly Arg Pro Ala Trp Val Val Thr Gly His Ala
35 40 45

Glu Ser Arg Ala Leu Leu Thr Asp Pro Arg Leu Ser Ala Asp Trp Gln
50 55 60

Asn Pro Ala Phe Pro Ser Pro Ala Pro Tyr Phe Glu Thr Leu Arg Lys
65 70 75 80

Val Arg Thr Pro Leu Leu Gly Val Asp Asp Pro Glu His Asn Thr Gln
85 90 95

Arg Arg Met Leu Ile Pro Ser Phe Ser Val Lys Arg Ala Ala Ala Leu
100 105 110

Arg Pro Arg Ile Gln Glu Ile Val Asp Arg Leu Leu Asp Ala Met Glu
115 120 125

Gln Gln Gly Pro Pro Ala Glu Leu Val Ser Ala Phe Ala Leu Pro Val
130 135 140

Pro Ser Met Val Ile Cys Ala Leu Leu Gly Val Pro Tyr Ala Asp His
145 150 155 160

Glu Leu Phe Glu Gly Leu Ser Arg Thr Leu Ala Gln Ser Ala Asp Pro
165 170 175

Gln Glu Val Thr Glu Ala Arg Asp Lys Leu Glu Asp Tyr Phe Thr Ala
180 185 190

Leu Val Glu Arg Lys Arg Lys Glu Pro Gly Asp Gly Leu Leu Asp Glu
195 200 205

Leu Ile Ala Glu Arg Leu Asp Ser Gly Glu Leu Gly His Arg Glu Leu
210 215 220

Val Arg Met Ala Met Leu Leu Leu Val Ala Gly His Glu Thr Thr Ser
225 230 235 240

Asn Met Leu Ser Leu Gly Thr Phe Thr Leu Leu Glu His Pro Glu Gln
245 250 255

Phe Ala Ala Leu Arg Ala Asp Pro Ser Leu Leu Pro Ala Ala Val Glu
260 265 270

Glu Leu Leu Arg Phe Leu Ser Ile Ala Asp Gly Met Val Arg Val Ala
275 280 285

Thr Glu Asp Ile Glu Ile Gly Gly Val Thr Ile Arg Ala Asp Asp Gly
290 295 300

Val Ile Phe Ser Thr Ser Val Val Asn Arg Asp Gly Ala Ala Tyr Ala
305 310 315 320

Ser Pro Asp Thr Leu Asp Trp Glu Arg Ser Ala Arg His His Val Ala
325 330 335

Phe Gly Phe Gly Val His Gln Cys Leu Gly Gln Asn Leu Ala Arg Ala

-continued

```
            340                 345                 350

Glu Met Glu Ile Ala Phe Gly Ala Leu Phe Ala Arg Phe Pro Gly Leu
        355                 360                 365

Arg Leu Ala Val Pro Ala Ala Glu Ile Pro Val Lys Pro Ala His Ala
    370                 375                 380

Leu Gln Gly Leu Val Glu Leu Pro Val Thr Trp
385                 390                 395
```